US012521437B2

(12) United States Patent
Ptacin et al.

(10) Patent No.: US 12,521,437 B2
(45) Date of Patent: Jan. 13, 2026

(54) IL-2 CONJUGATES AND METHODS OF USE THEREOF

(71) Applicant: Synthorx, Inc., La Jolla, CA (US)

(72) Inventors: Jerod Ptacin, San Diego, CA (US); Carolina E. Caffaro, San Diego, CA (US); Marcos Milla, Carlsbad, CA (US)

(73) Assignee: SYNTHORX, INC., Morristown, NJ (US)

( * ) Notice: Subject to any disclaimer, the term of this patent is extended or adjusted under 35 U.S.C. 154(b) by 1139 days.

(21) Appl. No.: 17/350,672

(22) Filed: Jun. 17, 2021

(65) Prior Publication Data

US 2022/0016249 A1 Jan. 20, 2022

Related U.S. Application Data

(60) Division of application No. 16/918,930, filed on Jul. 1, 2020, now Pat. No. 11,077,195, which is a continuation of application No. 16/783,095, filed on Feb. 5, 2020, now abandoned.

(60) Provisional application No. 62/940,173, filed on Nov. 25, 2019, provisional application No. 62/899,035, filed on Sep. 11, 2019, provisional application No. 62/870,581, filed on Jul. 3, 2019, provisional application No. 62/847,844, filed on May 14, 2019, provisional application No. 62/802,191, filed on Feb. 6, 2019.

(51) Int. Cl.
*A61K 38/00* (2006.01)
*A61K 47/34* (2017.01)

(52) U.S. Cl.
CPC .................................... *A61K 47/34* (2013.01)

(58) Field of Classification Search
CPC ........ A61K 47/34; A61K 38/00; A61K 47/60; A61K 38/2013; A61K 47/545; C07K 14/55; A61P 35/00; A61P 37/04
See application file for complete search history.

(56) References Cited

U.S. PATENT DOCUMENTS 3,687,808 A 8/1972 Merigan, Jr. et al.
4,469,863 A 9/1984 Ts'o et al.
4,476,301 A 10/1984 Imbach et al.
4,587,044 A 5/1986 Miller et al.
4,605,735 A 8/1986 Miyoshi et al.
4,667,025 A 5/1987 Miyoshi et al.
4,683,195 A 7/1987 Mullis et al.
4,683,202 A 7/1987 Mullis
4,762,779 A 8/1988 Snitman
4,766,106 A 8/1988 Katre et al.
4,789,737 A 12/1988 Miyoshi et al.
4,824,941 A 4/1989 Gordon et al.
4,828,979 A 5/1989 Klevan et al.
4,835,263 A 5/1989 Nguyen et al.
4,845,205 A 7/1989 Dinh et al.
4,849,513 A 7/1989 Smith et al.
4,876,335 A 10/1989 Yamane et al.
4,902,502 A 2/1990 Nitecki et al.
4,904,582 A 2/1990 Tullis
4,910,300 A 3/1990 Urdea et al.
4,931,544 A 6/1990 Katre et al.
4,948,882 A 8/1990 Ruth
4,958,013 A 9/1990 Letsinger
4,965,188 A 10/1990 Mullis et al.
4,981,957 A 1/1991 Lebleu et al.
5,015,733 A 5/1991 Smith et al.
5,023,243 A 6/1991 Tullis
5,034,506 A 7/1991 Summerton et al.
5,082,830 A 1/1992 Brakel et al.
5,093,232 A 3/1992 Urdea et al.
5,109,124 A 4/1992 Ramachandran et al.
5,112,963 A 5/1992 Pieles et al.
5,118,800 A 6/1992 Smith et al.
5,118,802 A 6/1992 Smith et al.
5,130,302 A 7/1992 Spielvogel et al.
5,134,066 A 7/1992 Rogers et al.
5,138,045 A 8/1992 Cook et al.
5,166,315 A 11/1992 Summerton et al.
5,175,273 A 12/1992 Bischofberger et al.
5,177,196 A 1/1993 Meyer, Jr. et al.
5,185,444 A 2/1993 Summerton et al.
5,188,897 A 2/1993 Suhadolnik et al.
5,206,344 A 4/1993 Katre et al.
5,214,134 A 5/1993 Weis et al.
5,214,136 A 5/1993 Lin et al.
5,216,141 A 6/1993 Benner
(Continued)

FOREIGN PATENT DOCUMENTS

CN 102665754 A 9/2012
CN 102838671 A 12/2012
(Continued)

OTHER PUBLICATIONS

Klinker et al. Polym. Chem., (2015). 6, pp. 4612-4623.*
Acimovic et al. Molecular Evolution of the Equilibrative Nucleoside Transporter Family: Identification of Novel Family Members in Prokaryotes and Eukaryotes, Mol Biol Evol 12:2199-2210 (2002).
Acsadi et al. Human Dystrophin Expression in mdx Mice After Intramuscular Injection of DNA Constructs. Nature 352:815-818 (1991).
Adhikary et al. Adaptive Mutations Alter Antibody Structure and Dynamics During Affinity Maturation. Biochemistry 54(11):2085-93 (2015).
Agris. Decoding the genome: a modified view. Nucleic Acids Res 32:223-238 (2004).
(Continued)

*Primary Examiner* — Jeanette M Lieb
(74) *Attorney, Agent, or Firm* — McNeill PLLC

(57) ABSTRACT

Disclosed herein are compositions, kits, and methods comprising interleukin (IL) conjugates (e.g., IL-2 conjugates) useful for the treatment of one or more indications. Also described herein are pharmaceutical compositions and kits comprising one or more of the interleukin conjugates (e.g., IL-2 conjugates).

33 Claims, 32 Drawing Sheets

Specification includes a Sequence Listing.

(56) References Cited

U.S. PATENT DOCUMENTS

| | | | |
|---|---|---|---|
| 5,218,105 | A | 6/1993 | Cook et al. |
| 5,229,109 | A | 7/1993 | Grimm et al. |
| 5,232,841 | A | 8/1993 | Hashimoto et al. |
| 5,235,033 | A | 8/1993 | Summerton et al. |
| 5,245,022 | A | 9/1993 | Weis et al. |
| 5,254,469 | A | 10/1993 | Warren, III et al. |
| 5,258,506 | A | 11/1993 | Urdea et al. |
| 5,262,536 | A | 11/1993 | Hobbs, Jr. |
| 5,264,423 | A | 11/1993 | Cohen et al. |
| 5,264,562 | A | 11/1993 | Matteucci |
| 5,264,564 | A | 11/1993 | Matteucci |
| 5,268,273 | A | 12/1993 | Buckholz |
| 5,272,250 | A | 12/1993 | Spielvogel et al. |
| 5,276,019 | A | 1/1994 | Cohen et al. |
| 5,278,302 | A | 1/1994 | Caruthers et al. |
| 5,286,717 | A | 2/1994 | Cohen et al. |
| 5,292,873 | A | 3/1994 | Rokita et al. |
| 5,317,098 | A | 5/1994 | Shizuya et al. |
| 5,319,080 | A | 6/1994 | Leumann |
| 5,321,131 | A | 6/1994 | Agrawal et al. |
| 5,359,044 | A | 10/1994 | Cook et al. |
| 5,367,066 | A | 11/1994 | Urdea et al. |
| 5,370,995 | A | 12/1994 | Hennecke et al. |
| 5,371,241 | A | 12/1994 | Brush |
| 5,389,529 | A | 2/1995 | Panayotatos et al. |
| 5,391,723 | A | 2/1995 | Priest |
| 5,393,878 | A | 2/1995 | Leumann |
| 5,399,676 | A | 3/1995 | Froehler |
| 5,405,938 | A | 4/1995 | Summerton et al. |
| 5,405,939 | A | 4/1995 | Suhadolnik et al. |
| 5,414,077 | A | 5/1995 | Lin et al. |
| 5,416,203 | A | 5/1995 | Letsinger |
| 5,432,272 | A | 7/1995 | Benner |
| 5,434,257 | A | 7/1995 | Matteucci et al. |
| 5,446,137 | A | 8/1995 | Maag et al. |
| 5,451,463 | A | 9/1995 | Nelson et al. |
| 5,453,496 | A | 9/1995 | Caruthers et al. |
| 5,455,233 | A | 10/1995 | Spielvogel et al. |
| 5,457,187 | A | 10/1995 | Gmeiner et al. |
| 5,459,255 | A | 10/1995 | Cook et al. |
| 5,466,677 | A | 11/1995 | Baxter et al. |
| 5,466,786 | A | 11/1995 | Buhr et al. |
| 5,470,719 | A | 11/1995 | Meng et al. |
| 5,470,967 | A | 11/1995 | Huie et al. |
| 5,476,925 | A | 12/1995 | Letsinger et al. |
| 5,484,908 | A | 1/1996 | Froehler et al. |
| 5,486,603 | A | 1/1996 | Buhr |
| 5,489,677 | A | 2/1996 | Sanghvi et al. |
| 5,502,177 | A | 3/1996 | Matteucci et al. |
| 5,510,475 | A | 4/1996 | Agrawal et al. |
| 5,512,439 | A | 4/1996 | Hornes et al. |
| 5,512,667 | A | 4/1996 | Reed et al. |
| 5,514,785 | A | 5/1996 | Ness et al. |
| 5,519,126 | A | 5/1996 | Hecht |
| 5,519,134 | A | 5/1996 | Acevedo et al. |
| 5,525,465 | A | 6/1996 | Haralambidis et al. |
| 5,525,711 | A | 6/1996 | Hawkins et al. |
| 5,536,821 | A | 7/1996 | Agrawal et al. |
| 5,539,082 | A | 7/1996 | Nielsen et al. |
| 5,541,306 | A | 7/1996 | Agrawal et al. |
| 5,541,307 | A | 7/1996 | Cook et al. |
| 5,541,313 | A | 7/1996 | Ruth |
| 5,545,730 | A | 8/1996 | Urdea et al. |
| 5,550,111 | A | 8/1996 | Suhadolnik et al. |
| 5,552,538 | A | 9/1996 | Urdea et al. |
| 5,552,540 | A | 9/1996 | Haralambidis |
| 5,561,225 | A | 10/1996 | Maddry et al. |
| 5,563,253 | A | 10/1996 | Agrawal et al. |
| 5,565,552 | A | 10/1996 | Magda et al. |
| 5,567,810 | A | 10/1996 | Weis et al. |
| 5,567,811 | A | 10/1996 | Misiura et al. |
| 5,571,799 | A | 11/1996 | Tkachuk et al. |
| 5,574,142 | A | 11/1996 | Meyer, Jr. et al. |
| 5,576,427 | A | 11/1996 | Cook et al. |
| 5,578,717 | A | 11/1996 | Urdea et al. |
| 5,578,718 | A | 11/1996 | Cook et al. |
| 5,580,731 | A | 12/1996 | Chang et al. |
| 5,585,481 | A | 12/1996 | Arnold, Jr. et al. |
| 5,587,361 | A | 12/1996 | Cook et al. |
| 5,587,371 | A | 12/1996 | Sessler et al. |
| 5,587,469 | A | 12/1996 | Cook et al. |
| 5,591,584 | A | 1/1997 | Chang et al. |
| 5,591,722 | A | 1/1997 | Montgomery et al. |
| 5,594,121 | A | 1/1997 | Froehler et al. |
| 5,595,726 | A | 1/1997 | Magda et al. |
| 5,595,899 | A | 1/1997 | Sato et al. |
| 5,596,086 | A | 1/1997 | Matteucci et al. |
| 5,596,091 | A | 1/1997 | Switzer |
| 5,597,696 | A | 1/1997 | Linn et al. |
| 5,597,909 | A | 1/1997 | Urdea et al. |
| 5,599,923 | A | 2/1997 | Sessler et al. |
| 5,599,928 | A | 2/1997 | Hemmi et al. |
| 5,602,240 | A | 2/1997 | Mesmaeker et al. |
| 5,608,046 | A | 3/1997 | Cook et al. |
| 5,610,289 | A | 3/1997 | Cook et al. |
| 5,610,300 | A | 3/1997 | Altmann et al. |
| 5,612,199 | A | 3/1997 | Western et al. |
| 5,614,185 | A | 3/1997 | Koths et al. |
| 5,614,617 | A | 3/1997 | Cook et al. |
| 5,618,704 | A | 4/1997 | Sanghvi et al. |
| 5,623,070 | A | 4/1997 | Cook et al. |
| 5,625,050 | A | 4/1997 | Beaton et al. |
| 5,627,053 | A | 5/1997 | Usman et al. |
| 5,633,360 | A | 5/1997 | Bischofberger et al. |
| 5,639,873 | A | 6/1997 | Barascut et al. |
| 5,643,564 | A | 7/1997 | Hamaguchi et al. |
| 5,645,985 | A | 7/1997 | Froehler et al. |
| 5,646,265 | A | 7/1997 | McGee |
| 5,648,247 | A | 7/1997 | Picataggio et al. |
| 5,656,493 | A | 8/1997 | Mullis et al. |
| 5,658,873 | A | 8/1997 | Bertsch-Frank et al. |
| 5,663,312 | A | 9/1997 | Chaturvedula |
| 5,670,633 | A | 9/1997 | Cook et al. |
| 5,677,437 | A | 10/1997 | Teng et al. |
| 5,677,439 | A | 10/1997 | Weis et al. |
| 5,681,941 | A | 10/1997 | Cook et al. |
| 5,688,941 | A | 11/1997 | Cook et al. |
| 5,700,920 | A | 12/1997 | Altmann et al. |
| 5,712,114 | A | 1/1998 | Mankovich et al. |
| 5,714,331 | A | 2/1998 | Buchardt et al. |
| 5,719,262 | A | 2/1998 | Buchardt et al. |
| 5,747,646 | A | 5/1998 | Hakimi et al. |
| 5,750,692 | A | 5/1998 | Cook et al. |
| 5,763,588 | A | 6/1998 | Matteucci et al. |
| 5,830,653 | A | 11/1998 | Froehler et al. |
| 5,834,594 | A | 11/1998 | Hakimi et al. |
| 5,846,818 | A | 12/1998 | Robinson et al. |
| 5,888,732 | A | 3/1999 | Hartley et al. |
| 5,932,474 | A | 8/1999 | Tsien et al. |
| 6,005,096 | A | 12/1999 | Matteucci et al. |
| 6,008,378 | A | 12/1999 | Tsien et al. |
| 6,010,871 | A | 1/2000 | Takahara et al. |
| 6,013,526 | A | 1/2000 | Takahara et al. |
| 6,054,271 | A | 4/2000 | Tsien et al. |
| 6,124,090 | A | 9/2000 | Rose et al. |
| 6,143,557 | A | 11/2000 | Hartley et al. |
| 6,171,861 | B1 | 1/2001 | Hartley et al. |
| 6,261,797 | B1 | 7/2001 | Sorge et al. |
| 6,268,490 | B1 | 7/2001 | Imanishi et al. |
| 6,270,969 | B1 | 8/2001 | Hartley et al. |
| 6,277,608 | B1 | 8/2001 | Hartley et al. |
| 6,288,302 | B1 | 9/2001 | Yu et al. |
| 6,294,323 | B1 | 9/2001 | Ullman et al. |
| 6,365,375 | B1 | 4/2002 | Dietmaier et al. |
| 6,391,544 | B1 | 5/2002 | Salituro et al. |
| 6,451,569 | B1 | 9/2002 | Tsien et al. |
| 6,525,191 | B1 | 2/2003 | Ramasamy |
| 6,670,461 | B1 | 12/2003 | Wengel et al. |
| 6,720,140 | B1 | 4/2004 | Hartley et al. |
| 6,770,748 | B2 | 8/2004 | Imanishi et al. |
| 6,794,499 | B2 | 9/2004 | Wengel et al. |
| 6,906,170 | B1 | 6/2005 | Lider et al. |
| 6,955,807 | B1 | 10/2005 | Shanafelt et al. |
| 7,034,133 | B2 | 4/2006 | Wengel et al. |

(56) References Cited

U.S. PATENT DOCUMENTS

| | | | |
|---|---|---|---|
| 7,045,337 | B2 | 5/2006 | Schultz et al. |
| 7,053,207 | B2 | 5/2006 | Wengel |
| 7,105,653 | B2 | 9/2006 | Shanafelt et al. |
| 7,393,632 | B2 | 7/2008 | Cheo et al. |
| 7,399,845 | B2 | 7/2008 | Seth et al. |
| 7,427,672 | B2 | 9/2008 | Imanishi et al. |
| 7,625,717 | B2 | 12/2009 | Chin et al. |
| 7,670,823 | B1 | 3/2010 | Hartley et al. |
| 7,741,457 | B2 | 6/2010 | Seth et al. |
| 7,744,861 | B2 | 6/2010 | Zhao et al. |
| 7,803,777 | B2 | 9/2010 | DeFrees |
| 8,012,465 | B2 | 9/2011 | Elias et al. |
| 8,252,743 | B2 | 8/2012 | Guyon et al. |
| 8,273,833 | B2 | 9/2012 | Bentley et al. |
| 8,420,792 | B2 | 4/2013 | Tian et al. |
| 8,501,805 | B2 | 8/2013 | Seth et al. |
| 8,546,556 | B2 | 10/2013 | Seth et al. |
| 8,557,776 | B2 | 10/2013 | Lehmann et al. |
| 8,604,127 | B2 | 12/2013 | Lee et al. |
| 8,609,383 | B2 | 12/2013 | Young et al. |
| 8,778,631 | B2 | 7/2014 | Voloshin et al. |
| 9,089,614 | B2 | 7/2015 | Lin et al. |
| 9,682,934 | B2 | 6/2017 | Stafford et al. |
| 9,732,134 | B2 | 8/2017 | Gavin et al. |
| 9,840,493 | B2 | 12/2017 | Yang et al. |
| 9,861,705 | B2 | 1/2018 | Bossard et al. |
| 9,938,516 | B2 | 4/2018 | Zimmerman et al. |
| 9,988,619 | B2 | 6/2018 | Zimmerman et al. |
| 10,610,571 | B2 | 4/2020 | Ptacin et al. |
| 10,851,144 | B2 | 12/2020 | Butz et al. |
| 10,960,079 | B2 | 3/2021 | Bossard et al. |
| 11,077,195 | B2 | 8/2021 | Ptacin et al. |
| 11,622,993 | B2 | 4/2023 | Ptacin et al. |
| 11,701,407 | B2 | 7/2023 | Ptacin et al. |
| 2002/0001804 | A1 | 1/2002 | Mitchell et al. |
| 2002/0007051 | A1 | 1/2002 | Cheo et al. |
| 2003/0083373 | A1 | 5/2003 | Tsien et al. |
| 2004/0171570 | A1 | 9/2004 | Allerson et al. |
| 2005/0112590 | A1 | 5/2005 | Boom et al. |
| 2005/0118623 | A1 | 6/2005 | Belousov et al. |
| 2005/0130923 | A1 | 6/2005 | Bhat et al. |
| 2006/0035254 | A1 | 2/2006 | Manoharan et al. |
| 2006/0074035 | A1 | 4/2006 | Hong et al. |
| 2006/0084136 | A1 | 4/2006 | Kudlicki et al. |
| 2006/0160187 | A1 | 7/2006 | Denis-Mize et al. |
| 2006/0263771 | A1 | 11/2006 | Hirao et al. |
| 2006/0269515 | A1 | 11/2006 | Denis-Mize et al. |
| 2007/0287831 | A1 | 12/2007 | Seth et al. |
| 2008/0025947 | A1 | 1/2008 | Gillies et al. |
| 2008/0039618 | A1 | 2/2008 | Allerson et al. |
| 2008/0300163 | A1 | 12/2008 | Cho et al. |
| 2009/0155844 | A1 | 6/2009 | Yokoyama et al. |
| 2010/0316595 | A1 | 12/2010 | Elias et al. |
| 2010/0323364 | A1 | 12/2010 | Sekine et al. |
| 2012/0022013 | A1 | 1/2012 | Sinclair et al. |
| 2012/0077252 | A1 | 3/2012 | Picataggio et al. |
| 2012/0244112 | A1 | 9/2012 | Ast et al. |
| 2012/0315245 | A1 | 12/2012 | Leon et al. |
| 2013/0333068 | A1 | 12/2013 | Coffin |
| 2014/0249076 | A1 | 9/2014 | Samant et al. |
| 2014/0255345 | A1 | 9/2014 | Grabstein et al. |
| 2014/0314864 | A1 | 10/2014 | Cheng et al. |
| 2014/0315245 | A1 | 10/2014 | Yam et al. |
| 2014/0328791 | A1 | 11/2014 | Bossard et al. |
| 2014/0336166 | A1 | 11/2014 | Briard et al. |
| 2016/0168187 | A1 | 6/2016 | Romesberg et al. |
| 2017/0029829 | A1 | 2/2017 | Romesberg et al. |
| 2017/0044229 | A1 | 2/2017 | Garcia et al. |
| 2017/0260137 | A1 | 9/2017 | Stafford et al. |
| 2017/0283469 | A1 | 10/2017 | Thanos et al. |
| 2017/0313753 | A1 | 11/2017 | Gavin et al. |
| 2017/0369871 | A1 | 12/2017 | Ptacin et al. |
| 2018/0051065 | A1 | 2/2018 | Yin |
| 2018/0086734 | A1 | 3/2018 | Yang et al. |
| 2018/0280551 | A1 | 10/2018 | Rashidian et al. |
| 2019/0376054 | A1 | 12/2019 | Ptacin et al. |
| 2020/0017540 | A1 | 1/2020 | Romesberg et al. |
| 2020/0024597 | A1 | 1/2020 | Ptacin et al. |
| 2020/0040027 | A1 | 2/2020 | Romesberg et al. |
| 2020/0095591 | A1 | 3/2020 | Romesberg et al. |
| 2020/0181220 | A1 | 6/2020 | Ptacin et al. |
| 2020/0188484 | A1 | 6/2020 | Ptacin et al. |
| 2020/0231644 | A1 | 7/2020 | Ptacin et al. |
| 2020/0299349 | A1 | 9/2020 | Garcia et al. |
| 2020/0368293 | A1 | 11/2020 | Olle |
| 2021/0023230 | A1 | 1/2021 | Bossard et al. |
| 2021/0024602 | A1 | 1/2021 | Sprogøe et al. |
| 2021/0046160 | A1 | 2/2021 | Ptacin et al. |
| 2021/0054040 | A1 | 2/2021 | Caffaro et al. |
| 2021/0060169 | A1 | 3/2021 | Ikeda et al. |
| 2021/0070827 | A1 | 3/2021 | Ptacin et al. |
| 2021/0139554 | A1 | 5/2021 | Butz et al. |
| 2021/0196796 | A1 | 7/2021 | Penaflor-Aspuria et al. |
| 2021/0221863 | A1 | 7/2021 | Kang et al. |
| 2021/0299222 | A1 | 9/2021 | Rodriguez et al. |
| 2021/0338829 | A1 | 11/2021 | Caffaro et al. |
| 2022/0016252 | A1 | 1/2022 | Abbadessa et al. |
| 2022/0273767 | A1 | 9/2022 | Caffaro et al. |
| 2022/0324792 | A1 | 10/2022 | Aerni et al. |
| 2023/0265148 | A1 | 8/2023 | Hu et al. |
| 2023/0277627 | A1 | 9/2023 | Caffaro et al. |
| 2023/0302089 | A1 | 9/2023 | Caffaro et al. |
| 2023/0416327 | A1 | 12/2023 | Caffaro et al. |
| 2024/0082359 | A1 | 3/2024 | Ptacin et al. |
| 2024/0226309 | A1 | 7/2024 | Abbadessa et al. |
| 2024/0287151 | A1 | 8/2024 | Caffaro et al. |

FOREIGN PATENT DOCUMENTS

| | | | |
|---|---|---|---|
| CN | 104231068 | A | 12/2014 |
| EP | 0154316 | B1 | 9/1989 |
| EP | 614907 | A1 | 9/1994 |
| EP | 629633 | A2 | 12/1994 |
| EP | 0811385 | B1 | 8/2003 |
| EP | 2130835 | A1 | 12/2009 |
| EP | 2581450 | B1 | 8/2018 |
| EP | 2382228 | B1 | 8/2020 |
| EP | 3280725 | B1 | 8/2020 |
| EP | 4011388 | A1 | 6/2022 |
| EP | 4209503 | A1 | 7/2023 |
| JP | 2007510401 | A | 4/2007 |
| WO | 9213869 | A1 | 8/1992 |
| WO | 9414226 | A1 | 6/1994 |
| WO | 1994014226 | A1 | 6/1994 |
| WO | 9422890 | A1 | 10/1994 |
| WO | 9735869 | A1 | 10/1997 |
| WO | 1997035869 | A1 | 10/1997 |
| WO | 9914226 | A2 | 3/1999 |
| WO | 9921013 | A1 | 4/1999 |
| WO | 9962923 | A2 | 12/1999 |
| WO | 0023456 | A1 | 4/2000 |
| WO | 0074724 | A2 | 12/2000 |
| WO | 0105801 | A1 | 1/2001 |
| WO | 0132887 | A1 | 5/2001 |
| WO | 0236626 | A1 | 5/2002 |
| WO | 02062816 | A1 | 8/2002 |
| WO | 02068216 | A1 | 9/2002 |
| WO | 02070533 | A2 | 9/2002 |
| WO | 03031464 | A2 | 4/2003 |
| WO | 03055898 | A1 | 7/2003 |
| WO | 03070918 | A2 | 8/2003 |
| WO | 2004007713 | A1 | 1/2004 |
| WO | 2004099231 | A2 | 11/2004 |
| WO | 2004106356 | A1 | 12/2004 |
| WO | 2005007121 | A2 | 1/2005 |
| WO | 2005021570 | A1 | 3/2005 |
| WO | 2005026187 | A1 | 3/2005 |
| WO | 2005045015 | A2 | 5/2005 |
| WO | 2005092928 | A1 | 10/2005 |
| WO | 2006049297 | A1 | 5/2006 |
| WO | 2004060300 | A3 | 7/2006 |
| WO | 2006082184 | A2 | 8/2006 |
| WO | 2006081510 | A3 | 1/2007 |
| WO | 2007015557 | A1 | 2/2007 |

(56) References Cited

FOREIGN PATENT DOCUMENTS

| | | | |
|---|---|---|---|
| WO | 2007066737 | A1 | 6/2007 |
| WO | 2007093599 | A1 | 8/2007 |
| WO | 2007085485 | A3 | 9/2007 |
| WO | 2007134181 | A2 | 11/2007 |
| WO | 2007090071 | A3 | 1/2008 |
| WO | 2008067825 | A1 | 6/2008 |
| WO | 2008101157 | A1 | 8/2008 |
| WO | 2008106186 | A2 | 9/2008 |
| WO | 2008150729 | A2 | 12/2008 |
| WO | 2008154401 | A2 | 12/2008 |
| WO | 2009006478 | A3 | 2/2009 |
| WO | 2009123216 | A1 | 10/2009 |
| WO | 2009155102 | A3 | 3/2010 |
| WO | 2010085495 | A1 | 7/2010 |
| WO | 2010023670 | A3 | 9/2010 |
| WO | 2011043385 | A1 | 4/2011 |
| WO | 2011053065 | A2 | 5/2011 |
| WO | 2011139699 | A2 | 11/2011 |
| WO | 2012065086 | A1 | 5/2012 |
| WO | 2015021432 | A1 | 2/2015 |
| WO | 2015038426 | A1 | 3/2015 |
| WO | 2015157555 | A2 | 10/2015 |
| WO | 2016025385 | A1 | 2/2016 |
| WO | 2016115168 | | 11/2016 |
| WO | 2017106767 | A1 | 6/2017 |
| WO | 2017112825 | A3 | 8/2017 |
| WO | 2017162828 | A1 | 9/2017 |
| WO | 2017223528 | A1 | 12/2017 |
| WO | 2019014262 | A1 | 1/2019 |
| WO | 2019014267 | A1 | 1/2019 |
| WO | 2019028419 | A1 | 2/2019 |
| WO | 2019028425 | A1 | 2/2019 |
| WO | 2019165453 | A1 | 8/2019 |
| WO | 2019173832 | A2 | 9/2019 |
| WO | 2020020783 | A1 | 1/2020 |
| WO | 2020056066 | A1 | 3/2020 |
| WO | 2020097325 | A1 | 5/2020 |
| WO | 2020146221 | A1 | 7/2020 |
| WO | 2020201095 | A1 | 10/2020 |
| WO | 2020219943 | A1 | 10/2020 |
| WO | 2020252418 | A2 | 12/2020 |
| WO | 2021030374 | A1 | 2/2021 |
| WO | 2021030483 | A1 | 2/2021 |
| WO | 2021030602 | A1 | 2/2021 |
| WO | 2021030706 | A1 | 2/2021 |
| WO | 2021041206 | A1 | 3/2021 |
| WO | 2021050554 | A1 | 3/2021 |
| WO | 2021091986 | A1 | 5/2021 |
| WO | 2021093633 | A1 | 5/2021 |
| WO | 2021133839 | A1 | 7/2021 |
| WO | 2021140416 | A2 | 7/2021 |
| WO | 2021263026 | A1 | 12/2021 |
| WO | 2022076853 | A1 | 4/2022 |
| WO | 2022076859 | A1 | 4/2022 |
| WO | 2022174101 | A1 | 8/2022 |
| WO | 2022256538 | A1 | 12/2022 |
| WO | 2023122750 | A1 | 6/2023 |
| WO | 2023137401 | A1 | 7/2023 |
| WO | 2024136899 | A1 | 6/2024 |

OTHER PUBLICATIONS

Akbergenov et al. ARC-1, a sequence element complementary to an internal 18S rRNA segment, enhances translation efficiency in plants when present in the leader or intercistronic region of mRNAs. Nucleic Acids Res 32 (1):239-247 (2004).
Allen et al. Roles of DNA polymerase I in leading and lagging-strand replication defined by a high-resolution mutation footprint of ColE1 plasmid replication. Nucleic Acids Res. 39:7020-7033 (2011).
Alpert et al. ABRF 2003: Precipitation of Large, High-Abundance Proteins from Serum With Organic Solvents. Poster No. P111-W (10 pgs) (2003).
Ambrogell Yet al. Pyrrolysine is not hardwired for cotranslational insertion at UAG condons. PNAS 104 (9):3141-3146 (2007).
Amiri et al. Deep origin of plastid/parasite ATP/ADP translocases. J. Mol. Evol. 56:137-150 (2003).
Arenas-Ramirez et al. Improved cancer immunotherapy by a CD25-mimobody conferring selectivity to human Interleukin-2. Sci Transl Med 8:367ra166 (2016).
Arie et al. Phylogenetic identification of n-alkane assimilating Candida yeasts based on nucleotide divergence in the 59 end of LSU rDNA gene. J Gen Appl Microbial. 46(5):257-262 (2000).
Ast et al. Diatom plastids depend on nucleotide import from the cytosol. PNAS USA 106:3621-3626 (2009).
Audia et al. Study of the five Rickettsia prowazekii proteins annotated as ATP/ADP translocases (Tic): Only Tlc1 transports ATP/ADP, while Tlc4 and T1c5 transport other ribonucleotides. J. Bacterial. 188:6261-6268 (2006).
Baba et al. Construction of *Escherichia coli* K-12 in-frame, single-gene knockout mutants: the Keio collection. Mol Syst Biol 2006. 0008 (2006).
Beigelman et al. Synthesis of 5'-C-Methyl-D-allo- & L-Talo-ribonucleoside 3' -0-Phosphoramidites & Their Incorporation into Hammerhead Ribozymes. Nucleosides and Nucleotides 14(3-5):901-905 (1995).
Bentebibel et al. The Novel IL-2 Cytokine Immune Agonist NKTR-214 Harnesses the Adaptive and Innate Immune System for the Treatment of Solid Cancers. Poster #P77. Society for Immunotherapy of Cancer 2017 Annual Meeting (SITC 2017).
Berger et al. Stability and selectivity of unnatural DNA with five-membered-ring nucleobase analogues. J Am Chem Soc 124(7):1222-6 (2002).
Berger et al. Stable and selective hybridization of oligonucleotides with unnatural hydrophobic bases. Angew Chem Int Ed Engl 39:2940-2942 (2000).
Berger et al. Universal bases for hybridization, replication and chain termination. Nucleic Acids Res 28 (15):2911-2914 (2000).
Betz et al. KlenTaq polymerase replicates unnatural base pairs by inducing a Watson-Crick geometry. Nat Chem Biol 8:612-614 (2012).
Betz et al. Structural Insights into DNA Replication without Hydrogen Bonds. J Am Chem Soc. 135:18637-18643 (2013).
Bhatt et al. Peripheral Blood Lymphocyte Responses in Patients with Renal Cell Carcinoma treated with High-Dose Interleukin-2. Poster (SITC 2018).
Biocentury Innovations publication Oct. 27, 2016 (26 pgs).
Bisztray et al. Improved efficiency in site-directed mutagenesis by PCR using a *Pyrococcus* sp. GB-D polymerase. Biotechniques 16:820-823 (1994).
Bohringer et al. Synthesis of 5'-deoxy-5'-methylphosphonate linked thymidine oligonucleotides. Tet Lett 34:2723-2726 (1993).
Bordo et al. Suggestions for "safe" residue substitutions in site-directed mutagenesis. J Mol Biol 217:721-729 (1991).
Boyman et al. Selective Stimulation of T Cell subsets with Antibody-Cytokine Immune Complexes. Science 311 :1924-1927 (2006).
Boyman et al. The role of interleukin-2 during homeostatis and activation of the immune system. Nature 12:180-190 (2012).
Braasch et al. Locked nucleic acid (LNA): fine-tuning the recognition of DNA and RNA. Chem. Biol 8:1-7 (2001).
Branca. Rekindling cancer vaccines. Nat Biotechnol 34(10):1019-1025 (2016).
Brauns et al. Studies On Lignin and Related Compounds: XII. Methanol Lignin. Canadian Journal of Research 13b (1):28-34 (1935).
Cann et al. A heterodimeric DNA polymerase: Evidence that members of Euryarchaeota possess a distinct DNA polymerase. PNAS USA 95:14250 (1998).
Capone et al. Amber, ochre and opal suppressor tRNA genes derived from a human serine tRNA gene. EMBO J 4 (1): 213-221 (1985).
Cariello et al. Fidelity of Thermococcus litoralis DNA polymerase (VentTM) in PCR determined by denaturing gradient gel electrophoresis Nucl Acid Res 19:4193-4198 (1991).
Carmenate et al. Human IL-2 Mutein with Higher Antitumor Efficacy Than Wild Type IL-2. Journal of Immunology 190(12):6230-6238 (2013).

(56) References Cited

OTHER PUBLICATIONS

Charych et al. Combining Complementary Mechanisms of Immune Activation: NKTR-214, a biased IL-2 Pathway Agonist and Immune Checkpoint Antagonists. Poster Abstract 3018. ESMO Annual Meeting (2016).
Charych et al. Modeling the receptor pharmacology, pharmacokinetis, and pharmacodynamics of NKTR-214, a kinetically-controlled interleukin-2 (IL2) receptor agonist for cancer immunotherapy. PLoS One 12(7):e0179431 (2017).
Charych et al. NKTR-214, an Engineered Cytokine with Biased IL2 Receptor Binding, Increased Tumor Exposure, and Marked Efficacy in Mouse Tumor Models. Clin Cancer Res 22(3):680-690 (2016).
Chastgner et al. Lack of intermediate-affinity interleukin-2 receptor in mice leads to dependence on interkeukin-2 receptor a, 13 and y chain expression for T cell growth. Eur J Immunol 26:201-206 (1996).
Chatterjee et al. A Versatile Platform for Single- and Multiple-Unnatural Amino Acid Mutagenesis in *Escherichia coli*. Biochemistry 52(10):1828-1837 (2013).
Chaturvedi et al. Stabilization of triple-stranded oligonucleotide complexes: use of probes containing alternating phosphodiester and stereo-uniform cationic phosphoramidate linkages. Nucleic Acids Res. 24:2318-2323 (1996).
Chatzkel et al. Coordinated pembrolizumab and high dose IL-2 (5-in-a-row schedule) for therapy therapy of metastatic clear cell renal cancer: a single-center, single-arm trial. Poster Abstract No. 244333 (2010).
Chen et al. A novel human IL-2 mutein with minimal systemic toxicity exerts greater antitumor efficacy than wild-type IL-2. Cell Death& Disease 9:989 (2018).
Chen et al. Directed polymerase evolution. FEBS Lett. 588(2):219-229 (2014).
Chen et al. Phosphonate Analogues of Cytosine Arabinoside Monophosphate. Phosphorus, Sulfur and Silicon 177:1783-1786 (2002).
Chen et al. The expanding world of DNA and RNA. Curr Opin Chem Biol 34:80-87 (2016).
Chen. Selective chemical labeling of proteins. Org. Biomol. Chem. 14:5417-5439 (2016).
Chien et al. Deoxyribonucleic acid polymerase from the extreme thermophile Thermus aquaticus. J Bacteriol 127:1550-1557 (1976).
Cleary et al. Production of complex nucleic acid libraries using highly parallel in situ oligonucleotide synthesis. Nat Methods 1 (3):241-248 (2004).
Collingwood et al. The Synthesis and Incorporation in Oligonucleotides of a Thymidine Dimer Containing an Internucleoside Phospinate Linkate. Synlett, 7:703-705 (1995).
Sharma et al. NKTR-214 enhances anti-tumor T cell immune responses induced by checkpoint blockade or vaccination. Poster (2017).
Shea et al. Synthesis, hybridization properties and antiviral activity of lipid oligodeoxynucleotide conjugates. Nucl. Acids Res. 18:3777-3783 (1990).
Shimizu et al. Cell-free translation systems for protein engineering. Febs J 273:4133-4140 (2006).
Shizuka et al. Site-specific functionalization of RNA molecules by an unnatural base pair transcription system via click chemistry. Chem. Comm. 48:10835-10837 (2012).
Siegel et al. Interleukin-2 Toxicity. J Clin Oncol 9(4):694-704 (1991).
Sierzputowska-Gracz et al. Chemistry and structure of modified uridines in the anticodon, wobble position of transfer RNA are determined by thiolation. J Am Chem Soc 109:7171-7177 (1987).
Sim et al. IL2 Variant Circumvents ICOS+ Regulatory T-cell Expansion and Promotes NK Cell Activation. Cancer Immunol Res. 4(11):983-995 (2016).
Singh et al. LNA (locked nucleic acids): synthesis and high-affinity nucleic acid recognition. Chem. Commun. 4:455-456 (1998).
Singh et al. Synthesis of 2'-Amino-LNA: A Novel Conformationally Restricted High Affinity Oligonucleotide Analogue with a Handle. J. Org. Chem. 63:10035-10039 (1998).
Sivakumar et al. Comparison of Vascular Leak Syndrome in Mice treated with IL21 or IL2. Comparative Medicine 63 (1):13-21 (2013).
Slagle et al. Click conjugation of cloaked peptide ligands to microbubbles. Bioconjugate Chem. 2018, 29:1534-1543 (2018).
Sockolosky et al. Selective targeting of engineered T cells using orthogonal IL-2 cytokine-receptor complexes. Science 359(6379):1037-1042 (2018).
Southern et al. Transformation of mammalian cells to antibiotic resistance with a bacterial gene under control of the SV40 early region promoter. J Mol Appl Genet 1 :327-341 (1982).
Spangler et al. Antibodies to Interleukin-2 Elicit Selective T Cell Subset Potentiation through Distinct Conformational Mechanism. Immunity 42:815-825 (2015).
Srivastava et al. Five- and Six-Membered Conformationally Locked 2',4'-Carbocyclic ribo-Thymidines: Synthesis, Structure, and Biochemical Studies. J. Am. Chem. Soc. 129(26):8362-8379 (2007).
Statement regarding IL-2 conjugates used in examples, 1 page (2021).
Stauber et al. Crystal Structure of the IL-2 signaling complex: Paradigm for a heterotrimeric cytokine receptor. PNAS 103(8):2788-2793 (2006).
Stenesh et al. DNA polymerase from mesophilic and thermophilic bacteria. III. Lack of fidelity in the replication of synthetic polydeoxyribonucleotides by DNA polymerase from Bacillus licheniformis and Bacillus stearothermophilus. Biochim Biophys Acta 475:32-41 (1977).
Sun et al. First-In-Human dose Selection of ALKS 4230, an Investigational Immunotherapeutic Agent. Poster 4088 (2017).
Sun et al. Pharmacokinetics and Pharmacodynamic Effects of ALKS 4230, an Investigational Immunotherapeutic Agent, in Cynomolgus Monkeys After Intravenous and Subcutaneous Administration. Poster (2018).
Svinarchuk et al. Inhibition of HIV proliferation in MT-4 cells by antisense oligonucleotide conjugated to lipophilic groups. Biochimie. 75:49-54 (1993).
Switzer et al. Enzymatic recognition of the base pair between isocytidine and isoguanosine. Biochemistry 32(39): 10489-10496 (1993).
Synthorx, Inc. Commission File No. 001-38756. Form 10-K Annual Report Pursuant to Section 13 or 15(d) of the Securities Exchange Act of 1934 for Fiscal Year End dated Dec. 31, 2018 (144 pgs).
Synthorx, Inc. Commission File No. 001-38756. Form 10-Q Annual Report Pursuant to Section 13 or 15(d) of the Securities Exchange Act of 1934 for Quarterly Period Ended Mar. 31, 2019.
Synthorx, Inc. Commission File No. 001-38756. Form 8-K Current Report Pursuant to Section 13 or 15(d) of the Securities Exchange Act of 1934 dated Apr. 2, 2019 (8 pgs).
Synthorx, Inc. Commission File No. 001-38756. Form 8-K Current Report Pursuant to Section 13 or 15(d) of the Securities Exchange Act of 1934 dated May 31, 2019 (15 pgs).
Synthorx, Inc. Registration No. 333-228355. Amendment No. 1 to Form S-1 Registration Statement Under The Securities Act of 1933 filed Nov. 27, 2018 (355 pgs.).
T Jalsma et al. Signal peptide-dependent protein transport in Bacillus subtilis: a genome-based survey of the secretome. Microbial Mol Biol Rev 64(3):515-547 (2000).
Tae et al. Efforts toward expansion of the genetic alphabet: replication of DNA with three base pairs. J. Am. Chem. Soc. 123:7439-7440 (2001).
Takagi et al. Characterization of DNA polymerase from *Pyrococcus* sp. strain KOD1 and its application to PCR. Appl Environ Microbiol 63(11):4504-4510 (1997).
Takai et al. A single uridine modification at the wobble position of an artificial tRNA enhances wobbling in an *Escherichia coli* cell-free translation system. FEBS Lett 447(1):1-4 (1999).
Tapp et al. Homogeneous scoring of single-nucleotide polymorphisms: comparison of the 5'-nuclease TaqMan assay and Molecular Beacon probes. Biotechniques 28(4):732-738 (Apr. 2000).

(56) References Cited

OTHER PUBLICATIONS

Tomizawa et al. Initiation of DNA synthesis in *Escherichia coli*. Annu. Rev. Biochem. 48:999-1034 (1979).
Tuerk. Systematic evolution of ligands by exponential enrichment: RNA ligands to bacteriophage T4 DNA polymerase. Science 249:505-510 (1990).
Tyagi et al. Molecular Beacons: Probes that Fluoresce Upon Hybridization. Nature Biotechnology 14(3):303-308 (1996).
U.S. Appl. No. 14/910,203 Office Action dated Feb. 5, 2019.
U.S. Appl. No. 14/910,203 Office Action dated Sep. 13, 2018.
U.S. Appl. No. 15/302,874 Office Action dated Jan. 28, 2019.
U.S. Appl. No. 15/302,874 Office Action dated Jul. 27, 2018.
U.S. Appl. No. 15/302,874 Office Action dated Jun. 19, 2019.
U.S. Appl. No. 15/302,874 Office Action dated Mar. 13, 2018.
U.S. Appl. No. 15/543,217 Office Action dated Aug. 7, 2019.
U.S. Appl. No. 15/543,217 Office Action dated Feb. 7, 2019.
U.S. Appl. No. 15/543,217 Office Action dated Nov. 18, 2019.
U.S. Appl. No. 15/543,217 Office Action dated Sep. 24, 2018.
U.S. Appl. No. 16/413,219 Office Action dated Aug. 22, 2019.
U.S. Appl. No. 16/434,999 Office Action dated Oct. 9, 2019.
Vaishampayan et al. A Phase 1 Trial of ALKS 4230, an Engineered Cytokine Activator of NK and Effector T Cells, in Patients with Advanced Solid Tumors. Poster for Abstract #TPS3111 (2017).
Vaishampayan et al. Safety, pharmacokinetics and pharmacodynamic effects of ALKS 4230 in patients with advanced solid tumors from the ongoing dose escalation portion of a first in human (FIH) study. Poster (2018).
Van Gool et al. Interleukin-5-producing group 2 innate lymphoid cells control eosinophilia induced by interleukin-2 therapy. Blood 124(24):3572-3576 (2014).
Co-pending U.S. Appl. No. 16/518,715, filed Jul. 22, 2019, also cited herein as US 2020/0040027.
Co-pending U.S. Appl. No. 16/530,742, filed Aug. 2, 2019, also cited herein as US 2019/0376054.
Co-pending U.S. Appl. No. 16/535,992, filed Aug. 8, 2019, also cited herein as US 2020/0017540.
Co-pending U.S. Appl. No. 16/577,347, filed Sep. 20, 2019, also cited herein as US 2020/0024597.
Co-pending U.S. Appl. No. 16/591,422, filed Oct. 2, 2019, also cited herein as US 2020/0095591.
Co-pending U.S. Appl. No. 16/634,479, filed Jan. 27, 2020, also cited herein as US 2020/0181120.
Co-pending U.S. Appl. No. 16/634,487, filed Jan. 27, 2020; also cited herein as US 2020/0231644.
Co-pending U.S. Appl. No. 16/803,816, filed Feb. 27, 2020; also cited herein as US 2020/0231644.
Co-pending U.S. Appl. No. 16/993,967, filed Aug. 14, 2020, also cited herein as US 2021/0046160.
Co-pending U.S. Appl. No. 17/001,965, filed Aug. 25, 2020; also cited herein as US 2020/0399338.
Crooke et al. Pharmacokinetic properties of several novel oligonucleotide analogs in mice. J Pharmacol Exp Ther 277:923-937 (1996).
Dahl et al. Discovery and validation of a series of aryl sulfonamides as selective inhibitors of tissue-nonspecific alkaline phosphatase (TNAP). J Med Chem 52(21):6919-6925 (2009).
De Mesmaeker et al. Amide-Modified Oligonucleotides with Preorganized Backbone and Furanose Rings: Highly Increased Thermodynamic Stability of the Duplexes Formed with their RNA and DNA Complements. Synlett 11:1287-1290 (1997).
Deiters et al. Site-specific PEGylation of proteins containing unnatural amino acids. Bioog Med Chem Lett 14 (23):5743-5745 (2004).
Dhami et al. Systematic exploration of a class of hydrophobic unnatural base pairs yields multiple new candidates for the expansion of the genetic alphabet. Nucleic Acids Res 42:10235-10244 (2014).
Diab et al. NKTR-214 (CD-122-biased agonist) plus nivolumab in patients with advanced solid tumors: Preliminary phase 1/2 results of PIVOT. Powerpoint presentation. ClinicalTrials.gov NCT02983045. 2018 ASCO Annual Meeting (2018).
Diab et al. Pivot-02: Preliminary safety, efficacy and biomarker results from dose escalation of the Phase 1/2 study of CD-122-biased agonist NKTR-214 plus nivolumab in patients with locally advanced/metastatic melanoma, renal cell carcinoma and non-small cell lung cancer. ClinicalTrials gov Identifier: NCT02983045 PowerPoint presentation. SITC (2017).
Diaz et al. Accuracy of replication in the polymerase chain reaction. Comparison between Thermotoga maritima DNA polymerase and Thermus aquaticus DNA polymerase. Braz J Med Res 31:1239-1242 (1998).
Dien et al. Eight-Letter DNA. Biochemistry 58:2581-2583 (2019).
Dien et al. Expansion of the genetic code via expansion of the genetic alphabet. Curr Opin Chem Biol 46:196-202 (2018).
Dien et al. Progress Toward a Semi-Synthetic Organism with an Unrestricted Expanded Genetic Alphabet. J Am Chem Soc. 140:16115-16123 (2018).
Dozier et al. Site-specific PEGylation of proteins containing unnatural amino acids. Int J Mol Sci 16:25831-25864 (2015).
Dranoff. Cytokines in cancer pathogenesis and cancer therapy. Nature Reviews Cancer 4:11-22 (2004).
Dufour. THOR-707, an engineered not-alpha IL-2, for the treatment of solid tumors induces strong immunological responses in vivo. CSCO Immunotherapy Seminar Shanghi, China. (2019).
Dumas et al. Designing logical codon reassignment—Expanding the chemistry in biology. Chem Sci 6:50-69 (2015).
Dupradeau et al. Differential salvation and tautomer stability of a model base pair within the minor and major grooves of DNA. J Am Chem Soc 127(44):15612-7 (2005).
Eggertsson et al. Transfer ribonucleic acid-mediated suppression of termination codons in *Escherichia coli*. Microbial Rev 52(3):354-374 (1988).
Egholm et al. PNA hybridizes to complementary oligonucleotides obeying the Watson-Crick hydrogen-bonding rules. Nature 365(6446):566-568 (1993).
El Yacoubi et al. Biosynthesis and function of posttranscriptional modifications of transfer RNAs. Annu Rev Genet 46:69-95 (2012).
Elayadi et al. Application of PNA and LNA oligomers to chemotherapy. Curr Opinion Invens Drugs 2:558-561 (2001).
Ellington et al. In vitro selection of RNA molecules that bind specific ligands. Nature 346:818-822 (1990).
Enablement Decision Tree, Example F, situation 1. 72 pages. http://www.uspto.gov/web/offices/pac/dapp/1oecba.htnn#7 > accessed Aug. 18, 2019.
Engleerg-Kukla et al. Chapter 60: Suppression of Termination Condons. *Escherichia coli* and *Salmonella* Cellular and Molecular Biology. 909-921 (1996).
Englisch et al. Chemically Modified Oligonucleotides as Probes and Inhibitors. Angew. Chem. Int. Ed. Eng. 30:613-629 (1991).
Eppacher et al., Synthesis and Incorporation of C(5')-Ethynylated Uracil-Derived Phosporamidites into RNA. Helvetica Chimica Acta. 87:3004-3020 (2004).
Fa et al. Expanding the substrate repertoire of a DNA polymerase by directed evolution. J Am Chem Soc 126 (6):1748-54 (2004).
Fairhurst et al. Synthesis and Hybridisation Properties of Phosphonamidate Ester Modified Nucleic Acid. Synlett, 4:467-472 (2001).
Fan et al. Rationally evolving tRNAPyl for efficient incorporation of noncanonical amino acids. Nucleic Acids Res 43 (22):e156 (2015).
Feldman et al. Chemical Stabilization of Unnatural Nucleotide Triphosphates for the in Vivo Expansion of the Genetic Alphabet. J Am Chem Soc 139(6):2464-2467 (2017).
Feldman et al. Optimization of Replication, Transcription, and Translation in a Semi-Synthetic Organism. J Am Chem Soc 141:10644-10653 (2019).
Feldman et al. In Vivo Structure-Activity Relationships and Optimization of an Unnatural Base Pair for Replication in a Semi-Synthetic Organism. J Am Chem Soc. 139:11427-11433 (2017).
Feldman et al. A Tool for the Import of Natural and Unnatural Nucleoside Triphosphates into Bacteria. J Am Chem Soc. 140:1447-1454 (2018).
Feldman. Expansion of the Genetic Alphabet: A Chemist's Approach to Synthetic Biology. Ace Chem Res 51 (2):394-403 (2018).

(56) References Cited

OTHER PUBLICATIONS

Fersht. Enzyme Structure and Mechanism, 2nd ed., W. H. Freeman & Co., New York. 350-351 (1985).
Fidanza et al. Site-specific labeling of DNA sequences containing phosphorothioate diesters. JAGS 114 (14):5509-5517 (2002).
Fisher et al. Chlamydia trachomatis Transports NAD via the Npt1 ATP/ADP Translocase. Journal of Bacteriology 195 (15):3381-3386 (2013).
Fidanza et al. Functionalization of oligonucleotides by the incorporation of thio-specific reporter groups. In Protocols for Oligonucleotide Conjugates. Protocols for Oligonucleotide Conjugates: Synthesis and Analytical Techniques 26:121-143 (1994).
Floros et al. Anticancer Cytokines: Biology and Clinical Effects of Interferon-a2, Interleukin (IL)-2, IL-15, IL-21, and IL-12. Semin Oncol 42(4):539-548 (2015).
Fourrey et al. Photo Rearrangement of Phenyl Selenide Derivatives Access to Selenium Substituted C Nucleosides. Tetrahedron Letters 21 :455-458 (1980).
Friedhoff et al. Quantitative polymerase chain reaction with oligodeoxynucleotide ligation assay/enzyme-linked immunosorbent assay detection. Anal Biochem 215(1):9-16 (1993).
Gallie et al. The 5'-leader sequence of tobacco mosaic virus RNA enhances the expression of foreign gene transcripts in vitro and in vivo. Nucleic Acids Res. 15(8):3257-3273 (1987).
Gallie. The 5'-leader of tobacco mosaic virus promotes translation through enhanced recruitment of elF4F. Nucleic Acids Res 30(15):3401-3411 (2002).
Gallier et al. Ex-Chiral-Pool Synthesis of B-Hydroxyphosphonate Nucleoside Analogues. Eur. J. Org. Chem., 925-933 (2007).
Gardner et al. Comparative Kinetics of Nucleotide Analog Incorporation by Vent DNA Polymerase. J Biol Chem 279 (12):11834-11842 (2004).
Gardner et al. Determinants of nucleotide sugar recognition in an archaeon DNA polymerase. Nucleic Acids Research 27(12):2545-2553 (1999).
Geze et al. Synthesis of sinefungin and its C-6' epimer. J. Am. Chem. Soc. 105(26):7638-7640 (1983).
Gillies et al. A Low-Toxicity IL-2-based Immunocytokine Retains Antitumor Activity Despite Its High Degree of IL-2 receptor Selectivity. Clin Cancer Res 17(11):3673-3686 (2011).
Goldberg et al. Re: Z. Ram et al. In situ retroviral-mediated gene transfer for the treatment of brain tumors in rats. Cancer Res. 53:83-88 (1993).
Gong. Recent advances in bioorthogonal reactions for site-specific protein labeling and engineering. Tett. Lett. 56:2123-2132 (2015).
Goodman. Error-prone repair DNA polymerases in prokaryotes and eukaryotes. Annu. Rev. Biochem. 71:17-50 (2002).
Guatelli et al. Isothermal, in vitro amplification of nucleic acids by a multienzyme reaction modeled after retroviral replication. PNAS USA 87(5): 1874-1878 (1990).
Haferkamp et al. Functional expression and characterisation of membrane transport proteins. Plant Biol. 14:675-690 (2012).
Haferkamp et al. Tapping the nucleotide pool of the host: novel nucleotide carrier proteins of Protochlamydia amoebophila. Mol. Microbial. 60:1534-1545 (2006).
Hampton et al. Synthesis of 6'-cyano-6'-deoxyhomoadenosine-6'-phosphonic acid and its phosphoryl and byrophosphoryl anhydrides and studies of their interactions with adenine nucleotide utilizing enzymes. J. Am. Chem. Soc. 95(13):4404-4414 (1973).
Hampton et al. Design of substrate-site-directed irreversible inhibitors of adenosine 5'-phosphate aminohydrolase. Effect of substrate substituents on affinity for the substrate site. J. Med. Chem. 19(8): 1029-1033 (1976).
Hampton et al. Design of substrate-site-directed inhibitors of adenylate kinase and hexokinase. Effect of substrate substituents on affinity for the adenine nucleotide sites. J. Med. Chem. 19:1371-1377 (1976).
Hancock et al. Expanding the Genetic Code of Yeast for Incorporation of Diverse Unnatural Amino Acids via a Pyrrolysyl-tRNA Synthetase/tRNA Pair. JAGS 132:14819-14824 (2010).
Hari et al. Optimization of the pyridyl nucleobase scaffold for polymerase recognition and unnatural base pair replication. Chembiochem 9(17):2796-2799 (2008).
Hatch et al. Adenine nucleotide and lysine transport in Chlamydia psittaci. J. Bacterial. 150:662-670 (1982).
Hayes et al. Combining computational and experimental screening for rapid optimization of protein properties. PNAS USA 99:15926-15931 (2002).
Heaton et al. Characterization of lymphokine-activated killing by human peripheral blood mononuclear cells stimulated with interleukin 2 (IL-2) analogs specific for the intermediate affinity IL-2 receptor. Cell Immunol 147:167-179 (1993).
Heaton et al. Human interleukin 2 analogues that preferentially bind the intermediate-affinity interleukin 2 receptor lead to reduced secondary cytokine secretion: implications for the use of these interleukin 2 analogues in cancer Immunotherapy. Cancer Res 53:2597-2602 (1993).
Henry et al. Beyond A, C, G and T: augmenting nature's alphabet. Curr Opin Chem Biol 7(6):727-33 (2003).
Henry et al. Determinants of unnatural nucleobase stability and polymerase recognition. J Am Chem Soc 125 (32):9638-9646 (2003).
Henry et al. Efforts to expand the genetic alphabet: identification of a replicable unnatural DNA self-pair. J Am Chem Soc 126(22):6923-31 (2004).
Hinnisdaels et al. Direct cloning of PCR products amplified with Pwo DNA polymerase. Biotechniques 20:186-188 (1996).
Hirao et al. An unnatural base pair between imidazolin-2-one and 2-amino-6-(2-thienyl)purine in replication and transcription. Nucleic Acids Res Suppl. 2(1):37-38 (2002).
Hirao et al., Unnatural base pair systems toward the expansion of the genetic alphabet in the central dogma. Proceedings of the Japan Academy, Series B, Phys Biol Sci. 88:345-367 (2012).
Horn et al. Bacterial endosymbionts of free-living amoebae. J. Eukaryot. Microbial. 5:509-514 (2004).
http://www.uspto.gov/web/offices/pac/dapp/1pecba.htm#7> Enablement Decision Tree, Example F, situation 1; accessed Aug. 18, 2019.
Hu et al. The Generation of Low Toxicity Interleukin-2 Fusion Proteins Devoid of Vasopermeability Activity. Blood 101 (12):4853-61 (2003).
Hurwitz et al. A Novel Immune Agonist, NKTR-214, Increases the No. of Activity of CD8+ Tumor Infiltrating Lymphocytes in Patients with Advance Renal Cell Carcinoma. Poster Abstract #454. Poster Session C. Asco (2017).
Hutter et al. From Phosphate to Bis(methylene) Sulfone: Non-Ionic Backbone Linkers in DNA. Helvetica Chimica Acta, 85:2777-2806 (2002).
Hwang et al. Polymerase recognition and stability of fluoro-substituted pyridone nucleobase analogues. Chembiochem 8:1606-1611 (2007).
Hwang et al. Substituent effects on the pairing and polymerase recognition of simple unnatural base pairs. Nucleic Acids Res 34(7):2037-45 (2006).
Hwang et al. The effects of unnatural base pairs and mispairs on DNA duplex stability and salvation. Nucleic Acids Res 37(14):4757-4763 (2009).
Hwang et al. Unnatural substrate repertoire of A, B, and X family DNA polymerases. J Am Chem Soc 130 (44):14872-14882 (2008).
Imran et al. Influence of architecture of high molecular weight linear and branched polyglycerols on their biocompatibility and biodistribution. Biomaterials 33:9135-9147 (2012).
Insight-Esprit Study Group et al. Interleukin-2 Therapy in Patients with HIV Infection. N Engl J Med. 361 (16):1548-59 (2009).
International Search Report and Written Opinion for PCT/US2014050423 dated Nov. 24, 2014.
International Search Report and Written Opinion for PCT/US2015/025175 dated Oct. 13, 2015.
International Search Report and Written Opinion for PCT/US2016/013095 dated Apr. 27, 2016.
International Search Report and Written Opinion for PCT/US2018/041509 dated Sep. 27, 2018.
International Search Report and Written Opinion for PCT/US2018/45265 dated Nov. 30, 2018.

(56) References Cited

OTHER PUBLICATIONS

International Search Report and Written Opinion for PCT/US2018/045257 dated Nov. 21, 2018.
International Search Report and Written Opinion for PCT/US2020/016885 dated Jun. 23, 2020.
International Search Report and Written Opinion for PCT/US2018/041503 dated Nov. 7, 2018.
Invitation to Pay Additional Fees for PCT/US2018/45257 dated Sep. 25, 2018.
Invitation to Pay Additional Fees for PCT/US2018/45265 dated Sep. 25, 2018.
Jager et al. Oligonucleotide N-Akylphosphoroamidates: Synthesis and Binding to Polynucleotides. Biochem. 27:7247-7246 (1988).
Zhang et al., "Site-specific PEGylation of interleukin-2 enhances immunosuppression via the sustained activation of regulatory T cells," Nature Biomed. Engin., 5: 1288-1305 (2021).
Dyson et al., "Chemistry of Synthetic Drugs," Publishing House "MIR", pp. 12-19 (1964); English language translation provided.
Pokrovsky, V.I., Popular Medical Encyclopedia, 4th Edition, p. 317 (1997); English language translation provided.
Pokrovsky, V.I., Small Medical Encyclopedia, Nephrolithiasis—toxicomanias, Scientific Engineering Library, vol. 5, pp. 90-96 (1996); English language translation provided.
Jiang et al. Role of IL-2 in cancer immunotherapy. Oncoimmunology 5(6):e1163462 (2016).
Johansson et al. The solution structures of mutant calbindin D9k's, as determined by NMR, show that the calcium-binding site can adopt different folds. Biochemistry 35(25):8429-8438 (1996).
Jones et al. A Subset of Latency-Reversing Agents Expose HIV-Infected Resting CD4+ T-Cells to Recognition by Cytotoxic T-Lymphocytes. PLoS Pathogens 12(4):e1005545 (2016).
Joseph et al. THOR-707, A novel not-alpha IL-2, elicits durable pharmacodynamic responses in non-human primates and, efficacy as single agent and in combination with anti PD-1 in multiple syngeneic mouse models. American Association of Cancer Research (AACR) Annual Meeting 2019 Poster (2019).
Jung et al. Synthesis of phosphonate derivatives of uridine, cytidine, and cytosine arabinoside. Bioorg. Med. Chem. 8:2501-2509 (2000).
Kabanov et al. A new class of antivirals: antisense oligonucleotides combined with a hydrophobic substituent effectively inhibit influenza virus reproduction and synthesis of virus-specific proteins in MDCK cells. FEBS Lett. 259:327-330 (1990).
Kandimalla et al. Effect of chemical modifications of cytosine and guanine in a CpG-motif of oligonucleotides: structure-immunostimulatory activity relationships. Bioorg. Med. Chem. 9:807-813 (2001).
Kappler et al. Species- or isozyme-selective enzyme inhibitors. 8. Synthesis of disubstituted two-substrate condensation products as inhibitors of rat adenylate kinases. J. Med. Chem. 25:1179-1184 (1982).
Kappler et al. Isozyme-specific enzyme inhibitors. 11. (L-homocysteine)-ATP S-C5' covalent adducts as inhibitors of rat methionine adenosyltransferases. J. Med. Chem. 29:1030-1038 (1986).
Kaur et al. Thermodynamic, Counterion, and Hydration Effects for the Incorporation of Locked Nucleic Acid Nucleotides into DNA Duplexes. Biochemistry 45(23):7347-7344 (2006).
Khalili et al. Mechanistic modeling of a new kinetically-controlled CD122 agonist for cancer immunotherapy: NKTR-214 pharmacokinetics, pharmacodynamics, and receptor pharmacology. Poster Abstract 1614. AACR Annual Meeting, Apr. 2017 (2017).
Kim et al. Stability and polymerase recognition of pyridine nucleobase analogues: role of minor-groove H-bond acceptors. Angew Chem Int Ed Engl 45(46):7809-12 (2006).
Kimoto et al. Generation of high-affinity DNA aptamers using an expanded genetic alphabet. Nat. Biotech. 31 (5):453-458 (2013).
Kivimae et al. Comprehensive Antitumor Immune Activation by a Novel TLR 7/8 Targeting Agent NKTR-262 Combined With CD122-Biased Immunostimulary Cytokine NKTR-214. Poster #3755 (2018).
Kivimae et al. Harnessing the innate and adaptive immune system to eradicate treated and distant untreated solid tumors. Poster #P275. Immunotherapy of Cancer 2017 Annual Meeting (2017).
Klein et al. Cergutuzumab amunaleukin (CEA-IL2v), a CEA-targeted IL-2 variant-based immunocytokine for combination cancer immunotherapy: Overcoming limitations of aldesleukin and conventional IL-2-based Immunocytokines. Oncoimmunology 6(3):e1277306 (2017).
Knab et al. Nucleotide parasitism by Simkania negevensis (Chlamydiae). J. Bacterial. 193:225-235 (2011).
Koshkin et al. LNA (Locked Nucleic Acids): Synthesis of the adenine, cytosine, guanine, 5-methylcytosine, thymine and uracil bicyclonucleoside monomers, oligomerisation, and unprecedented nucleic acid recognition. Tetrahedron. 54:3607-3630 (1998).
Kranaster et al. Increased single-nucleotide discrimination in allele-specific polymerase chain reactions through primer probes bearing nucleobase and 2'-deoxyribose modifications. Chem EurJ 13(21):6115-6122 (2007).
Krieg et al. Improved IL-2 immunotherapy by selective stimulation of IL-2 receptors on lymphocytes and endothelial cells. PNAS USA 107:11906-11911 (2010).
Kroschwitz. The Concise Encyclopedia of Polymer Science and Engineering. 858-859 (1990).
Kubelka et al. Synthesis of 2,6-disubstituted pyridin-3-yl C-2'-deoxyribonucleosides through chemoselective transformations of bromo-chloropyridine C-nucleosides. Org. Biomol. Chem. 11:4702-4718 (2013).
Kumar et al. The first analogues of LNA (Locked Nucleic Acids): Phosphorothioate-LNA and 2'-thio-LNA. Bioorg. Med. Chem. Lett. 8(16):2219-2222 (1998).
Kutyavin. Use of base-modified duplex-stabilizing deoxynucleoside 5'-triphosphates to enhance the hybridization properties of primers and probes in detection polymerase chain reaction. Biochemistry 4 7(51): 13666-13673 (2008).
Angowski et al. The CD122-biased immunostimulatory cytokine NKTR-214 combined with checkpoint blockade eads to mobilization of anti-tumor immunity and synergistic activity. Poster Abstract 311. 2016 CR-CIMT-EATIR-AACR Cancer Immunotherapy Conference (2016).
Lavergne et al. FRET Characterization of Complex Conformational Changes in a Large 16S Ribosomal RNA Fragment Site-Specifically Labeled Using Unnatural Base Pairs. ACS Chem Biol 11(5):1347-1353 (2016).
Lavergne et al. Major groove substituents and polymerase recognition of a class of predominantly hydrophobic unnatural base pairs. Chem. Eur. J. 18:1231-1239 (2012).
Lavergne et al. Expanding the Scope of Replicable Unnatural DNA: Stepwise Optimization of a Predominantly Hydrophobic Base Pair. J Am Chem Soc. 135:5408-5419 (2013).
Lazear et al. Targeting of IL-2 to cytotoxic lymphocytes as an improved method of cytokine-driven immunotherapy. Oncoimmunology 6(2):e1265721 (2017).
Leconte et al. Amplify this! DNA and RNA get a third base pair. Nat Meth 3:667-668 (2006).
Leconte et al. An efficiently extended class of unnatural base pairs. J Am Chem Soc 128(21):6780-6781 (2006).
Leconte et al. Chemical biology: a broader take on DNA. Nature 444:553-555 (2006).
Leconte et al. Directed Evolution of DNA Polymerases for Next-Generation Sequencing. Angew Chem Int Ed Engl 49(34):5921-5924 (2010).
Leconte et al. Discovery, characterization, and optimization of an unnatural base pair for expansion of the genetic alphabet. J Am Chem Soc 130(7):2336-2343 (2008).
Leconte et al. Efforts towards expansion of the genetic alphabet: pyridone and methyl pyridone nucleobases. Angew Chem Int Ed Engl 45(26):4326-9 (2006).
Leconte et al. Polymerase evolution: efforts toward expansion of the genetic code. J Am Chem Soc 127 (36): 12470-1 (2005).
Leconte et al. Selective Inactivation of the 3' to 5' exonuclease activity of *Escherichia coli* DNA polymerase I by heat. Nucl Acids Res 11 :7505-7515 (1983).

(56) References Cited

OTHER PUBLICATIONS

Ledbetter et al. Editorial overview: Expanding the genetic alphabet and code. Curr Opin Chem Biol 46:A1-A2 (2018).
Ledbetter et al. Reprograming the Replisome of a Semisynthetic Organism for the Expansion of the Genetic Alphabet. J Am Chem Soc. 140:758-765 (2018).
Ledbetter et al. Site-Specific Labeling of DNA via PCR with an Expanded Genetic Alphabet. Methods Mol Biol 1973:193-212 (2019).
Letourneau et al. IL-2/anti-IL-2 antibody complexes show strong biological activity by avoiding interaction with IL-2 receptor alpha subunit CD25. PNAS USA 107:2171-2176 (2010).
Letsinger et al. Cholesteryl-conjugated oligonucleotides: Synthesis, properties, and activity as inhibitors of replication of human immunodeficiency virus in cell culture. PNAS 86:6553-6556 (1989).
Levin et al. Exploiting a natural conformational switch to engineer an Interleukin-2 superkine. Nature 484 (7395):529-533 (2012).
Levin, It's prime time for reverse transcriptase. Cell 88:5-8 (1997).
Li et al. Improved Inhibition of Tumor Growth by Diabody-Drug Conjugates via Half-Life Extension. Bioconjugate Chem 30:1232-1243 (2019).
Li et al. Natural-like Replication of an Unnatural Base Pair for the Expansion of the Genetic Alphabet and Biotechnology Applications. J Am Chem Soc 136:826-829 (2014).
Li et al. Site-Specifically Arraying Small Molecules or Proteins on DNA Using An Expanded Genetic Alphabet. Chem Eur J 19:14205-14209 (2013).
Li et. al. Synthesis of linear polyether polyol derivatives as new materials for bioconjugation. Bioconjugate Chem. 20:780-789 (2009).
Lim et al. Site-specific albumination of a therapeutic protein with multi-subunit to prolong activity in vivo. J Control Release. 207:93-100 (2015).
Portnoff et al., "An antidote approach to reduce risk and broaden utility of antibody-based therapeutics", J Biol Chem, vol. 292, No. 20, pp. 8498-8506 (Mar. 3, 2017).
Emerson et al., "NMR Characterization of Interleukin-2 in Complexes with the IL-2R Receptor Component, and with Low Molecular Weight Compounds that Inhibit the IL-2/IL-R interaction", Protein Science, vol. 12 (Dec. 31, 2003).
Ghelani et al., "Defining the Threshold IL-2 Signal Required for Induction of Selective Treg Cell Responses Using Engineered IL-2 Muteins", Frontiers in Immunology, vol. 11, Article 1106, figure 2, (Jun. 30, 2020).
Levin et al., "Exploiting a Natural Conformational Switch to Engineer an Interleukin-2 Superkine", Nature, vol. 484, No. 7359, (Apr. 26, 2012).
Mei et al., "Site-Mutation of Hydrophobic Core Residues Synchronically Poise Super Interleukin 2 for Signaling: Identifying Distant Structural Effects through Affordable Computations", International Journal of Molecular Science, vol. 19, No. 3, Article 916 (Mar. 20, 2018).
Prometheus Laboratories Inc., FDA Label for Proleukin (Aldesleukin), 19 pages (2011).
Ptacin et al., "A CD25-biased interleukin-2 for autoimmune therapy engineered via a semi-synthetic organism", Communications Medicine, 4:58, pp. 1-16, (2024).
Rao et al., "Interleukin-2 Mutants with Enhanced A-Receptor Subunit Binding Affinity", Protein Engineering, vol. 16, No. 12, (Dec. 31, 2003).
National Institute of Cancer-understanding and related topics, accessed Aug. 18, 2019 at URL: https://www.cancer.gov/about-cancer/understanding/what-is-cancer (2019).
Nawrot et al. A Novel Class of DNA Analogs Bearing 5'-C-Phosphonothymidine Units: Synthesis and Physicochemical and Biochemical Properties. Oligonucleotides. 16(1):68-82 (2006).
Needleman et al. A general method applicable to the search for similarities in the amino acid sequence of two proteins. J. Mol. Biol. 48:443-453 (1970).
Nektar Therapeutics Presents New Clinical Data from Ongoing Phase 1 Dose-Escalation Study of NKTR-214 at the Society for Immunotherapy of Cancer (SITC) 2016 Annual Meeting. PRNewswire (2016).
Nektar Therapeutics. Investor Meeting presentation Jun. 3, 2017.
Nelson et al. N3'-P5 Oligodeoxyribonucleotide Phosphoramidates: A New Method of synthesis Based on a Phosphoramidite Amine-Exchange Reaction. J. Org. Chem. 62:7278-7287 (1997).
Neumann et al. Encoding multiple unnatural amino acids via evolution of a quadruplet-decoding ribosome. Nature. 464(7287): 441-444 (2010).
Nguyen et al. Genetic Encoding and Labeling of Aliphatic Azides and Alkynes in Recombinant Proteins via a Pyrrolysyl-tRNA Synthetase/tRNACUA Pair and Click Chemistry. JAGS 131:8720-8721 (2009).
Nicolini et al. The FAP-IL2v Immunocytokine is a Versatile Combination Partner for Cancer Immunotherapy. Poster (2018).
Nielsen et al. Sequence-selective recognition of DNA by strand displacement with a thymine-substituted polyamide. Science. 254:1497-1500 (1991).
Nordstrom et al. Characterization of bacteriophage T7 DNA polymerase purified to homogeneity by antithioredoxin immunoadsorbent chromatography. J Biol Chem 256:3112-3117(1981).
Oberhauser et al. Effective incorporation of 2'-O-methyl-oligoribonucleotides into liposomes and enhanced cell association through modification with thiocholesterol. Nucl. Acids Res. 20:533-538 (1992).
Obika et al. Synthesis of 2'-0,4'-C-methyleneuridine and -cytidine. Novel bicyclic nucleosides having a fixed C3'-endo sugar puckering. Tetrahedron Lett. 38(50):8735-8738 (1997).
Ogawa et al. Efforts toward the Expansion of the Genetic Alphabet: Information Storage and Replication with Unnatural Hydrophobic Base Pairs. J. Am. Chem. Soc. 122:3274-3278 (2000).
Ogawa et al. Rational Design of an Unnatural base Pair with Increased Kinetic Selectivity. J. Am. Chem. Soc. 122:8803-8804 (2000).
Ohtsuki et al. Unnatural base pairs for specific transcription. PNAS USA 98(9):4922-4925 (2001).
Okamoto. ECHO probes: a concept of fluorescence control for practical nucleic acid sensing. Chem. Soc. Rev. 40:5815-5828 (2011).
Oliphant et al. Defining the sequence specificity of DNA-binding proteins by selecting binding sites from random-sequence oligonucleotides: analysis of yeast GCN4 proteins. Mol. Cell Biol. 9:2944-2949 (1989).
Orum et al. Locked nucleic acids: a promising molecular family for gene-function analysis and antisense drug development. Curr Opinion Mol Ther 3:239-243 (2001).
Ostrov et al. Design, synthesis, and testing toward a 57-codon genome. Science 353(6301):819-822 (2016).
Owczarzy et al. Stability and mismatch discrimination of locked nucleic acid-DNA duplexes. Biochem. 50 (43):9352-9367 (2011).
Papanikolaou et al. Lipid production by Yarrowia lipolytica growing on industrial glycerol in a single-stage continuous culture. Bioresour Technol 82(1):43-9 (2002).
Parel et al. Triple-helix formation in the antiparallel binding motif of oligodeoxynucleotides containing N(9)- and N (7)-2-aminopurine deoxynucleosides. Nucleic Acids Res. 29(11):2260-2267 (2001).
Parisi et al. Enhanced expansion and tumor targeting of adoptively transferred T cells with NKTR-214. Poster Abstract #3566 (2018).
Parrish et al. Functional anatomy of a dsRNA trigger: differential requirement for the two trigger strands in RNA Interference. Mol Cell 6(5):1077-1087 (2000).
Paulous et al. Comparison of the capacity of different viral internal ribosome entry segments to direct translation initiation in poly(A)-dependent reticulocyte lysates. Nucleic Acids Res. 31(2):722-733 (2003).
Peyrottes et al. Oligodeoxynucleoside Phosphoramidates (P-NH 2 ): Synthesis and Thermal Stability of Duplexes With DNA and RNA Targets. Nucleic Acids Res. 24:1841-1848 (1996).
Pfannenstiel et al. A Novel, Individualized Xenograft Model of Cancer Immunotherapy and Tumor Growth Inhibition by ALKS 4230. Poster #P351 (2017).

(56) References Cited

OTHER PUBLICATIONS

Piccirilli et al. AC-nucleotide base pair: methylpseudouridine-directed incorporation of formycin triphosphate into RNA catalyzed by T7 RNA polymerase. Biochemistry 30(42): 10350-10356 (1991).
Piccirilli et al. Enzymatic incorporation of a new base pair into DNA and RNA extends the genetic alphabet. Nature 343:33-37 (1990).
Pieper et al. NKTR-214 in combination with radiation produces a potent in situ vaccine in the syngeneic B78 melanoma model. Poster (2018).
PLIETH. Cytokine therapy focus—interleukin-2 claims the early lead. EP Vantage. Evaluate Feb. 27, 2018 (Available at https://www.evaluate.com/vantage/articles/analysis/cytokine-therapy-focus-interleukin-2-claims-early-lead) (2018).
Quan et al. Circular polymerase extension cloning for high-throughput cloning of complex and combinatorial DNA libraries. Nat Protoc 6(2):242-251 (2011).
Ram et al., In situ retroviral-mediated gene transfer for the treatment of brain tumors in rats. Cancer Res. 53:83-88 (1993).
Roessler et al. Cooperative interactions between the interleukin 2 receptor a and 13 chains later the interleukin 2-binding affinity of the receptor subunits. PNAS USA 91:3344-3347 (1994).
Romesberg et al. Development of a universal nucleobase and modified nucleobases for expanding the genetic code. Curr Prot Nucleic Acid Chem Chapter 1 :Unit 1.5 (2002).
Rosentrater et al. Determination of the Relative potency of a Selective Agonist of the Intermediate-Affinity IL-2 Receptor on Lymphocytes from Human, Cynomolgus Monkey and Mouse. Poster for Abstract #4281 (No date available).
Saha et al. 5'-Methyl-DNA—A New Oligonucleotide Analog: Synthesis and Biochemical Properties. J. Org Chem. 60:788-789 (1995).
Saison-Behmoaras et al. Short modified antisense oligonucleotides directed against Ha-ras point mutation induce selective cleavage of the mRNA and inhibit T24 cells proliferation. EMBO J. 10:1111-1118 (1991).
Sakaguchi et al. Immunologic self-tolerance maintained by activated T cells expressing IL-2 receptor alpha-chains (CD25). Breakdown of a single mechanism of self-tolerance causes various autoimmune diseases. J Immunol 155 (3):1151-64 1995).
Sanghvi. Chapter 15, Antisense Research and Applications. Crookeand Lebleu Eds. CRC Press. 273-288 (1993).
Sauer. Site-specific recombination: developments and applications. Curr Opin Biotechnol 5(5):521-527 (1994).
Schmied et al. Efficient Multisite Unnatural Amino Acid Incorporation in Mammalian Cells via Optimized Pyrrolysyl RNA Synthetase/tRNA Expression and Engineered eRF1. JAGS 136:15577-15583 (2014).
Schultz et al. Oligo-2'-Fluoro-2'-Deoxynucleotide N3'->P5' Phosphoramidates: Synthesis and Properties. Nucleic Acids Res. 24:2966-2973 (1996).
Seo et al. Improved High-Efficiency Organic Solar Cells via Incorporation of a Conjugated Polyelectrolyte Interlayer. JAGS 133:8416-8419 (2011).
Seo et al. Major groove derivatization of an unnatural base pair. Chembiochem 10(14):2394-2400 (2009).
Seo et al. Optimization of an unnatural base pair toward natural-like replication. J Am Chem Soc 131 :3246-3252 (2009).
Seo et al. Site-specific labeling of DNA and RNA using an efficiently replicated and transcribed class of unnatural base pairs. J Am Chem Soc 133:19878-19888 (2011).
Seo et al. Transcription of an Expanded Genetic Alphabet. JAGS 131 (14):5046-5047 (2009).
Shaloiko et al. Effective non-viral leader for cap-independent translation in a eukaryotic cell-free system. Biotechnology and Bioengineering 88(6):730-739 (2004).
Liu et al. Adding new chemistries to the genetic code. Annu Rev Biochem 79:413-444 (2010).
Lizardi et al. Exponential amplification of recombinant-RNA hybridization probes. Nature Biotechnology 6:1197-1202 (1988).
Lopes et al. Characterization of the Pharmacodynamic Immune Response to a Novel Immunotherapeutic Agent, ALKS 4230, in Mice and Non-Human Primates. Poster 22 (Abstract #2663) (2017).
Lopes et al. Ex Vivo Expansion and Activation of Human Lymphocytes With a Selective Activator of Effector Cells. Abstract #3158 Poster (2015).
Losey et al. Abstract #4280: Utilizing a Selective Agonist of the Intermediate-Affinity IL-2 Receptor With an Improved Pharmacokinetic Profile Leads to an Enhanced Immunostimulatory Response With Reduced Toxicity in Mice. Proceedings: AACR 106th Annual Meeting Philadelphia, PA (2015).
Losey et al. Efficacy of ALKS 4230, a Novel Immunotherapeutic Agent, in Murine Syngeneic Tumor Models Alone and in Combination with Immune checkpoint Inhibitors. Poster 25 (Abstract #591) (2017).
Losey et al. Utilizing a Selective Agonist of the Intermediate-Affinity IL-2 Receptor With an Improved Pharmacokinetic Profile Leads to an Enhanced Immunostimulatory Response With Reduced Toxicity in Mice. Poster for Abstract #4280 (2015).
Lotze et al. In vivo administration of purified human interleukin 2. II. Half life, immunologic effects, and expansion of peripheral lymphoid cells in vivo with recombinant IL 2. J Immunol 135:2865-2875 (1985).
Lou et al. Fixing vascular leak in IL-2 immunotherapy. Sci BX 3(27):2 pgs (2010).
Ludwig et al. Rapid and efficient synthesis of nucleoside 5'-0-(1-thiotriphosphates), 5'-triphosphates and 2',3'- cyclophosphorothioates using 2-chloro-4H-1,3,2-benzodioxaphosphorin-4-one. J. Org. Chem. 54:631-635 (1989).
Lundberg et al. High-fidelity amplification using a thermostable DNA polymerase isolated from Pyrococcus furiosus. Gene 108:1-6 (1991).
Lyon et al. Self-hydrolyzing maleimides improve the stability and pharmacological properties of antibody-drug conjugates. Nat. Biotechnol. 32(10):1059-1062 (2014).
Malyshev et al. PCR with an Expanded Genetic Alphabet. JACS 131 (41):14620-14621 (2009).
Malyshev et al. Efficient and sequence-independent replication of DNA containing a third base pair establishes a functional six-letter genetic alphabet. Proc Natl Acad Sci USA. 109:12005-12010 (2012).
Malyshev et al. Solution structure, mechanism of replication, and optimization of an unnatural base pair. Chem Eur J 16:12650-12659 (2010).
Malyshev et al. The expanded genetic alphabet. Angew Chem Int Ed Engl 54:11930-11944 (2015).
Malyshev et al. A semi-synthetic organism with an expanded genetic alphabet. Nature. 509:385-388 (2014).
Manoharan et al. Chemical Modifications to Improve Uptake and Bioavailability of Antisense Oligonucleotides. Ann. KY. Acad. Sci. 660:306-309 (1992).
Manoharan et al. Introduction of a Lipohilic Thieother Tether in the Minor Groove of Nucleic Acids for Antisense Applications. Bioorg. Med. Chem. Let. 3:2765-2770 (1993).
Manoharan et al. Cholic Acid-Oligonucleotide Conjugates for Antisense Applications. Bioorg. Med. Chem. Let. 4:1053-1060 (1994).
Manoharan et al. Oligonucleotide Conjugates: Alteration of the Pharmacokinetic Properties of Antisense Agents. Nucleosides & Nucleotides. 14:969-973 (1995).
Manoharan et al. Lipidic Nucleic Acids. Tetrahedron Lett. 36:3651-3654 (1995).
Matsuda et al. Efforts toward expansion of the genetic alphabet: structure and replication of unnatural base pairs. J Am Chem Soc 129(34):10466-73 (2007).
Matsuda et al. Minor groove hydrogen bonds and the replication of unnatural base pairs. J Am Chem Soc 129 (17):5551-7 (2007).
Matsuda et al. Optimization of interstrand hydrophobic packing interactions within unnatural DNA base pairs. J Am Chem Soc 126(44):14419-27 (2004).
Matsuda et al. Optimization of unnatural base pair packing for polymerase recognition. J Am Chem Soc 128 (19):6369-75 (2006).
Matsuda et al. The effect of minor-groove hydrogen-bond acceptors and donors on the stability and replication of four unnatural base pairs. J Am Chem Soc 125(20):6134-9 (2003).

(56) References Cited

OTHER PUBLICATIONS

Matteucci. Oligonucleotide Analogs: an Overview in Oligonucleotides as Therapeutic Agents, (Chadwick and Cardew, ed.) John Wiley and Sons, New York, NY; Zon, 1993, Oligonucleoside Phosphorothioates in Protocols for Oligonucleotides and Analogs, Synthesis and Properties, Humana Press, pp. 165-190 (1997).
McMinn et al. Efforts toward Expansion of the Genetic Alphabet: DNA Polymerase Recognition of a Highly Stable, Self-Pairing Hydrophobic Base. J. Am. Chem. Soc. 121:11585-11586 (1999).
Meggers et al. A Novel Copper-Mediated DNA Base Pair. J. Am. Chem. Soc. 122:10714-10715 (2000).
Meghnem et al. Cutting Edge: Differential Fine-Tuning of IL-2- and IL-15-Dependent Functions by Targeting Their Common IL-2/15RI3/ yc Receptor. J Immunol 198(12):4563-4568 (2017).
Melero et al. Clinical activity safety, and PK/PD from a Phase 1 study of RO6874281, a fibroblast activation protein (FAP) targeted interleukin-2 variant (IL-cv). ESMO 2018 Congress Poster (2018).
Merchant et al. Preclinical characterization of IL-2 Superkines engineered with biased CD8+ T cell stimulating properties. Poster (2018).
Micklefield. Backbone Modification of Nucleic Acids: Synthesis, Structure and Therapeutic Applications. Curr. Med. Chem. 8:1157-1179 (2001).
Mignone et al. Untranslated regions of mRNAs. Genome Biol. 3(3):ReviewS0004 (2002).
Mignone et al. UTRdb and UTRsite: a collection of sequences and regulatory motifs of the untranslated regions of eukaryotic mRNAs. Nucleic Acids Res 33(Database issue):D141-D146 (2005).
Mikhailov et al. Substrate Properties of C'-Methylnucleoside and C'-Methyl-2'-deoxynucleoside 5'-Triphosphates in RNA and DNA Synthesis Reactions Catalysed by RNA and DNA Polymerases. Nucleosides & Nucleotides. 10 (1-3):339-343 (1991).
Milla et al. THOR-707: An engineered IL-2 for the treatment of solid tumors with superior pre-clinical efficacy and safety evidence. 2018 Society for Immunotherapy of Cancer (SITC) 33rd Annual Meeting Poster (2018).
Milla et al. THOR-707: Using Synthetic Biology to Reprogram the Therapeutic Activity of Interleukin-2 (IL-2). 2019 American Society of Clinical Oncology (ASCO) Annual Meeting Poster (2019).
Miller et al. Syntheses and Properties of Adenine and Thymine Nucleoside Alkyl Phosphotriesters, the Neutral Analogs of Dinucleoside Monophosphates. JACS 93:6657-6665 (1971).
Miroux et al. Over-production of proteins in *Escherichia coli*: mutant hosts that allow synthesis of some membrane proteins and globular proteins at high levels. J Mol Biol 260:289-298 (1996).
Mishra et al. Improved leishmanicidal effect of phosphorotioate antisense oligonucleotides by LDL-mediated delivery. Biochem. Biophys. Acta. 1264:229-237 (1995).
Montero et al. Nucleosides de synthese XVI: Sur une synthese selective de divers ribofuranosyl-1-purines. Journal of Heterocyclic Chemistry 15(6):929-935 (1978).
Morris et al. Synthetic Biology Parts for the Storage of Increased Genetic Information in Cells. ACS Synth Biol 6 (10):1834-1840 (2017).
Mulligan et al. Expression of a bacterial gene in mammalian cells. Science 209:1422-1427 (1980).
Mullis et al. Specific enzymatic amplification of DNA in vitro the polymerase chain reaction. Cold Spring Harbor Symp. Quant. Biol. 51 :263 (1986).
Myers et al. Optimal alignments in linear space. CABIOS 4:11-17 (1988).
Myers et al. Reverse transcription and DNA amplification by a Thermus thermophilus DNA polymerase. Biochemistry 30:7661-7666 (1991).
Nakazawa et al. UV and skin cancer: specific p53 gene mutation in normal skin as a biologically relevant exposure measurement. PNAS USA 91 (1):360-364 (1994).
Napolitano et al. Emergent rules for codon choice elucidated by editing rare argine codons in *Escherichia coli*. PNAS, 113(38): E5588-5597 (2016).
Van Haelst Pinsani et al. Administration of Interleukin-2 (IL-2) Results in Increased Plasma Concentrations of IL-5 and *Eosinophilia* in Patients with Cancer. Blood 78:1538-1544 (1991).
Vanbrunt et al. Genetically Encoded Azide Containing Amino Acid in Mammalian Cells Enables Site-Specific Antibody-Drug Conjugates Using Click Cycloaddition Chemistry. Bioconjug Chem. 26(11):2249-60 (2015).
Vazquez-Lombardi et al. Potent antitumour activity of the interleukin-2-Fc fusion proteins requires Fe-mediated depletion of regulatory T-cells. Nat Comm 8:15373 (2017).
Verma. Retroviral vectors for gene transfer. In: Microbiology (Leive Let al., eds., Ann. Soc. Microbial) American Society of Microbiology, Washington, DC, p. 229-232 (1985).
Verma. The reverse transcriptase. Biochim Biophys Acta. 473:1-38 (1977).
Vrudhula et al. Isozyme-specific enzyme inhibitors. 13. S-[5'(R)-['N-triphosphoamino)methyl]adenosyl]-L-homocysteine, a potent inhibitor of rat methionine adenosyltransferases. J. Med. Chem. 30:888-894 (1987).
Wahlestedt et al. Potent and nontoxic antisense oligonucleotides containing locked nucleic acids. Proc. Natl. Acad. Sci. USA. 97:5633-5638 (2000).
Waldmann et al. The Shared and Contrasting Roles of IL2 and IL 15 in the Life and Death of Normal and Neoplastic Lymphocytes: Implications for Cancer Therapy. Cancer Immunol Res 3(3):219-227 (2015).
Walker et al. Combination of NKTR-214 and Radiotherapy (RT) to reverse anergy and expand specific CD8 T cells. Poster (2017).
Wan et al. Pyrrolysyl-tRNA synthetase: an ordinary enzyme but an outstanding genetic code expansion tool. Biocheim Biophys Aceta 1844(6):1059-1070 (2014).
Wandry et al. Probing unnatural amino acid integration into enhanced green fluorescent protein by genetic code expansion with a high-throughput screening platform. J Biol Eng. 10:11 (2016).
Wang et al. Enhanced Anti-tumor Activity of the Combination of Entinostat and NKTR-214 in Renal and Colon Cancer Tumor Models. Poster. AACR Annual Meeting 2018 (2018).
Wang et al. Structure of the Quaternary Complex of Interleukin-2 with Its a, Is, and ye Receptors. Science 310:1159-63 (2005).
Wang et al. Biophysical and Biochemical Properties of Oligodeoxy-Nucleotides Containing 4'-C- and 5'-C-Substituted Thymidines. Bioorganic & Medicinal Chemistry Letters. 9:885-890 (1999).
Wang et al. Synthesis of Azole Nucleoside 5'-Monophosphate Mimics (P1Ms) and Their Inhibitory Properties of IMP Dehydrogenases. Nucleosides Nucleotides & Nucleic Acids. 23(1 & 2):317-337 (2004).
Webster et al. In vivo expansion of T reg cells with IL-2-mAb complexes: induction of resistance to EAE and long-term acceptance of islet allografts without immunosuppression. J Med Chem 206(4):751-760 (2009).
Winkler et al. Non-mitochondrial ATP transport. Trends Biochem. Sci. 24:64-68 (1999).
Winkler. Rickettsial permeability: an ADP-ATP transport system. J Biol Chem 251 :389-396 (1976).
Wolff et al. Direct gene transfer into mouse muscle in vivo. Science 247:1465-1468 (1990).
Wu et al. Efforts toward expansion of the genetic alphabet: Optimization of interbase hydrophobic interactions. J Am Chem Soc 122:7621-7632 (2000).
Wu et al. Enzymatic phosphorylation of unnatural nucleosides. J Am Chem Soc 124:14626-14630 (2002).
Wu et al. Reverse transcriptase. CRC Grit Rev Biochem 3:289-347 (1975).
Wu et al. Synthesis of Site-Specific Radiolabeled Antibodies for Radioimmunotherapy via Genetic Code Expansion. Bioconjugate Chem. 27:2460-2468 (2016).
Wu et al. Functionalization of the Sugar Moiety of Oligoribonucleotides on Solid Support. Bioconjugate Chem. 10:921-924 (1999).
Wu et al. Efforts toward Expansion of the Genetic Alphabet: Optimization of Interbase Hydrophobic Interactions. Helvetica Chimica Acta. 83:1127-1143 (2000).

(56) References Cited

OTHER PUBLICATIONS

Wurm et al. Squaric acid mediated synthesis and biological activity of a library of linear and hyperbranched poly (glycerol)-protein conjugates. Biomacromolecules. 13:1161-1171 (2012).
Xia et al. Directed evolution of novel polymerase activities: mutation of a DNA polymerase into an efficient RNA polymerase. PNAS USA 99(10):6597-602 (2002).
Yamaguchi et al. Role of IL-5 in IL-2-induced eosinophilia. In vivo and in vitro expression of IL-5 mRNA by IL-2. J Immunol 145:873-877 (1990).
Yamashige et al. Highly specific unnatural base pair systems as a third base pair for PCR amplification. Nucleic Acids Res. 40:2793-2806 (2012).
Yan et al. Nucleoside monophosphate kinases: structure, mechanism, and substrate specificity. Adv. Enzymol. Relat. Areas Mol. Biol. 73:103-134 (1999).
Young et al. Beyond the canonical 20 amino acids: expanding the genetic lexicon. J. of Biological Chemistry 285(15):11039-11044 (2010).
Yu et al. Polymerase recognition of unnatural base pairs. Angew Chem Int Ed Engl 41(20):3841-4 (2002).
Zalevsky. Jefferies 2016 Global Healthcare Conference. PowerPoint presentation (2016).
Zhang et al. A semisynthetic organism engineered for the stable expansion of the genetic alphabet. Proc Natl Acad Sci USA, 114:1317-1322 (2017).
Zhang et al. Semisynthetic Organisms with Expanded Genetic Codes. Biochemistry 57:2177-2178 (2018).
Zhang et al. Studies of nucleoside transporters using novel autofluorescent nucleoside probes. Biochemistry 45 (4):1087-1098 (2006).
Zhang et al. A semisynthetic organism engineered for the stable expansion of the genetic alphabet. Nature. 551 (7682): 644-647 (2017).
Zhou et al. Fine tuning of electrostatics around the internucleotidic phosphate through incorporation of modified 2',4'—carbocyclic-LNAs and -ENAs leads to significant modulation of antisense properties. J Org Chem 74:118-134 (2009).
Zon. Chapter 8: Oligonucleotide Phosphorothioates in Protocols for Oligonucleotides and Analogs, Synthesis and Properties. Humana Press (pp. 165-190) (1993).
Abbadessa et al., Co-pending U.S. Appl. No. 17/357,615, filed Jun. 24, 2021, also cited herein as US 2022/0016252.
Abbadessa et al., Co-pending U.S. Appl. No. 18/524,157, filed on Nov. 30, 2023, also cited herein as US 2024/0226309.
Aerni et al. Co-pending U.S. Appl. No. 17/845,495, filed Jun. 21, 2022, also cited herein as US 2022/0324792.
Caffaro et al., Co-pending U.S. Appl. No. 19/257,936, filed Jul. 2, 2025.
Caffaro et al., Co-pending U.S. Appl. No. 16/999,638, filed Aug. 21, 2020, also cited herein as US 2021/0054040.
Caffaro et al., Co-pending U.S. Appl. No. 17/313,579, filed May 6, 2021, also cited herein as US 2021/0338829.
Caffaro et al., Co-pending U.S. Appl. No. 17/735,564, filed May 3, 2022, also cited herein as US 2022/0273767.
Caffaro et al., Co-pending U.S. Appl. No. 18/179,198, filed on Mar. 6, 2023, also cited herein as US 2023/0302089.
Caffaro et al., Co-pending U.S. Appl. No. 18/296,710, filed Apr. 6, 2023, also cited herein as US 2023/0277627.
Caffaro et al., Co-pending U.S. Appl. No. 18/296,711, filed Apr. 6, 2023, also cited herein as US 2023/0416327.
Caffaro et al., Co-pending U.S. Appl. No. 18/415,445, filed Jan. 17, 2024, also cited herein as US 2024/0287151.
Caffaro et al., Co-pending U.S. Appl. No. 18/424,573, filed Jan. 26, 2024.
Ptacin et al., Co-pending U.S. Appl. No. 17/016,003, filed Sep. 9, 2020, also cited herein as US 2021/0070827.
Ptacin et al., Co-pending U.S. Appl. No. 18/327,535, filed Jun. 1, 2023, also cited herein as US 2024/0082359.
Ptacin et al., Co-pending U.S. Appl. No. 18/886,814, filed Sep. 16, 2024.
Ptacin et al., Co-pending U.S. Appl. No. 19/025,471, filed Jan. 16, 2025.

* cited by examiner

3

4

5

6

7

8

9

10

11

12

X = S, 13
X = O, 14

15

16

17

18

19

20

21

22

23

6 7 24 15 16

17 25 26 27 28

14 29 30 31

32 33 34 35

36 23 37 38 39

18 40 41 42 43

44 45 46 47 20

21 22 48 49 50

51

52, 53, 54, 55, 56, 57, 58-60, 61

62, 63, 64, 65, 66, 67, 68, 69, 70, 71

72, 73, 74, 75, 76, 77, 78-81, 82-86, 87

88, 89, 90, 91, 92, 93, 94, 95, 96, 97

1 2 3 4 5 6 7 8 9

10 11 12 13 14 15 16 17 18

19 20 21 22 23 24 25 26

27 28 29 30 31 32

33 34 35 36 37 38 39 40 41 42

43 44 45 46 47 48 49 50
51 52 53 54 55 56 57 58 59
60 61 62 63 64 65 66 67 68 69
70 71 72 73 74 75 76 77 78 79
80 81 82 83 84 85 86 87 88 89

90 91 92 93 94 95 96 97 98

99 100 101 102 103 104 105 106 107

108 109 110 111 112 113 114 115 116 117 118

119 120 121 122 123 124 125 126 127 128

Mean (±SD) Plasma Concentration versus Time Profiles Following a Single IV Bolus Dose of aldesleukin or P65_30KD and E62_30KD, E62_5KD to Female C57BL/6 mice

Sustained increase in peripheral blood pSTAT5+ CD8+ T in response to P65_30KD

P65_30KD did not induce the proliferation of CD4+ Tregs

White Blood Cell, Lymphocyte and Eosinophil Counts (Mean ±SD) following a Single IV Dose of P65_30KD to Male Cynomolgus monkeys

SEQUENCE LISTING

<160> NUMBER OF SEQ ID NOS: 87

<210> SEQ ID NO 1
<211> LENGTH: 133
<212> TYPE: PRT
<213> ORGANISM: Homo sapiens

<400> SEQUENCE: 1

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

<210> SEQ ID NO 2
<211> LENGTH: 153
<212> TYPE: PRT
<213> ORGANISM: Homo sapiens

<400> SEQUENCE: 2

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150
```

<210> SEQ ID NO 3
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 4
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 5
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (65)..(65)

<223> OTHER INFORMATION: Any unnatural amino acid

<400> SEQUENCE: 5

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Xaa Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 6
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (62)..(62)
<223> OTHER INFORMATION: Any unnatural amino acid

<400> SEQUENCE: 6

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Xaa Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 7
<211> LENGTH: 133
<212> TYPE: PRT
<213> ORGANISM: Artificial Sequence
<220> FEATURE:

-continued

<223> OTHER INFORMATION: Description of Artificial Sequence: Synthetic
      polypeptide
<220> FEATURE:
<221> NAME/KEY: MOD_RES
<222> LOCATION: (42)..(42)
<223> OTHER INFORMATION: Any unnatural amino acid

<400> SEQUENCE: 7

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Xaa Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130
```

<210> SEQ ID NO 8
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
<223> OTHER INFORMATION: Any unnatural amino acid

<400> SEQUENCE: 8

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Xaa Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130
```

```
<210> SEQ ID NO 9
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(35)
<223> OTHER INFORMATION: Any unnatural amino acid

<400> SEQUENCE: 9

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Xaa Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130


<210> SEQ ID NO 10
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (65)..(65)
<223> OTHER INFORMATION: N6-((2-azidoethoxy)-carbonyl)-L-lysine

<400> SEQUENCE: 10

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Lys Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125
```

```
Ile Ser Thr Leu Thr
    130


<210> SEQ ID NO 11
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (62)..(62)
<223> OTHER INFORMATION: N6-((2-azidoethoxy)-carbonyl)-L-lysine

<400> SEQUENCE: 11

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Lys Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130


<210> SEQ ID NO 12
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (42)..(42)
<223> OTHER INFORMATION: N6-((2-azidoethoxy)-carbonyl)-L-lysine

<400> SEQUENCE: 12

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95
```

-continued

Lys Gly Ser Glu Thr Thr Phe Met Cys Glu Tyr Ala Asp Glu Thr Ala
100 105 110

Thr Ile Val Glu Phe Leu Asn Arg Trp Ile Thr Phe Ser Gln Ser Ile
115 120 125

Ile Ser Thr Leu Thr
130

<210> SEQ ID NO 13
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (43)..(43)
<223> OTHER INFORMATION: N6-((2-azidoethoxy)-carbonyl)-L-lysine

<400> SEQUENCE: 13

Ala Pro Thr Ser Ser Ser Thr Lys Lys Thr Gln Leu Gln Leu Glu His
1 5 10 15

Leu Leu Leu Asp Leu Gln Met Ile Leu Asn Gly Ile Asn Asn Tyr Lys
20 25 30

Asn Pro Lys Leu Thr Arg Met Leu Thr Phe Lys Phe Tyr Met Pro Lys
35 40 45

Lys Ala Thr Glu Leu Lys His Leu Gln Cys Leu Glu Glu Glu Leu Lys
50 55 60

Pro Leu Glu Glu Val Leu Asn Leu Ala Gln Ser Lys Asn Phe His Leu
65 70 75 80

Arg Pro Arg Asp Leu Ile Ser Asn Ile Asn Val Ile Val Leu Glu Leu
85 90 95

Lys Gly Ser Glu Thr Thr Phe Met Cys Glu Tyr Ala Asp Glu Thr Ala
100 105 110

Thr Ile Val Glu Phe Leu Asn Arg Trp Ile Thr Phe Ser Gln Ser Ile
115 120 125

Ile Ser Thr Leu Thr
130

<210> SEQ ID NO 14
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (35)..(35)
<223> OTHER INFORMATION: N6-((2-azidoethoxy)-carbonyl)-L-lysine

<400> SEQUENCE: 14

Ala Pro Thr Ser Ser Ser Thr Lys Lys Thr Gln Leu Gln Leu Glu His
1 5 10 15

Leu Leu Leu Asp Leu Gln Met Ile Leu Asn Gly Ile Asn Asn Tyr Lys
20 25 30

Asn Pro Lys Leu Thr Arg Met Leu Thr Phe Lys Phe Tyr Met Pro Lys
35 40 45

Lys Ala Thr Glu Leu Lys His Leu Gln Cys Leu Glu Glu Glu Leu Lys
50 55 60

```
Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130


<210> SEQ ID NO 15
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (65)..(65)
<223> OTHER INFORMATION: N6-((2-azidoethoxy)-carbonyl)-L-lysine stably-
      conjugated to PEG
<220> FEATURE:
<223> OTHER INFORMATION: See specification as filed for detailed
      description of substitutions and preferred embodiments

<400> SEQUENCE: 15

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Lys Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130


<210> SEQ ID NO 16
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (62)..(62)
<223> OTHER INFORMATION: N6-((2-azidoethoxy)-carbonyl)-L-lysine stably-
      conjugated to PEG
<220> FEATURE:
<223> OTHER INFORMATION: See specification as filed for detailed
      description of substitutions and preferred embodiments
```

<400> SEQUENCE: 16

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Lys Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 17
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (42)..(42)
<223> OTHER INFORMATION: N6-((2-azidoethoxy)-carbonyl)-L-lysine stably-conjugated to PEG
<220> FEATURE:
<223> OTHER INFORMATION: See specification as filed for detailed description of substitutions and preferred embodiments

<400> SEQUENCE: 17

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 18
<211> LENGTH: 133
<212> TYPE: PRT

<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (43)..(43)
<223> OTHER INFORMATION: N6-((2-azidoethoxy)-carbonyl)-L-lysine stably-
conjugated to PEG
<220> FEATURE:
<223> OTHER INFORMATION: See specification as filed for detailed
description of substitutions and preferred embodiments

<400> SEQUENCE: 18

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130
```

<210> SEQ ID NO 19
<211> LENGTH: 133
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (35)..(35)
<223> OTHER INFORMATION: N6-((2-azidoethoxy)-carbonyl)-L-lysine stably-
conjugated to PEG
<220> FEATURE:
<223> OTHER INFORMATION: See specification as filed for detailed
description of substitutions and preferred embodiments

<400> SEQUENCE: 19

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95
```

Lys Gly Ser Glu Thr Thr Phe Met Cys Glu Tyr Ala Asp Glu Thr Ala
100 105 110

Thr Ile Val Glu Phe Leu Asn Arg Trp Ile Thr Phe Ser Gln Ser Ile
115 120 125

Ile Ser Thr Leu Thr
130

<210> SEQ ID NO 20
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (65)..(65)
<223> OTHER INFORMATION: N6-((2-azidoethoxy)-carbonyl)-L-lysine stably-conjugated to PEG
<220> FEATURE:
<223> OTHER INFORMATION: See specification as filed for detailed description of substitutions and preferred embodiments

<400> SEQUENCE: 20

Ala Pro Thr Ser Ser Ser Thr Lys Lys Thr Gln Leu Gln Leu Glu His
1 5 10 15

Leu Leu Leu Asp Leu Gln Met Ile Leu Asn Gly Ile Asn Asn Tyr Lys
20 25 30

Asn Pro Lys Leu Thr Arg Met Leu Thr Phe Lys Phe Tyr Met Pro Lys
35 40 45

Lys Ala Thr Glu Leu Lys His Leu Gln Cys Leu Glu Glu Glu Leu Lys
50 55 60

Lys Leu Glu Glu Val Leu Asn Leu Ala Gln Ser Lys Asn Phe His Leu
65 70 75 80

Arg Pro Arg Asp Leu Ile Ser Asn Ile Asn Val Ile Val Leu Glu Leu
85 90 95

Lys Gly Ser Glu Thr Thr Phe Met Cys Glu Tyr Ala Asp Glu Thr Ala
100 105 110

Thr Ile Val Glu Phe Leu Asn Arg Trp Ile Thr Phe Ser Gln Ser Ile
115 120 125

Ile Ser Thr Leu Thr
130

<210> SEQ ID NO 21
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (62)..(62)
<223> OTHER INFORMATION: N6-((2-azidoethoxy)-carbonyl)-L-lysine stably-conjugated to PEG
<220> FEATURE:
<223> OTHER INFORMATION: See specification as filed for detailed description of substitutions and preferred embodiments

<400> SEQUENCE: 21

Ala Pro Thr Ser Ser Ser Thr Lys Lys Thr Gln Leu Gln Leu Glu His
1 5 10 15

Leu Leu Leu Asp Leu Gln Met Ile Leu Asn Gly Ile Asn Asn Tyr Lys
20 25 30

```
Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Lys Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130


<210> SEQ ID NO 22
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (42)..(42)
<223> OTHER INFORMATION: N6-((2-azidoethoxy)-carbonyl)-L-lysine stably-
      conjugated to PEG
<220> FEATURE:
<223> OTHER INFORMATION: See specification as filed for detailed
      description of substitutions and preferred embodiments

<400> SEQUENCE: 22

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130


<210> SEQ ID NO 23
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
```

<223> OTHER INFORMATION: N6-((2-azidoethoxy)-carbonyl)-L-lysine stably-
conjugated to PEG
<220> FEATURE:
<223> OTHER INFORMATION: See specification as filed for detailed
description of substitutions and preferred embodiments

<400> SEQUENCE: 23

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130
```

<210> SEQ ID NO 24
<211> LENGTH: 133
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (35)..(35)
<223> OTHER INFORMATION: N6-((2-azidoethoxy)-carbonyl)-L-lysine stably-
conjugated to PEG
<220> FEATURE:
<223> OTHER INFORMATION: See specification as filed for detailed
description of substitutions and preferred embodiments

<400> SEQUENCE: 24

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110
```

Thr Ile Val Glu Phe Leu Asn Arg Trp Ile Thr Phe Ser Gln Ser Ile
        115                 120                 125

Ile Ser Thr Leu Thr
    130

<210> SEQ ID NO 25
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (65)..(65)
<223> OTHER INFORMATION: N6-((2-azidoethoxy)-carbonyl)-L-lysine stably-conjugated to PEG
<220> FEATURE:
<223> OTHER INFORMATION: See specification as filed for detailed description of substitutions and preferred embodiments

<400> SEQUENCE: 25

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Lys Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 26
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (62)..(62)
<223> OTHER INFORMATION: N6-((2-azidoethoxy)-carbonyl)-L-lysine stably-conjugated to PEG
<220> FEATURE:
<223> OTHER INFORMATION: See specification as filed for detailed description of substitutions and preferred embodiments

<400> SEQUENCE: 26

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Lys Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 27
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (42)..(42)
<223> OTHER INFORMATION: N6-((2-azidoethoxy)-carbonyl)-L-lysine stably-
      conjugated to PEG
<220> FEATURE:
<223> OTHER INFORMATION: See specification as filed for detailed
      description of substitutions and preferred embodiments

<400> SEQUENCE: 27

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 28
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)

<223> OTHER INFORMATION: N6-((2-azidoethoxy)-carbonyl)-L-lysine stably-
      conjugated to PEG
<220> FEATURE:
<223> OTHER INFORMATION: See specification as filed for detailed
      description of substitutions and preferred embodiments

<400> SEQUENCE: 28

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130
```

<210> SEQ ID NO 29
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (35)..(35)
<223> OTHER INFORMATION: N6-((2-azidoethoxy)-carbonyl)-L-lysine stably-
      conjugated to PEG
<220> FEATURE:
<223> OTHER INFORMATION: See specification as filed for detailed
      description of substitutions and preferred embodiments

<400> SEQUENCE: 29

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125
```

```
Ile Ser Thr Leu Thr
    130


<210> SEQ ID NO 30
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (64)..(64)
<223> OTHER INFORMATION: Any unnatural amino acid

<400> SEQUENCE: 30

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Xaa
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 31
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (61)..(61)
<223> OTHER INFORMATION: Any unnatural amino acid

<400> SEQUENCE: 31

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Xaa Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95
```

```
Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 32
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (41)..(41)
<223> OTHER INFORMATION: Any unnatural amino acid

<400> SEQUENCE: 32

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Xaa Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 33
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (42)..(42)
<223> OTHER INFORMATION: Any unnatural amino acid

<400> SEQUENCE: 33

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Xaa Phe Tyr Met Pro Lys Lys
        35                  40                  45

Ala Thr Glu Leu Lys His Leu Gln Cys Leu Glu Glu Glu Leu Lys Pro
    50                  55                  60
```

```
Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 34
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: Any unnatural amino acid

<400> SEQUENCE: 34

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Xaa Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 35
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (64)..(64)
<223> OTHER INFORMATION: N6-((2-azidoethoxy)-carbonyl)-L-lysine

<400> SEQUENCE: 35

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30
```

-continued

```
Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Lys
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 36
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (61)..(61)
<223> OTHER INFORMATION: N6-((2-azidoethoxy)-carbonyl)-L-lysine

<400> SEQUENCE: 36

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Lys Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 37
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (41)..(41)
<223> OTHER INFORMATION: N6-((2-azidoethoxy)-carbonyl)-L-lysine
```

<400> SEQUENCE: 37

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 38
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (42)..(42)
<223> OTHER INFORMATION: N6-((2-azidoethoxy)-carbonyl)-L-lysine

<400> SEQUENCE: 38

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 39
<211> LENGTH: 132
<212> TYPE: PRT
<213> ORGANISM: Artificial Sequence
<220> FEATURE:

<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: N6-((2-azidoethoxy)-carbonyl)-L-lysine

<400> SEQUENCE: 39

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 40
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (64)..(64)
<223> OTHER INFORMATION: N6-((2-azidoethoxy)-carbonyl)-L-lysine stably-
      conjugated to PEG
<220> FEATURE:
<223> OTHER INFORMATION: See specification as filed for detailed
      description of substitutions and preferred embodiments

<400> SEQUENCE: 40

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Lys
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

```
Ser Thr Leu Thr
    130


<210> SEQ ID NO 41
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (61)..(61)
<223> OTHER INFORMATION: N6-((2-azidoethoxy)-carbonyl)-L-lysine stably-
      conjugated to PEG
<220> FEATURE:
<223> OTHER INFORMATION: See specification as filed for detailed
      description of substitutions and preferred embodiments

<400> SEQUENCE: 41

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Lys Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 42
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (41)..(41)
<223> OTHER INFORMATION: N6-((2-azidoethoxy)-carbonyl)-L-lysine stably-
      conjugated to PEG
<220> FEATURE:
<223> OTHER INFORMATION: See specification as filed for detailed
      description of substitutions and preferred embodiments

<400> SEQUENCE: 42

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60
```

```
Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

```
<210> SEQ ID NO 43
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (42)..(42)
<223> OTHER INFORMATION: N6-((2-azidoethoxy)-carbonyl)-L-lysine stably-
      conjugated to PEG
<220> FEATURE:
<223> OTHER INFORMATION: See specification as filed for detailed
      description of substitutions and preferred embodiments

<400> SEQUENCE: 43

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

```
<210> SEQ ID NO 44
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: N6-((2-azidoethoxy)-carbonyl)-L-lysine stably-
      conjugated to PEG
<220> FEATURE:
<223> OTHER INFORMATION: See specification as filed for detailed
      description of substitutions and preferred embodiments
```

<400> SEQUENCE: 44

Pro Thr Ser Ser Ser Thr Lys Lys Thr Gln Leu Gln Leu Glu His Leu
1 5 10 15

Leu Leu Asp Leu Gln Met Ile Leu Asn Gly Ile Asn Asn Tyr Lys Asn
20 25 30

Pro Lys Leu Thr Arg Met Leu Thr Phe Lys Phe Tyr Met Pro Lys Lys
35 40 45

Ala Thr Glu Leu Lys His Leu Gln Cys Leu Glu Glu Glu Leu Lys Pro
50 55 60

Leu Glu Glu Val Leu Asn Leu Ala Gln Ser Lys Asn Phe His Leu Arg
65 70 75 80

Pro Arg Asp Leu Ile Ser Asn Ile Asn Val Ile Val Leu Glu Leu Lys
85 90 95

Gly Ser Glu Thr Thr Phe Met Cys Glu Tyr Ala Asp Glu Thr Ala Thr
100 105 110

Ile Val Glu Phe Leu Asn Arg Trp Ile Thr Phe Ser Gln Ser Ile Ile
115 120 125

Ser Thr Leu Thr
130

<210> SEQ ID NO 45
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (64)..(64)
<223> OTHER INFORMATION: N6-((2-azidoethoxy)-carbonyl)-L-lysine stably-conjugated to PEG
<220> FEATURE:
<223> OTHER INFORMATION: See specification as filed for detailed description of substitutions and preferred embodiments

<400> SEQUENCE: 45

Pro Thr Ser Ser Ser Thr Lys Lys Thr Gln Leu Gln Leu Glu His Leu
1 5 10 15

Leu Leu Asp Leu Gln Met Ile Leu Asn Gly Ile Asn Asn Tyr Lys Asn
20 25 30

Pro Lys Leu Thr Arg Met Leu Thr Phe Lys Phe Tyr Met Pro Lys Lys
35 40 45

Ala Thr Glu Leu Lys His Leu Gln Cys Leu Glu Glu Glu Leu Lys Lys
50 55 60

Leu Glu Glu Val Leu Asn Leu Ala Gln Ser Lys Asn Phe His Leu Arg
65 70 75 80

Pro Arg Asp Leu Ile Ser Asn Ile Asn Val Ile Val Leu Glu Leu Lys
85 90 95

Gly Ser Glu Thr Thr Phe Met Cys Glu Tyr Ala Asp Glu Thr Ala Thr
100 105 110

Ile Val Glu Phe Leu Asn Arg Trp Ile Thr Phe Ser Gln Ser Ile Ile
115 120 125

Ser Thr Leu Thr
130

<210> SEQ ID NO 46
<211> LENGTH: 132
<212> TYPE: PRT

<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (61)..(61)
<223> OTHER INFORMATION: N6-((2-azidoethoxy)-carbonyl)-L-lysine stably-conjugated to PEG
<220> FEATURE:
<223> OTHER INFORMATION: See specification as filed for detailed description of substitutions and preferred embodiments

<400> SEQUENCE: 46

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Lys Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

<210> SEQ ID NO 47
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (41)..(41)
<223> OTHER INFORMATION: N6-((2-azidoethoxy)-carbonyl)-L-lysine stably-conjugated to PEG
<220> FEATURE:
<223> OTHER INFORMATION: See specification as filed for detailed description of substitutions and preferred embodiments

<400> SEQUENCE: 47

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95
```

-continued

```
Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 48
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (42)..(42)
<223> OTHER INFORMATION: N6-((2-azidoethoxy)-carbonyl)-L-lysine stably-
      conjugated to PEG
<220> FEATURE:
<223> OTHER INFORMATION: See specification as filed for detailed
      description of substitutions and preferred embodiments

<400> SEQUENCE: 48

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 49
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: N6-((2-azidoethoxy)-carbonyl)-L-lysine stably-
      conjugated to PEG
<220> FEATURE:
<223> OTHER INFORMATION: See specification as filed for detailed
      description of substitutions and preferred embodiments

<400> SEQUENCE: 49

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30
```

```
Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 50
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (64)..(64)
<223> OTHER INFORMATION: N6-((2-azidoethoxy)-carbonyl)-L-lysine stably-
      conjugated to PEG
<220> FEATURE:
<223> OTHER INFORMATION: See specification as filed for detailed
      description of substitutions and preferred embodiments

<400> SEQUENCE: 50

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Lys
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 51
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (61)..(61)
```

<223> OTHER INFORMATION: N6-((2-azidoethoxy)-carbonyl)-L-lysine stably-
conjugated to PEG
<220> FEATURE:
<223> OTHER INFORMATION: See specification as filed for detailed
description of substitutions and preferred embodiments

<400> SEQUENCE: 51

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Lys Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

<210> SEQ ID NO 52
<211> LENGTH: 132
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (41)..(41)
<223> OTHER INFORMATION: N6-((2-azidoethoxy)-carbonyl)-L-lysine stably-
conjugated to PEG
<220> FEATURE:
<223> OTHER INFORMATION: See specification as filed for detailed
description of substitutions and preferred embodiments

<400> SEQUENCE: 52

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125
```

```
Ser Thr Leu Thr
    130


<210> SEQ ID NO 53
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (42)..(42)
<223> OTHER INFORMATION: N6-((2-azidoethoxy)-carbonyl)-L-lysine stably-
      conjugated to PEG
<220> FEATURE:
<223> OTHER INFORMATION: See specification as filed for detailed
      description of substitutions and preferred embodiments

<400> SEQUENCE: 53

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 54
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: N6-((2-azidoethoxy)-carbonyl)-L-lysine stably-
      conjugated to PEG
<220> FEATURE:
<223> OTHER INFORMATION: See specification as filed for detailed
      description of substitutions and preferred embodiments

<400> SEQUENCE: 54

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45
```

Ala Thr Glu Leu Lys His Leu Gln Cys Leu Glu Glu Glu Leu Lys Pro
50 55 60

Leu Glu Glu Val Leu Asn Leu Ala Gln Ser Lys Asn Phe His Leu Arg
65 70 75 80

Pro Arg Asp Leu Ile Ser Asn Ile Asn Val Ile Val Leu Glu Leu Lys
85 90 95

Gly Ser Glu Thr Thr Phe Met Cys Glu Tyr Ala Asp Glu Thr Ala Thr
100 105 110

Ile Val Glu Phe Leu Asn Arg Trp Ile Thr Phe Ser Gln Ser Ile Ile
115 120 125

Ser Thr Leu Thr
130

<210> SEQ ID NO 55
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (65)..(65)
<223> OTHER INFORMATION: N6-((2-azidoethoxy)-carbonyl)-L-lysine stably-conjugated to PEG
<220> FEATURE:
<223> OTHER INFORMATION: See specification as filed for detailed description of substitutions and preferred embodiments

<400> SEQUENCE: 55

Ala Pro Thr Ser Ser Ser Thr Lys Lys Thr Gln Leu Gln Leu Glu His
1 5 10 15

Leu Leu Leu Asp Leu Gln Met Ile Leu Asn Gly Ile Asn Asn Tyr Lys
20 25 30

Asn Pro Lys Leu Thr Arg Met Leu Thr Phe Lys Phe Tyr Met Pro Lys
35 40 45

Lys Ala Thr Glu Leu Lys His Leu Gln Cys Leu Glu Glu Glu Leu Lys
50 55 60

Lys Leu Glu Glu Val Leu Asn Leu Ala Gln Ser Lys Asn Phe His Leu
65 70 75 80

Arg Pro Arg Asp Leu Ile Ser Asn Ile Asn Val Ile Val Leu Glu Leu
85 90 95

Lys Gly Ser Glu Thr Thr Phe Met Cys Glu Tyr Ala Asp Glu Thr Ala
100 105 110

Thr Ile Val Glu Phe Leu Asn Arg Trp Ile Thr Phe Ser Gln Ser Ile
115 120 125

Ile Ser Thr Leu Thr
130

<210> SEQ ID NO 56
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (62)..(62)
<223> OTHER INFORMATION: N6-((2-azidoethoxy)-carbonyl)-L-lysine stably-conjugated to PEG
<220> FEATURE:

```
<223> OTHER INFORMATION: See specification as filed for detailed
      description of substitutions and preferred embodiments

<400> SEQUENCE: 56

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Lys Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130


<210> SEQ ID NO 57
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (42)..(42)
<223> OTHER INFORMATION: N6-((2-azidoethoxy)-carbonyl)-L-lysine stably-
      conjugated to PEG
<220> FEATURE:
<223> OTHER INFORMATION: See specification as filed for detailed
      description of substitutions and preferred embodiments

<400> SEQUENCE: 57

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130
```

<210> SEQ ID NO 58
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (43)..(43)
<223> OTHER INFORMATION: N6-((2-azidoethoxy)-carbonyl)-L-lysine stably-conjugated to PEG
<220> FEATURE:
<223> OTHER INFORMATION: See specification as filed for detailed description of substitutions and preferred embodiments

<400> SEQUENCE: 58

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130
```

<210> SEQ ID NO 59
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (35)..(35)
<223> OTHER INFORMATION: N6-((2-azidoethoxy)-carbonyl)-L-lysine stably-conjugated to PEG
<220> FEATURE:
<223> OTHER INFORMATION: See specification as filed for detailed description of substitutions and preferred embodiments

<400> SEQUENCE: 59

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80
```

```
Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130
```

<210> SEQ ID NO 60
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (65)..(65)
<223> OTHER INFORMATION: N6-((2-azidoethoxy)-carbonyl)-L-lysine stably-conjugated to PEG
<220> FEATURE:
<223> OTHER INFORMATION: See specification as filed for detailed description of substitutions and preferred embodiments

<400> SEQUENCE: 60

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Lys Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130
```

<210> SEQ ID NO 61
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (62)..(62)
<223> OTHER INFORMATION: N6-((2-azidoethoxy)-carbonyl)-L-lysine stably-conjugated to PEG
<220> FEATURE:
<223> OTHER INFORMATION: See specification as filed for detailed description of substitutions and preferred embodiments

<400> SEQUENCE: 61

```
Ala Pro Thr Ser Ser Ser Thr Lys Lys Thr Gln Leu Gln Leu Glu His
1               5                   10                  15
```

```
Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Lys Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130


<210> SEQ ID NO 62
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (42)..(42)
<223> OTHER INFORMATION: N6-((2-azidoethoxy)-carbonyl)-L-lysine stably-
      conjugated to PEG
<220> FEATURE:
<223> OTHER INFORMATION: See specification as filed for detailed
      description of substitutions and preferred embodiments

<400> SEQUENCE: 62

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130


<210> SEQ ID NO 63
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
```

-continued

<220> FEATURE:
<221> NAME/KEY: MOD_RES
<222> LOCATION: (43)..(43)
<223> OTHER INFORMATION: N6-((2-azidoethoxy)-carbonyl)-L-lysine stably-conjugated to PEG
<220> FEATURE:
<223> OTHER INFORMATION: See specification as filed for detailed description of substitutions and preferred embodiments

<400> SEQUENCE: 63

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130
```

<210> SEQ ID NO 64
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (35)..(35)
<223> OTHER INFORMATION: N6-((2-azidoethoxy)-carbonyl)-L-lysine stably-conjugated to PEG
<220> FEATURE:
<223> OTHER INFORMATION: See specification as filed for detailed description of substitutions and preferred embodiments

<400> SEQUENCE: 64

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110
```

```
Thr Ile Val Glu Phe Leu Asn Arg Trp Ile Thr Phe Ser Gln Ser Ile
        115                 120                 125

Ile Ser Thr Leu Thr
    130


<210> SEQ ID NO 65
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (65)..(65)
<223> OTHER INFORMATION: N6-((2-azidoethoxy)-carbonyl)-L-lysine stably-
      conjugated to PEG
<220> FEATURE:
<223> OTHER INFORMATION: See specification as filed for detailed
      description of substitutions and preferred embodiments

<400> SEQUENCE: 65

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Lys Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130


<210> SEQ ID NO 66
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (62)..(62)
<223> OTHER INFORMATION: N6-((2-azidoethoxy)-carbonyl)-L-lysine stably-
      conjugated to PEG
<220> FEATURE:
<223> OTHER INFORMATION: See specification as filed for detailed
      description of substitutions and preferred embodiments

<400> SEQUENCE: 66

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30
```

```
Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Lys Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130


<210> SEQ ID NO 67
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (42)..(42)
<223> OTHER INFORMATION: N6-((2-azidoethoxy)-carbonyl)-L-lysine stably-
      conjugated to PEG
<220> FEATURE:
<223> OTHER INFORMATION: See specification as filed for detailed
      description of substitutions and preferred embodiments

<400> SEQUENCE: 67

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130


<210> SEQ ID NO 68
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
```

<223> OTHER INFORMATION: N6-((2-azidoethoxy)-carbonyl)-L-lysine stably-
conjugated to PEG
<220> FEATURE:
<223> OTHER INFORMATION: See specification as filed for detailed
description of substitutions and preferred embodiments

<400> SEQUENCE: 68

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130
```

<210> SEQ ID NO 69
<211> LENGTH: 133
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (35)..(35)
<223> OTHER INFORMATION: N6-((2-azidoethoxy)-carbonyl)-L-lysine stably-
conjugated to PEG
<220> FEATURE:
<223> OTHER INFORMATION: See specification as filed for detailed
description of substitutions and preferred embodiments

<400> SEQUENCE: 69

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125
```

```
Ile Ser Thr Leu Thr
    130


<210> SEQ ID NO 70
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (64)..(64)
<223> OTHER INFORMATION: N6-((2-azidoethoxy)-carbonyl)-L-lysine
<220> FEATURE:
<223> OTHER INFORMATION: See specification as filed for detailed
      description of substitutions and preferred embodiments

<400> SEQUENCE: 70

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Lys
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 71
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (61)..(61)
<223> OTHER INFORMATION: N6-((2-azidoethoxy)-carbonyl)-L-lysine
<220> FEATURE:
<223> OTHER INFORMATION: See specification as filed for detailed
      description of substitutions and preferred embodiments

<400> SEQUENCE: 71

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Lys Leu Lys Pro
    50                  55                  60
```

Leu Glu Glu Val Leu Asn Leu Ala Gln Ser Lys Asn Phe His Leu Arg
65 70 75 80

Pro Arg Asp Leu Ile Ser Asn Ile Asn Val Ile Val Leu Glu Leu Lys
85 90 95

Gly Ser Glu Thr Thr Phe Met Cys Glu Tyr Ala Asp Glu Thr Ala Thr
100 105 110

Ile Val Glu Phe Leu Asn Arg Trp Ile Thr Phe Ser Gln Ser Ile Ile
115 120 125

Ser Thr Leu Thr
130

<210> SEQ ID NO 72
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (41)..(41)
<223> OTHER INFORMATION: N6-((2-azidoethoxy)-carbonyl)-L-lysine
<220> FEATURE:
<223> OTHER INFORMATION: See specification as filed for detailed description of substitutions and preferred embodiments

<400> SEQUENCE: 72

Pro Thr Ser Ser Ser Thr Lys Lys Thr Gln Leu Gln Leu Glu His Leu
1 5 10 15

Leu Leu Asp Leu Gln Met Ile Leu Asn Gly Ile Asn Asn Tyr Lys Asn
20 25 30

Pro Lys Leu Thr Arg Met Leu Thr Lys Lys Phe Tyr Met Pro Lys Lys
35 40 45

Ala Thr Glu Leu Lys His Leu Gln Cys Leu Glu Glu Glu Leu Lys Pro
50 55 60

Leu Glu Glu Val Leu Asn Leu Ala Gln Ser Lys Asn Phe His Leu Arg
65 70 75 80

Pro Arg Asp Leu Ile Ser Asn Ile Asn Val Ile Val Leu Glu Leu Lys
85 90 95

Gly Ser Glu Thr Thr Phe Met Cys Glu Tyr Ala Asp Glu Thr Ala Thr
100 105 110

Ile Val Glu Phe Leu Asn Arg Trp Ile Thr Phe Ser Gln Ser Ile Ile
115 120 125

Ser Thr Leu Thr
130

<210> SEQ ID NO 73
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (42)..(42)
<223> OTHER INFORMATION: N6-((2-azidoethoxy)-carbonyl)-L-lysine
<220> FEATURE:
<223> OTHER INFORMATION: See specification as filed for detailed description of substitutions and preferred embodiments

<400> SEQUENCE: 73

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 74
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (34)..(34)
<223> OTHER INFORMATION: N6-((2-azidoethoxy)-carbonyl)-L-lysine
<220> FEATURE:
<223> OTHER INFORMATION: See specification as filed for detailed description of substitutions and preferred embodiments

<400> SEQUENCE: 74

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 75
<211> LENGTH: 132
<212> TYPE: PRT

<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (64)..(64)
<223> OTHER INFORMATION: N6-((2-azidoethoxy)-carbonyl)-L-lysine
<220> FEATURE:
<223> OTHER INFORMATION: See specification as filed for detailed
description of substitutions and preferred embodiments

<400> SEQUENCE: 75

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Lys
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

<210> SEQ ID NO 76
<211> LENGTH: 132
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (61)..(61)
<223> OTHER INFORMATION: N6-((2-azidoethoxy)-carbonyl)-L-lysine
<220> FEATURE:
<223> OTHER INFORMATION: See specification as filed for detailed
description of substitutions and preferred embodiments

<400> SEQUENCE: 76

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Lys Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110
```

```
Ile Val Glu Phe Leu Asn Arg Trp Ile Thr Phe Ser Gln Ser Ile Ile
        115                 120                 125

Ser Thr Leu Thr
    130


<210> SEQ ID NO 77
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (41)..(41)
<223> OTHER INFORMATION: N6-((2-azidoethoxy)-carbonyl)-L-lysine
<220> FEATURE:
<223> OTHER INFORMATION: See specification as filed for detailed
      description of substitutions and preferred embodiments

<400> SEQUENCE: 77

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 78
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (42)..(42)
<223> OTHER INFORMATION: N6-((2-azidoethoxy)-carbonyl)-L-lysine
<220> FEATURE:
<223> OTHER INFORMATION: See specification as filed for detailed
      description of substitutions and preferred embodiments

<400> SEQUENCE: 78

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45
```

```
Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

<210> SEQ ID NO 79
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (34)..(34)
<223> OTHER INFORMATION: N6-((2-azidoethoxy)-carbonyl)-L-lysine
<220> FEATURE:
<223> OTHER INFORMATION: See specification as filed for detailed description of substitutions and preferred embodiments

<400> SEQUENCE: 79

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

<210> SEQ ID NO 80
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (64)..(64)
<223> OTHER INFORMATION: N6-((2-azidoethoxy)-carbonyl)-L-lysine
<220> FEATURE:
<223> OTHER INFORMATION: See specification as filed for detailed description of substitutions and preferred embodiments -continued

<400> SEQUENCE: 80

Pro Thr Ser Ser Ser Thr Lys Lys Thr Gln Leu Gln Leu Glu His Leu
1 5 10 15

Leu Leu Asp Leu Gln Met Ile Leu Asn Gly Ile Asn Asn Tyr Lys Asn
20 25 30

Pro Lys Leu Thr Arg Met Leu Thr Phe Lys Phe Tyr Met Pro Lys Lys
35 40 45

Ala Thr Glu Leu Lys His Leu Gln Cys Leu Glu Glu Glu Leu Lys Lys
50 55 60

Leu Glu Glu Val Leu Asn Leu Ala Gln Ser Lys Asn Phe His Leu Arg
65 70 75 80

Pro Arg Asp Leu Ile Ser Asn Ile Asn Val Ile Val Leu Glu Leu Lys
85 90 95

Gly Ser Glu Thr Thr Phe Met Cys Glu Tyr Ala Asp Glu Thr Ala Thr
100 105 110

Ile Val Glu Phe Leu Asn Arg Trp Ile Thr Phe Ser Gln Ser Ile Ile
115 120 125

Ser Thr Leu Thr
130

<210> SEQ ID NO 81
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (61)..(61)
<223> OTHER INFORMATION: N6-((2-azidoethoxy)-carbonyl)-L-lysine
<220> FEATURE:
<223> OTHER INFORMATION: See specification as filed for detailed description of substitutions and preferred embodiments

<400> SEQUENCE: 81

Pro Thr Ser Ser Ser Thr Lys Lys Thr Gln Leu Gln Leu Glu His Leu
1 5 10 15

Leu Leu Asp Leu Gln Met Ile Leu Asn Gly Ile Asn Asn Tyr Lys Asn
20 25 30

Pro Lys Leu Thr Arg Met Leu Thr Phe Lys Phe Tyr Met Pro Lys Lys
35 40 45

Ala Thr Glu Leu Lys His Leu Gln Cys Leu Glu Glu Lys Leu Lys Pro
50 55 60

Leu Glu Glu Val Leu Asn Leu Ala Gln Ser Lys Asn Phe His Leu Arg
65 70 75 80

Pro Arg Asp Leu Ile Ser Asn Ile Asn Val Ile Val Leu Glu Leu Lys
85 90 95

Gly Ser Glu Thr Thr Phe Met Cys Glu Tyr Ala Asp Glu Thr Ala Thr
100 105 110

Ile Val Glu Phe Leu Asn Arg Trp Ile Thr Phe Ser Gln Ser Ile Ile
115 120 125

Ser Thr Leu Thr
130

<210> SEQ ID NO 82
<211> LENGTH: 132
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (41)..(41)
<223> OTHER INFORMATION: N6-((2-azidoethoxy)-carbonyl)-L-lysine
<220> FEATURE:
<223> OTHER INFORMATION: See specification as filed for detailed
      description of substitutions and preferred embodiments

<400> SEQUENCE: 82

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Lys Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 83
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (42)..(42)
<223> OTHER INFORMATION: N6-((2-azidoethoxy)-carbonyl)-L-lysine
<220> FEATURE:
<223> OTHER INFORMATION: See specification as filed for detailed
      description of substitutions and preferred embodiments

<400> SEQUENCE: 83

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110
```

```
Ile Val Glu Phe Leu Asn Arg Trp Ile Thr Phe Ser Gln Ser Ile Ile
        115                 120                 125

Ser Thr Leu Thr
    130


<210> SEQ ID NO 84
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: N6-((2-azidoethoxy)-carbonyl)-L-lysine
<220> FEATURE:
<223> OTHER INFORMATION: See specification as filed for detailed
      description of substitutions and preferred embodiments

<400> SEQUENCE: 84

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130


<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Gly Gly Gly Ser
1               5


<210> SEQ ID NO 86
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid except Pro
```

-continued

```
<400> SEQUENCE: 86

Val Pro Gly Xaa Gly
1               5


<210> SEQ ID NO 87
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Phe Gln Ser Ser Ser Ser Lys Ala Pro Pro Pro Ser Leu Pro Ser Pro
1               5                   10                  15

Ser Arg Leu Pro Gly Pro Ser Asp Thr Pro Ile Leu Pro Gln
            20                  25                  30
```

IL-2 CONJUGATES AND METHODS OF USE THEREOF

CROSS-REFERENCE

This application is a divisional of U.S. patent application Ser. No. 16/918,930 filed on Jul. 1, 2020, which is a continuation of U.S. patent application Ser. No. 16/783,095 filed on Feb. 5, 2020, now abandoned, which claims the benefit of U.S. provisional patent application No. 62/802,191 filed on Feb. 6, 2019, U.S. provisional patent application No. 62/847,844 filed on May 14, 2019, U.S. provisional patent application No. 62/870,581 filed on Jul. 3, 2019, U.S. provisional patent application No. 62/899,035 filed on Sep. 11, 2019, and U.S. provisional patent application No. 62/940,173 filed on Nov. 25, 2019, all of which are incorporated by reference in their entirety.

SEQUENCE LISTING

The instant application contains a Sequence Listing which has been submitted electronically in ASCII format and is hereby incorporated by reference in its entirety. Said ASCII copy, created on Feb. 4, 2020, is named "46085-729203SL.txt" and is 121 KB in size.

BACKGROUND OF THE DISCLOSURE

Distinct populations of T cells modulate the immune system to maintain immune homeostasis and tolerance. For example, regulatory T (Treg) cells prevent inappropriate responses by the immune system by preventing pathological self-reactivity while cytotoxic T cells target and destroy infected cells and/or cancerous cells. In some instances, modulation of the different populations of T cells provides an option for treatment of a disease or indication.

SUMMARY OF THE DISCLOSURE

Described herein are IL-2 conjugates comprising the amino acid sequence of SEQ ID NO: 3 in which at least one amino acid residue in the IL-2 conjugate is replaced by the structure of Formula (I):

Formula (I)

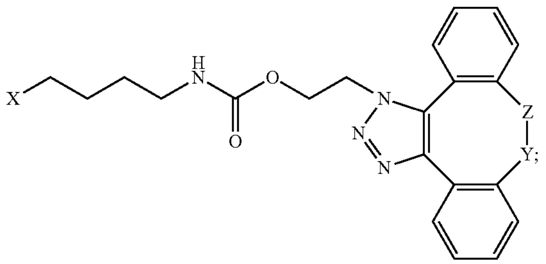

wherein:
Z is $CH_2$ and Y is

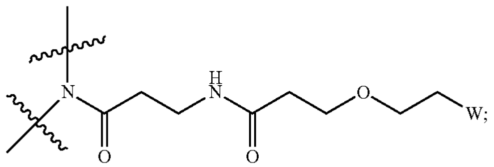

Y is $CH_2$ and Z is

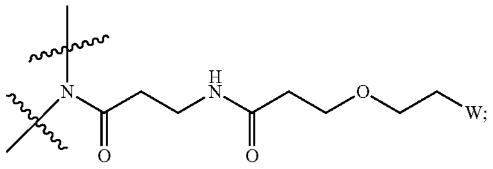

Z is $CH_2$ and Y is

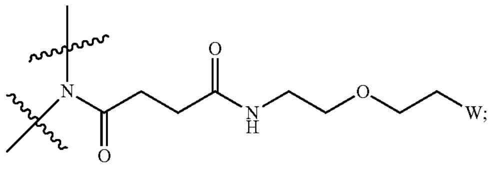

or
Y is $CH_2$ and Z is

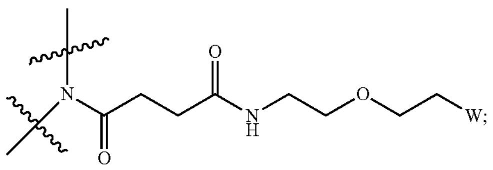

W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and
X has the structure:

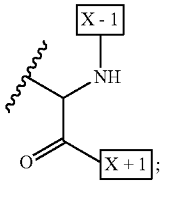 [SMILES: *C(NC)C(C)=O]

or a pharmaceutically acceptable salt, solvate, or hydrate thereof. In some embodiments of an IL-2 conjugate described herein, Z is $CH_2$ and Y is

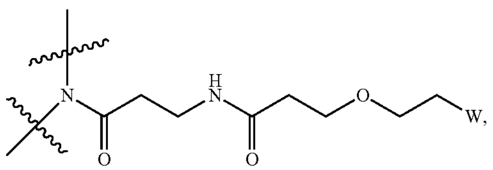

or a pharmaceutically acceptable salt, solvate, or hydrate thereof. In some embodiments of an IL-2 conjugate described herein, Y is $CH_2$ and Z is

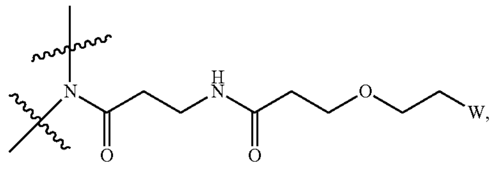

or a pharmaceutically acceptable salt, solvate, or hydrate thereof. In some embodiments of an IL-2 conjugate described herein, Z is $CH_2$ and Y is

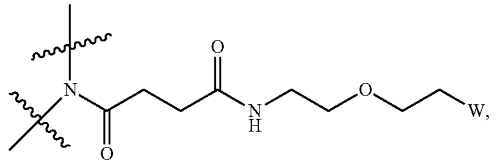

or a pharmaceutically acceptable salt, solvate, or hydrate thereof. In some embodiments of an IL-2 conjugate described herein, Z is $CH_2$ and Y is

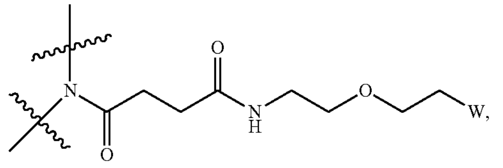

or a pharmaceutically acceptable salt, solvate, or hydrate thereof. In some embodiments of an IL-2 conjugate described herein, Y is $CH_2$ and Z is

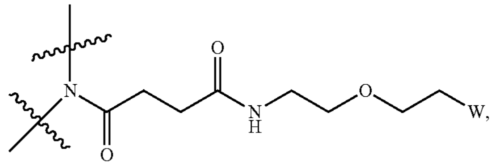

or a pharmaceutically acceptable salt, solvate, or hydrate thereof. In some embodiments of an IL-2 conjugate described herein, the PEG group has an average molecular weight selected from 5 kDa, 10 kDa, 20 kDa and 30 kDa, or a pharmaceutically acceptable salt, solvate, or hydrate thereof. In some embodiments of an IL-2 conjugate described herein, the PEG group has an average molecular weight of 5 kDa, or a pharmaceutically acceptable salt, solvate, or hydrate thereof. In some embodiments of an IL-2 conjugate described herein, the PEG group has an average molecular weight of 10 kDa, or a pharmaceutically acceptable salt, solvate, or hydrate thereof. In some embodiments of an IL-2 conjugate described herein, the PEG group has an average molecular weight of 15 kDa, or a pharmaceutically acceptable salt, solvate, or hydrate thereof. In some embodiments of an IL-2 conjugate described herein, the PEG group has an average molecular weight of 20 kDa, or a pharmaceutically acceptable salt, solvate, or hydrate thereof. In some embodiments of an IL-2 conjugate described herein, the PEG group has an average molecular weight of 25 kDa, or a pharmaceutically acceptable salt, solvate, or hydrate thereof. In some embodiments of an IL-2 conjugate described herein, the PEG group has an average molecular weight of 30 kDa, or a pharmaceutically acceptable salt, solvate, or hydrate thereof. In some embodiments of an IL-2 conjugate described herein, the PEG group has an average molecular weight of 35 kDa, or a pharmaceutically acceptable salt, solvate, or hydrate thereof. In some embodiments of an IL-2 conjugate described herein, the PEG group has an average molecular weight of 40 kDa, or a pharmaceutically acceptable salt, solvate, or hydrate thereof. In some embodiments of an IL-2 conjugate described herein, the PEG group has an average molecular weight of 45 kDa, or a pharmaceutically acceptable salt, solvate, or hydrate thereof. In some embodiments of an IL-2 conjugate described herein, the PEG group has an average molecular weight of 50 kDa, or a pharmaceutically acceptable salt, solvate, or hydrate thereof. In some embodiments of an IL-2 conjugate described herein, the PEG group has an average molecular weight of 60 kDa, or a pharmaceutically acceptable salt, solvate, or hydrate thereof. In some embodiments of an IL-2 conjugate described herein, the position of the structure of Formula (I) in the amino acid sequence of the IL-2 conjugate is selected from K35, F42, F44, K43, E62, P65, R38, T41, E68, Y45, V69, and L72, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is selected from F42, E62, and P65, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is K35, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is F42, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is F44, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is K43, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is E62, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is P65, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is R38, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is T41, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is E68, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is Y45, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is V69, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is L72, wherein the position of the structure of Formula (I) in the amino acid sequence of the IL-2 conjugate is in reference to the positions in SEQ ID NO: 1, or a pharmaceutically acceptable salt, solvate, or hydrate thereof.

Described herein are IL-2 conjugates comprising the amino acid sequence of SEQ ID NO: 4 in which at least one amino acid residue in the IL-2 conjugate is replaced by the structure of Formula (I):

Formula (I)

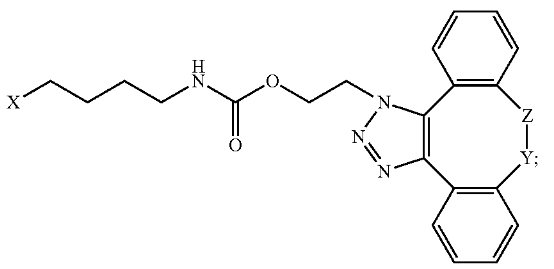

wherein:

Z is $CH_2$ and Y is

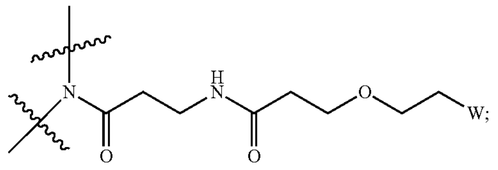

Y is $CH_2$ and Z is

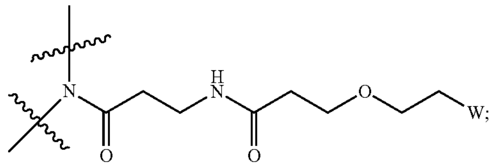

Z is $CH_2$ and Y is

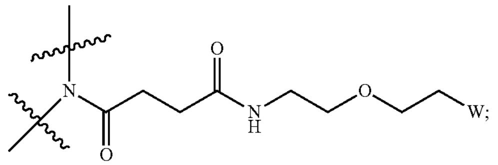

or

Y is $CH_2$ and Z is

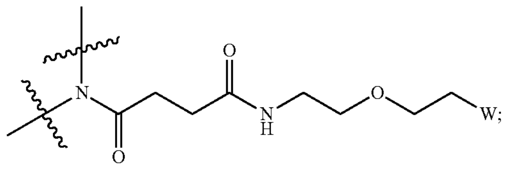

W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and X has the structure:

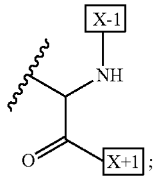

or a pharmaceutically acceptable salt, solvate, or hydrate thereof. In some embodiments of an IL-2 conjugate described herein, Z is $CH_2$ and Y is

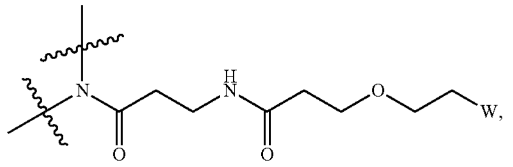

or a pharmaceutically acceptable salt, solvate, or hydrate thereof. In some embodiments of an IL-2 conjugate described herein, Y is $CH_2$ and Z is

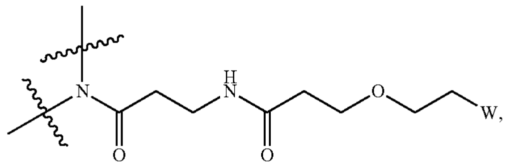

or a pharmaceutically acceptable salt, solvate, or hydrate thereof. In some embodiments of an IL-2 conjugate described herein, Z is $CH_2$ and Y is

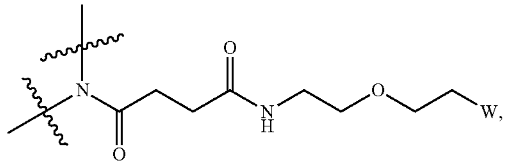

or a pharmaceutically acceptable salt, solvate, or hydrate thereof. In some embodiments of an IL-2 conjugate described herein, Z is $CH_2$ and Y is

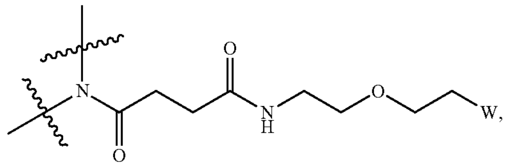

or a pharmaceutically acceptable salt, solvate, or hydrate thereof. In some embodiments of an IL-2 conjugate described herein, Y is $CH_2$ and Z is

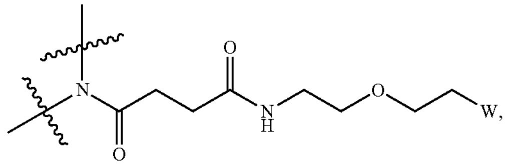

or a pharmaceutically acceptable salt, solvate, or hydrate thereof. In some embodiments of an IL-2 conjugate described herein, the PEG group has an average molecular weight selected from 5 kDa, 10 kDa, 20 kDa and 30 kDa, or a pharmaceutically acceptable salt, solvate, or hydrate thereof. In some embodiments of an IL-2 conjugate described herein, the PEG group has an average molecular weight of 5 kDa, or a pharmaceutically acceptable salt, solvate, or hydrate thereof. In some embodiments of an IL-2 conjugate described herein, the PEG group has an average molecular weight of 10 kDa, or a pharmaceutically acceptable salt, solvate, or hydrate thereof. In some embodiments of an IL-2 conjugate described herein, the PEG group has an average molecular weight of 15 kDa, or a pharmaceutically acceptable salt, solvate, or hydrate thereof. In some embodiments of an IL-2 conjugate described herein, the PEG group has an average molecular weight of 20 kDa, or a pharmaceutically acceptable salt, solvate, or hydrate thereof. In some embodiments of an IL-2 conjugate described herein, the PEG group has an average molecular weight of 25 kDa, or a pharmaceutically acceptable salt, solvate, or hydrate thereof. In some embodiments of an IL-2 conjugate described herein, the PEG group has an average molecular weight of 30 kDa, or a pharmaceutically acceptable salt, solvate, or hydrate thereof. In some embodiments of an IL-2 conjugate described herein, the PEG group has an average molecular weight of 35 kDa, or a pharmaceutically acceptable salt, solvate, or hydrate thereof. In some embodiments of an IL-2 conjugate described herein, the PEG group has an average molecular weight of 40 kDa, or a pharmaceutically acceptable salt, solvate, or hydrate thereof. In some embodiments of an IL-2 conjugate described herein, the PEG group has an average molecular weight of 45 kDa, or a pharmaceutically acceptable salt, solvate, or hydrate thereof. In some embodiments of an IL-2 conjugate described herein, the PEG group has an average molecular weight of 50 kDa, or a pharmaceutically acceptable salt, solvate, or hydrate thereof. In some embodiments of an IL-2 conjugate described herein, the PEG group has an average molecular weight of 60 kDa, or a pharmaceutically acceptable salt, solvate, or hydrate thereof. In some embodiments of an IL-2 conjugate described herein, the position of the structure of Formula (I) in the amino acid sequence of the IL-2 conjugate is selected from K35, F42, F44, K43, E62, P65, R38, T41, E68, Y45, V69, and L72, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is selected from F42, E62, and P65, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is K35, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is F42, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is F44, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is K43, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is E62, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is P65, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is R38, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is T41, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is E68, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is Y45, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is V69, wherein the position of the structure of Formula (I) in the amino acid sequence of the IL-2 conjugate is in reference to the positions in SEQ ID NO: 1, or a pharmaceutically acceptable salt, solvate, or hydrate thereof. In some embodiments of an IL-2 conjugate described herein, the position of the structure of Formula (I) in the amino acid sequence of the IL-2 conjugate is L72, wherein the position of the structure of Formula (I) in the amino acid sequence of the IL-2 conjugate is in reference to the positions in SEQ ID NO: 1, or a pharmaceutically acceptable salt, solvate, or hydrate thereof.

Described herein are IL-2 conjugates comprising the amino acid sequence of any one of SEQ ID NOS: 15-19, wherein [AzK_PEG] has the structure of Formula (II) or Formula (III), or a mixture of Formula (II) and Formula (III):

Formula (II)

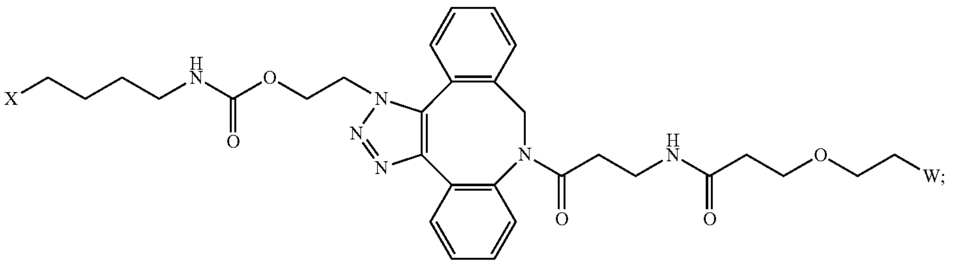

Formula (III)

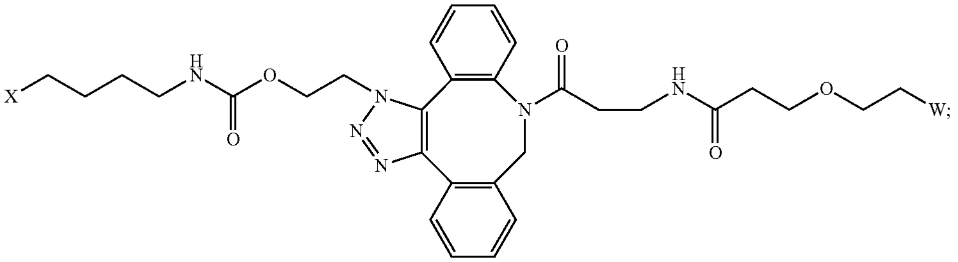

wherein:

W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and X has the structure:

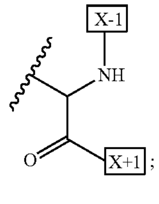

or a pharmaceutically acceptable salt, solvate, or hydrate thereof. In some embodiments of an IL-2 conjugate described herein, the [AzK_PEG] is a mixture of Formula (II) and Formula (III), or a pharmaceutically acceptable salt, solvate, or hydrate thereof. In some embodiments of an IL-2 conjugate described herein, the [AzK_PEG] has the structure of formula (II):

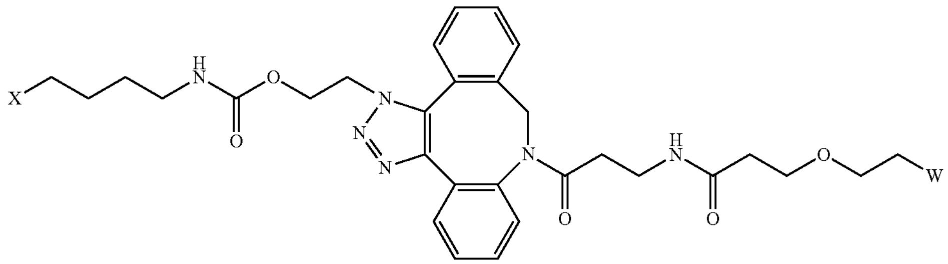

Formula (II); or a pharmaceutically acceptable salt, solvate, or hydrate thereof. In some embodiments of an IL-2 conjugate described herein, the IL-2 conjugate has the amino acid sequence of SEQ ID NO: 15, or a pharmaceutically acceptable salt, solvate, or hydrate thereof. In some embodiments of an IL-2 conjugate described herein, W is a PEG group having an average molecular weight selected from 5 kDa, 10 kDa, 15 kDa, 20 kDa, 25 kDa, and 30 kDa, or a pharmaceutically acceptable salt, solvate, or hydrate thereof. In some embodiments of an IL-2 conjugate described herein, W is a PEG group having an average molecular weight selected from 5 kDa and 30 kDa, or a pharmaceutically acceptable salt, solvate, or hydrate thereof. In some embodiments of an IL-2 conjugate described herein, W is a PEG group having an average molecular weight of 5 kDa, or a pharmaceutically acceptable salt, solvate, or hydrate thereof. In some embodiments of an IL-2 conjugate described herein, W is a PEG group having an average molecular weight of 30 kDa, or a pharmaceutically acceptable salt, solvate, or hydrate thereof. In some embodiments of an IL-2 conjugate described herein, the IL-2 conjugate has the amino acid sequence of SEQ ID NO: 16, or a pharmaceutically acceptable salt, solvate, or hydrate thereof. In some embodiments of an IL-2 conjugate described herein, W is a PEG group having an average molecular weight selected from 5 kDa, 10 kDa, 15 kDa, 20 kDa, 25 kDa, and 30 kDa, or a pharmaceutically acceptable salt, solvate, or hydrate thereof. In some embodiments of an IL-2 conjugate described herein, W is a PEG group having an average molecular weight selected from 5 kDa and 30 kDa, or a pharmaceutically acceptable salt, solvate, or hydrate thereof. In some embodiments of an IL-2 conjugate described herein, W is a PEG group having an average molecular weight of 5 kDa, or a pharmaceutically acceptable salt, solvate, or hydrate thereof. In some embodiments of an IL-2 conjugate described herein, W is a PEG group having an average molecular weight of 30 kDa, or a pharmaceutically acceptable salt, solvate, or hydrate thereof. In some embodiments of an IL-2 conjugate described herein, the IL-2 conjugate has the amino acid sequence of SEQ ID NO: 17, or a pharmaceutically acceptable salt, solvate, or hydrate thereof. In some embodiments of an IL-2 conjugate described herein, W is a PEG group having an average molecular weight selected from 5 kDa, 10 kDa, 15 kDa, 20 kDa, 25 kDa, and 30 kDa, or a pharmaceutically acceptable salt, solvate, or hydrate thereof. In some embodiments of an IL-2 conjugate described herein, W is a PEG group having an average molecular weight selected from 5 kDa and 30 kDa, or a pharmaceutically acceptable salt, solvate, or hydrate thereof. In some embodiments of an IL-2 conjugate described herein, W is a PEG group having an average molecular weight of 5 kDa, or a pharmaceutically acceptable salt, solvate, or hydrate thereof. In some embodiments of an IL-2 conjugate described herein, W is a PEG group having an average molecular weight of 30 kDa, or a pharmaceutically acceptable salt, solvate, or hydrate thereof. In some embodiments of an IL-2 conjugate described herein, the IL-2 conjugate has the amino acid sequence of SEQ ID NO: 18, or a pharmaceutically acceptable salt, solvate, or hydrate thereof. In some embodiments of an IL-2 conjugate described herein, W is a PEG group having an average molecular weight selected from 5 kDa, 10 kDa, 15 kDa, 20 kDa, 25 kDa, and 30 kDa, or a pharmaceutically acceptable salt, solvate, or hydrate thereof. In some embodiments of an IL-2 conjugate described herein, W is a PEG group having an average molecular weight selected from 5 kDa and 30 kDa, or a pharmaceutically acceptable salt, solvate, or hydrate thereof. In some embodiments of an IL-2 conjugate described herein, W is a PEG group having an average molecular weight of 5 kDa, or a pharmaceutically acceptable salt, solvate, or hydrate thereof. In some embodiments of an IL-2 conjugate described herein, W is a PEG group having an average molecular weight of 30 kDa, or a pharmaceutically acceptable salt, solvate, or hydrate thereof. In some embodiments of an IL-2 conjugate described herein, the IL-2 conjugate has the amino acid sequence of SEQ ID NO: 19, or a pharmaceutically acceptable salt, solvate, or hydrate thereof. In some embodiments of an IL-2 conjugate described herein, W is a PEG group having an average molecular weight selected from 5 kDa, 10 kDa, 15 kDa, 20 kDa, 25 kDa, and 30 kDa, or a pharmaceutically acceptable salt, solvate, or hydrate thereof. In some embodiments of an IL-2 conjugate described herein, W is a PEG group having an average molecular weight selected from 5 kDa and 30 kDa, or a pharmaceutically acceptable salt, solvate, or hydrate thereof. In some embodiments of an IL-2 conjugate described herein, W is a PEG group having an average molecular weight of 5 kDa, or a pharmaceutically acceptable salt, solvate, or hydrate thereof. In some embodiments of an IL-2 conjugate described herein, W is a PEG group having an average molecular weight of 30 kDa, or a pharmaceutically acceptable salt, solvate, or hydrate thereof. In some embodiments of an IL-2 conjugate described herein, the [AzK_PEG] has the structure of formula (III)

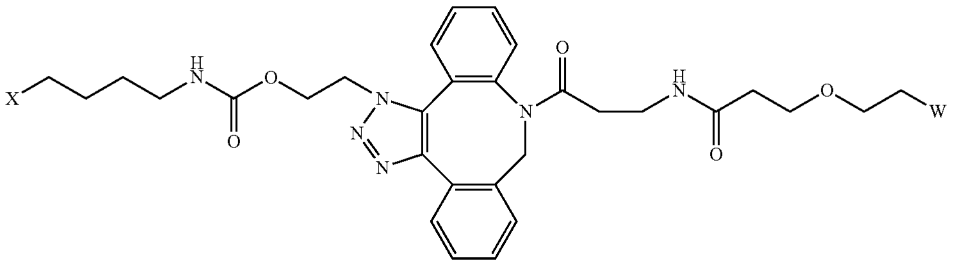

Formula (III); or a pharmaceutically acceptable salt, solvate, or hydrate thereof. In some embodiments of an IL-2 conjugate described herein, the IL-2 conjugate has the amino acid sequence of SEQ ID NO: 15, or a pharmaceutically acceptable salt, solvate, or hydrate thereof. In some embodiments of an IL-2 conjugate described herein, W is a PEG group having an average molecular weight selected from 5 kDa, 10 kDa, 15 kDa, 20 kDa, 25 kDa, and 30 kDa, or a pharmaceutically acceptable salt, solvate, or hydrate thereof. In some embodiments of an IL-2 conjugate described herein, W is a PEG group having an average molecular weight selected from 5 kDa and 30 kDa, or a pharmaceutically acceptable salt, solvate, or hydrate thereof. In some embodiments of an IL-2 conjugate described herein, W is a PEG group having an average molecular weight of 5 kDa, or a pharmaceutically acceptable salt, solvate, or hydrate thereof. In some embodiments of an IL-2 conjugate described herein, W is a PEG group having an average molecular weight of 30 kDa, or a pharmaceutically acceptable salt, solvate, or hydrate thereof. In some embodiments of an IL-2 conjugate described herein, the IL-2 conjugate has the amino acid sequence of SEQ ID NO: 16, or a pharmaceutically acceptable salt, solvate, or hydrate thereof. In some embodiments of an IL-2 conjugate described herein, W is a PEG group having an average molecular weight selected from 5 kDa, 10 kDa, 15 kDa, 20 kDa, 25 kDa, and 30 kDa, or a pharmaceutically acceptable salt, solvate, or hydrate thereof. In some embodiments of an IL-2 conjugate described herein, W is a PEG group having an average molecular weight selected from 5 kDa and 30 kDa, or a pharmaceutically acceptable salt, solvate, or hydrate thereof. In some embodiments of an IL-2 conjugate described herein, W is a PEG group having an average molecular weight of 5 kDa, or a pharmaceutically acceptable salt, solvate, or hydrate thereof. In some embodiments of an IL-2 conjugate described herein, W is a PEG group having an average molecular weight of 30 kDa, or a pharmaceutically acceptable salt, solvate, or hydrate thereof. In some embodiments of an IL-2 conjugate described herein, the IL-2 conjugate has the amino acid sequence of SEQ ID NO: 17, or a pharmaceutically acceptable salt, solvate, or hydrate thereof. In some embodiments of an IL-2 conjugate described herein, W is a PEG group having an average molecular weight selected from 5 kDa, 10 kDa, 15 kDa, 20 kDa, 25 kDa, and 30 kDa, or a pharmaceutically acceptable salt, solvate, or hydrate thereof. In some embodiments of an IL-2 conjugate described herein, W is a PEG group having an average molecular weight selected from 5 kDa and 30 kDa, or a pharmaceutically acceptable salt, solvate, or hydrate thereof. In some embodiments of an IL-2 conjugate described herein, W is a PEG group having an average molecular weight of 5 kDa, or a pharmaceutically acceptable salt, solvate, or hydrate thereof. In some embodiments of an IL-2 conjugate described herein, W is a PEG group having an average molecular weight of 30 kDa, or a pharmaceutically acceptable salt, solvate, or hydrate thereof. In some embodiments of an IL-2 conjugate described herein, the IL-2 conjugate has the amino acid sequence of SEQ ID NO: 18, or a pharmaceutically acceptable salt, solvate, or hydrate thereof. In some embodiments of an IL-2 conjugate described herein, W is a PEG group having an average molecular weight selected from 5 kDa, 10 kDa, 15 kDa, 20 kDa, 25 kDa, and 30 kDa, or a pharmaceutically acceptable salt, solvate, or hydrate thereof. In some embodiments of an IL-2 conjugate described herein, W is a PEG group having an average molecular weight selected from 5 kDa and 30 kDa, or a pharmaceutically acceptable salt, solvate, or hydrate thereof. In some embodiments of an IL-2 conjugate described herein, W is a PEG group having an average molecular weight of 5 kDa, or a pharmaceutically acceptable salt, solvate, or hydrate thereof. In some embodiments of an IL-2 conjugate described herein, W is a PEG group having an average molecular weight of 30 kDa, or a pharmaceutically acceptable salt, solvate, or hydrate thereof. In some embodiments of an IL-2 conjugate described herein, the IL-2 conjugate has the amino acid sequence of SEQ ID NO: 19, or a pharmaceutically acceptable salt, solvate, or hydrate thereof. In some embodiments of an IL-2 conjugate described herein, W is a PEG group having an average molecular weight selected from 5 kDa, 10 kDa, 15 kDa, 20 kDa, 25 kDa, and 30 kDa, or a pharmaceutically acceptable salt, solvate, or hydrate thereof. In some embodiments of an IL-2 conjugate described herein, W is a PEG group having an average molecular weight selected from 5 kDa and 30 kDa, or a pharmaceutically acceptable salt, solvate, or hydrate thereof. In some embodiments of an IL-2 conjugate described herein, W is a PEG group having an average molecular weight of 5 kDa, or a pharmaceutically acceptable salt, solvate, or hydrate thereof. In some embodiments of an IL-2 conjugate described herein, W is a PEG group having an average molecular weight of 30 kDa, or a pharmaceutically acceptable salt, solvate, or hydrate thereof. In some embodiments of an IL-2 conjugate described herein, W is a linear or branched PEG group, or a pharmaceutically acceptable salt, solvate, or hydrate thereof. In some embodiments of an IL-2 conjugate described herein, W is a linear PEG group, or a pharmaceutically acceptable salt, solvate, or hydrate thereof. In some embodiments of an IL-2 conjugate described herein, W is a branched PEG group, or a pharmaceutically acceptable salt, solvate, or hydrate thereof. In some embodiments of an IL-2 conjugate described herein, W is a methoxy PEG group, or a pharmaceutically acceptable salt, solvate, or hydrate thereof. In some embodiments of an IL-2 conjugate described herein, the methoxy PEG group is linear or branched, or a pharmaceutically acceptable salt, solvate, or hydrate thereof. In some embodiments of an IL-2 conjugate described herein, the methoxy PEG group is linear, or a pharmaceutically acceptable salt, solvate, or hydrate thereof. In some embodiments of an IL-2 conjugate described herein, the methoxy PEG group is branched, or a pharmaceutically acceptable salt, solvate, or hydrate thereof. An exemplary structure of a methoxy PEG group is illustrated in the mPEG-DBCO structure in Scheme 1 of Example 2.

In some embodiments of an IL-2 conjugate described herein having the amino acid sequence selected from any one of SEQ ID NO: 15, 16, 17, 18, and 19, [AzK_PEG] contains a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa. In some embodiments of an IL-2 conjugate described herein having the amino acid sequence selected from any one of SEQ ID NO: 15, 16, 17, 18, and 19, [AzK_PEG] contains a PEG group having an average molecular weight of 5 kDa. In some embodiments of an IL-2 conjugate described herein having the amino acid sequence selected from any one of SEQ ID NO: 15, 16, 17, 18, and 19, [AzK_PEG] contains a PEG group having an average molecular weight of 10 kDa. In some embodiments of an IL-2 conjugate described herein having the amino acid sequence selected from any one of SEQ ID NO: 15, 16, 17, 18, and 19, [AzK_PEG] contains a PEG group having an average molecular weight of 15 kDa. In some embodiments of an IL-2 conjugate described herein having the amino acid sequence selected from any one of SEQ ID NO: 15, 16, 17, 18, and 19, [AzK_PEG] contains a PEG group having an average molecular weight of 20 kDa. In some embodiments of an IL-2 conjugate described herein having the amino acid sequence selected from any one of SEQ ID NO: 15, 16, 17, 18, and 19, [AzK_PEG] contains a PEG group having an average molecular weight of 25 kDa. In some embodiments of an IL-2 conjugate described herein having the amino acid sequence selected from any one of SEQ ID NO: 15, 16, 17, 18, and 19, [AzK_PEG] contains a PEG group having an average molecular weight of 30 kDa. In some embodiments of an IL-2 conjugate described herein having the amino acid sequence selected from any one of SEQ ID NO: 15, 16, 17, 18, and 19, [AzK_PEG] contains a PEG group having an average molecular weight of 35 kDa. In some embodiments of an IL-2 conjugate described herein having the amino acid sequence selected from any one of SEQ ID NO: 15, 16, 17, 18, and 19, [AzK_PEG] contains a PEG group having an average molecular weight of 40 kDa. In some embodiments of an IL-2 conjugate described herein having the amino acid sequence selected from any one of SEQ ID NO: 15, 16, 17, 18, and 19, [AzK_PEG] contains a PEG group having an average molecular weight of 45 kDa. In some embodiments of an IL-2 conjugate described herein having the amino acid sequence selected from any one of SEQ ID NO: 15, 16, 17, 18, and 19, [AzK_PEG] contains a PEG group having an average molecular weight of 50 kDa. In some embodiments of an IL-2 conjugate described herein having the amino acid sequence selected from any one of SEQ ID NO: 15, 16, 17, 18, and 19, [AzK_PEG] contains a PEG group having an average molecular weight of 60 kDa. In some embodiments of an IL-2 conjugate described herein having the amino acid sequence selected from any one of SEQ ID NO: 15, 16, 17, 18, and 19, [AzK_PEG] contains a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa, wherein the PEG group is a methoxy PEG group, a linear methoxy PEG group, or a branched methoxy PEG group.

Described herein are IL-2 conjugates comprising the amino acid sequence of any one of SEQ ID NOS: 20-24, wherein [AzK_PEG5kD] has the structure of Formula (II) or Formula (III), or a mixture of Formula (II) and Formula (III):

Formula (II)

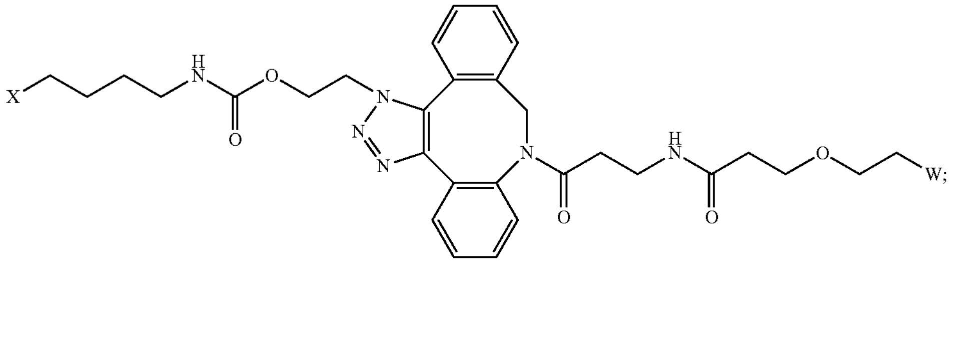

Formula (III)

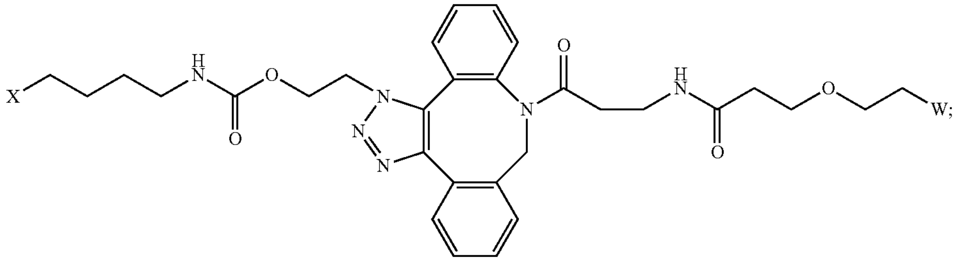

wherein:

W is a PEG group having an average molecular weight of 5 kDa; and

X has the structure:

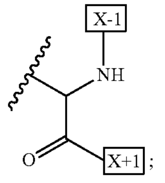

or a pharmaceutically acceptable salt, solvate, or hydrate thereof. In some embodiments of an IL-2 conjugate described herein, the IL-2 conjugate has the amino acid sequence of SEQ ID NO: 20, or a pharmaceutically acceptable salt, solvate, or hydrate thereof. In some embodiments of an IL-2 conjugate described herein, the IL-2 conjugate has the amino acid sequence of SEQ ID NO: 21, or a pharmaceutically acceptable salt, solvate, or hydrate thereof. In some embodiments of an IL-2 conjugate described herein, the IL-2 conjugate has the amino acid sequence of SEQ ID NO: 22, or a pharmaceutically acceptable salt, solvate, or hydrate thereof. In some embodiments of an IL-2 conjugate described herein, the IL-2 conjugate has the amino acid sequence of SEQ ID NO: 23, or a pharmaceutically acceptable salt, solvate, or hydrate thereof. In some embodiments of an IL-2 conjugate described herein, the IL-2 conjugate has the amino acid sequence of SEQ ID NO: 24, or a pharmaceutically acceptable salt, solvate, or hydrate thereof. In some embodiments of an IL-2 conjugate described herein, the [AzK_PEG5kD] has the structure of formula (III)

Formula (III)

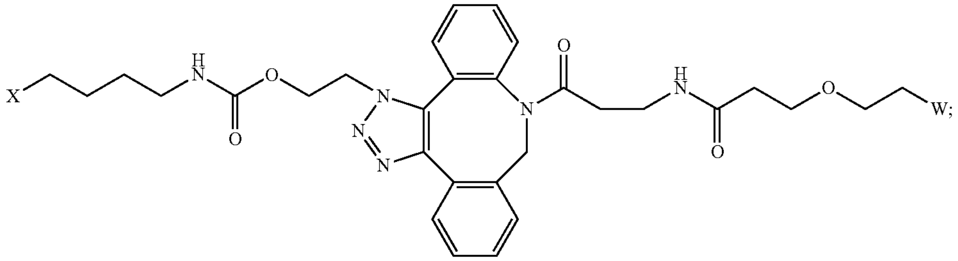

sequence of SEQ ID NO: 20, or a pharmaceutically acceptable salt, solvate, or hydrate thereof. In some embodiments of an IL-2 conjugate described herein, the IL-2 conjugate has the amino acid sequence of SEQ ID NO: 21, or a pharmaceutically acceptable salt, solvate, or hydrate thereof. In some embodiments of an IL-2 conjugate described herein, the IL-2 conjugate has the amino acid sequence of SEQ ID NO: 22, or a pharmaceutically acceptable salt, solvate, or hydrate thereof. In some embodiments of an IL-2 conjugate described herein, the IL-2 conjugate has the amino acid sequence of SEQ ID NO: 23, or a pharmaceutically acceptable salt, solvate, or hydrate thereof. In some embodiments of an IL-2 conjugate described herein, the IL-2 conjugate has the amino acid sequence of SEQ ID NO: 24, or a pharmaceutically acceptable salt, solvate, or hydrate thereof. In some embodiments of an IL-2 conjugate described herein, the [AzK_PEG5kD] has the structure of formula (II)

or a pharmaceutically acceptable salt, solvate, or hydrate thereof. In some embodiments of an IL-2 conjugate described herein, the IL-2 conjugate has the amino acid sequence of SEQ ID NO: 21, or a pharmaceutically acceptable salt, solvate, or hydrate thereof. In some embodiments of an IL-2 conjugate described herein, the IL-2 conjugate has the amino acid sequence of SEQ ID NO: 22, or a pharmaceutically acceptable salt, solvate, or hydrate thereof. In some embodiments of an IL-2 conjugate described herein, the IL-2 conjugate has the amino acid sequence of SEQ ID NO: 23, or a pharmaceutically acceptable salt, solvate, or hydrate thereof. In some embodiments of an IL-2 conjugate described herein, the IL-2 conjugate has the amino acid sequence of SEQ ID NO: 24, or a pharmaceutically acceptable salt, solvate, or hydrate thereof.

Described herein are IL-2 conjugates comprising the amino acid sequence of any one of SEQ ID NOS: 25-29, Formula (II)

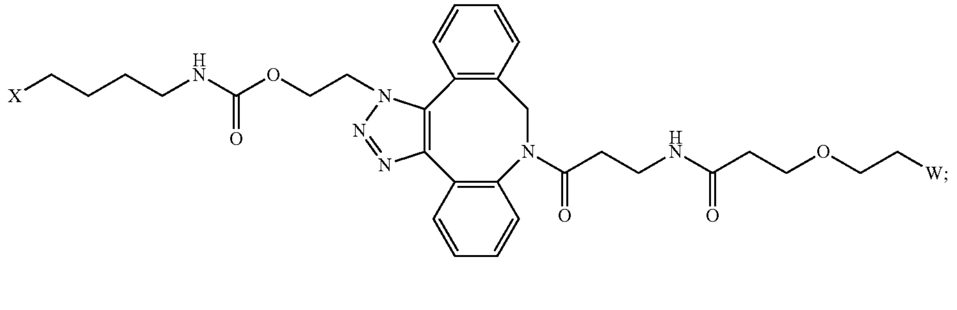

or a pharmaceutically acceptable salt, solvate, or hydrate thereof. In some embodiments of an IL-2 conjugate described herein, the IL-2 conjugate has the amino acid wherein [AzK_PEG30kD] has the structure of Formula (II) or Formula (III), or is a mixture of the structures of Formula (II) and Formula (III):

Formula (II)

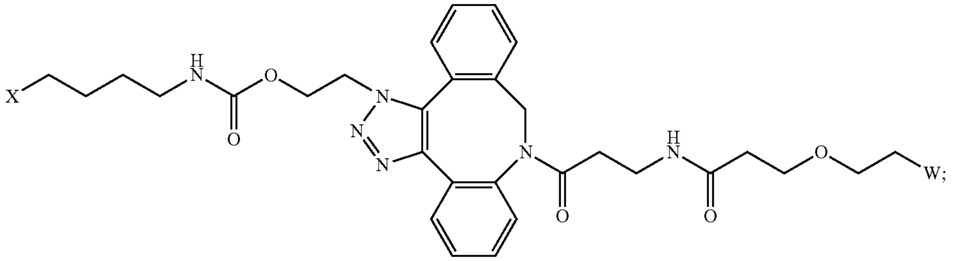

Formula (III)

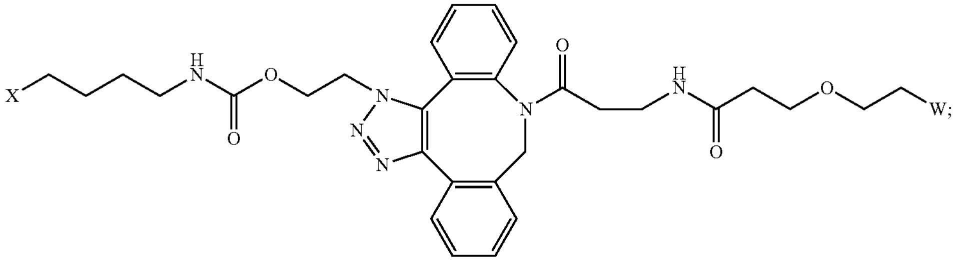

wherein:

W is a PEG group having an average molecular weight of 30 kDa; and

X has the structure:

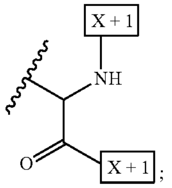

or a pharmaceutically acceptable salt, solvate, or hydrate thereof. In some embodiments of an IL-2 conjugate described herein, the IL-2 conjugate has the amino acid sequence of SEQ ID NO: 25, or a pharmaceutically acceptable salt, solvate, or hydrate thereof. In some embodiments of an IL-2 conjugate described herein, the IL-2 conjugate has the amino acid sequence of SEQ ID NO: 26, or a pharmaceutically acceptable salt, solvate, or hydrate thereof. In some embodiments of an IL-2 conjugate described herein, the IL-2 conjugate has the amino acid sequence of SEQ ID NO: 27, or a pharmaceutically acceptable salt, solvate, or hydrate thereof. In some embodiments of an IL-2 conjugate described herein, the IL-2 conjugate has the amino acid sequence of SEQ ID NO: 28, or a pharmaceutically acceptable salt, solvate, or hydrate thereof. In some embodiments of an IL-2 conjugate described herein, the IL-2 conjugate has the amino acid sequence of SEQ ID NO: 29, or a pharmaceutically acceptable salt, solvate, or hydrate thereof. In some embodiments of an IL-2 conjugate described herein, the [AzK_PEG30kD] has the structure of formula (II):

Formula (II)

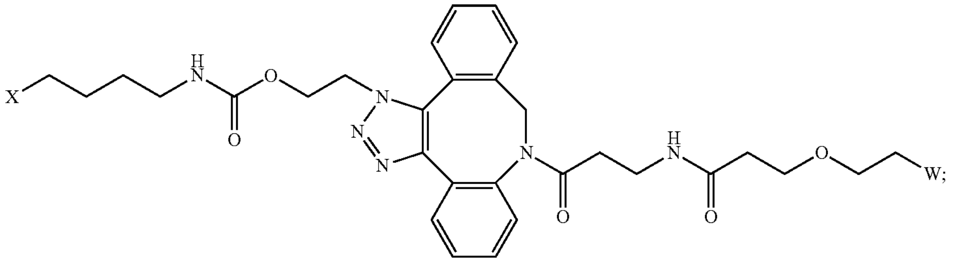

or a pharmaceutically acceptable salt, solvate, or hydrate thereof. In some embodiments of an IL-2 conjugate described herein, the IL-2 conjugate has the amino acid sequence of SEQ ID NO: 26, or a pharmaceutically acceptable salt, solvate, or hydrate thereof. In some embodiments of an IL-2 conjugate described herein, the IL-2 conjugate has the amino acid sequence of SEQ ID NO: 27, or a pharmaceutically acceptable salt, solvate, or hydrate thereof. In some embodiments of an IL-2 conjugate described herein, the IL-2 conjugate has the amino acid sequence of SEQ ID NO: 28, or a pharmaceutically acceptable salt, solvate, or hydrate thereof. In some embodiments of an IL-2 conjugate described herein, the IL-2 conjugate has the amino acid sequence of SEQ ID NO: 29, or a pharmaceutically acceptable salt, solvate, or hydrate thereof. In some embodiments of an IL-2 conjugate described herein, the [AzK_PEG30kD] has the structure of formula (III)

Formula (III)

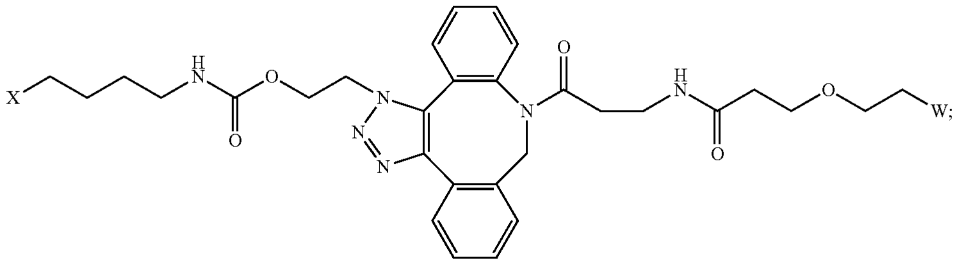

or a pharmaceutically acceptable salt, solvate, or hydrate thereof. In some embodiments of an IL-2 conjugate described herein, the IL-2 conjugate has the amino acid sequence of SEQ ID NO: 26, or a pharmaceutically acceptable salt, solvate, or hydrate thereof. In some embodiments of an IL-2 conjugate described herein, the IL-2 conjugate has the amino acid sequence of SEQ ID NO: 27, or a pharmaceutically acceptable salt, solvate, or hydrate thereof. In some embodiments of an IL-2 conjugate described herein, the IL-2 conjugate has the amino acid sequence of SEQ ID NO: 28, or a pharmaceutically acceptable salt, solvate, or hydrate thereof. In some embodiments of an IL-2 conjugate described herein, the IL-2 conjugate has the amino acid sequence of SEQ ID NO: 29, or a pharmaceutically acceptable salt, solvate, or hydrate thereof.

Described herein are IL-2 conjugates comprising the amino acid sequence of any one of SEQ ID NOS: 15-19, wherein [AzK_PEG] is a mixture of the structures of Formula (II) and Formula (III):

Formula (II)

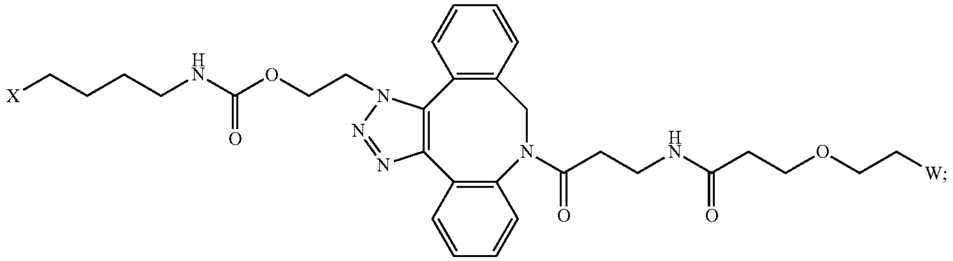

Formula (III)

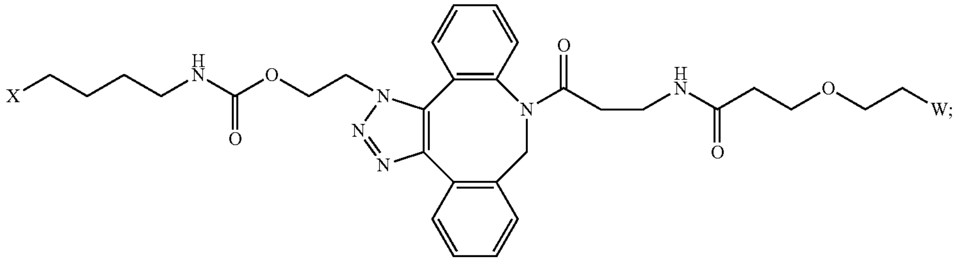

wherein:

W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and X has the structure:

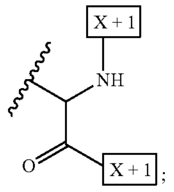 [SMILES: *C(NC)C(C)=O]

described herein, W is a branched PEG group, or a pharmaceutically acceptable salt, solvate, or hydrate thereof. In some embodiments of an IL-2 conjugate described herein, W is a methoxy PEG group, or a pharmaceutically acceptable salt, solvate, or hydrate thereof. In some embodiments of an IL-2 conjugate described herein, the methoxy PEG group is linear or branched, or a pharmaceutically acceptable salt, solvate, or hydrate thereof. In some embodiments of an IL-2 conjugate described herein, the methoxy PEG group is linear, or a pharmaceutically acceptable salt, solvate, or hydrate thereof. In some embodiments of an IL-2 conjugate described herein, the methoxy PEG group is branched, or a pharmaceutically acceptable salt, solvate, or hydrate thereof.

Described herein are IL-2 conjugates comprising the amino acid sequence of any one of SEQ ID NOS: 20 to 24, wherein [AzK_PEG5kD] is a mixture of the structures of Formula (II) and Formula (III):

Formula (II)

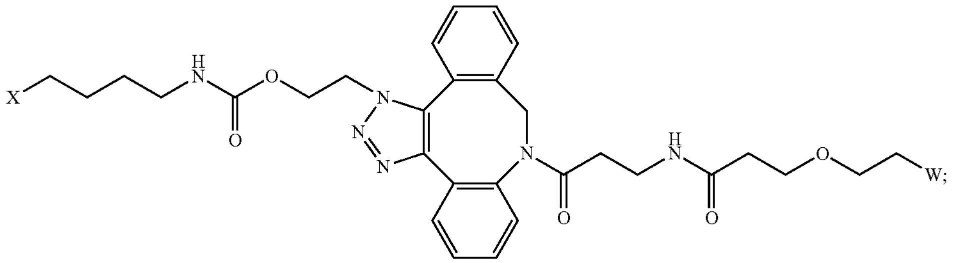

Formula (III)

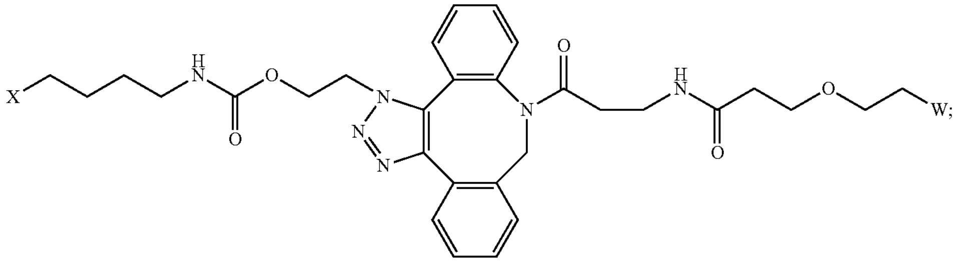

or a pharmaceutically acceptable salt, solvate, or hydrate thereof. In some embodiments of an IL-2 conjugate described herein, the ratio of the amount of the structure of Formula (II) to the amount of the structure of Formula (III) comprising the total amount of [AzK_PEG] in the IL-2 conjugate is about 1:1. In some embodiments of an IL-2 conjugate described herein, the ratio of the amount of the structure of Formula (II) to the amount of the structure of Formula (III) comprising the total amount of [AzK_PEG] in the IL-2 conjugate is greater than 1:1. In some embodiments of an IL-2 conjugate described herein, the ratio of the amount of the structure of Formula (II) to the amount of the structure of Formula (III) comprising the total amount of [AzK_PEG] in the IL-2 conjugate is less than 1:1. In some embodiments of an IL-2 conjugate described herein, W is a linear or branched PEG group, or a pharmaceutically acceptable salt, solvate, or hydrate thereof. In some embodiments of an IL-2 conjugate described herein, W is a linear PEG group, or a pharmaceutically acceptable salt, solvate, or hydrate thereof. In some embodiments of an IL-2 conjugate wherein:

W is a PEG group having an average molecular weight of 5 kDa; and

X has the structure:

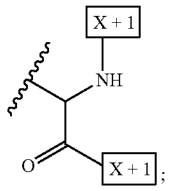

or a pharmaceutically acceptable salt, solvate, or hydrate thereof. In some embodiments of an IL-2 conjugate described herein, the ratio of the amount of the structure of Formula (II) to the amount of the structure of Formula (III) comprising the total amount of [AzK_PEG5kD] in the IL-2 conjugate is about 1:1. In some embodiments of an IL-2 conjugate described herein, the ratio of the amount of the structure of Formula (II) to the amount of the structure of Formula (III) comprising the total amount of [AzK_PEG5kD] in the IL-2 conjugate is greater than 1:1. In some embodiments of an IL-2 conjugate described herein, the ratio of the amount of the structure of Formula (II) to the amount of the structure of Formula (III) comprising the total amount of [AzK_PEG5kD] in the IL-2 conjugate is less than 1:1.

Described herein are IL-2 conjugates comprising the amino acid sequence of any one of SEQ ID NOS: 25-29, wherein [AzK_PEG30kD] is a mixture of the structures of Formula (II) and Formula (III):

Formula (II)

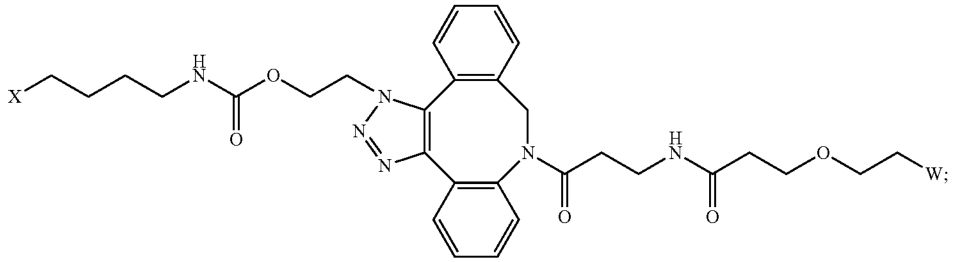

Formula (III)

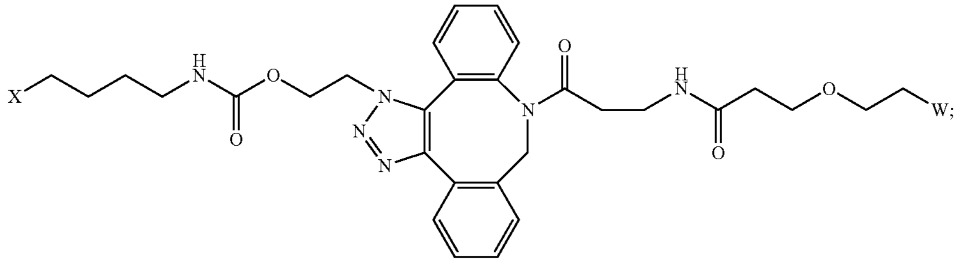

wherein:

W is a PEG group having an average molecular weight of 30 kDa; and

X has the structure:

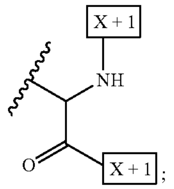

or a pharmaceutically acceptable salt, solvate, or hydrate thereof. In some embodiments of an IL-2 conjugate described herein, the ratio of the amount of the structure of Formula (II) to the amount of the structure of Formula (III) comprising the total amount of [AzK_PEG30kD] in the IL-2 conjugate is about 1:1. In some embodiments of an IL-2 conjugate described herein, the ratio of the amount of the structure of Formula (II) to the amount of the structure of Formula (III) comprising the total amount of [AzK_PEG30kD] in the IL-2 conjugate is greater than 1:1. In some embodiments of an IL-2 conjugate described herein, the ratio of the amount of the structure of Formula (II) to the amount of the structure of Formula (III) comprising the total amount of [AzK_PEG30kD] in the IL-2 conjugate is less than 1:1.

Described herein are IL-2 conjugates comprising the amino acid sequence of any one of SEQ ID NOS: 40-44, wherein [AzK_L1_PEG] has the structure of Formula (IV) or Formula (V), or a mixture of Formula (IV) and Formula (V):

Formula (IV)

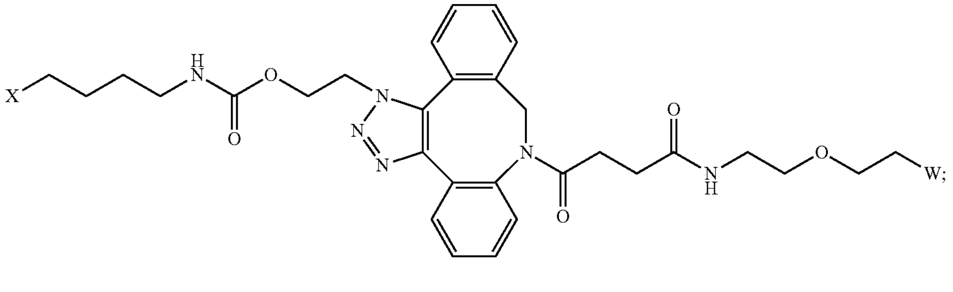

-continued

Formula (V)

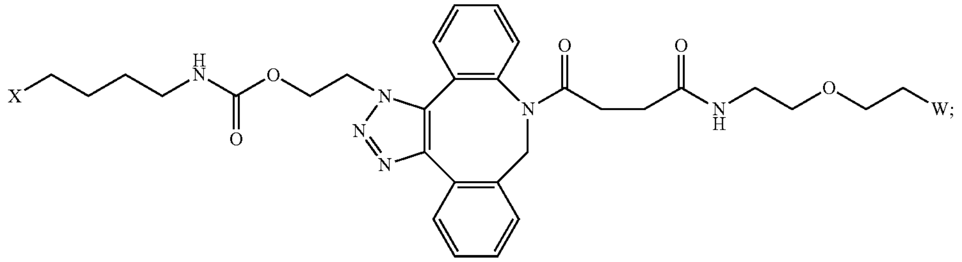

wherein:

W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and X has the structure:

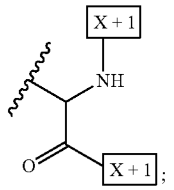 [SMILES: *C(NC)C(C)=O]

or a pharmaceutically acceptable salt, solvate, or hydrate thereof. In some embodiments of an IL-2 conjugate described herein, the [AzK_L1_PEG] is a mixture of Formula (IV) and Formula (V), or a pharmaceutically acceptable salt, solvate, or hydrate thereof. In some embodiments of an IL-2 conjugate described herein, the [AzK_L1_PEG] has the structure of Formula (IV):

ments of an IL-2 conjugate described herein, W is a PEG group having an average molecular weight of 30 kDa, or a pharmaceutically acceptable salt, solvate, or hydrate thereof. In some embodiments of an IL-2 conjugate described herein, the IL-2 conjugate has the amino acid sequence of SEQ ID NO: 41, or a pharmaceutically acceptable salt, solvate, or hydrate thereof. In some embodiments of an IL-2 conjugate described herein, W is a PEG group having an average molecular weight selected from 5 kDa, 10 kDa, 15 kDa, 20 kDa, 25 kDa, and 30 kDa, or a pharmaceutically acceptable salt, solvate, or hydrate thereof. In some embodiments of an IL-2 conjugate described herein, W is a PEG group having an average molecular weight selected from 5 kDa and 30 kDa, or a pharmaceutically acceptable salt, solvate, or hydrate thereof. In some embodiments of an IL-2 conjugate described herein, W is a PEG group having an average molecular weight of 5 kDa, or a pharmaceutically acceptable salt, solvate, or hydrate thereof. In some embodiments of an IL-2 conjugate described herein, W is a PEG group having an average molecular weight of 30 kDa, or a pharmaceutically acceptable salt, solvate, or hydrate thereof. In some embodiments of an IL-2 conjugate described herein, the IL-2

Formula (IV)

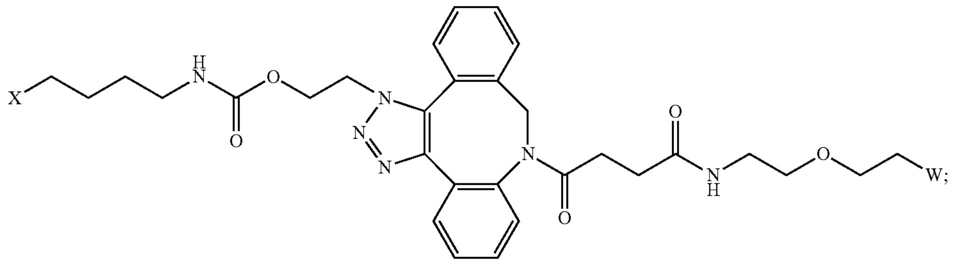

or a pharmaceutically acceptable salt, solvate, or hydrate thereof. In some embodiments of IL-2 conjugate described herein, the IL-2 conjugate has the amino acid sequence of SEQ ID NO: 40, or a pharmaceutically acceptable salt, solvate, or hydrate thereof. In some embodiments of an IL-2 conjugate described herein, W is a PEG group having an average molecular weight selected from 5 kDa, 10 kDa, 15 kDa, 20 kDa, 25 kDa, and 30 kDa, or a pharmaceutically acceptable salt, solvate, or hydrate thereof. In some embodiments of an IL-2 conjugate described herein, W is a PEG group having an average molecular weight selected from 5 kDa and 30 kDa, or a pharmaceutically acceptable salt, solvate, or hydrate thereof. In some embodiments of an IL-2 conjugate described herein, W is a PEG group having an average molecular weight of 5 kDa, or a pharmaceutically acceptable salt, solvate, or hydrate thereof. In some embodiments of an IL-2 conjugate described herein, W is a PEG group having an average molecular weight of 30 kDa, or a pharmaceutically acceptable salt, solvate, or hydrate thereof. In some embodiments of an IL-2 conjugate described herein, the IL-2 conjugate has the amino acid sequence of SEQ ID NO: 42, or a pharmaceutically acceptable salt, solvate, or hydrate thereof. In some embodiments of an IL-2 conjugate described herein, W is a PEG group having an average molecular weight selected from 5 kDa, 10 kDa, 15 kDa, 20 kDa, 25 kDa, and 30 kDa, or a pharmaceutically acceptable salt, solvate, or hydrate thereof. In some embodiments of an IL-2 conjugate described herein, W is a PEG group having an average molecular weight selected from 5 kDa and 30 kDa, or a pharmaceutically acceptable salt, solvate, or hydrate thereof. In some embodiments of an IL-2 conjugate described herein, W is a PEG group having an average molecular weight of 5 kDa, or a pharmaceutically acceptable salt, solvate, or hydrate thereof. In some embodiments of an IL-2 conjugate described herein, W is a PEG group having an average molecular weight of 30 kDa, or a pharmaceutically acceptable salt, solvate, or hydrate thereof. In some embodiments of an IL-2 conjugate described herein, the IL-2 conjugate has the amino acid sequence of SEQ ID NO: 43, or a pharmaceutically acceptable salt, solvate, or hydrate thereof. In some embodiments of an IL-2 conjugate described herein, W is a PEG group having an average molecular weight selected from 5 kDa, 10 kDa, 15 kDa, 20 kDa, 25 kDa, and 30 kDa, or a pharmaceutically acceptable salt, solvate, or hydrate thereof. In some embodiments of an IL-2 conjugate described herein, W is a PEG group having an average molecular weight selected from 5 kDa and 30 kDa, or a pharmaceutically acceptable salt, solvate, or hydrate thereof. In some embodiments of an IL-2 conjugate described herein, W is a PEG group having an average molecular weight of 5 kDa, or a pharmaceutically acceptable salt, solvate, or hydrate thereof.

In some embodiments of an IL-2 conjugate described herein, W is a PEG group having an average molecular weight of 30 kDa, or a pharmaceutically acceptable salt, solvate, or hydrate thereof. In some embodiments of an IL-2 conjugate described herein, the IL-2 conjugate has the amino acid sequence of SEQ ID NO: 44, or a pharmaceutically acceptable salt, solvate, or hydrate thereof. In some embodiments of an IL-2 conjugate described herein, W is a PEG group having an average molecular weight selected from 5 kDa, 10 kDa, 15 kDa, 20 kDa, 25 kDa, and 30 kDa, or a pharmaceutically acceptable salt, solvate, or hydrate thereof. In some embodiments of an IL-2 conjugate described herein, W is a PEG group having an average molecular weight selected from 5 kDa and 30 kDa, or a pharmaceutically acceptable salt, solvate, or hydrate thereof. In some embodiments of an IL-2 conjugate described herein, W is a PEG group having an average molecular weight of 5 kDa, or a pharmaceutically acceptable salt, solvate, or hydrate thereof. In some embodiments of an IL-2 conjugate described herein, W is a PEG group having an average molecular weight of 30 kDa, or a pharmaceutically acceptable salt, solvate, or hydrate thereof. In some embodiments of an IL-2 conjugate described herein, the [AzK_L1_PEG] has the structure of Formula (V)

ments of an IL-2 conjugate described herein, W is a PEG group having an average molecular weight of 5 kDa, or a pharmaceutically acceptable salt, solvate, or hydrate thereof. In some embodiments of an IL-2 conjugate described herein, W is a PEG group having an average molecular weight of 30 kDa, or a pharmaceutically acceptable salt, solvate, or hydrate thereof. In some embodiments of an IL-2 conjugate described herein, the IL-2 conjugate has the amino acid sequence of SEQ ID NO: 41, or a pharmaceutically acceptable salt, solvate, or hydrate thereof. In some embodiments of an IL-2 conjugate described herein, W is a PEG group having an average molecular weight selected from 5 kDa, 10 kDa, 15 kDa, 20 kDa, 25 kDa, and 30 kDa, or a pharmaceutically acceptable salt, solvate, or hydrate thereof. In some embodiments of an IL-2 conjugate described herein, W is a PEG group having an average molecular weight selected from 5 kDa and 30 kDa, or a pharmaceutically acceptable salt, solvate, or hydrate thereof. In some embodiments of an IL-2 conjugate described herein, W is a PEG group having an average molecular weight of 5 kDa, or a pharmaceutically acceptable salt, solvate, or hydrate thereof. In some embodiments of an IL-2 conjugate described herein, W is a PEG group having an average molecular weight of 30 kDa, or a pharmaceutically acceptable salt, solvate, or hydrate thereof. In some embodiments of an IL-2 conjugate described herein, the IL-2 conjugate has the amino acid sequence of SEQ ID NO: 42, or a pharmaceutically acceptable salt, solvate, or hydrate thereof. In some embodiments of an IL-2 conjugate described herein, W is a PEG group having an average molecular weight selected from 5 kDa, 10 kDa, 15 kDa, 20 kDa, 25 kDa, and 30 kDa, or a pharmaceutically acceptable salt, solvate, or hydrate thereof. In some embodiments of an IL-2 conjugate described herein, W is a PEG group having an average molecular weight selected from 5 kDa and 30 kDa, or a pharmaceutically acceptable salt, solvate, or hydrate thereof. In some embodiments of an IL-2 conjugate described herein, W is a PEG group having an average molecular weight of 5 kDa, or a pharmaceutically acceptable salt, solvate, or hydrate thereof. In some embodiments of an IL-2 conjugate described herein, W is a PEG group having an average molecular weight of 30 kDa, or a pharmaceutically acceptable salt, solvate, or Formula (V)

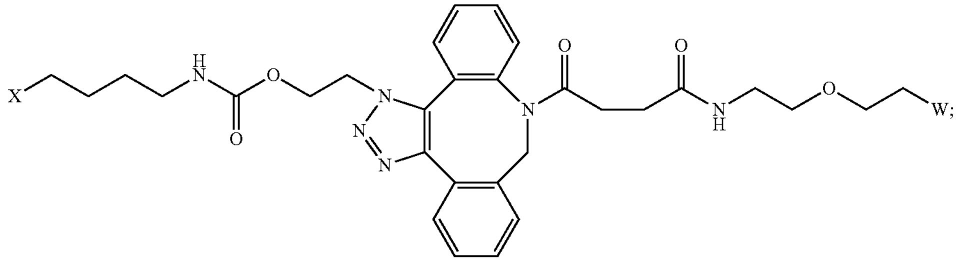

or a pharmaceutically acceptable salt, solvate, or hydrate thereof. In some embodiments of an IL-2 conjugate described herein, the IL-2 conjugate has the amino acid sequence of SEQ ID NO: 40, or a pharmaceutically acceptable salt, solvate, or hydrate thereof. In some embodiments of an IL-2 conjugate described herein, W is a PEG group having an average molecular weight selected from 5 kDa, 10 kDa, 15 kDa, 20 kDa, 25 kDa, and 30 kDa, or a pharmaceutically acceptable salt, solvate, or hydrate thereof. In some embodiments of an IL-2 conjugate described herein, W is a PEG group having an average molecular weight selected from 5 kDa and 30 kDa, or a pharmaceutically acceptable salt, solvate, or hydrate thereof. In some embodiments of an IL-2 conjugate described herein, W is a PEG hydrate thereof. In some embodiments of an IL-2 conjugate described herein, the IL-2 conjugate has the amino acid sequence of SEQ ID NO: 43, or a pharmaceutically acceptable salt, solvate, or hydrate thereof. In some embodiments of an IL-2 conjugate described herein, W is a PEG group having an average molecular weight selected from 5 kDa, 10 kDa, 15 kDa, 20 kDa, 25 kDa, and 30 kDa, or a pharmaceutically acceptable salt, solvate, or hydrate thereof. In some embodiments of an IL-2 conjugate described herein, W is a PEG group having an average molecular weight selected from 5 kDa and 30 kDa, or a pharmaceutically acceptable salt, solvate, or hydrate thereof. In some embodiments of an IL-2 conjugate described herein, W is a PEG group having an average molecular weight of 5 kDa, or a pharmaceutically acceptable salt, solvate, or hydrate thereof. In some embodiments of an IL-2 conjugate described herein, W is a PEG group having an average molecular weight of 30 kDa, or a pharmaceutically acceptable salt, solvate, or hydrate thereof. In some embodiments of an IL-2 conjugate described herein, the IL-2 conjugate has the amino acid sequence of SEQ ID NO: 44, or a pharmaceutically acceptable salt, solvate, or hydrate thereof. In some embodiments of an IL-2 conjugate described herein, W is a PEG group having an average molecular weight selected from 5 kDa, 10 kDa, 15 kDa, 20 kDa, 25 kDa, and 30 kDa, or a pharmaceutically acceptable salt, solvate, or hydrate thereof. In some embodiments of an IL-2 conjugate described herein, W is a PEG group having an average molecular weight selected from 5 kDa and 30 kDa, or a pharmaceutically acceptable salt, solvate, or hydrate thereof. In some embodiments of an IL-2 conjugate described herein, W is a PEG group having an average molecular weight of 5 kDa, or a pharmaceutically acceptable salt, solvate, or hydrate thereof. In some embodiments of an IL-2 conjugate described herein, W is a PEG group having an average molecular weight of 30 kDa, or a pharmaceutically acceptable salt, solvate, or hydrate thereof. In some embodiments of an IL-2 conjugate described herein, W is a linear or branched PEG group, or a pharmaceutically acceptable salt, solvate, or hydrate thereof. In some embodiments of an IL-2 conjugate described herein, W is a linear PEG group, or a pharmaceutically acceptable salt, solvate, or hydrate thereof. In some embodiments of an IL-2 conjugate described herein, W is a branched PEG group, or a pharmaceutically acceptable salt, solvate, or hydrate thereof. In some embodiments of an IL-2 conjugate described herein, W is a methoxy PEG group, or a pharmaceutically acceptable salt, solvate, or hydrate thereof. In some embodiments of an IL-2 conjugate described herein, the methoxy PEG group is linear or branched, or a pharmaceutically acceptable salt, solvate, or hydrate thereof. In some embodiments of an IL-2 conjugate described herein, the methoxy PEG group is linear, or a pharmaceutically acceptable salt, solvate, or hydrate thereof. In some embodiments of an IL-2 conjugate described herein, the methoxy PEG group is branched, or a pharmaceutically acceptable salt, solvate, or hydrate thereof. In some embodiments of an IL-2 conjugate described herein having the amino acid sequence selected from any one of SEQ ID NO: 40, 41, 42, 43, and 44, [AzK_L1_PEG] contains a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa. In some embodiments of an IL-2 conjugate described herein having the amino acid sequence selected from any one of SEQ ID NO: 40, 41, 42, 43, and 44, [AzK_L1_PEG] contains a PEG group having an average molecular weight of 5 kDa. In some embodiments of an IL-2 conjugate described herein having the amino acid sequence selected from any one of SEQ ID NO: 40, 41, 42, 43, and 44, [AzK_L1_PEG] contains a PEG group having an average molecular weight of 10 kDa. In some embodiments of an IL-2 conjugate described herein having the amino acid sequence selected from any one of SEQ ID NO: 40, 41, 42, 43, and 44, [AzK_L1_PEG] contains a PEG group having an average molecular weight of 15 kDa. In some embodiments of an IL-2 conjugate described herein having the amino acid sequence selected from any one of SEQ ID NO: 40, 41, 42, 43, and 44, [AzK_L1_PEG] contains a PEG group having an average molecular weight of 20 kDa. In some embodiments of an IL-2 conjugate described herein having the amino acid sequence selected from any one of SEQ ID NO: 40, 41, 42, 43, and 44, [AzK_L1_PEG] contains a PEG group having an average molecular weight of 25 kDa. In some embodiments of an IL-2 conjugate described herein having the amino acid sequence selected from any one of SEQ ID NO: 40, 41, 42, 43, and 44, [AzK_L1_PEG] contains a PEG group having an average molecular weight of 30 kDa. In some embodiments of an IL-2 conjugate described herein having the amino acid sequence selected from any one of SEQ ID NO: 40, 41, 42, 43, and 44, [AzK_L1_PEG] contains a PEG group having an average molecular weight of 35 kDa. In some embodiments of an IL-2 conjugate described herein having the amino acid sequence selected from any one of SEQ ID NO: 40, 41, 42, 43, and 44, [AzK_L1_PEG] contains a PEG group having an average molecular weight of 40 kDa. In some embodiments of an IL-2 conjugate described herein having the amino acid sequence selected from any one of SEQ ID NO: 40, 41, 42, 43, and 44, [AzK_L1_PEG] contains a PEG group having an average molecular weight of 45 kDa. In some embodiments of an IL-2 conjugate described herein having the amino acid sequence selected from any one of SEQ ID NO: 40, 41, 42, 43, and 44, [AzK_L1_PEG] contains a PEG group having an average molecular weight of 50 kDa. In some embodiments of an IL-2 conjugate described herein having the amino acid sequence selected from any one of SEQ ID NO: 40, 41, 42, 43, and 44, [AzK_L1_PEG] contains a PEG group having an average molecular weight of 60 kDa. In some embodiments of an IL-2 conjugate described herein having the amino acid sequence selected from any one of SEQ ID NO: 40, 41, 42, 43, and 44, [AzK_L1_PEG] contains a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa, wherein the PEG group is a methoxy PEG group, a linear methoxy PEG group, or a branched methoxy PEG group.

Described herein are IL-2 conjugates comprising the amino acid sequence of any one of SEQ ID NOS: 45-49, wherein [AzK_L1_PEG5kD] has the structure of Formula (IV) or Formula (V), or a mixture of Formula (IV) and Formula (V):

Formula (IV)

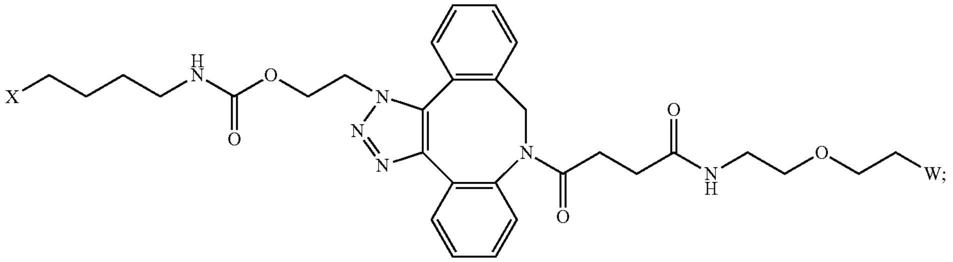

-continued

Formula (V)

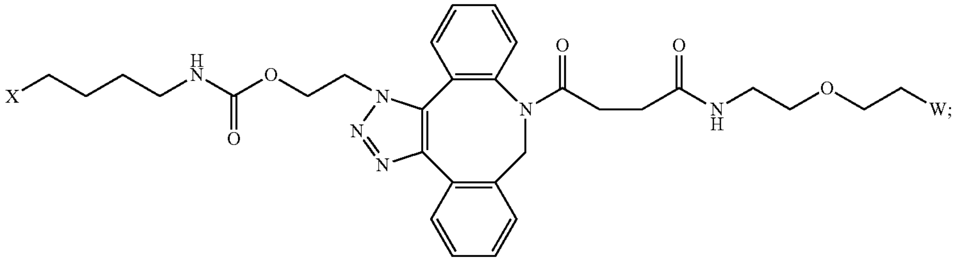

wherein:

W is a PEG group having an average molecular weight of 5 kDa; and

X has the structure:

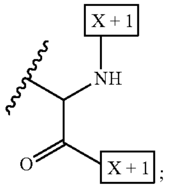

or a pharmaceutically acceptable salt, solvate, or hydrate thereof. In some embodiments of an IL-2 conjugate described herein, the IL-2 conjugate has the amino acid sequence of SEQ ID NO: 45, or a pharmaceutically acceptable salt, solvate, or hydrate thereof. In some embodiments of an IL-2 conjugate described herein, the IL-2 conjugate has the amino acid sequence of SEQ ID NO: 46, or a pharmaceutically acceptable salt, solvate, or hydrate thereof. In some embodiments of an IL-2 conjugate described herein, the IL-2 conjugate has the amino acid sequence of SEQ ID NO: 47, or a pharmaceutically acceptable salt, solvate, or hydrate thereof. In some embodiments of an IL-2 conjugate described herein, the IL-2 conjugate has the amino acid sequence of SEQ ID NO: 48, or a pharmaceutically acceptable salt, solvate, or hydrate thereof. In some embodiments of an IL-2 conjugate described herein, the IL-2 conjugate has the amino acid sequence of SEQ ID NO: 49, or a pharmaceutically acceptable salt, solvate, or hydrate thereof. In some embodiments of an IL-2 conjugate described herein, the [AzK_L1_PEG5kD] has the structure of Formula (IV)

Formula (IV)

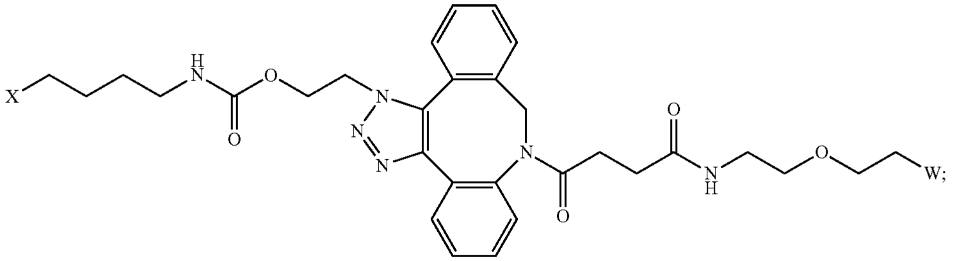

or a pharmaceutically acceptable salt, solvate, or hydrate thereof. In some embodiments of an IL-2 conjugate described herein, the IL-2 conjugate has the amino acid sequence of SEQ ID NO: 46, or a pharmaceutically acceptable salt, solvate, or hydrate thereof. In some embodiments of an IL-2 conjugate described herein, the IL-2 conjugate has the amino acid sequence of SEQ ID NO: 47, or a pharmaceutically acceptable salt, solvate, or hydrate thereof. In some embodiments of an IL-2 conjugate described herein, the IL-2 conjugate has the amino acid sequence of SEQ ID NO: 48, or a pharmaceutically acceptable salt, solvate, or hydrate thereof. In some embodiments of an IL-2 conjugate described herein, the IL-2 conjugate has the amino acid sequence of SEQ ID NO: 49, or a pharmaceutically acceptable salt, solvate, or hydrate thereof. In some embodiments of an IL-2 conjugate described herein, the [AzK_L1_PEG5kD] has the structure of Formula (V)

Formula (V)

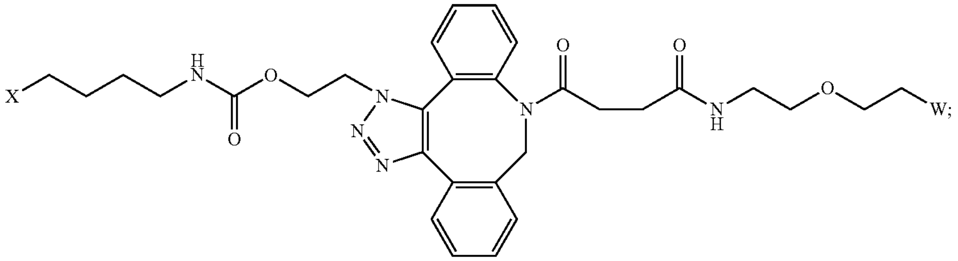

or a pharmaceutically acceptable salt, solvate, or hydrate thereof. In some embodiments of an IL-2 conjugate described herein, the IL-2 conjugate has the amino acid sequence of SEQ ID NO: 46, or a pharmaceutically acceptable salt, solvate, or hydrate thereof. In some embodiments of an IL-2 conjugate described herein, the IL-2 conjugate has the amino acid sequence of SEQ ID NO: 47, or a pharmaceutically acceptable salt, solvate, or hydrate thereof. In some embodiments of an IL-2 conjugate described herein, the IL-2 conjugate has the amino acid sequence of SEQ ID NO: 48, or a pharmaceutically acceptable salt, solvate, or hydrate thereof. In some embodiments of an IL-2 conjugate described herein, the IL-2 conjugate has the amino acid sequence of SEQ ID NO: 49, or a pharmaceutically acceptable salt, solvate, or hydrate thereof.

Described herein are IL-2 conjugates comprising the amino acid sequence of any one of SEQ ID NOS: 50-54, wherein [AzK_L1_PEG30kD] has the structure of Formula (IV) or Formula (V), or is a mixture of the structures of Formula (IV) and Formula (V):

Formula (IV)

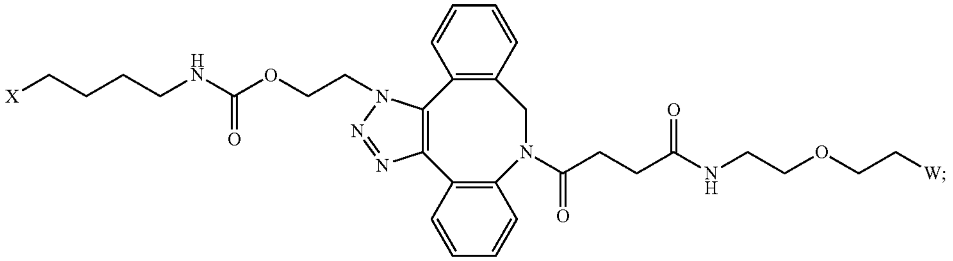

Formula (V)

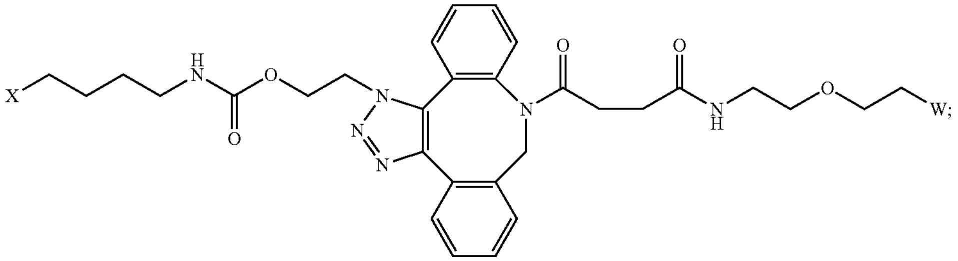

wherein:

W is a PEG group having an average molecular weight of 30 kDa; and

X has the structure:

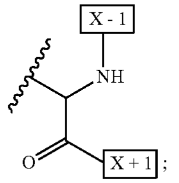

or a pharmaceutically acceptable salt, solvate, or hydrate thereof. In some embodiments of an IL-2 conjugate described herein, the IL-2 conjugate has the amino acid sequence of SEQ ID NO: 50, or a pharmaceutically acceptable salt, solvate, or hydrate thereof. In some embodiments of an IL-2 conjugate described herein, the IL-2 conjugate has the amino acid sequence of SEQ ID NO: 51, or a pharmaceutically acceptable salt, solvate, or hydrate thereof. In some embodiments of an IL-2 conjugate described herein, the IL-2 conjugate has the amino acid sequence of SEQ ID NO: 52, or a pharmaceutically acceptable salt, solvate, or hydrate thereof. In some embodiments of an IL-2 conjugate described herein, the IL-2 conjugate has the amino acid sequence of SEQ ID NO: 53, or a pharmaceutically acceptable salt, solvate, or hydrate thereof. In some embodiments of an IL-2 conjugate described herein, the IL-2 conjugate has the amino acid sequence of SEQ ID NO: 54, or a pharmaceutically acceptable salt, solvate, or hydrate thereof. In some embodiments of an IL-2 conjugate described herein, the [AzK_L1_PEG30kD] has the structure of Formula (IV):

Formula (IV)

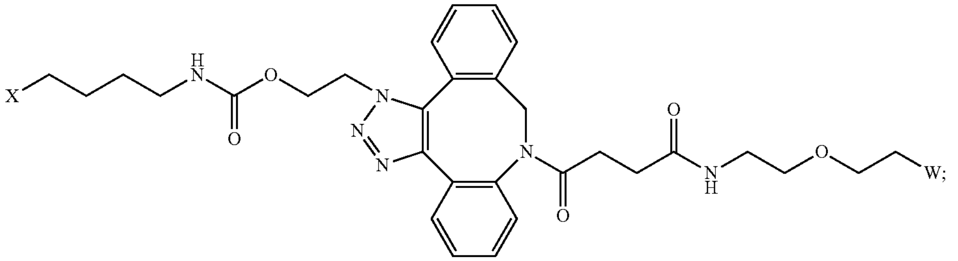

or a pharmaceutically acceptable salt, solvate, or hydrate thereof. In some embodiments of an IL-2 conjugate described herein, the IL-2 conjugate has the amino acid sequence of SEQ ID NO: 51, or a pharmaceutically acceptable salt, solvate, or hydrate thereof. In some embodiments of an IL-2 conjugate described herein, the IL-2 conjugate has the amino acid sequence of SEQ ID NO: 52, or a pharmaceutically acceptable salt, solvate, or hydrate thereof. In some embodiments of an IL-2 conjugate described herein, the IL-2 conjugate has the amino acid sequence of SEQ ID NO: 53, or a pharmaceutically acceptable salt, solvate, or hydrate thereof. In some embodiments of an IL-2 conjugate described herein, the IL-2 conjugate has the amino acid sequence of SEQ ID NO: 54, or a pharmaceutically acceptable salt, solvate, or hydrate thereof. In some embodiments of an IL-2 conjugate described herein, the [AzK_L1_PEG30kD] has the structure of Formula (V)

Formula (V)

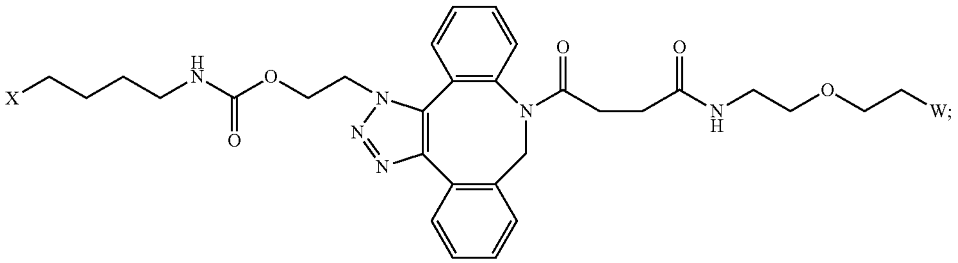

or a pharmaceutically acceptable salt, solvate, or hydrate thereof. In some embodiments of an IL-2 conjugate described herein, the IL-2 conjugate has the amino acid sequence of SEQ ID NO: 51, or a pharmaceutically acceptable salt, solvate, or hydrate thereof. In some embodiments of an IL-2 conjugate described herein, the IL-2 conjugate has the amino acid sequence of SEQ ID NO: 52, or a pharmaceutically acceptable salt, solvate, or hydrate thereof. In some embodiments of an IL-2 conjugate described herein, the IL-2 conjugate has the amino acid sequence of SEQ ID NO: 53, or a pharmaceutically acceptable salt, solvate, or hydrate thereof. In some embodiments of an IL-2 conjugate described herein, the IL-2 conjugate has the amino acid sequence of SEQ ID NO: 54, or a pharmaceutically acceptable salt, solvate, or hydrate thereof.

Described herein are IL-2 conjugates comprising the amino acid sequence of any one of SEQ ID NOS: 40-44, wherein [Azk_L1_PEG] is a mixture of the structures of Formula (IV) and Formula (V):

Formula (IV)

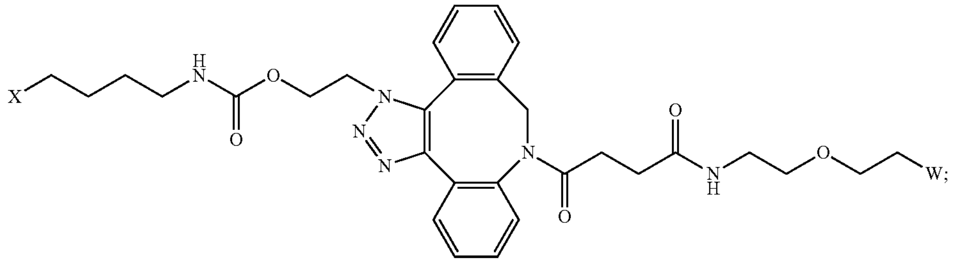

Formula (V)

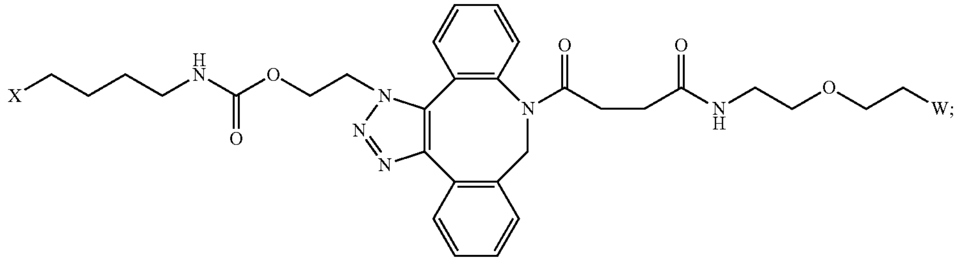

wherein:

W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and X has the structure:

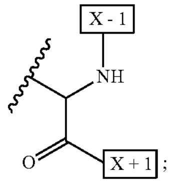

or a pharmaceutically acceptable salt, solvate, or hydrate thereof. In some embodiments of an IL-2 conjugate described herein, the ratio of the amount of the structure of Formula (IV) to the amount of the structure of Formula (V) comprising the total amount of [AzK_L1_PEG] in the IL-2 conjugate is about 1:1. In some embodiments of an IL-2 conjugate described herein, the ratio of the amount of the structure of Formula (IV) to the amount of the structure of Formula (V) comprising the total amount of [AzK_L1_PEG] in the IL-2 conjugate is greater than 1:1. In some embodiments of an IL-2 conjugate described herein, the ratio of the amount of the structure of Formula (IV) to the amount of the structure of Formula (V) comprising the total amount of [AzK_L1_PEG] in the IL-2 conjugate is less than 1:1. In some embodiments of an IL-2 conjugate described herein, W is a linear or branched PEG group, or a pharmaceutically acceptable salt, solvate, or hydrate thereof. In some embodiments of an IL-2 conjugate described herein, W is a linear PEG group, or a pharmaceutically acceptable salt, solvate, or hydrate thereof. In some embodiments of an IL-2 conjugate described herein, W is a branched PEG group, or a pharmaceutically acceptable salt, solvate, or hydrate thereof. In some embodiments of an IL-2 conjugate described herein, W is a methoxy PEG group, or a pharmaceutically acceptable salt, solvate, or hydrate thereof. In some embodiments of an IL-2 conjugate described herein, the methoxy PEG group is linear or branched, or a pharmaceutically acceptable salt, solvate, or hydrate thereof. In some embodiments of an IL-2 conjugate described herein, the methoxy PEG group is linear, or a pharmaceutically acceptable salt, solvate, or hydrate thereof. In some embodiments of an IL-2 conjugate described herein, the methoxy PEG group is branched, or a pharmaceutically acceptable salt, solvate, or hydrate thereof.

Described herein are IL-2 conjugates comprising the amino acid sequence of any one of SEQ ID NOS: 45 to 49, wherein [AzK_L1_PEG5kD] is a mixture of the structures of Formula (IV) and Formula (V):

Formula (IV)

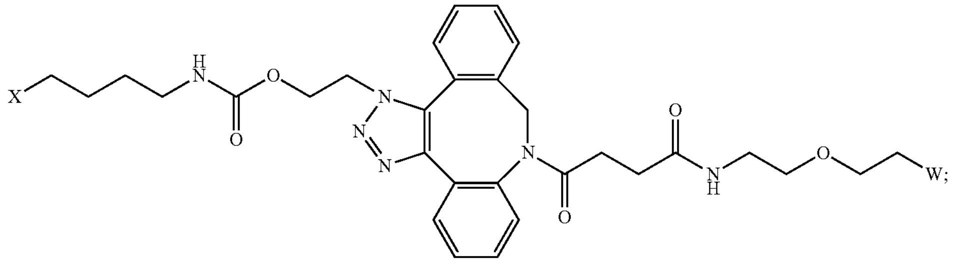

Formula (V)

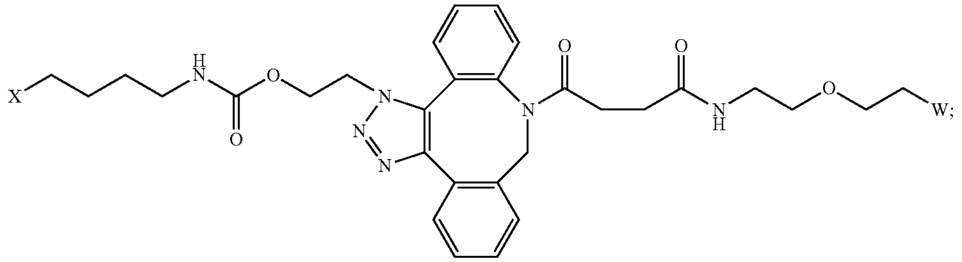

wherein:

W is a PEG group having an average molecular weight of 5 kDa; and

X has the structure:

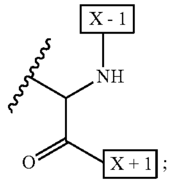

or a pharmaceutically acceptable salt, solvate, or hydrate thereof. In some embodiments of an IL-2 conjugate described herein, the ratio of the amount of the structure of Formula (IV) to the amount of the structure of Formula (V) comprising the total amount of [AzK_L1_PEG5kD] in the IL-2 conjugate is about 1:1. In some embodiments of an IL-2 conjugate described herein, the ratio of the amount of the structure of Formula (IV) to the amount of the structure of Formula (V) comprising the total amount of [AzK_L1_PEG5kD] in the IL-2 conjugate is greater than 1:1. In some embodiments of an IL-2 conjugate described herein, the ratio of the amount of the structure of Formula (IV) to the amount of the structure of Formula (V) comprising the total amount of [AzK_L1_PEG5kD] in the IL-2 conjugate is less than 1:1.

Described herein are IL-2 conjugates comprising the amino acid sequence of any one of SEQ ID NOS: 50-54, wherein [AzK_L1_PEG30kD] is a mixture of the structures of Formula (IV) and Formula (V):

Formula (IV)

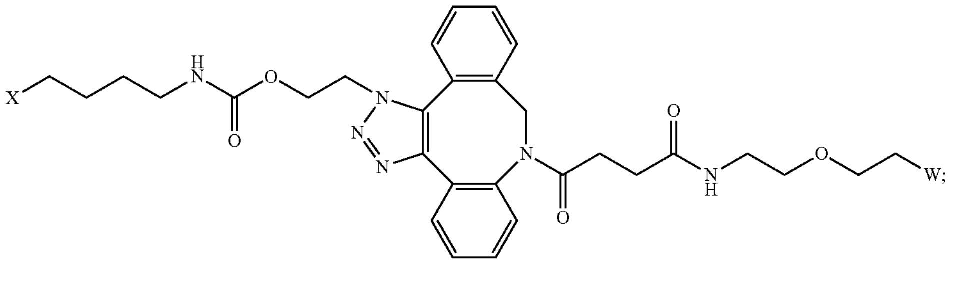

Formula (V)

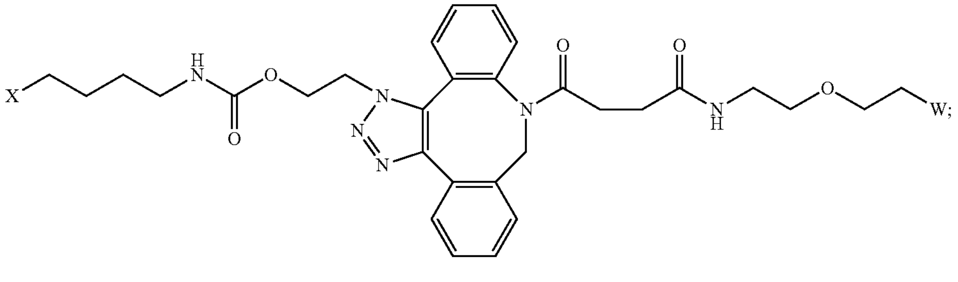

wherein:

W is a PEG group having an average molecular weight of 30 kDa; and

X has the structure:

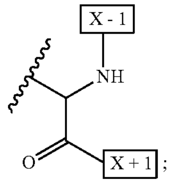

or a pharmaceutically acceptable salt, solvate, or hydrate thereof. In some embodiments of an IL-2 conjugate described herein, the ratio of the amount of the structure of Formula (IV) to the amount of the structure of Formula (V) comprising the total amount of [AzK_L1_PEG30kD] in the IL-2 conjugate is about 1:1. In some embodiments of an IL-2 conjugate described herein, the ratio of the amount of the structure of Formula (IV) to the amount of the structure of Formula (V) comprising the total amount of [AzK_L1_PEG30kD] in the IL-2 conjugate is greater than 1:1. In some embodiments of an IL-2 conjugate described herein, the ratio of the amount of the structure of Formula (IV) to the amount of the structure of Formula (V) comprising the total amount of [AzK_L1_PEG30kD] in the IL-2 conjugate is less than 1:1.

Described herein are IL-2 conjugates comprising the amino acid sequence of SEQ ID NO: 3 in which at least one amino acid residue in the IL-2 conjugate is replaced by the structure of Formula (VI) or (VII), or a mixture of (VI) and (VII):

Formula (VI)

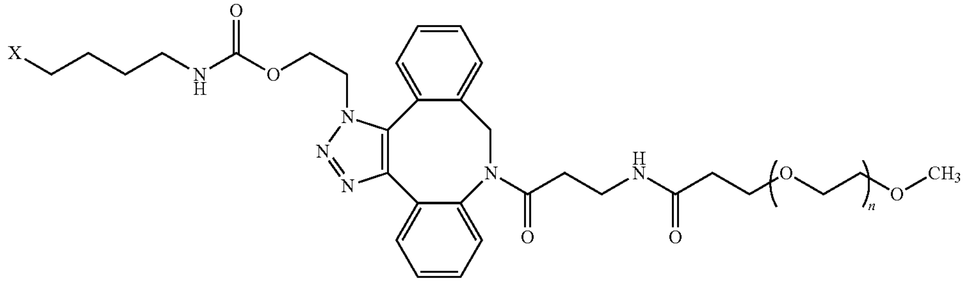

Formula (VII)

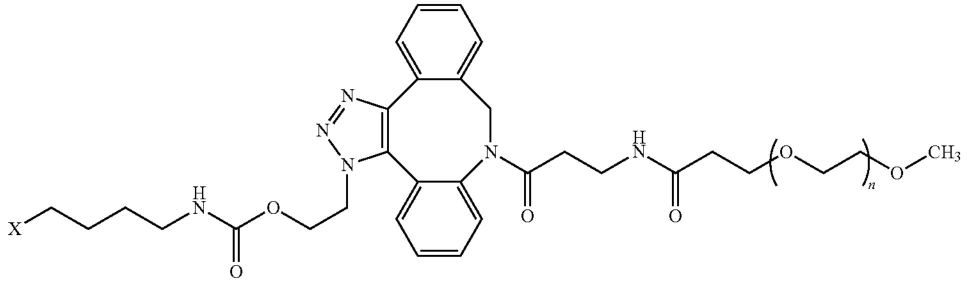

wherein:

n is an integer in the range from about 2 to about 5000; and

X has the structure:

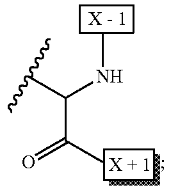

or a pharmaceutically acceptable salt, solvate, or hydrate thereof. In some embodiments of an IL-2 conjugate described herein, n in the compounds of Formula (VI) and (VII) is in the range from about 5 to about 4600, or from about 10 to about 4000, or from about 20 to about 3000, or from about 100 to about 3000, or from about 100 to about 2900, or from about 150 to about 2900, or from about 125 to about 2900, or from about 100 to about 2500, or from about 100 to about 2000, or from about 100 to about 1900, or from about 100 to about 1850, or from about 100 to about 1750, or from about 100 to about 1650, or from about 100 to about 1500, or from about 100 to about 1400, or from about 100 to about 1300, or from about 100 to about 1250, or from about 100 to about 1150, or from about 100 to about 1100, or from about 100 to about 1000, or from about 100 to about 900, or from about 100 to about 750, or from about 100 to about 700, or from about 100 to about 600, or from about 100 to about 575, or from about 100 to about 500, or from about 100 to about 450, or from about 100 to about to about 350, or from about 100 to about 275, or from about 100 to about 230, or from about 150 to about 475, or from about 150 to about 340, or from about 113 to about 340, or from about 450 to about 800, or from about 454 to about 796, or from about 454 to about 682, or from about 340 to about 795, or from about 341 to about 682, or from about 568 to about 909, or from about 227 to about 1500, or from about 225 to about 2280, or from about 460 to about 2160, or from about 460 to about 2050, or from about 341 to about 1820, or from about 341 to about 1710, or from about 341 to about 1250, or from about 225 to about 1250, or from about 341 to about 1250, or from about 341 to about 1136, or from about 341 to about 1023, or from about 341 to about 910, or from about 341 to about 796, or from about 341 to about 682, or from about 341 to about 568, or from about 114 to about 1000, or from about 114 to about 950, or from about 114 to about 910, or from about 114 to about 800, or from about 114 to about 690, or from about 114 to about 575. In some embodiments of an IL-2 conjugate described herein, n in the compounds of formula (VI) and (VII) is an integer selected from 2, 5, 10, 11, 22, 23, 113, 114, 227, 228, 340, 341, 454, 455, 568, 569, 680, 681, 682, 794, 795, 796, 908, 909, 910, 1021, 1022, 1023, 1135, 1136, 1137, 1249, 1250, 1251, 1362, 1363, 1364, 1476, 1477, 1478, 1589, 1590, 1591, 1703, 1704, 1705, 1817, 1818, 1819, 1930, 1931, 1932, 2044, 2045, 2046, 2158, 2159, 2160, 2271, 2272, 2273, 2839, 2840, 2841, 2953, 2954, 2955, 3408, 3409, 3410, 3976, 3977, 3978, 4544, 4545, and 4546. In some embodiments of an IL-2 conjugate described herein, the position of the structure of Formula (VI), Formula (VII), or a mixture of Formula (VI) and (VII) in the amino acid sequence of the IL-2 conjugate is selected from K34, F41, F43, K42, E61, P64, R37, T40, E67, Y44, V68, and L71, wherein the position of the structure of Formula (I) in the amino acid sequence of the IL-2 conjugate is in reference to the positions in SEQ ID NO: 3. In some embodiments of an IL-2 conjugate described herein, the position of the structure of Formula (VI), Formula (VII), or a mixture of Formula (VI) and (VII) in the amino acid sequence of the IL-2 conjugate of SEQ ID NO: 3 is selected from K34, F41, F43, K42, E61, P64, R37, T40, E67, Y44, V68, and L71. In some embodiments of an IL-2 conjugate described herein, the position of the structure of Formula (VI), Formula (VII), or a mixture of Formula (VI) and (VII) in the amino acid sequence of the IL-2 conjugate of SEQ ID NO: 3 is at position K34. In some embodiments of an IL-2 conjugate described herein, the position of the structure of Formula (VI), Formula (VII), or a mixture of Formula (VI) and (VII) in the amino acid sequence of the IL-2 conjugate of SEQ ID NO: 3 is at position F41. In some embodiments of an IL-2 conjugate described herein, the position of the structure of Formula (VI), Formula (VII), or a mixture of Formula (VI) and (VII) in the amino acid sequence of the IL-2 conjugate of SEQ ID NO: 3 is at position F43. In some embodiments of an IL-2 conjugate described herein, the position of the structure of Formula (VI), Formula (VII), or a mixture of Formula (VI) and (VII) in the amino acid sequence of the IL-2 conjugate of SEQ ID NO: 3 is at position K42. In some embodiments of an IL-2 conjugate described herein, the position of the structure of Formula (VI), Formula (VII), or a mixture of Formula (VI) and (VII) in the amino acid sequence of the IL-2 conjugate of SEQ ID NO: 3 is at position E61. In some embodiments of an IL-2 conjugate described herein, the position of the structure of Formula (VI), Formula (VII), or a mixture of Formula (VI) and (VII) in the amino acid sequence of the IL-2 conjugate of SEQ ID NO: 3 is at position P64. In some embodiments of an IL-2 conjugate described herein, the position of the structure of Formula (VI), Formula (VII), or a mixture of Formula (VI) and (VII) in the amino acid sequence of the IL-2 conjugate of SEQ ID NO: 3 is at position R37. In some embodiments of an IL-2 conjugate described herein, the position of the structure of Formula (VI), Formula (VII), or a mixture of Formula (VI) and (VII) in the amino acid sequence of the IL-2 conjugate of SEQ ID NO: 3 is at position T40. In some embodiments of an IL-2 conjugate described herein, the position of the structure of Formula (VI), Formula (VII), or a mixture of Formula (VI) and (VII) in the amino acid sequence of the IL-2 conjugate of SEQ ID NO: 3 is at position E67. In some embodiments of an IL-2 conjugate described herein, the position of the structure of Formula (VI), Formula (VII), or a mixture of Formula (VI) and (VII) in the amino acid sequence of the IL-2 conjugate of SEQ ID NO: 3 is at position Y44. In some embodiments of an IL-2 conjugate described herein, the position of the structure of Formula (VI), Formula (VII), or a mixture of Formula (VI) and (VII) in the amino acid sequence of the IL-2 conjugate of SEQ ID NO: 3 is at position V68. In some embodiments of an IL-2 conjugate described herein, the position of the structure of Formula (VI), Formula (VII), or a mixture of Formula (VI) and (VII) in the amino acid sequence of the IL-2 conjugate of SEQ ID NO: 3 is at position L71. In some embodiments of an IL-2 conjugate described herein, the ratio of the amount of the structure of Formula (VI) to the amount of the structure of Formula (VII) comprising the total amount of the IL-2 conjugate is about 1:1. In some embodiments of an IL-2 conjugate described herein, the ratio of the amount of the structure of Formula (VI) to the amount of the structure of Formula (VII) comprising the total amount of the IL-2 conjugate is greater than 1:1. In some embodiments of an IL-2 conjugate described herein, the ratio of the amount of the structure of Formula (VI) to the amount of the structure of Formula (VII) comprising the total amount of the IL-2 conjugate is less than 1:1.

In some embodiments described herein are IL-2 conjugates comprising the amino acid sequence of SEQ ID NO: 3 in which at least one amino acid residue in the IL-2 conjugate is replaced by the structure of Formula (VI) or (VII), or a mixture of (VI) and (VII), wherein the amino acid residue in in SEQ ID NO: 3 that is replaced is selected from K34, F41, F43, K42, E61, P64, R37, T40, E67, Y44, V68, and L71, and wherein n is an integer from 100 to about 1150, or from about 100 to about 1100, or from about 100 to about 1000, or from about 100 to about 900, or from about 100 to about 750, or from about 100 to about 700, or from about 100 to about 600, or from about 100 to about 575, or from about 100 to about 500, or from about 100 to about 450, or from about 100 to about to about 350, or from about 100 to about 275, or from about 100 to about 230, or from about 150 to about 475, or from about 150 to about 340, or from about 113 to about 340, or from about 450 to about 800, or from about 454 to about 796, or from about 454 to about 682, or from about 340 to about 795, or from about 341 to about 682, or from about 568 to about 909, or from about 227 to about 1500, or from about 225 to about 2280, or from about 460 to about 2160, or from about 460 to about 2050, or from about 341 to about 1820, or from about 341 to about 1710, or from about 341 to about 1250, or from about 225 to about 1250, or from about 341 to about 1250, or from about 341 to about 1136, or from about 341 to about 1023, or from about 341 to about 910, or from about 341 to about 796, or from about 341 to about 682, or from about 341 to about 568, or from about 114 to about 1000, or from about 114 to about 950, or from about 114 to about 910, or from about 114 to about 800, or from about 114 to about 690, or from about 114 to about 575. In some embodiments of an IL-2 conjugate described herein, n in the compounds of formula (VI) and (VII) is an integer selected from 2, 5, 10, 11, 22, 23, 113, 114, 227, 228, 340, 341, 454, 455, 568, 569, 680, 681, 682, 794, 795, 796, 908, 909, 910, 1021, 1022, 1023, 1135, 1136, 1137, 1249, 1250, 1251, 1362, 1363, 1364, 1476, 1477, 1478, 1589, 1590, 1591, 1703, 1704, 1705, 1817, 1818, 1819, 1930, 1931, 1932, 2044, 2045, 2046, 2158, 2159, 2160, 2271, 2272, 2273, 2839, 2840, 2841, 2953, 2954, 2955, 3408, 3409, 3410, 3976, 3977, 3978, 4544, 4545, and 4546.

In some embodiments described herein are IL-2 conjugates comprising the amino acid sequence of SEQ ID NO: 3 in which at least one amino acid residue in the IL-2 conjugate is replaced by the structure of Formula (VI) or (VII), or a mixture of (VI) and (VII), wherein the amino acid residue in in SEQ ID NO: 3 that is replaced is selected from F41, F43, K42, E61, and P64, and wherein n is an integer from about 450 to about 800, or from about 454 to about 796, or from about 454 to about 682, or from about 568 to about 909. In some embodiments of an IL-2 conjugate described herein, n in the compounds of formula (VI) and (VII) is an integer selected from 454, 455, 568, 569, 680, 681, 682, 794, 795, 796, 908, 909, 910, 1021, 1022, 1023, 1135, 1136, 1137, and 1249.

In some embodiments described herein are IL-2 conjugates comprising the amino acid sequence of SEQ ID NO: 3 in which at least one amino acid residue in the IL-2 conjugate is replaced by the structure of Formula (VI) or (VII), or a mixture of (VI) and (VII), wherein the amino acid residue in SEQ ID NO: 3 that is replaced is selected from E61 and P64, and wherein n is an integer from about 450 to about 800, or from about 454 to about 796, or from about 454 to about 682, or from about 568 to about 909. In some embodiments of an IL-2 conjugate described herein, n in the compounds of formula (VI) and (VII) is an integer selected from 454, 455, 568, 569, 680, 681, 682, 794, 795, 796, 908, 909, and 910.

In some embodiments described herein are IL-2 conjugates comprising the amino acid sequence of SEQ ID NO: 3 in which at least one amino acid residue in the IL-2 conjugate is replaced by the structure of Formula (VI) or (VII), or a mixture of (VI) and (VII), wherein the amino acid residue in SEQ ID NO: 3 that is replaced is E61, and wherein n is an integer from about 450 to about 800, or from about 454 to about 796, or from about 454 to about 682, or from about 568 to about 909. In some embodiments of an IL-2 conjugate described herein, n in the compounds of formula (VI) and (VII) is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681.

In some embodiments described herein are IL-2 conjugates comprising the amino acid sequence of SEQ ID NO: 3 in which at least one amino acid residue in the IL-2 conjugate is replaced by the structure of Formula (VI) or (VII), or a mixture of (VI) and (VII), wherein the amino acid residue in in SEQ ID NO: 3 that is replaced is P64, and wherein n is an integer from about 450 to about 800, or from about 454 to about 796, or from about 454 to about 682, or from about 568 to about 909. In some embodiments of an IL-2 conjugate described herein, n in the compounds of formula (VI) and (VII) is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681.

Described herein are IL-2 conjugates comprising the amino acid sequence of SEQ ID NO: 3 in which at least one amino acid residue in the IL-2 conjugate is replaced by the structure of Formula (VI) or (VII), or a mixture of (VI) and (VII), wherein n is an integer such that the molecular weight of the PEG moiety is in the range from about 1,000 Daltons about 200,000 Daltons, or from about 2,000 Daltons to about 150,000 Daltons, or from about 3,000 Daltons to about 125,000 Daltons, or from about 4,000 Daltons to about 100,000 Daltons, or from about 5,000 Daltons to about 100,000 Daltons, or from about 6,000 Daltons to about 90,000 Daltons, or from about 7,000 Daltons to about 80,000 Daltons, or from about 8,000 Daltons to about 70,000 Daltons, or from about 5,000 Daltons to about 70,000 Daltons, or from about 5,000 Daltons to about 65,000 Daltons, or from about 5,000 Daltons to about 60,000 Daltons, or from about 5,000 Daltons to about 50,000 Daltons, or from about 6,000 Daltons to about 50,000 Daltons, or from about 7,000 Daltons to about 50,000 Daltons, or from about 7,000 Daltons to about 45,000 Daltons, or from about 7,000 Daltons to about 40,000 Daltons, or from about 8,000 Daltons to about 40,000 Daltons, or from about 8,500 Daltons to about 40,000 Daltons, or from about 8,500 Daltons to about 35,000 Daltons, or from about 9,000 Daltons to about 50,000 Daltons, or from about 9,000 Daltons to about 45,000 Daltons, or from about 9,000 Daltons to about 40,000 Daltons, or from about 9,000 Daltons to about 35,000 Daltons, or from about 9,000 Daltons to about 30,000 Daltons, or from about 9,500 Daltons to about 35,000 Daltons, or from about 9,500 Daltons to about 30,000 Daltons, or from about 10,000 Daltons to about 50,000 Daltons, or from about 10,000 Daltons to about 45,000 Daltons, or from about 10,000 Daltons to about 40,000 Daltons, or from about 10,000 Daltons to about 35,000 Daltons, or from about 10,000 Daltons to about 30,000 Daltons, or from about 15,000 Daltons to about 50,000 Daltons, or from about 15,000 Daltons to about 45,000 Daltons, or from about 15,000 Daltons to about 40,000 Daltons, or from about 15,000 Daltons to about 35,000 Daltons, or from about 15,000 Daltons to about 30,000 Daltons, or from about 20,000 Daltons to about 50,000 Daltons, or from about 20,000 Daltons to about 45,000 Daltons, or from about 20,000 Daltons to about 40,000 Daltons, or from about 20,000 Daltons to about 35,000 Daltons, or from about 20,000 Daltons to about 30,000 Daltons. Described herein are IL-2 conjugates comprising the amino acid sequence of SEQ ID NO: 3 in which at least one amino acid residue in the IL-2 conjugate is replaced by the structure of Formula (VI) or (VII), or a mixture of (VI) and (VII), wherein n is an integer such that the molecular weight of the PEG moiety is about 5,000 Daltons, about 7,500 Daltons, about 10,000 Daltons, about 15,000 Daltons, about 20,000 Daltons, about 25,000 Daltons, about 30,000 Daltons, about 35,000 Daltons, about 40,000 Daltons, about 45,000 Daltons, about 50,000 Daltons, about 60,000 Daltons, about 70,000 Daltons, about 80,000 Daltons, about 90,000 Daltons, about 100,000 Daltons, about 125,000 Daltons, about 150,000 Daltons, about 175,000 Daltons or about 200,000 Daltons. Described herein are IL-2 conjugates comprising the amino acid sequence of SEQ ID NO: 3 in which at least one amino acid residue in the IL-2 conjugate is replaced by the structure of Formula (VI) or (VII), or a mixture of (VI) and (VII), wherein n is an integer such that the molecular weight of the PEG moiety is about 5,000 Daltons, about 7,500 Daltons, about 10,000 Daltons, about 15,000 Daltons, about 20,000 Daltons, about 25,000 Daltons, about 30,000 Daltons, about 35,000 Daltons, about 40,000 Daltons, about 45,000 Daltons, or about 50,000 Daltons.

Described herein are IL-2 conjugates comprising the amino acid sequence of SEQ ID NO: 3 in which at least one amino acid residue in the IL-2 conjugate is replaced by the structure of Formula (VIII) or (IX), or a mixture of (VIII) and (IX):

Formula (VIII)

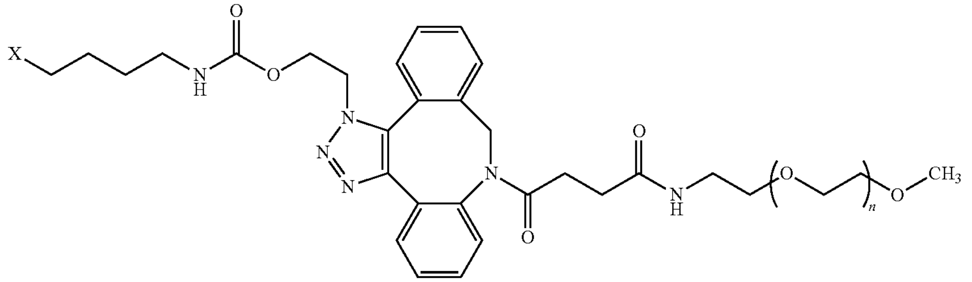

Formula (IX)

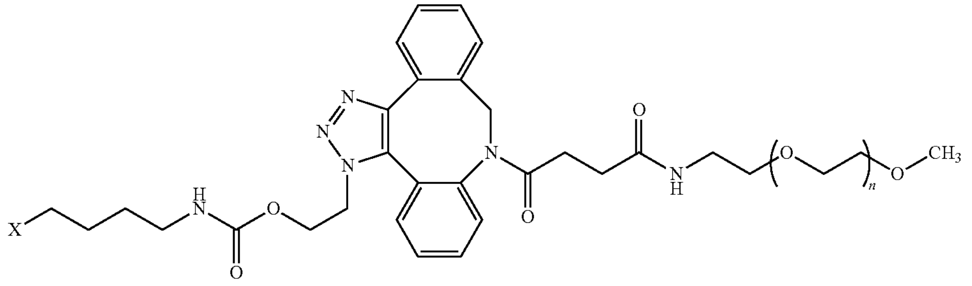

wherein:

n is an integer in the range from about 2 to about 5000; and

X has the structure:

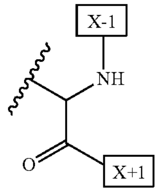
, or a pharmaceutically acceptable salt, solvate, or hydrate thereof. In some embodiments of an IL-2 conjugate described herein, n in the compounds of formula (VIII) and (IX) is in the range from about 5 to about 4600, or from about 10 to about 4000, or from about 20 to about 3000, or from about 100 to about 3000, or from about 100 to about 2900, or from about 150 to about 2900, or from about 125 to about 2900, or from about 100 to about 2500, or from about 100 to about 2000, or from about 100 to about 1900, or from about 100 to about 1850, or from about 100 to about 1750, or from about 100 to about 1650, or from about 100 to about 1500, or from about 100 to about 1400, or from about 100 to about 1300, or from about 100 to about 1250, or from about 100 to about 1150, or from about 100 to about 1100, or from about 100 to about 1000, or from about 100 to about 900, or from about 100 to about 750, or from about 100 to about 700, or from about 100 to about 600, or from about 100 to about 575, or from about 100 to about 500, or from about 100 to about 450, or from about 100 to about to about 350, or from about 100 to about 275, or from about 100 to about 230, or from about 150 to about 475, or from about 150 to about 340, or from about 113 to about 340, or from about 450 to about 800, or from about 454 to about 796, or from about 454 to about 682, or from about 340 to about 795, or from about 341 to about 682, or from about 568 to about 909, or from about 227 to about 1500, or from about 225 to about 2280, or from about 460 to about 2160, or from about 460 to about 2050, or from about 341 to about 1820, or from about 341 to about 1710, or from about 341 to about 1250, or from about 225 to about 1250, or from about 341 to about 1250, or from about 341 to about 1136, or from about 341 to about 1023, or from about 341 to about 910, or from about 341 to about 796, or from about 341 to about 682, or from about 341 to about 568, or from about 114 to about 1000, or from about 114 to about 950, or from about 114 to about 910, or from about 114 to about 800, or from about 114 to about 690, or from about 114 to about 575. In some embodiments of an IL-2 conjugate described herein, n in the compounds of formula (VIII) and (IX) is an integer selected from 2, 5, 10, 11, 22, 23, 113, 114, 227, 228, 340, 341, 454, 455, 568, 569, 680, 681, 682, 794, 795, 796, 908, 909, 910, 1021, 1022, 1023, 1135, 1136, 1137, 1249, 1250, 1251, 1362, 1363, 1364, 1476, 1477, 1478, 1589, 1590, 1591, 1703, 1704, 1705, 1817, 1818, 1819, 1930, 1931, 1932, 2044, 2045, 2046, 2158, 2159, 2160, 2271, 2272, 2273, 2839, 2840, 2841, 2953, 2954, 2955, 3408, 3409, 3410, 3976, 3977, 3978, 4544, 4545, and 4546. In some embodiments of an IL-2 conjugate described herein, the position of the structure of Formula (VIII), Formula (IX), or a mixture of Formula (VIII) and (IX) in the amino acid sequence of the IL-2 conjugate is selected from K34, F41, F43, K42, E61, P64, R37, T40, E67, Y44, V68, and L71, wherein the position of the structure of Formula (I) in the amino acid sequence of the IL-2 conjugate is in reference to the positions in SEQ ID NO: 3. In some embodiments of an IL-2 conjugate described herein, the position of the structure of Formula (VIII), Formula (IX), or a mixture of Formula (VIII) and (IX) in the amino acid sequence of the IL-2 conjugate of SEQ ID NO: 3 is selected from K34, F41, F43, K42, E61, P64, R37, T40, E67, Y44, V68, and L71. In some embodiments of an IL-2 conjugate described herein, the position of the structure of Formula (VIII), Formula (IX), or a mixture of Formula (VIII) and (IX) in the amino acid sequence of the IL-2 conjugate of SEQ ID NO: 3 is at position K34. In some embodiments of an IL-2 conjugate described herein, the position of the structure of Formula (VIII), Formula (IX), or a mixture of Formula (VIII) and (IX) in the amino acid sequence of the IL-2 conjugate of SEQ ID NO: 3 is at position F41. In some embodiments of an IL-2 conjugate described herein, the position of the structure of Formula (VIII), Formula (IX), or a mixture of Formula (VIII) and (IX) in the amino acid sequence of the IL-2 conjugate of SEQ ID NO: 3 is at position F43. In some embodiments of an IL-2 conjugate described herein, the position of the structure of Formula (VIII), Formula (IX), or a mixture of Formula (VIII) and (IX) in the amino acid sequence of the IL-2 conjugate of SEQ ID NO: 3 is at position K42. In some embodiments of an IL-2 conjugate described herein, the position of the structure of Formula (VIII), Formula (IX), or a mixture of Formula (VIII) and (IX) in the amino acid sequence of the IL-2 conjugate of SEQ ID NO: 3 is at position E61. In some embodiments of an IL-2 conjugate described herein, the position of the structure of Formula (VIII), Formula (IX), or a mixture of Formula (VIII) and (IX) in the amino acid sequence of the IL-2 conjugate of SEQ ID NO: 3 is at position P64. In some embodiments of an IL-2 conjugate described herein, the position of the structure of Formula (VIII), Formula (IX), or a mixture of Formula (VIII) and (IX) in the amino acid sequence of the IL-2 conjugate of SEQ ID NO: 3 is at position R37. In some embodiments of an IL-2 conjugate described herein, the position of the structure of Formula (VIII), Formula (IX), or a mixture of Formula (VIII) and (IX) in the amino acid sequence of the IL-2 conjugate of SEQ ID NO: 3 is at position T40. In some embodiments of an IL-2 conjugate described herein, the position of the structure of Formula (VIII), Formula (IX), or a mixture of Formula (VIII) and (IX) in the amino acid sequence of the IL-2 conjugate of SEQ ID NO: 3 is at position E67. In some embodiments of an IL-2 conjugate described herein, the position of the structure of Formula (VIII), Formula (IX), or a mixture of Formula (VIII) and (IX) in the amino acid sequence of the IL-2 conjugate of SEQ ID NO: 3 is at position Y44. In some embodiments of an IL-2 conjugate described herein, the position of the structure of Formula (VIII), Formula (IX), or a mixture of Formula (VIII) and (IX) in the amino acid sequence of the IL-2 conjugate of SEQ ID NO: 3 is at position V68. In some embodiments of an IL-2 conjugate described herein, the position of the structure of Formula (VIII), Formula (IX), or a mixture of Formula (VIII) and (IX) in the amino acid sequence of the IL-2 conjugate of SEQ ID NO: 3 is at position L71. In some embodiments of an IL-2 conjugate described herein, the ratio of the amount of the structure of Formula (VIII) to the amount of the structure of Formula (IX) comprising the total amount of the IL-2 conjugate is about 1:1. In some embodiments of an IL-2 conjugate described herein, the ratio of the amount of the structure of Formula (VIII) to the amount of the structure of Formula (IX) comprising the total amount of the IL-2 conjugate is greater than 1:1. In some embodiments of an IL-2 conjugate described herein, the ratio of the amount of the structure of Formula (VIII) to the amount of the structure of Formula (IX) comprising the total amount of the IL-2 conjugate is less than 1:1.

In some embodiments described herein are IL-2 conjugates comprising the amino acid sequence of SEQ ID NO: 3 in which at least one amino acid residue in the IL-2 conjugate is replaced by the structure of Formula (VIII) or (IX), or a mixture of (VIII) and (IX), wherein the amino acid residue in in SEQ ID NO: 3 that is replaced is selected from K34, F41, F43, K42, E61, P64, R37, T40, E67, Y44, V68, and L71, and wherein n is an integer from 100 to about 1150, or from about 100 to about 1100, or from about 100 to about 1000, or from about 100 to about 900, or from about 100 to about 750, or from about 100 to about 700, or from about 100 to about 600, or from about 100 to about 575, or from about 100 to about 500, or from about 100 to about 450, or from about 100 to about to about 350, or from about 100 to about 275, or from about 100 to about 230, or from about 150 to about 475, or from about 150 to about 340, or from about 113 to about 340, or from about 450 to about 800, or from about 454 to about 796, or from about 454 to about 682, or from about 340 to about 795, or from about 341 to about 682, or from about 568 to about 909, or from about 227 to about 1500, or from about 225 to about 2280, or from about 460 to about 2160, or from about 460 to about 2050, or from about 341 to about 1820, or from about 341 to about 1710, or from about 341 to about 1250, or from about 225 to about 1250, or from about 341 to about 1250, or from about 341 to about 1136, or from about 341 to about 1023, or from about 341 to about 910, or from about 341 to about 796, or from about 341 to about 682, or from about 341 to about 568, or from about 114 to about 1000, or from about 114 to about 950, or from about 114 to about 910, or from about 114 to about 800, or from about 114 to about 690, or from about 114 to about 575. In some embodiments of an IL-2 conjugate described herein, n in the compounds of formula (VIII) and (IX) is an integer selected from 2, 5, 10, 11, 22, 23, 113, 114, 227, 228, 340, 341, 454, 455, 568, 569, 680, 681, 682, 794, 795, 796, 908, 909, 910, 1021, 1022, 1023, 1135, 1136, 1137, 1249, 1250, 1251, 1362, 1363, 1364, 1476, 1477, 1478, 1589, 1590, 1591, 1703, 1704, 1705, 1817, 1818, 1819, 1930, 1931, 1932, 2044, 2045, 2046, 2158, 2159, 2160, 2271, 2272, 2273, 2839, 2840, 2841, 2953, 2954, 2955, 3408, 3409, 3410, 3976, 3977, 3978, 4544, 4545, and 4546.

In some embodiments described herein are IL-2 conjugates comprising the amino acid sequence of SEQ ID NO: 3 in which at least one amino acid residue in the IL-2 conjugate is replaced by the structure of Formula (VIII) or (IX), or a mixture of (VIII) and (IX), wherein the amino acid residue in in SEQ ID NO: 3 that is replaced is selected from F41, F43, K42, E61, and P64, and wherein n is an integer from about 450 to about 800, or from about 454 to about 796, or from about 454 to about 682, or from about 568 to about 909. In some embodiments of an IL-2 conjugate described herein, n in the compounds of formula (VIII) and (IX) is an integer selected from 454, 455, 568, 569, 680, 681, 682, 794, 795, 796, 908, 909, 910, 1021, 1022, 1023, 1135, 1136, 1137, and 1249.

In some embodiments described herein are IL-2 conjugates comprising the amino acid sequence of SEQ ID NO: 3 in which at least one amino acid residue in the IL-2 conjugate is replaced by the structure of Formula (VIII) or (IX), or a mixture of (VIII) and (IX), wherein the amino acid residue in SEQ ID NO: 3 that is replaced is selected from E61 and P64, and wherein n is an integer from about 450 to about 800, or from about 454 to about 796, or from about 454 to about 682, or from about 568 to about 909. In some embodiments of an IL-2 conjugate described herein, n in the compounds of formula (VIII) and (IX) is an integer selected from 454, 455, 568, 569, 680, 681, 682, 794, 795, 796, 908, 909, and 910.

In some embodiments described herein are IL-2 conjugates comprising the amino acid sequence of SEQ ID NO: 3 in which at least one amino acid residue in the IL-2 conjugate is replaced by the structure of Formula (VIII) or (IX), or a mixture of (VIII) and (IX), wherein the amino acid residue in SEQ ID NO: 3 that is replaced is E61, and wherein n is an integer from about 450 to about 800, or from about 454 to about 796, or from about 454 to about 682, or from about 568 to about 909. In some embodiments of an IL-2 conjugate described herein, n in the compounds of formula (VIII) and (IX) is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681.

In some embodiments described herein are IL-2 conjugates comprising the amino acid sequence of SEQ ID NO: 3 in which at least one amino acid residue in the IL-2 conjugate is replaced by the structure of Formula (VIII) or (IX), or a mixture of (VIII) and (IX), wherein the amino acid residue in in SEQ ID NO: 3 that is replaced is P64, and wherein n is an integer from about 450 to about 800, or from about 454 to about 796, or from about 454 to about 682, or from about 568 to about 909. In some embodiments of an IL-2 conjugate described herein, n in the compounds of formula (VIII) and (IX) is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681.

Described herein are IL-2 conjugates comprising the amino acid sequence of SEQ ID NO: 3 in which at least one amino acid residue in the IL-2 conjugate is replaced by the structure of Formula (VIII) or (IX), or a mixture of (VIII) and (IX), wherein n is an integer such that the molecular weight of the PEG moiety is in the range from about 1,000 Daltons about 200,000 Daltons, or from about 2,000 Daltons to about 150,000 Daltons, or from about 3,000 Daltons to about 125,000 Daltons, or from about 4,000 Daltons to about 100,000 Daltons, or from about 5,000 Daltons to about 100,000 Daltons, or from about 6,000 Daltons to about 90,000 Daltons, or from about 7,000 Daltons to about 80,000 Daltons, or from about 8,000 Daltons to about 70,000 Daltons, or from about 5,000 Daltons to about 70,000 Daltons, or from about 5,000 Daltons to about 65,000 Daltons, or from about 5,000 Daltons to about 60,000 Daltons, or from about 5,000 Daltons to about 50,000 Daltons, or from about 6,000 Daltons to about 50,000 Daltons, or from about 7,000 Daltons to about 50,000 Daltons, or from about 7,000 Daltons to about 45,000 Daltons, or from about 7,000 Daltons to about 40,000 Daltons, or from about 8,000 Daltons to about 40,000 Daltons, or from about 8,500 Daltons to about 40,000 Daltons, or from about 8,500 Daltons to about 35,000 Daltons, or from about 9,000 Daltons to about 50,000 Daltons, or from about 9,000 Daltons to about 45,000 Daltons, or from about 9,000 Daltons to about 40,000 Daltons, or from about 9,000 Daltons to about 35,000 Daltons, or from about 9,000 Daltons to about 30,000 Daltons, or from about 9,500 Daltons to about 35,000 Daltons, or from about 9,500 Daltons to about 30,000 Daltons, or from about 10,000 Daltons to about 50,000 Daltons, or from about 10,000 Daltons to about 45,000 Daltons, or from about 10,000 Daltons to about 40,000 Daltons, or from about 10,000 Daltons to about 35,000 Daltons, or from about 10,000 Daltons to about 30,000 Daltons, or from about 15,000 Daltons to about 50,000 Daltons, or from about 15,000 Daltons to about 45,000 Daltons, or from about 15,000 Daltons to about 40,000 Daltons, or from about 15,000 Daltons to about 35,000 Daltons, or from about 15,000 Daltons to about 30,000 Daltons, or from about 20,000 Daltons to about 50,000 Daltons, or from about 20,000 Daltons to about 45,000 Daltons, or from about 20,000 Daltons to about 40,000 Daltons, or from about 20,000 Daltons to about 35,000 Daltons, or from about 20,000 Daltons to about 30,000 Daltons. Described herein are IL-2 conjugates comprising the amino acid sequence of SEQ ID NO: 3 in which at least one amino acid residue in the IL-2 conjugate is replaced by the structure of Formula (VIII) or (IX), or a mixture of (VIII) and (IX), wherein n is an integer such that the molecular weight of the PEG moiety is about 5,000 Daltons, about 7,500 Daltons, about 10,000 Daltons, about 15,000 Daltons, about 20,000 Daltons, about 25,000 Daltons, about 30,000 Daltons, about 35,000 Daltons, about 40,000 Daltons, about 45,000 Daltons, about 50,000 Daltons, about 60,000 Daltons, about 70,000 Daltons, about 80,000 Daltons, about 90,000 Daltons, about 100,000 Daltons, about 125,000 Daltons, about 150,000 Daltons, about 175,000 Daltons or about 200,000 Daltons. Described herein are IL-2 conjugates comprising the amino acid sequence of SEQ ID NO: 3 in which at least one amino acid residue in the IL-2 conjugate is replaced by the structure of Formula (VIII) or (IX), or a mixture of (VIII) and (IX), wherein n is an integer such that the molecular weight of the PEG moiety is about 5,000 Daltons, about 7,500 Daltons, about 10,000 Daltons, about 15,000 Daltons, about 20,000 Daltons, about 25,000 Daltons, about 30,000 Daltons, about 35,000 Daltons, about 40,000 Daltons, about 45,000 Daltons, or about 50,000 Daltons.

Described herein are IL-2 conjugates comprising the amino acid sequence of SEQ ID NO: 3 in which at least one amino acid residue in the IL-2 conjugate is replaced by the structure of Formula (X) or (XI), or a mixture of (X) and (XI):

Formula (X)

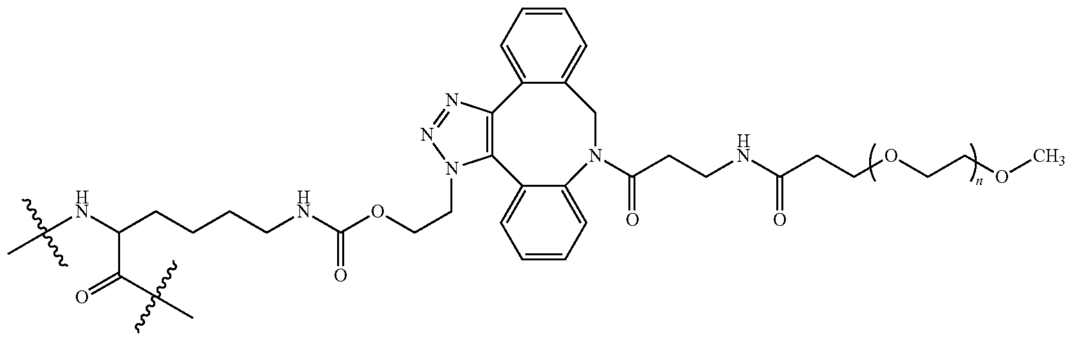

Formula (XI)

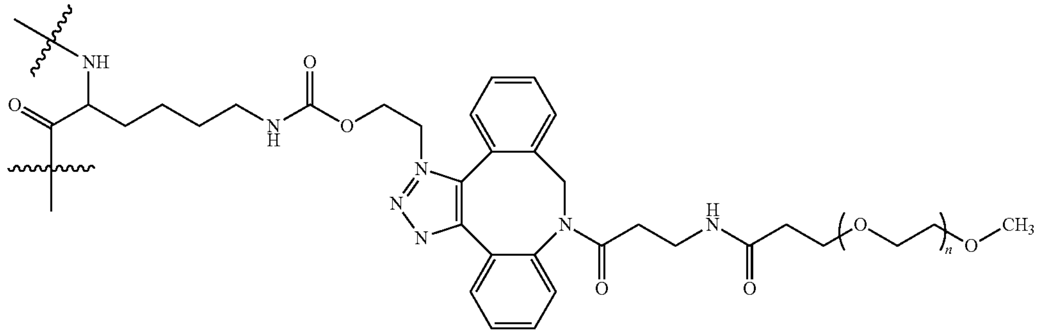

wherein:

n is an integer in the range from about 2 to about 5000; and the wavy lines indicate convalent bonds to amino acid residues within SEQ ID NO: 3 that are not replaced, or a pharmaceutically acceptable salt, solvate, or hydrate thereof.

In some embodiments, the stereochemistry of the chiral center within Formula (X) and Formula (XI) is racemic, is enriched in (R), is enriched in (S), is substantially (R), is substantially (S), is (R) or is (S). In some embodiments, the stereochemistry of the chiral center within Formula (X) and Formula (XI) is racemic. In some embodiments, the stereochemistry of the chiral center within Formula (X) and Formula (XI) is enriched in (R). In some embodiments, the stereochemistry of the chiral center within Formula (X) and Formula (XI) is enriched in (S). In some embodiments, the stereochemistry of the chiral center within Formula (X) and Formula (XI) is substantially (R). In some embodiments, the stereochemistry of the chiral center within Formula (X) and Formula (XI) is substantially (S). In some embodiments, the stereochemistry of the chiral center within Formula (X) and Formula (XI) is (R). In some embodiments, the stereochemistry of the chiral center within Formula (X) and Formula (XI) is (S).

In some embodiments of an IL-2 conjugate described herein, n in the compounds of Formula (X) and (XI) is in the range from about 5 to about 4600, or from about 10 to about 4000, or from about 20 to about 3000, or from about 100 to about 3000, or from about 100 to about 2900, or from about 150 to about 2900, or from about 125 to about 2900, or from about 100 to about 2500, or from about 100 to about 2000, or from about 100 to about 1900, or from about 100 to about 1850, or from about 100 to about 1750, or from about 100 to about 1650, or from about 100 to about 1500, or from about 100 to about 1400, or from about 100 to about 1300, or from about 100 to about 1250, or from about 100 to about 1150, or from about 100 to about 1100, or from about 100 to about 1000, or from about 100 to about 900, or from about 100 to about 750, or from about 100 to about 700, or from about 100 to about 600, or from about 100 to about 575, or from about 100 to about 500, or from about 100 to about 450, or from about 100 to about to about 350, or from about 100 to about 275, or from about 100 to about 230, or from about 150 to about 475, or from about 150 to about 340, or from about 113 to about 340, or from about 450 to about 800, or from about 454 to about 796, or from about 454 to about 682, or from about 340 to about 795, or from about 341 to about 682, or from about 568 to about 909, or from about 227 to about 1500, or from about 225 to about 2280, or from about 460 to about 2160, or from about 460 to about 2050, or from about 341 to about 1820, or from about 341 to about 1710, or from about 341 to about 1250, or from about 225 to about 1250, or from about 341 to about 1250, or from about 341 to about 1136, or from about 341 to about 1023, or from about 341 to about 910, or from about 341 to about 796, or from about 341 to about 682, or from about 341 to about 568, or from about 114 to about 1000, or from about 114 to about 950, or from about 114 to about 910, or from about 114 to about 800, or from about 114 to about 690, or from about 114 to about 575. In some embodiments of an IL-2 conjugate described herein, n in the compounds of Formula (X) and (XI) is an integer selected from 2, 5, 10, 11, 22, 23, 113, 114, 227, 228, 340, 341, 454, 455, 568, 569, 680, 681, 682, 794, 795, 796, 908, 909, 910, 1021, 1022, 1023, 1135, 1136, 1137, 1249, 1250, 1251, 1362, 1363, 1364, 1476, 1477, 1478, 1589, 1590, 1591, 1703, 1704, 1705, 1817, 1818, 1819, 1930, 1931, 1932, 2044, 2045, 2046, 2158, 2159, 2160, 2271, 2272, 2273, 2839, 2840, 2841, 2953, 2954, 2955, 3408, 3409, 3410, 3976, 3977, 3978, 4544, 4545, and 4546. In some embodiments of an IL-2 conjugate described herein, the position of the structure of Formula (X) and (XI) or a mixture of Formula (X) and (XI) in the amino acid sequence of the IL-2 conjugate is selected from K34, F41, F43, K42, E61, P64, R37, T40, E67, Y44, V68, and L71, wherein the position of the structure of Formula (I) in the amino acid sequence of the IL-2 conjugate is in reference to the positions in SEQ ID NO: 3. In some embodiments of an IL-2 conjugate described herein, the position of the structure of Formula (X) and (XI) or a mixture of Formula (X) and (XI) in the amino acid sequence of the IL-2 conjugate of SEQ ID NO: 3 is selected from K34, F41, F43, K42, E61, P64, R37, T40, E67, Y44, V68, and L71. In some embodiments of an IL-2 conjugate described herein, the position of the structure of Formula (X) and (XI) or a mixture of Formula (X) and (XI) in the amino acid sequence of the IL-2 conjugate of SEQ ID NO: 3 is at position K34. In some embodiments of an IL-2 conjugate described herein, the position of the structure of Formula (X) and (XI) or a mixture of Formula (X) and (XI) in the amino acid sequence of the IL-2 conjugate of SEQ ID NO: 3 is at position F41. In some embodiments of an IL-2 conjugate described herein, the position of the structure of Formula (X) and (XI) or a mixture of Formula (X) and (XI) in the amino acid sequence of the IL-2 conjugate of SEQ ID NO: 3 is at position F43. In some embodiments of an IL-2 conjugate described herein, the position of the structure of Formula (X) and (XI) or a mixture of Formula (X) and (XI) in the amino acid sequence of the IL-2 conjugate of SEQ ID NO: 3 is at position K42. In some embodiments of an IL-2 conjugate described herein, the position of the structure of Formula (X) and (XI) or a mixture of Formula (X) and (XI) in the amino acid sequence of the IL-2 conjugate of SEQ ID NO: 3 is at position E61. In some embodiments of an IL-2 conjugate described herein, the position of the structure of Formula (X) and (XI) or a mixture of Formula (X) and (XI) in the amino acid sequence of the IL-2 conjugate of SEQ ID NO: 3 is at position P64. In some embodiments of an IL-2 conjugate described herein, the position of the structure of Formula (X) and (XI) or a mixture of Formula (X) and (XI) in the amino acid sequence of the IL-2 conjugate of SEQ ID NO: 3 is at position R37. In some embodiments of an IL-2 conjugate described herein, the position of the structure of Formula (X) and (XI) or a mixture of Formula (X) and (XI) in the amino acid sequence of the IL-2 conjugate of SEQ ID NO: 3 is at position T40. In some embodiments of an IL-2 conjugate described herein, the position of the structure of Formula (X) and (XI) or a mixture of Formula (X) and (XI) in the amino acid sequence of the IL-2 conjugate of SEQ ID NO: 3 is at position E67. In some embodiments of an IL-2 conjugate described herein, the position of the structure of Formula (X) and (XI) or a mixture of Formula (X) and (XI) in the amino acid sequence of the IL-2 conjugate of SEQ ID NO: 3 is at position Y44. In some embodiments of an IL-2 conjugate described herein, the position of the structure of Formula (X) and (XI) or a mixture of Formula (X) and (XI) in the amino acid sequence of the IL-2 conjugate of SEQ ID NO: 3 is at position V68. In some embodiments of an IL-2 conjugate described herein, the position of the structure of Formula (X) and (XI) or a mixture of Formula (X) and (XI) in the amino acid sequence of the IL-2 conjugate of SEQ ID NO: 3 is at position L71. In some embodiments of an IL-2 conjugate described herein, the ratio of the amount of the structure of Formula (X) to the amount of the structure of Formula (XI) comprising the total amount of the IL-2 conjugate is about 1:1. In some embodiments of an IL-2 conjugate described herein, the ratio of the amount of the structure of Formula (X) to the amount of the structure of Formula (XI) comprising the total amount of the IL-2 conjugate is greater than 1:1. In some embodiments of an IL-2 conjugate described herein, the ratio of the amount of the structure of Formula (X) to the amount of the structure of Formula (XI) comprising the total amount of the IL-2 conjugate is less than 1:1.

In some embodiments described herein are IL-2 conjugates comprising the amino acid sequence of SEQ ID NO: 3 in which at least one amino acid residue in the IL-2 conjugate is replaced by the structure of Formula (X) or (XI), or a mixture of (X) and (XI), wherein the amino acid residue in in SEQ ID NO: 3 that is replaced is selected from K34, F41, F43, K42, E61, P64, R37, T40, E67, Y44, V68, and L71, and wherein n is an integer from 100 to about 1150, or from about 100 to about 1100, or from about 100 to about 1000, or from about 100 to about 900, or from about 100 to about 750, or from about 100 to about 700, or from about 100 to about 600, or from about 100 to about 575, or from about 100 to about 500, or from about 100 to about 450, or from about 100 to about to about 350, or from about 100 to about 275, or from about 100 to about 230, or from about 150 to about 475, or from about 150 to about 340, or from about 113 to about 340, or from about 450 to about 800, or from about 454 to about 796, or from about 454 to about 682, or from about 340 to about 795, or from about 341 to about 682, or from about 568 to about 909, or from about 227 to about 1500, or from about 225 to about 2280, or from about 460 to about 2160, or from about 460 to about 2050, or from about 341 to about 1820, or from about 341 to about 1710, or from about 341 to about 1250, or from about 225 to about 1250, or from about 341 to about 1250, or from about 341 to about 1136, or from about 341 to about 1023, or from about 341 to about 910, or from about 341 to about 796, or from about 341 to about 682, or from about 341 to about 568, or from about 114 to about 1000, or from about 114 to about 950, or from about 114 to about 910, or from about 114 to about 800, or from about 114 to about 690, or from about 114 to about 575. In some embodiments of an IL-2 conjugate described herein, n in the compounds of formula (VI) and (VII) is an integer selected from 2, 5, 10, 11, 22, 23, 113, 114, 227, 228, 340, 341, 454, 455, 568, 569, 680, 681, 682, 794, 795, 796, 908, 909, 910, 1021, 1022, 1023, 1135, 1136, 1137, 1249, 1250, 1251, 1362, 1363, 1364, 1476, 1477, 1478, 1589, 1590, 1591, 1703, 1704, 1705, 1817, 1818, 1819, 1930, 1931, 1932, 2044, 2045, 2046, 2158, 2159, 2160, 2271, 2272, 2273, 2839, 2840, 2841, 2953, 2954, 2955, 3408, 3409, 3410, 3976, 3977, 3978, 4544, 4545, and 4546.

In some embodiments described herein are IL-2 conjugates comprising the amino acid sequence of SEQ ID NO: 3 in which at least one amino acid residue in the IL-2 conjugate is replaced by the structure of Formula (X) or (XI), or a mixture of (X) and (XI), wherein the amino acid residue in in SEQ ID NO: 3 that is replaced is selected from F41, F43, K42, E61, and P64, and wherein n is an integer from about 450 to about 800, or from about 454 to about 796, or from about 454 to about 682, or from about 568 to about 909. In some embodiments of an IL-2 conjugate described herein, n in the compounds of formula (X) and (XI) is an integer selected from 454, 455, 568, 569, 680, 681, 682, 794, 795, 796, 908, 909, 910, 1021, 1022, 1023, 1135, 1136, 1137, and 1249.

In some embodiments described herein are IL-2 conjugates comprising the amino acid sequence of SEQ ID NO: 3 in which at least one amino acid residue in the IL-2 conjugate is replaced by the structure of Formula (X) or (XI), or a mixture of (X) and (XI), wherein the amino acid residue in SEQ ID NO: 3 that is replaced is selected from E61 and P64, and wherein n is an integer from about 450 to about 800, or from about 454 to about 796, or from about 454 to about 682, or from about 568 to about 909. In some embodiments of an IL-2 conjugate described herein, n in the compounds of formula (X) and (XI) is an integer selected from 454, 455, 568, 569, 680, 681, 682, 794, 795, 796, 908, 909, and 910.

In some embodiments described herein are IL-2 conjugates comprising the amino acid sequence of SEQ ID NO: 3 in which at least one amino acid residue in the IL-2 conjugate is replaced by the structure of Formula (X) or (XI), or a mixture of (X) and (XI), wherein the amino acid residue in SEQ ID NO: 3 that is replaced is E61, and wherein n is an integer from about 450 to about 800, or from about 454 to about 796, or from about 454 to about 682, or from about 568 to about 909. In some embodiments of an IL-2 conjugate described herein, n in the compounds of formula (X) and (XI) is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681.

In some embodiments described herein are IL-2 conjugates comprising the amino acid sequence of SEQ ID NO: 3 in which at least one amino acid residue in the IL-2 conjugate is replaced by the structure of Formula (X) or (XI), or a mixture of (X) and (XI), wherein the amino acid residue in in SEQ ID NO: 3 that is replaced is P64, and wherein n is an integer from about 450 to about 800, or from about 454 to about 796, or from about 454 to about 682, or from about 568 to about 909. In some embodiments of an IL-2 conjugate described herein, n in the compounds of formula (X) and (XI) is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681.

Described herein are IL-2 conjugates comprising the amino acid sequence of SEQ ID NO: 3 in which at least one amino acid residue in the IL-2 conjugate is replaced by the structure of Formula (X) or (XI), or a mixture of (X) and (XI), wherein n is an integer such that the molecular weight of the PEG moiety is in the range from about 1,000 Daltons about 200,000 Daltons, or from about 2,000 Daltons to about 150,000 Daltons, or from about 3,000 Daltons to about 125,000 Daltons, or from about 4,000 Daltons to about 100,000 Daltons, or from about 5,000 Daltons to about 100,000 Daltons, or from about 6,000 Daltons to about 90,000 Daltons, or from about 7,000 Daltons to about 80,000 Daltons, or from about 8,000 Daltons to about 70,000 Daltons, or from about 5,000 Daltons to about 70,000 Daltons, or from about 5,000 Daltons to about 65,000 Daltons, or from about 5,000 Daltons to about 60,000 Daltons, or from about 5,000 Daltons to about 50,000 Daltons, or from about 6,000 Daltons to about 50,000 Daltons, or from about 7,000 Daltons to about 50,000 Daltons, or from about 7,000 Daltons to about 45,000 Daltons, or from about 7,000 Daltons to about 40,000 Daltons, or from about 8,000 Daltons to about 40,000 Daltons, or from about 8,500 Daltons to about 40,000 Daltons, or from about 8,500 Daltons to about 35,000 Daltons, or from about 9,000 Daltons to about 50,000 Daltons, or from about 9,000 Daltons to about 45,000 Daltons, or from about 9,000 Daltons to about 40,000 Daltons, or from about 9,000 Daltons to about 35,000 Daltons, or from about 9,000 Daltons to about 30,000 Daltons, or from about 9,500 Daltons to about 35,000 Daltons, or from about 9,500 Daltons to about 30,000 Daltons, or from about 10,000 Daltons to about 50,000 Daltons, or from about 10,000 Daltons to about 45,000 Daltons, or from about 10,000 Daltons to about 40,000 Daltons, or from about 10,000 Daltons to about 35,000 Daltons, or from about 10,000 Daltons to about 30,000 Daltons, or from about 15,000 Daltons to about 50,000 Daltons, or from about 15,000 Daltons to about 45,000 Daltons, or from about 15,000 Daltons to about 40,000 Daltons, or from about 15,000 Daltons to about 35,000 Daltons, or from about 15,000 Daltons to about 30,000 Daltons, or from about 20,000 Daltons to about 50,000 Daltons, or from about 20,000 Daltons to about 45,000 Daltons, or from about 20,000 Daltons to about 40,000 Daltons, or from about 20,000 Daltons to about 35,000 Daltons, or from about 20,000 Daltons to about 30,000 Daltons. Described herein are IL-2 conjugates comprising the amino acid sequence of SEQ ID NO: 3 in which at least one amino acid residue in the IL-2 conjugate is replaced by the structure of Formula (X) or (XI), or a mixture of (X) and (XI), wherein n is an integer such that the molecular weight of the PEG moiety is about 5,000 Daltons, about 7,500 Daltons, about 10,000 Daltons, about 15,000 Daltons, about 20,000 Daltons, about 25,000 Daltons, about 30,000 Daltons, about 35,000 Daltons, about 40,000 Daltons, about 45,000 Daltons, about 50,000 Daltons, about 60,000 Daltons, about 70,000 Daltons, about 80,000 Daltons, about 90,000 Daltons, about 100,000 Daltons, about 125,000 Daltons, about 150,000 Daltons, about 175,000 Daltons or about 200,000 Daltons. Described herein are IL-2 conjugates comprising the amino acid sequence of SEQ ID NO: 3 in which at least one amino acid residue in the IL-2 conjugate is replaced by the structure of Formula (X) or (XI), or a mixture of (X) and (XI), wherein n is an integer such that the molecular weight of the PEG moiety is about 5,000 Daltons, about 7,500 Daltons, about 10,000 Daltons, about 15,000 Daltons, about 20,000 Daltons, about 25,000 Daltons, about 30,000 Daltons, about 35,000 Daltons, about 40,000 Daltons, about 45,000 Daltons, or about 50,000 Daltons.

Described herein are IL-2 conjugates comprising the amino acid sequence of SEQ ID NO: 3 in which at least one amino acid residue in the IL-2 conjugate is replaced by the structure of Formula (XII) or (XIII), or a mixture of (XII) and (XIII):

Formula (XII)

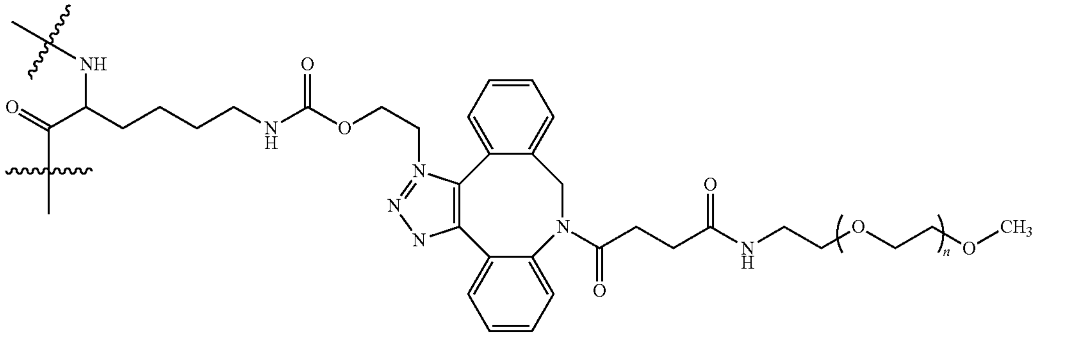

Formula (XIII)

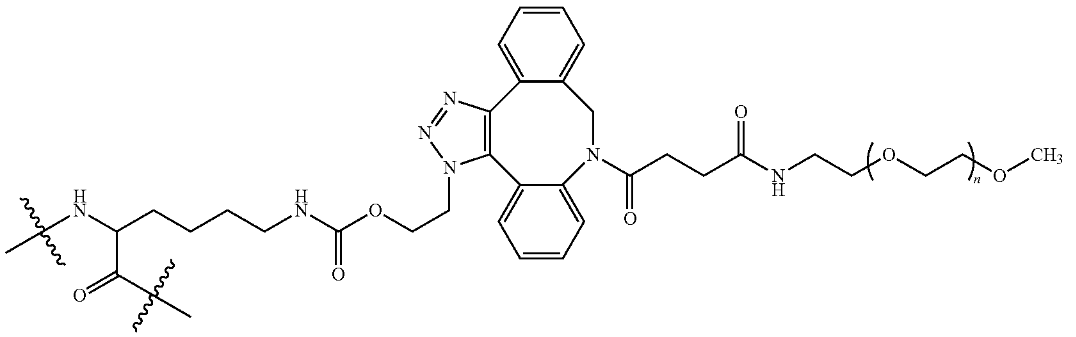

wherein:

n is an integer in the range from about 2 to about 5000; and the wavy lines indicate convalent bonds to amino acid residues within SEQ ID NO: 3 that are not replaced, or a pharmaceutically acceptable salt, solvate, or hydrate thereof.

In some embodiments, the stereochemistry of the chiral center within Formula (XII) and Formula (XIII) is racemic, is enriched in (R), is enriched in (S), is substantially (R), is substantially (S), is (R) or is (S). In some embodiments, the stereochemistry of the chiral center within Formula (XII) and Formula (XIII) is racemic. In some embodiments, the stereochemistry of the chiral center within Formula (XII) and Formula (XIII) is enriched in (R). In some embodiments, the stereochemistry of the chiral center within Formula (XII) and Formula (XIII) is enriched in (S). In some embodiments, the stereochemistry of the chiral center within Formula (XII) and Formula (XIII) is substantially (R). In some embodiments, the stereochemistry of the chiral center within Formula (XII) and Formula (XIII) is substantially (S). In some embodiments, the stereochemistry of the chiral center within Formula (XII) and Formula (XIII) is (R). In some embodiments, the stereochemistry of the chiral center within Formula (XII) and Formula (XIII) is (S).

In some embodiments of an IL-2 conjugate described herein, n in the compounds of Formula (XII) and (XIII) is in the range from about 5 to about 4600, or from about 10 to about 4000, or from about 20 to about 3000, or from about 100 to about 3000, or from about 100 to about 2900, or from about 150 to about 2900, or from about 125 to about 2900, or from about 100 to about 2500, or from about 100 to about 2000, or from about 100 to about 1900, or from about 100 to about 1850, or from about 100 to about 1750, or from about 100 to about 1650, or from about 100 to about 1500, or from about 100 to about 1400, or from about 100 to about 1300, or from about 100 to about 1250, or from about 100 to about 1150, or from about 100 to about 1100, or from about 100 to about 1000, or from about 100 to about 900, or from about 100 to about 750, or from about 100 to about 700, or from about 100 to about 600, or from about 100 to about 575, or from about 100 to about 500, or from about 100 to about 450, or from about 100 to about to about 350, or from about 100 to about 275, or from about 100 to about 230, or from about 150 to about 475, or from about 150 to about 340, or from about 113 to about 340, or from about 450 to about 800, or from about 454 to about 796, or from about 454 to about 682, or from about 340 to about 795, or from about 341 to about 682, or from about 568 to about 909, or from about 227 to about 1500, or from about 225 to about 2280, or from about 460 to about 2160, or from about 460 to about 2050, or from about 341 to about 1820, or from about 341 to about 1710, or from about 341 to about 1250, or from about 225 to about 1250, or from about 341 to about 1250, or from about 341 to about 1136, or from about 341 to about 1023, or from about 341 to about 910, or from about 341 to about 796, or from about 341 to about 682, or from about 341 to about 568, or from about 114 to about 1000, or from about 114 to about 950, or from about 114 to about 910, or from about 114 to about 800, or from about 114 to about 690, or from about 114 to about 575. In some embodiments of an IL-2 conjugate described herein, n in the compounds of Formula (XII) and (XIII) is an integer selected from 2, 5, 10, 11, 22, 23, 113, 114, 227, 228, 340, 341, 454, 455, 568, 569, 680, 681, 682, 794, 795, 796, 908, 909, 910, 1021, 1022, 1023, 1135, 1136, 1137, 1249, 1250, 1251, 1362, 1363, 1364, 1476, 1477, 1478, 1589, 1590, 1591, 1703, 1704, 1705, 1817, 1818, 1819, 1930, 1931, 1932, 2044, 2045, 2046, 2158, 2159, 2160, 2271, 2272, 2273, 2839, 2840, 2841, 2953, 2954, 2955, 3408, 3409, 3410, 3976, 3977, 3978, 4544, 4545, and 4546. In some embodiments of an IL-2 conjugate described herein, the position of the structure of Formula (XII) and (XIII) or a mixture of Formula (XII) and (XIII) in the amino acid sequence of the IL-2 conjugate is selected from K34, F41, F43, K42, E61, P64, R37, T40, E67, Y44, V68, and L71, wherein the position of the structure of Formula (I) in the amino acid sequence of the IL-2 conjugate is in reference to the positions in SEQ ID NO: 3. In some embodiments of an IL-2 conjugate described herein, the position of the structure of Formula (XII) and (XIII) or a mixture of Formula (XII) and (XIII) in the amino acid sequence of the IL-2 conjugate of SEQ ID NO: 3 is selected from K34, F41, F43, K42, E61, P64, R37, T40, E67, Y44, V68, and L71. In some embodiments of an IL-2 conjugate described herein, the position of the structure of Formula (XII) and (XIII) or a mixture of Formula (XII) and (XIII) in the amino acid sequence of the IL-2 conjugate of SEQ ID NO: 3 is at position K34. In some embodiments of an IL-2 conjugate described herein, the position of the structure of Formula (XII) and (XIII) or a mixture of Formula (XII) and (XIII) in the amino acid sequence of the IL-2 conjugate of SEQ ID NO: 3 is at position F41. In some embodiments of an IL-2 conjugate described herein, the position of the structure of Formula (XII) and (XIII) or a mixture of Formula (XII) and (XIII) in the amino acid sequence of the IL-2 conjugate of SEQ ID NO: 3 is at position F43. In some embodiments of an IL-2 conjugate described herein, the position of the structure of Formula (XII) and (XIII) or a mixture of Formula (XII) and (XIII) in the amino acid sequence of the IL-2 conjugate of SEQ ID NO: 3 is at position K42. In some embodiments of an IL-2 conjugate described herein, the position of the structure of Formula (XII) and (XIII) or a mixture of Formula (XII) and (XIII) in the amino acid sequence of the IL-2 conjugate of SEQ ID NO: 3 is at position E61. In some embodiments of an IL-2 conjugate described herein, the position of the structure of Formula (XII) and (XIII) or a mixture of Formula (XII) and (XIII) in the amino acid sequence of the IL-2 conjugate of SEQ ID NO: 3 is at position P64. In some embodiments of an IL-2 conjugate described herein, the position of the structure of Formula (XII) and (XIII) or a mixture of Formula (XII) and (XIII) in the amino acid sequence of the IL-2 conjugate of SEQ ID NO: 3 is at position R37. In some embodiments of an IL-2 conjugate described herein, the position of the structure of Formula (XII) and (XIII) or a mixture of Formula (XII) and (XIII) in the amino acid sequence of the IL-2 conjugate of SEQ ID NO: 3 is at position T40. In some embodiments of an IL-2 conjugate described herein, the position of the structure of Formula (XII) and (XIII) or a mixture of Formula (XII) and (XIII) in the amino acid sequence of the IL-2 conjugate of SEQ ID NO: 3 is at position E67. In some embodiments of an IL-2 conjugate described herein, the position of the structure of Formula (XII) and (XIII) or a mixture of Formula (XII) and (XIII) in the amino acid sequence of the IL-2 conjugate of SEQ ID NO: 3 is at position Y44. In some embodiments of an IL-2 conjugate described herein, the position of the structure of Formula (XII) and (XIII) or a mixture of Formula (XII) and (XIII) in the amino acid sequence of the IL-2 conjugate of SEQ ID NO: 3 is at position V68. In some embodiments of an IL-2 conjugate described herein, the position of the structure of Formula (XII) and (XIII) or a mixture of Formula (XII) and (XIII) in the amino acid sequence of the IL-2 conjugate of SEQ ID NO: 3 is at position L71. In some embodiments of an IL-2 conjugate described herein, the ratio of the amount of the structure of Formula (XII) to the amount of the structure of Formula (XIII) comprising the total amount of the IL-2 conjugate is about 1:1. In some embodiments of an IL-2 conjugate described herein, the ratio of the amount of the structure of Formula (XII) to the amount of the structure of Formula (XIII) comprising the total amount of the IL-2 conjugate is greater than 1:1. In some embodiments of an IL-2 conjugate described herein, the ratio of the amount of the structure of Formula (XII) to the amount of the structure of Formula (XIII) comprising the total amount of the IL-2 conjugate is less than 1:1.

In some embodiments described herein are IL-2 conjugates comprising the amino acid sequence of SEQ ID NO: 3 in which at least one amino acid residue in the IL-2 conjugate is replaced by the structure of Formula (XII) or (XIII), or a mixture of (XII) and (XIII), wherein the amino acid residue in in SEQ ID NO: 3 that is replaced is selected from K34, F41, F43, K42, E61, P64, R37, T40, E67, Y44, V68, and L71, and wherein n is an integer from 100 to about 1150, or from about 100 to about 1100, or from about 100 to about 1000, or from about 100 to about 900, or from about 100 to about 750, or from about 100 to about 700, or from about 100 to about 600, or from about 100 to about 575, or from about 100 to about 500, or from about 100 to about 450, or from about 100 to about to about 350, or from about 100 to about 275, or from about 100 to about 230, or from about 150 to about 475, or from about 150 to about 340, or from about 113 to about 340, or from about 450 to about 800, or from about 454 to about 796, or from about 454 to about 682, or from about 340 to about 795, or from about 341 to about 682, or from about 568 to about 909, or from about 227 to about 1500, or from about 225 to about 2280, or from about 460 to about 2160, or from about 460 to about 2050, or from about 341 to about 1820, or from about 341 to about 1710, or from about 341 to about 1250, or from about 225 to about 1250, or from about 341 to about 1250, or from about 341 to about 1136, or from about 341 to about 1023, or from about 341 to about 910, or from about 341 to about 796, or from about 341 to about 682, or from about 341 to about 568, or from about 114 to about 1000, or from about 114 to about 950, or from about 114 to about 910, or from about 114 to about 800, or from about 114 to about 690, or from about 114 to about 575. In some embodiments of an IL-2 conjugate described herein, n in the compounds of formula (XII) and (XIII) is an integer selected from 2, 5, 10, 11, 22, 23, 113, 114, 227, 228, 340, 341, 454, 455, 568, 569, 680, 681, 682, 794, 795, 796, 908, 909, 910, 1021, 1022, 1023, 1135, 1136, 1137, 1249, 1250, 1251, 1362, 1363, 1364, 1476, 1477, 1478, 1589, 1590, 1591, 1703, 1704, 1705, 1817, 1818, 1819, 1930, 1931, 1932, 2044, 2045, 2046, 2158, 2159, 2160, 2271, 2272, 2273, 2839, 2840, 2841, 2953, 2954, 2955, 3408, 3409, 3410, 3976, 3977, 3978, 4544, 4545, and 4546.

In some embodiments described herein are IL-2 conjugates comprising the amino acid sequence of SEQ ID NO:

3 in which at least one amino acid residue in the IL-2 conjugate is replaced by the structure of Formula (XII) or (XIII), or a mixture of (XII) and (XIII), wherein the amino acid residue in in SEQ ID NO: 3 that is replaced is selected from F41, F43, K42, E61, and P64, and wherein n is an integer from about 450 to about 800, or from about 454 to about 796, or from about 454 to about 682, or from about 568 to about 909. In some embodiments of an IL-2 conjugate described herein, n in the compounds of formula (XII) and (XIII) is an integer selected from 454, 455, 568, 569, 680, 681, 682, 794, 795, 796, 908, 909, 910, 1021, 1022, 1023, 1135, 1136, 1137, and 1249.

In some embodiments described herein are IL-2 conjugates comprising the amino acid sequence of SEQ ID NO: 3 in which at least one amino acid residue in the IL-2 conjugate is replaced by the structure of Formula (XII) or (XIII), or a mixture of (XII) and (XIII), wherein the amino acid residue in SEQ ID NO: 3 that is replaced is selected from E61 and P64, and wherein n is an integer from about 450 to about 800, or from about 454 to about 796, or from about 454 to about 682, or from about 568 to about 909. In some embodiments of an IL-2 conjugate described herein, n in the compounds of formula (XII) and (XIII) is an integer selected from 454, 455, 568, 569, 680, 681, 682, 794, 795, 796, 908, 909, and 910.

In some embodiments described herein are IL-2 conjugates comprising the amino acid sequence of SEQ ID NO: 3 in which at least one amino acid residue in the IL-2 conjugate is replaced by the structure of Formula (XII) or (XIII), or a mixture of (XII) and (XIII), wherein the amino acid residue in SEQ ID NO: 3 that is replaced is E61, and wherein n is an integer from about 450 to about 800, or from about 454 to about 796, or from about 454 to about 682, or from about 568 to about 909. In some embodiments of an IL-2 conjugate described herein, n in the compounds of formula (XII) and (XIII) is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681.

In some embodiments described herein are IL-2 conjugates comprising the amino acid sequence of SEQ ID NO: 3 in which at least one amino acid residue in the IL-2 conjugate is replaced by the structure of Formula (XII) or (XIII), or a mixture of (XII) and (XIII), wherein the amino acid residue in in SEQ ID NO: 3 that is replaced is P64, and wherein n is an integer from about 450 to about 800, or from about 454 to about 796, or from about 454 to about 682, or from about 568 to about 909. In some embodiments of an IL-2 conjugate described herein, n in the compounds of formula (XII) and (XIII) is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681.

Described herein are IL-2 conjugates comprising the amino acid sequence of SEQ ID NO: 3 in which at least one amino acid residue in the IL-2 conjugate is replaced by the structure of Formula (XII) or (XIII), or a mixture of (XII) and (XIII), wherein n is an integer such that the molecular weight of the PEG moiety is in the range from about 1,000 Daltons about 200,000 Daltons, or from about 2,000 Daltons to about 150,000 Daltons, or from about 3,000 Daltons to about 125,000 Daltons, or from about 4,000 Daltons to about 100,000 Daltons, or from about 5,000 Daltons to about 100,000 Daltons, or from about 6,000 Daltons to about 90,000 Daltons, or from about 7,000 Daltons to about 80,000 Daltons, or from about 8,000 Daltons to about 70,000 Daltons, or from about 5,000 Daltons to about 70,000 Daltons, or from about 5,000 Daltons to about 65,000 Daltons, or from about 5,000 Daltons to about 60,000 Daltons, or from about 5,000 Daltons to about 50,000 Daltons, or from about 6,000 Daltons to about 50,000 Daltons, or from about 7,000 Daltons to about 50,000 Daltons, or from about 7,000 Daltons to about 45,000 Daltons, or from about 7,000 Daltons to about 40,000 Daltons, or from about 8,000 Daltons to about 40,000 Daltons, or from about 8,500 Daltons to about 40,000 Daltons, or from about 8,500 Daltons to about 35,000 Daltons, or from about 9,000 Daltons to about 50,000 Daltons, or from about 9,000 Daltons to about 45,000 Daltons, or from about 9,000 Daltons to about 40,000 Daltons, or from about 9,000 Daltons to about 35,000 Daltons, or from about 9,000 Daltons to about 30,000 Daltons, or from about 9,500 Daltons to about 35,000 Daltons, or from about 9,500 Daltons to about 30,000 Daltons, or from about 10,000 Daltons to about 50,000 Daltons, or from about 10,000 Daltons to about 45,000 Daltons, or from about 10,000 Daltons to about 40,000 Daltons, or from about 10,000 Daltons to about 35,000 Daltons, or from about 10,000 Daltons to about 30,000 Daltons, or from about 15,000 Daltons to about 50,000 Daltons, or from about 15,000 Daltons to about 45,000 Daltons, or from about 15,000 Daltons to about 40,000 Daltons, or from about 15,000 Daltons to about 35,000 Daltons, or from about 15,000 Daltons to about 30,000 Daltons, or from about 20,000 Daltons to about 50,000 Daltons, or from about 20,000 Daltons to about 45,000 Daltons, or from about 20,000 Daltons to about 40,000 Daltons, or from about 20,000 Daltons to about 35,000 Daltons, or from about 20,000 Daltons to about 30,000 Daltons. Described herein are IL-2 conjugates comprising the amino acid sequence of SEQ ID NO: 3 in which at least one amino acid residue in the IL-2 conjugate is replaced by the structure of Formula (XII) or (XIII), or a mixture of (XII) and (XIII), wherein n is an integer such that the molecular weight of the PEG moiety is about 5,000 Daltons, about 7,500 Daltons, about 10,000 Daltons, about 15,000 Daltons, about 20,000 Daltons, about 25,000 Daltons, about 30,000 Daltons, about 35,000 Daltons, about 40,000 Daltons, about 45,000 Daltons, about 50,000 Daltons, about 60,000 Daltons, about 70,000 Daltons, about 80,000 Daltons, about 90,000 Daltons, about 100,000 Daltons, about 125,000 Daltons, about 150,000 Daltons, about 175,000 Daltons or about 200,000 Daltons. Described herein are IL-2 conjugates comprising the amino acid sequence of SEQ ID NO: 3 in which at least one amino acid residue in the IL-2 conjugate is replaced by the structure of Formula (XII) or (XIII), or a mixture of (XII) and (XIII), wherein n is an integer such that the molecular weight of the PEG moiety is about 5,000 Daltons, about 7,500 Daltons, about 10,000 Daltons, about 15,000 Daltons, about 20,000 Daltons, about 25,000 Daltons, about 30,000 Daltons, about 35,000 Daltons, about 40,000 Daltons, about 45,000 Daltons, or about 50,000 Daltons.

Described herein are IL-2 conjugates comprising the amino acid sequence of SEQ ID NO: 3 in which at least one amino acid residue in the IL-2 conjugate is replaced by the structure of Formula (XIV) or (XV), or a mixture of (XIV) and (XV):

Formula (XIV)

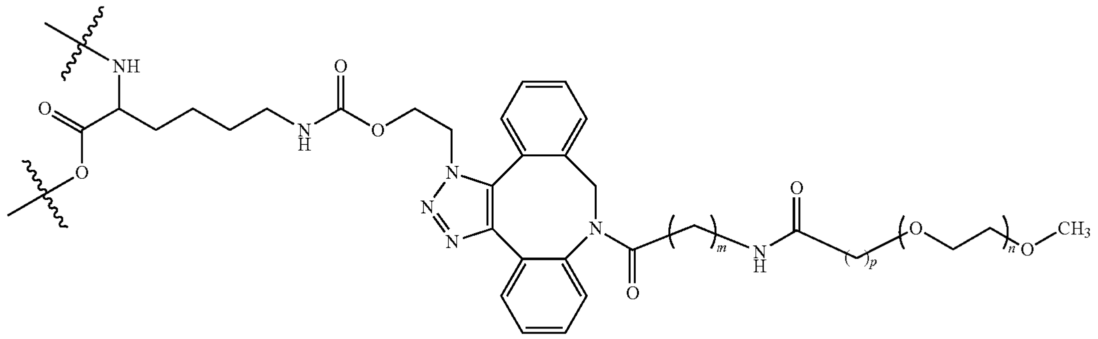

Formula (XV)

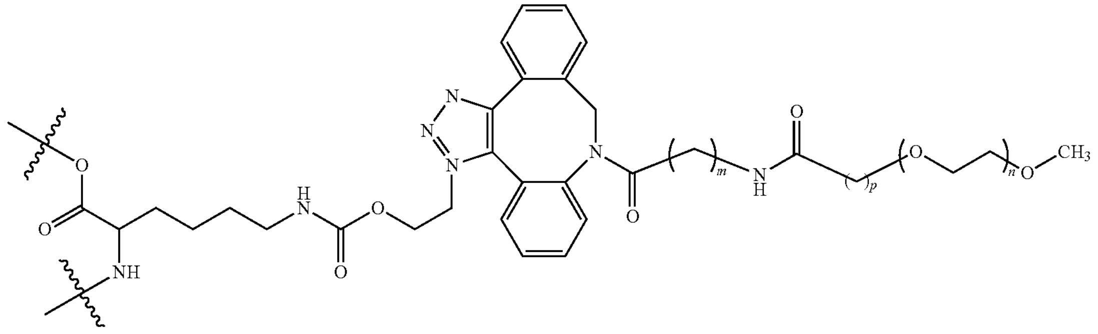

wherein:

m is an integer from 0 to 20;

p is an integer from 0 to 20;

n is an integer in the range from about 2 to about 5000; and the wavy lines indicate covalent bonds to amino acid residues within SEQ ID NO: 3 that are not replaced, or a pharmaceutically acceptable salt, solvate, or hydrate thereof.

In some embodiments, the stereochemistry of the chiral center within Formula (XIV) and Formula (XV) is racemic, is enriched in (R), is enriched in (S), is substantially (R), is substantially (S), is (R) or is (S). In some embodiments, the stereochemistry of the chiral center within Formula (XIV) and Formula (XV) is racemic. In some embodiments, the stereochemistry of the chiral center within Formula (XIV) and Formula (XV) is enriched in (R). In some embodiments, the stereochemistry of the chiral center within Formula (XIV) and Formula (XV) is enriched in (S). In some embodiments, the stereochemistry of the chiral center within Formula (XIV) and Formula (XV) is substantially (R). In some embodiments, the stereochemistry of the chiral center within Formula (XIV) and Formula (XV) is substantially (S). In some embodiments, the stereochemistry of the chiral center within Formula (XIV) and Formula (XV) is (R). In some embodiments, the stereochemistry of the chiral center within Formula (XIV) and Formula (XV) is (S).

In some embodiments of an IL-2 conjugate described herein, m in the compounds of Formula (XIV) and (XV) is from 0 to 20, or from 0 to 18, or from 0 to 16, or from 0 to 14, or from 0 to 12, or from 0 to 10, or from 0 to 9, or from 0 to 8, or from 0 to 7, or from 0 to 6, or from 0 to 5, or from 0 to 4, or from 0 to 3, or from 0 to 2. In some embodiments of an IL-2 conjugate described herein, m in the compounds of Formula (XIV) and (XV) is 0. In some embodiments of an IL-2 conjugate described herein, m in the compounds of Formula (XIV) and (XV) is 1. In some embodiments of an IL-2 conjugate described herein, m in the compounds of Formula (XIV) and (XV) is 2. In some embodiments of an IL-2 conjugate described herein, m in the compounds of Formula (XIV) and (XV) is 3. In some embodiments of an IL-2 conjugate described herein, m in the compounds of Formula (XIV) and (XV) is 4. In some embodiments of an IL-2 conjugate described herein, m in the compounds of Formula (XIV) and (XV) is 5. In some embodiments of an IL-2 conjugate described herein, m in the compounds of Formula (XIV) and (XV) is 6. In some embodiments of an IL-2 conjugate described herein, m in the compounds of Formula (XIV) and (XV) is 7. In some embodiments of an IL-2 conjugate described herein, m in the compounds of Formula (XIV) and (XV) is 8. In some embodiments of an IL-2 conjugate described herein, m in the compounds of Formula (XIV) and (XV) is 9. In some embodiments of an IL-2 conjugate described herein, m in the compounds of Formula (XIV) and (XV) is 10. In some embodiments of an IL-2 conjugate described herein, m in the compounds of Formula (XIV) and (XV) is 11. In some embodiments of an IL-2 conjugate described herein, m in the compounds of Formula (XIV) and (XV) is 12. In some embodiments of an IL-2 conjugate described herein, m in the compounds of Formula (XIV) and (XV) is 13. In some embodiments of an IL-2 conjugate described herein, m in the compounds of Formula (XIV) and (XV) is 14. In some embodiments of an IL-2 conjugate described herein, m in the compounds of Formula (XIV) and (XV) is 15. In some embodiments of an IL-2 conjugate described herein, m in the compounds of Formula (XIV) and (XV) is 16. In some embodiments of an IL-2 conjugate described herein, m in the compounds of Formula (XIV) and (XV) is 17. In some embodiments of an IL-2 conjugate described herein, m in the compounds of Formula (XIV) and (XV) is 18. In some embodiments of an IL-2 conjugate described herein, m in the compounds of Formula (XIV) and (XV) is 19. In some embodiments of an IL-2 conjugate described herein, m in the compounds of Formula (XIV) and (XV) is 20.

In some embodiments of an IL-2 conjugate described herein, p in the compounds of Formula (XIV) and (XV) is from 0 to 20, or from 0 to 18, or from 0 to 16, or from 0 to 14, or from 0 to 12, or from 0 to 10, or from 0 to 9, or from 0 to 8, or from 0 to 7, or from 0 to 6, or from 0 to 5, or from 0 to 4, or from 0 to 3, or from 0 to 2. In some embodiments of an IL-2 conjugate described herein, p in the compounds of Formula (XIV) and (XV) is 0. In some embodiments of an IL-2 conjugate described herein, p in the compounds of Formula (XIV) and (XV) is 1. In some embodiments of an IL-2 conjugate described herein, p in the compounds of Formula (XIV) and (XV) is 2. In some embodiments of an IL-2 conjugate described herein, p in the compounds of Formula (XIV) and (XV) is 3. In some embodiments of an IL-2 conjugate described herein, p in the compounds of Formula (XIV) and (XV) is 4. In some embodiments of an IL-2 conjugate described herein, p in the compounds of Formula (XIV) and (XV) is 5. In some embodiments of an IL-2 conjugate described herein, p in the compounds of Formula (XIV) and (XV) is 6. In some embodiments of an IL-2 conjugate described herein, p in the compounds of Formula (XIV) and (XV) is 7. In some embodiments of an IL-2 conjugate described herein, p in the compounds of Formula (XIV) and (XV) is 8. In some embodiments of an IL-2 conjugate described herein, p in the compounds of Formula (XIV) and (XV) is 9. In some embodiments of an IL-2 conjugate described herein, p in the compounds of Formula (XIV) and (XV) is 10. In some embodiments of an IL-2 conjugate described herein, p in the compounds of Formula (XIV) and (XV) is 11. In some embodiments of an IL-2 conjugate described herein, p in the compounds of Formula (XIV) and (XV) is 12. In some embodiments of an IL-2 conjugate described herein, p in the compounds of Formula (XIV) and (XV) is 13. In some embodiments of an IL-2 conjugate described herein, p in the compounds of Formula (XIV) and (XV) is 14. In some embodiments of an IL-2 conjugate described herein, p in the compounds of Formula (XIV) and (XV) is 15. In some embodiments of an IL-2 conjugate described herein, m in the compounds of Formula (XIV) and (XV) is 16. In some embodiments of an IL-2 conjugate described herein, p in the compounds of Formula (XIV) and (XV) is 17. In some embodiments of an IL-2 conjugate described herein, p in the compounds of Formula (XIV) and (XV) is 18. In some embodiments of an IL-2 conjugate described herein, p in the compounds of Formula (XIV) and (XV) is 19. In some embodiments of an IL-2 conjugate described herein, p in the compounds of Formula (XIV) and (XV) is 20.

In some embodiments of an IL-2 conjugate described herein, n in the compounds of Formula (XIV) and (XV) is in the range from about 5 to about 4600, or from about 10 to about 4000, or from about 20 to about 3000, or from about 100 to about 3000, or from about 100 to about 2900, or from about 150 to about 2900, or from about 125 to about 2900, or from about 100 to about 2500, or from about 100 to about 2000, or from about 100 to about 1900, or from about 100 to about 1850, or from about 100 to about 1750, or from about 100 to about 1650, or from about 100 to about 1500, or from about 100 to about 1400, or from about 100 to about 1300, or from about 100 to about 1250, or from about 100 to about 1150, or from about 100 to about 1100, or from about 100 to about 1000, or from about 100 to about 900, or from about 100 to about 750, or from about 100 to about 700, or from about 100 to about 600, or from about 100 to about 575, or from about 100 to about 500, or from about 100 to about 450, or from about 100 to about to about 350, or from about 100 to about 275, or from about 100 to about 230, or from about 150 to about 475, or from about 150 to about 340, or from about 113 to about 340, or from about 450 to about 800, or from about 454 to about 796, or from about 454 to about 682, or from about 340 to about 795, or from about 341 to about 682, or from about 568 to about 909, or from about 227 to about 1500, or from about 225 to about 2280, or from about 460 to about 2160, or from about 460 to about 2050, or from about 341 to about 1820, or from about 341 to about 1710, or from about 341 to about 1250, or from about 225 to about 1250, or from about 341 to about 1250, or from about 341 to about 1136, or from about 341 to about 1023, or from about 341 to about 910, or from about 341 to about 796, or from about 341 to about 682, or from about 341 to about 568, or from about 114 to about 1000, or from about 114 to about 950, or from about 114 to about 910, or from about 114 to about 800, or from about 114 to about 690, or from about 114 to about 575.

In some embodiments of an IL-2 conjugate described herein in the compounds of Formula (XIV) and (XV), m is an integer from 0 to 6, p is an integer from 0 to 6, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is an integer from 1 to 6, p is an integer from 1 to 6, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is an integer from 2 to 6, p is an integer from 2 to 6, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is an integer from 2 to 4, p is an integer from 2 to 4, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 1, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 2, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 3, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 4, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 5, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 6, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 7, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 8, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 9, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 10, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 11, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 11, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 2, p is 2, and n is an integer selected from 680, 681, 682, 794, 795, 796, 908, 909, 910, 1021, 1022, 1023, 1135, 1136, and 1137.

In some embodiments of an IL-2 conjugate described herein, n in the compounds of Formula (XIV) and (XV) is an integer selected from 2, 5, 10, 11, 22, 23, 113, 114, 227, 228, 340, 341, 454, 455, 568, 569, 680, 681, 682, 794, 795, 796, 908, 909, 910, 1021, 1022, 1023, 1135, 1136, 1137, 1249, 1250, 1251, 1362, 1363, 1364, 1476, 1477, 1478, 1589, 1590, 1591, 1703, 1704, 1705, 1817, 1818, 1819, 1930, 1931, 1932, 2044, 2045, 2046, 2158, 2159, 2160, 2271, 2272, 2273, 2839, 2840, 2841, 2953, 2954, 2955, 3408, 3409, 3410, 3976, 3977, 3978, 4544, 4545, and 4546. In some embodiments of an IL-2 conjugate described herein, the position of the structure of Formula (XIV) and (XV) or a mixture of Formula (XIV) and (XV) in the amino acid sequence of the IL-2 conjugate is selected from K34, F41, F43, K42, E61, P64, R37, T40, E67, Y44, V68, and L71, wherein the position of the structure of Formula (I) in the amino acid sequence of the IL-2 conjugate is in reference to the positions in SEQ ID NO: 3. In some embodiments of an IL-2 conjugate described herein, the position of the structure of Formula (XIV) and (XV) or a mixture of Formula (XIV) and (XV) in the amino acid sequence of the IL-2 conjugate of SEQ ID NO: 3 is selected from K34, F41, F43, K42, E61, P64, R37, T40, E67, Y44, V68, and L71. In some embodiments of an IL-2 conjugate described herein, the position of the structure of Formula (XIV) and (XV) or a mixture of Formula (XIV) and (XV) in the amino acid sequence of the IL-2 conjugate of SEQ ID NO: 3 is at position K34. In some embodiments of an IL-2 conjugate described herein, the position of the structure of Formula (XIV) and (XV) or a mixture of Formula (XIV) and (XV) in the amino acid sequence of the IL-2 conjugate of SEQ ID NO: 3 is at position F41. In some embodiments of an IL-2 conjugate described herein, the position of the structure of Formula (XIV) and (XV) or a mixture of Formula (XIV) and (XV) in the amino acid sequence of the IL-2 conjugate of SEQ ID NO: 3 is at position F43. In some embodiments of an IL-2 conjugate described herein, the position of the structure of Formula (XIV) and (XV) or a mixture of Formula (XIV) and (XV) in the amino acid sequence of the IL-2 conjugate of SEQ ID NO: 3 is at position K42. In some embodiments of an IL-2 conjugate described herein, the position of the structure of Formula (XIV) and (XV) or a mixture of Formula (XIV) and (XV) in the amino acid sequence of the IL-2 conjugate of SEQ ID NO: 3 is at position E61. In some embodiments of an IL-2 conjugate described herein, the position of the structure of Formula (XIV) and (XV) or a mixture of Formula (XIV) and (XV) in the amino acid sequence of the IL-2 conjugate of SEQ ID NO: 3 is at position P64. In some embodiments of an IL-2 conjugate described herein, the position of the structure of Formula (XIV) and (XV) or a mixture of Formula (XIV) and (XV) in the amino acid sequence of the IL-2 conjugate of SEQ ID NO: 3 is at position R37. In some embodiments of an IL-2 conjugate described herein, the position of the structure of Formula (XIV) and (XV) or a mixture of Formula (XIV) and (XV) in the amino acid sequence of the IL-2 conjugate of SEQ ID NO: 3 is at position T40. In some embodiments of an IL-2 conjugate described herein, the position of the structure of Formula (XIV) and (XV) or a mixture of Formula (XIV) and (XV) in the amino acid sequence of the IL-2 conjugate of SEQ ID NO: 3 is at position E67. In some embodiments of an IL-2 conjugate described herein, the position of the structure of Formula (XIV) and (XV) or a mixture of Formula (XIV) and (XV) in the amino acid sequence of the IL-2 conjugate of SEQ ID NO: 3 is at position Y44. In some embodiments of an IL-2 conjugate described herein, the position of the structure of Formula (XIV) and (XV) or a mixture of Formula (XIV) and (XV) in the amino acid sequence of the IL-2 conjugate of SEQ ID NO: 3 is at position V68. In some embodiments of an IL-2 conjugate described herein, the position of the structure of Formula (XIV) and (XV) or a mixture of Formula (XIV) and (XV) in the amino acid sequence of the IL-2 conjugate of SEQ ID NO: 3 is at position L71. In some embodiments of an IL-2 conjugate described herein, the ratio of the amount of the structure of Formula (XIV) to the amount of the structure of Formula (XV) comprising the total amount of the IL-2 conjugate is about 1:1. In some embodiments of an IL-2 conjugate described herein, the ratio of the amount of the structure of Formula (XIV) to the amount of the structure of Formula (XV) comprising the total amount of the IL-2 conjugate is greater than 1:1. In some embodiments of an IL-2 conjugate described herein, the ratio of the amount of the structure of Formula (XIV) to the amount of the structure of Formula (XV) comprising the total amount of the IL-2 conjugate is less than 1:1.

In some embodiments described herein are IL-2 conjugates comprising the amino acid sequence of SEQ ID NO: 3 in which at least one amino acid residue in the IL-2 conjugate is replaced by the structure of Formula (XIV) or (XV), or a mixture of (XIV) and (XV), wherein the amino acid residue in in SEQ ID NO: 3 that is replaced is selected from K34, F41, F43, K42, E61, P64, R37, T40, E67, Y44, V68, and L71, and wherein n is an integer from 100 to about 1150, or from about 100 to about 1100, or from about 100 to about 1000, or from about 100 to about 900, or from about 100 to about 750, or from about 100 to about 700, or from about 100 to about 600, or from about 100 to about 575, or from about 100 to about 500, or from about 100 to about 450, or from about 100 to about to about 350, or from about 100 to about 275, or from about 100 to about 230, or from about 150 to about 475, or from about 150 to about 340, or from about 113 to about 340, or from about 450 to about 800, or from about 454 to about 796, or from about 454 to about 682, or from about 340 to about 795, or from about 341 to about 682, or from about 568 to about 909, or from about 227 to about 1500, or from about 225 to about 2280, or from about 460 to about 2160, or from about 460 to about 2050, or from about 341 to about 1820, or from about 341 to about 1710, or from about 341 to about 1250, or from about 225 to about 1250, or from about 341 to about 1250, or from about 341 to about 1136, or from about 341 to about 1023, or from about 341 to about 910, or from about 341 to about 796, or from about 341 to about 682, or from about 341 to about 568, or from about 114 to about 1000, or from about 114 to about 950, or from about 114 to about 910, or from about 114 to about 800, or from about 114 to about 690, or from about 114 to about 575. In some embodiments of an IL-2 conjugate described herein, n in the compounds of formula (XIV) and (XV) is an integer selected from 2, 5, 10, 11, 22, 23, 113, 114, 227, 228, 340, 341, 454, 455, 568, 569, 680, 681, 682, 794, 795, 796, 908, 909, 910, 1021, 1022, 1023, 1135, 1136, 1137, 1249, 1250, 1251, 1362, 1363, 1364, 1476, 1477, 1478, 1589, 1590, 1591, 1703, 1704, 1705, 1817, 1818, 1819, 1930, 1931, 1932, 2044, 2045, 2046, 2158, 2159, 2160, 2271, 2272, 2273, 2839, 2840, 2841, 2953, 2954, 2955, 3408, 3409, 3410, 3976, 3977, 3978, 4544, 4545, and 4546.

In some embodiments described herein are IL-2 conjugates comprising the amino acid sequence of SEQ ID NO: 3 in which at least one amino acid residue in the IL-2 conjugate is replaced by the structure of Formula (XIV) or (XV), or a mixture of (XIV) and (XV), wherein the amino acid residue in in SEQ ID NO: 3 that is replaced is selected from F41, F43, K42, E61, and P64, and wherein n is an integer from about 450 to about 800, or from about 454 to about 796, or from about 454 to about 682, or from about 568 to about 909. In some embodiments of an IL-2 conjugate described herein, n in the compounds of formula (XIV) and (XV) is an integer selected from 454, 455, 568, 569, 680, 681, 682, 794, 795, 796, 908, 909, 910, 1021, 1022, 1023, 1135, 1136, 1137, and 1249.

In some embodiments described herein are IL-2 conjugates comprising the amino acid sequence of SEQ ID NO: 3 in which at least one amino acid residue in the IL-2 conjugate is replaced by the structure of Formula (XIV) or (XV), or a mixture of (XIV) and (XV), wherein the amino acid residue in SEQ ID NO: 3 that is replaced is selected from E61 and P64, and wherein n is an integer from about 450 to about 800, or from about 454 to about 796, or from about 454 to about 682, or from about 568 to about 909. In some embodiments of an IL-2 conjugate described herein, n in the compounds of formula (XIV) and (XV) is an integer selected from 454, 455, 568, 569, 680, 681, 682, 794, 795, 796, 908, 909, and 910.

In some embodiments described herein are IL-2 conjugates comprising the amino acid sequence of SEQ ID NO: 3 in which at least one amino acid residue in the IL-2 conjugate is replaced by the structure of Formula (XIV) or (XV), or a mixture of (XIV) and (XV), wherein the amino acid residue in SEQ ID NO: 3 that is replaced is E61, and wherein n is an integer from about 450 to about 800, or from about 454 to about 796, or from about 454 to about 682, or from about 568 to about 909. In some embodiments of an IL-2 conjugate described herein, n in the compounds of formula (XIV) and (XV) is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681.

In some embodiments described herein are IL-2 conjugates comprising the amino acid sequence of SEQ ID NO: 3 in which at least one amino acid residue in the IL-2 conjugate is replaced by the structure of Formula (XIV) or (XV), or a mixture of (XIV) and (XV), wherein the amino acid residue in in SEQ ID NO: 3 that is replaced is P64, and wherein n is an integer from about 450 to about 800, or from about 454 to about 796, or from about 454 to about 682, or from about 568 to about 909. In some embodiments of an IL-2 conjugate described herein, n in the compounds of formula (XIV) and (XV) is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681.

Described herein are IL-2 conjugates comprising the amino acid sequence of SEQ ID NO: 3 in which at least one amino acid residue in the IL-2 conjugate is replaced by the structure of Formula (XIV) or (XV), or a mixture of (XIV) and (XV), wherein n is an integer such that the molecular weight of the PEG moiety is in the range from about 1,000 Daltons about 200,000 Daltons, or from about 2,000 Daltons to about 150,000 Daltons, or from about 3,000 Daltons to about 125,000 Daltons, or from about 4,000 Daltons to about 100,000 Daltons, or from about 5,000 Daltons to about 100,000 Daltons, or from about 6,000 Daltons to about 90,000 Daltons, or from about 7,000 Daltons to about 80,000 Daltons, or from about 8,000 Daltons to about 70,000 Daltons, or from about 5,000 Daltons to about 70,000 Daltons, or from about 5,000 Daltons to about 65,000 Daltons, or from about 5,000 Daltons to about 60,000 Daltons, or from about 5,000 Daltons to about 50,000 Daltons, or from about 6,000 Daltons to about 50,000 Daltons, or from about 7,000 Daltons to about 50,000 Daltons, or from about 7,000 Daltons to about 45,000 Daltons, or from about 7,000 Daltons to about 40,000 Daltons, or from about 8,000 Daltons to about 40,000 Daltons, or from about 8,500 Daltons to about 40,000 Daltons, or from about 8,500 Daltons to about 35,000 Daltons, or from about 9,000 Daltons to about 50,000 Daltons, or from about 9,000 Daltons to about 45,000 Daltons, or from about 9,000 Daltons to about 40,000 Daltons, or from about 9,000 Daltons to about 35,000 Daltons, or from about 9,000 Daltons to about 30,000 Daltons, or from about 9,500 Daltons to about 35,000 Daltons, or from about 9,500 Daltons to about 30,000 Daltons, or from about 10,000 Daltons to about 50,000 Daltons, or from about 10,000 Daltons to about 45,000 Daltons, or from about 10,000 Daltons to about 40,000 Daltons, or from about 10,000 Daltons to about 35,000 Daltons, or from about 10,000 Daltons to about 30,000 Daltons, or from about 15,000 Daltons to about 50,000 Daltons, or from about 15,000 Daltons to about 45,000 Daltons, or from about 15,000 Daltons to about 40,000 Daltons, or from about 15,000 Daltons to about 35,000 Daltons, or from about 15,000 Daltons to about 30,000 Daltons, or from about 20,000 Daltons to about 50,000 Daltons, or from about 20,000 Daltons to about 45,000 Daltons, or from about 20,000 Daltons to about 40,000 Daltons, or from about 20,000 Daltons to about 35,000 Daltons, or from about 20,000 Daltons to about 30,000 Daltons. Described herein are IL-2 conjugates comprising the amino acid sequence of SEQ ID NO: 3 in which at least one amino acid residue in the IL-2 conjugate is replaced by the structure of Formula (XIV) or (XV), or a mixture of (XIV) and (XV), wherein n is an integer such that the molecular weight of the PEG moiety is about 5,000 Daltons, about 7,500 Daltons, about 10,000 Daltons, about 15,000 Daltons, about 20,000 Daltons, about 25,000 Daltons, about 30,000 Daltons, about 35,000 Daltons, about 40,000 Daltons, about 45,000 Daltons, about 50,000 Daltons, about 60,000 Daltons, about 70,000 Daltons, about 80,000 Daltons, about 90,000 Daltons, about 100,000 Daltons, about 125,000 Daltons, about 150,000 Daltons, about 175,000 Daltons or about 200,000 Daltons. Described herein are IL-2 conjugates comprising the amino acid sequence of SEQ ID NO: 3 in which at least one amino acid residue in the IL-2 conjugate is replaced by the structure of Formula (XIV) or (XV), or a mixture of (XIV) and (XV), wherein n is an integer such that the molecular weight of the PEG moiety is about 5,000 Daltons, about 7,500 Daltons, about 10,000 Daltons, about 15,000 Daltons, about 20,000 Daltons, about 25,000 Daltons, about 30,000 Daltons, about 35,000 Daltons, about 40,000 Daltons, about 45,000 Daltons, or about 50,000 Daltons.

In some embodiments described herein are IL-2 conjugates comprising the amino acid sequence of SEQ ID NO: 3 in which at least one amino acid residue in the IL-2 conjugate is replaced by the structure of Formula (XIV) or (XV), or a mixture of (XIV) and (XV), wherein the amino acid residue in in SEQ ID NO: 3 that is replaced is selected from F41, F43, K42, E61, and P64, m is an integer from 0 to 6, p is an integer from 0 to 6, and n is an integer from about 450 to about 800, or from about 454 to about 796, or from about 454 to about 682, or from about 568 to about 909. In some embodiments of an IL-2 conjugate described herein in the compounds of formula (XIV) and (XV), m is 2, p is 2, and n is an integer selected from 454, 455, 568, 569, 680, 681, 682, 794, 795, 796, 908, 909, 910, 1021, 1022, 1023, 1135, 1136, 1137, and 1249.

In some embodiments described herein are IL-2 conjugates comprising the amino acid sequence of SEQ ID NO: 3 in which at least one amino acid residue in the IL-2 conjugate is replaced by the structure of Formula (XIV) or (XV), or a mixture of (XIV) and (XV), wherein the amino acid residue in SEQ ID NO: 3 that is replaced is selected from E61 and P64, and wherein m is an integer from 0 to 6, p is an integer from 0 to 6, and n is an integer from about 450 to about 800, or from about 454 to about 796, or from about 454 to about 682, or from about 568 to about 909. In some embodiments of an IL-2 conjugate described herein in the compounds of formula (XIV) and (XV), m is 2, p is 2, and n is an integer selected from 454, 455, 568, 569, 680, 681, 682, 794, 795, 796, 908, 909, and 910.

In some embodiments described herein are IL-2 conjugates comprising the amino acid sequence of SEQ ID NO: 3 in which at least one amino acid residue in the IL-2 conjugate is replaced by the structure of Formula (XIV) or (XV), or a mixture of (XIV) and (XV), wherein the amino acid residue in SEQ ID NO: 3 that is replaced is E61, and wherein m is an integer from 0 to 6, p is an integer from 0 to 6, and n is an integer from about 450 to about 800, or from about 454 to about 796, or from about 454 to about 682, or from about 568 to about 909. In some embodiments of an IL-2 conjugate described herein in the compounds of formula (XIV) and (XV), m is 2, p is 2, and n is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681.

In some embodiments described herein are IL-2 conjugates comprising the amino acid sequence of SEQ ID NO: 3 in which at least one amino acid residue in the IL-2 conjugate is replaced by the structure of Formula (XIV) or (XV), or a mixture of (XIV) and (XV), wherein the amino acid residue in in SEQ ID NO: 3 that is replaced is P64, and wherein m is an integer from 0 to 6, p is an integer from 0 to 6, and n is an integer from about 450 to about 800, or from about 454 to about 796, or from about 454 to about 682, or from about 568 to about 909. In some embodiments of an IL-2 conjugate described herein in the compounds of formula (XIV) and (XV), m is 2, p is 2, and n is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681.

Described herein are IL-2 conjugates comprising the amino acid sequence of SEQ ID NO: 3 in which at least one amino acid residue in the IL-2 conjugate is replaced by the structure of Formula (XVI) or (XVII), or a mixture of (XVI) and (XVII):

Formula (XVI)

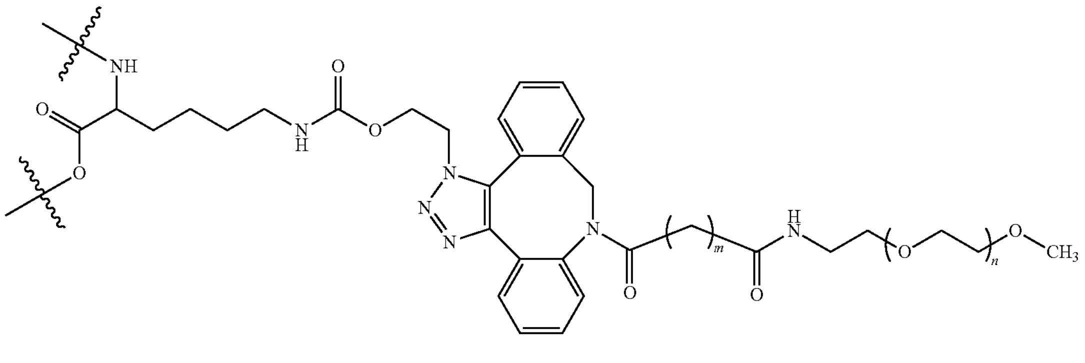

-continued

Formula (XVII)

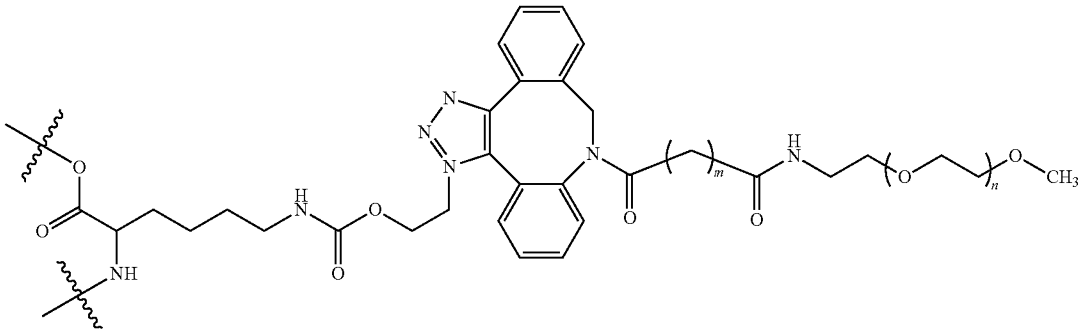

wherein:

m is an integer from 0 to 20;

n is an integer in the range from about 2 to about 5000; and the wavy lines indicate covalent bonds to amino acid residues within SEQ ID NO: 3 that are not replaced, or a pharmaceutically acceptable salt, solvate, or hydrate thereof.

In some embodiments, the stereochemistry of the chiral center within Formula (XVI) and Formula (XVII) is racemic, is enriched in (R), is enriched in (S), is substantially (R), is substantially (S), is (R) or is (S). In some embodiments, the stereochemistry of the chiral center within Formula (XVI) and Formula (XVII) is racemic. In some embodiments, the stereochemistry of the chiral center within Formula (XVI) and Formula (XVII) is enriched in (R). In some embodiments, the stereochemistry of the chiral center within Formula (XVI) and Formula (XVII) is enriched in (S). In some embodiments, the stereochemistry of the chiral center within Formula (XVI) and Formula (XVII) is substantially (R). In some embodiments, the stereochemistry of the chiral center within Formula (XVI) and Formula (XVII) is substantially (S). In some embodiments, the stereochemistry of the chiral center within Formula (XVI) and Formula (XVII) is (R). In some embodiments, the stereochemistry of the chiral center within Formula (XVI) and Formula (XVII) is (S).

In some embodiments of an IL-2 conjugate described herein, m in the compounds of Formula (XVI) and (XVII) is from 0 to 20, or from 0 to 18, or from 0 to 16, or from 0 to 14, or from 0 to 12, or from 0 to 10, or from 0 to 9, or from 0 to 8, or from 0 to 7, or from 0 to 6, or from 0 to 5, or from 0 to 4, or from 0 to 3, or from 0 to 2. In some embodiments of an IL-2 conjugate described herein, m in the compounds of Formula (XVI) and (XVII) is 0. In some embodiments of an IL-2 conjugate described herein, m in the compounds of Formula (XVI) and (XVII) is 1. In some embodiments of an IL-2 conjugate described herein, m in the compounds of Formula (XVI) and (XVII) is 2. In some embodiments of an IL-2 conjugate described herein, m in the compounds of Formula (XVI) and (XVII) is 3. In some embodiments of an IL-2 conjugate described herein, m in the compounds of Formula (XVI) and (XVII) is 4. In some embodiments of an IL-2 conjugate described herein, m in the compounds of Formula (XVI) and (XVII) is 5. In some embodiments of an IL-2 conjugate described herein, m in the compounds of Formula (XVI) and (XVII) is 6. In some embodiments of an IL-2 conjugate described herein, m in the compounds of Formula (XVI) and (XVII) is 7. In some embodiments of an IL-2 conjugate described herein, m in the compounds of Formula (XVI) and (XVII) is 8. In some embodiments of an IL-2 conjugate described herein, m in the compounds of Formula (XVI) and (XVII) is 9. In some embodiments of an IL-2 conjugate described herein, m in the compounds of Formula (XVI) and (XVII) is 10. In some embodiments of an IL-2 conjugate described herein, m in the compounds of Formula (XVI) and (XVII) is 11. In some embodiments of an IL-2 conjugate described herein, m in the compounds of Formula (XVI) and (XVII) is 12. In some embodiments of an IL-2 conjugate described herein, m in the compounds of Formula (XVI) and (XVII) is 13. In some embodiments of an IL-2 conjugate described herein, m in the compounds of Formula (XVI) and (XVII) is 14. In some embodiments of an IL-2 conjugate described herein, m in the compounds of Formula (XVI) and (XVII) is 15. In some embodiments of an IL-2 conjugate described herein, m in the compounds of Formula (XVI) and (XVII) is 16. In some embodiments of an IL-2 conjugate described herein, m in the compounds of Formula (XVI) and (XVII) is 17. In some embodiments of an IL-2 conjugate described herein, m in the compounds of Formula (XVI) and (XVII) is 18. In some embodiments of an IL-2 conjugate described herein, m in the compounds of Formula (XVI) and (XVII) is 19. In some embodiments of an IL-2 conjugate described herein, m in the compounds of Formula (XVI) and (XVII) is 20.

In some embodiments of an IL-2 conjugate described herein, n in the compounds of Formula (XVI) and (XVII) is in the range from about 5 to about 4600, or from about 10 to about 4000, or from about 20 to about 3000, or from about 100 to about 3000, or from about 100 to about 2900, or from about 150 to about 2900, or from about 125 to about 2900, or from about 100 to about 2500, or from about 100 to about 2000, or from about 100 to about 1900, or from about 100 to about 1850, or from about 100 to about 1750, or from about 100 to about 1650, or from about 100 to about 1500, or from about 100 to about 1400, or from about 100 to about 1300, or from about 100 to about 1250, or from about 100 to about 1150, or from about 100 to about 1100, or from about 100 to about 1000, or from about 100 to about 900, or from about 100 to about 750, or from about 100 to about 700, or from about 100 to about 600, or from about 100 to about 575, or from about 100 to about 500, or from about 100 to about 450, or from about 100 to about to about 350, or from about 100 to about 275, or from about 100 to about 230, or from about 150 to about 475, or from about 150 to about 340, or from about 113 to about 340, or from about 450 to about 800, or from about 454 to about 796, or from about 454 to about 682, or from about 340 to about 795, or from about 341 to about 682, or from about 568 to about 909, or from about 227 to about 1500, or from about 225 to about 2280, or from about 460 to about 2160, or from about 460 to about 2050, or from about 341 to about 1820, or from about 341 to about 1710, or from about 341 to about 1250, or from about 225 to about 1250, or from about 341 to about 1250, or from about 341 to about 1136, or from about 341 to about 1023, or from about 341 to about 910, or from about 341 to about 796, or from about 341 to about 682, or from about 341 to about 568, or from about 114 to about 1000, or from about 114 to about 950, or from about 114 to about 910, or from about 114 to about 800, or from about 114 to about 690, or from about 114 to about 575.

In some embodiments of an IL-2 conjugate described herein in the compounds of Formula (XVI) and (XVII), m is an integer from 0 to 6, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is an integer from 1 to 6, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is an integer from 2 to 6, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is an integer from 2 to 4, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 1, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 3, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 4, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 5, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 6, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 7, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 8, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 9, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 10, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 11, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 12, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 2, and n is an integer selected from 680, 681, 682, 794, 795, 796, 908, 909, 910, 1021, 1022, 1023, 1135, 1136, and 1137.

In some embodiments of an IL-2 conjugate described herein, n in the compounds of Formula (XVI) and (XVII) is an integer selected from 2, 5, 10, 11, 22, 23, 113, 114, 227, 228, 340, 341, 454, 455, 568, 569, 680, 681, 682, 794, 795, 796, 908, 909, 910, 1021, 1022, 1023, 1135, 1136, 1137, 1249, 1250, 1251, 1362, 1363, 1364, 1476, 1477, 1478, 1589, 1590, 1591, 1703, 1704, 1705, 1817, 1818, 1819, 1930, 1931, 1932, 2044, 2045, 2046, 2158, 2159, 2160, 2271, 2272, 2273, 2839, 2840, 2841, 2953, 2954, 2955, 3408, 3409, 3410, 3976, 3977, 3978, 4544, 4545, and 4546. In some embodiments of an IL-2 conjugate described herein, the position of the structure of Formula (XVI) and (XVII) or a mixture of Formula (XVI) and (XVII) in the amino acid sequence of the IL-2 conjugate is selected from K34, F41, F43, K42, E61, P64, R37, T40, E67, Y44, V68, and L71, wherein the position of the structure of Formula (I) in the amino acid sequence of the IL-2 conjugate is in reference to the positions in SEQ ID NO: 3. In some embodiments of an IL-2 conjugate described herein, the position of the structure of Formula (XVI) and (XVII) or a mixture of Formula (XVI) and (XVII) in the amino acid sequence of the IL-2 conjugate of SEQ ID NO: 3 is selected from K34, F41, F43, K42, E61, P64, R37, T40, E67, Y44, V68, and L71. In some embodiments of an IL-2 conjugate described herein, the position of the structure of Formula (XVI) and (XVII) or a mixture of Formula (XVI) and (XVII) in the amino acid sequence of the IL-2 conjugate of SEQ ID NO: 3 is at position K34. In some embodiments of an IL-2 conjugate described herein, the position of the structure of Formula (XVI) and (XVII) or a mixture of Formula (XVI) and (XVII) in the amino acid sequence of the IL-2 conjugate of SEQ ID NO: 3 is at position F41. In some embodiments of an IL-2 conjugate described herein, the position of the structure of Formula (XVI) and (XVII) or a mixture of Formula (XVI) and (XVII) in the amino acid sequence of the IL-2 conjugate of SEQ ID NO: 3 is at position F43. In some embodiments of an IL-2 conjugate described herein, the position of the structure of Formula (XVI) and (XVII) or a mixture of Formula (XVI) and (XVII) in the amino acid sequence of the IL-2 conjugate of SEQ ID NO: 3 is at position K42. In some embodiments of an IL-2 conjugate described herein, the position of the structure of Formula (XVI) and (XVII) or a mixture of Formula (XVI) and (XVII) in the amino acid sequence of the IL-2 conjugate of SEQ ID NO: 3 is at position E61. In some embodiments of an IL-2 conjugate described herein, the position of the structure of Formula (XVI) and (XVII) or a mixture of Formula (XVI) and (XVII) in the amino acid sequence of the IL-2 conjugate of SEQ ID NO: 3 is at position P64. In some embodiments of an IL-2 conjugate described herein, the position of the structure of Formula (XVI) and (XVII) or a mixture of Formula (XVI) and (XVII) in the amino acid sequence of the IL-2 conjugate of SEQ ID NO: 3 is at position R37. In some embodiments of an IL-2 conjugate described herein, the position of the structure of Formula (XVI) and (XVII) or a mixture of Formula (XVI) and (XVII) in the amino acid sequence of the IL-2 conjugate of SEQ ID NO: 3 is at position T40. In some embodiments of an IL-2 conjugate described herein, the position of the structure of Formula (XVI) and (XVII) or a mixture of Formula (XVI) and (XVII) in the amino acid sequence of the IL-2 conjugate of SEQ ID NO: 3 is at position E67. In some embodiments of an IL-2 conjugate described herein, the position of the structure of Formula (XVI) and (XVII) or a mixture of Formula (XVI) and (XVII) in the amino acid sequence of the IL-2 conjugate of SEQ ID NO: 3 is at position Y44. In some embodiments of an IL-2 conjugate described herein, the position of the structure of Formula (XVI) and (XVII) or a mixture of Formula (XVI) and (XVII) in the amino acid sequence of the IL-2 conjugate of SEQ ID NO: 3 is at position V68. In some embodiments of an IL-2 conjugate described herein, the position of the structure of Formula (XVI) and (XVII) or a mixture of Formula (XVI) and (XVII) in the amino acid sequence of the IL-2 conjugate of SEQ ID NO: 3 is at position L71. In some embodiments of an IL-2 conjugate described herein, the ratio of the amount of the structure of Formula (XVI) to the amount of the structure of Formula (XVII) comprising the total amount of the IL-2 conjugate is about 1:1. In some embodiments of an IL-2 conjugate described herein, the ratio of the amount of the structure of Formula (XVI) to the amount of the structure of Formula (XVII) comprising the total amount of the IL-2 conjugate is greater than 1:1. In some embodiments of an IL-2 conjugate described herein, the ratio of the amount of the structure of Formula (XVI) to the amount of the structure of Formula (XVII) comprising the total amount of the IL-2 conjugate is less than 1:1.

In some embodiments described herein are IL-2 conjugates comprising the amino acid sequence of SEQ ID NO: 3 in which at least one amino acid residue in the IL-2 conjugate is replaced by the structure of Formula (XVI) or (XVII), or a mixture of (XVI) and (XVII), wherein the amino acid residue in in SEQ ID NO: 3 that is replaced is selected from K34, F41, F43, K42, E61, P64, R37, T40, E67, Y44, V68, and L71, and wherein n is an integer from 100 to about 1150, or from about 100 to about 1100, or from about 100 to about 1000, or from about 100 to about 900, or from about 100 to about 750, or from about 100 to about 700, or from about 100 to about 600, or from about 100 to about 575, or from about 100 to about 500, or from about 100 to about 450, or from about 100 to about to about 350, or from about 100 to about 275, or from about 100 to about 230, or from about 150 to about 475, or from about 150 to about 340, or from about 113 to about 340, or from about 450 to about 800, or from about 454 to about 796, or from about 454 to about 682, or from about 340 to about 795, or from about 341 to about 682, or from about 568 to about 909, or from about 227 to about 1500, or from about 225 to about 2280, or from about 460 to about 2160, or from about 460 to about 2050, or from about 341 to about 1820, or from about 341 to about 1710, or from about 341 to about 1250, or from about 225 to about 1250, or from about 341 to about 1250, or from about 341 to about 1136, or from about 341 to about 1023, or from about 341 to about 910, or from about 341 to about 796, or from about 341 to about 682, or from about 341 to about 568, or from about 114 to about 1000, or from about 114 to about 950, or from about 114 to about 910, or from about 114 to about 800, or from about 114 to about 690, or from about 114 to about 575. In some embodiments of an IL-2 conjugate described herein, n in the compounds of formula (XVI) and (XVII) is an integer selected from 2, 5, 10, 11, 22, 23, 113, 114, 227, 228, 340, 341, 454, 455, 568, 569, 680, 681, 682, 794, 795, 796, 908, 909, 910, 1021, 1022, 1023, 1135, 1136, 1137, 1249, 1250, 1251, 1362, 1363, 1364, 1476, 1477, 1478, 1589, 1590, 1591, 1703, 1704, 1705, 1817, 1818, 1819, 1930, 1931, 1932, 2044, 2045, 2046, 2158, 2159, 2160, 2271, 2272, 2273, 2839, 2840, 2841, 2953, 2954, 2955, 3408, 3409, 3410, 3976, 3977, 3978, 4544, 4545, and 4546.

In some embodiments described herein are IL-2 conjugates comprising the amino acid sequence of SEQ ID NO: 3 in which at least one amino acid residue in the IL-2 conjugate is replaced by the structure of Formula (XVI) or (XVII), or a mixture of (XVI) and (XVII), wherein the amino acid residue in in SEQ ID NO: 3 that is replaced is selected from F41, F43, K42, E61, and P64, and wherein n is an integer from about 450 to about 800, or from about 454 to about 796, or from about 454 to about 682, or from about 568 to about 909. In some embodiments of an IL-2 conjugate described herein, n in the compounds of formula (XVI) and (XVII) is an integer selected from 454, 455, 568, 569, 680, 681, 682, 794, 795, 796, 908, 909, 910, 1021, 1022, 1023, 1135, 1136, 1137, and 1249.

In some embodiments described herein are IL-2 conjugates comprising the amino acid sequence of SEQ ID NO: 3 in which at least one amino acid residue in the IL-2 conjugate is replaced by the structure of Formula (XVI) or (XVII), or a mixture of (XVI) and (XVII), wherein the amino acid residue in SEQ ID NO: 3 that is replaced is selected from E61 and P64, and wherein n is an integer from about 450 to about 800, or from about 454 to about 796, or from about 454 to about 682, or from about 568 to about 909. In some embodiments of an IL-2 conjugate described herein, n in the compounds of formula (XVI) and (XVII) is an integer selected from 454, 455, 568, 569, 680, 681, 682, 794, 795, 796, 908, 909, and 910.

In some embodiments described herein are IL-2 conjugates comprising the amino acid sequence of SEQ ID NO: 3 in which at least one amino acid residue in the IL-2 conjugate is replaced by the structure of Formula (XVI) or (XVII), or a mixture of (XVI) and (XVII), wherein the amino acid residue in SEQ ID NO: 3 that is replaced is E61, and wherein n is an integer from about 450 to about 800, or from about 454 to about 796, or from about 454 to about 682, or from about 568 to about 909. In some embodiments of an IL-2 conjugate described herein, n in the compounds of formula (XVI) and (XVII) is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681.

In some embodiments described herein are IL-2 conjugates comprising the amino acid sequence of SEQ ID NO: 3 in which at least one amino acid residue in the IL-2 conjugate is replaced by the structure of Formula (XVI) or (XVII), or a mixture of (XVI) and (XVII), wherein the amino acid residue in in SEQ ID NO: 3 that is replaced is P64, and wherein n is an integer from about 450 to about 800, or from about 454 to about 796, or from about 454 to about 682, or from about 568 to about 909. In some embodiments of an IL-2 conjugate described herein, n in the compounds of formula (XVI) and (XVII) is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681.

Described herein are IL-2 conjugates comprising the amino acid sequence of SEQ ID NO: 3 in which at least one amino acid residue in the IL-2 conjugate is replaced by the structure of Formula (XVI) or (XVII), or a mixture of (XVI) and (XVII), wherein n is an integer such that the molecular weight of the PEG moiety is in the range from about 1,000 Daltons about 200,000 Daltons, or from about 2,000 Daltons to about 150,000 Daltons, or from about 3,000 Daltons to about 125,000 Daltons, or from about 4,000 Daltons to about 100,000 Daltons, or from about 5,000 Daltons to about 100,000 Daltons, or from about 6,000 Daltons to about 90,000 Daltons, or from about 7,000 Daltons to about 80,000 Daltons, or from about 8,000 Daltons to about 70,000 Daltons, or from about 5,000 Daltons to about 70,000 Daltons, or from about 5,000 Daltons to about 65,000 Daltons, or from about 5,000 Daltons to about 60,000 Daltons, or from about 5,000 Daltons to about 50,000 Daltons, or from about 6,000 Daltons to about 50,000 Daltons, or from about 7,000 Daltons to about 50,000 Daltons, or from about 7,000 Daltons to about 45,000 Daltons, or from about 7,000 Daltons to about 40,000 Daltons, or from about 8,000 Daltons to about 40,000 Daltons, or from about 8,500 Daltons to about 40,000 Daltons, or from about 8,500 Daltons to about 35,000 Daltons, or from about 9,000 Daltons to about 50,000 Daltons, or from about 9,000 Daltons to about 45,000 Daltons, or from about 9,000 Daltons to about 40,000 Daltons, or from about 9,000 Daltons to about 35,000 Daltons, or from about 9,000 Daltons to about 30,000 Daltons, or from about 9,500 Daltons to about 35,000 Daltons, or from about 9,500 Daltons to about 30,000 Daltons, or from about 10,000 Daltons to about 50,000 Daltons, or from about 10,000 Daltons to about 45,000 Daltons, or from about 10,000 Daltons to about 40,000 Daltons, or from about 10,000 Daltons to about 35,000 Daltons, or from about 10,000 Daltons to about 30,000 Daltons, or from about 15,000 Daltons to about 50,000 Daltons, or from about 15,000 Daltons to about 45,000 Daltons, or from about 15,000 Daltons to about 40,000 Daltons, or from about 15,000 Daltons to about 35,000 Daltons, or from about 15,000 Daltons to about 30,000 Daltons, or from about 20,000 Daltons to about 50,000 Daltons, or from about 20,000 Daltons to about 45,000 Daltons, or from about 20,000 Daltons to about 40,000 Daltons, or from about 20,000 Daltons to about 35,000 Daltons, or from about 20,000 Daltons to about 30,000 Daltons. Described herein are IL-2 conjugates comprising the amino acid sequence of SEQ ID NO: 3 in which at least one amino acid residue in the IL-2 conjugate is replaced by the structure of Formula (XVI) or (XVII), or a mixture of (XVI) and (XVII), wherein n is an integer such that the molecular weight of the PEG moiety is about 5,000 Daltons, about 7,500 Daltons, about 10,000 Daltons, about 15,000 Daltons, about 20,000 Daltons, about 25,000 Daltons, about 30,000 Daltons, about 35,000 Daltons, about 40,000 Daltons, about 45,000 Daltons, about 50,000 Daltons, about 60,000 Daltons, about 70,000 Daltons, about 80,000 Daltons, about 90,000 Daltons, about 100,000 Daltons, about 125,000 Daltons, about 150,000 Daltons, about 175,000 Daltons or about 200,000 Daltons. Described herein are IL-2 conjugates comprising the amino acid sequence of SEQ ID NO: 3 in which at least one amino acid residue in the IL-2 conjugate is replaced by the structure of Formula (XVI) or (XVII), or a mixture of (XVI) and (XVII), wherein n is an integer such that the molecular weight of the PEG moiety is about 5,000 Daltons, about 7,500 Daltons, about 10,000 Daltons, about 15,000 Daltons, about 20,000 Daltons, about 25,000 Daltons, about 30,000 Daltons, about 35,000 Daltons, about 40,000 Daltons, about 45,000 Daltons, or about 50,000 Daltons.

In some embodiments described herein are IL-2 conjugates comprising the amino acid sequence of SEQ ID NO: 3 in which at least one amino acid residue in the IL-2 conjugate is replaced by the structure of Formula (XVI) or (XVII), or a mixture of (XVI) and (XVII), wherein the amino acid residue in in SEQ ID NO: 3 that is replaced is selected from F41, F43, K42, E61, and P64, m is an integer from 0 to 6, and n is an integer from about 450 to about 800, or from about 454 to about 796, or from about 454 to about 682, or from about 568 to about 909. In some embodiments of an IL-2 conjugate described herein in the compounds of formula (XVI) and (XVII), m is 2, and n is an integer selected from 454, 455, 568, 569, 680, 681, 682, 794, 795, 796, 908, 909, 910, 1021, 1022, 1023, 1135, 1136, 1137, and 1249.

In some embodiments described herein are IL-2 conjugates comprising the amino acid sequence of SEQ ID NO: 3 in which at least one amino acid residue in the IL-2 conjugate is replaced by the structure of Formula (XVI) or (XVII), or a mixture of (XVI) and (XVII), wherein the amino acid residue in SEQ ID NO: 3 that is replaced is selected from E61 and P64, and wherein m is an integer from 0 to 6, and n is an integer from about 450 to about 800, or from about 454 to about 796, or from about 454 to about 682, or from about 568 to about 909. In some embodiments of an IL-2 conjugate described herein in the compounds of formula (XVI) and (XVII), m is 2, and n is an integer selected from 454, 455, 568, 569, 680, 681, 682, 794, 795, 796, 908, 909, and 910.

In some embodiments described herein are IL-2 conjugates comprising the amino acid sequence of SEQ ID NO: 3 in which at least one amino acid residue in the IL-2 conjugate is replaced by the structure of Formula (XVI) or (XVII), or a mixture of (XVI) and (XVII), wherein the amino acid residue in SEQ ID NO: 3 that is replaced is E61, and wherein m is an integer from 0 to 6, and n is an integer from about 450 to about 800, or from about 454 to about 796, or from about 454 to about 682, or from about 568 to about 909. In some embodiments of an IL-2 conjugate described herein in the compounds of formula (XVI) and (XVII), m is 2, and n is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681.

In some embodiments described herein are IL-2 conjugates comprising the amino acid sequence of SEQ ID NO: 3 in which at least one amino acid residue in the IL-2 conjugate is replaced by the structure of Formula (XVI) or (XVII), or a mixture of (XVI) and (XVII), wherein the amino acid residue in in SEQ ID NO: 3 that is replaced is P64, and wherein m is an integer from 0 to 6, and n is an integer from about 450 to about 800, or from about 454 to about 796, or from about 454 to about 682, or from about 568 to about 909. In some embodiments of an IL-2 conjugate described herein in the compounds of formula (XVI) and (XVII), m is 2, and n is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681.

Described herein are pharmaceutical compositions comprising an effective amount of an IL-conjugate described herein and one or more pharmaceutically acceptable excipients.

Described herein are methods of treating cancer in a subject, comprising administering to a subject in need thereof an effective amount of an IL-2 conjugate described herein. In some embodiments of a method of treating cancer described herein, the cancer in the subject is selected from renal cell carcinoma (RCC), non-small cell lung cancer (NSCLC), head and neck squamous cell cancer (HNSCC), classical Hodgkin lymphoma (cHL), primary mediastinal large B-cell lymphoma (PMBCL), urothelial carcinoma, microsatellite unstable cancer, microsatellite stable cancer, gastric cancer, cervical cancer, hepatocellular carcinoma (HCC), Merkel cell carcinoma (MCC), melanoma, small cell lung cancer (SCLC), esophageal, glioblastoma, mesothelioma, breast cancer, triple-negative breast cancer, prostate cancer, castrate-resistant prostate cancer, metastatic castrate-resistant prostate cancer, metastatic castrate-resistant prostate cancer having DNA damage response (DDR) defects, bladder cancer, ovarian cancer, tumors of moderate to low mutational burden, cutaneous squamous cell carcinoma (CSCC), squamous cell skin cancer (SCSC), tumors of low- to non-expressing PD-L1, tumors disseminated systemically to the liver and CNS beyond their primary anatomic originating site, and diffuse large B-cell lymphoma. Described herein are methods of treating cancer in a subject, comprising administering to a subject in need thereof an effective amount of an IL-2 conjugate described herein. In some embodiments of a method of treating cancer described herein, the cancer in the subject is cholangiocarcinoma. In some embodiments of a method of treating cancer described herein, the cancer in the subject is selected from renal cell carcinoma (RCC), non-small cell lung cancer (NSCLC), urothelial carcinoma, and melanoma. In some embodiments of a method of treating cancer described herein, the IL-2 conjugate is administered to the subject in need thereof once every two weeks, once every three weeks, once every 4 weeks, once every 5 weeks, once every 6 weeks, once every 7 weeks, or once every 8 weeks. In some embodiments of a method of treating cancer described herein, the IL-2 conjugate is administered to the subject in need thereof once per week or once every two weeks. In some embodiments of a method of treating cancer described herein, the IL-2 conjugate is administered to the subject in need thereof once per week. In some embodiments of a method of treating cancer described herein, the IL-2 conjugate is administered to the subject in need thereof once every two weeks. In some embodiments of a method of treating cancer described herein, administration of the effective amount of the IL-2 conjugate to the subject does not cause vascular leak syndrome in the subject. In some embodiments of a method of treating cancer described herein, administration of the effective amount of the IL-2 conjugate to the subject does not cause Grade 2, Grade 3, or Grade 4 vascular leak syndrome in the subject. In some embodiments of a method of treating cancer described herein, administration of the effective amount of the IL-2 conjugate to the subject does not cause Grade 2 vascular leak syndrome in the subject. In some embodiments of a method of treating cancer described herein, administration of the effective amount of the IL-2 conjugate to the subject does not cause Grade 3 vascular leak syndrome in the subject. In some embodiments of a method of treating cancer described herein, administration of the effective amount of the IL-2 conjugate to the subject does not cause Grade 4 vascular leak syndrome in the subject. In some embodiments of a method of treating cancer described herein, administration of the effective amount of the IL-2 conjugate to the subject does not cause loss of vascular tone in the subject. In some embodiments of a method of treating cancer described herein, administration of the effective amount of the IL-2 conjugate to the subject does not cause extravasation of plasma proteins and fluid into the extravascular space in the subject. In some embodiments of a method of treating cancer described herein, administration of the effective amount of the IL-2 conjugate to the subject does not cause hypotension and reduced organ perfusion in the subject. In some embodiments of a method of treating cancer described herein, administration of the effective amount of the IL-2 conjugate to the subject does not cause impaired neutrophil function in the subject. In some embodiments of a method of treating cancer described herein, administration of the effective amount of the IL-2 conjugate to the subject does not cause reduced chemotaxis in the subject. In some embodiments of a method of treating cancer described herein, administration of the effective amount of the IL-2 conjugate to the subject is not associated with an increased risk of disseminated infection in the subject. In some embodiments of a method of treating cancer described herein, the disseminated infection is sepsis or bacterial endocarditis. In some embodiments of a method of treating cancer described herein, the disseminated infection is sepsis. In some embodiments of a method of treating cancer described herein, the disseminated infection is bacterial endocarditis. In some embodiments of a method of treating cancer described herein, the subject is treated for any preexisting bacterial infections prior to administration of the IL-2 conjugate. In some embodiments of a method of treating cancer described herein, the subject is treated with an antibacterial agent selected from oxacillin, nafcillin, ciprofloxacin, and vancomycin prior to administration of the IL-2 conjugate. In some embodiments of a method of treating cancer described herein, administration of the effective amount of the IL-2 conjugate to the subject does not exacerbate a pre-existing or initial presentation of an autoimmune disease or an inflammatory disorder in the subject. In some embodiments of a method of treating cancer described herein, the administration of the effective amount of the IL-2 conjugate to the subject does not exacerbate a pre-existing or initial presentation of an autoimmune disease in the subject. In some embodiments of a method of treating cancer described herein, the administration of the effective amount of the IL-2 conjugate to the subject does not exacerbate a pre-existing or initial presentation of an inflammatory disorder in the subject. In some embodiments of a method of treating cancer described herein, the autoimmune disease or inflammatory disorder in the subject is selected from Crohn's disease, scleroderma, thyroiditis, inflammatory arthritis, diabetes mellitus, oculo-bulbar myasthenia gravis, crescentic IgA glomerulonephritis, cholecystitis, cerebral vasculitis, Stevens-Johnson syndrome and bullous pemphigoid. In some embodiments of a method of treating cancer described herein, the autoimmune disease or inflammatory disorder in the subject is Crohn's disease. In some embodiments of a method of treating cancer described herein, the autoimmune disease or inflammatory disorder in the subject is scleroderma. In some embodiments of a method of treating cancer described herein, the autoimmune disease or inflammatory disorder in the subject is thyroiditis. In some embodiments of a method of treating cancer described herein, the autoimmune disease or inflammatory disorder in the subject is inflammatory arthritis. In some embodiments of a method of treating cancer described herein, the autoimmune disease or inflammatory disorder in the subject is diabetes mellitus. In some embodiments of a method of treating cancer described herein, the autoimmune disease or inflammatory disorder in the subject is oculo-bulbar myasthenia gravis. In some embodiments of a method of treating cancer described herein, the autoimmune disease or inflammatory disorder in the subject is crescentic IgA glomerulonephritis. In some embodiments of a method of treating cancer described herein, the autoimmune disease or inflammatory disorder in the subject is cholecystitis. In some embodiments of a method of treating cancer described herein, the autoimmune disease or inflammatory disorder in the subject is cerebral vasculitis. In some embodiments of a method of treating cancer described herein, the autoimmune disease or inflammatory disorder in the subject is Stevens-Johnson syndrome. In some embodiments of a method of treating cancer described herein, the autoimmune disease or inflammatory disorder in the subject is bullous pemphigoid. In some embodiments of a method of treating cancer described herein, administration of the effective amount of the IL-2 conjugate to the subject does not cause changes in mental status, speech difficulties, cortical blindness, limb or gait ataxia, hallucinations, agitation, obtundation, or coma in the subject. In some embodiments of a method of treating cancer described herein, administration of the effective amount of the IL-2 conjugate to the subject does not cause seizures in the subject. In some embodiments of a method of treating cancer described herein, administration of the effective amount of the IL-2 conjugate to the subject is not contraindicated in subjects having a known seizure disorder. In some embodiments of a method of treating cancer described herein, administration of the effective amount of the IL-2 conjugate to the subject does not cause capillary leak syndrome in the subject. In some embodiments of a method of treating cancer described herein, administration of the effective amount of the IL-2 conjugate to the subject does not cause Grade 2, Grade 3, or Grade 4 capillary leak syndrome in the subject. In some embodiments of a method of treating cancer described herein, administration of the effective amount of the IL-2 conjugate to the subject does not cause Grade 2 capillary leak syndrome in the subject. In some embodiments of a method of treating cancer described herein, administration of the effective amount of the IL-2 conjugate to the subject does not cause Grade 3 capillary leak syndrome in the subject. In some embodiments of a method of treating cancer described herein, administration of the effective amount of the IL-2 conjugate to the subject does not cause Grade 4 capillary leak syndrome in the subject. In some embodiments of a method of treating cancer described herein, administration of the effective amount of the IL-2 conjugate to the subject does not cause a drop in mean arterial blood pressure in the subject following administration of the IL-2 conjugate to the subject. In some embodiments of a method of treating cancer described herein, administration of the effective amount of the IL-2 conjugate to the subject does not cause hypotension in the subject following administration of the IL-2 conjugate to the subject. In some embodiments of a method of treating cancer described herein, administration of the effective amount of the IL-2 conjugate to the subject does not cause the subject to experience a systolic blood pressure below 90 mm Hg or a 20 mm Hg drop from baseline systolic pressure following administration of the IL-2 conjugate to the subject. In some embodiments of a method of treating cancer described herein, administration of the effective amount of the IL-2 conjugate to the subject does not cause edema in the subject following administration of the IL-2 conjugate to the subject. In some embodiments of a method of treating cancer described herein, administration of the effective amount of the IL-2 conjugate to the subject does not cause impairment of kidney or liver function in the subject following administration of the IL-2 conjugate to the subject. In some embodiments of a method of treating cancer described herein, administration of the effective amount of the IL-2 conjugate to the subject does not cause eosinophilia in the subject following administration of the IL-2 conjugate to the subject. In some embodiments of a method of treating cancer described herein, administration of the effective amount of the IL-2 conjugate to the subject does not cause the eosinophil count in the peripheral blood of the subject to exceed 500 per L following administration of the IL-2 conjugate to the subject. In some embodiments of a method of treating cancer described herein, administration of the effective amount of the IL-2 conjugate to the subject does not cause the eosinophil count in the peripheral blood of the subject to exceed 500 μL to 1500 per μL following administration of the IL-2 conjugate to the subject. In some embodiments of a method of treating cancer described herein, administration of the effective amount of the IL-2 conjugate to the subject does not cause the eosinophil count in the peripheral blood of the subject to exceed 1500 per L to 5000 per μL following administration of the IL-2 conjugate to the subject. In some embodiments of a method of treating cancer described herein, administration of the effective amount of the IL-2 conjugate to the subject does not cause the eosinophil count in the peripheral blood of the subject to exceed 5000 per L following administration of the IL-2 conjugate to the subject. In some embodiments of a method of treating cancer described herein, administration of the effective amount of the IL-2 conjugate to the subject is not contraindicated in subjects on an existing regimen of psychotropic drugs.

In some embodiments of a method of treating cancer described herein, administration of the effective amount of the IL-2 conjugate to the subject is not contraindicated in subjects on an existing regimen of nephrotoxic, myelotoxic, cardiotoxic, or hepatotoxic drugs. In some embodiments of a method of treating cancer described herein, administration of the effective amount of the IL-2 conjugate to the subject is not contraindicated in subjects on an existing regimen of aminoglycosides, cytotoxic chemotherapy, doxorubicin, methotrexate, or asparaginase. In some embodiments of a method of treating cancer described herein, administration of the effective amount of the IL-2 conjugate to the subject is not contraindicated in subjects receiving combination regimens containing antineoplastic agents. In some embodiments of a method of treating cancer described herein, the antineoplastic agent is selected from dacarbazine, cis-platinum, tamoxifen and interferon-alfa. In some embodiments of a method of treating cancer described herein, administration of the effective amount of the IL-2 conjugate to the subject does not cause one or more Grade 4 adverse events in the subject following administration of the IL-2 conjugate to the subject. In some embodiments of a method of treating cancer described herein, the one or more Grade 4 adverse events are selected from hypothermia; shock; bradycardia; ventricular extrasystoles; myocardial ischemia; syncope; hemorrhage; atrial arrhythmia; phlebitis; AV block second degree; endocarditis; pericardial effusion; peripheral gangrene; thrombosis; coronary artery disorder; stomatitis; nausea and vomiting; liver function tests abnormal; gastrointestinal hemorrhage; hematemesis; bloody diarrhea; gastrointestinal disorder; intestinal perforation; pancreatitis; anemia; leukopenia; leukocytosis; hypocalcemia; alkaline phosphatase increase; blood urea nitrogen (BUN) increase; hyperuricemia; non-protein nitrogen (NPN) increase; respiratory acidosis; somnolence; agitation; neuropathy; paranoid reaction; convulsion; grand mal convulsion; delirium; asthma, lung edema; hyperventilation; hypoxia; hemoptysis; hypoventilation; pneumothorax; mydriasis; pupillary disorder; kidney function abnormal; kidney failure; and acute tubular necrosis. In some embodiments of a method of treating cancer described herein, administration of the effective amount of the IL-2 conjugate to a group of subjects does not cause one or more Grade 4 adverse events in greater than 1% of the subjects following administration of the IL-2 conjugate to the subjects. In some embodiments of a method of treating cancer described herein, the one or more Grade 4 adverse events are selected from hypothermia; shock; bradycardia; ventricular extrasystoles; myocardial ischemia; syncope; hemorrhage; atrial arrhythmia; phlebitis; AV block second degree; endocarditis; pericardial effusion; peripheral gangrene; thrombosis; coronary artery disorder; stomatitis; nausea and vomiting; liver function tests abnormal; gastrointestinal hemorrhage; hematemesis; bloody diarrhea; gastrointestinal disorder; intestinal perforation; pancreatitis; anemia; leukopenia; leukocytosis; hypocalcemia; alkaline phosphatase increase; blood urea nitrogen (BUN) increase; hyperuricemia; non-protein nitrogen (NPN) increase; respiratory acidosis; somnolence; agitation; neuropathy; paranoid reaction; convulsion; grand mal convulsion; delirium; asthma, lung edema; hyperventilation; hypoxia; hemoptysis; hypoventilation; pneumothorax; mydriasis; pupillary disorder; kidney function abnormal; kidney failure; and acute tubular necrosis. In some embodiments of a method of treating cancer described herein, administration of the effective amount of the IL-2 conjugate to a group of subjects does not cause one or more adverse events in greater than 1% of the subjects following administration of the IL-2 conjugate to the subjects, wherein the one or more adverse events is selected from duodenal ulceration; bowel necrosis; myocarditis; supraventricular tachycardia; permanent or transient blindness secondary to optic neuritis; transient ischemic attacks; meningitis; cerebral edema; pericarditis; allergic interstitial nephritis; and tracheo-esophageal fistula. In some embodiments of a method of treating cancer described herein, administration of the effective amount of the IL-2 conjugate to a group of subjects does not cause one or more adverse events in greater than 1% of the subjects following administration of the IL-2 conjugate to the subjects, wherein the one or more adverse events is selected from malignant hyperthermia; cardiac arrest; myocardial infarction; pulmonary emboli; stroke; intestinal perforation; liver or renal failure; severe depression leading to suicide; pulmonary edema; respiratory arrest; respiratory failure. In some embodiments of a method of treating cancer described herein, administration of the effective amount of the IL-2 conjugate to a subject does not result in the production of neutralizing antibodies to the IL-2 conjugate. In some embodiments of a method of treating cancer described herein, administration of the IL-2 conjugate to the subject increases the number of peripheral CD8+ T and NK cells in the subject without increasing the number of peripheral CD4+ regulatory T cells in the subject. In some embodiments of a method of treating cancer described herein, administration of the IL-2 conjugate to the subject increases the number of peripheral CD8+ T and NK cells in the subject without increasing the number of peripheral eosinophils in the subject. In some embodiments of a method of treating cancer described herein, administration of the IL-2 conjugate to the subject increases the number of intratumoral CD8+ T and NK cells in the subject without increasing the number of intratumoral CD4+ regulatory T cells in the subject. In some embodiments of a method of treating cancer described herein, administration of the effective amount of the IL-2 conjugate to the subject does not require the availability of an intensive care facility or skilled specialists in cardiopulmonary or intensive care medicine. In some embodiments of a method of treating cancer described herein, administration of the effective amount of the IL-2 conjugate to the subject does not require the availability of an intensive care facility. In some embodiments of a method of treating cancer described herein, administration of the effective amount of the IL-2 conjugate to the subject does not require the availability of skilled specialists in cardiopulmonary or intensive care medicine.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A illustrates exemplary lysine derivatives. FIG. 2B illustrates exemplary phenylalanine derivatives.

FIG. 3B—UAA #43-89; FIG. 3C—UAA #90-128; FIG. 3D—UAA #129-167). FIGS. 3A-3D are adopted from Table 1 of Dumas et al., *Chemical Science* 2015, 6, 50-69.

FIG. 4A shows SPR analysis of IL-2 variants binding to immobilized IL-2 Rα. FIG. 4B shows SPR analysis of IL-2 variants binding to immobilized IL-2 Rβ. FIG. 4C shows SPR analysis of recombinant IL-2 and IL-2 variant F42_30kD binding to immobilized IL-2 Ra and IL-2 Rβ.

FIG. 5A: native IL-2; FIG. 5B: P65_30kD; FIG. 5C: K64_30kD; FIG. 5D: K43_30kD; FIG. 5E: K35_30kD, and FIG. 5F: F42_30kD.

FIG. 6A: native IL-2; FIG. 6B: E62K; FIG. 6C: E62_30 kD.

FIG. 11A shows memory CD8+CD44+ T cell proliferation at 72, 96 and 120 hours. FIG. 11B shows flow cytometry analysis of those cells at the 120 h time point.

FIG. 12A shows percentage of NK, CD8+ T and CD4+ T reg cells in P65_30kD-treated vs untreated (vehicle) animals at Day 5 of treatment. FIG. 12B shows the ratio of CD8+/CD4+ Treg cells in P65_30 kD-treated and control (vehicle) animals. Data were analyzed using uinpaired Student t test. *** designate P values<0.001.

FIG. 13A shows cytokine levels for aldesleukin-dosed animals and FIG. 13B for P65_30 kD-dosed animals.

FIG. 16A shows immune cell expansion after treatment with IL-2 (control). FIG. 16B shows immune cell expansion after treatment with P65_30kD.

DETAILED DESCRIPTION OF THE DISCLOSURE

Figure 1:
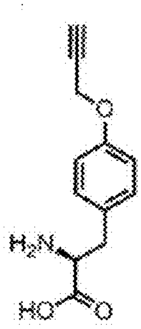
FIG. 1 shows exemplary unnatural amino acids. This figure is adapted from FIG. 2 of Young et al., "Beyond the canonical 20 amino acids: expanding the genetic lexicon," *J. of Biological Chemistry* 285(15): 11039-11044 (2010).
Figure 1:
Figure 1:
Figure 1:
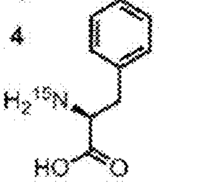
Figure 1:
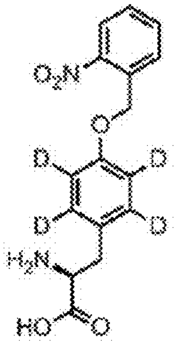
Figure 1:
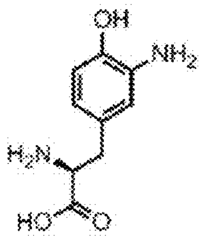
Figure 1:
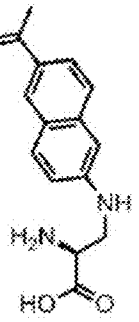
Figure 1:
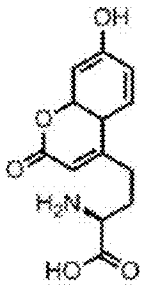
Figure 1:
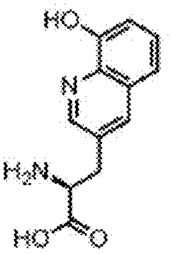
Figure 1:
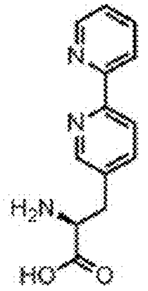
Figure 1:
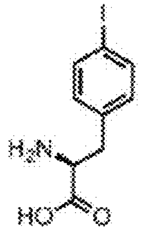
Figure 1:
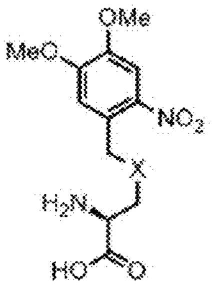
Figure 1:
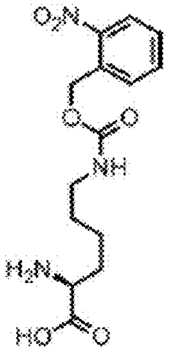
Figure 1:
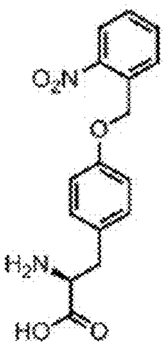
Figure 1:
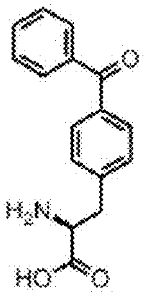
Figure 1:
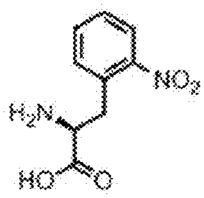
Figure 1:
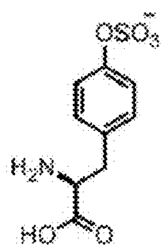
Figure 1:
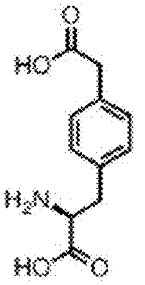
Figure 1:
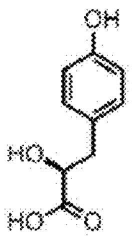
Figure 1:
Figure 1:
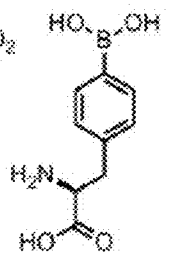

Cytokines comprise a family of cell signaling proteins such as chemokines, interferons, interleukins, lymphokines, tumor necrosis factors, and other growth factors playing roles in innate and adaptive immune cell homeostasis. Cytokines are produced by immune cells such as macrophages, B lymphocytes, T lymphocytes and mast cells, endothelial cells, fibroblasts, and different stromal cells. In some instances, cytokines modulate the balance between humoral and cell-based immune responses.

Interleukins are signaling proteins which modulate the development and differentiation of T and B lymphocytes, cell of the monocytic lineage, neutrophils, basophils, eosinophils, megakaryocytes, and hematopoietic cells. Interleukins are produced by helper CD4 T and B lymphocytes, monocytes, macrophages, endothelial cells, and other tissue residents.

Interleukin 2 (IL-2) is a pleiotropic type-1 cytokine whose structure comprises a 15.5 kDa four α-helix bundle. The precursor form of IL-2 is 153 amino acid residues in length, with the first 20 amino acids forming a signal peptide and residues 21-153 forming the mature form. IL-2 is produced primarily by CD4+ T cells post antigen stimulation and to a lesser extent, by CD8+ cells, Natural Killer (NK) cells, and Natural killer T (NKT) cells, activated dendritic cells (DCs), and mast cells. IL-2 signaling occurs through interaction with specific combinations of IL-2 receptor (IL-2R) subunits, IL-2Rα (also known as CD25), IL-2Rβ (also known as CD122), and IL-2Rβγ (also known as CD132). Interaction of IL-2 with the IL-2Rα forms the “low-affinity” IL-2 receptor complex with a $K_d$ of about $10^{-8}$ M. Interaction of IL-2 with IL-2Rβ and IL-2Rγ forms the “intermediate-affinity” IL-2 receptor complex with a $K_d$ of about $10^{-9}$ M. Interaction of IL-2 with all three subunits, IL-2Rα, IL-2Rβ, and IL-2Rβγ, forms the “high-affinity” IL-2 receptor complex with a $K_d$ of about $>10^{-11}$ M.

In some instances, IL-2 signaling via the “high-affinity” IL-2Rαβγ complex modulates the activation and proliferation of regulatory T cells. Regulatory T cells, or $CD4^+$ $CD25^+Foxp3^+$ regulatory T (Treg) cells, mediate maintenance of immune homeostasis by suppression of effector cells such as $CD4^+$ T cells, $CD8^+$ T cells, B cells, NK cells, and NKT cells. In some instances, Treg cells are generated from the thymus (tTreg cells) or are induced from naïve T cells in the periphery (pTreg cells). In some cases, Treg cells are considered as the mediator of peripheral tolerance. Indeed, in one study, transfer of CD25-depleted peripheral $CD4^+$ T cells produced a variety of autoimmune diseases in nude mice, whereas cotransfer of $CD4^+CD25^+$ T cells suppressed the development of autoimmunity (Sakaguchi, et al., "Immunologic self-tolerance maintained by activated T cells expressing IL-2 receptor alpha-chains (CD25)," *J. Immunol.* 155(3): 1151-1164 (1995)). Augmentation of the Treg cell population down-regulates effector T cell proliferation and suppresses autoimmunity and T cell anti-tumor responses.

IL-2 signaling via the "intermediate-affinity" IL-2Rβγ complex modulates the activation and proliferation of CD8+ effector T (Teff) cells, NK cells, and NKT cells. CD8+ Teff cells (also known as cytotoxic T cells, Tc cells, cytotoxic T lymphocytes, CTLs, T-killer cells, cytolytic T cells, Tcon, or killer T cells) are T lymphocytes that recognize and kill damaged cells, cancerous cells, and pathogen-infected cells. NK and NKT cells are types of lymphocytes that, similar to CD8+ Teff cells, target cancerous cells and pathogen-infected cells.

In some instances, IL-2 signaling is utilized to modulate T cell responses and subsequently for treatment of a cancer. For example, IL-2 is administered in a high-dose form to induce expansion of Teff cell populations for treatment of a cancer. However, high-dose IL2 further leads to concomitant stimulation of Treg cells that dampen anti-tumor immune responses. High-dose IL-2 also induces toxic adverse events mediated by the engagement of IL-2R alpha chain-expressing cells in the vasculature, including type 2 innate immune cells (ILC-2), eosinophils and endothelial cells. This leads to eosinophilia, capillary leak and vascular leak syndrome VLS).

Adoptive cell therapy enables physicians to effectively harness a patient's own immune cells to fight diseases such as proliferative disease (e.g., cancer) as well as infectious disease. In one non-limiting example, T lymphocytes may be harvested from the patient, reengineered to target a specific antigen on the surface of malignant cells, and reintroduced into the body of the patient to specifically target the malignant cells. In addition, adoptive cell therapies provide a sustained response in the body by signaling to the immune cells to grow and divide long after the reintroduction of the reengineered cells into the patient's immune system.

Disclosed herein, in certain embodiments, is a method of selectively upregulating distinct population(s) of lymphocytes (e.g., CD4+ helper cells, CD8+ effector naïve and memory cells, NK cells, or NKT cells) through cytokine/cytokine receptor signaling. In some instances, the cytokine comprises an interleukin, an interferon, or a tumor necrosis factor. In some cases, the cytokine is a cytokine conjugate, e.g., an interleukin conjugate, an interferon conjugate, or a tumor necrosis factor conjugate. In additional cases, described herein comprise pharmaceutical compositions and kits comprising one or more cytokine conjugates described herein.

In some embodiments, also described herein is a method of selectively upregulating CD4+ helper cell, CD8+ effector naïve and memory cell, NK cell, and/or NKT cell populations through IL-2/IL-2R signaling. In some instances, IL-2 is an IL-2 conjugate, which interacts with the "intermediate-affinity" IL-2Rβγ complex, optionally with a similar potency as the IL-2Rαβγ complex, and with a weakened IL-2Rα interaction relative to wild-type IL-2. In some embodiments, further described herein are methods of treating a cancer with use of an IL-2 conjugate described herein. In additional embodiments, described herein are pharmaceutical compositions and kits which comprise one or more IL-2 conjugates described herein. In some embodiments, the IL-2 conjugates comprise conjugating moieties (e.g., a PEG) that contribute to an increase or a decrease in "clearance rate," or plasma half-life in a subject, without affecting the pharmacokinetics, including the desired cytokine-receptor interactions and immune cell expansion.

Disclosed herein, in some embodiments, are reagents that may be used to develop adoptive cell therapies comprising cells engineered to express modified cytokines that result in selective cytokine-receptor interactions and immune cell expansion. In some embodiments, the reagents comprise a nucleic acid construct encoding the IL-2 conjugates described above. Also disclosed are adoptive cell therapies comprising the IL-2 conjugates described above that may be useful for the treatment of proliferative or infectious disease described herein.

Disclosed herein, in some embodiments, are compositions that result in selective cytokine-receptor interactions and immune cell expansion. In some embodiments, the reagents comprise a nucleic acid construct encoding the IL-2 conjugates described above. Also disclosed are pharmaceutical compositions comprising the IL-2 conjugates described above that may be useful for the treatment of proliferative or infectious disease described herein.

Cytokine Conjugates

In some embodiments, described herein are cytokine conjugates. In some instances, the cytokine comprises an interleukins, a tumor necrosis factor, an interferon, a chemokine, a lymphokine, or a growth factor. In some instances, the cytokine is an interleukin. In some cases, the cytokine is an interferon. In additional cases, the cytokine is a tumor necrosis factor. In further cases, the cytokine is a growth factor.

In some embodiments, described herein is an interleukin conjugate. Exemplary interleukins include, but are not limited to interleukin 2 (IL-2).

IL-2 Conjugates

Described herein are polypeptides shown in Table 20. In some embodiments, IL-2 conjugates described herein are exemplified in Table 20.

TABLE 20

| Name | Sequence | SEQ ID NO: |
|---|---|---|
| IL-2 (*homo sapiens*) (mature form) | APTSSSTKKTQLQLEHLLLDLQMILNGINNYKNPKLTRML TFKFYMPKKATELKEILQCLEEELKPLEEVLNLAQSKNFEIL RPRDLISNINVIVLELKGSETTFMCEYADETATIVEFLNRWI TFCQSIISTLT | 1 |
| IL-2 (*homo sapiens*) (precursor) | MYRMQLLSCIALSLALVTNSAPTSSSTKKTQLQLEHLLLDL QMILNGINNYKNPKLTRMLTFKFYMPKKATELKHLQCLEE ELKPLEEVLNLAQSKNFHLRPRDLISNINVIVLELKGSETTF | 2 |

TABLE 20 -continued

| Name | Sequence | SEQ ID NO: |
|---|---|---|
| NCBI Accession No.: AAB46883.1 | MCEYADETATIVEFLNRWITFCQSIISTLT | |
| aldesleukin | PTSSSTKKTQLQLEHLLLDLQMILNGINNYKNPKLTRMLTF KFYMPKKATELKEILQCLEEELKPLEEVLNLAQSKNFHLRP RDLISNINVIVLELKGSETTFMCEYADETATIVEFLNRWITF SQSIISTLT | 3 |
| IL-2_C125S | APTSSSTKKTQLQLEHLLLDLQMILNGINNYKNPKLTRML TFKFYMPKKATELKEILQCLEEELKPLEEVLNLAQSKNFEIL RPRDLISNINVIVLELKGSETTFMCEYADETATIVEFLNRWI TFSQSIISTLT | 4 |
| IL-2_P65X | APTSSSTKKTQLQLEHLLLDLQMILNGINNYKNPKLTRML TFKFYMPKKATELKEILQCLEEELK**X**LEEVLNLAQSKNFEIL RPRDLISNINVIVLELKGSETTFMCEYADETATIVEFLNRWI TFSQSIISTLT | 5 |
| IL-2_E62X | APTSSSTKKTQLQLEEILLLDLQMILNGINNYKNPKLTRML TFKFYMPKKATELKHLQCLEE**X**LKPLEEVLNLAQSKNFHL RPRDLISNINVIVLELKGSETTFMCEYADETATIVEFLNRWI TFSQSIISTLT | 6 |
| IL-2_F42X | APTSSSTKKTQLQLEFILLLDLQMILNGINNYKNPKLTRML T**X**KFYMPKKATELKEILQCLEEELKPLEEVLNLAQSKNFEIL RPRDLISNINVIVLELKGSETTFMCEYADETATIVEFLNRWI TFSQSIISTLT | 7 |
| IL-2_K43X | APTSSSTKKTQLQLEFILLLDLQMILNGINNYKNPKLTRML TF**X**FYMPKKATELKEILQCLEEELKPLEEVLNLAQSKNFEIL RPRDLISNINVIVLELKGSETTFMCEYADETATIVEFLNRWI TFSQSIISTLT | 8 |
| IL-2_K35X | APTSSSTKKTQLQLEFILLLDLQMILNGINNYKNP**X**LTRML TFKFYMPKKATELKEILQCLEEELKPLEEVLNLAQSKNFEIL RPRDLISNINVIVLELKGSETTFMCEYADETATIVEFLNRWI TFSQSIISTLT | 9 |
| IL-2_P65[AzK] | APTSSSTKKTQLQLEFILLLDLQMILNGINNYKNPKLTRML TFKFYMPKKATELKEILQCLEEELK[**AzK**]LEEVLNLAQSKN FHLRPRDLISNINVIVLELKGSETTFMCEYADETATIVEFLN RWITFSQSIISTLT | 10 |
| IL-2_E62[AzK] | APTSSSTKKTQLQLEFILLLDLQMILNGINNYKNPKLTRML TFKFYMPKKATELKEILQCLEE[**AzK**]LKPLEEVLNLAQSKN FHLRPRDLISNINVIVLELKGSETTFMCEYADETATIVEFLN RWITFSQSIISTLT | 11 |
| IL-2_F42[AzK] | APTSSSTKKTQLQLEFILLLDLQMILNGINNYKNPKLTRML T[**AzK**]KFYMPKKATELKHLQCLEEELKPLEEVLNLAQSKN FHLRPRDLISNINVIVLELKGSETTFMCEYADETATIVEFLN RWITFSQSIISTLT | 12 |
| IL-2_K43[AzK] | APTSSSTKKTQLQLEFILLLDLQMILNGINNYKNPKLTRML TF[**AzK**]FYMPKKATELKHLQCLEEELKPLEEVLNLAQSKN FHLRPRDLISNINVIVLELKGSETTFMCEYADETATIVEFLN RWITFSQSIISTLT | 13 |
| IL-2_K35[AzK] | APTSSSTKKTQLQLEFILLLDLQMILNGINNYKNP[**AzK**]LTR MLTFKFYMPKKATELKEILQCLEEELKPLEEVLNLAQSKNF HLRPRDLISNINVIVLELKGSETTFMCEYADETATIVEFLNR WITFSQSIISTLT | 14 |
| IL-2_P65[AzK_PEG] | APTSSSTKKTQLQLEFILLLDLQMILNGINNYKNPKLTRML TFKFYMPKKATELKEILQCLEEELK[**AzK_PEG**]LEEVLNLA QSKNFHLRPRDLISNINVIVLELKGSETTFMCEYADETATIV EFLNRWITFSQSIISTLT | 15 |
| IL-2_E62[AzK_PEG] | APTSSSTKKTQLQLEFILLLDLQMILNGINNYKNPKLTRML TFKFYMPKKATELKHLQCLEE[**AzK_PEG**]LKPLEEVLNLA QSKNFHLRPRDLISNINVIVLELKGSETTFMCEYADETATIV EFLNRWITFSQSIISTLT | 16 |
| IL-2_F42[AzK_PEG] | APTSSSTKKTQLQLEFILLLDLQMILNGINNYKNPKLTRML T[**AzK_PEG**]KFYMPKKATELKEILQCLEEELKPLEEVLNLA | 17 |

TABLE 20 -continued

| Name | Sequence | SEQ ID NO: |
|---|---|---|
| | QSKNFHLRPRDLISNINVIVLELKGSETTFMCEYADETATIV<br>EFLNRWITFSQSIISTLT | |
| IL-2_K43[AzK_PEG] | APTSSSTKKTQLQLEFILLLDLQMILNGINNYKNPKLTRML<br>TF[**AzK PEG**]FYMPKKATELKEILQCLEEELKPLEEVLNLA<br>QSKNFHLRPRDLISNINVIVLELKGSETTFMCEYADETATIV<br>EFLNRWITFSQSIISTLT | 18 |
| IL-2_K35[AzK_PEG] | APTSSSTKKTQLQLEFILLLDLQMILNGINNYKNP[**AzK PEG**]<br>LTRMLTFKFYMPKKATELKHLQCLEEELKPLEEVLNLA<br>QSKNFHLRPRDLISNINVIVLELKGSETTFMCEYADETATIV<br>EFLNRWITFSQSIISTLT | 19 |
| IL-2_P65[AzK_PEG5kD] | APTSSSTKKTQLQLEFILLLDLQMILNGINNYKNPKLTRML<br>TFKFYMPKKATELKEILQCLEEELK[**AzK PEG5kD**]LEEVL<br>NLAQSKNFHLRPRDLISNINVIVLELKGSETTFMCEYADET<br>ATIVEFLNRWITFSQSIISTLT | 20 |
| IL-2_E62[AzK_PEG5kD] | APTSSSTKKTQLQLEFILLLDLQMILNGINNYKNPKLTRML<br>TFKFYMPKKATELKHLQCLEE[**AzK PEG5kD**]LKPLEEVL<br>NLAQSKNFHLRPRDLISNINVIVLELKGSETTFMCEYADET<br>ATIVEFLNRWITFSQSIISTLT | 21 |
| IL-2_F42[AzK_PEG5kD] | APTSSSTKKTQLQLEFILLLDLQMILNGINNYKNPKLTRML<br>T[**AzK PEG5kD**]KFYMPKKATELKEILQCLEEELKPLEEVL<br>NLAQSKNFHLRPRDLISNINVIVLELKGSETTFMCEYADET<br>ATIVEFLNRWITFSQSIISTLT | 22 |
| IL-2_K43[AzK_PEG5kD] | APTSSSTKKTQLQLEFILLLDLQMILNGINNYKNPKLTRML<br>TF[**AzK PEG5kD**]FYMPKKATELKEILQCLEEELKPLEEVLN<br>LAQSKNFHLRPRDLISNINVIVLELKGSETTFMCEYADETA<br>TIVEFLNRWITFSQSIISTLT | 23 |
| IL-2_K35[AzK_PEG5kD] | APTSSSTKKTQLQLEFILLLDLQMILNGINNYKNP[**AzK<br>PEG5kD**]LTRMLTFKFYMPKKATELKEILQCLEEELKPLEEVL<br>NLAQSKNFHLRPRDLISNINVIVLELKGSETTFMCEYADET<br>ATIVEFLNRWITFSQSIISTLT | 24 |
| IL-2_P65[AzK_PEG30D] | APTSSSTKKTQLQLEFILLLDLQMILNGINNYKNPKLTRML<br>TFKFYMPKKATELKEILQCLEEELK[**AzK PEG30kD**]LEEVL<br>NLAQSKNFHLRPRDLISNINVIVLELKGSETTFMCEYADET<br>ATIVEFLNRWITFSQSIISTLT | 25 |
| IL-2_E62[AzK_PEG30kD] | APTSSSTKKTQLQLEFILLLDLQMILNGINNYKNPKLTRML<br>TFKFYMPKKATELKHLQCLEE[**AzK PEG30kD**]LKPLEEVL<br>NLAQSKNFHLRPRDLISNINVIVLELKGSETTFMCEYADET<br>ATIVEFLNRWITFSQSIISTLT | 26 |
| IL-2_F42[AzK_PEG30kD] | APTSSSTKKTQLQLEFILLLDLQMILNGINNYKNPKLTRML<br>T[**AzK PEG30kD**]KFYMPKKATELKEILQCLEEELKPLEEVL<br>NLAQSKNFHLRPRDLISNINVIVLELKGSETTFMCEYADET<br>ATIVEFLNRWITFSQSIISTLT | 27 |
| IL-2_K43[AzK_PEG30kD] | APTSSSTKKTQLQLEFILLLDLQMILNGINNYKNPKLTRML<br>TF[**AzK PEG30kD**]FYMPKKATELKEILQCLEEELKPLEEVL<br>NLAQSKNFHLRPRDLISNINVIVLELKGSETTFMCEYADET<br>ATIVEFLNRWITFSQSIISTLT | 28 |
| IL-2_K35[AzK_PEG30kD] | APTSSSTKKTQLQLEFILLLDLQMILNGINNYKNP[**AzK<br>PEG30kD**]LTRNILTFKFYMPKKATELKEILQCLEEELKPLE<br>EVLNLAQSKNFHLRPRDLISNINVIVLELKGSETTFMCEYAD<br>ETATIVEFLNRWITFSQSIISTLT | 29 |
| IL-2_P65X-1 | PTSSSTKKTQLQLEHLLLDLQMILNGINNYKNPKLTRMLTF<br>KFYMPKKATELKEILQCLEEELK**X**LEEVLNLAQSKNFHLRP<br>RDLISNINVIVLELKGSETTFMCEYADETATIVEFLNRWITF<br>SQSIISTLT | 30 |
| IL-2_E62X-1 | PTSSSTKKTQLQLEHLLLDLQMILNGINNYKNPKLTRMLTF<br>KFYMPKKATELKHLQCLEE**X**LKPLEEVLNLAQSKNFHLRP<br>RDLISNINVIVLELKGSETTFMCEYADETATIVEFLNRWITF<br>SQSIISTLT | 31 |

TABLE 20 -continued

| Name | Sequence | SEQ ID NO: |
|---|---|---|
| IL-2_F42X-1 | PTSSSTKKTQLQLEHLLLDLQMILNGINNYKNPKLTRMLT**X**KFYMPKKATELKHLQCLEEELKPLEEVLNLAQSKNFHLRPRDLISNINVIVLELKGSETTFMCEYADETATIVEFLNRWITFSQSIISTLT | 32 |
| IL-2_K43X-1 | PTSSSTKKTQLQLEHLLLDLQMILNGINNYKNPKLTRMLTF**X**FYMPKKATELKHLQCLEEELKPLEEVLNLAQSKNFHLRPRDLISNINVIVLELKGSETTFMCEYADETATIVEFLNRWITFSQSIISTLT | 33 |
| IL-2_K35X-1 | PTSSSTKKTQLQLEHLLLDLQMILNGINNYKNP**X**LTRMLTFKFYMPKKATELKHLQCLEEELKPLEEVLNLAQSKNFHLRPRDLISNINVIVLELKGSETTFMCEYADETATIVEFLNRWITFSQSIISTLT | 34 |
| IL-2_P65[AzK]-1 | PTSSSTKKTQLQLEHLLLDLQMILNGINNYKNPKLTRNILTFKFYMPKKATELKHLQCLEEELK[**AzK**]LEEVLNLAQSKNFHLRPRDLISNINVIVLELKGSETTFMCEYADETATIVEFLNRWITFSQSIISTLT | 35 |
| IL-2_E62[AzK]-1 | PTSSSTKKTQLQLEHLLLDLQMILNGINNYKNPKLTRNILTFKFYMPKKATELKHLQCLEE[**AzK**]LKPLEEVLNLAQSKNFHLRPRDLISNINVIVLELKGSETTFMCEYADETATIVEFLNRWITFSQSIISTLT | 36 |
| IL-2_F42[AzK]-1 | PTSSSTKKTQLQLEHLLLDLQMILNGINNYKNPKLTRNILT[**AzK**]KFYMPKKATELKHLQCLEEELKPLEEVLNLAQSKNFHLRPRDLISNINVIVLELKGSETTFMCEYADETATIVEFLNRWITFSQSIISTLT | 37 |
| IL-2_K43[AzK]-1 | PTSSSTKKTQLQLEHLLLDLQMILNGINNYKNPKLTRNILTF[**AzK**]FYMPKKATELKHLQCLEEELKPLEEVLNLAQSKNFHLRPRDLISNINVIVLELKGSETTFMCEYADETATIVEFLNRWITFSQSIISTLT | 38 |
| IL-2_K35[AzK]-1 | PTSSSTKKTQLQLEHLLLDLQMILNGINNYKNP[**AzK**]LTRMLTFKFYMPKKATELKHLQCLEEELKPLEEVLNLAQSKNFHLRPRDLISNINVIVLELKGSETTFMCEYADETATIVEFLNRWITFSQSIISTLT | 39 |
| IL-2_P65 [AzK_L1_PEG]-1 | PTSSSTKKTQLQLEHLLLDLQMILNGINNYKNPKLTRNILTFKFYMPKKATELKHLQCLEEELK[**AzK L1 PEG**]LEEVLNLAQSKNFHLRPRDLISNINVIVLELKGSETTFMCEYADETATIVEFLNRWITFSQSIISTLT | 40 |
| IL-2_E62 [AzK_L1_PEG]-1 | PTSSSTKKTQLQLEHLLLDLQMILNGINNYKNPKLTRNILTFKFYMPKKATELKHLQCLEE[**AzK L1 PEG**]LKPLEEVLNLAQSKNFHLRPRDLISNINVIVLELKGSETTFMCEYADETATIVEFLNRWITFSQSIISTLT | 41 |
| IL-2_F42 [AzK_L1_PEG]-1 | PTSSSTKKTQLQLEHLLLDLQMILNGINNYKNPKLTRMLT[**AzK L1 PEG**]KFYMPKKATELKHLQCLEEELKPLEEVLNLAQSKNFHLRPRDLISNINVIVLELKGSETTFMCEYADETATIVEFLNRWITFSQSIISTLT | 42 |
| IL-2_K43 [AzK_L1_PEG]-1 | PTSSSTKKTQLQLEHLLLDLQMILNGINNYKNPKLTRNILTF[**AzK L1 PEG**]FYMPKKATELKELQCLEEELKPLEEVLNLAQSKNFHLRPRDLISNINVIVLELKGSETTFMCEYADETATIVEFLNRWITFSQSIISTLT | 43 |
| IL-2_K35 [AzK_L1_PEG]-1 | PTSSSTKKTQLQLEHLLLDLQMILNGINNYKNP[**AzK L1 PEG**]LTRNILTFKFYMPKKATELKHLQCLEEELKPLEEVLNLAQSKNFHLRPRDLISNINVIVLELKGSETTFMCEYADETATIVEFLNRWITFSQSIISTLT | 44 |
| IL-2_P65 [AzK_L1_PEG5kD]-1 | PTSSSTKKTQLQLEHLLLDLQMILNGINNYKNPKLTRNILTFKFYMPKKATELKELQCLEEELK[**AzK L1 PEG5kD**]LEEVLNLAQSKNFHLRPRDLISNINVIVLELKGSETTFMCEYADETATIVEFLNRWITFSQSIISTLT | 45 |
| IL-2_E62 [AzK_L1_PEG5kD]-1 | PTSSSTKKTQLQLEHLLLDLQMILNGINNYKNPKLTRNILTFKFYMPKKATELKELQCLEE[**AzK L1 PEG5kD**]LKPLEEVLNLAQSKNFHLRPRDLISNINVIVLELKGSETTFMCEYADETATIVEFLNRWITFSQSIISTLT | 46 |

TABLE 20 -continued

| Name | Sequence | SEQ ID NO: |
|---|---|---|
| IL-2_F42 [AzK_L1_PEG5kD]-1 | PTSSSTKKTQLQLEHLLLDLQMILNGINNYKNPKLTRMLT [AzK L1 PEG5kD]KFYMPKKATELKELQCLEEELKPLEEV LNLAQSKNFHLRPRDLISNINVIVLELKGSETTFMCEYADE TATIVEFLNRWITFSQSIISTLT | 47 |
| IL-2_K43 [AzK_L1_PEG5kD]-1 | PTSSSTKKTQLQLEHLLLDLQMILNGINNYKNPKLTRNILTF [AzK L1 PEG5kD]FYMPKKATELKELQCLEEELKPLEEVL NLAQSKNFHLRPRDLISNINVIVLELKGSETTFMCEYADET ATIVEFLNRWITFSQSIISTLT | 48 |
| IL-2_K35 [AzK_L1_PEG5kD]-1 | PTSSSTKKTQLQLEHLLLDLQMILNGINNYKNP[AzK L1 PEG5kD]LTRNILTFKFYMPKKATELKEILQCLEEELKPLEEVL NLAQSKNFHLRPRDLISNINVIVLELKGSETTFMCEYADET ATIVEFLNRWITFSQSIISTLT | 49 |
| IL-2_P65 [AzK_L1_PEG5kD]-1 | PTSSSTKKTQLQLEHLLLDLQMILNGINNYKNPKLTRNILTF KFYMPKKATELKELQCLEEELK[AzK L1 PEG5kD]LEEV LNLAQSKNFHLRPRDLISNINVIVLELKGSETTFMCEYADE TATIVEFLNRWITFSQSIISTLT | 50 |
| IL-2_E62 [AzK_L1_PEG30kD]-1 | PTSSSTKKTQLQLEHLLLDLQMILNGINNYKNPKLTRNILTF KFYMPKKATELKELQCLEE[AzK L1 PEG30kD]LKPLEEV LNLAQSKNFHLRPRDLISNINVIVLELKGSETTFMCEYADE TATIVEFLNRWITFSQSIISTLT | 51 |
| IL-2_F42 [AzK_L1_PEG30kD]-1 | PTSSSTKKTQLQLEHLLLDLQMILNGINNYKNPKLTRMLT [AzK L1 PEG30kD]KFYMPKKATELKELQCLEEELKPLEE VLNLAQSKNFHLRPRDLISNINVIVLELKGSETTFMCEYAD ETATIVEFLNRWITFSQSIISTLT | 52 |
| IL-2_K43 [AzK_L1_PEG30kD]-1 | PTSSSTKKTQLQLEHLLLDLQMILNGINNYKNPKLTRNILTF [AzK L1 PEG30kD]FYMPKKATELKELQCLEEELKPLEEV LNLAQSKNFHLRPRDLISNINVIVLELKGSETTFMCEYADE TATIVEFLNRWITFSQSIISTLT | 53 |
| IL-2_K35 [AzK_L1_PEG30kD]-1 | PTSSSTKKTQLQLEHLLLDLQMILNGINNYKNP[AzK L1 PEG30kD]LTRNILTFKFYMPKKATELKEILQCLEEELKPLEEV LNLAQSKNFHLRPRDLISNINVIVLELKGSETTFMCEYADE TATIVEFLNRWITFSQSIISTLT | 54 |
| IL-2_P65 [AzK_L1_PEG]-2 | APTSSSTKKTQLQLEFILLLDLQMILNGINNYKNPKLTRNIL TFKFYMPKKATELKELQCLEEELK[AzK L1 PEG]LEEVL NLAQSKNFHLRPRDLISNINVIVLELKGSETTFMCEYADET ATIVEFLNRWITFSQSIISTLT | 55 |
| IL-2_E62 [AzK_L1_PEG]-2 | APTSSSTKKTQLQLEFILLLDLQMILNGINNYKNPKLTRNIL TFKFYMPKKATELKHLQCLEE[AzK_L1_PEG]LKPLEEVLN LAQSKNFHLRPRDLISNINVIVLELKGSETTFMCEYADETA TIVEFLNRWITFSQSITSTLT | 56 |
| IL-2_F42 [AzK_L1_PEG]-2 | APTSSSTKKTQLQLEFILLLDLQMILNGINNYKNPKLTRML T[AzK_L1_PEG]KFYMPKKATELKHLQCLEEELKPLEEVL NLAQSKNFHLRPRDLISNINVIVLELKGSETTFMCEYADET ATIVEFLNRWITFSQSIISTLT | 57 |
| IL-2_K43 [AzK_L1_PEG]-2 | APTSSSTKKTQLQLEFILLLDLQMILNGINNYKNPKLTRML TF[AzK_L1_PEG]FYMPKKATELKEILQCLEEELKPLEEVLN LAQSKNFHLRPRDLISNINVIVLELKGSETTFMCEYADETA TIVEFLNRWITFSQSIISTLT | 58 |
| IL-2_K35 [AzK_L1_PEG]-2 | APTSSSTKKTQLQLEFILLLDLQMILNGINNYKNP[AzK_L1 PEG]LTRNILTFKFYMPKKATELKEILQCLEEELKPLEEVLN LAQSKNFHLRPRDLISNINVIVLELKGSETTFMCEYADETA TIVEFLNRWITFSQSIISTLT | 59 |
| IL-2_P65 [AzK_L1_PEG5kD]-2 | APTSSSTKKTQLQLEFILLLDLQMILNGINNYKNPKLTRML TFKFYMPKKATELKELQCLEEELK[AzK L1 PEG5kD]LEE VLNLAQSKNFHLRPRDLISNINVIVLELKGSETTFMCEYAD ETATIVEFLNRWITFSQSIISTLT | 60 |
| IL-2_E62 [AzK_L1_PEG5kD]-2 | APTSSSTKKTQLQLEFILLLDLQMILNGINNYKNPKLTRML TFKFYMPKKATELKHLQCLEE[AzK L1 PEG5kD]LKPLEE VLNLAQSKNFHLRPRDLISNINVIVLELKGSETTFMCEYAD ETATIVEFLNRWITFSQSIISTLT | 61 |

TABLE 20 -continued

| Name | Sequence | SEQ ID NO: |
|---|---|---|
| IL-2_F42 [AzK_L1_PEG5kD]-2 | APTSSSTKKTQLQLEFILLLDLQMILNGINNYKNPKLTRML T[**AzK L1 PEG5kD**]KFYMPKKATELKEILQCLEEELKPLEE VLNLAQSKNFHLRPRDLISNINVIVLELKGSETTFMCEYAD ETATIVEFLNRWITFSQSIISTLT | 62 |
| IL-2_K43 [AzK_L1_PEG5kD]-2 | APTSSSTKKTQLQLEFILLLDLQMILNGINNYKNPKLTRML TF[**AzK L1 PEG5kD**]FYMPKKATELKEILQCLEEELKPLEE VLNLAQSKNFHLRPRDLISNINVIVLELKGSETTFMCEYAD ETATIVEFLNRWITFSQSIISTLT | 63 |
| IL-2_K35 [AzK_L1_PEG5kD]-2 | APTSSSTKKTQLQLEFILLLDLQMILNGINNYKNP[**AzK L1 PEG5kD**]LTRNILTFKFYMPKKATELKEILQCLEEELKPLEEV LNLAQSKNFHLRPRDLISNINVIVLELKGSETTFMCEYADE TATIVEFLNRWITFSQSIISTLT | 64 |
| IL-2_P65 [AzK_L1_PEG30kD]-2 | APTSSSTKKTQLQLEFILLLDLQMILNGINNYKNPKLTRML TFKFYMPKKATELKELQCLEEELK[**AzK L1 PEG30kD**]LE EVLNLAQSKNFHLRPRDLISNINVIVLELKGSETTFMCEYA DETATIVEFLNRWITFSQSIISTLT | 65 |
| IL-2_E62 [AzK_L1_PEG30kD]-2 | APTSSSTKKTQLQLEFILLLDLQMILNGINNYKNPKLTRML TFKFYMPKKATELKHLQCLEE[**AzK L1 PEG30kD**]LKPLE EVLNLAQSKNFHLRPRDLISNINVIVLELKGSETTFMCEYA DETATIVEFLNRWITFSQSIISTLT | 66 |
| IL-2_F42 [AzK_L1_PEG30kD]-2 | APTSSSTKKTQLQLEFILLLDLQMILNGINNYKNPKLTRML T[**AzK L1 PEG30kD**]KFYMPKKATELKHLQCLEEELKPLE EVLNLAQSKNFHLRPRDLISNINVIVLELKGSETTFMCEYA DETATIVEFLNRWITFSQSIISTLT | 67 |
| IL-2_K43 [AzK_L1_PEG30kD]-2 | APTSSSTKKTQLQLEFILLLDLQMILNGINNYKNPKLTRNIL TF[**AzK L1 PEG30kD**]FYMPKKATELKEILQCLEEELKPLE EVLNLAQSKNFHLRPRDLISNINVIVLELKGSETTFMCEYA DETATIVEFLNRWITFSQSIISTLT | 68 |
| IL-2_K35 [AzK_L1_PEG30kD]-2 | APTSSSTKKTQLQLEFILLLDLQMILNGINNYKNP[**AzK L1 PEG30kD**]LTRMLTFKFYMPKKATELKHLQCLEEELKPLEE VLNLAQSKNFHLRPRDLISNINVIVLELKGSETTFMCEYAD ETATIVEFLNRWITFSQSIISTLT | 69 |
| IL-2_P65[AzK_PEG]-1 | PTSSSTKKTQLQLEHLLLDLQMILNGINNYKNPKLTRNILTF KFYMPKKATELKEILQCLEEELK[**AzK_PEG**]LEEVLNLAQS KNFHLRPRDLISNINVIVLELKGSETTFMCEYADETATIVEF LNRWITFSQSIISTLT | 70 |
| IL-2_E62[AzK_PEG]-1 | PTSSSTKKTQLQLEHLLLDLQMILNGINNYKNPKLTRNILTF KFYMPKKATELKEILQCLEE[**AzK_PEG**]LKPLEEVLNLAQS KNFHLRPRDLISNINVIVLELKGSETTFMCEYADETATIVEF LNRWITFSQSIISTLT | 71 |
| IL-2_F42[AzK_PEG]-1 | PTSSSTKKTQLQLEHLLLDLQMILNGINNYKNPKLTRMLT [**AzK_PEG**]KFYMPKKATELKHLQCLEEELKPLEEVLNLAQ SKNFHLRPRDLISNINVIVLELKGSETTFMCEYADETATIVE FLNRWITFSQSIISTLT | 72 |
| IL-2_K43[AzK_PEG]-1 | PTSSSTKKTQLQLEHLLLDLQMILNGINNYKNPKLTRNILTF [**AzK_PEG**]FYMPKKATELKEILQCLEEELKPLEEVLNLAQS KNFHLRPRDLISNINVIVLELKGSETTFMCEYADETATIVEF LNRWITFSQSIISTLT | 73 |
| IL-2_K35[AzK_PEG]-1 | PTSSSTKKTQLQLEHLLLDLQMILNGINNYKNP[**AzK_PEG**] LTRMLTFKFYMPKKATELKEILQCLEEELKPLEEVLNLAQS KNFHLRPRDLISNINVIVLELKGSETTFMCEYADETATIVEF LNRWITFSQSIISTLT | 74 |
| IL-2_P65 [AzK PEG5kD]-1 | PTSSSTKKTQLQLEHLLLDLQMILNGINNYKNPKLTRNILTF KFYMPKKATELKEILQCLEEELK[**AzK PEG5kD**]LEEVLNL SKNFHLRPRDLISNINVIVLELKGSETTFMCEYADETATI VEFLNRWITFSQSIISTLT | 75 |
| IL-2_E62 [AzK PEG5kD]-1 | PTSSSTKKTQLQLEHLLLDLQMILNGINNYKNPKLTRNILTF KFYMPKKATELKEILQCLEE[**AzK PEG5kD**]LKPLEEVLNL AQSKNFHLRPRDLISNINVIVLELKGSETTFMCEYADETATI VEFLNRWITFSQSIISTLT | 76 |

TABLE 20 -continued

| Name | Sequence | SEQ ID NO: |
|---|---|---|
| IL-2_F42<br>[AzK_PEG5kD]-1 | PTSSSTKKTQLQLEHLLLDLQMILNGINNYKNPKLTRMLT<br>[**AzK PEG5kD**]KFYMPKKATELKEILQCLEEELKPLEEVLNL<br>AQSKNFHLRPRDLISNINVIVLELKGSETTFMCEYADETATI<br>VEFLNRWITFSQSIISTLT | 77 |
| IL-2_K43<br>[AzK_PEG5kD]-1 | PTSSSTKKTQLQLEHLLLDLQMILNGINNYKNPKLTRNILTF<br>[**AzK PEG5kD**]FYMPKKATELKEILQCLEEELKPLEEVLNL<br>AQSKNFHLRPRDLISNINVIVLELKGSETTFMCEYADETATI<br>VEFLNRWITFSQSIISTLT | 78 |
| IL-2_K35<br>[AzK_PEG5kD]-1 | PTSSSTKKTQLQLEHLLLDLQMILNGINNYKNP[**AzK PEG5kD**]<br>LTRNILTFKFYMPKKATELKHLQCLEEELKPLEEVLNL<br>AQSKNFHLRPRDLISNINVIVLELKGSETTFMCEYADETATI<br>VEFLNRWITFSQSIISTLT | 79 |
| IL-2_P65<br>[AzK_PEG30kD]-1 | PTSSSTKKTQLQLEHLLLDLQMILNGINNYKNPKLTRNILTF<br>KFYMPKKATELKEILQCLEEELK[**AzK PEG30kD**]LEEVLN<br>LAQSKNFEILRPRDLISNINVIVLELKGSETTFMCEYADETA<br>TIVEFLNRWITFSQSIISTLT | 80 |
| IL-2_E62<br>[AzK_PEG30kD]-1 | PTSSSTKKTQLQLEFILLLDLQIVIILNGINNYKNPKLTRMLTF<br>KFYMPKKATELKEILQCLEE[**AzK PEG30kD**]LKPLEEVLN<br>LAQSKNFEILRPRDLISNINVIVLELKGSETTFMCEYADETA<br>TIVEFLNRWITFSQSIISTLT | 81 |
| IL-2_F42<br>[AzK_PEG30kD]-1 | PTSSSTKKTQLQLEFILLLDLQIVIILNGINNYKNPKLTRMLT<br>[**AzK PEG30kD**]KFYMPKKATELKEILQCLEEELKPLEEVLN<br>LAQSKNFEILRPRDLISNINVIVLELKGSETTFMCEYADETA<br>TIVEFLNRWITFSQSIISTLT | 82 |
| IL-2_K43<br>[AzK_PEG30kD]-1 | PTSSSTKKTQLQLEFILLLDLQIVIILNGINNYKNPKLTRMLTF<br>[**AzK PEG30kD**]FYMPKKATELKEILQCLEEELKPLEEVLNL<br>AQSKNFEILRPRDLISNINVIVLELKGSETTFMCEYADETATI<br>VEFLNRWITFSQSIISTLT | 83 |
| IL-2_K35<br>[AzK_PEG30kD]-1 | PTSSSTKKTQLQLEFILLLDLQMILNGINNYKNP[**AzK PEG30kD**]<br>LTRMLTFKFYMPKKATELKEILQCLEEELKPLEEVLNL<br>AQSKNFEILRPRDLISNINVIVLELKGSETTFMCEYADETATI<br>VEFLNRWITFSQSIISTLT | 84 |

X = site comprising an unnatural amino acid.

Figure 3A:
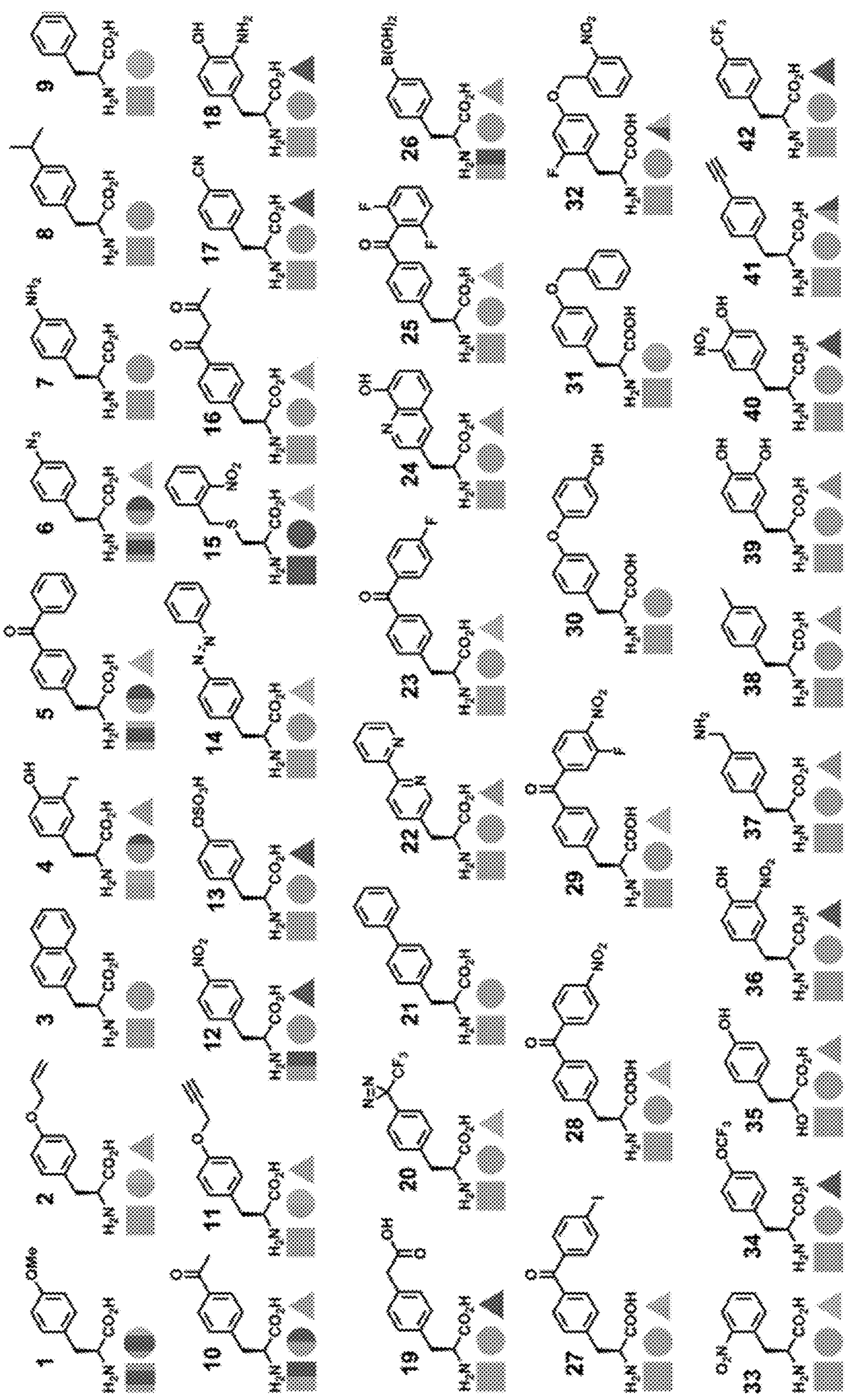
FIGS. 3A-FIG. 3D illustrate exemplary unnatural amino acids. These unnatural amino acids (UAAs) have been genetically encoded in proteins (FIG. 3A—UAA #1-42.
Figure 3B:
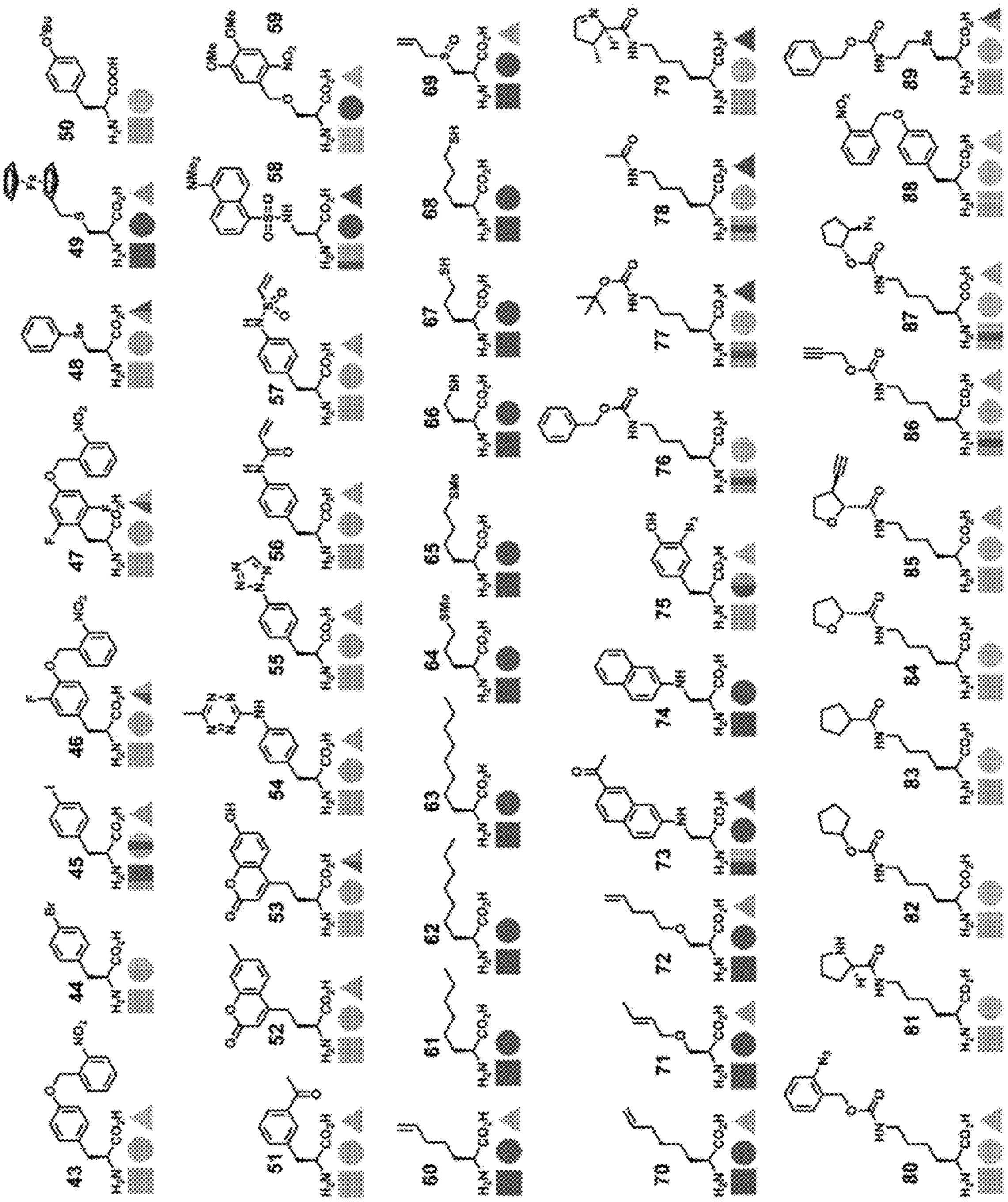
Figure 3C:
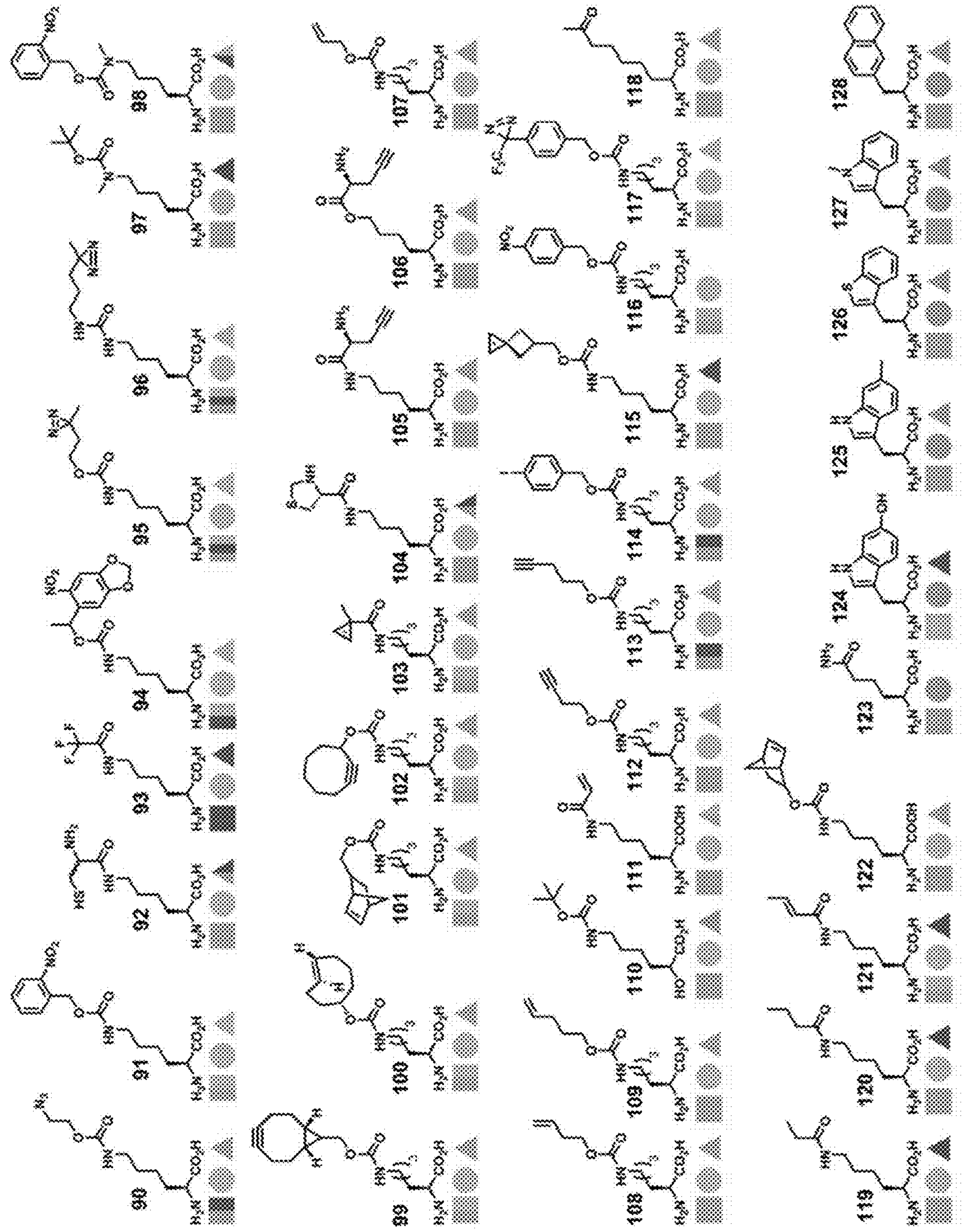
Figure 3D:
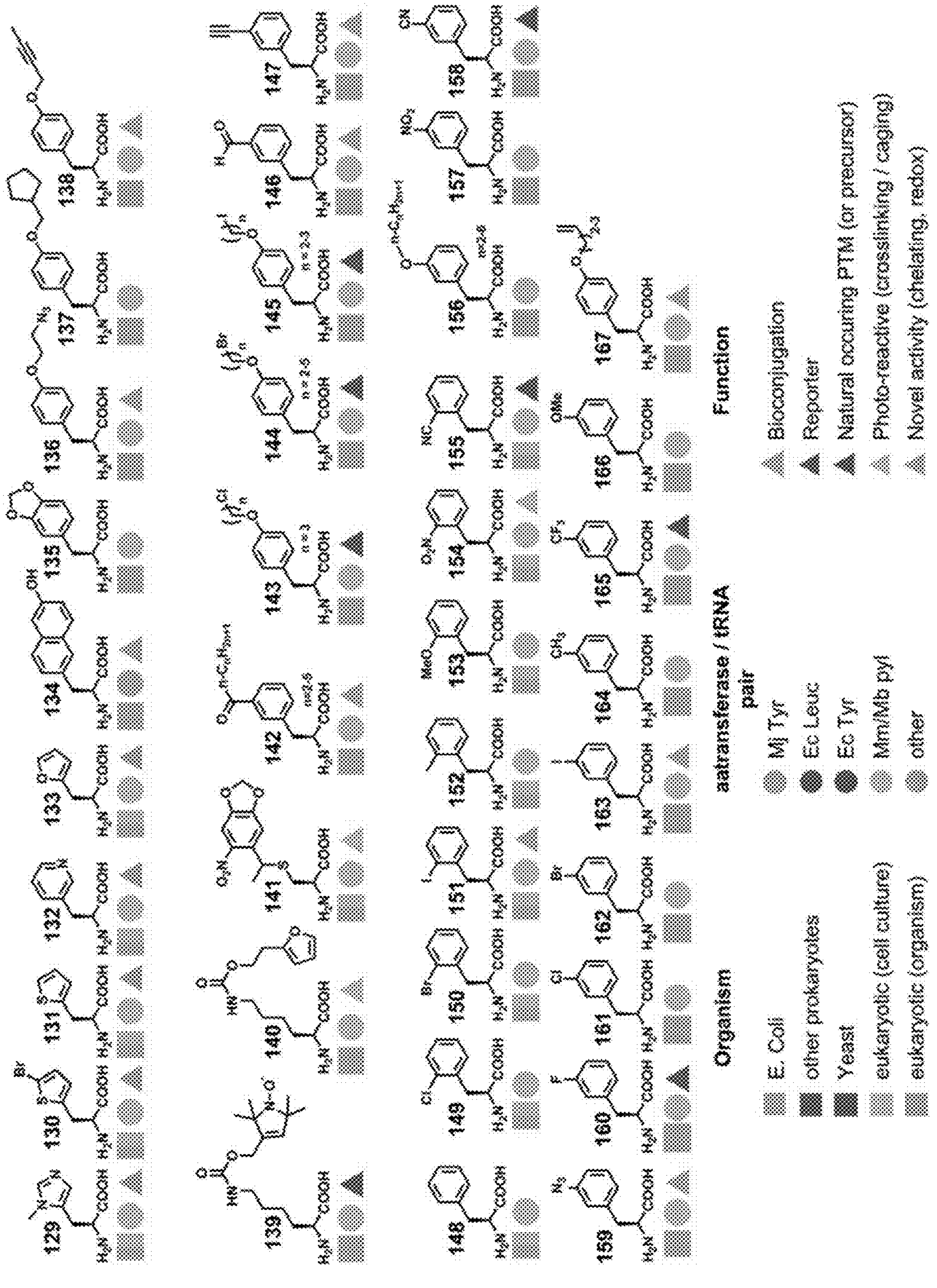

[AzK]=N6-((2-azidoethoxy)-carbonyl)-L-lysine (the structure of which is disclosed as compound 90 in FIG. 3C). The compound has Chemical Abstracts Registry No. 1167421-25-1.

[AzK_PEG]=N6-((2-azidoethoxy)-carbonyl)-L-lysine stably-conjugated to PEG via DBCO-mediated click chemistry, to form a compound comprising a structure of Formula (II) or Formula (III). For example, if specified, PEG5kD indicates a linear polyethylene glycol chain with an average molecular weight of 5 kiloDaltons, capped with a methoxy group. The ratio of regioisomers generated from the click reaction is about 1:1 or greater than 1:1. The term "DBCO" means a chemical moiety comprising a dibenzocyclooctyne group, such as comprising the mPEG-DBCO compound illustrated in Scheme 1 of Example 2. An exemplary structure of a methoxy PEG group is illustrated in the mPEG-DBCO structure in Scheme 1 of Example 2

[AzK_L1_PEG]=N6-((2-azidoethoxy)-carbonyl)-L-lysine stably-conjugated to PEG via DBCO-mediated click chemistry to form a compound comprising a structure of Formula (IV) or Formula (V). For example, if specified, PEG5kD indicates a linear polyethylene glycol chain with an average molecular weight of 5 kiloDaltons, capped with a methoxy group. The ratio of regioisomers generated from the click reaction is about 1:1 or greater than 1:1. The term "DBCO" means a chemical moiety comprising a dibenzocyclooctyne group, such as comprising the mPEG-DBCO compound illustrated in Scheme 1 of Example 2.

In some embodiments, described herein are IL-2 conjugates modified at an amino acid position. In some instances, the modification is to a natural amino acid. In some instances, the modification is to an unnatural amino acid. In some instances, described herein is an isolated and modified IL-2 polypeptide that comprises at least one unnatural amino acid. In some instances, the IL-2 polypeptide is an isolated and purified mammalian IL-2, for example, a rodent IL-2 protein, or a human IL-2 protein. In some cases, the IL-2 polypeptide is a human IL-2 protein. In some cases, the IL-2 polypeptide comprises about 80%, 85%, 90%, 95%, 96%, 97%, 98%, or 99% sequence identity to SEQ ID NO: 1. In some cases, the IL-2 polypeptide comprises the sequence of SEQ ID NO: 1. In some cases, the IL-2 polypeptide consists of the sequence of SEQ ID NO: 1. In additional cases, the IL-2 polypeptide comprises about 80%, 85%, 90%, 95%, 96%, 97%, 98%, or 99% sequence identity to SEQ ID NO: 2. In additional cases, the IL-2 polypeptide comprises the sequence of SEQ ID NO: 2. In additional cases, the IL-2 polypeptide consists of the sequence of SEQ ID NO: 2. In some cases, the IL-2 polypeptide comprises about 80%, 85%, 90%, 95%, 96%, 97%, 98%, or 99% sequence identity to SEQ ID NO: 3. In some cases, the IL-2 polypeptide comprises the sequence of SEQ ID NO: 3. In some cases, the IL-2 polypeptide consists of the sequence of SEQ ID NO: 3. In additional cases, the IL-2 polypeptide comprises about 80%, 85%, 90%, 95%, 96%, 97%, 98%, or 99% sequence identity to SEQ ID NO: 4. In additional cases, the IL-2 polypeptide comprises the sequence of SEQ ID NO: 4. In additional cases, the IL-2 polypeptide consists of the sequence of SEQ ID NO: 4. In some cases, the IL-2 polypeptide comprises about 80%, 85%, 90%, 95%, 96%, 97%, 98%, or 99% sequence identity to SEQ ID NO: 5. In some cases, the IL-2 polypeptide comprises the sequence of SEQ ID NO: 5. In some cases, the IL-2 polypeptide consists of the sequence of SEQ ID NO: 5. In additional cases, the IL-2 polypeptide comprises about 80%, 85%, 90%, 95%, 96%, 97%, 98%, or 99% sequence identity to SEQ ID NO: 6. In additional cases, the IL-2 polypeptide comprises the sequence of SEQ ID NO: 6. In additional cases, the IL-2 polypeptide consists of the sequence of SEQ ID NO: 6. In some cases, the IL-2 polypeptide comprises about 80%, 85%, 90%, 95%, 96%, 97%, 98%, or 99% sequence identity to SEQ ID NO: 7. In some cases, the IL-2 polypeptide comprises the sequence of SEQ ID NO: 7. In some cases, the IL-2 polypeptide consists of the sequence of SEQ ID NO: 7. In additional cases, the IL-2 polypeptide comprises about 80%, 85%, 90%, 95%, 96%, 97%, 98%, or 99% sequence identity to SEQ ID NO: 8. In additional cases, the IL-2 polypeptide comprises the sequence of SEQ ID NO: 8. In additional cases, the IL-2 polypeptide consists of the sequence of SEQ ID NO: 8. In some cases, the IL-2 polypeptide comprises about 80%, 85%, 90%, 95%, 96%, 97%, 98%, or 99% sequence identity to SEQ ID NO: 9. In some cases, the IL-2 polypeptide comprises the sequence of SEQ ID NO: 9. In some cases, the IL-2 polypeptide consists of the sequence of SEQ ID NO: 9. In some cases, the IL-2 polypeptide comprises about 80%, 85%, 90%, 95%, 96%, 97%, 98%, or 99% sequence identity to SEQ ID NO: 10. In some cases, the IL-2 polypeptide comprises the sequence of SEQ ID NO: 10. In some cases, the IL-2 polypeptide consists of the sequence of SEQ ID NO: 10. In some cases, the IL-2 polypeptide comprises about 80%, 85%, 90%, 95%, 96%, 97%, 98%, or 99% sequence identity to SEQ ID NO: 11. In some cases, the IL-2 polypeptide comprises the sequence of SEQ ID NO: 11. In some cases, the IL-2 polypeptide consists of the sequence of SEQ ID NO: 11. In some cases, the IL-2 polypeptide comprises about 80%, 85%, 90%, 95%, 96%, 97%, 98%, or 99% sequence identity to SEQ ID NO: 12. In some cases, the IL-2 polypeptide comprises the sequence of SEQ ID NO: 12. In some cases, the IL-2 polypeptide consists of the sequence of SEQ ID NO: 12. In some cases, the IL-2 polypeptide comprises about 80%, 85%, 90%, 95%, 96%, 97%, 98%, or 99% sequence identity to SEQ ID NO: 13. In some cases, the IL-2 polypeptide comprises the sequence of SEQ ID NO: 13. In some cases, the IL-2 polypeptide consists of the sequence of SEQ ID NO: 13. In some cases, the IL-2 polypeptide comprises about 80%, 85%, 90%, 95%, 96%, 97%, 98%, or 99% sequence identity to SEQ ID NO: 14. In some cases, the IL-2 polypeptide comprises the sequence of SEQ ID NO: 14. In some cases, the IL-2 polypeptide consists of the sequence of SEQ ID NO: 14. In some cases, the IL-2 polypeptide comprises about 80%, 85%, 90%, 95%, 96%, 97%, 98%, or 99% sequence identity to SEQ ID NO: 15. In some cases, the IL-2 polypeptide comprises the sequence of SEQ ID NO: 15. In some cases, the IL-2 polypeptide consists of the sequence of SEQ ID NO: 15. In some cases, the IL-2 polypeptide comprises about 80%, 85%, 90%, 95%, 96%, 97%, 98%, or 99% sequence identity to SEQ ID NO: 16. In some cases, the IL-2 polypeptide comprises the sequence of SEQ ID NO: 16. In some cases, the IL-2 polypeptide consists of the sequence of SEQ ID NO: 16. In some cases, the IL-2 polypeptide comprises about 80%, 85%, 90%, 95%, 96%, 97%, 98%, or 99% sequence identity to SEQ ID NO: 17. In some cases, the IL-2 polypeptide comprises the sequence of SEQ ID NO: 17. In some cases, the IL-2 polypeptide consists of the sequence of SEQ ID NO: 17. In some cases, the IL-2 polypeptide comprises about 80%, 85%, 90%, 95%, 96%, 97%, 98%, or 99% sequence identity to SEQ ID NO: 18. In some cases, the IL-2 polypeptide comprises the sequence of SEQ ID NO: 18. In some cases, the IL-2 polypeptide consists of the sequence of SEQ ID NO: 18. In some cases, the IL-2 polypeptide comprises about 80%, 85%, 90%, 95%, 96%, 97%, 98%, or 99% sequence identity to SEQ ID NO: 19. In some cases, the IL-2 polypeptide comprises the sequence of SEQ ID NO: 19. In some cases, the IL-2 polypeptide consists of the sequence of SEQ ID NO: 19. In some cases, the IL-2 polypeptide comprises about 80%, 85%, 90%, 95%, 96%, 97%, 98%, or 99% sequence identity to SEQ ID NO: 20. In some cases, the IL-2 polypeptide comprises the sequence of SEQ ID NO: 20. In some cases, the IL-2 polypeptide consists of the sequence of SEQ ID NO: 20. In some cases, the IL-2 polypeptide comprises about 80%, 85%, 90%, 95%, 96%, 97%, 98%, or 99% sequence identity to SEQ ID NO: 21. In some cases, the IL-2 polypeptide comprises the sequence of SEQ ID NO: 21. In some cases, the IL-2 polypeptide consists of the sequence of SEQ ID NO: 21. In some cases, the IL-2 polypeptide comprises about 80%, 85%, 90%, 95%, 96%, 97%, 98%, or 99% sequence identity to SEQ ID NO: 22. In some cases, the IL-2 polypeptide comprises the sequence of SEQ ID NO: 22. In some cases, the IL-2 polypeptide consists of the sequence of SEQ ID NO: 22. In some cases, the IL-2 polypeptide comprises about 80%, 85%, 90%, 95%, 96%, 97%, 98%, or 99% sequence identity to SEQ ID NO: 23. In some cases, the IL-2 polypeptide comprises the sequence of SEQ ID NO: 23. In some cases, the IL-2 polypeptide consists of the sequence of SEQ ID NO: 23. In some cases, the IL-2 polypeptide comprises about 80%, 85%, 90%, 95%, 96%, 97%, 98%, or 99% sequence identity to SEQ ID NO: 24. In some cases, the IL-2 polypeptide comprises the sequence of SEQ ID NO: 24. In some cases, the IL-2 polypeptide consists of the sequence of SEQ ID NO: 24. In additional cases, the IL-2 polypeptide comprises about 80%, 85%, 90%, 95%, 96%, 97%, 98%, or 99% sequence identity to SEQ ID NO: 25. In additional cases, the IL-2 polypeptide comprises the sequence of SEQ ID NO: 25. In additional cases, the IL-2 polypeptide consists of the sequence of SEQ ID NO: 25. In some cases, the IL-2 polypeptide comprises about 80%, 85%, 90%, 95%, 96%, 97%, 98%, or 99% sequence identity to SEQ ID NO: 26. In some cases, the IL-2 polypeptide comprises the sequence of SEQ ID NO: 26. In some cases, the IL-2 polypeptide consists of the sequence of SEQ ID NO: 26. In additional cases, the IL-2 polypeptide comprises about 80%, 85%, 90%, 95%, 96%, 97%, 98%, or 99% sequence identity to SEQ ID NO: 27. In additional cases, the IL-2 polypeptide comprises the sequence of SEQ ID NO: 27. In additional cases, the IL-2 polypeptide consists of the sequence of SEQ ID NO: 27. In some cases, the IL-2 polypeptide comprises about 80%, 85%, 90%, 95%, 96%, 97%, 98%, or 99% sequence identity to SEQ ID NO: 28. In some cases, the IL-2 polypeptide comprises the sequence of SEQ ID NO: 28. In some cases, the IL-2 polypeptide consists of the sequence of SEQ ID NO: 28. In additional cases, the IL-2 polypeptide comprises about 80%, 85%, 90%, 95%, 96%, 97%, 98%, or 99% sequence identity to SEQ ID NO: 29. In additional cases, the IL-2 polypeptide comprises the sequence of SEQ ID NO: 29. In additional cases, the IL-2 polypeptide consists of the sequence of SEQ ID NO: 29. In some cases, the IL-2 polypeptide comprises about 80%, 85%, 90%, 95%, 96%, 97%, 98%, or 99% sequence identity to SEQ ID NO: 30. In some cases, the IL-2 polypeptide comprises the sequence of SEQ ID NO: 30. In some cases, the IL-2 polypeptide consists of the sequence of SEQ ID NO: 30. In some cases, the IL-2 polypeptide comprises about 80%, 85%, 90%, 95%, 96%, 97%, 98%, or 99% sequence identity to SEQ ID NO: 31. In some cases, the IL-2 polypeptide comprises the sequence of SEQ ID NO: 31. In some cases, the IL-2 polypeptide consists of the sequence of SEQ ID NO: 31. In additional cases, the IL-2 polypeptide comprises about 80%, 85%, 90%, 95%, 96%, 97%, 98%, or 99% sequence identity to SEQ ID NO: 32. In additional cases, the IL-2 polypeptide comprises the sequence of SEQ ID NO: 32. In additional cases, the IL-2 polypeptide consists of the sequence of SEQ ID NO: 32. In some cases, the IL-2 polypeptide comprises about 80%, 85%, 90%, 95%, 96%, 97%, 98%, or 99% sequence identity to SEQ ID NO: 33. In some cases, the IL-2 polypeptide comprises the sequence of SEQ ID NO: 33. In some cases, the IL-2 polypeptide consists of the sequence of SEQ ID NO: 33. In additional cases, the IL-2 polypeptide comprises about 80%, 85%, 90%, 95%, 96%, 97%, 98%, or 99% sequence identity to SEQ ID NO: 34. In additional cases, the IL-2 polypeptide comprises the sequence of SEQ ID NO: 34. In additional cases, the IL-2 polypeptide consists of the sequence of SEQ ID NO: 34. In some cases, the IL-2 polypeptide comprises about 80%, 85%, 90%, 95%, 96%, 97%, 98%, or 99% sequence identity to SEQ ID NO: 35. In some cases, the IL-2 polypeptide comprises the sequence of SEQ ID NO: 35. In some cases, the IL-2 polypeptide consists of the sequence of SEQ ID NO: 35. In additional cases, the IL-2 polypeptide comprises about 80%, 85%, 90%, 95%, 96%, 97%, 98%, or 99% sequence identity to SEQ ID NO: 36. In additional cases, the IL-2 polypeptide comprises the sequence of SEQ ID NO: 36. In additional cases, the IL-2 polypeptide consists of the sequence of SEQ ID NO: 36. In some cases, the IL-2 polypeptide comprises about 80%, 85%, 90%, 95%, 96%, 97%, 98%, or 99% sequence identity to SEQ ID NO: 37. In some cases, the IL-2 polypeptide comprises the sequence of SEQ ID NO: 37. In some cases, the IL-2 polypeptide consists of the sequence of SEQ ID NO: 37. In additional cases, the IL-2 polypeptide comprises about 80%, 85%, 90%, 95%, 96%, 97%, 98%, or 99% sequence identity to SEQ ID NO: 38. In additional cases, the IL-2 polypeptide comprises the sequence of SEQ ID NO: 38. In additional cases, the IL-2 polypeptide consists of the sequence of SEQ ID NO: 38. In some cases, the IL-2 polypeptide comprises about 80%, 85%, 90%, 95%, 96%, 97%, 98%, or 99% sequence identity to SEQ ID NO: 39. In some cases, the IL-2 polypeptide comprises the sequence of SEQ ID NO: 39. In some cases, the IL-2 polypeptide consists of the sequence of SEQ ID NO: 39. In some cases, the IL-2 polypeptide comprises about 80%, 85%, 90%, 95%, 96%, 97%, 98%, or 99% sequence identity to SEQ ID NO: 40. In some cases, the IL-2 polypeptide comprises the sequence of SEQ ID NO: 40. In some cases, the IL-2 polypeptide consists of the sequence of SEQ ID NO: 40. In some cases, the IL-2 polypeptide comprises about 80%, 85%, 90%, 95%, 96%, 97%, 98%, or 99% sequence identity to SEQ ID NO: 41. In some cases, the IL-2 polypeptide comprises the sequence of SEQ ID NO: 41. In some cases, the IL-2 polypeptide consists of the sequence of SEQ ID NO: 41. In some cases, the IL-2 polypeptide comprises about 80%, 85%, 90%, 95%, 96%, 97%, 98%, or 99% sequence identity to SEQ ID NO: 42. In some cases, the IL-2 polypeptide comprises the sequence of SEQ ID NO: 42. In some cases, the IL-2 polypeptide consists of the sequence of SEQ ID NO: 42. In some cases, the IL-2 polypeptide comprises about 80%, 85%, 90%, 95%, 96%, 97%, 98%, or 99% sequence identity to SEQ ID NO: 43. In some cases, the IL-2 polypeptide comprises the sequence of SEQ ID NO: 43. In some cases, the IL-2 polypeptide consists of the sequence of SEQ ID NO: 43. In some cases, the IL-2 polypeptide comprises about 80%, 85%, 90%, 95%, 96%, 97%, 98%, or 99% sequence identity to SEQ ID NO: 44. In some cases, the IL-2 polypeptide comprises the sequence of SEQ ID NO: 44. In some cases, the IL-2 polypeptide consists of the sequence of SEQ ID NO: 44. In some cases, the IL-2 polypeptide comprises about 80%, 85%, 90%, 95%, 96%, 97%, 98%, or 99% sequence identity to SEQ ID NO: 45. In some cases, the IL-2 polypeptide comprises the sequence of SEQ ID NO: 45. In some cases, the IL-2 polypeptide consists of the sequence of SEQ ID NO: 45. In some cases, the IL-2 polypeptide comprises about 80%, 85%, 90%, 95%, 96%, 97%, 98%, or 99% sequence identity to SEQ ID NO: 46. In some cases, the IL-2 polypeptide comprises the sequence of SEQ ID NO: 46. In some cases, the IL-2 polypeptide consists of the sequence of SEQ ID NO: 46. In some cases, the IL-2 polypeptide comprises about 80%, 85%, 90%, 95%, 96%, 97%, 98%, or 99% sequence identity to SEQ ID NO: 47. In some cases, the IL-2 polypeptide comprises the sequence of SEQ ID NO: 47. In some cases, the IL-2 polypeptide consists of the sequence of SEQ ID NO: 47. In some cases, the IL-2 polypeptide comprises about 80%, 85%, 90%, 95%, 96%, 97%, 98%, or 99% sequence identity to SEQ ID NO: 48. In some cases, the IL-2 polypeptide comprises the sequence of SEQ ID NO: 48. In some cases, the IL-2 polypeptide consists of the sequence of SEQ ID NO: 48. In some cases, the IL-2 polypeptide comprises about 80%, 85%, 90%, 95%, 96%, 97%, 98%, or 99% sequence identity to SEQ ID NO: 49. In some cases, the IL-2 polypeptide comprises the sequence of SEQ ID NO: 49. In some cases, the IL-2 polypeptide consists of the sequence of SEQ ID NO: 49. In some cases, the IL-2 polypeptide comprises about 80%, 85%, 90%, 95%, 96%, 97%, 98%, or 99% sequence identity to SEQ ID NO: 50. In some cases, the IL-2 polypeptide comprises the sequence of SEQ ID NO: 50. In some cases, the IL-2 polypeptide consists of the sequence of SEQ ID NO: 50. In some cases, the IL-2 polypeptide comprises about 80%, 85%, 90%, 95%, 96%, 97%, 98%, or 99% sequence identity to SEQ ID NO: 51. In some cases, the IL-2 polypeptide comprises the sequence of SEQ ID NO: 51. In some cases, the IL-2 polypeptide consists of the sequence of SEQ ID NO: 51. In some cases, the IL-2 polypeptide comprises about 80%, 85%, 90%, 95%, 96%, 97%, 98%, or 99% sequence identity to SEQ ID NO: 52. In some cases, the IL-2 polypeptide comprises the sequence of SEQ ID NO: 52. In some cases, the IL-2 polypeptide consists of the sequence of SEQ ID NO: 52. In some cases, the IL-2 polypeptide comprises about 80%, 85%, 90%, 95%, 96%, 97%, 98%, or 99% sequence identity to SEQ ID NO: 53. In some cases, the IL-2 polypeptide comprises the sequence of SEQ ID NO: 53. In some cases, the IL-2 polypeptide consists of the sequence of SEQ ID NO: 53. In some cases, the IL-2 polypeptide comprises about 80%, 85%, 90%, 95%, 96%, 97%, 98%, or 99% sequence identity to SEQ ID NO: 54. In some cases, the IL-2 polypeptide comprises the sequence of SEQ ID NO: 54. In some cases, the IL-2 polypeptide consists of the sequence of SEQ ID NO: 54. In additional cases, the IL-2 polypeptide comprises about 80%, 85%, 90%, 95%, 96%, 97%, 98%, or 99% sequence identity to SEQ ID NO: 55. In additional cases, the IL-2 polypeptide comprises the sequence of SEQ ID NO: 55. In additional cases, the IL-2 polypeptide consists of the sequence of SEQ ID NO: 55. In some cases, the IL-2 polypeptide comprises about 80%, 85%, 90%, 95%, 96%, 97%, 98%, or 99% sequence identity to SEQ ID NO: 56. In some cases, the IL-2 polypeptide comprises the sequence of SEQ ID NO: 56. In some cases, the IL-2 polypeptide consists of the sequence of SEQ ID NO: 56. In additional cases, the IL-2 polypeptide comprises about 80%, 85%, 90%, 95%, 96%, 97%, 98%, or 99% sequence identity to SEQ ID NO: 57. In additional cases, the IL-2 polypeptide comprises the sequence of SEQ ID NO: 57. In additional cases, the IL-2 polypeptide consists of the sequence of SEQ ID NO: 57. In some cases, the IL-2 polypeptide comprises about 80%, 85%, 90%, 95%, 96%, 97%, 98%, or 99% sequence identity to SEQ ID NO: 58. In some cases, the IL-2 polypeptide comprises the sequence of SEQ ID NO: 58. In some cases, the IL-2 polypeptide consists of the sequence of SEQ ID NO: 58. In additional cases, the IL-2 polypeptide comprises about 80%, 85%, 90%, 95%, 96%, 97%, 98%, or 99% sequence identity to SEQ ID NO: 59. In additional cases, the IL-2 polypeptide comprises the sequence of SEQ ID NO: 59. In additional cases, the IL-2 polypeptide consists of the sequence of SEQ ID NO: 59. In some cases, the IL-2 polypeptide comprises about 80%, 85%, 90%, 95%, 96%, 97%, 98%, or 99% sequence identity to SEQ ID NO: 60. In some cases, the IL-2 polypeptide comprises the sequence of SEQ ID NO: 60. In some cases, the IL-2 polypeptide consists of the sequence of SEQ ID NO: 60. In some cases, the IL-2 polypeptide comprises about 80%, 85%, 90%, 95%, 96%, 97%, 98%, or 99% sequence identity to SEQ ID NO: 61. In some cases, the IL-2 polypeptide comprises the sequence of SEQ ID NO: 61. In some cases, the IL-2 polypeptide consists of the sequence of SEQ ID NO: 61. In additional cases, the IL-2 polypeptide comprises about 80%, 85%, 90%, 95%, 96%, 97%, 98%, or 99% sequence identity to SEQ ID NO: 62. In additional cases, the IL-2 polypeptide comprises the sequence of SEQ ID NO: 62. In additional cases, the IL-2 polypeptide consists of the sequence of SEQ ID NO: 62. In some cases, the IL-2 polypeptide comprises about 80%, 85%, 90%, 95%, 96%, 97%, 98%, or 99% sequence identity to SEQ ID NO: 63. In some cases, the IL-2 polypeptide comprises the sequence of SEQ ID NO: 63. In some cases, the IL-2 polypeptide consists of the sequence of SEQ ID NO: 63. In additional cases, the IL-2 polypeptide comprises about 80%, 85%, 90%, 95%, 96%, 97%, 98%, or 99% sequence identity to SEQ ID NO: 64. In additional cases, the IL-2 polypeptide comprises the sequence of SEQ ID NO: 64. In additional cases, the IL-2 polypeptide consists of the sequence of SEQ ID NO: 64. In some cases, the IL-2 polypeptide comprises about 80%, 85%, 90%, 95%, 96%, 97%, 98%, or 99% sequence identity to SEQ ID NO: 65. In some cases, the IL-2 polypeptide comprises the sequence of SEQ ID NO: 65. In some cases, the IL-2 polypeptide consists of the sequence of SEQ ID NO: 65. In additional cases, the IL-2 polypeptide comprises about 80%, 85%, 90%, 95%, 96%, 97%, 98%, or 99% sequence identity to SEQ ID NO: 66. In additional cases, the IL-2 polypeptide comprises the sequence of SEQ ID NO: 66. In additional cases, the IL-2 polypeptide consists of the sequence of SEQ ID NO: 66. In some cases, the IL-2 polypeptide comprises about 80%, 85%, 90%, 95%, 96%, 97%, 98%, or 99% sequence identity to SEQ ID NO: 67. In some cases, the IL-2 polypeptide comprises the sequence of SEQ ID NO: 67. In some cases, the IL-2 polypeptide consists of the sequence of SEQ ID NO: 67. In additional cases, the IL-2 polypeptide comprises about 80%, 85%, 90%, 95%, 96%, 97%, 98%, or 99% sequence identity to SEQ ID NO: 68. In additional cases, the IL-2 polypeptide comprises the sequence of SEQ ID NO: 68. In additional cases, the IL-2 polypeptide consists of the sequence of SEQ ID NO: 68. In some cases, the IL-2 polypeptide comprises about 80%, 85%, 90%, 95%, 96%, 97%, 98%, or 99% sequence identity to SEQ ID NO: 69. In some cases, the IL-2 polypeptide comprises the sequence of SEQ ID NO: 69. In some cases, the IL-2 polypeptide consists of the sequence of SEQ ID NO: 69. In some cases, the IL-2 polypeptide comprises about 80%, 85%, 90%, 95%, 96%, 97%, 98%, or 99% sequence identity to SEQ ID NO: 70. In some cases, the IL-2 polypeptide comprises the sequence of SEQ ID NO: 70. In some cases, the IL-2 polypeptide consists of the sequence of SEQ ID NO: 70. In some cases, the IL-2 polypeptide comprises about 80%, 85%, 90%, 95%, 96%, 97%, 98%, or 99% sequence identity to SEQ ID NO: 71. In some cases, the IL-2 polypeptide comprises the sequence of SEQ ID NO: 71. In some cases, the IL-2 polypeptide consists of the sequence of SEQ ID NO: 71. In some cases, the IL-2 polypeptide comprises about 80%, 85%, 90%, 95%, 96%, 97%, 98%, or 99% sequence identity to SEQ ID NO: 72. In some cases, the IL-2 polypeptide comprises the sequence of SEQ ID NO: 72. In some cases, the IL-2 polypeptide consists of the sequence of SEQ ID NO: 72. In some cases, the IL-2 polypeptide comprises about 80%, 85%, 90%, 95%, 96%, 97%, 98%, or 99% sequence identity to SEQ ID NO: 73. In some cases, the IL-2 polypeptide comprises the sequence of SEQ ID NO: 73. In some cases, the IL-2 polypeptide consists of the sequence of SEQ ID NO: 73. In some cases, the IL-2 polypeptide comprises about 80%, 85%, 90%, 95%, 96%, 97%, 98%, or 99% sequence identity to SEQ ID NO: 74. In some cases, the IL-2 polypeptide comprises the sequence of SEQ ID NO: 74. In some cases, the IL-2 polypeptide consists of the sequence of SEQ ID NO: 74. In some cases, the IL-2 polypeptide comprises about 80%, 85%, 90%, 95%, 96%, 97%, 98%, or 99% sequence identity to SEQ ID NO: 75. In some cases, the IL-2 polypeptide comprises the sequence of SEQ ID NO: 75. In some cases, the IL-2 polypeptide consists of the sequence of SEQ ID NO: 75. In some cases, the IL-2 polypeptide comprises about 80%, 85%, 90%, 95%, 96%, 97%, 98%, or 99% sequence identity to SEQ ID NO: 76. In some cases, the IL-2 polypeptide comprises the sequence of SEQ ID NO: 76. In some cases, the IL-2 polypeptide consists of the sequence of SEQ ID NO: 76. In some cases, the IL-2 polypeptide comprises about 80%, 85%, 90%, 95%, 96%, 97%, 98%, or 99% sequence identity to SEQ ID NO: 77. In some cases, the IL-2 polypeptide comprises the sequence of SEQ ID NO: 77. In some cases, the IL-2 polypeptide consists of the sequence of SEQ ID NO: 77. In some cases, the IL-2 polypeptide comprises about 80%, 85%, 90%, 95%, 96%, 97%, 98%, or 99% sequence identity to SEQ ID NO: 78. In some cases, the IL-2 polypeptide comprises the sequence of SEQ ID NO: 78. In some cases, the IL-2 polypeptide consists of the sequence of SEQ ID NO: 78. In some cases, the IL-2 polypeptide comprises about 80%, 85%, 90%, 95%, 96%, 97%, 98%, or 99% sequence identity to SEQ ID NO: 79. In some cases, the IL-2 polypeptide comprises the sequence of SEQ ID NO: 79. In some cases, the IL-2 polypeptide consists of the sequence of SEQ ID NO: 79. In some cases, the IL-2 polypeptide comprises about 80%, 85%, 90%, 95%, 96%, 97%, 98%, or 99% sequence identity to SEQ ID NO: 80. In some cases, the IL-2 polypeptide comprises the sequence of SEQ ID NO: 80. In some cases, the IL-2 polypeptide consists of the sequence of SEQ ID NO: 80. In some cases, the IL-2 polypeptide comprises about 80%, 85%, 90%, 95%, 96%, 97%, 98%, or 99% sequence identity to SEQ ID NO: 81. In some cases, the IL-2 polypeptide comprises the sequence of SEQ ID NO: 81. In some cases, the IL-2 polypeptide consists of the sequence of SEQ ID NO: 81. In some cases, the IL-2 polypeptide comprises about 80%, 85%, 90%, 95%, 96%, 97%, 98%, or 99% sequence identity to SEQ ID NO: 82. In some cases, the IL-2 polypeptide comprises the sequence of SEQ ID NO: 82. In some cases, the IL-2 polypeptide consists of the sequence of SEQ ID NO: 82. In some cases, the IL-2 polypeptide comprises about 80%, 85%, 90%, 95%, 96%, 97%, 98%, or 99% sequence identity to SEQ ID NO: 83. In some cases, the IL-2 polypeptide comprises the sequence of SEQ ID NO: 83. In some cases, the IL-2 polypeptide consists of the sequence of SEQ ID NO: 83. In some cases, the IL-2 polypeptide comprises about 80%, 85%, 90%, 95%, 96%, 97%, 98%, or 99% sequence identity to SEQ ID NO: 84. In some cases, the IL-2 polypeptide comprises the sequence of SEQ ID NO: 84. In some cases, the IL-2 polypeptide consists of the sequence of SEQ ID NO: 84.

In some instances, the IL-2 polypeptide is a truncated variant. In some instances, the truncation is an N-terminal deletion. In other instances, the truncation is a C-terminal deletion. In additional instances, the truncation comprises both N-terminal and C-terminal deletions. For example, the truncation can be a deletion of at least or about 1, 2, 3, 4, 5, 6, 7, 8, 9, 10, 11, 12, 13, 14, 15, 20, or more residues from either the N-terminus or the C-terminus, or both termini. In some cases, the IL-2 polypeptide comprises an N-terminal deletion of at least or about 1, 2, 3, 4, 5, 6, 7, 8, 9, 10, 11, 12, 13, 14, 15, 20, or more residues. In some cases, the IL-2 polypeptide comprises an N-terminal deletion of at least or about 1, 2, 3, 4, 5, 6, 7, 8, 9, or 10 residues. In some cases, the IL-2 polypeptide comprises an N-terminal deletion of at least or about 2 residues. In some cases, the IL-2 polypeptide comprises an N-terminal deletion of at least or about 3 residues. In some cases, the IL-2 polypeptide comprises an N-terminal deletion of at least or about 4 residues. In some cases, the IL-2 polypeptide comprises an N-terminal deletion of at least or about 5 residues. In some cases, the IL-2 polypeptide comprises an N-terminal deletion of at least or about 6 residues. In some cases, the IL-2 polypeptide comprises an N-terminal deletion of at least or about 7 residues. In some cases, the IL-2 polypeptide comprises an N-terminal deletion of at least or about 8 residues. In some cases, the IL-2 polypeptide comprises an N-terminal deletion of at least or about 9 residues. In some cases, the IL-2 polypeptide comprises an N-terminal deletion of at least or about 10 residues.

In some embodiments, the IL-2 polypeptide is a functionally active fragment. In some cases, the functionally active fragment comprises IL-2 region 10-133, 20-133, 30-133, 10-130, 20-130, 30-130, 10-125, 20-125, 30-125, 1-130, or 1-125, wherein the residue positions are in reference to the positions in SEQ ID NO: 1. In some cases, the functionally active fragment comprises IL-2 region 10-133, wherein the residue positions are in reference to the positions in SEQ ID NO: 1. In some cases, the functionally active fragment comprises IL-2 region 20-133, wherein the residue positions are in reference to the positions in SEQ ID NO: 1. In some cases, the functionally active fragment comprises IL-2 region 30-133, wherein the residue positions are in reference to the positions in SEQ ID NO: 1. In some cases, the functionally active fragment comprises IL-2 region 10-125, wherein the residue positions are in reference to the positions in SEQ ID NO: 1. In some cases, the functionally active fragment comprises IL-2 region 20-125, wherein the residue positions are in reference to the positions in SEQ ID NO: 1. In some cases, the functionally active fragment comprises IL-2 region 1-130, wherein the residue positions are in reference to the positions in SEQ ID NO: 1. In some cases, the functionally active fragment comprises IL-2 region 1-125, wherein the residue positions are in reference to the positions in SEQ ID NO: 1.

In some embodiments, described herein is an IL-2 conjugate that comprises an isolated, purified, and modified IL-2 polypeptide and a conjugating moiety. In some instances, the IL-2 conjugate has a decreased affinity to an IL-2 receptor α (IL-2Rα) subunit relative to a wild-type IL-2 polypeptide. In some cases, the conjugating moiety is bound to an amino acid residue that interacts with IL-2Rα (e.g., at the IL-2/IL-2Rα interface). In some cases, the conjugating moiety is bound to an amino acid residue that is proximal to the IL-2/IL-2Rα interface (e.g., about 5 Å, about 10 Å, about 15 Å, or about 20 Å away from the IL-2/IL-2Rα interface). As used herein, the residues involved in the IL-2/IL-2Rα interface comprise IL-2 residues that form hydrophobic interactions, hydrogen bonds, or ionic interactions with residues from the IL-2Rα subunit.

In some instances, the conjugating moiety is bound to an amino acid residue selected from an amino acid position Y31, K32, N33, P34, K35, T37, R38, T41, F42, K43, F44, Y45, P47, K48, Q57, E60, E61, E62, L63, K64, P65, E68, V69, N71, L72, Q74, S75, K76, N77, M104, C105, E106, Y107, A108, D109, E110, T111, or A112, in which the numbering of the amino acid residues corresponds to SEQ ID NO: 1. In some instances, the amino acid position is selected from Y31, K32, N33, P34, K35, T37, R38, T41, F42, K43, F44, Y45, P47, K48, E61, E62, E68, K64, P65, V69, L72, Q74, S75, K76, N77, M104, C105, E106, Y107, A108, D109, E110, T111, and A112. In some instances, the amino acid position is selected from N33, P34, K35, T37, R38, M39, T41, F42, K43, F44, Y45, Q57, E60, E61, E62, L63, K64, P65, E68, V69, N71, L72, M104, C105, E106, Y107, A108, D109, E110, T111, and A112. In some instances, the amino acid position is selected from K35, T37, R38, T41, F42, K43, F44, Y45, E61, E62, E68, K64, P65, V69, L72, and Y107. In some instances, the amino acid position is selected from T37, R38, T41, F42, F44, Y45, E61, E62, E68, K64, P65, V69, L72, and Y107. In some instances, the amino acid position is selected from T37, R38, T41, F42, F44, Y45, E61, E62, E68, P65, V69, L72, and Y107. In some instances, the amino acid position is selected from T37, T41, F42, F44, Y45, P65, V69, L72, and Y107. In some instances, the amino acid position is selected from R38 and K64. In some instances, the amino acid position is selected from E61, E62, and E68. In some cases, the amino acid position is at K35. In some cases, the amino acid position is at T37. In some cases, the amino acid position is at R38. In some cases, the amino acid position is at T41. In some cases, the amino acid position is at F42. In some cases, the amino acid position is at K43. In some cases, the amino acid position is at F44. In some cases, the amino acid position is at Y45. In some cases, the amino acid position is at E61. In some cases, the amino acid position is at E62. In some cases, the amino acid position is at K64. In some cases, the amino acid position is at E68. In some cases, the amino acid position is at P65. In some cases, the amino acid position is at V69. In some cases, the amino acid position is at L72. In some cases, the amino acid position is at Y107. In some cases, the amino acid position is at L72. In some cases, the amino acid position is at D109.

In some instances, the IL-2 conjugate further comprises an additional mutation. In some cases, the additional mutation is at an amino acid position selected from K35, T37, R38, T41, F42, K43, F44, Y45, E61, E62, E68, K64, P65, V69, L72, and Y107. In such cases, the amino acid is conjugated to an additional conjugating moiety for increase in serum half-life, stability, or a combination thereof. Alternatively, the amino acid is first mutated to a natural amino acid such as lysine, cysteine, histidine, arginine, aspartic acid, glutamic acid, serine, threonine, or tyrosine; or to an unnatural amino acid prior to binding to the additional conjugating moiety.

In some embodiments, the decreased affinity of the modified IL-2 polypeptide to an IL-2 receptor α (IL-2Rα) subunit relative to a wild-type IL-2 polypeptide without the unnatural amino acid modification (e.g., a wild-type IL-2 polypeptide) is about 10%, 20%, 30%, 40%, 50%, 60%, 70%, 80%, 90%, 95%, or 99%, or greater than 99%. In some cases, the decreased affinity is about 10%. In some cases, the decreased affinity is about 20%. In some cases, the decreased affinity is about 40%. In some cases, the decreased affinity is about 50%. In some cases, the decreased affinity is about 60%. In some cases, the decreased affinity is about 80%. In some cases, the decreased affinity is about 90%. In some cases, the decreased affinity is about 99%. In some cases, the decreased affinity is greater than 99%. In some cases, the decreased affinity is about 80%. In some cases, the decreased affinity is about 100%.

In some embodiments, the decreased affinity of the modified IL-2 polypeptide to an IL-2 receptor α (IL-2Rα) subunit relative to an equivalent IL-2 polypeptide without the unnatural amino acid modification (e.g., a wild-type IL-2 polypeptide) is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 400-fold, 500-fold, 1,000-fold, or more. In some cases, the decreased affinity is about 1-fold. In some cases, the decreased affinity is about 2-fold. In some cases, the decreased affinity is about 4-fold. In some cases, the decreased affinity is about 5-fold. In some cases, the decreased affinity is about 6-fold. In some cases, the decreased affinity is about 8-fold. In some cases, the decreased affinity is about 10-fold. In some cases, the decreased affinity is about 30-fold. In some cases, the decreased affinity is about 50-fold. In some cases, the decreased affinity is about 100-fold. In some cases, the decreased affinity is about 300-fold. In some cases, the decreased affinity is about 500-fold. In some cases, the decreased affinity is about 1000-fold. In some cases, the decreased affinity is more than 1,000-fold.

In some cases, the modified IL-2 polypeptide does not interact with IL-2Rα. In some instances, the modified IL-2 polypeptide is further conjugated to a conjugating moiety. In some cases, the IL-2 conjugate does not interact with IL-2Rα.

In some embodiments, the modified IL-2 polypeptide exhibits a first receptor signaling potency to an IL-2βγ signaling complex and a second receptor signaling potency to an IL-2αβγ signaling complex, and wherein a difference between the first receptor signaling potency and the second receptor signaling potency is less than 10-fold. In some embodiments, the modified IL-2 polypeptide exhibits a first receptor signaling potency to an IL-2βγ signaling complex and a second receptor signaling potency to an IL-2αβγ signaling complex, and wherein a difference between the first receptor signaling potency and the second receptor signaling potency is less than 5-fold. In some instances, the difference is less than 9-fold, less than 8-fold, less than 7-fold, less than 6-fold, less than 5-fold, less than 4-fold, less than 3-fold, less than 2-fold, or less than 1-fold. In some instances, the modified IL-2 polypeptide is a partial agonist, e.g., an agonist that activates a receptor (e.g., an IL-2βγ signaling complex or an IL-2αβγ signaling complex) but has only a partial efficacy at the receptor relative to a full agonist. In some instances, the modified IL-2 polypeptide is a full agonist, e.g., an agonist that activates a receptor (e.g., an IL-2βγ signaling complex or an IL-2αβγ signaling complex) at a maximum response.

In some instances, the receptor signaling potency is measured by an EC50 value. In some instances, the modified IL-2 polypeptide provides a first EC50 value for activating IL-2βγ signaling complex and a second EC50 value for activating IL-2αβγ signaling complex, and wherein a difference between the first EC50 and the second EC50 value is less than 10-fold. In some instances, the modified IL-2 polypeptide provides a first EC50 value for activating IL-2βγ signaling complex and a second EC50 value for activating IL-2αβγ signaling complex, and wherein a difference between the first EC50 and the second EC50 value is less than 5-fold. In some cases, the difference is less than 9-fold, less than 8-fold, less than 7-fold, less than 6-fold, less than 5-fold, less than 4-fold, less than 3-fold, less than 2-fold, or less than 1-fold.

In some instances, the receptor signaling potency is measured by an ED50 value. In some instances, the modified IL-2 polypeptide provides a first ED50 value for activating IL-2βγ signaling complex and a second ED50 value for activating IL-2αβγ signaling complex, and wherein a difference between the first ED50 and the second ED50 value is less than 10-fold. In some instances, the modified IL-2 polypeptide provides a first ED50 value for activating IL-2βγ signaling complex and a second ED50 value for activating IL-2αβγ signaling complex, and wherein a difference between the first ED50 and the second ED50 value is less than 5-fold. In some cases, the difference is less than 9-fold, less than 8-fold, less than 7-fold, less than 6-fold, less than 5-fold, less than 4-fold, less than 3-fold, less than 2-fold, or less than 1-fold.

In some embodiments, the conjugating moiety is linked to the N-terminus or the C-terminus of an IL-2 polypeptide, either directly or indirectly through a linker peptide. In some cases, the conjugating moiety (e.g., a polymer, a protein, or a peptide) is genetically fused to the IL-2, at the N-terminus or the C-terminus of IL-2, and either directly or indirectly through a linker peptide. In some instances, the conjugating moiety is linked to the N-terminus or the C-terminus amino acid residue. In some instances, the conjugating moiety is linked to a reactive group that is bound to the N-terminus or C-terminus amino acid residue.

In some embodiments, the IL-2 conjugate with reduced binding affinity to IL-2Rα is capable of expanding CD4+ helper cell, CD8+ effector naïve and memory T cell, Natural Killer (NK) cell, or Natural killer T (NKT) cell populations. In some cases, the conjugating moiety impairs or blocks binding of IL-2 with IL-2Rα.

In some cases, activation of CD4+ helper cell, CD8+ effector naïve and memory cell, Natural Killer (NK) cell, or Natural killer T (NKT) cell population via the IL-2Rβγ complex by the modified IL-2 polypeptide retains significant potency of activation of said cell population relative to a wild-type IL-2 polypeptide. In some instances, the activation by the modified IL-2 polypeptide is equivalent to that of the wild-type IL-2 polypeptide. In other instances, the activation by the modified IL-2 polypeptide is higher than that of the wild-type IL-2 polypeptide. In some cases, the receptor signaling potency of the modified IL-2 polypeptide to the IL-2Rβγ complex is higher than a receptor signaling potency of the wild-type IL-2 polypeptide to the IL-2Rβγ complex. In some cases, the receptor signaling potency of the modified IL-2 polypeptide is at least 1-fold higher than the respective potency of the wild-type IL-2 polypeptide. In some cases, the receptor signaling potency of the modified IL-2 polypeptide is about or at least 2-fold, 3-fold, 4-fold, 5-fold, 6-fold, 7-fold, 8-fold, 9-fold, 10-fold, 15-fold, 20-fold, 25-fold, 30-fold, 40-fold, 50-fold, 60-fold, 70-fold, 80-fold, 90-fold, 100-fold, 150-fold, 200-fold, 300-fold, 400-fold, 500-fold, 1,000-fold, or higher than the respective potency of the wild-type IL-2 polypeptide. In such cases, the dose or concentration of the modified IL-2 polypeptide used for achieving a similar level of activation of the CD4+ helper cell, CD8+ effector naïve and memory cell, Natural Killer (NK) cell, or Natural killer T (NKT) cell population as a wild-type Il-2 polypeptide is lower than a dose or concentration used for the wild-type IL-2 polypeptide.

In some embodiments, activation of CD4+ helper cell, CD8+ effector naïve and memory cell, Natural Killer (NK) cell, or Natural killer T (NKT) cell population via the IL-2Rβγ complex by the modified IL-2 polypeptide retains significant potency of activation of said cell population by a wild-type IL-2 polypeptide. In some cases, the receptor signaling potency of the modified IL-2 polypeptide the IL-2Rβγ complex is lower than a receptor signaling potency of the wild-type IL-2 polypeptide the IL-2Rβγ complex. In some cases, the receptor signaling potency of the modified IL-2 polypeptide is about or at least 1-fold, 2-fold, 3-fold, 4-fold, 5-fold, 10-fold, 20-fold, or 50-fold lower than the respective potency of the wild-type IL-2 polypeptide.

In some embodiments, the modified IL-2 polypeptide exhibits a first receptor signaling potency to IL-2Rβγ and a second receptor signaling potency to IL-2Rαβγ. In some instances, the first receptor signaling potency to IL-2Rβγ is an improved potency relative to a wild-type IL-2 polypeptide. In some instances, the second receptor signaling potency to IL-2Rαβγ is an impaired potency relative to the wild-type IL-2 polypeptide. In some embodiments, the modified IL-2 polypeptide exhibits a first receptor signaling potency to IL-2Rβγ and a second receptor signaling potency to IL-2Rαβγ, and wherein the first receptor signaling potency is at least 1-fold, 2-fold, 3-fold, 4-fold, 5-fold, 6-fold, 7-fold, 8-fold, 9-fold, 10-fold, 20-fold, 30-fold, 50-fold, 100-fold, 500-fold, 1000-fold, or higher than the second receptor signaling potency. In some instances, the first receptor signaling potency is at least 1-fold or higher than the second receptor signaling potency. In some instances, the first receptor signaling potency is at least 2-fold or higher than the second receptor signaling potency. In some instances, the first receptor signaling potency is at least 5-fold or higher than the second receptor signaling potency. In some instances, the first receptor signaling potency is at least 10-fold or higher than the second receptor signaling potency. In some instances, the first receptor signaling potency is at least 20-fold or higher than the second receptor signaling potency. In some instances, the first receptor signaling potency is at least 50-fold or higher than the second receptor signaling potency. In some instances, the first receptor signaling potency is at least 100-fold or higher than the second receptor signaling potency. In some instances, the first receptor signaling potency is at least 500-fold or higher than the second receptor signaling potency. In some instances, the first receptor signaling potency is at least 1000-fold or higher than the second receptor signaling potency. In some instances, the first receptor signaling potency of the modified IL-2 polypeptide is higher than a receptor signaling potency of the wild-type IL-2 polypeptide to the IL-2Rβγ, and the second receptor signaling potency of the modified IL-2 polypeptide is lower than a receptor signaling potency of the wild-type IL-2 polypeptide to the IL-2Rαβγ. In some cases, both receptor signaling potencies are lower than their respective potencies in a wild-type IL-2 polypeptide. In other cases, both receptor signaling potencies are higher than their respective potencies in a wild-type IL-2 polypeptide.

In some embodiments, the IL-2 conjugate decreases a toxic adverse event in a subject administered with the IL-2 conjugate. Exemplary toxic adverse events include eosinophilia, capillary leak, and vascular leak syndrome (VLS). In some instances, the IL-2 conjugate decreases the occurrence of a toxic adverse event in the subject by about 10%, 20%, 30%, 40%, 50%, 60%, 70%, 80%, 90%, 95%, 99%, or about 100%, relative to a second subject administered with a wild-type IL-2 or aldesleukin. In some instances, the IL-2 conjugate decreases the severity of a toxic adverse event in the subject by about 10%, 20%, 30%, 40%, 50%, 60%, 70%, 80%, 90%, 95%, 99%, or about 100%, relative to a second subject administered with a wild-type IL-2 or aldesleukin.

In some instances, the toxic adverse event is eosinophilia. In some cases, the IL-2 conjugate decreases the occurrence of eosinophilia in the subject by about 10%, 20%, 30%, 40%, 50%, 60%, 70%, 80%, 90%, 95%, 99%, or about 100%, relative to a second subject administered with a wild-type IL-2 or aldesleukin. In some cases, the IL-2 conjugate decreases the severity of eosinophilia in the subject by about 10%, 20%, 30%, 40%, 50%, 60%, 70%, 80%, 90%, 95%, 99%, or about 100%, relative to a second subject administered with a wild-type IL-2 or aldesleukin.

In some instances, the toxic adverse event is capillary leak. In some cases, the IL-2 conjugate decreases the occurrence of capillary leak in the subject by about 10%, 20%, 30%, 40%, 50%, 60%, 70%, 80%, 90%, 95%, 99%, or about 100%, relative to a second subject administered with a wild-type IL-2 or aldesleukin. In some cases, the IL-2 conjugate decreases the severity of capillary leak in the subject by about 10%, 20%, 30%, 40%, 50%, 60%, 70%, 80%, 90%, 95%, 99%, or about 100%, relative to a second subject administered with a wild-type IL-2 or aldesleukin.

In some instances, the toxic adverse event is VLS. In some cases, the IL-2 conjugate decreases the occurrence of VLS in the subject by about 10%, 20%, 30%, 40%, 50%, 60%, 70%, 80%, 90%, 95%, 99%, or about 100%, relative to a second subject administered with a wild-type IL-2 or aldesleukin. In some cases, the IL-2 conjugate decreases the severity of VLS in the subject by about 10%, 20%, 30%, 40%, 50%, 60%, 70%, 80%, 90%, 95%, 99%, or about 100%, relative to a second subject administered with a wild-type IL-2 or aldesleukin.

In some embodiments, the IL-2 conjugate comprises a plasma half-life of greater than 1 hour, 2 hours, 3 hours, 4 hours, 5 hours, 6 hours, 7 hours, 8 hours, 9 hours, 10 hours, 12 hours, 18 hours, 24 hours, 2 days, 3 days, 4 days, 5 days, 6 days, 7 days, or more. In some embodiments, the IL-2 conjugate comprises a plasma half-life of greater than 1 hour, 2 hours, 3 hours, 4 hours, 5 hours, 6 hours, 7 hours, 8 hours, 9 hours, 10 hours, or more. In some embodiments, the IL-2 conjugate comprises a plasma half-life of greater than 1 hour. In some embodiments, the IL-2 conjugate comprises a plasma half-life of greater than 2 hours. In some embodiments, the IL-2 conjugate comprises a plasma half-life of greater than 3 hours. In some embodiments, the IL-2 conjugate comprises a plasma half-life of greater than 4 hours. In some embodiments, the IL-2 conjugate comprises a plasma half-life of greater than 5 hours. In some embodiments, the IL-2 conjugate comprises a plasma half-life of greater than 6 hours. In some embodiments, the IL-2 conjugate comprises a plasma half-life of greater than 7 hours. In some embodiments, the IL-2 conjugate comprises a plasma half-life of greater than 8 hours. In some embodiments, the IL-2 conjugate comprises a plasma half-life of greater than 9 hours. In some embodiments, the IL-2 conjugate comprises a plasma half-life of greater than 10 hours. In some embodiments, the IL-2 conjugate comprises a plasma half-life of greater than 12 hours. In some embodiments, the IL-2 conjugate comprises a plasma half-life of greater than 18 hours. In some embodiments, the IL-2 conjugate comprises a plasma half-life of greater than 24 hours.

In some embodiments, the IL-2 conjugate comprises a plasma half-life of at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more. In some embodiments, the IL-2 conjugate comprises a plasma half-life of at least 1 hour, 2 hours, 3 hours, 4 hours, 5 hours, 6 hours, 7 hours, 8 hours, 9 hours, 10 hours, 12 hours, 15 hours, 18 hours, 24 hours, or more. In some embodiments, the IL-2 conjugate comprises a plasma half-life of at least 1 hour. In some embodiments, the IL-2 conjugate comprises a plasma half-life of at least 2 hours. In some embodiments, the IL-2 conjugate comprises a plasma half-life of at least 3 hours. In some embodiments, the IL-2 conjugate comprises a plasma half-life of at least 4 hours. In some embodiments, the IL-2 conjugate comprises a plasma half-life of at least 5 hours. In some embodiments, the IL-2 conjugate comprises a plasma half-life of at least 6 hours. In some embodiments, the IL-2 conjugate comprises a plasma half-life of at least 7 hours. In some embodiments, the IL-2 conjugate comprises a plasma half-life of at least 8 hours. In some embodiments, the IL-2 conjugate comprises a plasma half-life of at least 9 hours. In some embodiments, the IL-2 conjugate comprises a plasma half-life of at least 10 hours. In some embodiments, the IL-2 conjugate comprises a plasma half-life of at least 12 hours. In some embodiments, the IL-2 conjugate comprises a plasma half-life of at least 18 hours. In some embodiments, the IL-2 conjugate comprises a plasma half-life of at least 24 hours.

In some embodiments, the IL-2 conjugate comprises a plasma half-life of from about 1 hour to about 7 days, from about 12 hours to about 7 days, from about 18 hours to about 7 days, from about 24 hours to about 7 days, from about 1 hours to about 5 days, from about 12 hours to about 5 days, from about 24 hours to about 5 days, from about 2 days to about 5 days, or from about 2 days to about 3 days.

In some embodiments, the IL-2 conjugate comprises a plasma half-life of from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours.

In some embodiments, the IL-2 conjugate comprises a plasma half-life that is capable of proliferating and/or expanding a CD4+ helper cell, CD8+ effector naïve and memory T cell, NK cell, NKT cell, or a combination thereof, but does not exert a deleterious effect such as apoptosis.

In some embodiments, the IL-2 conjugate comprises an extended plasma half-life, e.g., by at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more relative to a wild-type IL-2. In some embodiments, the IL-2 conjugate comprises an extended plasma half-life, e.g., by at least 1 hour, 2 hours, 3 hours, 4 hours, 5 hours, 6 hours, 7 hours, 8 hours, 9 hours, 10 hours, 12 hours, 15 hours, 18 hours, 24 hours, or more relative to a wild-type IL-2.

In some embodiments, the IL-2 conjugate comprises an extended plasma half-life, e.g., from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours relative to a wild-type IL-2.

In some embodiments, the IL-2 conjugate comprises an extended plasma half-life, e.g., by at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more relative to aldesleukin. In some embodiments, the IL-2 conjugate comprises an extended plasma half-life, e.g., by at least 1 hour, 2 hours, 3 hours, 4 hours, 5 hours, 6 hours, 7 hours, 8 hours, 9 hours, 10 hours, 12 hours, 15 hours, 18 hours, 24 hours, or more relative to aldesleukin.

In some embodiments, the IL-2 conjugate comprises an extended plasma half-life, e.g., from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours relative to aldesleukin.

In some embodiments, the IL-2 conjugate comprises an extended plasma half-life with a reduced toxicity. In some instances, the IL-2 conjugate comprises an extended plasma half-life of at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more with a reduced toxicity. In some instances, the IL-2 conjugate comprises an extended plasma half-life of at least 1 hour, 2 hours, 3 hours, 4 hours, 5 hours, 6 hours, 7 hours, 8 hours, 9 hours, 10 hours, 12 hours, 15 hours, 18 hours, 24 hours, or more with a reduced toxicity. In some instances, the IL-2 conjugate comprises an extended plasma half-life of from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours with a reduced toxicity. In some cases, the reduced toxicity is at least 1-fold, 2-fold, 3-fold, 4-fold, 5-fold, 6-fold, 7-fold, 8-fold, 9-fold, 10-fold, 20-fold, 30-fold, 50-fold, 100-fold, or more reduced relative to a wild-type IL2. In some cases, the reduced toxicity is at least 10%, 20%, 30%, 40%, 50%, 60%, 70%, 80%, 90%, 100%, 200%, 300%, 400%, 500%, or more reduced relative to a wild-type IL-2.

In some embodiments, the IL-2 conjugate comprises an extended plasma half-life with a reduced toxicity. In some instances, the IL-2 conjugate comprises an extended plasma half-life of at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more with a reduced toxicity. In some instances, the IL-2 conjugate comprises an extended plasma half-life of at least 1 hour, 2 hours, 3 hours, 4 hours, 5 hours, 6 hours, 7 hours, 8 hours, 9 hours, 10 hours, 12 hours, 15 hours, 18 hours, 24 hours, or more with a reduced toxicity. In some instances, the IL-2 conjugate comprises an extended plasma half-life of from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours with a reduced toxicity. In some cases, the reduced toxicity is at least 1-fold, 2-fold, 3-fold, 4-fold, 5-fold, 6-fold, 7-fold, 8-fold, 9-fold, 10-fold, 20-fold, 30-fold, 50-fold, 100-fold, or more reduced relative to aldesleukin. In some cases, the reduced toxicity is at least 10%, 20%, 30%, 40%, 50%, 60%, 70%, 80%, 90%, 100%, 200%, 300%, 400%, 500%, or more reduced relative to aldesleukin.

In some embodiments, the IL-2 conjugate comprises a conjugating moiety in which the size (e.g., the volume or length) of the conjugating moiety enhances plasma stability but does not reduce potency. In some instances, the size of the conjugating moiety extends plasma half-life by at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more. In some instances, the size of the conjugating moiety extends plasma half-life by at least 1 hour, 2 hours, 3 hours, 4 hours, 5 hours, 6 hours, 7 hours, 8 hours, 9 hours, 10 hours, 12 hours, 15 hours, 18 hours, 24 hours, or more. In some instances, the size of the conjugating moiety extends plasma half-life from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours. In some instances, the size of the conjugating moiety reduces the potency by less than 5%, 4%, 3%, 2%, 1%, or less relative to aldesleukin.

In some embodiments, the IL-2 conjugate comprises a conjugating moiety in which the size (e.g., the volume or length) of the conjugating moiety enhances plasma stability and potency. In some instances, the size of the conjugating moiety extends plasma half-life by at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more. In some instances, the size of the conjugating moiety extends plasma half-life by at least 1 hour, 2 hours, 3 hours, 4 hours, 5 hours, 6 hours, 7 hours, 8 hours, 9 hours, 10 hours, 12 hours, 15 hours, 18 hours, 24 hours, or more. In some instances, the size of the conjugating moiety extends plasma half-life from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours. In some instances, the size of the conjugating moiety further enhances the potency by more than 5%, 10%, 20%, 30%, 40%, 50%, 60%, 70%, 80%, 90%, 100%, 200%, or more relative to aldesleukin.

In some embodiments, described herein is an IL-2 conjugate comprising an unnatural amino acid covalently attached to a conjugating moiety, wherein the unnatural amino acid is located in region 35-107, and wherein the region 35-107 corresponds to residues K35-Y107 of SEQ ID NO: 1.

In some embodiments, described herein is an interleukin 2 βγ receptor (IL-2Rβγ) binding protein, wherein the binding affinity for an interleukin 2α receptor (IL-2Rα) of said binding protein is less than that of wild-type human IL-2 (hIL-2), wherein the binding affinity for an interleukin 2α receptor (IL-2Rα) of said binding protein is less than that of wild-type human IL-2 (hIL-2). In some embodiments, described herein is an interleukin 2 βγ receptor (IL-2Rβγ) binding protein, wherein the binding affinity for an interleukin 2α receptor (IL-2Rα) of said binding protein is less than that of wild-type human IL-2 (hIL-2), and wherein said binding protein comprises at least one unnatural amino acid. In some instances, said binding protein is a modified IL-2 polypeptide or a functionally active fragment thereof, wherein the modified IL-2 polypeptide comprises at least one unnatural amino acid. In some instances, the at least one unnatural amino acid is located in region 35-107, and wherein the region 35-107 corresponds to residues K35-Y107 of SEQ ID NO: 1.

In some embodiments, described herein is an IL-2/IL-2Rβγ complex comprising a modified IL-2 polypeptide comprising a mutation and an IL-2Rβγ, wherein the modified IL-2 polypeptide has a reduced binding affinity toward IL-2Rα, and wherein the reduced binding affinity is compared to a binding affinity between a wild-type IL-2 polypeptide and IL-2Rα. In some instances, the modified IL-2 polypeptide further comprises a conjugating moiety covalently attached to site of mutation. In some instances, the site of mutation comprises an amino acid mutated to a natural amino acid. In some cases, the site of mutation comprises an amino acid mutated to a cysteine residue. In other cases, the site of mutation comprises an amino acid mutated to a lysine residue.

In some embodiments, described herein is an IL-2/IL-2Rβγ complex comprising a modified IL-2 polypeptide comprising an unnatural amino acid and an IL-2Rβγ, wherein the modified IL-2 polypeptide has a reduced binding affinity toward IL-2Rα, and wherein the reduced binding affinity is compared to a binding affinity between a wild-type IL-2 polypeptide and IL-2Rα. In some instances, the modified IL-2 polypeptide further comprises a conjugating moiety covalently attached to the unnatural amino acid.

In some embodiments, described herein is an IL-2/IL-2Rβγ complex comprising a modified IL-2 polypeptide comprising an unnatural amino acid and an IL-2Rβγ, wherein the modified IL-2 polypeptide has a reduced receptor signaling potency toward IL-2Rα, and wherein the reduced receptor signaling potency is compared to a receptor signaling potency between a wild-type IL-2 polypeptide and IL-2Rα. In some instances, the modified IL-2 polypeptide further comprises a conjugating moiety covalently attached to the unnatural amino acid.

In some embodiments, described herein is an activator of a CD4+ helper cell, CD8+ effector naïve and memory T cell, Natural Killer (NK) cell, or a Natural killer T (NKT) cell that selectively expands CD4+ helper cells, CD8+ effector naïve and memory T cells, NK cells, NKT cells, or a combination thereof in a cell population, wherein said activator comprises a modified interleukin 2 (IL-2) polypeptide comprising at least one mutation. In some instances, the mutation is to a natural amino acid. In other instances, the mutation is to an unnatural amino acid. In some embodiments, described herein is an activator of a CD4+ helper cell, CD8+ effector naïve and memory T cell, Natural Killer (NK) cell, or a Natural killer T (NKT) cell that selectively expands CD4+ helper cells, CD8+ effector naïve and memory T cells, NK cells, NKT cells, or a combination thereof in a cell population, wherein said activator comprises a modified interleukin 2 (IL-2) polypeptide comprising at least one unnatural amino acid. In some instances, said activator expands CD4+ T regulatory (Treg) cells by less than 20%, 15%, 10%, 5%, 1%, or less than 0.1% when said activator is in contact with said CD3+ cell population compared to an expansion of CD4+ Treg cells in the CD3+ cell population contacted with a wild-type IL-2 polypeptide. In some instances, said activator does not expand Treg cells in said cell population. In some instances, said cell population is an in vivo cell population. In some instances, said cell population is an in vitro cell population. In some instances, said cell population is an ex vivo cell population.

In some instances, also described herein is a method of expanding a CD4+ helper cell, CD8+ effector naïve and memory T cell, Natural Killer (NK) cell, or a Natural killer T (NKT) cell population, comprising contacting said cell population with a therapeutically effective amount of a CD4+ helper cell, CD8+ effector naïve and memory T cell, Natural Killer (NK) cell, or a Natural killer T (NKT) cell activator, in which said activator comprises a modified interleukin 2 (IL-2) polypeptide comprising at least one mutation, thereby expanding the CD4+ helper cell, CD8+ effector naïve and memory T cell, Natural Killer (NK) cell, or Natural killer T (NKT) cell population. In some instances, the mutation is to a natural amino acid. In other instances, the mutation is to an unnatural amino acid. In some instances, also described herein is a method of expanding a CD4+ helper cell, CD8+ effector naïve and memory T cell, Natural Killer (NK) cell, or a Natural killer T (NKT) cell population, comprising contacting said cell population with a therapeutically effective amount of a CD4+ helper cell, CD8+ effector naïve and memory T cell, Natural Killer (NK) cell, or a Natural killer T (NKT) cell activator, in which said activator comprises a modified interleukin 2 (IL-2) polypeptide comprising at least one unnatural amino acid, thereby expanding the CD4+ helper cell, CD8+ effector naïve and memory T cell, Natural Killer (NK) cell, or Natural killer T (NKT) cell population.

In some embodiments, the modified IL-2 polypeptide comprising a mutation at K35 corresponding to residue position 35, of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα

In some embodiments, the modified IL-2 polypeptide comprising a mutation at residue T37 corresponding to a position 37 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα.

In some instances, the conjugating moiety is bound to an amino acid residue selected from an amino acid position P2, T3, S4, S5, S6, T7, K8, K9, Q11, L12, E15, H16, L18, L19, D20, Q22, M23, N26, G27, N29, N30, Y31, K32, K35, T37, M46, K47, K48, A50, T51, E52, K53, H55, Q57, E60, E67, N71, Q74, S75, K76, N77, F78, H79, R81, P82, R83, D84, S87, N88, N89, V91, 192, L94, E95, K97, G98, S99, E100, T101, T102, F103, M104, C105, E106, Y107, A108, D109, E110, T111, A112, T113, E116, N119, R120, T123, A125, Q126, S127, S130, T131, L132, and T133, in which the numbering of the amino acid residues corresponds to SEQ ID NO: 1. In some instances, the amino acid position is selected from K8, K9, Q11, L12, E15, H16, L18, L19, D20, Q22, M23, N26, R81, D84, S87, N88, V91, 192, L94, E95, E116, N119, R120, T123, A125, Q126, 5127, S130, T131, L132, and T133. In some instances, the amino acid position is selected from P2, T3, S4, S5, S6, T7, G27, N29, N30, Y31, K32, K35, T37, M46, K47, K48, A50, T51, E52, K53, H55, Q57, E60, E67, N71, Q74, S75, K76, N77, F78, H79, P82, R83, N89, K97, G98, S99, E100, T101, T102, F103, M104, C105, E106, Y107, A108, D109, E110, T111, A112, and T113. In some instances, the amino acid position is selected from K8, K9, L12, E15, H16, L19, D20, Q22, M23, N26, D84, N88, E95, and Q126. In some instances, the amino acid position is selected from K8, K9, and H16. In some instances, the amino acid position is selected from Q22, N26, N88, and Q126. In some instances, the amino acid position is selected from E15, D20, D84, and E95. In some instances, the amino acid position is selected from L12, L19, and M23. In some instances, the amino acid position is selected from Q22 and N26. In some cases, the amino acid position is at K8. In some cases, the amino acid position is at K9. In some cases, the amino acid position is at Q11. In some cases, the amino acid position is at L12. In some cases, the amino acid position is at E15. In some cases, the amino acid position is at H16. In some cases, the amino acid position is at L18. In some cases, the amino acid position is at L19. In some cases, the amino acid position is at D20. In some cases, the amino acid position is at Q22. In some cases, the amino acid position is at M23. In some cases, the amino acid position is at N26. In some cases, the amino acid position is at R81. In some cases, the amino acid position is at D84. In some cases, the amino acid position is at S87. In some cases, the amino acid position is at N88. In some cases, the amino acid position is at V91. In some cases, the amino acid position is at 192. In some cases, the amino acid position is at L94. In some cases, the amino acid position is at E95. In some cases, the amino acid position is at E116. In some cases, the amino acid position is at N119. In some cases, the amino acid position is at R120. In some cases, the amino acid position is at T123. In some cases, the amino acid position is at A125. In some cases, the amino acid position is at Q126. In some cases, the amino acid position is at S127. In some cases, the amino acid position is at S130. In some cases, the amino acid position is at T131. In some cases, the amino acid position is at L132. In some cases, the amino acid position is at T133.

In some instances, the IL-2 conjugate further comprises an additional mutation. In such cases, the amino acid is conjugated to an additional conjugating moiety for increase in serum half-life, stability, or a combination thereof. Alternatively, the amino acid is first mutated to a natural amino acid such as lysine, cysteine, histidine, arginine, aspartic acid, glutamic acid, serine, threonine, or tyrosine; or to an unnatural amino acid prior to binding to the additional conjugating moiety.

In some embodiments, the IL-2 conjugate has a decreased binding affinity to IL-2 receptor β(IL-2Rβ) subunit, IL-2 receptor γ (IL-2Rγ) subunit, or a combination thereof, of the IL-2Rαβγ complex, relative to a wild-type IL-2 polypeptide. In some instances, the decreased affinity of the IL-2 conjugate to IL-2 receptor β (IL-2Rβ) subunit, IL-2 receptor γ (IL-2Rγ) subunit, or a combination thereof, relative to a wild-type IL-2 polypeptide, is about 10%, 20%, 30%, 40%, 50%, 60%, 70%, 80%, 90%, 95%, 99%, or greater than 99%. In some cases, the decreased affinity is about 10%. In some cases, the decreased affinity is about 20%. In some cases, the decreased affinity is about 40%. In some cases, the decreased affinity is about 50%. In some cases, the decreased affinity is about 60%. In some cases, the decreased affinity is about 80%. In some cases, the decreased affinity is about 90%. In some cases, the decreased affinity is about 99%. In some cases, the decreased affinity is greater than 99%. In some cases, the decreased affinity is about 80%. In some cases, the decreased affinity is about 100%.

In some embodiments, the decreased binding affinity of the IL-2 conjugate to IL-2 receptor β (IL-2Rβ) subunit, IL-2 receptor γ (IL-2Rγ) subunit, or a combination thereof, relative to a wild-type IL-2 polypeptide, is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 400-fold, 500-fold, 1,000-fold, or more. In some cases, the decreased affinity is about 1-fold. In some cases, the decreased affinity is about 2-fold. In some cases, the decreased affinity is about 4-fold. In some cases, the decreased affinity is about 5-fold. In some cases, the decreased affinity is about 6-fold. In some cases, the decreased affinity is about 8-fold. In some cases, the decreased affinity is about 10-fold. In some cases, the decreased affinity is about 30-fold. In some cases, the decreased affinity is about 50-fold. In some cases, the decreased affinity is about 100-fold. In some cases, the decreased affinity is about 300-fold. In some cases, the decreased affinity is about 500-fold. In some cases, the decreased affinity is about 1000-fold. In some cases, the decreased affinity is more than 1,000-fold.

In some embodiments, the IL-2 conjugate has a reduced IL-2Rγ subunit recruitment to the IL-2/IL-2R3 complex. In some cases, the reduced recruitment is compared to an IL-2Rγ subunit recruitment by an equivalent IL-2 polypeptide without the unnatural amino acid (e.g., a wild-type IL-2 polypeptide). In some cases, the decrease in IL-2Rγ subunit recruitment is about 10%, 20%, 30%, 40%, 50%, 60%, 70%, 80%, 90%, 95%, 99%, or greater than 99% decrease relative to an equivalent IL-2 polypeptide without the unnatural amino acid modification. In some cases, the decrease in IL-2Rγ subunit recruitment is about 10%. In some cases, the decrease in IL-2Rγ subunit recruitment is about 20%. In some cases, the decrease in IL-2Rγ subunit recruitment is about 40%. In some cases, the decrease in IL-2Rγ subunit recruitment is about 50%. In some cases, the decrease in IL-2Rγ subunit recruitment is about 60%. In some cases, the decrease in IL-2Rγ subunit recruitment is about 70%. In some cases, the decrease in IL-2Rγ subunit recruitment is about 80%. In some cases, the decrease in IL-2Rγ subunit recruitment is about 90%. In some cases, the decrease in IL-2Rγ subunit recruitment is about 99%. In some cases, the decrease in IL-2Rγ subunit recruitment is greater than 99%. In some cases, the decrease in IL-2Rγ subunit recruitment is about 100%. In some instances, the IL-2 conjugate further has an increase in IL-2Rα subunit recruitment.

In some embodiments, the decrease in IL-2Rγ subunit recruitment is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 400-fold, 500-fold, 1,000-fold, or more relative to an equivalent IL-2 polypeptide without the unnatural amino acid modification (e.g., a wild-type IL-2 polypeptide). In some cases, the decrease in IL-2Rγ subunit recruitment is about 1-fold. In some cases, the decrease in IL-2Rγ subunit recruitment is about 2-fold. In some cases, the decrease in IL-2Rγ subunit recruitment is about 4-fold. In some cases, the decrease in IL-2Rγ subunit recruitment is about 5-fold. In some cases, the decrease in IL-2Rγ subunit recruitment is about 6-fold. In some cases, the decrease in IL-2Rγ subunit recruitment is about 8-fold. In some cases, the decrease in IL-2Rγ subunit recruitment is about 10-fold. In some cases, the decrease in IL-2Rγ subunit recruitment is about 30-fold. In some cases, the decrease in IL-2Rγ subunit recruitment is about 50-fold. In some cases, the decrease in IL-2Rγ subunit recruitment is about 100-fold. In some cases, the decrease in IL-2Rγ subunit recruitment is about 300-fold. In some cases, the decrease in IL-2Rγ subunit recruitment is about 500-fold. In some cases, the decrease in IL-2Rγ subunit recruitment is about 1000-fold. In some cases, the decrease in IL-2Rγ subunit recruitment is more than 1,000-fold. In some instances, the IL-2 conjugate further has an increase in IL-2Rα subunit recruitment.

In some embodiments, the IL-2 conjugate has an increase in IL-2Rα subunit recruitment to the IL-2 polypeptide. In some cases, the reduced recruitment is compared to an IL-2Rα subunit recruitment by an equivalent IL-2 polypeptide without the unnatural amino acid (e.g., a wild-type IL-2 polypeptide). In some cases, the increase in IL-2Rα subunit recruitment is about 10%, 20%, 30%, 40%, 50%, 60%, 70%, 80%, 90%, 95%, 99%, or greater than 99% increase relative to an equivalent IL-2 polypeptide without the unnatural amino acid modification. In some cases, the increase in IL-2Rα subunit recruitment is about 10%. In some cases, the increase in IL-2Rα subunit recruitment is about 20%. In some cases, the increase in IL-2Rα subunit recruitment is about 40%. In some cases, the increase in IL-2Rα subunit recruitment is about 50%. In some cases, the increase in IL-2Rα subunit recruitment is about 60%. In some cases, the increase in IL-2Rα subunit recruitment is about 70%. In some cases, the increase in IL-2Rα subunit recruitment is about 80%. In some cases, the increase in IL-2Rα subunit recruitment is about 90%. In some cases, the increase in IL-2Rα subunit recruitment is about 99%. In some cases, the increase in IL-2Rα subunit recruitment is greater than 99%. In some cases, the increase in IL-2Rα subunit recruitment is about 100%. In some instances, the IL-2 conjugate further has a decrease in recruitment of an IL-2Rβ subunit and/or IL-2Rγ subunit.

In some embodiments, the increase in IL-2Rα subunit recruitment is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 400-fold, 500-fold, 1,000-fold, or more relative to an equivalent IL-2 polypeptide without the unnatural amino acid modification (e.g., a wild-type IL-2 polypeptide). In some cases, the increase in IL-2Rα subunit recruitment is about 1-fold. In some cases, the increase in IL-2Rα subunit recruitment is about 2-fold. In some cases, the increase in IL-2Rα subunit recruitment is about 4-fold. In some cases, the increase in IL-2Rα subunit recruitment is about 5-fold. In some cases, the increase in IL-2Rα subunit recruitment is about 6-fold. In some cases, the increase in IL-2Rα subunit recruitment is about 8-fold. In some cases, the increase in IL-2Rα subunit recruitment is about 10-fold. In some cases, the increase in IL-2Rα subunit recruitment is about 30-fold. In some cases, the increase in IL-2Rα subunit recruitment is about 50-fold. In some cases, the increase in IL-2Rα subunit recruitment is about 100-fold. In some cases, the increase in IL-2Rα subunit recruitment is about 300-fold. In some cases, the increase in IL-2Rα subunit recruitment is about 500-fold. In some cases, the increase in IL-2Rα subunit recruitment is about 1000-fold. In some cases, the increase in IL-2Rα subunit recruitment is more than 1,000-fold. In some instances, the IL-2 conjugate further has a decrease in recruitment of an IL-2Rβ subunit and/or IL-2Rγ subunit.

In some embodiments, an IL-2 polypeptide described herein has a decrease in receptor signaling potency to IL-2Rβγ. In some instances, the decrease in receptor signaling potency is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 400-fold, 500-fold, 1000-fold, or more to IL-2Rβγ relative to a wild-type IL-2 polypeptide. In some cases, the decrease in receptor signaling potency is about 2-fold. In some cases, the decrease in receptor signaling potency is about 5-fold. In some cases, the decrease in receptor signaling potency is about 10-fold. In some cases, the decrease in receptor signaling potency is about 20-fold. In some cases, the decrease in receptor signaling potency is about 30-fold. In some cases, the decrease in receptor signaling potency is about 40-fold. In some cases, the decrease in receptor signaling potency is about 50-fold. In some cases, the decrease in receptor signaling potency is about 100-fold. In some cases, the decrease in receptor signaling potency is about 200-fold. In some cases, the decrease in receptor signaling potency is about 300-fold. In some cases, the decrease in receptor signaling potency is about 400-fold. In some cases, the decrease in receptor signaling potency is about 500-fold. In some cases, the decrease in receptor signaling potency is about 1000-fold.

In some instances, the receptor signaling potency is measured by an EC50 value. In some cases, the decrease in receptor signaling potency is an increase in EC50. In some instances, the increase in EC50 is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 400-fold, 500-fold, 1000-fold, or more relative to a wild-type IL-2 polypeptide.

In some instances, the receptor signaling potency is measured by an ED50 value. In some cases, the decrease in receptor signaling potency is an increase in ED50. In some instances, the increase in ED50 is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 400-fold, 500-fold, 1000-fold, or more relative to a wild-type IL-2 polypeptide.

In some embodiments, an IL-2 polypeptide described herein has an expanded therapeutic window compared to a therapeutic window of a wild-type IL-2 polypeptide. In some instances, the expanded therapeutic window is due to a decrease in binding between the IL-2 polypeptide and interleukin 2 receptor βγ (IL-2Rβγ), a decrease in receptor signaling potency to IL-2Rβγ, a decrease in recruitment of an IL-2Rγ subunit to the IL-2/IL-2Rβ complex, or an increase in recruitment of an IL-2Rα subunit to the IL-2 polypeptide. In some instances, the IL-2 polypeptide does not have an impaired activation of interleukin 2 αβγ receptor (IL-2Rαβγ).

In some embodiments, the modified IL-2 polypeptide exhibits a first receptor signaling potency to an IL-2βγ signaling complex and a second receptor signaling potency to an IL-2αβγ signaling complex, and wherein a difference between the first receptor signaling potency and the second receptor signaling potency is at least 1-fold. In some instances, the difference is at least 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 1000-fold, or more. In some instances, the first receptor signaling potency is less than the second receptor signaling potency. In some instances, the first receptor signaling potency is at least 1-fold, 2-fold, 3-fold, 4-fold, 5-fold, 6-fold, 7-fold, 8-fold, 9-fold, 10-fold, 20-fold, 30-fold, 50-fold, 100-fold, 500-fold, 1000-fold, or lower than the second receptor signaling potency. In some cases, the modified IL-2 polypeptide has a lower receptor signaling potency to an IL-2βγ signaling complex than a second receptor signaling potency to an IL-2αβγ signaling complex. In some cases, the first receptor signaling potency of the modified IL-2 polypeptide is at least 1-fold lower than a receptor signaling potency of the wild-type IL-2 polypeptide. In some cases, the first receptor signaling potency of the modified IL-2 polypeptide is at least 2-fold, 3-fold, 4-fold, 5-fold, 10-fold, 20-fold, 50-fold, 100-fold, 200-fold, or 500-fold lower than a receptor signaling potency of the wild-type IL-2 polypeptide. In some cases, the first receptor signaling potency and the second receptor signaling potency are both lower that the respective potencies of the wild-type IL-2 polypeptide, but the first receptor signaling potency is lower than the second receptor signaling potency. In some cases, the difference between the first receptor signaling potency and the second receptor signaling potency increases the therapeutic window for the modified IL-2 polypeptide.

In some instances, the conjugating moiety impairs or blocks the receptor signaling potency of IL-2 with IL-2Rβγ, or reduces recruitment of the IL-2Rγ subunit to the IL-2/IL-2Rβ complex.

In some instances, the modified IL-2 polypeptide with the decrease in receptor signaling potency to IL-2Rβγ is capable of expanding CD4+ T regulatory (Treg) cells.

In some embodiments, CD4+ Treg cell proliferation by the modified IL-2/IL-2Rαβγ complex is equivalent or greater to that of a wild-type IL-2 polypeptide.

In some embodiments, the IL-2/IL-2Rαβγ complex induces proliferation of the CD4+ Treg cells to a population that is sufficient to modulate a disease course in an animal model.

In some embodiments, described herein is an interleukin 2 αβγ receptor (IL-2Rαβγ) binding protein, wherein the receptor signaling potency for an interleukin 2 βγ receptor (IL-2Rβγ) of said binding protein is less than that of wild-type human IL-2 (hIL-2), and wherein said binding protein comprises at least one unnatural amino acid. In some cases, said binding protein is a modified IL-2 polypeptide or a functionally active fragment thereof, wherein the modified IL-2 polypeptide comprises at least one unnatural amino acid.

In some embodiments, described herein is an interleukin 2 αβγ receptor (IL-2Rαβγ) binding protein, wherein a recruitment of an IL-2Rγ subunit to an IL-2/IL-2Rβ complex by said binding protein is less than that of wild-type human IL-2 (hIL-2), and wherein said binding protein comprises at least one unnatural amino acid. In some cases, said binding protein is a modified IL-2 polypeptide or a functionally active fragment thereof, wherein the modified IL-2 polypeptide comprises at least one unnatural amino acid.

In some embodiments, described herein is an interleukin 2 αβγ receptor (IL-2Rαβγ) binding protein, wherein the binding affinity for an interleukin 2 βγ receptor (IL-2Rβγ) of said binding protein is less than that of wild-type human IL-2 (hIL-2), and wherein said binding protein comprises at least one unnatural amino acid. In such cases, said binding protein is a modified IL-2 polypeptide or a functionally active fragment thereof, wherein the modified IL-2 polypeptide comprises at least one unnatural amino acid.

In some embodiments, described herein is an IL-2/IL-2Rαβγ complex comprising a modified IL-2 polypeptide comprising an unnatural amino acid and an IL-2Rαβγ, wherein the modified IL-2 polypeptide has a reduced receptor signaling potency toward IL-2Rβγ, and wherein the reduced receptor signaling potency is compared to a binding affinity between a wild-type IL-2 polypeptide and IL-2Rβγ. In some cases, the modified IL-2 polypeptide further comprises a conjugating moiety covalently attached to the unnatural amino acid.

In some embodiments, described herein is an IL-2/IL-2Rαβγ complex comprising a modified IL-2 polypeptide comprising an unnatural amino acid and an IL-2Rαβγ, wherein a recruitment of an IL-2Rγ subunit to an IL-2/IL-2Rβ complex by said modified IL-2 polypeptide is less than that of a wild-type IL-2 polypeptide. In some cases, the modified IL-2 polypeptide further comprises a conjugating moiety covalently attached to the unnatural amino acid.

In some embodiments, described herein is an IL-2/IL-2Rαβγ complex comprising a modified IL-2 polypeptide comprising an unnatural amino acid and an IL-2Rαβγ, wherein the modified IL-2 polypeptide has a reduced binding affinity toward IL-2Rβγ, and wherein the reduced binding affinity is compared to a binding affinity between a wild-type IL-2 polypeptide and IL-2Rβγ. In some embodiments, described herein is an IL-2/IL-2Rαβγ complex comprising a modified IL-2 polypeptide comprising an unnatural amino acid and an IL-2Rαβγ, wherein a recruitment of an IL-2Rγ subunit to an IL-2/IL-2Rβ complex by said modified IL-2 polypeptide is less than that of a wild-type IL-2 polypeptide. In some instances, the modified IL-2 polypeptide further comprises a conjugating moiety covalently attached to the unnatural amino acid.

In some embodiments, described herein is a CD4+ Treg cell activator that selectively expands CD4+ Treg cells in a cell population, wherein said activator comprises a modified IL-2 polypeptide comprising at least one unnatural amino acid. In some instances, said activator expands CD8+ effector T cell and/or Natural Killer cells by less than 20%, 15%, 10%, 5%, 1%, or 0.1% in the CD3+ cell population when said activator is in contact with said CD3+ cell population, relative to an expansion of CD8+ effector T cell and/or Natural Killer cells in the CD3+ cell population contacted by a wild-type IL-2 polypeptide. In some instances, said cell population is an in vivo cell population. In some instances, said cell population is an in vitro cell population. In some instances, said cell population is an ex vivo cell population.

In some embodiments, the modified IL-2 polypeptide comprising a mutation at residue R38 corresponding to a position 38 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da.

In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at resident T41 corresponding to a position 41 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue F42 corresponding to a position 42 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue K43 corresponding to a position 43 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue F44 corresponding to a position 44 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue Y45 corresponding to a position 45 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue E60 corresponding to a position 60 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue E61 corresponding to a position 61 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue E62 corresponding to a position 62 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue K64 corresponding to a position 64 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue P65 corresponding to a position 65 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue E68 corresponding to a position 68 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue V69 corresponding to a position 69 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue N71 corresponding to a position 71 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue L72 corresponding to a position 72 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue M104 corresponding to a position 104 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at C105 corresponding to a position 105 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue Y107 corresponding to a position 107 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα.

Cytokines Conjugate Precursors

Described herein are cytokine conjugate precursors, comprising a mutant cytokine (such as IL-2), wherein one or more amino acids have been mutated from the wild type amino acid. Such precursors are often used with the methods described herein for the treatment of diseases or conditions. In some embodiments, a cytokine precursor is not conjugated. Such mutations variously comprise additions, deletions, or substitutions. In some embodiments, the mutation comprises substitution to a different natural amino acid. In some instances, the mutant cytokine comprises a mutation at amino acid position Y31, K32, N33, P34, K35, T37, R38, T41, F42, K43, F44, Y45, P47, K48, Q57, E60, E61, E62, L63, K64, P65, E68, V69, N71, L72, Q74, S75, K76, N77, M104, C105, E106, Y107, A108, D109, E110, T111, or A112, in which the numbering of the amino acid residues corresponds to SEQ ID NO: 1. In some instances, the amino acid position is selected from Y31, K32, N33, P34, K35, T37, R38, T41, F42, K43, F44, Y45, P47, K48, E61, E62, E68, K64, P65, V69, L72, Q74, S75, K76, N77, M104, C105, E106, Y107, A108, D109, E110, T111, and A112. In some instances, the amino acid position is selected from N33, P34, K35, T37, R38, M39, T41, F42, K43, F44, Y45, Q57, E60, E61, E62, L63, K64, P65, E68, V69, N71, L72, M104, C105, E106, Y107, A108, D109, E110, T111, and A112. In some instances, the amino acid position is selected from K35, T37, R38, T41, F42, K43, F44, Y45, E61, E62, E68, K64, P65, V69, L72, and Y107. In some instances, the amino acid position is selected from T37, R38, T41, F42, F44, Y45, E61, E62, E68, K64, P65, V69, L72, and Y107. In some instances, the amino acid position is selected from T37, R38, T41, F42, F44, Y45, E61, E62, E68, P65, V69, L72, and Y107. In some instances, the amino acid position is selected from T37, T41, F42, F44, Y45, P65, V69, L72, and Y107. In some instances, the amino acid position is selected from R38 and K64. In some instances, the amino acid position is selected from E61, E62, and E68. In some cases, the amino acid position is at K35. In some cases, the amino acid position is at T37. In some cases, the amino acid position is at R38. In some cases, the amino acid position is at T41. In some cases, the amino acid position is at F42. In some cases, the amino acid position is at K43. In some cases, the amino acid position is at F44. In some cases, the amino acid position is at Y45. In some cases, the amino acid position is at E61. In some cases, the amino acid position is at E62. In some cases, the amino acid position is at K64. In some cases, the amino acid position is at E68. In some cases, the amino acid position is at P65. In some cases, the amino acid position is at V69. In some cases, the amino acid position is at L72. In some cases, the amino acid position is at Y107. In some cases, the amino acid position is at L72. In some cases, the amino acid position is at D109. In some embodiments, a cytokine mutant comprises a conjugation moiety, wherein the conjugation moiety is attached to a mutated site in the mutant cytokine.

Cytokine mutants described herein often comprise one or more mutations to natural amino acids. In some embodiments, a cytokine mutant comprises SEQ ID NO:1, and at least one mutation. In some embodiments, the cytokine mutant comprises SEQ ID NO:1 and an E62K mutation. In some embodiments, the cytokine mutant comprises SEQ ID NO:1 and an E62C mutation. In some embodiments, the cytokine mutant comprises SEQ ID NO:1 and an E62A mutation. In some embodiments, the cytokine mutant comprises SEQ ID NO:1 and an E62I mutation. In some embodiments, the cytokine mutant comprises SEQ ID NO:1 and an E62L mutation. In some embodiments, the cytokine mutant comprises SEQ ID NO:1 and an E62Y mutation. In some embodiments, the cytokine mutant comprises SEQ ID NO:1 and an E62W mutation. In some embodiments, the cytokine mutant comprises SEQ ID NO:1 and an E62N mutation. In some embodiments, the cytokine mutant comprises SEQ ID NO:1 and an E62R mutation. In some embodiments, the cytokine mutant comprises SEQ ID NO:1 and an E62D mutation. In some embodiments, the cytokine mutant comprises SEQ ID NO:1 and an E62Q mutation. In some embodiments, the cytokine mutant comprises SEQ ID NO:1 and an E62G mutation. In some embodiments, the cytokine mutant comprises SEQ ID NO:1 and an E62H mutation. In some embodiments, the cytokine mutant comprises SEQ ID NO:1 and an E62M mutation. In some embodiments, the cytokine mutant comprises SEQ ID NO:1 and an E62F mutation. In some embodiments, the cytokine mutant comprises SEQ ID NO:1 and an E62P mutation. In some embodiments, the cytokine mutant comprises SEQ ID NO:1 and an E62S mutation. In some embodiments, the cytokine mutant comprises SEQ ID NO:1 and an E62T mutation. In some embodiments, the cytokine mutant comprises SEQ ID NO:1 and an E62V mutation.

In some embodiments, a cytokine mutant comprises SEQ ID NO:1, and at least one mutation. In some embodiments, the cytokine mutant comprises SEQ ID NO:1 and a P65K mutation. In some embodiments, the cytokine mutant comprises SEQ ID NO:1 and a P65C mutation. In some embodiments, the cytokine mutant comprises SEQ ID NO:1 and a P65A mutation. In some embodiments, the cytokine mutant comprises SEQ ID NO:1 and a P65I mutation. In some embodiments, the cytokine mutant comprises SEQ ID NO:1 and a P65L mutation. In some embodiments, the cytokine mutant comprises SEQ ID NO:1 and a P65Y mutation. In some embodiments, the cytokine mutant comprises SEQ ID NO:1 and a P65W mutation. In some embodiments, the cytokine mutant comprises SEQ ID NO:1 and a P65N mutation. In some embodiments, the cytokine mutant comprises SEQ ID NO:1 and a P65R mutation. In some embodiments, the cytokine mutant comprises SEQ ID NO:1 and a P65D mutation. In some embodiments, the cytokine mutant comprises SEQ ID NO:1 and a P65Q mutation. In some embodiments, the cytokine mutant comprises SEQ ID NO:1 and a P65G mutation. In some embodiments, the cytokine mutant comprises SEQ ID NO:1 and a P65H mutation. In some embodiments, the cytokine mutant comprises SEQ ID NO:1 and a P65M mutation. In some embodiments, the cytokine mutant comprises SEQ ID NO:1 and a P65F mutation. In some embodiments, the cytokine mutant comprises SEQ ID NO:1 and a P65E mutation. In some embodiments, the cytokine mutant comprises SEQ ID NO:1 and a P65S mutation. In some embodiments, the cytokine mutant comprises SEQ ID NO:1 and a P65T mutation. In some embodiments, the cytokine mutant comprises SEQ ID NO:1 and a P65V mutation.

Protein or Peptide Fusions

In some embodiments, a cytokine conjugate described herein comprises a cytokine (e.g., IL-2, or other cytokine) that is fused to a peptide or protein (fusion). In some embodiments, the peptide or protein is an antibody or antibody fragment. In some embodiments, a cytokine conjugate described herein comprises a cytokine (e.g., IL-2, or other cytokine) that is fused to an antibody, or its binding fragments thereof. In some embodiments, a cytokine described herein is fused to multiple proteins or peptides. In some embodiments, a cytokine conjugate comprises a cytokine fusion to a protein or peptide, and at least one conjugating moiety. In some instances, an antibody or its binding fragments thereof comprise a humanized antibody or binding fragment thereof, murine antibody or binding fragment thereof, chimeric antibody or binding fragment thereof, monoclonal antibody or binding fragment thereof, monovalent Fab', divalent $Fab_2$, $F(ab)'_3$ fragments, single-chain variable fragment (scFv), bis-scFv, $(scFv)_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof. Such fusion proteins in some instances are generated directly through translation. In some embodiments, fusions are generated using chemical or other enzymatic ligation method. In some embodiments, a cytokine conjugate comprises a fused peptide or protein is attached by a linker. In some embodiments, the linker is a peptide. In some embodiments, a cytokine conjugate comprises an N-terminal peptide or protein fusion. In some embodiments, a cytokine conjugate comprises a C-terminal peptide or protein fusion. In some cases, the cytokine fused to the peptide or protein is further conjugated to one or more conjugation moieties described below.

In some instances, the cytokine conjugate comprises a fusion to an scFv, bis-scFv, $(scFv)_2$, dsFv, or sdAb fusion. In some cases, the fusion comprises a scFv. In some cases, the cytokine conjugate comprises a fusion to bis-scFv. In some cases, the cytokine conjugate comprises a fusion to $(scFv)_2$. In some cases, the cytokine conjugate comprises a fusion to dsFv. In some cases, the cytokine conjugate comprises a fusion to sdAb. In some cases, the cytokine fused to the scFv, bis-scFv, $(scFv)_2$, dsFv, or sdAb is further conjugated to one or more conjugation moieties described below.

In some instances, the cytokine conjugate comprises a fusion to an Fc portion of an antibody, e.g., of IgG, IgA, IgM, IgE, or IgD. In some instances, the cytokine conjugate comprises a fusion to an Fc portion of IgG (e.g., $IgG_1$, $IgG_3$, or $IgG_4$). In some cases, the cytokine fused to the Fc portion is further conjugated to one or more conjugation moieties described below.

In some cases, a cytokine (e.g., an interleukin, IFN, or TNF) polypeptide is fused to an antibody, or its binding fragments thereof. In some cases, the cytokine polypeptide is fused to a humanized antibody or binding fragment thereof, murine antibody or binding fragment thereof, chimeric antibody or binding fragment thereof, monoclonal antibody or binding fragment thereof, monovalent Fab', divalent $Fab_2$, $F(ab)'_3$ fragments, single-chain variable fragment (scFv), bis-scFv, $(scFv)_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof. In additional cases, the cytokine polypeptide is fused to an Fc portion of an antibody. In additional cases, the cytokine polypeptide is fused to an Fc portion of IgG (e.g., $IgG_1$, $IgG_3$, or $IgG_4$). In some cases, the cytokine fused to the antibody, or its binding fragments thereof is further conjugated to one or more conjugation moieties described below.

In some cases, an IL-2 polypeptide is fused to an antibody, or its binding fragments thereof. In some cases, the IL-2 polypeptide is fused to a humanized antibody or binding fragment thereof, murine antibody or binding fragment thereof, chimeric antibody or binding fragment thereof, monoclonal antibody or binding fragment thereof, monovalent Fab', divalent $Fab_2$, F(ab)'3 fragments, single-chain variable fragment (scFv), bis-scFv, $(scFv)_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof. In additional cases, the IL-2 polypeptide is fused to an Fc portion of an antibody. In additional cases, the IL-2 polypeptide is fused to an Fc portion of IgG (e.g., $IgG_1$, $IgG_3$, or $IgG_4$). In some cases, the IL-2 polypeptide fused to the antibody, or its binding fragments thereof is further conjugated to one or more conjugation moieties described below.

Natural and Unnatural Amino Acids

In some embodiments, an amino acid residue described herein (e.g., within a cytokine such as IL-2) is mutated to lysine, cysteine, histidine, arginine, aspartic acid, glutamic acid, serine, threonine, or tyrosine prior to binding to (or reacting with) a conjugating moiety. For example, the side chain of lysine, cysteine, histidine, arginine, aspartic acid, glutamic acid, serine, threonine, or tyrosine may bind to a conjugating moiety described herein. In some instances, the amino acid residue is mutated to cysteine, lysine, or histidine. In some cases, the amino acid residue is mutated to cysteine. In some cases, the amino acid residue is mutated to lysine. In some cases, the amino acid residue is mutated to histidine. In some cases, the amino acid residue is mutated to tyrosine. In some cases, the amino acid residue is mutated to tryptophan. In some embodiments, an unnatural amino acid is not conjugated with a conjugating moiety. In some embodiments, a cytokine described herein comprises an unnatural amino acid, wherein the cytokine is conjugated to the protein, wherein the point of attachment is not the unnatural amino acid.

In some embodiments, an amino acid residue described herein (e.g., within a cytokine such as IL-2) is mutated to an unnatural amino acid prior to binding to a conjugating moiety. In some cases, the mutation to an unnatural amino acid prevents or minimizes a self-antigen response of the immune system. As used herein, the term "unnatural amino acid" or "non-canonical amino acid" refers to an amino acid other than the 20 amino acids that occur naturally in protein. Non-limiting examples of unnatural amino acids include: p-acetyl-L-phenylalanine, p-iodo-L-phenylalanine, p-methoxyphenylalanine, O-methyl-L-tyrosine, p-propargyloxyphenylalanine, p-propargyl-phenylalanine, L-3-(2-naphthyl)alanine, 3-methyl-phenylalanine, O-4-allyl-L-tyrosine, 4-propyl-L-tyrosine, tri-O-acetyl-GlcNAcp-serine, L-Dopa, fluorinated phenylalanine, isopropyl-L-phenylalanine, p-azido-L-phenylalanine, p-acyl-L-phenylalanine, p-benzoyl-L-phenylalanine, p-Boronophenylalanine, O-propargyltyrosine, L-phosphoserine, phosphonoserine, phosphonotyrosine, p-bromophenylalanine, selenocysteine, p-amino-L-phenylalanine, isopropyl-L-phenylalanine, N6-(2-azidoethoxy)-carbonyl-L-lysine (AzK; the chemical structure of which is shown as compound 90 in FIG. 3C), an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an a-hydroxy containing acid; an amino thio acid; an u, a disubstituted amino acid; a p-amino acid; a cyclic amino acid other than proline or histidine, and an aromatic amino acid other than phenylalanine, tyrosine or tryptophan.

In some embodiments, the unnatural amino acid comprises a selective reactive group, or a reactive group for site-selective labeling of a target polypeptide. In some instances, the chemistry is a biorthogonal reaction (e.g., biocompatible and selective reactions). In some cases, the chemistry is a Cu(I)-catalyzed or "copper-free" alkyne-azide triazole-forming reaction, the Staudinger ligation, inverse-electron-demand Diels-Alder (IEDDA) reaction, "photo-click" chemistry, or a metal-mediated process such as olefin metathesis and Suzuki-Miyaura or Sonogashira cross-coupling.

In some embodiments, the unnatural amino acid comprises a photoreactive group, which crosslinks, upon irradiation with, e.g., UV.

In some embodiments, the unnatural amino acid comprises a photo-caged amino acid.

In some instances, the unnatural amino acid is a para-substituted, meta-substituted, or an ortho-substituted amino acid derivative.

In some instances, the unnatural amino acid comprises p-acetyl-L-phenylalanine, p-azidomethyl-L-phenylalanine (pAMF), p-iodo-L-phenylalanine, O-methyl-L-tyrosine, p-methoxyphenylalanine, p-propargyloxyphenylalanine, p-propargyl-phenylalanine, L-3-(2-naphthyl)alanine, 3-methyl-phenylalanine, O-4-allyl-L-tyrosine, 4-propyl-L-tyrosine, tri-O-acetyl-GlcNAcp-serine, L-Dopa, fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-bromophenylalanine, p-amino-L-phenylalanine, or isopropyl-L-phenylalanine.

In some cases, the unnatural amino acid is 3-aminotyrosine, 3-nitrotyrosine, 3,4-dihydroxy-phenylalanine, or 3-iodotyrosine.

In some cases, the unnatural amino acid is phenylselenocysteine.

In some instances, the unnatural amino acid is a benzophenone, ketone, iodide, methoxy, acetyl, benzoyl, or azide containing phenylalanine derivative.

In some instances, the unnatural amino acid is a benzophenone, ketone, iodide, methoxy, acetyl, benzoyl, or azide containing lysine derivative.

In some instances, the unnatural amino acid comprises an aromatic side chain.

In some instances, the unnatural amino acid does not comprise an aromatic side chain.

In some instances, the unnatural amino acid comprises an azido group.

In some instances, the unnatural amino acid comprises a Michael-acceptor group. In some instances, Michael-acceptor groups comprise an unsaturated moiety capable of forming a covalent bond through a 1,2-addition reaction. In some instances, Michael-acceptor groups comprise electron-deficient alkenes or alkynes. In some instances, Michael-acceptor groups include but are not limited to alpha,beta unsaturated: ketones, aldehydes, sulfoxides, sulfones, nitriles, imines, or aromatics.

In some instances, the unnatural amino acid is dehydroalanine.

In some instances, the unnatural amino acid comprises an aldehyde or ketone group.

In some instances, the unnatural amino acid is a lysine derivative comprising an aldehyde or ketone group.

In some instances, the unnatural amino acid is a lysine derivative comprising one or more O, N, Se, or S atoms at the beta, gamma, or delta position. In some instances, the unnatural amino acid is a lysine derivative comprising O, N, Se, or S atoms at the gamma position.

In some instances, the unnatural amino acid is a lysine derivative wherein the epilson N atom is replaced with an oxygen atom.

In some instances, the unnatural amino acid is a lysine derivative that is not naturally-occurring post-translationally modified lysine.

In some instances, the unnatural amino acid is an amino acid comprising a side chain, wherein the sixth atom from the alpha position comprises a carbonyl group. In some instances, the unnatural amino acid is an amino acid comprising a side chain, wherein the sixth atom from the alpha position comprises a carbonyl group, and the fifth atom from the alpha position is a nitrogen. In some instances, the unnatural amino acid is an amino acid comprising a side chain, wherein the seventh atom from the alpha position is an oxygen atom.

In some instances, the unnatural amino acid is a serine derivative comprising selenium. In some instances, the unnatural amino acid is selenoserine (2-amino-3-hydroselenopropanoic acid). In some instances, the unnatural amino acid is 2-amino-3-((2-((3-(benzyloxy)-3-oxopropyl)amino)ethyl)selanyl)propanoic acid. In some instances, the unnatural amino acid is 2-amino-3-(phenylselanyl)propanoic acid. In some instances, the unnatural amino acid comprises selenium, wherein oxidation of the selenium results in the formation of an unnatural amino acid comprising an alkene.

In some instances, the unnatural amino acid comprises a cyclooctynyl group.

In some instances, the unnatural amino acid comprises a transcycloctenyl group.

In some instances, the unnatural amino acid comprises a norbornenyl group.

In some instances, the unnatural amino acid comprises a cyclopropenyl group.

In some instances, the unnatural amino acid comprises a diazirine group.

In some instances, the unnatural amino acid comprises a tetrazine group.

In some instances, the unnatural amino acid is a lysine derivative, wherein the side-chain nitrogen is carbamylated. In some instances, the unnatural amino acid is a lysine derivative, wherein the side-chain nitrogen is acylated. In some instances, the unnatural amino acid is 2-amino-6-{[(tert-butoxy)carbonyl]amino}hexanoic acid. In some instances, the unnatural amino acid is 2-amino-6-{[(tert-butoxy)carbonyl]amino}hexanoic acid. In some instances, the unnatural amino acid is N6-Boc-N6-methyllysine. In some instances, the unnatural amino acid is N6-acetyllysine. In some instances, the unnatural amino acid is pyrrolysine. In some instances, the unnatural amino acid is N6-trifluoroacetyllysine. In some instances, the unnatural amino acid is 2-amino-6-{[(benzyloxy)carbonyl]amino}hexanoic acid. In some instances, the unnatural amino acid is 2-amino-6-{[(p-iodobenzyloxy)carbonyl]amino}hexanoic acid. In some instances, the unnatural amino acid is 2-amino-6-{[(p-nitrobenzyloxy)carbonyl]amino}hexanoic acid. In some instances, the unnatural amino acid is N6-prolyllysine. In some instances, the unnatural amino acid is 2-amino-6-{[(cyclopentyloxy)carbonyl]amino}hexanoic acid. In some instances, the unnatural amino acid is N6-(cyclopentanecarbonyl)lysine. In some instances, the unnatural amino acid is N6-(tetrahydrofuran-2-carbonyl)lysine. In some instances, the unnatural amino acid is N6-(3-ethynyltetrahydrofuran-2-carbonyl)lysine. In some instances, the unnatural amino acid is N6-((prop-2-yn-1-yloxy)carbonyl)lysine.

In some instances, the unnatural amino acid is 2-amino-6-{[(2-azidocyclopentyloxy)carbonyl]amino}hexanoic acid. In some instances, the unnatural amino acid is N6-(2-azidoethoxy)-carbonyl-lysine. In some instances, the unnatural amino acid is 2-amino-6-{[(2-nitrobenzyloxy)carbonyl]amino}hexanoic acid. In some instances, the unnatural amino acid is 2-amino-6-{[(2-cyclooctynyloxy)carbonyl]amino}hexanoic acid. In some instances, the unnatural amino acid is N6-(2-aminobut-3-ynoyl)lysine. In some instances, the unnatural amino acid is 2-amino-6-((2-aminobut-3-ynoyl)oxy)hexanoic acid. In some instances, the unnatural amino acid is N6-(allyloxycarbonyl)lysine. In some instances, the unnatural amino acid is N6-(butenyl-4-oxycarbonyl)lysine. In some instances, the unnatural amino acid is N6-(pentenyl-5-oxycarbonyl)lysine. In some instances, the unnatural amino acid is N6-((but-3-yn-1-yloxy)carbonyl)-lysine. In some instances, the unnatural amino acid is N6-((pent-4-yn-1-yloxy)carbonyl)-lysine. In some instances, the unnatural amino acid is N6-(thiazolidine-4-carbonyl)lysine. In some instances, the unnatural amino acid is 2-amino-8-oxononanoic acid. In some instances, the unnatural amino acid is 2-amino-8-oxooctanoic acid. In some instances, the unnatural amino acid is N6-(2-oxoacetyl)lysine.

In some instances, the unnatural amino acid is N6-propionyllysine. In some instances, the unnatural amino acid is N6-butyryllysine. In some instances, the unnatural amino acid is N6-(but-2-enoyl)lysine, In some instances, the unnatural amino acid is N6-((bicyclo[2.2.1]hept-5-en-2-yloxy)carbonyl)lysine. In some instances, the unnatural amino acid is N6-((spiro[2.3]hex-1-en-5-ylmethoxy)carbonyl)lysine. In some instances, the unnatural amino acid is N6-(((4-(1-(trifluoromethyl)cycloprop-2-en-1-yl)benzyl)oxy)carbonyl)lysine. In some instances, the unnatural amino acid is N6-((bicyclo[2.2.1]hept-5-en-2-ylmethoxy)carbonyl)lysine. In some instances, the unnatural amino acid is cysteinyllysine. In some instances, the unnatural amino acid is N6-((1-(6-nitrobenzo[d][1,3]dioxol-5-yl)ethoxy)carbonyl)lysine. In some instances, the unnatural amino acid is N6-((2-(3-methyl-3H-diazirin-3-yl)ethoxy)carbonyl)lysine. In some instances, the unnatural amino acid is N6-((3-(3-methyl-3H-diazirin-3-yl)propoxy)carbonyl)lysine. In some instances, the unnatural amino acid is N6-((meta nitrobenzyloxy)N6-methylcarbonyl)lysine. In some instances, the unnatural amino acid is N6-((bicyclo[6.1.0]non-4-yn-9-ylmethoxy)carbonyl)-lysine. In some instances, the unnatural amino acid is N6-((cyclohept-3-en-1-yloxy)carbonyl)-L-lysine.

In some instances, the unnatural amino acid is 2-amino-3-(((((benzyloxy)carbonyl)amino)methyl)selanyl)propanoic acid.

In some embodiments, the unnatural amino acid is incorporated into the cytokine (e.g., the IL polypeptide) by a repurposed amber, opal, or ochre stop codon.

In some embodiments, the unnatural amino acid is incorporated into the cytokine (e.g., the IL polypeptide) by a 4-base codon.

In some embodiments, the unnatural amino acid is incorporated into the cytokine (e.g., the IL polypeptide) by a repurposed rare sense codon.

In some embodiments, the unnatural amino acid is incorporated into the cytokine (e.g., the IL polypeptide) by a synthetic codon comprising an unnatural nucleic acid.

In some instances, the unnatural amino acid is incorporated into the cytokine by an orthogonal, modified synthetase/tRNA pair. Such orthogonal pairs comprise an unnatural synthetase that is capable of charging the unnatural tRNA with the unnatural amino acid, while minimizing charging of a) other endogenous amino acids onto the unnatural tRNA and b) unnatural amino acids onto other endogenous tRNAs. Such orthogonal pairs comprise tRNAs that are capable of being charged by the unnatural synthetase, while avoiding being charged with a) other endogenous amino acids by endogenous synthetases. In some embodiments, such pairs are identified from various organisms, such as bacteria, yeast, Archaea, or human sources. In some embodiments, an orthogonal synthetase/tRNA pair comprises components from a single organism. In some embodiments, an orthogonal synthetase/tRNA pair comprises components from two different organisms. In some embodiments, an orthogonal synthetase/tRNA pair comprising components that prior to modification, promote translation of two different amino acids. In some embodiments, an orthogonal synthetase is a modified alanine synthetase. In some embodiments, an orthogonal synthetase is a modified arginine synthetase. In some embodiments, an orthogonal synthetase is a modified asparagine synthetase. In some embodiments, an orthogonal synthetase is a modified aspartic acid synthetase. In some embodiments, an orthogonal synthetase is a modified cysteine synthetase. In some embodiments, an orthogonal synthetase is a modified glutamine synthetase. In some embodiments, an orthogonal synthetase is a modified glutamic acid synthetase. In some embodiments, an orthogonal synthetase is a modified alanine glycine. In some embodiments, an orthogonal synthetase is a modified histidine synthetase. In some embodiments, an orthogonal synthetase is a modified leucine synthetase. In some embodiments, an orthogonal synthetase is a modified isoleucine synthetase. In some embodiments, an orthogonal synthetase is a modified lysine synthetase. In some embodiments, an orthogonal synthetase is a modified methionine synthetase. In some embodiments, an orthogonal synthetase is a modified phenylalanine synthetase. In some embodiments, an orthogonal synthetase is a modified proline synthetase. In some embodiments, an orthogonal synthetase is a modified serine synthetase. In some embodiments, an orthogonal synthetase is a modified threonine synthetase. In some embodiments, an orthogonal synthetase is a modified tryptophan synthetase. In some embodiments, an orthogonal synthetase is a modified tyrosine synthetase. In some embodiments, an orthogonal synthetase is a modified valine synthetase. In some embodiments, an orthogonal synthetase is a modified phosphoserine synthetase. In some embodiments, an orthogonal tRNA is a modified alanine tRNA. In some embodiments, an orthogonal tRNA is a modified arginine tRNA. In some embodiments, an orthogonal tRNA is a modified asparagine tRNA. In some embodiments, an orthogonal tRNA is a modified aspartic acid tRNA. In some embodiments, an orthogonal tRNA is a modified cysteine tRNA. In some embodiments, an orthogonal tRNA is a modified glutamine tRNA. In some embodiments, an orthogonal tRNA is a modified glutamic acid tRNA. In some embodiments, an orthogonal tRNA is a modified alanine glycine. In some embodiments, an orthogonal tRNA is a modified histidine tRNA. In some embodiments, an orthogonal tRNA is a modified leucine tRNA. In some embodiments, an orthogonal tRNA is a modified isoleucine tRNA. In some embodiments, an orthogonal tRNA is a modified lysine tRNA. In some embodiments, an orthogonal tRNA is a modified methionine tRNA. In some embodiments, an orthogonal tRNA is a modified phenylalanine tRNA. In some embodiments, an orthogonal tRNA is a modified proline tRNA. In some embodiments, an orthogonal tRNA is a modified serine tRNA. In some embodiments, an orthogonal tRNA is a modified threonine tRNA. In some embodiments, an orthogonal tRNA is a modified tryptophan tRNA. In some embodiments, an orthogonal tRNA is a modified tyrosine tRNA. In some embodiments, an orthogonal tRNA is a modified valine tRNA. In some embodiments, an orthogonal tRNA is a modified phosphoserine tRNA.

In some embodiments, the unnatural amino acid is incorporated into the cytokine (e.g., the IL polypeptide) by an aminoacyl (aaRS or RS)-tRNA synthetase-tRNA pair. Exemplary aaRS-tRNA pairs include, but are not limited to, *Methanococcus jannaschii* (Mj-Tyr) aaRS/tRNA pairs, *E. coli* TyrRS (Ec-Tyr)/*B. stearothermophilus* $tRNA_{CUA}$ pairs, *E. coli* LeuRS (Ec-Leu)/*B. stearothermophilus* $tRNA_{CUA}$ pairs, and pyrrolysyl-tRNA pairs. In some instances, the unnatural amino acid is incorporated into the cytokine (e.g., the IL polypeptide) by a Mj-TyrRS/tRNA pair. Exemplary UAAs that can be incorporated by a Mj-TyrRS/tRNA pair include, but are not limited to, para-substituted phenylalanine derivatives such as p-aminophenylalanine and p-methoyphenylalanine; meta-substituted tyrosine derivatives such as 3-aminotyrosine, 3-nitrotyrosine, 3,4-dihydroxyphenylalanine, and 3-iodotyrosine; phenylselenocysteine; p-boronopheylalanine; and o-nitrobenzyltyrosine.

In some instances, the unnatural amino acid is incorporated into the cytokine (e.g., the IL polypeptide) by a Ec-Tyr/$tRNA_{CUA}$ or a Ec-Leu/$tRNA_{CUA}$ pair. Exemplary UAAs that can be incorporated by a Ec-Tyr/$tRNA_{CUA}$ or a Ec-Leu/$tRNA_{CUA}$ pair include, but are not limited to, phenylalanine derivatives containing benzophenoe, ketone, iodide, or azide substituents; O-propargyltyrosine; α-aminocaprylic acid, O-methyl tyrosine, 0-nitrobenzyl cysteine; and 3-(naphthalene-2-ylamino)-2-amino-propanoic acid.

In some instances, the unnatural amino acid is incorporated into the cytokine (e.g., the IL polypeptide) by a pyrrolysyl-tRNA pair. In some cases, the PylRS is obtained from an archaebacterial, e.g., from a methanogenic archaebacterial. In some cases, the PylRS is obtained from *Methanosarcina barkeri, Methanosarcina mazei*, or *Methanosarcina acetivorans*. Exemplary UAAs that can be incorporated by a pyrrolysyl-tRNA pair include, but are not limited to, amide and carbamate substituted lysines such as 2-amino-6-((R)-tetrahydrofuran-2-carboxamido)hexanoic acid, N-ε-D-prolyl-L-lysine, and N-ε-cyclopentyloxycarbonyl-L-lysine; N-ε-Acryloyl-L-lysine; N-s-[(1-(6-nitrobenzo[d][1,3]dioxol-5-yl)ethoxy)carbonyl]-L-lysine; and N-ε-(1-methylcyclopro-2-enecarboxamido)lysine. In some emobodiments, the IL-2 conjugates disclosed herein may be prepared by use of *M. mazei* Pyl tRNA which is selectively charged with a non-natural amino acid such as N6-((2-azidoethoxy)-carbonyl)-L-lysine (AzK) by the *M. barkeri* pyrrolysyl-tRNA synthetase (Mb PylRS). Other methods are known to those of ordinary skill in the art, such as those disclosed in Zhang et al., Nature 2017, 551(7682): 644-647.

In some instances, an unnatural amino acid is incorporated into a cytokine described herein (e.g., the IL polypeptide) by a synthetase disclosed in U.S. Pat. Nos. 9,988,619 and 9,938,516. Exemplary UAAs that can be incorporated by such synthetases include para-methylazido-L-phenylalanine, aralkyl, heterocyclyl, heteroaralkyl unnatural amino acids, and others. In some embodiments, such UAAs comprise pyridyl, pyrazinyl, pyrazolyl, triazolyl, oxazolyl, thiazolyl, thiophenyl, or other heterocycle. Such amino acids in some embodiments comprise azides, tetrazines, or other chemical group capable of conjugation to a coupling partner, such as a water soluble moiety. In some embodiments, such synthetases are expressed and used to incorporate UAAs into cytokines in-vivo. In some embodiments, such synthetases are used to incorporate UAAs into cytokines using a cell-free translation system.

In some instances, an unnatural amino acid is incorporated into a cytokine described herein (e.g., the IL polypeptide) by a naturally occurring synthetase. In some embodiments, an unnatural amino acid is incorporated into a cytokine by an organism that is auxotrophic for one or more amino acids. In some embodiments, synthetases corresponding to the auxotrophic amino acid are capable of charging the corresponding tRNA with an unnatural amino acid. In some embodiments, the unnatural amino acid is selenocysteine, or a derivative thereof. In some embodiments, the unnatural amino acid is selenomethionine, or a derivative thereof. In some embodiments, the unnatural amino acid is an aromatic amino acid, wherein the aromatic amino acid comprises an aryl halide, such as an iodide. In embodiments, the unnatural amino acid is structurally similar to the auxotrophic amino acid.

In some instances, the unnatural amino acid comprises an unnatural amino acid illustrated in FIG. 1.

Figure 2A:
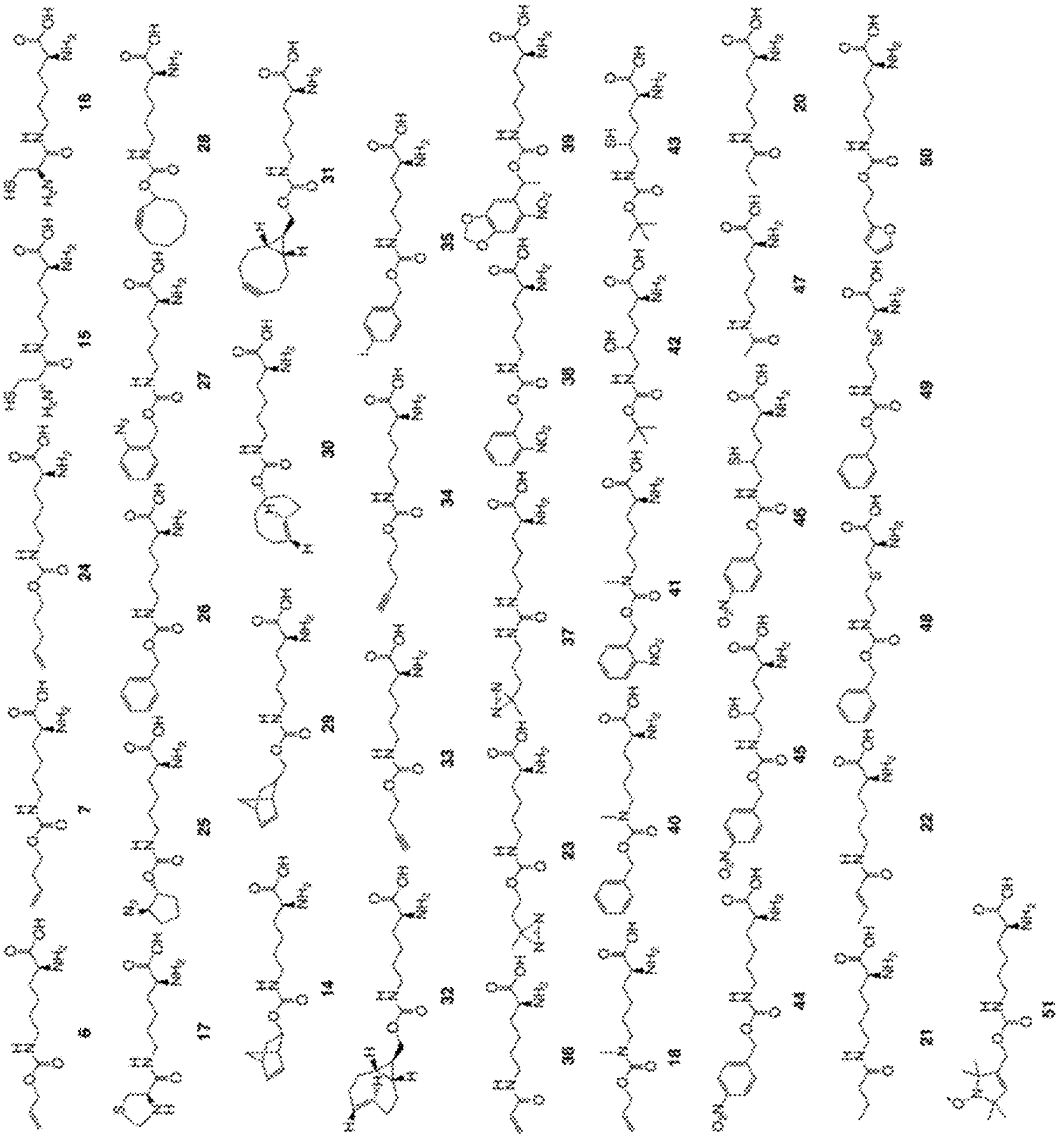
FIGS. 2A-FIG. 2B illustrate exemplary unnatural amino acids.
Figure 2B:
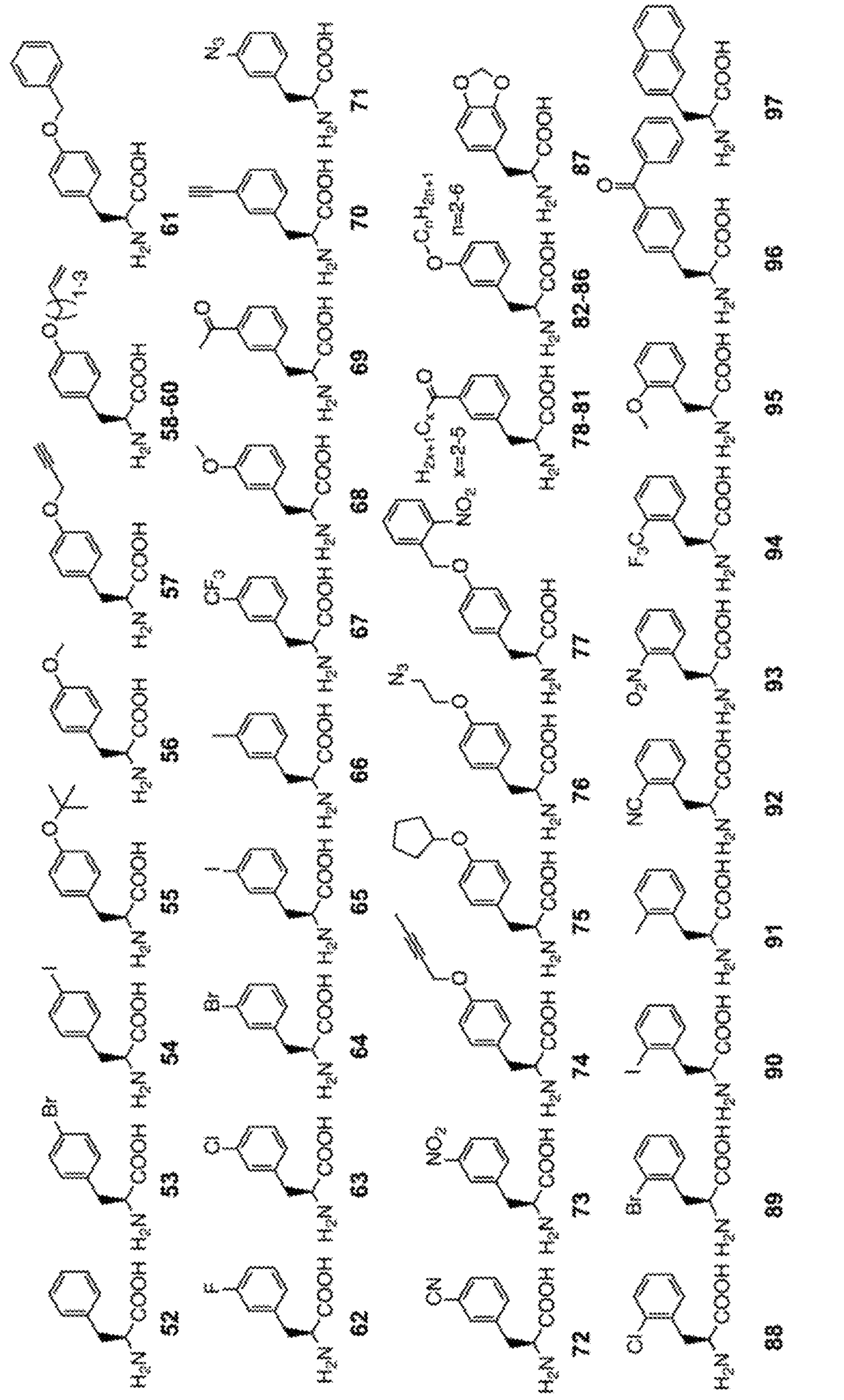

In some instances, the unnatural amino acid comprises a lysine or phenylalanine derivative or analogue. In some instances, the unnatural amino acid comprises a lysine derivative or a lysine analogue. In some instances, the unnatural amino acid comprises a pyrrolysine (Pyl). In some instances, the unnatural amino acid comprises a phenylalanine derivative or a phenylalanine analogue. In some instances, the unnatural amino acid is an unnatural amino acid described in Wan, et al., "Pyrrolysyl-tRNA synthetase: an ordinary enzyme but an outstanding genetic code expansion tool," Biocheim Biophys Aceta 1844(6): 1059-4070 (2014). In some instances, the unnatural amino acid comprises an unnatural amino acid illustrated in FIG. 2 (e.g., FIG. 2A and FIG. 2B).

In some embodiments, the unnatural amino acid comprises an unnatural amino acid illustrated in FIG. 3A-FIG. 3D (adopted from Table 1 of Dumas et al., *Chemical Science* 2015, 6, 50-69).

In some embodiments, an unnatural amino acid incorporated into a cytokine described herein (e.g., the IL polypeptide) is disclosed in U.S. Pat. Nos. 9,840,493; 9,682,934; US 2017/0260137; U.S. Pat. No. 9,938,516; or US 2018/0086734. Exemplary UAAs that can be incorporated by such synthetases include para-methylazido-L-phenylalanine, aralkyl, heterocyclyl, and heteroaralkyl, and lysine derivative unnatural amino acids. In some embodiments, such UAAs comprise pyridyl, pyrazinyl, pyrazolyl, triazolyl, oxazolyl, thiazolyl, thiophenyl, or other heterocycle. Such amino acids in some embodiments comprise azides, tetrazines, or other chemical group capable of conjugation to a coupling partner, such as a water soluble moiety. In some embodiments, a UAA comprises an azide attached to an aromatic moiety via an alkyl linker. In some embodiments, an alkyl linker is a $C_1$-$C_{10}$ linker. In some embodiments, a UAA comprises a tetrazine attached to an aromatic moiety via an alkyl linker. In some embodiments, a UAA comprises a tetrazine attached to an aromatic moiety via an amino group. In some embodiments, a UAA comprises a tetrazine attached to an aromatic moiety via an alkylamino group. In some embodiments, a UAA comprises an azide attached to the terminal nitrogen (e.g., N6 of a lysine derivative, or N5, N4, or N3 of a derivative comprising a shorter alkyl side chain) of an amino acid side chain via an alkyl chain. In some embodiments, a UAA comprises a tetrazine attached to the terminal nitrogen of an amino acid side chain via an alkyl chain. In some embodiments, a UAA comprises an azide or tetrazine attached to an amide via an alkyl linker. In some embodiments, the UAA is an azide or tetrazine-containing carbamate or amide of 3-aminoalanine, serine, lysine, or derivative thereof. In some embodiments, such UAAs are incorporated into cytokines in-vivo. In some embodiments, such UAAs are incorporated into cytokines in a cell-free system.

Conjugating Moieties

In certain embodiments, disclosed herein are conjugating moieties that are bound to one or more cytokines (e.g., interleukins, IFNs, or TNFs) described supra. In some instances, the conjugating moiety is a molecule that perturbs the interaction of a cytokine with its receptor. In some instances, the conjugating moiety is any molecule that when bond to the cytokine, enables the cytokine conjugate to modulate an immune response. In some instances, the conjugating moiety is bound to the cytokine through a covalent bond. In some instances, a cytokine described herein is attached to a conjugating moiety with a triazole group. In some instances, a cytokine described herein is attached to a conjugating moiety with a dihydropyridazine or pyridazine group. In some instances, the conjugating moiety comprises a water-soluble polymer. In other instances, the conjugating moiety comprises a protein or a binding fragment thereof. In additional instances, the conjugating moiety comprises a peptide. In additional instances, the conjugating moiety comprises a nucleic acid. In additional instances, the conjugating moiety comprises a small molecule. In additional instances, the conjugating moiety comprises a bioconjugate (e.g., a TLR agonist such as a TLR1, TLR2, TLR3, TLR4, TLR5, TLR6, TLR7, TLR8, or TLR9 agonist; or a synthetic ligand such as Pam3Cys, CFA, MALP2, Pam2Cys, FSL-1, Hib-OMPC, Poly I:C, poly A:U, AGP, MPL A, RC-529, MDF2β, CFA, or Flagellin). In some cases, the conjugating moiety increases serum half-life, and/or improves stability. In some cases, the conjugating moiety reduces cytokine interaction with one or more cytokine receptor domains or subunits. In additional cases, the conjugating moiety blocks cytokine interaction with one or more cytokine domains or subunits with its cognate receptor(s). In some embodiments, cytokine conjugates described herein comprise multiple conjugating moieties. In some embodiments, a conjugating moiety is attached to an unnatural or natural amino acid in the cytokine peptide. In some embodiments, a cytokine conjugate comprises a conjugating moiety attached to a natural amino acid. In some embodiments, a cytokine conjugate is attached to an unnatural amino acid in the cytokine peptide. In some embodiments, a conjugating moiety is attached to the N or C terminal amino acid of the cytokine peptide. Various combinations sites are disclosed herein, for example, a first conjugating moiety is attached to an unnatural or natural amino acid in the cytokine peptide, and a second conjugating moiety is attached to the N or C terminal amino acid of the cytokine peptide. In some embodiments, a single conjugating moiety is attached to multiple residues of the cytokine peptide (e.g. a staple). In some embodiments, a conjugating moiety is attached to both the N and C terminal amino acids of the cytokine peptide.

Water-Soluble Polymers

In some embodiments, a conjugating moiety descried herein is a water-soluble polymer. In some instances, the water-soluble polymer is a nonpeptidic, nontoxic, and biocompatible. As used herein, a substance is considered biocompatible if the beneficial effects associated with use of the substance alone or with another substance (e.g., an active agent such as a cytokine moiety) in connection with living tissues (e.g., administration to a patient) outweighs any deleterious effects as evaluated by a clinician, e.g., a physician, a toxicologist, or a clinical development specialist. In some instances, a water-soluble polymer is further non-immunogenic. In some instances, a substance is considered non-immunogenic if the intended use of the substance in vivo does not produce an undesired immune response (e.g., the formation of antibodies) or, if an immune response is produced, that such a response is not deemed clinically significant or important as evaluated by a clinician, e.g., a physician, a toxicologist, or a clinical development specialist.

In some instances, the water-soluble polymer is characterized as having from about 2 to about 300 termini. Exemplary water soluble polymers include, but are not limited to, poly(alkylene glycols) such as polyethylene glycol ("PEG"), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol) (PVA), polyacrylamide (PAAm), poly(N-(2-hydroxypropyl) methacrylamide) (PHPMA), polydimethylacrylamide (PDAAm), polyphosphazene, polyoxazolines ("POZ") (which are described in WO 2008/106186), poly(N-acryloylmorpholine), and combinations of any of the foregoing.

In some cases, the water-soluble polymer is not limited to a particular structure. In some cases, the water-soluble polymer is linear (e.g., an end capped, e.g., alkoxy PEG or a bifunctional PEG), branched or multi-armed (e.g., forked PEG or PEG attached to a polyol core), a dendritic (or star) architecture, each with or without one or more degradable linkages. Moreover, the internal structure of the water-soluble polymer can be organized in any number of different repeat patterns and can be selected from the group consisting of homopolymer, alternating copolymer, random copolymer, block copolymer, alternating tripolymer, random tripolymer, and block tripolymer.

In some instances, the water-soluble polymer is represented by a length of repeating polymeric units, for example, a number n of polyethylene glycol units. In some instances, the water-soluble polymer has the structure:

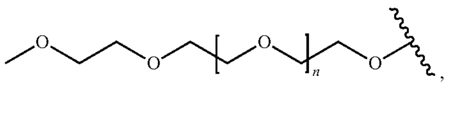

wherein the wavy line indicates attachment to a linker, reactive group, or unnatural amino acid, and n is 1-5000. In some instances, the water-soluble polymer has the structure:

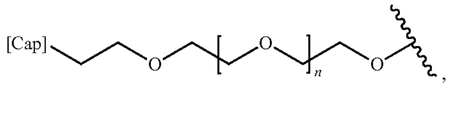

wherein the wavy line indicates attachment to a linker, reactive group, or unnatural amino acid, "Cap" indicates a capping group (for example, such as $-OCH_3$, $-O(C_1-C_6$ alkyl), —SMe, $-S(C_1-C_6$ alkyl), $-CO_2H$, $-CO_2(C_1-C_6$ alkyl), $-CONH_2$, $-CONH(C_1-C_6$ alkyl), $-CON(C_1-C_6$ alkyl$)_2$, $-NH_2$, —SH, or OH) and n is 1-5000. In some embodiments, n is 100-2000, 200-1000, 300-750, 400-600, 450-550, 400-2000, 750-3000, or 100-750. In some embodiments, n is about 100, 200, 300, 400, 500, 600, 700, 800, 900, or about 1000. In some embodiments, n is at least 100, 200, 300, 400, 500, 600, 700, 800, 900, or at least 1000. In some embodiments, n is no more than 100, 200, 300, 400, 500, 600, 700, 800, 900, or no more than 1000. In some embodiments, the n is represented as an average length of the water-soluble polymer.

In some embodiments, the weight-average molecular weight of the water-soluble polymer in the IL-2 conjugate is from about 100 Daltons to about 150,000 Daltons. Exemplary ranges include, for example, weight-average molecular weights in the range of greater than 5,000 Daltons to about 100,000 Daltons, in the range of from about 6,000 Daltons to about 90,000 Daltons, in the range of from about 10,000 Daltons to about 85,000 Daltons, in the range of greater than 10,000 Daltons to about 85,000 Daltons, in the range of from about 20,000 Daltons to about 85,000 Daltons, in the range of from about 53,000 Daltons to about 85,000 Daltons, in the range of from about 25,000 Daltons to about 120,000 Daltons, in the range of from about 29,000 Daltons to about 120,000 Daltons, in the range of from about 35,000 Daltons to about 120,000 Daltons, and in the range of from about 40,000 Daltons to about 120,000 Daltons.

Exemplary weight-average molecular weights for the water-soluble polymer include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. Branched versions of the water-soluble polymer (e.g., a branched 40,000 Dalton water-soluble polymer comprised of two 20,000 Dalton polymers) having a total molecular weight of any of the foregoing can also be used. In one or more embodiments, the conjugate will not have any PEG moieties attached, either directly or indirectly, with a PEG having a weight average molecular weight of less than about 6,000 Daltons.

PEGs will typically comprise a number of $(OCH_2CH_2)$ monomers [or $(CH_2CH_2O)$ monomers, depending on how the PEG is defined]. As used herein, the number of repeating units is identified by the subscript "n" in "$(OCH_2CH_2)_n$." Thus, the value of (n) typically falls within one or more of the following ranges: from 2 to about 3400, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the total weight-average molecular weight of the polymer by the molecular weight of the repeating monomer.

In some instances, the water-soluble polymer is an end-capped polymer, that is, a polymer having at least one terminus capped with a relatively inert group, such as a lower $C_{1-6}$ alkoxy group, or a hydroxyl group. When the polymer is PEG, for example, a methoxy-PEG (commonly referred to as mPEG) may be used, which is a linear form of PEG wherein one terminus of the polymer is a methoxy $(-OCH_3)$ group, while the other terminus is a hydroxyl or other functional group that can be optionally chemically modified.

In some embodiments, the PEG group comprising the IL-2 conjugates disclosed herein is a linear or branched PEG group. In some embodiments, the PEG group is a linear PEG group. In some embodiments, the PEG group is a branched PEG group. In some embodiments, the PEG group is a methoxy PEG group. In some embodiments, the PEG group is a linear or branched methoxy PEG group. In some embodiments, the PEG group is a linear methoxy PEG group. In some embodiments, the PEG group is a branched methoxy PEG group. In some embodiments, the PEG group is a linear or branched PEG group having an average molecular weight of from about 100 Daltons to about 150,000 Daltons. Exemplary ranges include, for example, weight-average molecular weights in the range of greater than 5,000 Daltons to about 100,000 Daltons, in the range of from about 6,000 Daltons to about 90,000 Daltons, in the range of from about 10,000 Daltons to about 85,000 Daltons, in the range of greater than 10,000 Daltons to about 85,000 Daltons, in the range of from about 20,000 Daltons to about 85,000 Daltons, in the range of from about 53,000 Daltons to about 85,000 Daltons, in the range of from about 25,000 Daltons to about 120,000 Daltons, in the range of from about 29,000 Daltons to about 120,000 Daltons, in the range of from about 35,000 Daltons to about 120,000 Daltons, and in the range of from about 40,000 Daltons to about 120,000 Daltons. Exemplary weight-average molecular weights for the PEG group include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, about 75,000 Daltons, about 80,000 Daltons, about 90,000 Daltons, about 95,000 Daltons, and about 100,000 Daltons. In some embodiments, the PEG group is a linear PEG group having an average molecular weight as disclosed above. In some embodiments, the PEG group is a branched PEG group having an average molecular weight as disclosed above. In some embodiments, the PEG group comprising the IL-2 conjugates disclosed herein is a linear or branched PEG group having a defined molecular weight±10%, or 15% or 20% or 25%. For example, included within the scope of the present disclosure are IL-2 conjugates comprising a PEG group having a molecular weight of 30,000 Da±3000 Da, or 30,000 Da±4,500 Da, or 30,000 Da±6,000 Da.

In some embodiments, the PEG group comprising the IL-2 conjugates disclosed herein is a linear or branched PEG group having an average molecular weight of from about 5,000 Daltons to about 60,000 Daltons. In some embodiments, the PEG group is a linear or branched PEG group having an average molecular weight of about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, about 75,000 Daltons, about 80,000 Daltons, about 90,000 Daltons, about 95,000 Daltons, and about 100,000 Daltons. In some embodiments, the PEG group is a linear or branched PEG group having an average molecular weight of about 5,000 Daltons, about 10,000 Daltons, about 20,000 Daltons, about 30,000 Daltons, about 50,000 Daltons, or about 60,000 Daltons. In some embodiments, the PEG group is a linear or branched PEG group having an average molecular weight of about 5,000 Daltons, about 30,000 Daltons, about 50,000 Daltons, or about 60,000 Daltons. In some embodiments, the PEG group is a linear PEG group having an average molecular of about 5,000 Daltons, about 10,000 Daltons, about 20,000 Daltons, about 30,000 Daltons, about 50,000 Daltons, or about 60,000 Daltons. In some embodiments, the PEG group is a branched PEG group having an average molecular weight of about 5,000 Daltons, about 10,000 Daltons, about 20,000 Daltons, about 30,000 Daltons, about 50,000 Daltons, or about 60,000 Daltons.

In some embodiments, the PEG group comprising the IL-2 conjugates disclosed herein is a linear methoxy PEG group having an average molecular weight of from about 5,000 Daltons to about 60,000 Daltons. In some embodiments, the PEG group is a linear methoxy PEG group having an average molecular weight of about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, about 75,000 Daltons, about 80,000 Daltons, about 90,000 Daltons, about 95,000 Daltons, and about 100,000 Daltons. In some embodiments, the PEG group is a linear methoxy PEG group having an average molecular weight of about 5,000 Daltons, about 10,000 Daltons, about 20,000 Daltons, about 30,000 Daltons, about 50,000 Daltons, or about 60,000 Daltons. In some embodiments, the PEG group is a linear methoxy PEG group having an average molecular weight of about 5,000 Daltons, about 30,000 Daltons, about 50,000 Daltons, or about 60,000 Daltons. In some embodiments, the PEG group is a linear methoxy PEG group having an average molecular of about 5,000 Daltons, about 10,000 Daltons, about 20,000 Daltons, about 30,000 Daltons, about 50,000 Daltons, or about 60,000 Daltons. In some embodiments, the PEG group is a linear methoxy PEG group having an average molecular of about 5,000 Daltons. In some embodiments, the PEG group is a linear methoxy PEG group having an average molecular of about 10,000 Daltons. In some embodiments, the PEG group is a linear methoxy PEG group having an average molecular of about 20,000 Daltons. In some embodiments, the PEG group is a linear methoxy PEG group having an average molecular of about 30,000 Daltons. In some embodiments, the PEG group is a linear methoxy PEG group having an average molecular of about 50,000 Daltons. In some embodiments, the PEG group is a linear methoxy PEG group having an average molecular of about 60,000 Daltons. In some embodiments, the PEG group comprising the IL-2 conjugates disclosed herein is a linear methoxy PEG group having a defined molecular weight±10%, or 15% or 20% or 25%. For example, included within the scope of the present disclosure are IL-2 conjugates comprising a linear methoxy PEG group having a molecular weight of 30,000 Da±3000 Da, or 30,000 Da±4,500 Da, or 30,000 Da±6,000 Da.

In some embodiments, the PEG group comprising the IL-2 conjugates disclosed herein is a branched methoxy PEG group having an average molecular weight of from about 5,000 Daltons to about 60,000 Daltons. In some embodiments, the PEG group is a branched methoxy PEG group having an average molecular weight of about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, about 75,000 Daltons, about 80,000 Daltons, about 90,000 Daltons, about 95,000 Daltons, and about 100,000 Daltons. In some embodiments, the PEG group is a branched methoxy PEG group having an average molecular weight of about 5,000 Daltons, about 10,000 Daltons, about 20,000 Daltons, about 30,000 Daltons, about 50,000 Daltons, or about 60,000 Daltons. In some embodiments, the PEG group is a branched methoxy PEG group having an average molecular weight of about 5,000 Daltons, about 30,000 Daltons, about 50,000 Daltons, or about 60,000 Daltons. In some embodiments, the PEG group is a branched methoxy PEG group having an average molecular of about 5,000 Daltons, about 10,000 Daltons, about 20,000 Daltons, about 30,000 Daltons, about 50,000 Daltons, or about 60,000 Daltons. In some embodiments, the PEG group is a branched methoxy PEG group having an average molecular of about 5,000 Daltons, about 10,000 Daltons, about 20,000 Daltons, about 30,000 Daltons, about 50,000 Daltons, or about 60,000 Daltons. In some embodiments, the PEG group is a branched methoxy PEG group having an average molecular of about 5,000 Daltons. In some embodiments, the PEG group is a branched methoxy PEG group having an average molecular of about 10,000 Daltons. In some embodiments, the PEG group is a branched methoxy PEG group having an average molecular of about 20,000 Daltons. In some embodiments, the PEG group is a branched methoxy PEG group having an average molecular of about 30,000 Daltons. In some embodiments, the PEG group is a branched methoxy PEG group having an average molecular of about 50,000 Daltons. In some embodiments, the PEG group is a branched methoxy PEG group having an average molecular of about 60,000 Daltons. In some embodiments, the PEG group comprising the IL-2 conjugates disclosed herein is a branched methoxy PEG group having a defined molecular weight±10%, or 15% or 20% or 25%. For example, included within the scope of the present disclosure are IL-2 conjugates comprising a branched methoxy PEG group having a molecular weight of 30,000 Da±3000 Da, or 30,000 Da±4,500 Da, or 30,000 Da 6,000 Da.

In some embodiments, exemplary water-soluble polymers include, but are not limited to, linear or branched discrete PEG (dPEG) from Quanta Biodesign, Ltd; linear, branched, or forked PEGs from Nektar Therapeutics; and Y-shaped PEG derivatives from JenKem Technology.

In some embodiments, a cytokine (e.g., an interleukin, IFN, or TNF) polypeptide described herein is conjugated to a water-soluble polymer selected from poly(alkylene glycols) such as polyethylene glycol ("PEG"), poly(propylene glycol) ("PPG"), copolymers of ethylene glycol and propylene glycol and the like, poly(oxyethylated polyol), poly (olefinic alcohol), poly(vinylpyrrolidone), poly(hydroxyalkylmethacrylamide), poly(hydroxyalkylmethacrylate), poly (saccharides), poly(α-hydroxy acid), poly(vinyl alcohol) (PVA), polyacrylamide (PAAm), polydimethylacrylamide (PDAAm), poly(N-(2-hydroxypropyl) methacrylamide) (PHPMA), polyphosphazene, polyoxazolines ("POZ"), poly (N-acryloylmorpholine), and a combination thereof. In some instances, the cytokine polypeptide is conjugated to PEG (e.g., PEGylated). In some instances, the cytokine polypeptide is conjugated to PPG. In some instances, the cytokine polypeptide is conjugated to POZ. In some instances, the cytokine polypeptide is conjugated to PVP.

In some embodiments, an IL-2 polypeptide described herein is conjugated to a water-soluble polymer selected from poly(alkylene glycols) such as polyethylene glycol ("PEG"), poly(propylene glycol) ("PPG"), copolymers of ethylene glycol and propylene glycol and the like, poly (oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol) (PVA), polyacrylamide (PAAm), polydimethylacrylamide (PDAAm), poly(N-(2-hydroxypropyl) methacrylamide) (PHPMA), polyphosphazene, polyoxazolines ("POZ"), poly(N-acryloylmorpholine), and a combination thereof. In some instances, the IL-2 polypeptide is conjugated to PEG (e.g., PEGylated). In some instances, the IL-2 polypeptide is conjugated to PPG. In some instances, the IL-2 polypeptide is conjugated to POZ. In some instances, the IL-2 polypeptide is conjugated to PVP.

In some instances, a water-soluble polymer comprises a polyglycerol (PG). In some cases, the polyglycerol is a hyperbranched PG (HPG) (e.g., as described by Imran, et al. "Influence of architecture of high molecular weight linear and branched polyglycerols on their biocompatibility and biodistribution," *Biomaterials* 33:9135-9147 (2012)). In other cases, the polyglycerol is a linear PG (LPG). In additional cases, the polyglycerol is a midfunctional PG, a linear-block-hyperbranched PG (e.g., as described by Wurm et. Al., "Squaric acid mediated synthesis and biological activity of a library of linear and hyperbranched poly (glycerol)-protein conjugates," *Biomacromolecules* 13:1161-1171 (2012)), or a side-chain functional PG (e.g., as described by Li, et. al., "Synthesis of linear polyether polyol derivatives as new materials for bioconjugation," *Bioconjugate Chem.* 20:780-789 (2009).

In some instances, a cytokine (e.g., an interleukin, IFN, or TNF) polypeptide described herein is conjugated to a PG, e.g., a HPG, a LPG, a midfunctional PG, a linear-block-hyperbranched PG, or a side-chain functional PG. In some instances, the cytokine is an IL-2 polypeptide. In some cases, the IL-2 polypeptide is conjugated to a PG, a midfunctional PG, a linear-block-hyperbranched PG.

In some embodiments, a water-soluble polymer is a degradable synthetic PEG alternative. Exemplary degradable synthetic PEG alternatives include, but are not limited to, poly[oligo(ethylene glycol)methyl methacrylate] (POEGMA); backbone modified PEG derivatives generated by polymerization of telechelic, or di-end-functionalized PEG-based macromonomers; PEG derivatives comprising comonomers comprising degradable linkage such as poly [(ethylene oxide)-co-(methylene ethylene oxide)][P(EO-co-MEO)], cyclic ketene acetals such as 5,6-benzo-2-methylene-1,3-dioxepane (BMDO), 2-methylene-1,3-dioxepane (MDO), and 2-methylene-4-phenyl-1,3-dioxolane (MPDL) copolymerized with OEGMA; or poly-(ε-caprolactone)-graft-poly(ethylene oxide) (PCL-g-PEO).

In some instances, a cytokine (e.g., an interleukin, IFN, or TNF) polypeptide described herein is conjugated to a degradable synthetic PEG alternative, such as for example, POEGM; backbone modified PEG derivatives generated by polymerization of telechelic, or di-end-functionalized PEG-based macromonomers; P(EO-co-MEO); cyclic ketene acetals such as BMDO, MDO, and MPDL copolymerized with OEGMA; or PCL-g-PEO. In some instances, the cytokine is an IL-2 polypeptide. In some cases, the IL-2 polypeptide is conjugated to a degradable synthetic PEG alternative, such as for example, POEGM; backbone modified PEG derivatives generated by polymerization of telechelic, or di-end-functionalized PEG-based macromonomers; P(EO-co-MEO); cyclic ketene acetals such as BMDO, MDO, and MPDL copolymerized with OEGMA; or PCL-g-PEO.

In some embodiments, a water-soluble polymer comprises a poly(zwitterions). Exemplary poly(zwitterions) include, but are not limited to, poly(sulfobetaine methacrylate) (PSBMA), poly(carboxybetaine methacrylate) (PCBMA), and poly(2-methyacryloyloxyethyl phosphorylcholine) (PMPC). In some instances, a cytokine (e.g., an interleukin, IFN, or TNF) polypeptide described herein is conjugated to a poly(zwitterion) such as PSBMA, PCBMA, or PMPC. In some cases, the cytokine is an IL-2 polypeptide. In some cases, the IL-2 polypeptide is conjugated to a poly(zwitterion) such as PSBMA, PCBMA, or PMPC.

In some embodiments, a water-soluble polymer comprises a polycarbonate. Exemplary polycarbones include, but are not limited to, pentafluorophenyl 5-methyl-2-oxo-1,3-dioxane-5-carboxylate (MTC-$OC_6F_5$). In some instances, a cytokine (e.g., an interleukin, IFN, or TNF) polypeptide described herein is conjugated to a polycarbonate such as MTC-$OC_6F_5$. In some cases, the cytokine is an IL-2 polypeptide. In some cases, the IL-2 polypeptide is conjugated to a polycarbonate such as MTC-$OC_6F_5$.

In some embodiments, a water-soluble polymer comprises a polymer hybrid, such as for example, a polycarbonate/PEG polymer hybrid, a peptide/protein-polymer conjugate, or a hydroxylcontaining and/or zwitterionic derivatized polymer (e.g., a hydroxylcontaining and/or zwitterionic derivatized PEG polymer). In some instances, a cytokine (e.g., an interleukin, IFN, or TNF) polypeptide described herein is conjugated to a polymer hybrid such as a polycarbonate/PEG polymer hybrid, a peptide/protein-polymer conjugate, or a hydroxylcontaining and/or zwitterionic derivatized polymer (e.g., a hydroxylcontaining and/or zwitterionic derivatized PEG polymer). In some cases, the cytokine is an IL-2 polypeptide. In some cases, the IL-2 polypeptide is conjugated to a polymer hybrid such as a polycarbonate/PEG polymer hybrid, a peptide/protein-polymer conjugate, or a hydroxylcontaining and/or zwitterionic derivatized polymer (e.g., a hydroxylcontaining and/or zwitterionic derivatized PEG polymer).

In some instances, a water-soluble polymer comprises a polysaccharide. Exemplary polysaccharides include, but are not limited to, dextran, polysialic acid (PSA), hyaluronic acid (HA), amylose, heparin, heparan sulfate (HS), dextrin, or hydroxyethyl-starch (HES). In some cases, a cytokine (e.g., an interleukin, IFN, or TNF) polypeptide is conjugated to a polysaccharide. In some cases, an IL-2 polypeptide is conjugated to dextran. In some cases, an IL-2 polypeptide is conjugated to PSA. In some cases, an IL-2 polypeptide is conjugated to HA. In some cases, an IL-2 polypeptide is conjugated to amylose. In some cases, an IL-2 polypeptide is conjugated to heparin. In some cases, an IL-2 polypeptide is conjugated to HS. In some cases, an IL-2 polypeptide is conjugated to dextrin. In some cases, an IL-2 polypeptide is conjugated to HES.

In some cases, a water-soluble polymer comprises a glycan. Exemplary classes of glycans include N-linked glycans, O-linked glycans, glycolipids, O-GlcNAc, and glycosaminoglycans. In some cases, a cytokine (e.g., an interleukin, IFN, or TNF) polypeptide is conjugated to a glycan. In some cases, an IL-2 polypeptide is conjugated to N-linked glycans. In some cases, an IL-2 polypeptide is conjugated to O-linked glycans. In some cases, an IL-2 polypeptide is conjugated to glycolipids. In some cases, an IL-2 polypeptide is conjugated to O-GlcNAc. In some cases, an IL-2 polypeptide is conjugated to glycosaminoglycans.

In some embodiments, a water-soluble polymer comprises a polyoxazoline polymer. A polyoxazoline polymer is a linear synthetic polymer, and similar to PEG, comprises a low polydispersity. In some instances, a polyoxazoline polymer is a polydispersed polyoxazoline polymer, characterized with an average molecule weight. In some cases, the average molecule weight of a polyoxazoline polymer includes, for example, 1000, 1500, 2000, 2500, 3000, 3500, 4000, 4500, 5000, 5500, 6000, 6500, 7000, 7500, 8000, 10,000, 12,000, 20,000, 35,000, 40,000, 50,000, 60,000, 100,000, 200,000, 300,000, 400,000, or 500,000 Da. In some instances, a polyoxazoline polymer comprises poly(2-methyl 2-oxazoline) (PMOZ), poly(2-ethyl 2-oxazoline) (PEOZ), or poly (2-propyl 2-oxazoline) (PPOZ). In some cases, a cytokine (e.g., an interleukin, IFN, or TNF) polypeptide is conjugated to a polyoxazoline polymer. In some cases, an IL-2 polypeptide is conjugated to a polyoxazoline polymer. In some cases, an IL-2 polypeptide is conjugated to PMOZ. In some cases, an IL-2 polypeptide is conjugated to PEOZ. In some cases, an IL-2 polypeptide is conjugated to PPOZ.

In some instances, a water-soluble polymer comprises a polyacrylic acid polymer. In some cases, a cytokine (e.g., an interleukin, IFN, or TNF) polypeptide is conjugated to a polyacrylic acid polymer. In some cases, an IL-2 polypeptide is conjugated to a polyacrylic acid polymer.

In some instances, a water-soluble polymer comprises polyamine. Polyamine is an organic polymer comprising two or more primary amino groups. In some embodiments, a polyamine includes a branched polyamine, a linear polyamine, or cyclic polyamine. In some cases, a polyamine is a low-molecular-weight linear polyamine. Exemplary polyamines include putrescine, cadaverine, spermidine, spermine, ethylene diamine, 1,3-diaminopropane, hexamethylenediamine, tetraethylmethylenediamine, and piperazine. In some cases, a cytokine (e.g., an interleukin, IFN, or TNF) polypeptide is conjugated to a polyamine. In some cases, an IL-2 polypeptide is conjugated to polyamine. In some cases, an IL-2 polypeptide is conjugated to putrescine, cadaverine, spermidine, spermine, ethylene diamine, 1,3-diaminopropane, hexamethylenediamine, tetraethylmethylenediamine, or piperazine.

In some instances, a water-soluble polymer is described in U.S. Pat. Nos. 7,744,861, 8,273,833, and 7,803,777. In some instances, a cytokine (e.g., an interleukin, IFN, or TNF) polypeptide is conjugated to a linker described in U.S. Pat. Nos. 7,744,861, 8,273,833, or 7,803,777. In some cases, an IL-2 polypeptide is conjugated to a linker described in U.S. Pat. Nos. 7,744,861, 8,273,833, or 7,803,777.

Lipids

In some embodiments, a conjugating moiety descried herein is a lipid. In some instances, the lipid is a fatty acid. In some cases, the fatty acid is a saturated fatty acid. In other cases, the fatty acid is an unsaturated fatty acid. Exemplary fatty acids include, but are not limited to, fatty acids comprising from about 6 to about 26 carbon atoms, from about 6 to about 24 carbon atoms, from about 6 to about 22 carbon atoms, from about 6 to about 20 carbon atoms, from about 6 to about 18 carbon atoms, from about 20 to about 26 carbon atoms, from about 12 to about 26 carbon atoms, from about 12 to about 24 carbon atoms, from about 12 to about 22 carbon atoms, from about 12 to about 20 carbon atoms, or from about 12 to about 18 carbon atoms. In some cases, the lipid binds to one or more serum proteins, thereby increasing serum stability and/or serum half-life.

In some embodiments, the lipid is conjugated to IL-2. In some instances, the lipid is a fatty acid, e.g., a saturated fatty acid or an unsaturated fatty acid. In some cases, the fatty acid is from about 6 to about 26 carbon atoms, from about 6 to about 24 carbon atoms, from about 6 to about 22 carbon atoms, from about 6 to about 20 carbon atoms, from about 6 to about 18 carbon atoms, from about 20 to about 26 carbon atoms, from about 12 to about 26 carbon atoms, from about 12 to about 24 carbon atoms, from about 12 to about 22 carbon atoms, from about 12 to about 20 carbon atoms, or from about 12 to about 18 carbon atoms. In some cases, the fatty acid comprises about 6, 7, 8, 9, 10, 11, 12, 13, 14, 15, 16, 17, 18, 19, 20, 21, 22, 23, 24, 25, or 26 carbon atoms in length. In some cases, the fatty acid comprises caproic acid (hexanoic acid), enanthic acid (heptanoic acid), caprylic acid (octanoic acid), pelargonic acid (nonanoic acid), capric acid (decanoic acid), undecylic acid (undecanoic acid), lauric acid (dodecanoic acid), tridecylic acid (tridecanoic acid), myristic acid (tetradecanoic acid), pentadecylic acid (pentadecanoic acid), palmitic acid (hexadecanoic acid), margaric acid (heptadecanoic acid), stearic acid (octadecanoic acid), nonadecylic acid (nonadecanoic acid), arachidic acid (eicosanoic acid), heneicosylic acid (heneicosanoic acid), behenic acid (docosanoic acid), tricosylic acid (tricosanoic acid), lignoceric acid (tetracosanoic acid), pentacosylic acid (pentacosanoic acid), or cerotic acid (hexacosanoic acid).

In some embodiments, the IL-2 lipid conjugate enhances serum stability and/or serum half-life.

Proteins

In some embodiments, a conjugating moiety descried herein is a protein or a binding fragment thereof. Exemplary proteins include albumin, transferrin, or transthyretin. In some instances, the protein or a binding fragment thereof comprises an antibody, or its binding fragments thereof. In some cases, a cytokine conjugate comprises a protein or a binding fragment thereof. In some cases, an IL-2 conjugate comprising a protein or a binding fragment thereof has an increased serum half-life, and/or stability. In some cases, an IL-2 conjugate comprising a protein or a binding fragment thereof has a reduced IL-2 interaction with one or more IL-2R subunits. In additional cases, the protein or a binding fragment thereof blocks IL-2 interaction with one or more IL-2R subunits.

In some embodiments, the conjugating moiety is albumin. Albumin is a family of water-soluble globular proteins. It is commonly found in blood plasma, comprising about 55-60% of all plasma proteins. Human serum albumin (HSA) is a 585 amino acid polypeptide in which the tertiary structure is divided into three domains, domain I (amino acid residues 1-195), domain II (amino acid residues 196-383), and domain III (amino acid residues 384-585). Each domain further comprises a binding site, which can interact either reversibly or irreversibly with endogenous ligands such as long- and medium-chain fatty acids, bilirubin, or hemin, or exogenous compounds such as heterocyclic or aromatic compounds.

In some cases, a cytokine (e.g., an interleukin, IFN, or TNF) polypeptide is conjugated to albumin. In some cases, the cytokine polypeptide is conjugated to human serum albumin (HSA). In additional cases, the cytokine polypeptide is conjugated to a functional fragment of albumin.

In some instances, an IL-2 polypeptide is conjugated to albumin. In some cases, the IL-2 polypeptide is conjugated to human serum albumin (HSA). In additional cases, the IL-2 polypeptide is conjugated to a functional fragment of albumin.

In some embodiments, the conjugating moiety is transferrin. Transferrin is a 679 amino acid polypeptide that is about 80 kDa in size and comprises two $Fe^{3+}$ binding sites with one at the N-terminal domain and the other at the C-terminal domain. In some instances, human transferrin has a half-life of about 7-12 days.

In some instances, a cytokine (e.g., an interleukin, IFN, or TNF) polypeptide is conjugated to transferrin. In some cases, the cytokine polypeptide is conjugated to human transferrin. In additional cases, the cytokine polypeptide is conjugated to a functional fragment of transferrin.

In some instances, an IL-2 polypeptide is conjugated to transferrin. In some cases, the IL-2 polypeptide is conjugated to human transferrin. In additional cases, the IL-2 polypeptide is conjugated to a functional fragment of transferrin.

In some embodiments, the conjugating moiety is transthyretin (TTR). Transthyretin is a transport protein located in the serum and cerebrospinal fluid which transports the thyroid hormone thyroxine ($T_4$) and retinol-binding protein bound to retinol.

In some instances, a cytokine (e.g., an interleukin, IFN, or TNF) polypeptide is conjugated to transthyretin (via one of its termini or via an internal hinge region). In some cases, the cytokine polypeptide is conjugated to a functional fragment of transthyretin.

In some instances, an IL-2 polypeptide is conjugated to transthyretin (via one of its termini or via an internal hinge region). In some cases, the IL-2 polypeptide is conjugated to a functional fragment of transthyretin.

In some embodiments, the conjugating moiety is an antibody, or its binding fragments thereof. In some instances, an antibody or its binding fragments thereof comprise a humanized antibody or binding fragment thereof, murine antibody or binding fragment thereof, chimeric antibody or binding fragment thereof, monoclonal antibody or binding fragment thereof, monovalent Fab', divalent $Fab_2$, $F(ab)'_3$ fragments, single-chain variable fragment (scFv), bis-scFv, $(scFv)_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof.

In some instances, the conjugating moiety comprises a scFv, bis-scFv, $(scFv)_2$, dsFv, or sdAb. In some cases, the conjugating moiety comprises a scFv. In some cases, the conjugating moiety comprises a bis-scFv. In some cases, the conjugating moiety comprises a $(scFv)_2$. In some cases, the conjugating moiety comprises a dsFv. In some cases, the conjugating moiety comprises a sdAb.

In some instances, the conjugating moiety comprises an Fc portion of an antibody, e.g., of IgG, IgA, IgM, IgE, or IgD. In some instances, the moiety comprises an Fc portion of IgG (e.g., $IgG_1$, $IgG_3$, or $IgG_4$).

In some cases, a cytokine (e.g., an interleukin, IFN, or TNF) polypeptide is conjugated to an antibody, or its binding fragments thereof. In some cases, the cytokine polypeptide is conjugated to a humanized antibody or binding fragment thereof, murine antibody or binding fragment thereof, chimeric antibody or binding fragment thereof, monoclonal antibody or binding fragment thereof, monovalent Fab', divalent $Fab_2$, $F(ab)'_3$ fragments, single-chain variable fragment (scFv), bis-scFv, $(scFv)_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof. In additional cases, the cytokine polypeptide is conjugated to an Fc portion of an antibody. In additional cases, the cytokine polypeptide is conjugated to an Fc portion of IgG (e.g., $IgG_1$, $IgG_3$, or $IgG_4$).

In some cases, an IL-2 polypeptide is conjugated to an antibody, or its binding fragments thereof. In some cases, the IL-2 polypeptide is conjugated to a humanized antibody or binding fragment thereof, murine antibody or binding fragment thereof, chimeric antibody or binding fragment thereof, monoclonal antibody or binding fragment thereof, monovalent Fab', divalent $Fab_2$, $F(ab)'_3$ fragments, single-chain variable fragment (scFv), bis-scFv, $(scFv)_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof. In additional cases, the IL-2 polypeptide is conjugated to an Fc portion of an antibody. In additional cases, the IL-2 polypeptide is conjugated to an Fc portion of IgG (e.g., $IgG_1$, $IgG_3$, or $IgG_4$).

In some embodiments, an IL-2 polypeptide is conjugated to a water-soluble polymer (e.g., PEG) and an antibody or binding fragment thereof. In some cases, the antibody or binding fragments thereof comprises a humanized antibody or binding fragment thereof, murine antibody or binding fragment thereof, chimeric antibody or binding fragment thereof, monoclonal antibody or binding fragment thereof, monovalent Fab', divalent $Fab_2$, $F(ab)'_3$ fragments, single-chain variable fragment (scFv), bis-scFv, $(scFv)_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof. In some cases, the antibody or binding fragments thereof comprises a scFv, bis-scFv, $(scFv)_2$, dsFv, or sdAb. In some cases, the antibody or binding fragments thereof comprises a scFv. In some cases, the antibody or binding fragment thereof guides the IL-2 conjugate to a target cell of interest and the water-soluble polymer enhances stability and/or serum half-life.

In some instances, one or more IL-2 polypeptide-water-soluble polymer (e.g., PEG) conjugates are further bound to an antibody or binding fragments thereof. In some instances, the ratio of the IL-2 conjugate to the antibody is about 1:1, 2:1, 3:1, 4:1, 5:1, 6:1, 7:1, 8:1, 9:1, 10:1, 11:1, or 12:1. In some cases, the ratio of the IL-2 conjugate to the antibody is about 1:1. In other cases, the ratio of the IL-2 conjugate to the antibody is about 2:1, 3:1, or 4:1. In additional cases, the ratio of the IL-2 conjugate to the antibody is about 6:1 or higher.

In some embodiments, the one or more IL-2 polypeptide-water-soluble polymer (e.g., PEG) conjugates are directly bound to the antibody or binding fragments thereof. In other instances, the IL-2 conjugate is indirectly bound to the antibody or binding fragments thereof with a linker. Exemplary linkers include homobifunctional linkers, heterobifunctional linkers, maleimide-based linkers, zero-trace linkers, self-immolative linkers, spacers, and the like.

In some embodiments, the antibody or binding fragments thereof is bound either directly or indirectly to the IL-2 polypeptide portion of the IL-2 polypeptide-water-soluble polymer (e.g., PEG) conjugate. In such cases, the conjugation site of the antibody to the IL-2 polypeptide is at a site that will not impede binding of the IL-2 polypeptide with the IL-2Rβγ. In additional cases, the conjugation site of the antibody to the IL-2 polypeptide is at a site that partially blocks binding of the IL-2 polypeptide with the IL-2Rβγ. In additional cases, the conjugation site of the antibody to the IL-2 polypeptide is at a site that will impede or further impede binding of the IL-2 polypeptide with the IL-2Rα. In other embodiments, the antibody or binding fragments thereof is bound either directly or indirectly to the water-soluble polymer portion of the IL-2 polypeptide-water-soluble polymer (e.g., PEG) conjugate.

Peptides

In some embodiments, a conjugating moiety descried herein is a peptide. In some instances, the peptide is a non-structured peptide. In some cases, a cytokine (e.g., an interleukin, IFN, or TNF) polypeptide is conjugated to a peptide. In some cases, the IL-2 conjugate comprising a peptide has an increased serum half-life, and/or stability. In some cases, the IL-2 conjugate comprising a peptide has a reduced IL-2 interaction with one or more IL-2R subunits. In additional cases, the peptide blocks IL-2 interaction with one or more IL-2R subunits.

In some instances, the conjugating moiety is a XTEN™ peptide (Amunix Operating Inc.) and the modification is referred to as XTENylation. XTENylation is the genetic fusion of a nucleic acid encoding a polypeptide of interest with a nucleic acid encoding a XTEN™ peptide (Amunix Operating Inc.), a long unstructured hydrophilic peptide comprising different percentage of six amino acids: Ala, Glu, Gly, Ser, and Thr. In some instances, a XTEN™ peptide is selected based on properties such as expression, genetic stability, solubility, aggregation resistance, enhanced half-life, increased potency, and/or increased in vitro activity in combination with a polypeptide of interest. In some cases, a cytokine (e.g., an interleukin, IFN, or TNF) polypeptide is conjugated to a XTEN peptide. In some cases, an IL-2 polypeptide is conjugated to a XTEN peptide.

In some instances, the conjugating moiety is a glycine-rich homoamino acid polymer (HAP) and the modification is referred to as HAPylation. HAPylation is the genetic fusion of a nucleic acid encoding a polypeptide of interest with a nucleic acid encoding a glycine-rich homoamino acid polymer (HAP). In some instances, the HAP polymer comprises a $(Gly_4Ser)_n$ repeat motif (SEQ ID NO: 85) and sometimes are about 50, 100, 150, 200, 250, 300, or more residues in length. In some cases, a cytokine (e.g., an interleukin, IFN, or TNF) polypeptide is conjugated to HAP. In some cases, an IL-2 polypeptide is conjugated to HAP.

In some embodiments, the conjugating moiety is a PAS polypeptide and the modification is referred to as PASylation. PASylation is the genetic fusion of a nucleic acid encoding a polypeptide of interest with a nucleic acid encoding a PAS polypeptide. A PAS polypeptide is a hydrophilic uncharged polypeptide consisting of Pro, Ala and Ser residues. In some instances, the length of a PAS polypeptide is at least about 100, 200, 300, 400, 500, or 600 amino acids. In some cases, a cytokine (e.g., an interleukin, IFN, or TNF) polypeptide is conjugated to a PAS polypeptide. In some cases, an IL-2 polypeptide is conjugated to a PAS polypeptide.

In some embodiments, the conjugating moiety is an elastin-like polypeptide (ELP) and the modification is referred to as ELPylation. ELPylation is the genetic fusion of a nucleic acid encoding a polypeptide of interest with a nucleic acid encoding an elastin-like polypeptide (ELPs). An ELP comprises a VPGxG repeat motif (SEQ ID NO: 86) in which x is any amino acid except proline. In some cases, a cytokine (e.g., an interleukin, IFN, or TNF) polypeptide is conjugated to ELP. In some cases, an IL-2 polypeptide is conjugated to ELP.

In some embodiments, the conjugating moiety is a CTP peptide. A CTP peptide comprises a 31 amino acid residue peptide FQSSSS*KAPPPS*LPSPS*RLPGPS*DTPILPQ (SEQ ID NO: 87) in which the S* denotes O-glycosylation sites (OPKO). In some instances, a CTP peptide is genetically fused to a cytokine polypeptide (e.g., an IL-2 polypeptide). In some cases, a cytokine polypeptide (e.g., an IL-2 polypeptide) is conjugated to a CTP peptide.

In some embodiments, a cytokine (e.g., an IL-2 polypeptide) is modified by glutamylation. Glutamylation (or polyglutamylation) is a reversible posttranslational modification of glutamate, in which the γ-carboxy group of glutamate forms a peptide-like bond with the amino group of a free glutamate in which the α-carboxy group extends into a polyglutamate chain.

In some embodiments, a cytokine (e.g., an IL-2 polypeptide) is modified by a gelatin-like protein (GLK) polymer. In some instances, the GLK polymer comprises multiple repeats of Gly-Xaa-Yaa wherein Xaa and Yaa primarily comprise proline and 4-hydroxyproline, respectively. In some cases, the GLK polymer further comprises amino acid residues Pro, Gly, Glu, Qln, Asn, Ser, and Lys. In some cases, the length of the GLK polymer is about 20, 30, 40, 50, 60, 70, 80, 90, 100, 110, 120, 150 residues or longer.

Additional Conjugating Moieties

In some instances, the conjugating moiety comprises an extracellular biomarker. In some instances, the extracellular biomarker is a tumor antigen. In some instances, exemplary extracellular biomarker comprises CD19, PSMA, B7-H3, B7-H6, CD70, CEA, CSPG4, EGFRvIII, EphA3, EpCAM, EGFR, ErbB2 (HER2), FAP, FRα, GD2, GD3, Lewis-Y, mesothelin, Muc1, Muc16, ROR1, TAG72, VEGFR2, CD11, Gr-1, CD204, CD16, CD49b, CD3, CD4, CD8, and B220. In some instances, the conjugating moiety is bond or conjugated to the cytokine (e.g., IL-2). In some cases, the conjugating moiety is genetically fused, for example, at the N-terminus or the C-terminus, of the cytokine (e.g., IL-2).

In some instances, the conjugating moiety comprises a molecule from a post-translational modification. In some instances, examples of post-translational modification include myristoylation, palmitoylation, isoprenylation (or prenylation) (e.g., farnesylation or geranylgeranylation), glypiation, acylation (e.g., O-acylation, N-acylation, S-acylation), alkylation (e.g., additional of alkyl groups such as methyl or ethyl groups), amidation, glycosylation, hydroxylation, iodination, nucleotide addition, oxidation, phosphorylation, succinylation, sulfation, glycation, carbamylation, glutamylation, or deamidation. In some instances, the cytokine (e.g., IL-2) is modified by a post-translational modification such as myristoylation, palmitoylation, isoprenylation (or prenylation) (e.g., farnesylation or geranylgeranylation), glypiation, acylation (e.g., O-acylation, N-acylation, S-acylation), alkylation (e.g., additional of alkyl groups such as methyl or ethyl groups), amidation, glycosylation, hydroxylation, iodination, nucleotide addition, oxidation, phosphorylation, succinylation, sulfation, glycation, carbamylation, glutamylation, or deamidation.

Conjugation

Linkers

In some embodiments, useful functional reactive groups for conjugating or binding a conjugating moiety to a cytokine polypeptide (e.g., an IL-2 polypeptide) described herein include, for example, zero or higher-order linkers. In some instances, an unnatural amino acid incorporated into an interleukin described herein comprises a functional reactive group. In some instances, a linker comprises a functional reactive group that reacts with an unnatural amino acid incorporated into an interleukin described herein. In some instances, a conjugating moiety comprises a functional reactive group that reacts with an unnatural amino acid incorporated into an interleukin described herein. In some instances, a conjugating moiety comprises a functional reactive group that reacts with a linker (optionally pre-attached to a cytokine peptide) described herein. In some embodiments, a linker comprises a reactive group that reacts with a natural amino acid in a cytokine peptide described herein. In some cases, higher-order linkers comprise bifunctional linkers, such as homobifunctional linkers or heterobifunctional linkers. Exemplary homobifunctional linkers include, but are not limited to, Lomant's reagent dithiobis (succinimidylpropionate) DSP, 3'3'-dithiobis(sulfosuccinimidyl proprionate (DTSSP), disuccinimidyl suberate (DSS), bis(sulfosuccinimidyl)suberate (BS), disuccinimidyl tartrate (DST), disulfosuccinimidyl tartrate (sulfo DST), ethylene glycobis(succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-3'-(2'-pyridyldithio)propionamido)butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[D-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide).

In some embodiments, the bifunctional linker comprises a heterobifunctional linker. Exemplary heterobifunctional linker include, but are not limited to, amine-reactive and sulfhydryl cross-linkers such as N-succinimidyl 3-(2-pyridyldithio)propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6-[α-methyl-α-(2-pyridyldithio)toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl(4-iodoacteyl)aminobenzoate (sIAB), sulfosuccinimidyl(4-iodoacteyl)aminobenzoate (sulfo-sIAB), succinimidyl-4-(p-maleimidophenyl)butyrate (sMPB), sulfosuccinimidyl-4-(p-maleimidophenyl) butyrate (sulfo-sMPB), N-(γ-maleimidobutyryloxy) succinimide ester (GMBs), N-(γ-maleimidobutyryloxy) sulfosuccinimide ester (sulfo-GMBs), succinimidyl 6-((iodoacetyl)amino)hexanoate (sIAX), succinimidyl 6-[6-(((iodoacetyl)amino)hexanoyl)amino]hexanoate (sIAXX), succinimidyl 4-(((iodoacetyl)amino)methyl)cyclohexane-1-carboxylate (sIAC), succinimidyl 6-((((4-iodoacetyl)amino) methyl)cyclohexane-1-carbonyl)amino) hexanoate (sIACX), p-nitrophenyl iodoacetate (NPIA), carbonyl-reactive and sulfhydryl-reactive cross-linkers such as 4-(4-N-maleimidophenyl)butyric acid hydrazide (MPBH), 4-(N-maleimidomethyl)cyclohexane-1-carboxyl-hydrazide-8 (M2C2H), 3-(2-pyridyldithio)propionyl hydrazide (PDPH), amine-reactive and photoreactive cross-linkers such as N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido)hexanoate (sulfo-NHs-LC-AsA), sulfosuccinimidyl-2-(ρ-azidosalicylamido) ethyl-1,3'-dithiopropionate (sAsD), N-hydroxysuccinimidyl-4-azidobenzoate (HsAB), N-hydroxysulfosuccinimidyl-4-azidobenzoate (sulfo- HsAB), N-succinimidyl-6-(4'-azido-2'-nitrophenylamino) hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4(4-azidophenyl)1,3'-dithiopropionate (sADP), N-sulfosuccinimidyl(4-azidophenyl)-1,3'-dithiopropionate (sulfo-sADP), sulfosuccinimidyl 4-(ρ-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), ρ-nitrophenyl diazopyruvate (pNPDP), ρ-nitrophenyl-2-diazo-3,3,3-trifluoropropionate (PNP-DTP), sulfhydryl-reactive and photoreactive cross-linkers such as 1-(ρ-Azidosalicylamido)-4-(iodoacetamido)butane (AsIB), N-[4-(ρ-azidosalicylamido)butyl]-3'-(2'-pyridyldithio)propionamide (APDP), benzophenone-4-iodoacetamide, benzophenone-4-maleimide carbonyl-reactive and photoreactive cross-linkers such as ρ-azidobenzoyl hydrazide (ABH), carboxylate-reactive and photoreactive cross-linkers such as 4-(ρ-azidosalicylamido)butylamine (AsBA), and arginine-reactive and photoreactive cross-linkers such as ρ-azidophenyl glyoxal (APG).

In some instances, the reactive functional group comprises a nucleophilic group that is reactive to an electrophilic group present on a binding moiety (e.g., on a conjugating moiety or on IL-2). Exemplary electrophilic groups include carbonyl groups-such as aldehyde, ketone, carboxylic acid, ester, amide, enone, acyl halide or acid anhydride. In some embodiments, the reactive functional group is aldehyde. Exemplary nucleophilic groups include hydrazide, oxime, amino, hydrazine, thiosemicarbazone, hydrazine carboxylate, and arylhydrazide. In some embodiments, an unnatural amino acid incorporated into an interleukin described herein comprises an electrophilic group.

In some embodiments, the linker is a cleavable linker. In some embodiments, the cleavable linker is a dipeptide linker. In some embodiments, the dipeptide linker is valine-citrulline (Val-Cit), phenylalanine-lysine (Phe-Lys), valine-alanine (Val-Ala) and valine-lysine (Val-Lys). In some embodiments, the dipeptide linker is valine-citrulline.

In some embodiments, the linker is a peptide linker comprising, e.g., at least 2, 3, 4, 5, 6, 7, 8, 9, 10, 11, 12, 15, 20, 25, 30, 35, 40, 45, 50, or more amino acids. In some instances, the peptide linker comprises at most 2, 3, 4, 5, 6, 7, 8, 9, 10, 11, 12, 15, 20, 25, 30, 35, 40, 45, 50, or less amino acids. In additional cases, the peptide linker comprises about 2, 3, 4, 5, 6, 7, 8, 9, 10, 11, 12, 15, 20, 25, 30, 35, 40, 45, or 50 amino acids.

In some embodiments, the linker comprises a self-immolative linker moiety. In some embodiments, the self-immolative linker moiety comprises p-aminobenzyl alcohol (PAB), p-aminobenzyoxycarbonyl (PABC), or derivatives or analogs thereof. In some embodiments, the linker comprises a dipeptide linker moiety and a self-immolative linker moiety. In some embodiments, the self-immolative linker moiety is such as described in U.S. Pat. No. 9,089,614 and WIPO Application No. WO2015038426.

In some embodiments, the cleavable linker is glucuronide. In some embodiments, the cleavable linker is an acid-cleavable linker. In some embodiments, the acid-cleavable linker is hydrazine. In some embodiments, the cleavable linker is a reducible linker.

In some embodiments, the linker comprises a maleimide group. In some instances, the maleimide group is also referred to as a maleimide spacer. In some instances, the maleimide group further comprises a caproic acid, forming maleimidocaproyl (mc). In some cases, the linker comprises maleimidocaproyl (mc). In some cases, linker is maleimidocaproyl (mc). In other instances, the maleimide group comprises a maleimidomethyl group, such as succinimidyl-4-(N-maleimidomethyl)cyclohexane-1-carboxylate (sMCC) or sulfosuccinimidyl-4-(N-maleimidomethyl)cyclohexane-1-carboxylate (sulfo-sMCC) described above.

In some embodiments, the maleimide group is a self-stabilizing maleimide. In some instances, the self-stabilizing maleimide utilizes diaminopropionic acid (DPR) to incorporate a basic amino group adjacent to the maleimide to provide intramolecular catalysis of tiosuccinimide ring hydrolysis, thereby eliminating maleimide from undergoing an elimination reaction through a retro-Michael reaction. In some instances, the self-stabilizing maleimide is a maleimide group described in Lyon, et al., "Self-hydrolyzing maleimides improve the stability and pharmacological properties of antibody-drug conjugates," *Nat. Biotechnol.* 32(10): 1059-1062 (2014). In some instances, the linker comprises a self-stabilizing maleimide. In some instances, the linker is a self-stabilizing maleimide.

Conjugation Chemistry

Various conjugation reactions are used to conjugate linkers, conjugation moieties, and unnatural amino acids incorporated into cytokine peptides described herein. Such conjugation reactions are often compatible with aqueous conditions, such as "bioorthogonal" reactions. In some embodiments, conjugation reactions are mediated by chemical reagents such as catalysts, light, or reactive chemical groups found on linkers, conjugation moieties, or unnatural amino acids. In some embodiments, conjugation reactions are mediated by enzymes. In some embodiments, a conjugation reaction used herein is described in Gong, Y., Pan, L. Tett. Lett. 2015, 56, 2123. In some embodiments, a conjugation reaction used herein is described in Chen, X.; Wu. Y—W. Org. Biomol. Chem. 2016, 14, 5417.

In some embodiments described herein, a conjugation reaction comprises reaction of a ketone or aldehyde with a nucleophile. In some embodiments, a conjugation reaction comprises reaction of a ketone with an aminoxy group to form an oxime. In some embodiments, a conjugation reaction comprises reaction of a ketone with an aryl or heteroaryl amine group to form an imine. In some embodiments, a conjugation reaction comprises reaction of an aldehyde with an aryl or heteroaryl amine group to form an imine. In some embodiments, a conjugation reaction described herein results in cytokine peptide comprising a linker or conjugation moiety attached via an oxime. In some embodiments, a conjugation reaction comprises a Pictet-Spengler reaction of an aldehyde or ketone with a tryptamine nucleophile. In some embodiments, a conjugation reaction comprises a hydrazino-Pictet-Spengler reaction. In some embodiments, a conjugation reaction comprises a Pictet-Spengler ligation.

In some embodiments described herein, a conjugation reaction described herein comprises reaction of an azide and a phosphine (Staudinger ligation). In some embodiments, the phosphine is an aryl phosphine. In some embodiments, the aryl phosphine comprises an ortho ester group. In some embodiments, the phosphine comprises the structure methyl 2-(diphenylphosphaneyl)benzoate. In some embodiments, a conjugation reaction described herein results in cytokine peptide comprising a linker or conjugation moiety attached via an arylamide. In some embodiments, a conjugation reaction described herein results in cytokine peptide comprising a linker or conjugation moiety attached via an amide.

In some embodiments described herein, a conjugation reaction described herein comprises a 1,3-dipolar cycloaddition reaction. In some embodiments, the 1,3-dipolar cycloaddition reaction comprises reaction of an azide and a phosphine ("Click" reaction). In some embodiments, the conjugation reaction is catalyzed by copper. In some embodiments, a conjugation reaction described herein results in cytokine peptide comprising a linker or conjugation moiety attached via a triazole. In some embodiments, a conjugation reaction described herein comprises reaction of an azide with a strained olefin. In some embodiments, a conjugation reaction described herein comprises reaction of an azide with a strained alkyne. In some embodiments, a conjugation reaction described herein comprises reaction of an azide with a cycloalkyne, for example, OCT, DIFO, DIFBO, DIBO, BARAC, TMTH, or other strained cycloalkyne, the structures of which are shown in Gong, Y., Pan, L. Tett. Lett. 2015, 56, 2123. In some embodiments, a 1,3-dipolar cycloaddition reaction is catalyzed by light ("photoclick"). In some embodiments, a conjugation reaction described herein comprises reaction of a terminal allyl group with a tetrazole and light. In some embodiments, a conjugation reaction described herein comprises reaction of a terminal alkynyl group with a tetrazole and light. In some embodiments, a conjugation reaction described herein comprises reaction of an O-allyl amino acid with a tetrazine and light. In some embodiments, a conjugation reaction described herein comprises reaction of O-allyl tyrosine with a tetrazine and light.

In some embodiments described herein, a conjugation reaction described herein comprises:

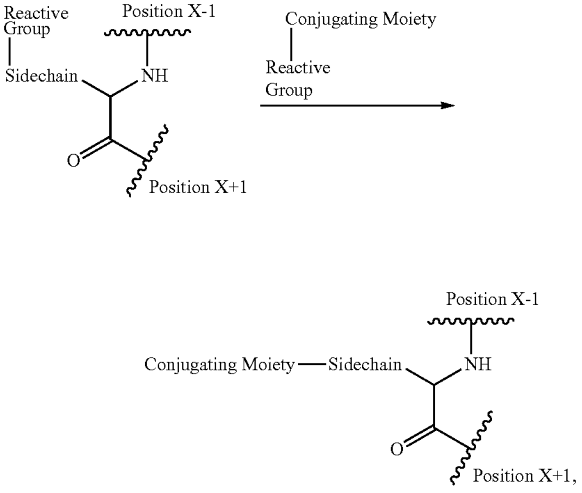

wherein X is the position in the IL-2 conjugate comprising an unnatural amino acid, such as in any one of SEQ ID NOS: 5, 6, 7, 8, 9, 30, 31, 32, 33, and 34. In some embodiments, the conjugating moiety comprises water soluble polymer. In some embodiments, a reactive group comprises an alkyne or azide. In some embodiments described herein, a conjugation reaction described herein comprises:

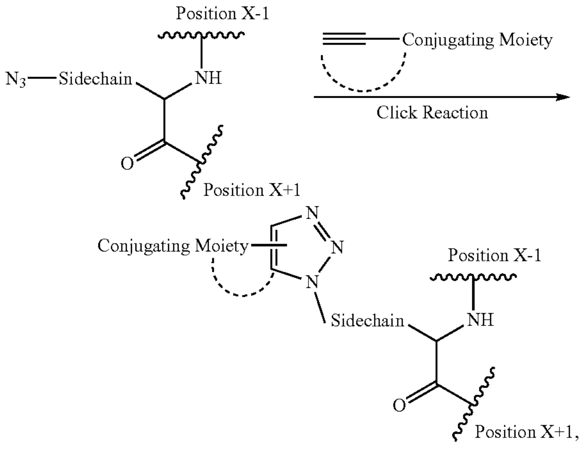

wherein X is the position in the IL-2 conjugate comprising an unnatural amino acid, such as in any one of SEQ ID NOS: 5, 6, 7, 8, 9, 30, 31, 32, 33, and 34. In some embodiments described herein, a conjugation reaction described herein comprises:

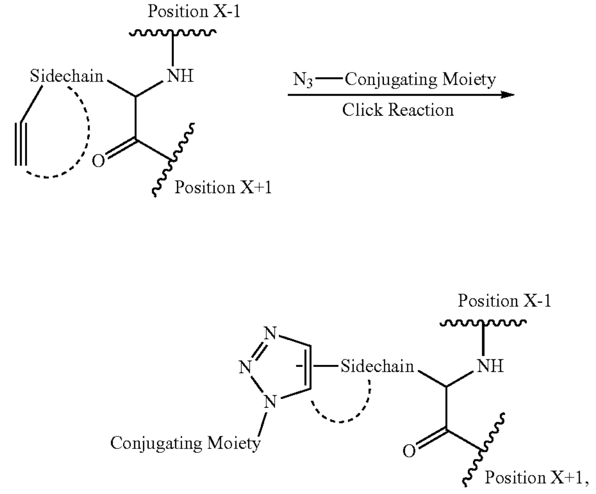

wherein X is the position in the IL-2 conjugate comprising an unnatural amino acid, such as in any one of SEQ ID NOS: 5, 6, 7, 8, 9, 30, 31, 32, 33, and 34. In some embodiments described herein, a conjugation reaction described herein comprises:

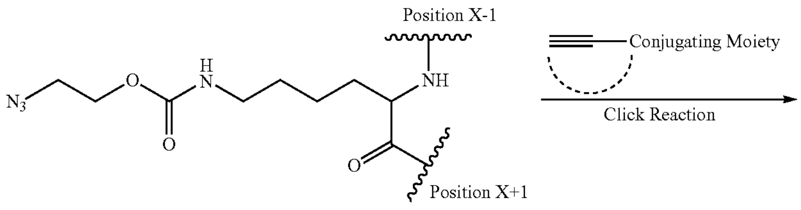

-continued

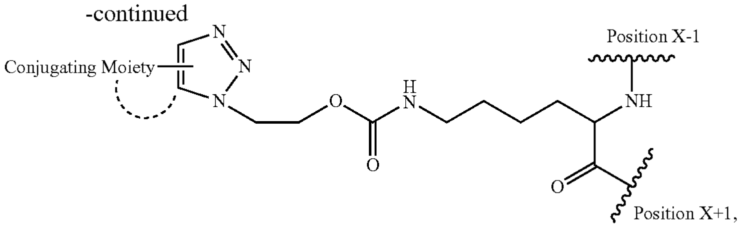

wherein X is the position in the IL-2 conjugate comprising an unnatural amino acid, such as in any one of SEQ ID NOS: 5, 6, 7, 8, 9, 30, 31, 32, 33, and 34. In some embodiments described herein, a conjugation reaction described herein comprises:

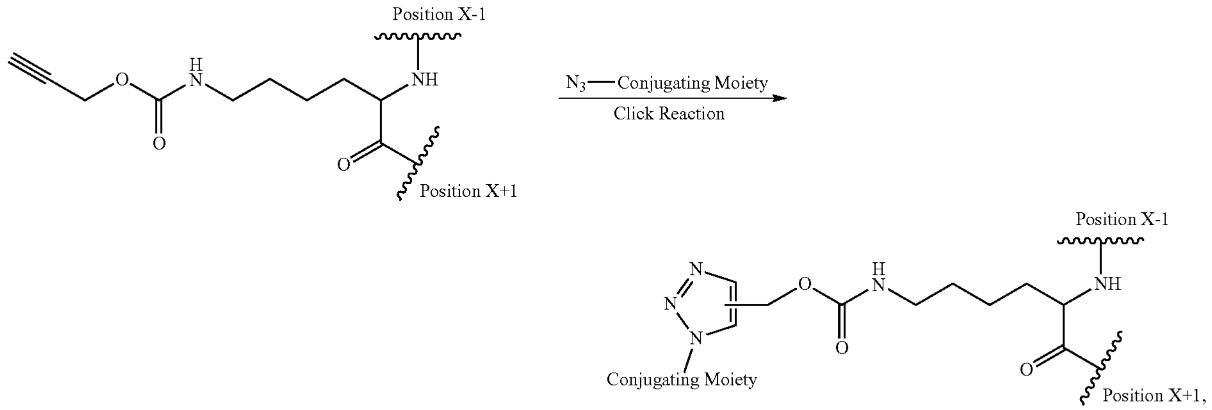

wherein X is the position in the IL-2 conjugate comprising an unnatural amino acid, such as in any one of SEQ ID NOS: 5, 6, 7, 8, 9, 30, 31, 32, 33, and 34. In some embodiments, a conjugation reaction described herein results in an IL-2 variant of Table 20.

In some embodiments described herein, a conjugation reaction described herein comprises are cycloaddition reaction between an azide moiety, such as that contained in a protein containing an amino acid residue derived from N6-((2-azidoethoxy)-carbonyl)-L-lysine (AzK), and a strained cycloalkyne, such as that derived from DBCO, which is a chemical moiety comprising a dibenzocyclooctyne group. PEG groups comprising a DBCO moiety are commercially available or may be prepared by methods known to those of ordinary skill in the art.

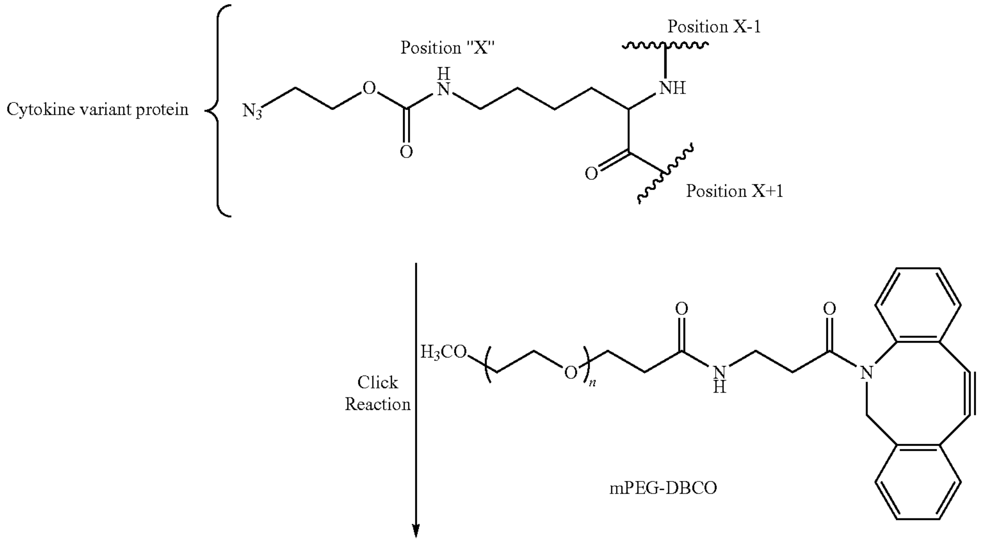

mPEG-DBCO

-continued
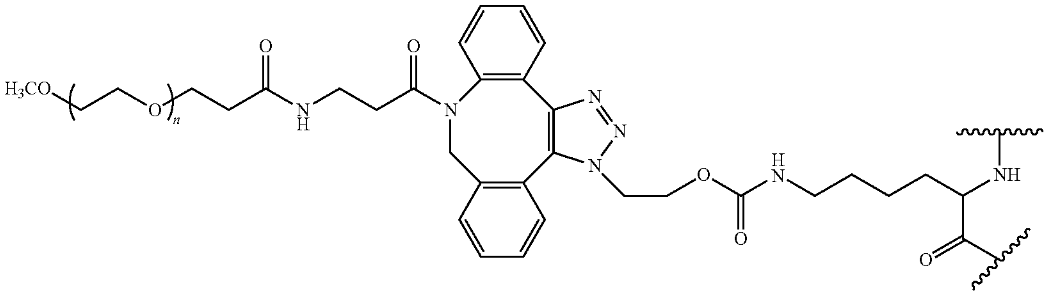
+
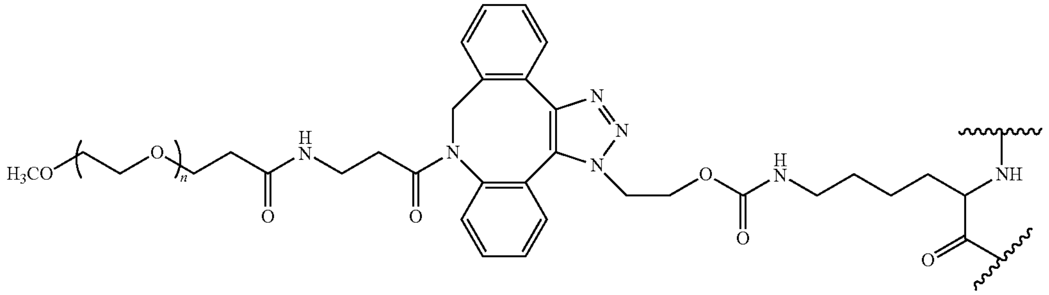
Cytokine Azk_PEG variant proteins
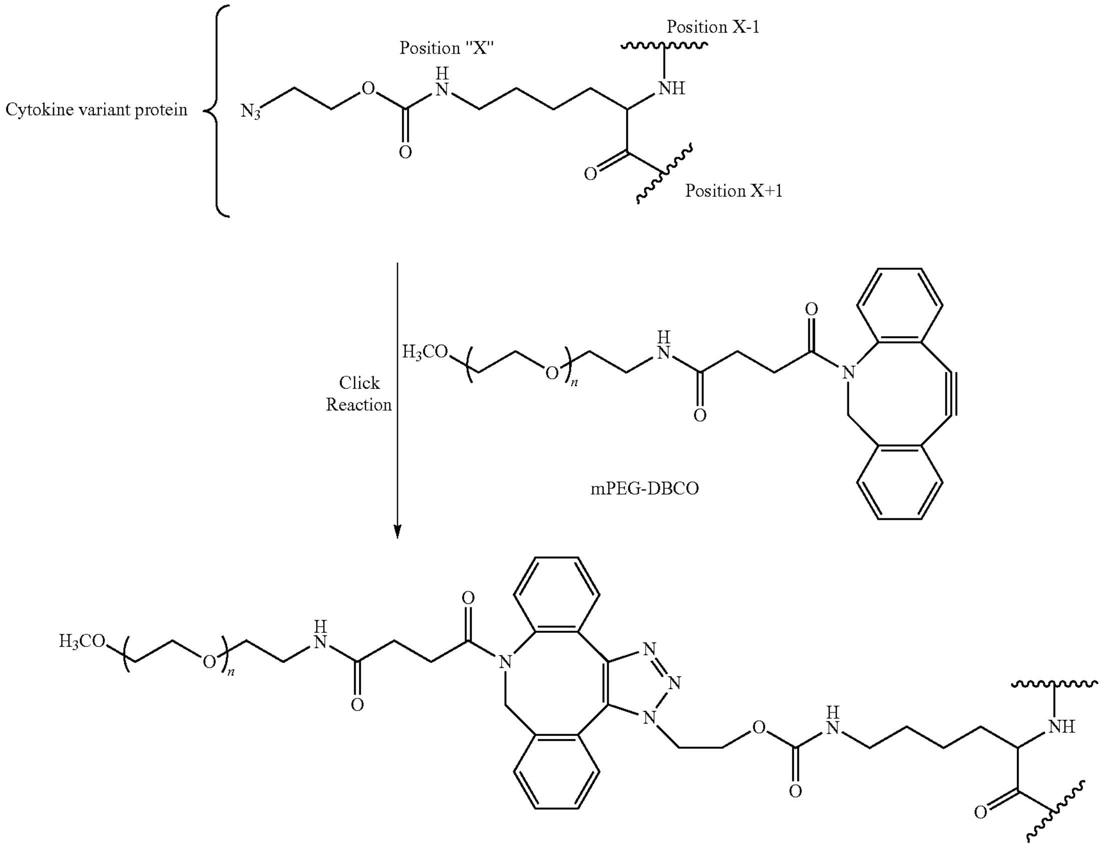
+

-continued

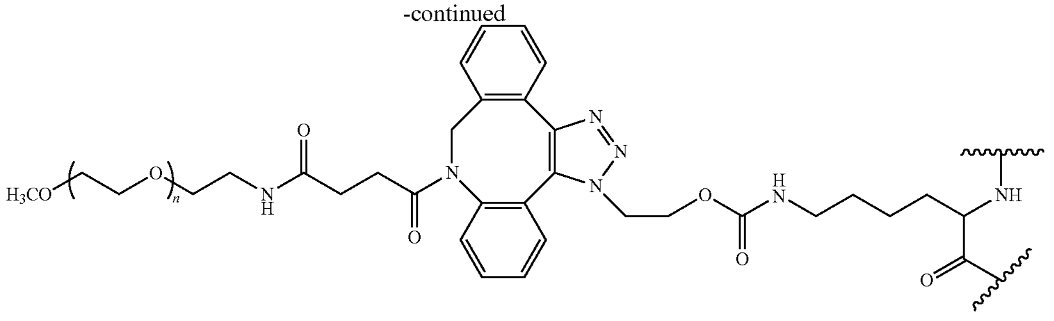

Cytokine Azk_L1_PEG variant proteins

Conjugation reactions such as a click reaction described herein may generate a single regioisomer, or a mixture of regioisomers. In some instances the ratio of regioisomers is about 1:1. In some instances the ratio of regioisomers is about 2:1. In some instances the ratio of regioisomers is about 1.5:1. In some instances the ratio of regioisomers is about 1.2:1. In some instances the ratio of regioisomers is about 1.1:1. In some instances the ratio of regioisomers is greater than 1:1.

Described herein are IL-2 conjugates having the structure of Formula (I):

Formula (I)

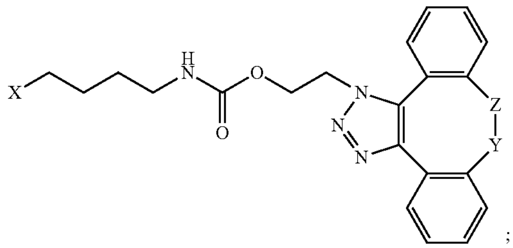

;

wherein:

Z is $CH_2$ and Y is

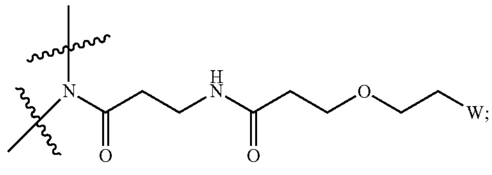

W;

or

Y is $CH_2$ and Z is

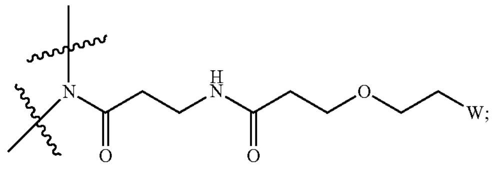

W;

W is a PEG group having an average molecular weight selected from 5 kDa, 10 kDa, 15 kDa, 20 kDa, 25 kDa, 30 kDa, 35 kDa, 40 kDa, 45 kDa, and 50 kDa; and X is an amino acid position of a recombinant human IL-2, wherein the amino acid position is in reference to the positions in SEQ ID NO: 1; or a pharmaceutically acceptable salt, solvate, or hydrate thereof. In some embodiments of an IL-2 conjugate of Formula (I), Z is $CH_2$ and Y is

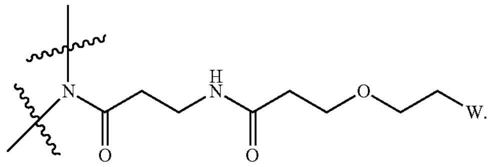

W.

In some embodiments of an IL-2 conjugate of Formula (I), Y is $CH_2$ and Z is

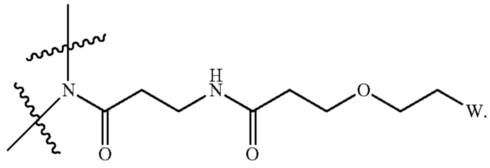

W.

In some embodiments of an IL-2 conjugate of Formula (I), the PEG group has an average molecular weight selected from 5 kDa, 10 kDa, and 30 kDa. In some embodiments of an IL-2 conjugate of Formula (I), the PEG group has an average molecular weight of 5 kDa. In some embodiments of an IL-2 conjugate of Formula (I), the PEG group has an average molecular weight of 10 kDa. In some embodiments of an IL-2 conjugate of Formula (I), the PEG group has an average molecular weight of 20 kDa. In some embodiments of an IL-2 conjugate of Formula (I), the PEG group has an average molecular weight of 30 kDa. In some embodiments of an IL-2 conjugate of Formula (I), the PEG group has an average molecular weight of 40 kDa. In some embodiments of an IL-2 conjugate of Formula (I), the PEG group has an average molecular weight of 50 kDa. In some embodiments of an IL-2 conjugate of Formula (I), X is K35. In some embodiments of an IL-2 conjugate of Formula (I), X is F42. In some embodiments of an IL-2 conjugate of Formula (I), X is K43. In some embodiments of an IL-2 conjugate of Formula (I), X is E62. In some embodiments of an IL-2 conjugate of Formula (I), X is P65. In some embodiments of an IL-2 conjugate of Formula (I), X is R38. In some embodiments of an IL-2 conjugate of Formula (I), X is T41.

In some embodiments of an IL-2 conjugate of Formula (I), X is E68. In some embodiments of an IL-2 conjugate of Formula (I), X is Y45. In some embodiments of an IL-2 conjugate of Formula (I), X is V69. In some embodiments of an IL-2 conjugate of Formula (I), X is selected from K35, F42, K43, E62, P65, R38, T41, E68, Y45, and V69. In some embodiments of an IL-2 conjugate of Formula (I), X is selected from F42, K43, E62, and P65. In some embodiments an IL-2 conjugate of Formula (I) comprises the sequence of any one of SEQ ID NOs: 5-84. In some embodiments an IL-2 conjugate of Formula (I) comprises SEQ ID NOs.: 15-29. In some embodiments an IL-2 conjugate of Formula (I) comprises SEQ ID NOs.: 40-54. In some embodiments an IL-2 conjugate of Formula (I) comprises SEQ ID NOs.: 55-69. In some embodiments an IL-2 conjugate of Formula (I) comprises SEQ ID NOs.: 70-84. In some embodiments an IL-2 conjugate of Formula (I) comprises the sequence of SEQ ID NO: 3. In some embodiments an IL-2 conjugate of Formula (I) comprises the sequence of SEQ ID NO: 4. In some embodiments an IL-2 conjugate of Formula (I) comprises the sequence of SEQ ID NO: 5. In some embodiments an IL-2 conjugate of Formula (I) comprises the sequence of SEQ ID NO: 6. In some embodiments an IL-2 conjugate of Formula (I) comprises the sequence of SEQ ID NO: 7. In some embodiments an IL-2 conjugate of Formula (I) comprises the sequence of SEQ ID NO: 8. In some embodiments an IL-2 conjugate of Formula (I) comprises the sequence of SEQ ID NO: 9. In some embodiments an IL-2 conjugate of Formula (I) comprises the sequence of SEQ ID NO: 10. In some embodiments an IL-2 conjugate of Formula (I) comprises the sequence of SEQ ID NO: 11. In some embodiments an IL-2 conjugate of Formula (I) comprises the sequence of SEQ ID NO: 12. In some embodiments an IL-2 conjugate of Formula (I) comprises the sequence of SEQ ID NO: 13. In some embodiments an IL-2 conjugate of Formula (I) comprises the sequence of SEQ ID NO: 14. In some embodiments an IL-2 conjugate of Formula (I) comprises the sequence of SEQ ID NO: 15. In some embodiments an IL-2 conjugate of Formula (I) comprises the sequence of SEQ ID NO: 16. In some embodiments an IL-2 conjugate of Formula (I) comprises the sequence of SEQ ID NO: 17. In some embodiments an IL-2 conjugate of Formula (I) comprises the sequence of SEQ ID NO: 18. In some embodiments an IL-2 conjugate of Formula (I) comprises the sequence of SEQ ID NO: 19. In some embodiments an IL-2 conjugate of Formula (I) comprises the sequence of SEQ ID NO: 20. In some embodiments an IL-2 conjugate of Formula (I) comprises the sequence of SEQ ID NO: 21. In some embodiments an IL-2 conjugate of Formula (I) comprises the sequence of SEQ ID NO: 22. In some embodiments an IL-2 conjugate of Formula (I) comprises the sequence of SEQ ID NO: 23. In some embodiments an IL-2 conjugate of Formula (I) comprises the sequence of SEQ ID NO: 24. In some embodiments an IL-2 conjugate of Formula (I) comprises the sequence of SEQ ID NO: 25. In some embodiments an IL-2 conjugate of Formula (I) comprises the sequence of SEQ ID NO: 26. In some embodiments an IL-2 conjugate of Formula (I) comprises the sequence of SEQ ID NO: 27. In some embodiments an IL-2 conjugate of Formula (I) comprises the sequence of SEQ ID NO: 28. In some embodiments an IL-2 conjugate of Formula (I) comprises the sequence of SEQ ID NO: 29. In some embodiments an IL-2 conjugate of Formula (I) comprises the sequence of SEQ ID NO: 30. In some embodiments an IL-2 conjugate of Formula (I) comprises the sequence of SEQ ID NO: 31. In some embodiments an IL-2 conjugate of Formula (I) comprises the sequence of SEQ ID NO: 32. In some embodiments an IL-2 conjugate of Formula (I) comprises the sequence of SEQ ID NO: 33. In some embodiments an IL-2 conjugate of Formula (I) comprises the sequence of SEQ ID NO: 34. In some embodiments an IL-2 conjugate of Formula (I) comprises the sequence of SEQ ID NO: 35. In some embodiments an IL-2 conjugate of Formula (I) comprises the sequence of SEQ ID NO: 36. In some embodiments an IL-2 conjugate of Formula (I) comprises the sequence of SEQ ID NO: 37. In some embodiments an IL-2 conjugate of Formula (I) comprises the sequence of SEQ ID NO: 38. In some embodiments an IL-2 conjugate of Formula (I) comprises the sequence of SEQ ID NO: 39. In some embodiments an IL-2 conjugate of Formula (I) comprises the sequence of SEQ ID NO: 40. In some embodiments an IL-2 conjugate of Formula (I) comprises the sequence of SEQ ID NO: 41. In some embodiments an IL-2 conjugate of Formula (I) comprises the sequence of SEQ ID NO: 42. In some embodiments an IL-2 conjugate of Formula (I) comprises the sequence of SEQ ID NO: 43. In some embodiments an IL-2 conjugate of Formula (I) comprises the sequence of SEQ ID NO: 44. In some embodiments an IL-2 conjugate of Formula (I) comprises the sequence of SEQ ID NO: 45. In some embodiments an IL-2 conjugate of Formula (I) comprises the sequence of SEQ ID NO: 46. In some embodiments an IL-2 conjugate of Formula (I) comprises the sequence of SEQ ID NO: 47. In some embodiments an IL-2 conjugate of Formula (I) comprises the sequence of SEQ ID NO: 48. In some embodiments an IL-2 conjugate of Formula (I) comprises the sequence of SEQ ID NO: 49. In some embodiments an IL-2 conjugate of Formula (I) comprises the sequence of SEQ ID NO: 50. In some embodiments an IL-2 conjugate of Formula (I) comprises the sequence of SEQ ID NO: 51. In some embodiments an IL-2 conjugate of Formula (I) comprises the sequence of SEQ ID NO: 52. In some embodiments an IL-2 conjugate of Formula (I) comprises the sequence of SEQ ID NO: 53. In some embodiments an IL-2 conjugate of Formula (I) comprises the sequence of SEQ ID NO: 54. In some embodiments an IL-2 conjugate of Formula (I) comprises the sequence of SEQ ID NO: 55. In some embodiments an IL-2 conjugate of Formula (I) comprises the sequence of SEQ ID NO: 56. In some embodiments an IL-2 conjugate of Formula (I) comprises the sequence of SEQ ID NO: 57. In some embodiments an IL-2 conjugate of Formula (I) comprises the sequence of SEQ ID NO: 58. In some embodiments an IL-2 conjugate of Formula (I) comprises the sequence of SEQ ID NO: 59. In some embodiments an IL-2 conjugate of Formula (I) comprises the sequence of SEQ ID NO: 60. In some embodiments an IL-2 conjugate of Formula (I) comprises the sequence of SEQ ID NO: 61. In some embodiments an IL-2 conjugate of Formula (I) comprises the sequence of SEQ ID NO: 62. In some embodiments an IL-2 conjugate of Formula (I) comprises the sequence of SEQ ID NO: 63. In some embodiments an IL-2 conjugate of Formula (I) comprises the sequence of SEQ ID NO: 64. In some embodiments an IL-2 conjugate of Formula (I) comprises the sequence of SEQ ID NO: 65. In some embodiments an IL-2 conjugate of Formula (I) comprises the sequence of SEQ ID NO: 66. In some embodiments an IL-2 conjugate of Formula (I) comprises the sequence of SEQ ID NO: 67. In some embodiments an IL-2 conjugate of Formula (I) comprises the sequence of SEQ ID NO: 68. In some embodiments an IL-2 conjugate of Formula (I) comprises the sequence of SEQ ID NO: 69. In some embodiments an IL-2 conjugate of Formula (I) comprises the sequence of SEQ ID NO: 70. In some embodiments an IL-2 conjugate of Formula (I) comprises the sequence of SEQ ID NO: 71. In some embodiments an IL-2 conjugate of Formula (I) comprises the sequence of SEQ ID NO: 72. In some embodiments an IL-2 conjugate of Formula (I) comprises the sequence of SEQ ID NO: 73. In some embodiments an IL-2 conjugate of Formula (I) comprises the sequence of SEQ ID NO: 74. In some embodiments an IL-2 conjugate of Formula (I) comprises the sequence of SEQ ID NO: 75. In some embodiments an IL-2 conjugate of Formula (I) comprises the sequence of SEQ ID NO: 76. In some embodiments an IL-2 conjugate of Formula (I) comprises the sequence of SEQ ID NO: 77. In some embodiments an IL-2 conjugate of Formula (I) comprises the sequence of SEQ ID NO: 78. In some embodiments an IL-2 conjugate of Formula (I) comprises the sequence of SEQ ID NO: 79. In some embodiments an IL-2 conjugate of Formula (I) comprises the sequence of SEQ ID NO: 80. In some embodiments an IL-2 conjugate of Formula (I) comprises the sequence of SEQ ID NO: 81. In some embodiments an IL-2 conjugate of Formula (I) comprises the sequence of SEQ ID NO: 82. In some embodiments an IL-2 conjugate of Formula (I) comprises the sequence of SEQ ID NO: 83. In some embodiments an IL-2 conjugate of Formula (I) comprises the sequence of SEQ ID NO: 84.

Described herein are IL-2 conjugates having the structure of Formula (II):

Formula (II)

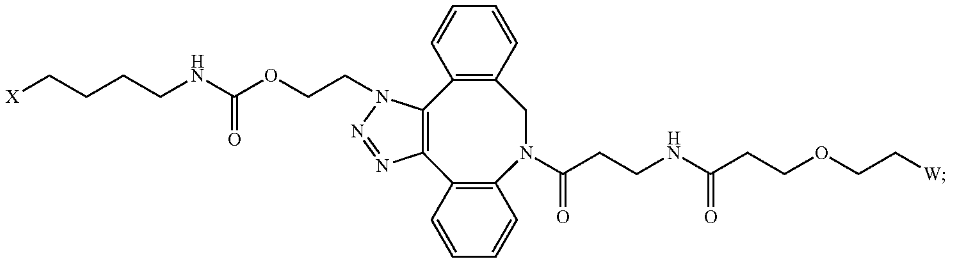

wherein W is a PEG group having an average molecular weight selected from 5 kDa, 10 kDa, and 30 kDa; and X is an amino acid position having the structure:

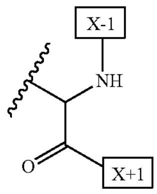

of a recombinant human IL-2 selected from F42, K43, E62, and P65, wherein the amino acid position corresponds to the positions in SEQ ID NO: 1.

Described herein are IL-2 conjugates having the structure of Formula (III):

Formula (III)

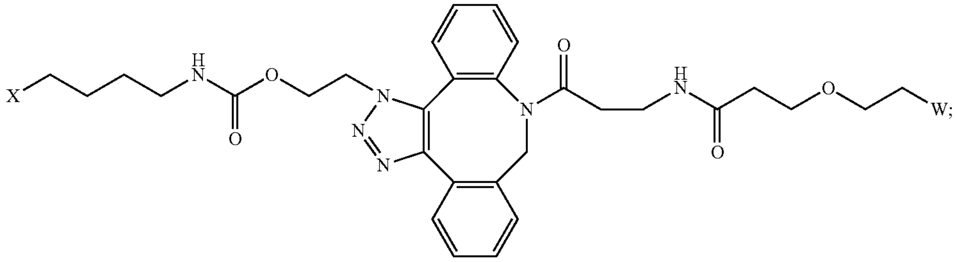

wherein W is a PEG group having an average molecular weight selected from 5 kDa, 10 kDa, and 30 kDa; and X is an amino acid position having the structure

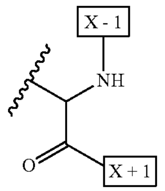 [SMILES: *C(NC)C(C)=O]

of a recombinant human IL-2 selected from F42, K43, E62, and P65, wherein the amino acid corresponds to the positions in SEQ ID NO: 1.

In some embodiments of an IL-2 conjugate of Formula (II) or Formula (III), X is the F42 position of a recombinant human IL-2. In some embodiments of an IL-2 conjugate of Formula (II) or Formula (III), the PEG group has an average molecular weight of 5 kDa and X is the F42 position of a recombinant human IL-2. In some embodiments of an IL-2 conjugate of Formula (II) or Formula (III), X is the K43 position of a recombinant human IL-2. In some embodiments of an IL-2 conjugate of Formula (II) or Formula (III), the PEG group has an average molecular weight of 5 kDa and X is the K43 position of a recombinant human IL-2. In some embodiments of an IL-2 conjugate of Formula (II) or Formula (III), X is the E62 position of a recombinant human IL-2. In some embodiments of an IL-2 conjugate of Formula (II) or Formula (III), the PEG group has an average molecular weight of 5 kDa and X is the E62 position of a recombinant human IL-2. In some embodiments of an IL-2 conjugate of Formula (II) or Formula (III), X is the P65 position of a recombinant human IL-2. In some embodiments of an IL-2 conjugate of Formula (II) or Formula (III), the PEG group has an average molecular weight of 5 kDa and X is the P65 position of a recombinant human IL-2. In some embodiments of an IL-2 conjugate of Formula (II) or Formula (III), X is the F42 position of a recombinant human IL-2 and W is a PEG group having an average molecular weight of 10 kDa. In some embodiments of an IL-2 conjugate of Formula (II) or Formula (III), X is the K43 position of a recombinant human IL-2 and W is a PEG group having an average molecular weight of 10 kDa. In some embodiments of an IL-2 conjugate of Formula (II) or Formula (III), X is the E62 position of a recombinant human IL-2 and W is a PEG group having an average molecular weight of 10 kDa. In some embodiments of an IL-2 conjugate of Formula (II) or Formula (III), the P65 position of a recombinant human IL-2 and W is a PEG group having an average molecular weight of 10 kDa. In some embodiments of an IL-2 conjugate of Formula (II) or Formula (III), the F42 position of a recombinant human IL-2 and W is a PEG group having an average molecular weight of 30 kDa. In some embodiments of an IL-2 conjugate of Formula (II) or Formula (III), the K43 position of a recombinant human IL-2 and W is a PEG group having an average molecular weight of 30 kDa. In some embodiments of an IL-2 conjugate of Formula (II) or Formula (III), the E62 position of a recombinant human IL-2 and W is a PEG group having an average molecular weight of 30 kDa. In some embodiments of an IL-2 conjugate of Formula (II) or Formula (III), the P65 position of a recombinant human IL-2 and W is a PEG group having an average molecular weight of 30 kDa. In some embodiments an IL-2 conjugate of Formula (II) or Formula (III) comprises the sequence of any one of SEQ NOs: 3-29 and 70-84. In some embodiments an IL-2 conjugate of Formula (II) or Formula (III) comprises the sequence of SEQ ID NO: 3. In some embodiments an IL-2 conjugate of Formula (II) or Formula (III) comprises the sequence of SEQ ID NO: 4. In some embodiments an IL-2 conjugate of Formula (II) or Formula (III) comprises the sequence of SEQ ID NO: 5. In some embodiments an IL-2 conjugate of Formula (II) or Formula (III) comprises the sequence of SEQ ID NO: 6. In some embodiments an IL-2 conjugate of Formula (II) or Formula (III) comprises the sequence of SEQ ID NO: 7. In some embodiments an IL-2 conjugate of Formula (II) or Formula (III) comprises the sequence of SEQ ID NO: 8. In some embodiments an IL-2 conjugate of Formula (II) or Formula (III) comprises the sequence of SEQ ID NO: 9. In some embodiments an IL-2 conjugate of Formula (II) or Formula (III) comprises the sequence of SEQ ID NO: 10. In some embodiments an IL-2 conjugate of Formula (II) or Formula (III) comprises the sequence of SEQ ID NO: 11. In some embodiments an IL-2 conjugate of Formula (II) or Formula (III) comprises the sequence of SEQ ID NO: 12. In some embodiments an IL-2 conjugate of Formula (II) or Formula (III) comprises the sequence of SEQ ID NO: 13. In some embodiments an IL-2 conjugate of Formula (II) or Formula (III) comprises the sequence of SEQ ID NO: 14. In some embodiments an IL-2 conjugate of Formula (II) or Formula (III) comprises the sequence of SEQ ID NO: 15. In some embodiments an IL-2 conjugate of Formula (II) or Formula (III) comprises the sequence of SEQ ID NO: 16. In some embodiments an IL-2 conjugate of Formula (II) or Formula (III) comprises the sequence of SEQ ID NO: 17. In some embodiments an IL-2 conjugate of Formula (II) or Formula (III) comprises the sequence of SEQ ID NO: 18. In some embodiments an IL-2 conjugate of Formula (II) or Formula (III) comprises the sequence of SEQ ID NO: 19. In some embodiments an IL-2 conjugate of Formula (II) or Formula (III) comprises the sequence of SEQ ID NO: 20. In some embodiments an IL-2 conjugate of Formula (II) or Formula (III) comprises the sequence of SEQ ID NO: 21. In some embodiments an IL-2 conjugate of Formula (II) or Formula (III) comprises the sequence of SEQ ID NO: 22. In some embodiments an IL-2 conjugate of Formula (II) or Formula (III) comprises the sequence of SEQ ID NO: 23. In some embodiments an IL-2 conjugate of Formula (II) or Formula (III) comprises the sequence of SEQ ID NO: 24. In some embodiments an IL-2 conjugate of Formula (II) or Formula (III) comprises the sequence of SEQ ID NO: 25. In some embodiments an IL-2 conjugate of Formula (II) or Formula (III) comprises the sequence of SEQ ID NO: 26. In some embodiments an IL-2 conjugate of Formula (II) or Formula (III) comprises the sequence of SEQ ID NO: 27. In some embodiments an IL-2 conjugate of Formula (II) or Formula (III) comprises the sequence of SEQ ID NO: 28. In some embodiments an IL-2 conjugate of Formula (II) or Formula (III) comprises the sequence of SEQ ID NO: 29. In some embodiments an IL-2 conjugate of Formula (II) or Formula (III) comprises the sequence of SEQ ID NO: 70. In some embodiments an IL-2 conjugate of Formula (II) or Formula (III) comprises the sequence of SEQ ID NO: 71. In some embodiments an IL-2 conjugate of Formula (II) or Formula (III) comprises the sequence of SEQ ID NO: 72. In some embodiments an IL-2 conjugate of Formula (II) or Formula (III) comprises the sequence of SEQ ID NO: 73. In some embodiments an IL-2 conjugate of Formula (II) or Formula (III) comprises the sequence of SEQ ID NO: 74. In some embodiments an IL-2 conjugate of Formula (II) or Formula (III) comprises the sequence of SEQ ID NO: 75. In some embodiments an IL-2 conjugate of Formula (II) or Formula (III) comprises the sequence of SEQ ID NO: 76. In some embodiments an IL-2 conjugate of Formula (II) or Formula (III) comprises the sequence of SEQ ID NO: 77. In some embodiments an IL-2 conjugate of Formula (II) or Formula (III) comprises the sequence of SEQ ID NO: 78. In some embodiments an IL-2 conjugate of Formula (II) or Formula (III) comprises the sequence of SEQ ID NO: 79. In some embodiments an IL-2 conjugate of Formula (II) or Formula (III) comprises the sequence of SEQ ID NO: 80. In some embodiments an IL-2 conjugate of Formula (II) or Formula (III) comprises the sequence of SEQ ID NO: 81. In some embodiments an IL-2 conjugate of Formula (II) or Formula (III) comprises the sequence of SEQ ID NO: 82. In some embodiments an IL-2 conjugate of Formula (II) or Formula (III) comprises the sequence of SEQ ID NO: 83. In some embodiments an IL-2 conjugate of Formula (II) or Formula (III) comprises the sequence of SEQ ID NO: 84.

Described herein are pharmaceutical compositions of Formula (I), Formula (II), or Formula (III). In some embodiments, a pharmaceutical compositions of Formula (I), Formula (II), or Formula (III) comprises a sequence comprising any one of SEQ ID NOS: 3-29 and 70-84. In some embodiments, a pharmaceutical compositions of Formula (I), Formula (II), or Formula (III) comprises a sequence comprising SEQ ID NO: 3. In some embodiments, a pharmaceutical compositions of Formula (I), Formula (II), or Formula (III) comprises a sequence comprising SEQ ID NO: 4.

Described herein are IL-2 conjugates having the structure of Formula (IV):

Formula (IV)

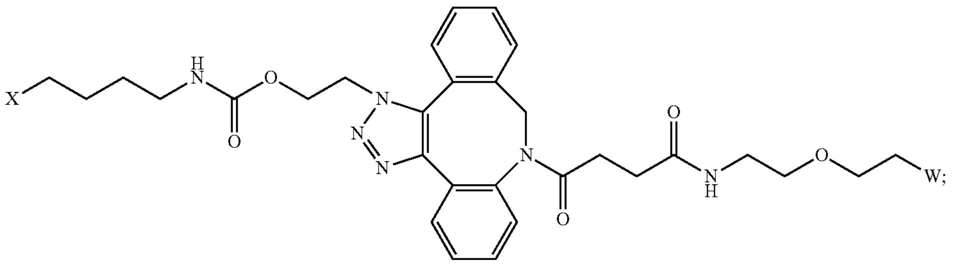

wherein W is a PEG group having an average molecular weight selected from 5 kDa, 10 kDa, and 30 kDa; and X is an amino acid position having the structure:

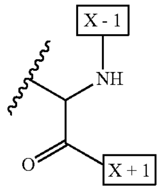 [SMILES: *C(NC)C(C)=O]

of a recombinant human IL-2 selected from F42, K43, E62, and P65, wherein the amino acid position corresponds to the positions in SEQ ID NO: 1.

Described herein are IL-2 conjugates having the structure of Formula (V):

Formula (V)

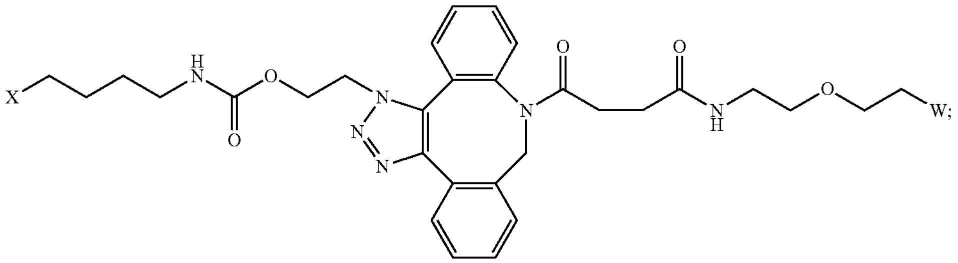

wherein W is a PEG group having an average molecular weight selected from 5 kDa, 10 kDa, and 30 kDa; and X is an amino acid position having the structure

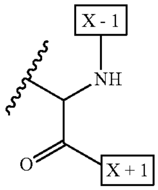 [SMILES: *C(NC)C(C)=O]

of a recombinant human IL-2 selected from F42, K43, E62, and P65, wherein the amino acid corresponds to the positions in SEQ ID NO: 1.

In some embodiments of an IL-2 conjugate of Formula (IV) or Formula (V), X is the F42 position of a recombinant human IL-2. In some embodiments of an IL-2 conjugate of Formula (IV) or Formula (V), the PEG group has an average molecular weight of 5 kDa and X is the F42 position of a recombinant human IL-2. In some embodiments of an IL-2 conjugate of Formula (IV) or Formula (V), X is the K43 position of a recombinant human IL-2. In some embodiments of an IL-2 conjugate of Formula (IV) or Formula (V), the PEG group has an average molecular weight of 5 kDa and X is the K43 position of a recombinant human IL-2. In some embodiments of an IL-2 conjugate of Formula (IV) or Formula (V), X is the E62 position of a recombinant human IL-2. In some embodiments of an IL-2 conjugate of Formula (IV) or Formula (V), the PEG group has an average molecular weight of 5 kDa and X is the E62 position of a recombinant human IL-2. In some embodiments of an IL-2 conjugate of Formula (IV) or Formula (V), X is the P65 position of a recombinant human IL-2. In some embodiments of an IL-2 conjugate of Formula (IV) or Formula (V), the PEG group has an average molecular weight of 5 kDa and X is the P65 position of a recombinant human IL-2. In some embodiments of an IL-2 conjugate of Formula (IV) or Formula (V), X is the F42 position of a recombinant human IL-2 and W is a PEG group having an average molecular weight of 10 kDa. In some embodiments of an IL-2 conjugate of Formula (IV) or Formula (V), X is the K43 position of a recombinant human IL-2 and W is a PEG group having an average molecular weight of 10 kDa. In some embodiments of an IL-2 conjugate of Formula (IV) or Formula (V), X is the E62 position of a recombinant human IL-2 and W is a PEG group having an average molecular weight of 10 kDa. In some embodiments of an IL-2 conjugate of Formula (IV) or Formula (V), the P65 position of a recombinant human IL-2 and W is a PEG group having an average molecular weight of 10 kDa. In some embodiments of an IL-2 conjugate of Formula (IV) or Formula (V), the F42 position of a recombinant human IL-2 and W is a PEG group having an average molecular weight of 30 kDa. In some embodiments of an IL-2 conjugate of Formula (IV) or Formula (V), the K43 position of a recombinant human IL-2 and W is a PEG group having an average molecular weight of 30 kDa. In some embodiments of an IL-2 conjugate of Formula (IV) or Formula (V), the E62 position of a recombinant human IL-2 and W is a PEG group having an average molecular weight of 30 kDa. In some embodiments of an IL-2 conjugate of Formula (IV) or Formula (V), the P65 position of a recombinant human IL-2 and W is a PEG group having an average molecular weight of 30 kDa. In some embodiments an IL-2 conjugate of Formula (IV) or Formula (V) comprises the sequence of any one of SEQ NOs: 3, 4, 40-69. In some embodiments an IL-2 conjugate of Formula (IV) or Formula (V) comprises the sequence of SEQ ID NO: 3. In some embodiments an IL-2 conjugate of Formula (IV) or Formula (V) comprises the sequence of SEQ ID NO: 4. In some embodiments an IL-2 conjugate of Formula (IV) or Formula (V) comprises the sequence of SEQ ID NO: 40. In some embodiments an IL-2 conjugate of Formula (IV) or Formula (V) comprises the sequence of SEQ ID NO: 41. In some embodiments an IL-2 conjugate of Formula (IV) or Formula (V) comprises the sequence of SEQ ID NO: 42. In some embodiments an IL-2 conjugate of Formula (IV) or Formula (V) comprises the sequence of SEQ ID NO: 43. In some embodiments an IL-2 conjugate of Formula (IV) or Formula (V) comprises the sequence of SEQ ID NO: 44. In some embodiments an IL-2 conjugate of Formula (IV) or Formula (V) comprises the sequence of SEQ ID NO: 45. In some embodiments an IL-2 conjugate of Formula (IV) or Formula (V) comprises the sequence of SEQ ID NO: 46. In some embodiments an IL-2 conjugate of Formula (IV) or Formula (V) comprises the sequence of SEQ ID NO: 47. In some embodiments an IL-2 conjugate of Formula (IV) or Formula (V) comprises the sequence of SEQ ID NO: 48. In some embodiments an IL-2 conjugate of Formula (IV) or Formula (V) comprises the sequence of SEQ ID NO: 49. In some embodiments an IL-2 conjugate of Formula (IV) or Formula (V) comprises the sequence of SEQ ID NO: 50. In some embodiments an IL-2 conjugate of Formula (IV) or Formula (V) comprises the sequence of SEQ ID NO: 51. In some embodiments an IL-2 conjugate of Formula (IV) or Formula (V) comprises the sequence of SEQ ID NO: 52. In some embodiments an IL-2 conjugate of Formula (IV) or Formula (V) comprises the sequence of SEQ ID NO: 53. In some embodiments an IL-2 conjugate of Formula (IV) or Formula (V) comprises the sequence of SEQ ID NO: 54. In some embodiments an IL-2 conjugate of Formula (IV) or Formula (V) comprises the sequence of SEQ ID NO: 55. In some embodiments an IL-2 conjugate of Formula (IV) or Formula (V) comprises the sequence of SEQ ID NO: 56. In some embodiments an IL-2 conjugate of Formula (IV) or Formula (V) comprises the sequence of SEQ ID NO: 57. In some embodiments an IL-2 conjugate of Formula (IV) or Formula (V) comprises the sequence of SEQ ID NO: 58. In some embodiments an IL-2 conjugate of Formula (IV) or Formula (V) comprises the sequence of SEQ ID NO: 59. In some embodiments an IL-2 conjugate of Formula (IV) or Formula (V) comprises the sequence of SEQ ID NO: 60. In some embodiments an IL-2 conjugate of Formula (IV) or Formula (V) comprises the sequence of SEQ ID NO: 61. In some embodiments an IL-2 conjugate of Formula (IV) or Formula (V) comprises the sequence of SEQ ID NO: 62. In some embodiments an IL-2 conjugate of Formula (IV) or Formula (V) comprises the sequence of SEQ ID NO: 63. In some embodiments an IL-2 conjugate of Formula (IV) or Formula (V) comprises the sequence of SEQ ID NO: 64. In some embodiments an IL-2 conjugate of Formula (IV) or Formula (V) comprises the sequence of SEQ ID NO: 65. In some embodiments an IL-2 conjugate of Formula (IV) or Formula (V) comprises the sequence of SEQ ID NO: 66. In some embodiments an IL-2 conjugate of Formula (IV) or Formula (V) comprises the sequence of SEQ ID NO: 67. In some embodiments an IL-2 conjugate of Formula (IV) or Formula (V) comprises the sequence of SEQ ID NO: 68. In some embodiments an IL-2 conjugate of Formula (IV) or Formula (V) comprises the sequence of SEQ ID NO: 69.

Described herein are pharmaceutical compositions of Formula (I), Formula (IV), or Formula (V). In some embodiments, a pharmaceutical compositions of Formula (I), Formula (IV), or Formula (V) comprises a sequence comprising any one of SEQ ID NOS: 3, 4, and 40-69. In some embodiments, a pharmaceutical compositions of Formula (I), Formula (IV), or Formula (V) comprises a sequence comprising SEQ ID NO: 3.

In some embodiments described herein, a conjugation reaction described herein comprises an inverse-electron demand cycloaddition reaction comprising a diene and a dienophile. In some embodiments, the diene comprises a tetrazine. In some embodiments, the dienophile comprises an alkene. In some embodiments, the dienophile comprises an alkyne. In some embodiments, the alkyne is a strained alkyne. In some embodiments, the alkene is a strained diene. In some embodiments, the alkyne is a trans-cyclooctyne. In some embodiments, the alkyne is a cyclooctene. In some embodiments, the alkene is a cyclopropene. In some embodiments, the alkene is a fluorocyclopropene. In some embodiments, a conjugation reaction described herein results in the formation of a cytokine peptide attached to a linker or conjugation moiety via a 6-membered ring heterocycle comprising two nitrogen atoms in the ring.

In some embodiments described herein, a conjugation reaction described herein comprises an olefin metathesis reaction. In some embodiments, a conjugation reaction described herein comprises reaction of an alkene and an alkyne with a ruthenium catalyst. In some embodiments, a conjugation reaction described herein comprises reaction of two alkenes with a ruthenium catalyst. In some embodiments, a conjugation reaction described herein comprises reaction of two alkynes with a ruthenium catalyst. In some embodiments, a conjugation reaction described herein comprises reaction of an alkene or alkyne with a ruthenium catalyst and an amino acid comprising an allyl group. In some embodiments, a conjugation reaction described herein comprises reaction of an alkene or alkyne with a ruthenium catalyst and an amino acid comprising an allyl sulfide or selenide. In some embodiments, a ruthenium catalyst is Hoveda-Grubbs $2^{nd}$ generation catalyst. In some embodiments, an olefin metathesis reaction comprises reaction of one or more strained alkenes or alkynes.

In some embodiments described herein, a conjugation reaction described herein comprises a cross-coupling reaction. In some embodiments, cross-coupling reactions comprise transition metal catalysts, such as iridium, gold, ruthenium, rhodium, palladium, nickel, platinum, or other transition metal catalyst and one or more ligands. In some embodiments, transition metal catalysts are water-soluble. In some embodiments described herein, a conjugation reaction described herein comprises a Suzuki-Miyaura cross-coupling reaction. In some embodiments described herein, a conjugation reaction described herein comprises reaction of an aryl halide (or triflate, or tosylate), an aryl or alkenyl boronic acid, and a palladium catalyst. In some embodiments described herein, a conjugation reaction described herein comprises a Sonogashira cross-coupling reaction. In some embodiments described herein, a conjugation reaction described herein comprises reaction of an aryl halide (or triflate, or tosylate), an alkyne, and a palladium catalyst. In some embodiments, cross-coupling reactions result in attachment of a linker or conjugating moiety to a cytokine peptide via a carbon-carbon bond.

In some embodiments described herein, a conjugation reaction described herein comprises a deprotection or "uncaging" reaction of a reactive group prior to conjugation. In some embodiments, a conjugation reaction described herein comprises uncaging of a reactive group with light, followed by a conjugation reaction. In some embodiments, a reactive group is protected with an aralkyl moiety comprising one or more nitro groups. In some embodiments, uncaging of a reactive group results in a free amine, sulfide, or other reactive group. In some embodiments, a conjugation reaction described herein comprises uncaging of a reactive group with a transition metal catalyst, followed by a conjugation reaction. In some embodiments, the transition metal catalyst comprises palladium and one or more ligands. In some embodiments, a reactive group is protected with an allyl moiety. In some embodiments, a reactive group is protected with an allylic carbamate. In some embodiments, a reactive group is protected with a propargylic moiety. In some embodiments, a reactive group is protected with a propargyl carbamate. In some embodiments, a reactive group is protected with a dienophile, wherein exposure to a diene (such as a tetrazine) results in deprotection of the reactive group.

In some embodiments described herein, a conjugation reaction described herein comprises a ligand-directed reaction, wherein a ligand (optionally) attached to a reactive group) facilitates the site of conjugation between the reactive group and the cytokine peptide. In some embodiments, the ligand is cleaved during or after reaction of the cytokine peptide with the reactive group. In some embodiments, the conjugation site of the cytokine peptide is a natural amino acid. In some embodiments, the conjugation site of the cytokine peptide is a lysine, cysteine, or serine. In some embodiments, the conjugation site of the cytokine peptide is an unnatural amino acid described herein. In some embodiments the reactive group comprises a leaving group, such as an electron-poor aryl or heteroaryl group. In some embodiments the reactive group comprises a leaving group, such as an electron-poor alkyl group that is displaced by the cytokine peptide. In some embodiments, a conjugation reaction described herein comprises reaction of a radical trapping agent with a radical species. In some embodiments, a conjugation reaction described herein comprises an oxidative radical addition reaction. In some embodiments, a radical trapping agent is an arylamine. In some embodiments, a radical species is a tyrosyl radical. In some embodiments, radical species are generated by a ruthenium catalyst (such as $[Ru(bpy)_3]$) and light.

Enzymatic reactions are optionally used for conjugation reactions described herein. Exemplary enzymatic conjugations include SortA-mediated conjugation, a TGs-mediated conjugation, or an FGE-mediated conjugation. In some embodiments, a conjugation reaction described herein comprises native protein ligation (NPL) of a terminal 1-amino-2-thio group with a thioester to form an amide bond.

Various conjugation reactions are described herein for reacting a linker or conjugating moiety with a cytokine peptide, wherein the reaction occurs with a natural ("canonical") amino acid in the cytokine peptide. In some embodiments, the natural amino acid is found at a conjugation position is found in a wild type sequence, or alternatively the position has been mutated. In some embodiments, a conjugation reaction comprises formation of a disulfide bond at a cysteine residue. In some embodiments, a conjugation reaction comprises a 1,4 Michael addition reaction of a cysteine or lysine. In some embodiments, a conjugation reaction comprises a cyanobenzothiazole ligation of a cysteine. In some embodiments, a conjugation reaction comprises crosslinking with an acetone moiety, such as 1,3-dichloro-2-propionone. In some embodiments, a conjugation reaction comprises a 1,4 Michael addition to a dehydroalanine, formed by reaction of cysteine with O-mesitylenesulfonylhydroxylamine. In some embodiments a conjugation reaction comprises reaction of a tyrosine with a triazolinedione (TAD), or TAD derivative. In some embodiments a conjugation reaction comprises reaction of a tryptophan with a rhodium carbenoid.

Methods of Use

Proliferative Diseases or Conditions

In some embodiments, described herein is a method of treating a proliferative disease or condition in a subject in need thereof, which comprises administering to the subject a therapeutically effective amount of a cytokine conjugate (e.g., an IL-2 conjugate) described herein. In some instances, the cytokine conjugate comprising SEQ ID NOS: 5-84. In some embodiments, the IL-2 conjugate comprises SEQ ID NOs.: 15-29. In some embodiments, the IL-2 conjugate comprises SEQ ID NOs.: 40-54. In some embodiments, the IL-2 conjugate comprises SEQ ID NOs.: 55-69. In some embodiments, the IL-2 conjugate comprises SEQ ID NOs.: 70-84. In some instances, the IL-2 conjugate comprises an isolated and purified IL-2 polypeptide and a conjugating moiety, wherein the IL-2 conjugate has a decreased affinity to an IL-2 receptor α (IL-2Rα) subunit relative to a wild-type IL-2 polypeptide. In some instances, the IL-2 conjugate comprises an isolated and purified IL-2 polypeptide; and a conjugating moiety that binds to the isolated and purified IL-2 polypeptide at an amino acid position selected from K35, T37, R38, T41, F42, K43, F44, Y45, E60, E61, E62, K64, P65, E68, V69, N71, L72, M104, C105, and Y107, wherein the numbering of the amino acid residues corresponds to SEQ ID NO: 1. In some cases, the IL-2 conjugate preferentially interact with the IL-2Rβ and IL-2Rβγ subunits to form a IL-2/IL-2Rβγ complex. In some cases, the IL-2/IL-2Rβγ complex stimulates and/or enhances expansion of CD4+ helper cells, CD8+ effector naïve and memory T cells, NK cells, and/or NKT cells. In additional cases, the expansion of Teff cells skews the Teff:Treg ratio toward the Teff population. In some embodiments, the IL-2 conjugate comprising a mutation at residue F42, wherein the residue corresponds to positions 42 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG correspondence with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal affect, on the receptor signaling potency of the modified IL-2 polypeptide to the IL-2βγ or IL-2αβγ signaling complexes. In some embodiments, the molecular weight of the PEG does not affect, or has minimal affect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα.

In some embodiments, described herein is a method of treating a proliferative disease or condition in a subject in need thereof, which comprises administering to the subject a therapeutically effective amount of a cytokine conjugate (e.g., an IL-2 conjugate) described Table 20. In some embodiments, the IL-2 conjugate comprises SEQ ID NOs.: 1-84. In some embodiments, the IL-2 conjugate comprises SEQ ID NOs.: 15-29. In some embodiments, the IL-2 conjugate comprises SEQ ID NOs.: 40-54. In some embodiments, the IL-2 conjugate comprises SEQ ID NOs.: 55-69. In some embodiments, the IL-2 conjugate comprises SEQ ID NOs.: 70-84. In some embodiments, the IL-2 conjugate comprises a structure of Formula (I). In some embodiments, the IL-2 conjugate comprises a structure of Formula (II). In some embodiments, the IL-2 conjugate comprises a structure of Formula (III). In some embodiments, the IL-2 conjugate comprises a structure of Formula (IV). In some embodiments, the IL-2 conjugate comprises a structure of Formula (V). In some embodiments, the IL-2 conjugate comprises SEQ ID NO: 1. In some embodiments, the IL-2 conjugate comprises SEQ ID NO: 2. In some embodiments, the IL-2 conjugate comprises SEQ ID NO: 3. In some embodiments, the IL-2 conjugate comprises SEQ ID NO: 4. In some embodiments, the IL-2 conjugate comprises SEQ ID NO: 5. In some embodiments, the IL-2 conjugate comprises SEQ ID NO: 6. In some embodiments, the IL-2 conjugate comprises SEQ ID NO: 7. In some embodiments, the IL-2 conjugate comprises SEQ ID NO: 8. In some embodiments, the IL-2 conjugate comprises SEQ ID NO: 9. In some embodiments, the IL-2 conjugate comprises SEQ ID NO: 10. In some embodiments, the IL-2 conjugate comprises SEQ ID NO: 11. In some embodiments, the IL-2 conjugate comprises SEQ ID NO: 12. In some embodiments, the IL-2 conjugate comprises SEQ ID NO: 13. In some embodiments, the IL-2 conjugate comprises SEQ ID NO: 14. In some embodiments, the IL-2 conjugate comprises SEQ ID NO: 15. In some embodiments, the IL-2 conjugate comprises SEQ ID NO: 16. In some embodiments, the IL-2 conjugate comprises SEQ ID NO: 17. In some embodiments, the IL-2 conjugate comprises SEQ ID NO: 18. In some embodiments, the IL-2 conjugate comprises SEQ ID NO: 19. In some embodiments, the IL-2 conjugate comprises SEQ ID NO: 20. In some embodiments, the IL-2 conjugate comprises SEQ ID NO: 21. In some embodiments, the IL-2 conjugate comprises SEQ ID NO: 22. In some embodiments, the IL-2 conjugate comprises SEQ ID NO: 23. In some embodiments, the IL-2 conjugate comprises SEQ ID NO: 24. In some embodiments, the IL-2 conjugate comprises SEQ ID NO: 25. In some embodiments, the IL-2 conjugate comprises SEQ ID NO: 26. In some embodiments, the IL-2 conjugate comprises SEQ ID NO: 27. In some embodiments, the IL-2 conjugate comprises SEQ ID NO: 28. In some embodiments, the IL-2 conjugate comprises SEQ ID NO: 24. In some embodiments, the IL-2 conjugate comprises SEQ ID NO: 25. In some embodiments, the IL-2 conjugate comprises SEQ ID NO: 26. In some embodiments, the IL-2 conjugate comprises SEQ ID NO: 27. In some embodiments, the IL-2 conjugate comprises SEQ ID NO: 28. In some embodiments, the IL-2 conjugate comprises SEQ ID NO: 29. In some embodiments, the IL-2 conjugate comprises SEQ ID NO: 30. In some embodiments, the IL-2 conjugate comprises SEQ ID NO: 31. In some embodiments, the IL-2 conjugate comprises SEQ ID NO: 32. In some embodiments, the IL-2 conjugate comprises SEQ ID NO: 33. In some embodiments, the IL-2 conjugate comprises SEQ ID NO: 34. In some embodiments, the IL-2 conjugate comprises SEQ ID NO: 35. In some embodiments, the IL-2 conjugate comprises SEQ ID NO: 36. In some embodiments, the IL-2 conjugate comprises SEQ ID NO: 37. In some embodiments, the IL-2 conjugate comprises SEQ ID NO: 38. In some embodiments, the IL-2 conjugate comprises SEQ ID NO: 39. In some embodiments, the IL-2 conjugate comprises SEQ ID NO: 40. In some embodiments, the IL-2 conjugate comprises SEQ ID NO: 41. In some embodiments, the IL-2 conjugate comprises SEQ ID NO: 42. In some embodiments, the IL-2 conjugate comprises SEQ ID NO: 43. In some embodiments, the IL-2 conjugate comprises SEQ ID NO: 44. In some embodiments, the IL-2 conjugate comprises SEQ ID NO: 45. In some embodiments, the IL-2 conjugate comprises SEQ ID NO: 46. In some embodiments, the IL-2 conjugate comprises SEQ ID NO: 47. In some embodiments, the IL-2 conjugate comprises SEQ ID NO: 48. In some embodiments, the IL-2 conjugate comprises SEQ ID NO: 49. In some embodiments, the IL-2 conjugate comprises SEQ ID NO: 50. In some embodiments, the IL-2 conjugate comprises SEQ ID NO: 51. In some embodiments, the IL-2 conjugate comprises SEQ ID NO: 52. In some embodiments, the IL-2 conjugate comprises SEQ ID NO: 53. In some embodiments, the IL-2 conjugate comprises SEQ ID NO: 54. In some embodiments, the IL-2 conjugate comprises SEQ ID NO: 55. In some embodiments, the IL-2 conjugate comprises SEQ ID NO: 56. In some embodiments, the IL-2 conjugate comprises SEQ ID NO: 57. In some embodiments, the IL-2 conjugate comprises SEQ ID NO: 58. In some embodiments, the IL-2 conjugate comprises SEQ ID NO: 59. In some embodiments, the IL-2 conjugate comprises SEQ ID NO: 60. In some embodiments, the IL-2 conjugate comprises SEQ ID NO: 61. In some embodiments, the IL-2 conjugate comprises SEQ ID NO: 62. In some embodiments, the IL-2 conjugate comprises SEQ ID NO: 63. In some embodiments, the IL-2 conjugate comprises SEQ ID NO: 64. In some embodiments, the IL-2 conjugate comprises SEQ ID NO: 65. In some embodiments, the IL-2 conjugate comprises SEQ ID NO: 66. In some embodiments, the IL-2 conjugate comprises SEQ ID NO: 67. In some embodiments, the IL-2 conjugate comprises SEQ ID NO: 68. In some embodiments, the IL-2 conjugate comprises SEQ ID NO: 69. In some embodiments, the IL-2 conjugate comprises SEQ ID NO: 70. In some embodiments, the IL-2 conjugate comprises SEQ ID NO: 71. In some embodiments, the IL-2 conjugate comprises SEQ ID NO: 72. In some embodiments, the IL-2 conjugate comprises SEQ ID NO: 73. In some embodiments, the IL-2 conjugate comprises SEQ ID NO: 74. In some embodiments, the IL-2 conjugate comprises SEQ ID NO: 75. In some embodiments, the IL-2 conjugate comprises SEQ ID NO: 76. In some embodiments, the IL-2 conjugate comprises SEQ ID NO: 77. In some embodiments, the IL-2 conjugate comprises SEQ ID NO: 78. In some embodiments, the IL-2 conjugate comprises SEQ ID NO: 79. In some embodiments, the IL-2 conjugate comprises SEQ ID NO: 80. In some embodiments, the IL-2 conjugate comprises SEQ ID NO: 81. In some embodiments, the IL-2 conjugate comprises SEQ ID NO: 82. In some embodiments, the IL-2 conjugate comprises SEQ ID NO: 83. In some embodiments, the IL-2 conjugate comprises SEQ ID NO: 84.

In some embodiments, the proliferative disease or condition is a cancer. In some cases, the cancer is a solid tumor. Exemplary solid tumors include, but are not limited to, bladder cancer, bone cancer, brain cancer, breast cancer, colorectal cancer, esophageal cancer, eye cancer, head and neck cancer, kidney cancer, lung cancer, melanoma, ovarian cancer, pancreatic cancer, or prostate cancer. In some cases, the solid tumor is a metastatic cancer. In some cases, the solid tumor is a relapsed or refractory cancer. In some cases, the solid tumor is castrate-resistant prostate cancer, metastatic castrate-resistant prostate cancer, or metastatic castrate-resistant prostate cancer having DNA damage response (DDR) defects.

In some instances, a cytokine (e.g., interleukin, IFN, or TNF) conjugate described herein is administered to a subject in need thereof, for treating a solid tumor. In such cases, the subject has bladder cancer, bone cancer, brain cancer, breast cancer, colorectal cancer, esophageal cancer, eye cancer, head and neck cancer, kidney cancer, lung cancer, melanoma, ovarian cancer, pancreatic cancer, or prostate cancer. In some cases, the solid tumor is a metastatic cancer. In some cases, the solid tumor is a relapsed or refractory cancer. In some cases, the solid tumor is castrate-resistant prostate cancer, metastatic castrate-resistant prostate cancer, or metastatic castrate-resistant prostate cancer having DNA damage response (DDR) defects.

In some instances, an IL-2 conjugate described herein is administered to a subject in need thereof, for treating a solid tumor. In such cases, the subject has a bladder cancer, a bone cancer, a brain cancer, a breast cancer, a colorectal cancer, an esophageal cancer, an eye cancer, a head and neck cancer, a kidney cancer, a lung cancer, a melanoma, an ovarian cancer, a pancreatic cancer, or a prostate cancer. In some cases, the IL-2 conjugate is administered to a subject for the treatment of a bladder cancer. In some cases, the IL-2 conjugate is administered to a subject for the treatment of a breast cancer. In some cases, the IL-2 conjugate is administered to a subject for the treatment of a colorectal cancer. In some cases, the IL-2 conjugate is administered to a subject for the treatment of an esophageal cancer. In some cases, the IL-2 conjugate is administered to a subject for the treatment of a head and neck cancer. In some cases, the IL-2 conjugate is administered to a subject for the treatment of a kidney cancer. In some cases, the IL-2 conjugate is administered to a subject for the treatment of a lung cancer. In some cases, the IL-2 conjugate is administered to a subject for the treatment of a melanoma. In some cases, the IL-2 conjugate is administered to a subject for the treatment of an ovarian cancer. In some cases, the IL-2 conjugate is administered to a subject for the treatment of a pancreatic cancer. In some cases, the IL-2 conjugate is administered to a subject for the treatment of a prostate cancer. In some cases, the IL-2 conjugate is administered to a subject for the treatment of castrate-resistant prostate cancer, metastatic castrate-resistant prostate cancer, or metastatic castrate-resistant prostate cancer having DNA damage response (DDR) defects.

In some embodiments, the IL-2 conjugate is administered to a subject for the treatment of a metastatic cancer. In some instances, the metastatic cancer comprises a metastatic bladder cancer, metastatic bone cancer, metastatic brain cancer, metastatic breast cancer, metastatic colorectal cancer, metastatic esophageal cancer, metastatic eye cancer, metastatic head and neck cancer, metastatic kidney cancer, metastatic lung cancer, metastatic melanoma, metastatic ovarian cancer, metastatic pancreatic cancer, or metastatic prostate cancer. In some cases, the IL-2 conjugate is administered to a subject for the treatment of metastatic bladder cancer, metastatic bone cancer, metastatic brain cancer, metastatic breast cancer, metastatic colorectal cancer, metastatic esophageal cancer, metastatic eye cancer, metastatic head and neck cancer, metastatic kidney cancer, metastatic lung cancer, metastatic melanoma, metastatic ovarian cancer, metastatic pancreatic cancer, or metastatic prostate cancer. In some cases, the IL-2 conjugate is administered to a subject for the treatment of castrate-resistant prostate cancer, metastatic castrate-resistant prostate cancer, or metastatic castrate-resistant prostate cancer having DNA damage response (DDR) defects.

In some instances, the IL-2 conjugate is administered to a subject for the treatment of a relapsed or refractory cancer. In some instances, the relapsed or refractory cancer comprises a relapsed or refractory bladder cancer, relapsed or refractory bone cancer, relapsed or refractory brain cancer, relapsed or refractory breast cancer, relapsed or refractory colorectal cancer, relapsed or refractory esophageal cancer, relapsed or refractory eye cancer, relapsed or refractory head and neck cancer, relapsed or refractory kidney cancer, relapsed or refractory lung cancer, relapsed or refractory melanoma, relapsed or refractory ovarian cancer, relapsed or refractory pancreatic cancer, or relapsed or refractory prostate cancer. In some cases, the IL-2 conjugate is administered to a subject for the treatment of a relapsed or refractory bladder cancer, relapsed or refractory bone cancer, relapsed or refractory brain cancer, relapsed or refractory breast cancer, relapsed or refractory colorectal cancer, relapsed or refractory esophageal cancer, relapsed or refractory eye cancer, relapsed or refractory head and neck cancer, relapsed or refractory kidney cancer, relapsed or refractory lung cancer, relapsed or refractory melanoma, relapsed or refractory ovarian cancer, relapsed or refractory pancreatic cancer, or relapsed or refractory prostate cancer.

In some embodiments, the cancer is a treatment-naïve cancer. In such cases, the treatment-naïve cancer is a cancer that has not been treated by a therapy. In some cases, the treatment-naive cancer is a solid tumor, such as bladder cancer, a bone cancer, a brain cancer, a breast cancer, a colorectal cancer, an esophageal cancer, an eye cancer, a head and neck cancer, a kidney cancer, a lung cancer, a melanoma, an ovarian cancer, a pancreatic cancer, or a prostate cancer. In some embodiments, described herein is a method of treating a treatment-naive solid tumor in a subject in need thereof which comprises administering to the subject a cytokine conjugate (e.g., an IL-2 conjugate) described herein.

In some embodiments, the cancer is a hematologic malignancy. In some instances, the hematologic malignancy comprises a leukemia, a lymphoma, or a myeloma. In some cases, the hematologic malignancy is a T-cell malignancy. In other cases, the hematological malignancy is a B-cell malignancy. Exemplary hematologic malignancies include, but are not limited to, chronic lymphocytic leukemia (CLL), small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some cases, the hematologic malignancy is a metastatic cancer. In some cases, the metastatic cancer is a metastatic T-cell malignancy or a metastatic B-cell malignancy.

In some cases, the hematologic malignancy is a relapsed or refractory cancer. In some cases, the relapsed or refractory cancer is a relapsed or refractory T-cell malignancy or a relapsed or refractory B-cell malignancy.

In some instances, a cytokine (e.g., interleukin, IFN, or TNF) described herein is administered to a subject in need thereof, for treating a hematologic malignancy. In some cases, the subject has a T-cell malignancy. In some cases, the subject has a B-cell malignancy. In some cases, the subject has chronic lymphocytic leukemia (CLL), small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some instances, an IL-2 conjugate described herein is administered to a subject in need thereof, for treating a hematologic malignancy. In some cases, the subject has a T-cell malignancy. In some cases, the subject has a B-cell malignancy. In some cases, the subject has chronic lymphocytic leukemia (CLL), small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some cases, the IL-2 conjugate is administered to a subject for the treatment of CLL. In some cases, the IL-2 conjugate is administered to a subject for the treatment of SLL. In some cases, the IL-2 conjugate is administered to a subject for the treatment of FL. In some cases, the IL-2 conjugate is administered to a subject for the treatment of DLBCL. In some cases, the IL-2 conjugate is administered to a subject for the treatment of MCL. In some cases, the IL-2 conjugate is administered to a subject for the treatment of Waldenstrom's macroglobulinemia. In some cases, the IL-2 conjugate is administered to a subject for the treatment of multiple myeloma. In some cases, the IL-2 conjugate is administered to a subject for the treatment of Burkitt's lymphoma.

In some cases, the IL-2 conjugate is administered to a subject for the treatment of a metastatic hematologic malignancy. In some cases, the IL-2 conjugate is administered to a subject for the treatment of a metastatic T-cell malignancy. In some cases, the IL-2 conjugate is administered to a subject for the treatment of a metastatic B-cell malignancy. In some cases, the IL-2 conjugate is administered to a subject for the treatment of a metastatic chronic lymphocytic leukemia (CLL), small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or metastatic lymphomatoid granulomatosis.

In some cases, the IL-2 conjugate is administered to a subject for the treatment of a relapsed or refractory hematologic malignancy. In some cases, the IL-2 conjugate is administered to a subject for the treatment of a relapsed or refractory T-cell malignancy. In some cases, the IL-2 conjugate is administered to a subject for the treatment of a relapsed or refractory B-cell malignancy. In some cases, the IL-2 conjugate is administered to a subject for the treatment of a relapsed or refractory chronic lymphocytic leukemia (CLL), small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

Additional Therapeutic Agents

In some embodiments, an additional therapeutic agent is further administered to the subject. In some cases, the additional therapeutic agent is administered simultaneously with a cytokine conjugate (e.g., an IL-2 conjugate). In other cases, the additional therapeutic agent and the IL-2 conjugate are administered sequentially, e.g., the cytokine conjugate (e.g., IL-2 conjugate) is administered prior to the additional therapeutic agent or that the cytokine conjugate (e.g., IL-2 conjugate) is administered after administration of the additional therapeutic agent.

In some cases, the additional therapeutic agent comprises a chemotherapeutic agent, an immunotherapeutic agent, a targeted therapy, radiation therapy, or a combination thereof. Illustrative additional therapeutic agents include, but are not limited to, alkylating agents such as altretamine, busulfan, carboplatin, carmustine, chlorambucil, cisplatin, cyclophosphamide, dacarbazine, lomustine, melphalan, oxalaplatin, temozolomide, or thiotepa; antimetabolites such as 5-fluorouracil (5-FU), 6-mercaptopurine (6-MP), capecitabine, cytarabine, floxuridine, fludarabine, gemcitabine, hydroxyurea, methotrexate, or pemetrexed; anthracyclines such as daunorubicin, doxorubicin, epirubicin, or idarubicin; topoisomerase I inhibitors such as topotecan or irinotecan (CPT-11); topoisomerase II inhibitors such as etoposide (VP-16), teniposide, or mitoxantrone; mitotic inhibitors such as docetaxel, estramustine, ixabepilone, paclitaxel, vinblastine, vincristine, or vinorelbine; or corticosteroids such as prednisone, methylprednisolone, or dexamethasone.

In some cases, the additional therapeutic agent comprises a first-line therapy. As used herein, "first-line therapy" comprises a primary treatment for a subject with a cancer. In some instances, the cancer is a primary cancer. In other instances, the cancer is a metastatic or recurrent cancer. In some cases, the first-line therapy comprises chemotherapy. In other cases, the first-line treatment comprises radiation therapy. A skilled artisan would readily understand that different first-line treatments may be applicable to different type of cancers.

In some cases, a cytokine conjugate (e.g., IL-2 conjugate) is administered with an additional therapeutic agent selected from an alkylating agent such as altretamine, busulfan, carboplatin, carmustine, chlorambucil, cisplatin, cyclophosphamide, dacarbazine, lomustine, melphalan, oxalaplatin, temozolomide, or thiotepa; an antimetabolite such as 5-fluorouracil (5-FU), 6-mercaptopurine (6-MP), capecitabine, cytarabine, floxuridine, fludarabine, gemcitabine, hydroxyurea, methotrexate, or pemetrexed; an anthracycline such as daunorubicin, doxorubicin, epirubicin, or idarubicin; a topoisomerase I inhibitor such as topotecan or irinotecan (CPT-11); a topoisomerase II inhibitor such as etoposide (VP-16), teniposide, or mitoxantrone; a mitotic inhibitor such as docetaxel, estramustine, ixabepilone, paclitaxel, vinblastine, vincristine, or vinorelbine; or a corticosteroid such as prednisone, methylprednisolone, or dexamethasone.

In some instances, a cytokine conjugate (e.g., IL-2 conjugate) described herein is administered with an inhibitor of the enzyme poly ADP ribose polymerase (PARP). Exemplary PARP inhibitors include, but are not limited to, olaparib (AZD-2281, Lynparza®, from Astra Zeneca), rucaparib (PF-01367338, Rubraca®, from Clovis Oncology), niraparib (MK-4827, Zejula®, from Tesaro), talazoparib (BMN-673, from BioMarin Pharmaceutical Inc.), veliparib (ABT-888, from AbbVie), CK-102 (formerly CEP 9722, from Teva Pharmaceutical Industries Ltd.), E7016 (from Eisai), iniparib (BSI 201, from Sanofi), and pamiparib (BGB-290, from BeiGene). In some cases, the cytokine conjugate (e.g., IL-2 conjugate) is administered in combination with a PARP inhibitor such as olaparib, rucaparib, niraparib, talazoparib, veliparib, CK-102, E7016, iniparib, or pamiparib.

In some instances, a cytokine conjugate (e.g., IL-2 conjugate) described herein is administered with an immune checkpoint inhibitor. Exemplary checkpoint inhibitors include:

PD-L1 inhibitors such as Genentech's MPDL3280A (RG7446), Anti-mouse PD-L1 antibody Clone 10F.9G2 (Cat #BE0101) from BioXcell, anti-PD-L1 monoclonal antibody MDX-1105 (BMS-936559) and BMS-935559 from Bristol-Meyer's Squibb, MSB0010718C, mouse anti-PD-L1 Clone 29E.2A3, AstraZeneca's MEDI4736, atezolizumab (also known as Tecentriq®), bavelizumab (also known as Imfinzi®), and avelumab (also known as Bavencio®);

PD-L2 inhibitors such as GlaxoSmithKline's AMP-224 (Amplimmune), and rHIgM12B7;

PD-1 inhibitors such as anti-mouse PD-1 antibody Clone J43 (Cat #BE0033-2) from BioXcell, anti-mouse PD-1 antibody Clone RMP1-14 (Cat #BE0146) from BioXcell, mouse anti-PD-1 antibody Clone EH12, Merck's MK-3475 anti-mouse PD-1 antibody (Keytruda, pembrolizumab, lambrolizumab), AnaptysBio's anti-PD-1 antibody known as ANB011, antibody MDX-1 106 (ONO-4538), Bristol-Myers Squibb's human IgG4 monoclonal antibody nivolumab (Opdivo®, BMS-936558, MDX1106), AstraZeneca's AMP-514 and AMP-224, cemiplimab from Regeneron, and Pidilizumab (CT-011) from CureTech Ltd;

CTLA-4 inhibitors such as Bristol Meyers Squibb's anti-CTLA-4 antibody ipilimumab (also known as Yervoy®, MDX-010, BMS-734016 and MDX-101), anti-CTLA4 antibody clone 9H10 from Millipore, Pfizer's tremelimumab (CP-675,206, ticilimumab), and anti-CTLA4 antibody clone BNI3 from Abcam;

LAG3 inhibitors such as anti-Lag-3 antibody clone eBioC9B7W (C9B7W) from eBioscience, anti-Lag3 antibody LS-B2237 from LifeSpan Biosciences, IMP321 (ImmuFact) from Immutep, anti-Lag3 antibody BMS-986016, and the LAG-3 chimeric antibody A9H12;

B7-H3 inhibitors such as MGA271;

KIR inhibitors such as Lirilumab (IPH2101);

CD137 inhibitors such as urelumab (BMS-663513, Bristol-Myers Squibb), PF-05082566 (anti-4-1BB, PF-2566, Pfizer), or XmAb-5592 (Xencor);

PS inhibitors such as Bavituximab;

and inhibitors such as an antibody or fragments (e.g., a monoclonal antibody, a human, humanized, or chimeric antibody) thereof, RNAi molecules, or small molecules to TIM3, CD52, CD30, CD20, CD33, CD27, OX40, GITR, ICOS, BTLA (CD272), CD160, 2B4, LAIR1, TIGHT, LIGHT, DR3, CD226, CD2, or SLAM.

In some instances, the cytokine conjugate (e.g., IL-2 conjugate) is administered in combination with pembrolizumab, nivolumab, tremelimumab, or ipilimumab.

In some instances, a cytokine conjugate (e.g., IL-2 conjugate) described herein is administered with an antibody such as alemtuzumab, trastuzumab, ibritumomab tiuxetan, brentuximab vedotin, ado-trastuzumab emtansine, or blinatumomab.

In some instances, a cytokine conjugate (e.g., IL-2 conjugate) is administered with an additional therapeutic agent selected from a receptor agonist. In some instances, the receptor agonist comprises a Toll-like receptor (TLR) ligand. In some cases, the TLR ligand comprises TLR1, TLR2, TLR3, TLR4, TLR5, TLR6, TLR7, TLR8, or TLR9. In some cases, the TLR ligand comprises a synthetic ligand such as, for example, Pam3Cys, CFA, MALP2, Pam2Cys, FSL-1, Hib-OMPC, Poly I:C, poly A:U, AGP, MPL A, RC-529, MDF2β, CFA, or Flagellin. In some cases, the cytokine conjugate (e.g., IL-2 conjugate) is administered with one or more TLR agonists selected from TLR1, TLR2, TLR3, TLR4, TLR5, TLR6, TLR7, TLR8, and TLR9. In some cases, the cytokine conjugate (e.g., IL-2 conjugate) is administered with one or more TLR agonists selected from Pam3Cys, CFA, MALP2, Pam2Cys, FSL-1, Hib-OMPC, Poly I:C, poly A:U, AGP, MPL A, RC-529, MDF2β, CFA, and Flagellin.

In some embodiments, a cytokine conjugate (e.g., IL-2 conjugate) is used in conjunction with an adoptive T cell transfer (ACT) therapy. In one embodiment, ACT involves identification of autologous T lymphocytes in a subject with, e.g., anti-tumor activity, expansion of the autologous T lymphocytes in vitro, and subsequent reinfusion of the expanded T lymphocytes into the subject. In another embodiment, ACT comprises use of allogeneic T lymphocytes with, e.g., anti-tumor activity, expansion of the T lymphocytes in vitro, and subsequent infusion of the expanded allogeneic T lymphocytes into a subject in need thereof. In some instances, a cytokine conjugate (e.g., IL-2 conjugate) described herein is used in conjunction with an autologous T lymphocytes as part of an ACT therapy. In other instances, a cytokine conjugate (e.g., IL-2 conjugate) described herein is used in conjunction with an allogeneic T lymphocytes as part of an ACT therapy. In some cases, the cytokine conjugate (e.g., IL-2 conjugate) is administered simultaneously with the ACT therapy to a subject in need thereof. In other cases, the cytokine conjugate (e.g., IL-2 conjugate) is administered sequentially with the ACT therapy to a subject in need thereof.

In some embodiments, a cytokine conjugate (e.g., IL-2 conjugate) is used for an ex vivo activation and/or expansion of an autologous and/or allogenic T cell transfer. In such cases, the cytokine conjugate (e.g., IL-2 conjugate) is used to activate and/or expand a sample comprising autologous and/or allogenic T cells and the cytokine conjugate (e.g., IL-2 conjugate) is optionally removed from the sample prior to administering the sample to a subject in need thereof.

In some embodiments, a cytokine conjugate (e.g., IL-2 conjugate) is administered with a vaccine. In some instances, a cytokine conjugate (e.g., IL-2 conjugate) is utilized in combination with an oncolytic virus. In such cases, the cytokine conjugate (e.g., IL-2 conjugate) acts as a stimulatory agent to modulate the immune response. In some instances, the cytokine conjugate (e.g., IL-2 conjugate) is used with an oncolytic virus as part of an adjuvant therapy. Exemplary oncolytic viruses include T-Vec (Amgen), G47A (Todo et al.), JX-594 (Sillajen), CG0070 (Cold Genesys), and Reolysin (Oncolytics Biotech). In some cases, the cytokine conjugate (e.g., IL-2 conjugate) is used in combination with an oncolytic virus such as T-Vec, G47Δ, JX-594, CG0070, or Reolysin.

In some embodiments, a cytokine conjugate (e.g., IL-2 conjugate) is administered in combination with a radiation therapy.

In some embodiments, a cytokine conjugate (e.g., IL-2 conjugate) is administered in combination with surgery.

Pathogenic Infections

In some embodiments, described herein is a method of treating a pathogenic infection in a subject in need thereof, which comprises administering to the subject a therapeutically effective amount of a cytokine conjugate (e.g., an IL-2 conjugate) described herein. In some instances, the IL-2 conjugate comprises an isolated and purified IL-2 polypeptide and a conjugating moiety, wherein the IL-2 conjugate has a decreased affinity to an IL-2 receptor α (IL-2Rα) subunit relative to a wild-type IL-2 polypeptide. In some instances, the IL-2 conjugate comprises an isolated and purified IL-2 polypeptide; and a conjugating moiety that binds to the isolated and purified IL-2 polypeptide at an amino acid position selected from K35, T37, R38, T41, F42, K43, F44, Y45, E60, E61, E62, K64, P65, E68, V69, N71, L72, M104, C105, and Y107, wherein the numbering of the amino acid residues corresponds to SEQ ID NO: 1. In some cases, the IL-2 conjugate preferentially interact with the IL-2Rβ and IL-2Rβγ subunits to form a IL-2/IL-2Rβγ complex, which stimulates and/or enhances expansion of CD4+ helper cells, CD8+ effector naïve and memory cells, NK cells, and/or NKT cells. In additional cases, the IL-2 conjugate facilitates recognition of pathogenic reservoir by CD8+ T-cells. In some embodiments, the IL-2 conjugate comprising a mutation at residue F42, wherein the residue corresponds to position 42 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG correspondence with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal affect, on the receptor signaling potency of the modified IL-2 polypeptide to the IL-2βγ or IL-2αβγ signaling complexes. In some embodiments, the molecular weight of the PEG does not affect, or has minimal affect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα.

In some embodiments, the pathogenic infection is a viral infection, in which upon treatment with an antiviral therapy, a viral reservoir (e.g., resting CD4+ T cells) persists in a treated host. In such instances, a cytokine conjugate (e.g., an IL-2 conjugate) described herein induces recognition of the viral reservoir by CD8+ T cells (or cytotoxic T cells). In some cases, the cytokine conjugate (e.g., IL-2 conjugate) is utilized as a monotherapy to redirect CD8+ T cells to infected resting cells for elimination. In some cases, the cytokine conjugate (e.g., IL-2 conjugate) is utilized in combination with an additional therapy to redirect CD8+ T cells to infected resting cells for elimination. Exemplary additional therapy comprises antiviral treatments such as acyclovir, brivudine, docosanol, famciclovir, foscarnet, idoxuridine, penciclovir, trifluridine, valacyclovir, and pritelivir.

In some embodiments, the virus is a DNA virus or an RNA virus. The DNA viruses include single-stranded (ss) DNA viruses, double-stranded (ds) DNA viruses, or DNA viruses that contain both ss and ds DNA regions. The RNA viruses include single-stranded (ss) RNA viruses or double-stranded (ds) RNA viruses. In some cases, the ssRNA viruses are further classified into positive-sense RNA viruses or negative-sense RNA viruses.

Exemplary dsDNA viruses include viruses from the family: Myoviridae, Podoviridae, Siphoviridae, Alloherpesviridae, Herpesviridae, Malacoherpesviridae, Lipothrixviridae, Rudiviridae, Adenoviridae, Ampullaviridae, Ascoviridae, Asfaviridae, Baculoviridae, Bicaudaviridae, Clavaviridae, Corticoviridae, Fuselloviridae, Globuloviridae, Guttaviridae, Hytrosaviridae, Iridoviridae, Marseilleviridae, Mimiviridae, Nimaviridae, Pandoraviridae, Papillomaviridae, Phycodnaviridae, Plasmaviridae, Polydnaviruses, Polyomaviridae, Poxviridae, Sphaerolipoviridae, and Tectiviridae.

Exemplary ssDNA viruses include viruses from the family: Anelloviridae, Bacillariodnaviridae, Bidnaviridae, Circoviridae, Geminiviridae, Inoviridae, Microviridae, Nanoviridae, Parvoviridae, and Spiraviridae.

Exemplary DNA viruses that contain both ss and ds DNA regions include viruses from the group of pleolipoviruses. In some cases, the pleolipoviruses include *Haloarcula hispanica* pleomorphic virus 1, *Halogeometricum pleomorphic* virus 1, *Halorubrum pleomorphic* virus 1, *Halorubrum pleomorphic* virus 2, *Halorubrum pleomorphic virus* 3, and *Halorubrum pleomorphic* virus 6.

Exemplary dsRNA viruses include viruses from the family: Bimaviridae, Chrysoviridae, Cystoviridae, Endomaviridae, Hypoviridae, Megavimaviridae, Partitiviridae, Picobimaviridae, Reoviridae, Rotavirus, and Totiviridae.

Exemplary positive-sense ssRNA viruses include viruses from the family: Alphaflexiviridae, Alphatetraviridae, Alvernaviridae, Arteriviridae, Astroviridae, Bamaviridae, Betaflexiviridae, Bromoviridae, Caliciviridae, Carmotetraviridae, Closteroviridae, Coronaviridae, Dicistroviridae, Flaviviridae, Gammaflexiviridae, Iflaviridae, Leviviridae, Luteoviridae, Mamaviridae, Mesoniviridae, Namaviridae, Nodaviridae, Permutotetraviridae, Picomaviridae, Potyviridae, Roniviridae, Retroviridae, Secoviridae, Togaviridae, Tombusviridae, Tymoviridae, and Virgaviridae.

Exemplary negative-sense ssRNA viruses include viruses from the family: Arenaviridae, Bomaviridae, Bunyaviridae, Filoviridae, Nyamiviridae, Ophioviridae, Orthomyxoviridae, Paramyxoviridae, and Rhabdoviridae.

In some embodiments, the pathogenic infection is caused by Abelson leukemia virus, Abelson murine leukemia virus, Abelson's virus, Acute laryngotracheobronchitis virus, Adelaide River virus, Adeno associated virus group, Adenovirus, African horse sickness virus, African swine fever virus, AIDS virus, Aleutian mink disease parvovirus, Alpharetrovirus, Aiphavirus, ALV related virus, Amapari virus, Aphthovirus, Aquareovirus, Arbovirus, Arbovirus C, arbovirus group A, arbovirus group B, Arenavirus group, Argentine hemorrhagic fever virus, Argentine hemorrhagic fever virus, Arterivirus, Astrovirus, Ateline herpesvirus group, Aujezky's disease virus, Aura virus, Ausduk disease virus, Australian bat lyssavirus, Aviadenovirus, avian erythroblastosis virus, avian infectious bronchitis virus, avian leukemia virus, avian leukosis virus, avian lymphomatosis virus, avian myeloblastosis virus, avian paramyxovirus, avian pneumoencephalitis virus, avian reticuloendotheliosis virus, avian sarcoma virus, avian type C retrovirus group, Avihepadnavirus, Avipoxvirus, B virus, B19 virus, Babanki virus, baboon herpesvirus, baculovirus, Barmah Forest virus, Bebaru virus, Berrimah virus, Betaretrovirus, Birnavirus, Bittner virus, BK virus, Black Creek Canal virus, bluetongue virus, Bolivian hemorrhagic fever virus, Boma disease virus, border disease of sheep virus, borna virus, bovine alphaherpesvirus 1, bovine alphaherpesvirus 2, bovine coronavirus, bovine ephemeral fever virus, bovine immunodeficiency virus, bovine leukemia virus, bovine leukosis virus, bovine mammillitis virus, bovine papillomavirus, bovine papular stomatitis virus, bovine parvovirus, bovine syncytial virus, bovine type C oncovirus, bovine viral diarrhea virus, Buggy Creek virus, bullet shaped virus group, Bunyamwera virus supergroup, Bunyavirus, Burkitt's lymphoma virus, Bwamba Fever, CA virus, Calicivirus, California encephalitis virus, camelpox virus, canarypox virus, canid herpesvirus, canine coronavirus, canine distemper virus, canine herpesvirus, canine minute virus, canine parvovirus, Cano Delgadito virus, caprine arthritis virus, caprine encephalitis virus, Caprine Herpes Virus, Capripox virus, Cardiovirus, caviid herpesvirus 1, Cercopithecid herpesvirus 1, cercopithecine herpesvirus 1, Cercopithecine herpesvirus 2, Chandipura virus, Changuinola virus, channel catfish virus, Charleville virus, chickenpox virus, Chikungunya virus, chimpanzee herpesvirus, chub reovirus, chum salmon virus, Cocal virus, Coho salmon reovirus, coital exanthema virus, Colorado tick fever virus, Coltivirus, Columbia SK virus, common cold virus, contagious eethyma virus, contagious pustular dermatitis virus, Coronavirus, Corriparta virus, coryza virus, cowpox virus, coxsackie virus, CPV (cytoplasmic polyhedrosis virus), cricket paralysis virus, Crimean-Congo hemorrhagic fever virus, croup associated virus, Cryptovirus, Cypovirus, Cytomegalovirus, cytomegalovirus group, cytoplasmic polyhedrosis virus, deer papillomavirus, deltaretrovirus, dengue virus, Densovirus, Dependovirus, Dhori virus, diploma virus, *Drosophila* C virus, duck hepatitis B virus, duck hepatitis virus 1, duck hepatitis virus 2, duovirus, Duvenhage virus, Deformed wing virus DWV, eastern equine encephalitis virus, eastern equine encephalomyelitis virus, EB virus, Ebola virus, Ebola-like virus, echo virus, echovirus, echovirus 10, echovirus 28, echovirus 9, ectromelia virus, EEE virus, EIA virus, EIA virus, encephalitis virus, encephalomyocarditis group virus, encephalomyocarditis virus, Enterovirus, enzyme elevating virus, enzyme elevating virus (LDH), epidemic hemorrhagic fever virus, epizootic hemorrhagic disease virus, Epstein-Barr virus, equid alphaherpesvirus 1, equid alphaherpesvirus 4, equid herpesvirus 2, equine abortion virus, equine arteritis virus, equine encephalosis virus, equine infectious anemia virus, equine morbillivirus, equine rhinopneumonitis virus, equine rhinovirus, Eubenangu virus, European elk papillomavirus, European swine fever virus, Everglades virus, Eyach virus, felid herpesvirus 1, feline calicivirus, feline fibrosarcoma virus, feline herpesvirus, feline immunodeficiency virus, feline infectious peritonitis virus, feline leukemia/sarcoma virus, feline leukemia virus, feline panleukopenia virus, feline parvovirus, feline sarcoma virus, feline syncytial virus, Filovirus, Flanders virus, Flavivirus, foot and mouth disease virus, Fort Morgan virus, Four Corners hantavirus, fowl adenovirus 1, fovlpox virus, Friend virus, Gammaretrovirus, GB hepatitis virus, GB virus, German measles virus, Getah virus, gibbon ape leukemia virus, glandular fever virus, goatpox virus, golden shinner virus, Gonometa virus, goose parvovirus, granulosis virus, Gross' virus, ground squirrel hepatitis B virus, group A arbovirus, Guanarito virus, guinea pig cytomegalovirus, guinea pig type C virus, H-antaan virus, Hantavirus, hard clam reovirus, hare fibroma virus, HCMV (human cytomegalovirus), hemadsorption virus 2, hemagglutinating virus of Japan, hemorrhagic fever virus, hendra virus, lenipaviruses, Hepadnavirus, hepatitis A virus, hepatitis B virus group, hepatitis C virus, hepatitis D virus, hepatitis delta virus, hepatitis F virus, hepatitis F virus, hepatitis G virus, hepatitis nonA nonB virus, hepatitis virus, hepatitis virus (nonhuman), hepatoencephalomyelitis reovirus 3, Hepatovirus, heron hepatitis B virus, herpes B virus, herpes simplex virus, herpes simplex virus 1, herpes simplex virus 2, herpesvirus, herpesvirus 7, Herpesvirus ateles, *Herpesvirus hominis*, Herpesvirus infection, Herpesvirus saimiri, Herpesvirus suis, Herpesvirus varicellae, Highlands J virus, Hirame rhabdovirus, hog cholera virus, human adenovirus 2, human alphaherpesvirus 1, human alphaherpesvirus 2, human alphaherpesvirus 3, human B lymphotropic virus, human betaherpesvirus 5, human coronavirus, human cytomegalovirus group, human foamy virus, human gammaherpesvirus 4, human gammaherpesvirus 6, human hepatitis A virus, human herpesvirus 1 group, human herpesvirus 2 group, human herpesvirus 3 group, human herpesvirus 4 group, human herpesvirus 6, human herpesvirus 8, human immodeficiency virus, human immodeficiency virus 1, human immunodeficiency virus 2, human papillomavirus, human T cell leukemia virus, human T cell leukemia virus I, human T cell leukemia virus H, human T cell leukemia virus II, human T cell lymphoma virus I, human T cell lymphoma virus II, human T cell lymphotropic virus type 1, human T cell lymphotropic virus type 2, human T lymphotropic virus I, human T lymphotropic virus 11, human T lymphotropic virus III, Ichnovirus, infantile gastroenteritis virus, infectious bovine rhinotracheitis virus, infectious haematopoietic necrosis virus, infectious pancreatic necrosis virus, influenza virus A, influenza virus B, influenza virus C, influenza virus D, influenza virus pr8, insect iridescent virus, insect virus, iridovirus, Japanese B virus, Japanese encephalitis virus, JC virus, Junin virus, Kaposi's sarcoma-associated herpesvirus, Kemerovo virus, Kilham's rat virus, Klamath virus, Kolongo virus, Korean hemorrhagic fever virus, kumba virus, Kysanur forest disease virus, Ky zylagach virus, La Crosse virus, lactic dehydrogenase elevating virus, lactic dehydrogenase virus, Lagos bat virus, Langur virus, lapine parvovirus, Lassa fever virus, Lassa virus, latent rat virus, LCM virus, Leaky virus, Lentivirus, Leporipoxvirus, leukemia virus, leukovirus, lumpy skin disease virus, lymphadenopathy associated virus, Lymphocryptovirus, lymphocytic choriomeningitis virus, lymphoproliferative virus group, Machupo virus, mad itch virus, mammalian type B oncovirus group, mammalian type B retroviruses, mammalian type C rsetrovirus group, miminialian type D retroviruses, mammary tumor virus, Mapuera virus, Marburg virus, Marburg-like virus, Mason Pfizer monkey virus, Mastadenovirus, Mayaro virus, ME virus, measles virus, Menangle virus, Mengo virus, Mengovirus, Middelburg virus, milkers nodule virus, mink enteritis virus, minute virus of mice, MLV related virus, MM virus, Mokola virus, Molluscipoxvirus, Molluscum contagiosum virus, monkey B virus, monkeypox virus, Mononegavirales, Morbillivirus, Mount Elgon bat virus, mouse cytomegalovirus, mouse encephalomyelitis virus, mouse hepatitis virus, mouse K virus, mouse leukemia virus, mouse mammary tumor virus, mouse minute virus, mouse pneumonia virus, mouse poliomyelitis virus, mouse polyiomavirus, mouse sarcoma virus, mousepox virus, Mozambique virus, Mucambo virus, mucosal disease virus, mumps virus, murid betaherpesvirus 1, murid cytomegalovirus 2, murine cytomegalovirus group, murine encephalomyelitis virus, murne hepatitis virus, murine leukemia virus, murine nodule inducing virus, murine polyomavirus, murine sarcoma virus Muromegalovirus, Murray Valley encephalitis virus, myxoina virus, Myxovirus, Myxovirus miltiforme, Myxovirus parotitidis, Nairobi sheep disease virus, Nairovirus, Nanirnavirus, Nariva virus, Ndumo virus, Neethling virus, Nelson Bay virus, neurotropic virus, New World Arenavirus, newborn pneumonitis virus, Newcastle disease virus, Nipah virus, noncytopathogenic virus, Norwalk virus, nuclear polyhedrosis virus (NPV), nipple neck virus, O'nyong'nyong virus, Ockelbo virus, oncogenic virus, oncogenic viruslike particle, oncornavirus, Orbivirus, Orf virus, Oropouche virus, Orthohepadnavirus, Orthomyxovirus, Orthopoxvirus, Orthoreovirus, Orungo, ovine papillomavirus, ovine catarrhal fever virus, owl monkey herpesvirus, Palyam virus, Papillomavirus, Papillomavirus sylvilagi, Papovavirus, parainfluenza virus, parainfluenza virus type 1, parainfluenza virus type 2, parainfluenza virus type 3, parainfluenza virus type 4, Paramyxovirus, Parapoxvirus, paravaccinia virus, Parvovirus, Parvovirus B19, parvovirus group, Pestivirus, Phlebovirus, phocine distemper virus, Picodnavirus, Picornavirus, pig cytomegalovirus-pigeonpox virus, Piry virus, Pixuna virus, pneumonia virus of mice, Pneumovirus, poliomyelitis virus, poliovirus, Polydnavirus, polyhedral virus, polyorna virus, Polyomavirus, Polyomavirus *bovis*, Polyomavirus cercopitheci, Polyomavirus *hominis* 2, Polyomavirus maccacae 1, Polyomavirus *muris* 1, Polyomavirus *muris* 2, Polyomavirus papionis 1, Polyomavirus papionis 2, Polyomavirus sylvilagi, Pongine herpesvirus 1, porcine epidemic diarrhea virus, porcine beiagglutinating encephalomyelitis virus, porcine parvovirus, porcine transmissible gastroenteritis virus, porcine type C virus, pox virus, poxvirus, poxvirus variolae, Prospect-Hill virus, Provirus, pseudocowvpox virus, pseudorabies virus, psittacinepox virus, quailpox virus, rabbit fibroma virus, rabbit kidney vaculolating virus, rabbit papillomavirus, rabies virus, raccoon parvovirus, raccoonpox virus, Ranikhet virus, rat cytomegalovirus, rat parvovirus, rat virus, Rauscher's virus, recombinant vaccinia virus, recombinant virus, reovirus, reovirus 1, reovirus 2, reovirus 3, reptilian type C virus, respiratory infection virus, respiratory syncytial virus, respiratory virus, reticuloendotheliosis virus, Rhabdovirus, Rhabdovirus carpia, Rhadinovirus, Rhinovirus, Rhizidiovirus, Rift Valley fever virus, Riley's virus, rinderpest virus, RNA tumor virus, Ross River virus, Rotavirus, rougeole virus, Rous sarcoma virus, rubella virus, rubeola virus, Rubivirus, Russian autumn encephalitis virus, SA 11 simian virus, SA2 virus, Sabia virus, Sagiyama virus, Saimirine herpesvirus 1, salivary gland virus, sandfly fever virus group, Sandjimba virus, SARS virus, SDAV (sialodacryoadenitis virus), sealpox virus, Semliki Forest Virus, Seoul virus, sheeppox virus, Shope fibroma virus, Shope papilloma virus, simian foamy virus, simian hepatitis A virus, simian human immunodeficiency virus, simian immunodeficiency virus, simian parainfluenza virus, simian T cell lymphotrophic virus, simian virus, simian virus 40, Simplexvirus, Sin Nombre virus, Sindbis virus, smallpox virus, South American hemorrhagic fever viruses, sparrowpox virus, Spumavirus, squirrel fibroma virus, squirrel monkey retrovirus, SSV 1 virus group, STLV (simian T lymphotropic virus) type I, STLV (simian T lymphotropic virus) type II, STLV (simian T lymphotropic virus) type III, stomatitis papulosa virus, submaxillary virus, suid alphaherpesvirus 1, suid herpesvirus 2, Suipoxvirus, swamp fever virus, swinepox virus, Swiss mouse leukemia virus, TAC virus, Tacaribe complex virus, Tacaribe virus, Tanapox virus, Taterapox virus, Tench reovirus, Theiler's encephalomyelitis virus, Theiler's virus, Thogoto virus, Thottapalayam virus, Tick borne encephalitis virus, Tioman virus, Togavirus, Torovirus, tumor virus, Tupaia virus, turkey rhinotracheitis virus, turkeypox virus, type C retroviruses, type D oncovirus, type D retrovirus group, ulcerative disease rhabdovirus, Una virus, Uukuniemi virus group, vaccinia virus, vacuolating virus, vanicella zoster virus, Varicellovirus, Varicola virus, variola major virus, variola virus, Vasin Gishu disease virus, VEE virus, Venezuelan equine encephalitis virus, Venezuelan equine encephalomyelitis virus, Venezuelan hemorrhagic fever virus, vesicular stomatitis virus, Vesiculovirus, Vilyuisk virus, viper retrovirus, viral haemorrhagic septicemia virus, Visna Maedi virus, Visna virus, volepox virus, VSV (vesicular stomatitis virus), Wallal virus, Warrego virus, wart virus, WEE virus, West Nile virus, western equine encephalitis virus, western equine encephalomyelitis virus, Whataroa virus, Winter Vomiting Virus, woodchuck hepatitis B virus, woolly monkey sarcoma virus, wound tumor virus, WRSV virus, Yaba monkey tumor virus, Yaba virus, Yatapoxvirus, yellow fever virus, or the Yug Bogdanovac virus.

In some embodiments, the pathogenic infection is caused by a retrovirus. Exemplary retroviruses include, but are not limited to, human immunodefiency virus (HIV), human T-cell leukemia viruses (HTLV), moloney murine leukemia virus (MuLV), murine mammary tumor virus (MMTV), avian leucosis and sarcoma viruses, or Mason-Pfizer monkey virus.

In some embodiments, a cytokine conjugate (e.g., an IL-2 conjugate) described herein is administered to a subject with a retroviral infection or during a latency period to reduce and/or eliminate infected cells that are in a resting period. In some cases, the retrovirus comprises human immunodefiency virus (HIV), human T-cell leukemia viruses (HTLV), moloney murine leukemia virus (MuLV), murine mammary tumor virus (MMTV), avian leucosis and sarcoma viruses, or Mason-Pfizer monkey virus. In some cases, the cytokine conjugate redirects CD8+ T cells to recognize and eliminate infected cells that are in a resting period.

In some cases, the cytokine conjugate is an IL-2 conjugate. In some instances, the IL-2 conjugate is administered to a subject with a retroviral infection or during a latency period to reduce and/or eliminate infected cells that are in a resting period. In some cases, the retrovirus comprises human immunodefiency virus (HIV), human T-cell leukemia viruses (HTLV), moloney murine leukemia virus (MuLV), murine mammary tumor virus (MMTV), avian leucosis and sarcoma viruses, or Mason-Pfizer monkey virus. In some cases, the IL-2 conjugate redirects CD8+ T cells to recognize and eliminate infected cells that are in a resting period. In additional cases, the IL-2 conjugate is administered to the subject in combination with an antiretroviral therapy.

In some embodiments, the retrovirus is HIV. In some instances, a cytokine conjugate (e.g., an IL-2 conjugate) described herein is administered to a subject having acquired immune deficiency syndrome (AIDS) or during a latency period to reduce and/or eliminate HIV-infected cells (e.g., CD4+ T cells) that are in a resting period. In some cases, the cytokine conjugate is an IL-2 conjugate. In some cases, the IL-2 conjugate is administered to the subject in combination with an antiretroviral therapy. Exemplary HIV antiretroviral therapy includes: (a) nucleoside reverse transcriptase inhibitors (NRTIs) such as abacavir, emtricitabine, lamivudine, tenofovir disoproxil fumarate, and zidovudine; (b) non-nucleoside reverse transcriptase inhibitors (NNRTIs) such as efavirenz, etravirine, nevirapine, or rilpivirine; (c) protease inhibitors (PIs) such as atazanavir, darunavir, fosamprenavir, ritonavir, saquinavir, and tipranavir; (d) fusion inhibitors such as enfuvirtide; (e) CCR5 antagonists such as maraviroc; (f) integrase inhibitors such as dolutegravir and raltegravir; (g) post-attachment inhibitors such as ibalizumab; (h) pharmacokinetic enhancers such ac cobicistat; and (i) cocktails such as abacavir and lamivudine; abacavir, dolutegravir, and lamivudine; abacavir, lamivudine, and zidovudine; atazanavir and cobicistat; bictegravir, emtricitabine, and tenofovir alafenamide; darunavir and cobicistat; dolutegravir and rilpivirine; efavirenz, emtricitabine, and tenofovir disoproxil fumarate; efavirenz, lamivudine, and tenofovir disoproxil fumarate; efavirenz, lamivudine, and tenofovir disoproxil fumarate; elvitegravir, cobicistat, emtricitabine, and tenofovir alafenamide fumarate; elvitegravir, cobicistat, emtricitabine, and tenofovir disoproxil fumarate; emtricitabine, rilpivirine, and tenofovir alafenamide; emtricitabine, rilpivirine, and tenofovir disoproxil fumarate; emtricitabine and tenofovir alafenamide; emtricitabine and tenofovir disoproxil fumarate; lamivudine and tenofovir disoproxil fumarate; lamivudine and zidovudine; and lopinavir and ritonavir.

In some cases, the IL-2 conjugate is administered to the subject in combination with an antiretroviral therapy such as nucleoside reverse transcriptase inhibitors (NRTIs) such as abacavir, emtricitabine, lamivudine, tenofovir disoproxil fumarate, and zidovudine; non-nucleoside reverse transcriptase inhibitors (NNRTIs) such as efavirenz, etravirine, nevirapine, or rilpivirine; protease inhibitors (PIs) such as atazanavir, darunavir, fosamprenavir, ritonavir, saquinavir, and tipranavir; fusion inhibitors such as enfuvirtide; CCR5 antagonists such as maraviroc; integrase inhibitors such as dolutegravir and raltegravir; post-attachment inhibitors such as ibalizumab; pharmacokinetic enhancers such ac cobicistat; or cocktails such as abacavir and lamivudine; abacavir, dolutegravir, and lamivudine; abacavir, lamivudine, and zidovudine; atazanavir and cobicistat; bictegravir, emtricitabine, and tenofovir alafenamide; darunavir and cobicistat; dolutegravir and rilpivirine; efavirenz, emtricitabine, and tenofovir disoproxil fumarate; efavirenz, lamivudine, and tenofovir disoproxil fumarate; efavirenz, lamivudine, and tenofovir disoproxil fumarate; elvitegravir, cobicistat, emtricitabine, and tenofovir alafenamide fumarate; elvitegravir, cobicistat, emtricitabine, and tenofovir disoproxil fumarate; emtricitabine, rilpivirine, and tenofovir alafenamide; emtricitabine, rilpivirine, and tenofovir disoproxil fumarate; emtricitabine and tenofovir alafenamide; emtricitabine and tenofovir disoproxil fumarate; lamivudine and tenofovir disoproxil fumarate; lamivudine and zidovudine; and lopinavir and ritonavir.

In some embodiments, the virus is a hepatitis virus, e.g., hepatitis A, B, C, D, or E. In some instances, a cytokine conjugate (e.g., an IL-2 conjugate) described herein is administered to a subject with a hepatitis infection or during a latency period to reduce and/or eliminate infected cells that are in a resting period. In some cases, the cytokine conjugate redirects CD8+ T cells to recognize and eliminate infected cells that are in a resting period.

In some cases, the cytokine conjugate is an IL-2 conjugate. In some instances, the IL-2 conjugate is administered to a subject with a hepatitis infection or during a latency period to reduce and/or eliminate infected cells that are in a resting period. In some cases, the IL-2 conjugate redirects CD8+ T cells to recognize and eliminate infected cells that are in a resting period. In some cases, the IL-2 conjugate is administered to the subject in combination with an antiviral therapy. Exemplary antiviral therapy for hepatitis include ribavirin; NS3/4A protease inhibitors such as paritaprevir, simeprevir, and grazoprevir; NS5A protease inhibitors such as ledipasvir, ombitasvir, elbasvir, and daclatasvir; NS5B nucleotide/nucleoside and nonnucleoside polymerase inhibitors such as sofosbuvir and dasabuvir; and combinations such as ledipasvir-sofosbuvir, dasabuvir-ombitasvir-paritaprevir-ritonavir; elbasvir-grazoprevir, ombitasvir-paritaprevir-ritonavir, sofosbuvir-velpatasvir, sofosbuvir-velpatasvir-voxilaprevir, and glecaprevir-pibrentasvir; and interferons such as peginterferon alfa-2a, peginterferon alfa-2b, and interferon alfa-2b. In some cases, e IL-2 conjugate is administered to the subject in combination with an antiviral therapy such as ribavirin; NS3/4A protease inhibitors such as paritaprevir, simeprevir, and grazoprevir; NS5A protease inhibitors such as ledipasvir, ombitasvir, elbasvir, and daclatasvir; NS5B nucleotide/nucleoside and non-nucleoside polymerase inhibitors such as sofosbuvir and dasabuvir; and combinations such as ledipasvir-sofosbuvir, dasabuvir-ombitasvir-paritaprevir-ritonavir; elbasvir-grazoprevir, ombitasvir-paritaprevir-ritonavir, sofosbuvir-velpatasvir, sofosbuvir-velpatasvir-voxilaprevir, and glecaprevir-pibrentasvir; and interferons such as peginterferon alfa-2a, peginterferon alfa-2b, and interferon alfa-2b.

Autoimmune Disease or Disorder

In some embodiments, also described herein is a method of treating an autoimmune disease or disorder in a subject in need thereof, which comprises administering to the subject a therapeutically effective amount of a cytokine conjugate (e.g., IL-2 conjugate) described herein. In some instances, the IL-2 conjugate comprises an isolated and purified IL-2 polypeptide and a conjugating moiety, wherein the IL-2 conjugate has a decreased affinity to IL-2 receptor β (IL-2Rβ) subunit, IL-2 receptor γ (IL-2Rγ) subunit, or a combination thereof, relative to a wild-type IL-2 polypeptide. In some instances, the IL-2 conjugate comprises an isolated and purified IL-2 polypeptide; and a conjugating moiety that binds to the isolated and purified IL-2 polypeptide at an amino acid residue selected from P2, T3, S4, S5, S6, T7, K8, K9, Q11, L12, E15, H16, L18, L19, D20, Q22, M23, N26, G27, N29, N30, Y31, K32, K35, T37, M46, K47, K48, A50, T51, E52, K53, H55, Q57, E60, E67, N71, Q74, S75, K76, N77, F78, H79, R81, P82, R83, D84, S87, N88, N89, V91, 192, L94, E95, K97, G98, S99, E100, T101, T102, F103, M104, C105, E106, Y107, A108, D109, E110, T111, A112, T113, E116, N119, R120, T123, A125, Q126, S127, S130, T131, L132, and T133, wherein the numbering of the amino acid residues corresponds to SEQ ID NO: 1. In some instances, the amino acid residue is selected from K8, K9, Q11, L12, E15, H16, L18, L19, D20, Q22, M23, N26, R81, D84, S87, N88, V91, 192, L94, E95, E116, N119, R120, T123, A125, Q126, 5127, S130, T131, L132, and T133. In some instances, the amino acid residue is selected from K8, K9, L12, E15, H16, L19, D20, Q22, M23, N26, D84, N88, E95, and Q126. In some cases, the IL-2 conjugate interacts with an IL-2Rαβγ complex but with a reduced affinity toward the IL-2Rβ and IL-2Rγ subunits, or will decrease the recruitment of the IL-2R γ subunit to the IL-2/IL-2R3 complex. In some cases, the modified IL-2 polypeptide maintains the binding affinity toward IL-2Rα relative to a wild-type IL-2 polypeptide. In such cases, the IL-2/IL-2Rαβγ complex stimulates or enhances expansion of CD4+ Treg cells. In additional cases, the modified IL-2 polypeptide increases the dose required for activation of the Teff and/or NK cells via the IL-2Rβγ complex, thereby expanding the dose ranges for activation of Treg cells via the IL-2Rαβγ complex (or expanding the therapeutic window of the IL-2 for activation of Treg cells via the IL-2Rαβγ complex).

In some instances, the autoimmune disease or disorder comprises alopecia areata, autoimmune hemolytic anemia, autoimmune hepatitis, dermatomyositis, type 1 diabetes, juvenile idiopathic arthritis, glomerulonephritis, Graves' disease, Guillain-Barré syndrome, idiopathic thrombocytepenic purpura, myasthenia gravis, multiple sclerosis, pemphigus/pemphigoid, pernicious anemia, polyarteritis *nodosa*, polymyositis, primary biliary cirrhosis, psoriasis, rheumatoid arthritis, scleroderma, Sjögren's syndrome, systemic lupus erythematosus, thyroiditis, uveitis, vitiligo, or Wegener's granulomatosis.

In some cases, a cytokine (e.g., interleukin, IFN, or TNF) conjugate is administered to a subject having alopecia areata, autoimmune hemolytic anemia, autoimmune hepatitis, dermatomyositis, type 1 diabetes, juvenile idiopathic arthritis, glomerulonephritis, Graves' disease, Guillain-Barré syndrome, idiopathic thrombocytepenic purpura, myasthenia gravis, multiple sclerosis, pemphigus/pemphigoid, pernicious anemia, polyarteritis *nodosa*, polymyositis, primary biliary cirrhosis, psoriasis, rheumatoid arthritis, scleroderma, Sjögren's syndrome, systemic lupus erythematosus, thyroiditis, uveitis, vitiligo, or Wegener's granulomatosis.

In some cases, an IL-2 conjugate is administered to a subject having alopecia areata, autoimmune hemolytic anemia, autoimmune hepatitis, dermatomyositis, type 1 diabetes, juvenile idiopathic arthritis, glomerulonephritis, Graves' disease, Guillain-Barré syndrome, idiopathic thrombocytepenic purpura, myasthenia gravis, multiple sclerosis, pemphigus/pemphigoid, pernicious anemia, polyarteritis *nodosa*, polymyositis, primary biliary cirrhosis, psoriasis, rheumatoid arthritis, scleroderma, Sjögren's syndrome, systemic lupus erythematosus, thyroiditis, uveitis, vitiligo, or Wegener's granulomatosis. In some cases, the IL-2 conjugate is administered to a subject having type 1 diabetes. In some cases, the IL-2 conjugate is administered to a subject having Graves' disease. In some cases, the IL-2 conjugate is administered to a subject having multiple sclerosis. In some cases, the IL-2 conjugate is administered to a subject having psoriasis. In some cases, the IL-2 conjugate is administered to a subject having rheumatoid arthritis. In some cases, the IL-2 conjugate is administered to a subject having Sjögren's syndrome. In some cases, the IL-2 conjugate is administered to a subject having systemic lupus erythematosus. In some cases, the IL-2 conjugate is administered to a subject having uveitis. In some cases, the IL-2 conjugate is administered to a subject having Wegener's granulomatosis.

In some cases, a cytokine conjugate (e.g., an IL-2 conjugate) is administered to a subject for the treatment of a Graft-versus-Host disease (GVHD).

In some embodiments, an additional therapeutic agent is further administered to the subject. In some cases, the additional therapeutic agent is administered simultaneously with a cytokine conjugate (e.g., IL-2 conjugate). In other cases, the additional therapeutic agent and the cytokine conjugate (e.g., IL-2 conjugate) are administered sequentially, e.g., the cytokine conjugate (e.g., IL-2 conjugate) is administered prior to the additional therapeutic agent or that the cytokine conjugate (e.g., IL-2 conjugate) is administered after administration of the additional therapeutic agent.

Exemplary additional therapeutic agents for the treatment of an autoimmune disease or disorder include, but are not limited to, corticosteroids such as prednisone, budesonide, or prednisolone; calcineurin inhibitors such as cyclosporine or tacrolimus; mTOR inhibitors such as sirolimus or everolimus; IVDH inhibitors such as azathioprine, leflunomide, or mycophenolate; biologics such as abatacept, adalimumab, anakinra, certolizumab, etanercept, golimumab, infliximab, ixekizumab, natalizumab, rituximab, secukinumab, tocilizumab, ustekinumab, or vedolizumab; and monoclonal antibodies such as basiliximab, daclizumab, or muromonab.

In some cases, a cytokine conjugate (e.g., IL-2 conjugate) is administered with an additional therapeutic agent selected from a corticosteroid such as prednisone, budesonide, or prednisolone; a calcineurin inhibitor such as cyclosporine or tacrolimus; an mTOR inhibitor such as sirolimus or everolimus; an IMDH inhibitor such as azathioprine, leflunomide, or mycophenolate; a biologics such as abatacept, adalimumab, anakinra, certolizumab, etanercept, golimumab, infliximab, ixekizumab, natalizumab, rituximab, secukinumab, tocilizumab, ustekinumab, or vedolizumab; and a monoclonal antibody such as basiliximab, daclizumab, or muromonab.

Development of Adoptive Cell Therapies

Disclosed herein, in some embodiments, are methods of generating an adoptive cell therapy composition useful for the treatment of a disease or condition described herein (e.g., proliferative disease or condition, pathogenic infection, and/or autoimmune disease or condition) in a subject in need thereof, comprising: a) providing immune cells obtained from a subject in need thereof; b) engineering the immune cells to express a modified IL-2 polypeptide, a IL-2 conjugate, aIL-2Rβγ binding protein, or an activator of the immune cell, wherein the immune cell comprises a CD4+ helper cell, a CD8+ effector naïve and memory cell, a CD8+ cytotoxic T cell, a suppressor T Cell, a Natural Killer (NK) cell, or a Natural killer T (NKT) cell. In some embodiments, the immune cell is engineered to additionally express a chimeric antigen receptor (CAR). In some embodiments, the engineering step (b) comprises contacting the immune cells obtained from the subject to a vector (e.g., polynucleotide sequence) encoding the modified IL-2 polypeptide, the IL-2 conjugate, the IL-2Rβγ binding protein, or the activator of the immune cell. In some instances, the vector comprises the articles of manufacture disclosed herein. In some instances, the methods of generating the adoptive cell therapy are performed using the kits disclosed herein. In some embodiments, the subject is treated with the adoptive cell therapy, by administering a therapeutically effective amount of the adoptive cell therapy. In some instances, the subject is diagnosed with the disease or condition. In some instances, the adoptive cell therapy is effective to treat the disease or condition in the subject. In some embodiments, the disease or condition comprises a proliferative disease (e.g., cancer). In some embodiments, the disease or condition comprises a pathogenic infection. In some instances, the disease or condition comprises an autoimmune disease. is a cancer, such as those described herein.

Disclosed herein, in some embodiments, are methods of generating an adoptive cell therapy composition useful for the treatment of a disease or condition described herein (e.g., proliferative disease or condition, pathogenic infection, and/or autoimmune disease or condition) in a subject in need thereof, comprising: a) providing immune cells obtained from a subject in need thereof; b) contacting the immune cells to with a modified IL-2 polypeptide, an IL-2 conjugate, an IL-2Rβγ binding protein, or an activator of the immune cell, wherein the immune cell comprises a CD4+ helper cell, a CD8+ effector naïve and memory cell, a CD8+ cytotoxic T cell, a suppressor T Cell, a Natural Killer (NK) cell, or a Natural killer T (NKT) cell. In some embodiments, the immune cell is engineered to additionally express a chimeric antigen receptor (CAR). In some instances, the modified IL-2 polypeptide, the IL-2 conjugate, the IL-2Rβγ binding protein, or the activator of the immune cell comprises the articles of manufacture disclosed herein. In some instances, the methods of generating the adoptive cell therapy are performed using the kits disclosed herein. In some embodiments, the subject is treated with the adoptive cell therapy, by administering a therapeutically effective amount of the adoptive cell therapy. In some instances, the subject is diagnosed with the disease or condition. In some instances, the adoptive cell therapy is effective to treat the disease or condition in the subject. In some embodiments, the disease or condition comprises a proliferative disease (e.g., cancer).

In some embodiments, the disease or condition comprises a pathogenic infection. In some instances, the disease or condition comprises an autoimmune disease. is a cancer, such as those described herein.

In some embodiments, the modified IL-2 polypeptide or the IL-2 conjugate comprises a mutation at residue F42 corresponding to position 42 of SEQ ID NO: 1, and comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da.

In some embodiments, the modified IL-2 polypeptide or the IL-2 conjugate comprises a mutation at residue P65 corresponding to position 65 of SEQ ID NO: 1, and comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da.

In some embodiments, the modified IL-2 polypeptide or the IL-2 conjugate comprises a mutation at residue E62 corresponding to position 62 of SEQ ID NO: 1, and comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da.

In some instances, the molecular weight of the PEG is effective to improve the manufacturing process of the IL-2 polypeptide or the IL-2 conjugate as a reagent for adoptive cell therapies. In some embodiments, the molecular weight of the PEG improves the solubility of the IL-2 polypeptide or IL-2 conjugate. In some instances, the molecular weight of the PEG improves the purification process of manufacturing the adoptive cell therapy. In some instances, the molecular weight of the PEG improves the stability of the IL-2 polypeptide or the IL-2 conjugate.

Disclosed herein, in some embodiments, are methods of treating an autoimmune disease or disorder in a subject in need thereof, which comprises administering to the subject an adoptive cell therapy described herein. In some instances, the adoptive cell therapy is developed using the methods described herein. In some instances, the adoptive cell therapy is administered to the subject in addition to the cytokine conjugate (e.g., IL-2 conjugate) described herein. In some instances, the cytokine conjugate is administered before the adoptive cell therapy. In some instances, the cytokine conjugate is administered after the adoptive cell therapy. In some instances, the adoptive cell therapy is effective to expand a population of immune cells in the subject (e.g., CD4+ helper cell, CD8+ effector naïve and memory cell, NK cell, and/or NKT cell populations, Treg cell population).

Disclosed herein, in some embodiments are methods of treating a pathogenic infection in a subject in need thereof, which comprises administering to the subject a therapeutically effective amount of an adoptive cell therapy described herein. In some instances, the adoptive cell therapy is developed using the methods described herein. In some instances, the adoptive cell therapy is administered to the subject in addition to the cytokine conjugate (e.g., IL-2 conjugate) described herein. In some instances, the cytokine conjugate is administered before the adoptive cell therapy. In some instances, the cytokine conjugate is administered after the adoptive cell therapy. In some instances, the adoptive cell therapy is effective to expand a population of immune cells in the subject (e.g., CD4+ helper cell, CD8+ effector naïve and memory cell, NK cell, and/or NKT cell populations, Treg cell population).

Disclosed herein, in some embodiments, are methods of treating an a *prolifer* disease or disorder (e.g., cancer) in a subject in need thereof, which comprises administering to the subject an adoptive cell therapy described herein. In some instances, the adoptive cell therapy is developed using the methods described herein. In some instances, the adoptive cell therapy is administered to the subject in addition to the cytokine conjugate (e.g., IL-2 conjugate) described herein. In some instances, the cytokine conjugate is administered before the adoptive cell therapy. In some instances, the cytokine conjugate is administered after the adoptive cell therapy. In some instances, the adoptive cell therapy is effective to expand a population of immune cells in the subject (e.g., CD4+ helper cell, CD8+ effector naïve and memory cell, NK cell, and/or NKT cell populations, Treg cell population).

Methods of Cell Population Expansion

In some embodiments, additionally described herein are methods of expanding lymphocyte populations, e.g., CD4+ helper cell, CD8+ effector naïve and memory cell, NK cell, and/or NKT cell populations, or methods of expanding a Treg cell population. In some instances, the method comprises contacting a cell with a cytokine conjugate described herein and interacting the cytokine with a cytokine receptor to form a complex, wherein the complex stimulates expansion of a distinct lymphocyte population.

In some instances, the method of expanding a CD4+ helper cell, CD8+ effector naïve and memory cell, Natural Killer (NK) cell, or Natural killer T (NKT) cell population comprises contacting a cell population with an isolated and modified IL-2 polypeptide described above for a time sufficient to induce formation of a complex with an IL-2Rβ, thereby stimulating the expansion of the Teff and/or NK cell population. In some instances, the method of expanding CD4+ helper cell, CD8+ effector naïve and memory cell, NK cell, and/or NKT cell populations comprises (a) contacting a cell population with an IL-2 conjugate described herein;

and (b) interacting the IL-2 with IL-2Rβ and IL-2Rγ subunits to form an IL-2/IL-2Rβγ complex; wherein the IL-2 conjugate has a decreased affinity to IL-2Rα subunit, and wherein the IL-2/IL-2Rβγ complex stimulates the expansion of CD4+ helper cells, CD8+ effector naïve and memory cells, NK cells, and/or NKT cells. As described above, the IL-2 conjugate comprises an isolated and purified IL-2 polypeptide; and a conjugating moiety that binds to the isolated and purified IL-2 polypeptide at an amino acid position selected from K35, T37, R38, T41, F42, K43, F44, Y45, E60, E61, E62, K64, P65, E68, V69, N71, L72, M104, C105, and Y107, wherein the numbering of the amino acid residues corresponds to SEQ ID NO: 1. In some instances, the amino acid position is selected from K35, T37, R38, T41, F42, K43, F44, Y45, E61, E62, E68, K64, P65, V69, L72, and Y107. In some instances, the amino acid position is selected from T37, R38, T41, F42, F44, Y45, E61, E62, E68, K64, P65, V69, L72, and Y107. In some instances, the amino acid position is selected from T37, R38, T41, F42, F44, Y45, E61, E62, E68, P65, V69, L72, and Y107. In some instances, the amino acid position is selected from T37, T41, F42, F44, Y45, P65, V69, L72, and Y107. In some instances, the amino acid position is selected from R38 and K64. In some instances, the amino acid position is selected from E61, E62, and E68. In some cases, the amino acid position is at E62.

In some instances, the IL-2 conjugate expands CD4+ T regulatory (Treg) cells by less than 20%, 15%, 10%, 5%, or 1% in the cell population. In some instances, the IL-2 conjugate does not expand CD4+ Treg cells in the cell population. In some instances, the ratio of the Teff cells to Treg cells in the cell population after incubation with the isolated and modified IL-2 polypeptide is at least 2:1, 3:1, 4:1, 5:1, 6:1, 7:1, 8:1, 9:1, 10:1, 20:1, 50:1, or 100:1. In some instances, the ratio of the Teff cells to Treg cells in the cell population after incubation with the isolated and modified IL-2 polypeptide is about 2:1, 3:1, 4:1, 5:1, 6:1, 7:1, 8:1, 9:1, 10:1, 20:1, 50:1, or 100:1.

In some instances, the time sufficient to induce formation of a complex with an IL-2Rβ is at least 5 minutes, 10 minutes, 15 minutes, 20 minutes, 30 minutes, 1 hour, 2 hours, 3 hours, 4 hours, 5 hours, 8 hours, 10 hours, 12 hours, 18 hours, 24 hours, 2 days, 3 days, 4 days, 5 days, 6 days, or 7 days. In some instances, the time sufficient to induce formation of a complex with an IL-2Rβ is about 5 minutes, 10 minutes, 15 minutes, 20 minutes, 30 minutes, 1 hour, 2 hours, 3 hours, 4 hours, 5 hours, 8 hours, 10 hours, 12 hours, 18 hours, 24 hours, 2 days, 3 days, 4 days, 5 days, 6 days, or 7 days.

In some instances, the method is an in vivo method.

In some instances, the method is an in vitro method.

In some instances, the method is an ex vivo method.

Cytokine Polypeptide Production

In some instances, the cytokine (e.g., interleukin, IFN, or TNF) polypeptides described herein, either containing a natural amino acid mutation or an unnatural amino acid mutation, are generated recombinantly or are synthesized chemically. In some instances, the cytokine (e.g., IL-2) polypeptides described herein are generated recombinantly, for example, either by a host cell system, or in a cell-free system.

In some instances, the cytokine (e.g., IL-2) polypeptides are generated recombinantly through a host cell system. In some cases, the host cell is a eukaryotic cell (e.g., mammalian cell, insect cells, yeast cells or plant cell) or a prokaryotic cell (e.g., gram-positive bacterium or a gram-negative bacterium). In some cases, a eukaryotic host cell is a mammalian host cell. In some cases, a mammalian host cell is a stable cell line, or a cell line that has incorporated a genetic material of interest into its own genome and has the capability to express the product of the genetic material after many generations of cell division. In other cases, a mammalian host cell is a transient cell line, or a cell line that has not incorporated a genetic material of interest into its own genome and does not have the capability to express the product of the genetic material after many generations of cell division.

Exemplary mammalian host cells include 293T cell line, 293A cell line, 293FT cell line, 293F cells, 293H cells, A549 cells, MDCK cells, CHO DG44 cells, CHO-S cells, CHO-K1 cells, Expi293F™ cells, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cells, FreeStyle™ CHO-S cells, GripTite™ 293 MSR cell line, GS-CHO cell line, HepaRG™ cells, T-REx™ Jurkat cell line, Per.C6 cells, T-REx™-293 cell line, T-REx™-CHO cell line, and T-REx™-HeLa cell line.

In some embodiments, an eukaryotic host cell is an insect host cell. Exemplary insect host cell include *Drosophila* S2 cells, Sf9 cells, Sf21 cells, High Five™ cells, and expresSF+® cells.

In some embodiments, a eukaryotic host cell is a yeast host cell. Exemplary yeast host cells include *Pichia pastoris* yeast strains such as GS115, KM71H, SIMD1168, SIMD1168H, and X-33, and *Saccharomyces cerevisiae* yeast strain such as INVSc1.

In some embodiments, an eukaryotic host cell is a plant host cell. In some instances, the plant cells comprise a cell from algae. Exemplary plant cell lines include strains from *Chlamydomonas reinhardtii* 137c, or Synechococcus *elongatus* PPC 7942.

In some embodiments, a host cell is a prokaryotic host cell. Exemplary prokaryotic host cells include BL21, Mach1™, DH10B™, TOP10, DH5α, DH10Bac™, OmniMax™, MegaX™, DH12S™, INV110, TOP10F', INVαF, TOP10/P3, ccdB Survival, PIR1, PIR2, Stbl2™, Stbl3™, or Stbl4™.

In some instances, suitable polynucleic acid molecules or vectors for the production of an IL-2 polypeptide described herein include any suitable vectors derived from either a eukaryotic or prokaryotic source. Exemplary polynucleic acid molecules or vectors include vectors from bacteria (e.g., *E. coli*), insects, yeast (e.g., *Pichia pastoris*), algae, or mammalian source. Bacterial vectors include, for example, pACYC177, pASK75, pBAD vector series, pBADM vector series, pET vector series, pETM vector series, pGEX vector series, pHAT, pHAT2, pMal-c2, pMal-p2, pQE vector series, pRSET A, pRSET B, pRSET C, pTrcHis2 series, pZA31-Luc, pZE21-MCS-1, pFLAG ATS, pFLAG CTS, pFLAG MAC, pFLAG Shift-12c, pTAC-MAT-1, pFLAG CTC, or pTAC-MAT-2.

Insect vectors include, for example, pFastBacl, pFastBac DUAL, pFastBac ET, pFastBac HTa, pFastBac HTb, pFastBac HTc, pFastBac M30a, pFastBact M30b, pFastBac, M30c, pVL1392, pVL1393, pVL1393 M10, pVL1393 M1, pVL1393 M12, FLAG vectors such as pPolh-FLAG1 or pPolh-MAT 2, or MAT vectors such as pPolh-MAT1, or pPolh-MAT2.

Yeast vectors include, for example, Gateway® pDEST™ 14 vector, Gateway® pDEST™ 15 vector, Gateway® pDEST™ 17 vector, Gateway® pDEST™ 24 vector, Gateway® pYES-DEST52 vector, pBAD-DEST49 Gateway® destination vector, pAO815 Pichia vector, pFLD1 *Pichi*

*pastoris* vector, pGAPZA, B, & C *Pichia pastoris* vector, pPIC3.5K *Pichia* vector, pPIC6 A, B, & C *Pichia* vector, pPIC9K *Pichia* vector, pTEFI/Zeo, pYES2 yeast vector, pYES2/CT yeast vector, pYES2/NT A, B, & C yeast vector, or pYES3/CT yeast vector.

Algae vectors include, for example, pChlamy-4 vector or MCS vector.

Mammalian vectors include, for example, transient expression vectors or stable expression vectors. Exemplary mammalian transient expression vectors include p3×FLAG-CMV 8, pFLAG-Myc-CMV 19, pFLAG-Myc-CMV 23, pFLAG-CMV 2, pFLAG-CMV 6a,b,c, pFLAG-CMV 5.1, pFLAG-CMV 5a,b,c, p3×FLAG-CMV 7.1, pFLAG-CMV 20, p3×FLAG-Myc-CMV 24, pCMV-FLAG-MAT1, pCMV-FLAG-MAT2, pBICEP-CMV 3, or pBICEP-CMV 4. Exemplary mammalian stable expression vectors include pFLAG-CMV 3, p3×FLAG-CMV 9, p3×FLAG-CMV 13, pFLAG-Myc-CMV 21, p3×FLAG-Myc-CMV 25, pFLAG-CMV 4, p3×FLAG-CMV 10, p3×FLAG-CMV 14, pFLAG-Myc-CMV 22, p3×FLAG-Myc-CMV 26, pBICEP-CMV 1, or pBICEP-CMV 2.

In some instances, a cell-free system is used for the production of a cytokine (e.g., IL-2) polypeptide described herein. In some cases, a cell-free system comprises a mixture of cytoplasmic and/or nuclear components from a cell and is suitable for in vitro nucleic acid synthesis. In some instances, a cell-free system utilizes prokaryotic cell components. In other instances, a cell-free system utilizes eukaryotic cell components. Nucleic acid synthesis is obtained in a cell-free system based on, for example, *Drosophila* cell, *Xenopus* egg, Archaea, or HeLa cells. Exemplary cell-free systems include *E. coli* S30 Extract system, *E. coli* T7 S30 system, or PURExpress®, XpressCF, and XpressCF+.

Cell-free translation systems variously comprise components such as plasmids, mRNA, DNA, tRNAs, synthetases, release factors, ribosomes, chaperone proteins, translation initiation and elongation factors, natural and/or unnatural amino acids, and/or other components used for protein expression. Such components are optionally modified to improve yields, increase synthesis rate, increase protein product fidelity, or incorporate unnatural amino acids. In some embodiments, cytokines described herein are synthesized using cell-free translation systems described in U.S. Pat. No. 8,778,631; US 2017/0283469; US 2018/0051065; US 2014/0315245; or U.S. Pat. No. 8,778,631. In some embodiments, cell-free translation systems comprise modified release factors, or even removal of one or more release factors from the system. In some embodiments, cell-free translation systems comprise a reduced protease concentration. In some embodiments, cell-free translation systems comprise modified tRNAs with re-assigned codons used to code for unnatural amino acids. In some embodiments, the synthetases described herein for the incorporation of unnatural amino acids are used in cell-free translation systems. In some embodiments, tRNAs are pre-loaded with unnatural amino acids using enzymatic or chemical methods before being added to a cell-free translation system. In some embodiments, components for a cell-free translation system are obtained from modified organisms, such as modified bacteria, yeast, or other organism.

In some embodiments, a cytokine (e.g., IL-2) polypeptide is generated as a circularly permuted form, either via an expression host system or through a cell-free system.

Production of Cytokine Polypeptide Comprising an Unnatural Amino Acid

An orthogonal or expanded genetic code can be used in the present disclosure, in which one or more specific codons present in the nucleic acid sequence of a cytokine (e.g., IL-2) polypeptide are allocated to encode the unnatural amino acid so that it can be genetically incorporated into the cytokine (e.g., IL-2) by using an orthogonal tRNA synthetase/tRNA pair. The orthogonal tRNA synthetase/tRNA pair is capable of charging a tRNA with an unnatural amino acid and is capable of incorporating that unnatural amino acid into the polypeptide chain in response to the codon.

In some instances, the codon is the codon amber, ochre, opal or a quadruplet codon. In some cases, the codon corresponds to the orthogonal tRNA which will be used to carry the unnatural amino acid. In some cases, the codon is amber. In other cases, the codon is an orthogonal codon.

In some instances, the codon is a quadruplet codon, which can be decoded by an orthogonal ribosome ribo-Q1. In some cases, the quadruplet codon is as illustrated in Neumann, et al., "Encoding multiple unnatural amino acids via evolution of a quadruplet-decoding ribosome," *Nature,* 464(7287): 441-444 (2010).

In some instances, a codon used in the present disclosure is a recoded codon, e.g., a synonymous codon or a rare codon that is replaced with alternative codon. In some cases, the recoded codon is as described in Napolitano, et al., "Emergent rules for codon choice elucidated by editing rare argine codons in *Escherichia coli,*" *PNAS,* 113(38): E5588-5597 (2016). In some cases, the recoded codon is as described in Ostrov et al., "Design, synthesis, and testing toward a 57-codon genome," *Science* 353(6301): 819-822 (2016).

In some instances, unnatural nucleic acids are utilized leading to incorporation of one or more unnatural amino acids into the cytokine (e.g., IL-2). Exemplary unnatural nucleic acids include, but are not limited to, uracil-5-yl, hypoxanthin-9-yl (I), 2-aminoadenin-9-yl, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifiuoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Certain unnatural nucleic acids, such as 5-substituted pyrimidines, 6-azapyrimidines and N-2 substituted purines, N-6 substituted purines, 0-6 substituted purines, 2-aminopropyladenine, 5-propynyluracil, 5-propynylcytosine, 5-methylcytosine, those that increase the stability of duplex formation, universal nucleic acids, hydrophobic nucleic acids, promiscuous nucleic acids, size-expanded nucleic acids, fluorinated nucleic acids, 5-substituted pyrimidines, 6-azapyrimidines and N-2, N-6 and 0-6 substituted purines, including 2-aminopropyladenine, 5-propynyluracil and 5-propynylcytosine. 5-methylcytosine (5-me-C), 5-hydroxymethyl cytosine, xanthine, hypoxanthine, 2-aminoadenine, 6-methyl, other alkyl derivatives of adenine and guanine, 2-propyl and other alkyl derivatives of adenine and guanine, 2-thiouracil, 2-thiothymine and 2-thiocytosine, 5-halouracil, 5-halocytosine, 5-propynyl ($-C\equiv C-CH_3$) uracil, 5-propynyl cytosine, other alkynyl derivatives of pyrimidine nucleic acids, 6-azo uracil, 6-azo cytosine, 6-azo thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl, other 5-substituted uracils and cytosines, 7-methylguanine, 7-methyladenine, 2-F-adenine, 2-amino-adenine, 8-azaguanine, 8-azaadenine, 7-deazaguanine, 7-deazaadenine, 3-deazaguanine, 3-deazaadenine, tricyclic pyrimidines, phenoxazine cytidine ([5,4-b][1,4]benzoxazin-2(3H)-one), phenothiazine cytidine (1H-pyrimido[5,4-b][1,4]benzothiazin-2(3H)-one), G-clamps, phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3', 2': 4,5]pyrrolo[2,3-d]pyrimidin-2-one), those in which the purine or pyrimidine base is replaced with other heterocycles, 7-deaza-adenine, 7-deazaguanosine, 2-aminopyridine, 2-pyridone, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 2-amino-adenine, 6-thio-guanine, 2-thio-thymine, 4-thio-thymine, 5-propynyl-uracil, 4-thiouracil, N4-ethylcytosine, 7-deazaguanine, 7-deaza-8-azaguanine, 5-hydroxycytosine, 2'-deoxyuridine, 2-amino-2'-deoxyadenosine, and those described in U.S. Pat. Nos. 3,687,808; 4,845,205; 4,910,300; 4,948,882; 5,093,232; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096; WO 99/62923; Kandimalla et al., (2001) Bioorg. Med. Chem. 9:807-813; The Concise Encyclopedia of Polymer Science and Engineering, Kroschwitz, J. I., Ed., John Wiley & Sons, 1990, 858-859; Englisch et al., Angewandte Chemie, International Edition, 1991, 30, 613; and Sanghvi, Chapter 15, Antisense Research and Applications, Crooke and Lebleu Eds., CRC Press, 1993, 273-288. Additional base modifications can be found, for example, in U.S. Pat. No. 3,687,808; Englisch et al., Angewandte Chemie, International Edition, 1991, 30, 613; and Sanghvi, Chapter 15, Antisense Research and Applications, pages 289-302, Crooke and Lebleu ed., CRC Press, 1993.

Unnatural nucleic acids comprising various heterocyclic bases and various sugar moieties (and sugar analogs) are available in the art, and the nucleic acids in some cases include one or several heterocyclic bases other than the principal five base components of naturally-occurring nucleic acids. For example, the heterocyclic base includes, in some cases, uracil-5-yl, cytosin-5-yl, adenin-7-yl, adenin-8-yl, guanin-7-yl, guanin-8-yl, 4-aminopyrrolo [2.3-d] pyrimidin-5-yl, 2-amino-4-oxopyrolo [2,3-d]pyrimidin-5-yl, 2-amino-4-oxopyrrolo [2.3-d] pyrimidin-3-yl groups, where the purines are attached to the sugar moiety of the nucleic acid via the 9-position, the pyrimidines via the 1-position, the pyrrolopyrimidines via the 7-position and the pyrazolopyrimidines via the 1-position.

In some embodiments, nucleotide analogs are also modified at the phosphate moiety. Modified phosphate moieties include, but are not limited to, those with modification at the linkage between two nucleotides and contains, for example, a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides are through a 3'-5' linkage or a 2'-5' linkage, and the linkage contains inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

In some embodiments, unnatural nucleic acids include 2', 3'-dideoxy-2', 3'-didehydro-nucleosides (PCT/US2002/006460), 5'-substituted DNA and RNA derivatives (PCT/US2011/033961; Saha et al., J. Org Chem., 1995, 60, 788-789; Wang et al., Bioorganic & Medicinal Chemistry Letters, 1999, 9, 885-890; and Mikhailov et al., Nucleosides & Nucleotides, 1991, 10(1-3), 339-343; Leonid et al., 1995, 14(3-5), 901-905; and Eppacher et al., Helvetica Chimica Acta, 2004, 87, 3004-3020; PCT/JP2000/004720; PCT/JP2003/002342; PCT/JP2004/013216; PCT/JP2005/020435; PCT/JP2006/315479; PCT/JP2006/324484; PCT/JP2009/056718; PCT/JP2010/067560), or 5'-substituted monomers made as the monophosphate with modified bases (Wang et al., Nucleosides Nucleotides & Nucleic Acids, 2004, 23 (1 & 2), 317-337).

In some embodiments, unnatural nucleic acids include modifications at the 5'-position and the 2'-position of the sugar ring (PCT/US94/02993), such as 5'-$CH_2$-substituted 2'-O-protected nucleosides (Wu et al., Helvetica Chimica Acta, 2000, 83, 1127-1143 and Wu et al., Bioconjugate Chem. 1999, 10, 921-924). In some cases, unnatural nucleic acids include amide linked nucleoside dimers have been prepared for incorporation into oligonucleotides wherein the 3' linked nucleoside in the dimer (5' to 3') comprises a 2'-$OCH_3$ and a 5'-(S)—$CH_3$ (Mesmaeker et al., Synlett, 1997, 1287-1290). Unnatural nucleic acids can include 2'-substituted 5'-$CH_2$ (or O) modified nucleosides (PCT/US92/01020). Unnatural nucleic acids can include 5'-methylenephosphonate DNA and RNA monomers, and dimers (Bohringer et al., Tet. Lett., 1993, 34, 2723-2726; Collingwood et al., Synlett, 1995, 7, 703-705; and Hutter et al., Helvetica Chimica Acta, 2002, 85, 2777-2806). Unnatural nucleic acids can include 5'-phosphonate monomers having a 2'-substitution (US2006/0074035) and other modified 5'-phosphonate monomers (WO1997/35869). Unnatural nucleic acids can include 5'-modified methylenephosphonate monomers (EP614907 and EP629633). Unnatural nucleic acids can include analogs of 5' or 6'-phosphonate ribonucleosides comprising a hydroxyl group at the 5' and/or 6'-position (Chen et al., Phosphorus, Sulfur and Silicon, 2002, 777, 1783-1786; Jung et al., Bioorg. Med. Chem., 2000, 8, 2501-2509; Gallier et al., Eur. J. Org. Chem., 2007, 925-933; and Hampton et al., J. Med. Chem., 1976, 19(8), 1029-1033). Unnatural nucleic acids can include 5'-phosphonate deoxyribonucleoside monomers and dimers having a 5'-phosphate group (Nawrot et al., Oligonucleotides, 2006, 16(1), 68-82). Unnatural nucleic acids can include nucleosides having a 6'-phosphonate group wherein the 5' or/and 6'-position is unsubstituted or substituted with a thio-tert-butyl group ($SC(CH_3)_3$) (and analogs thereof); a methyleneamino group ($CH_2NH_2$) (and analogs thereof) or a cyano group (CN) (and analogs thereof) (Fairhurst et al., Synlett, 2001, 4, 467-472; Kappler et al., J. Med. Chem., 1986, 29, 1030-1038; Kappler et al., J. Med. Chem., 1982, 25, 1179-1184; Vrudhula et al., J. Med. Chem., 1987, 30, 888-894; Hampton et al., J. Med. Chem., 1976, 19, 1371-1377; Geze et al., J. Am. Chem. Soc, 1983, 105(26), 7638-7640; and Hampton et al., J. Am. Chem. Soc, 1973, 95(13), 4404-4414).

In some embodiments, unnatural nucleic acids also include modifications of the sugar moiety. In some cases, nucleic acids contain one or more nucleosides wherein the sugar group has been modified. Such sugar modified nucleosides may impart enhanced nuclease stability, increased binding affinity, or some other beneficial biological property. In certain embodiments, nucleic acids comprise a chemically modified ribofuranose ring moiety. Examples of chemically modified ribofuranose rings include, without limitation, addition of substituent groups (including 5' and/or 2' substituent groups; bridging of two ring atoms to form bicyclic nucleic acids (BNA); replacement of the ribosyl ring oxygen atom with S, N(R), or $C(R_1)(R_2)$ (R═H, $C_1$-$C_{12}$ alkyl or a protecting group); and combinations thereof. Examples of chemically modified sugars can be found in WO2008/101157, US2005/0130923, and WO2007/134181.

In some instances, a modified nucleic acid comprises modified sugars or sugar analogs. Thus, in addition to ribose and deoxyribose, the sugar moiety can be pentose, deoxypentose, hexose, deoxyhexose, glucose, arabinose, xylose, lyxose, or a sugar "analog" cyclopentyl group. The sugar can be in a pyranosyl or furanosyl form. The sugar moiety may be the furanoside of ribose, deoxyribose, arabinose or 2'-O-alkylribose, and the sugar can be attached to the respective heterocyclic bases either in [alpha] or [beta] anomeric configuration. Sugar modifications include, but are not limited to, 2'-alkoxy-RNA analogs, 2'-amino-RNA analogs, 2'-fluoro-DNA, and 2'-alkoxy- or amino-RNA/DNA chimeras. For example, a sugar modification may include 2'-O-methyl-uridine or 2'-O-methyl-cytidine. Sugar modifications include 2'-O-alkyl-substituted deoxyribonucleosides and 2'-O-ethyleneglycol like ribonucleosides. The preparation of these sugars or sugar analogs and the respective "nucleosides" wherein such sugars or analogs are attached to a heterocyclic base (nucleic acid base) is known. Sugar modifications may also be made and combined with other modifications.

Modifications to the sugar moiety include natural modifications of the ribose and deoxy ribose as well as unnatural modifications. Sugar modifications include, but are not limited to, the following modifications at the 2' position: OH; F; O—, S—, or N-alkyl; O—, S-, or N-alkenyl; O—, S- or N-alkynyl; or O-alkyl-O-alkyl, wherein the alkyl, alkenyl and alkynyl may be substituted or unsubstituted $C_1$ to $C_{10}$, alkyl or $C_2$ to $C_{10}$ alkenyl and alkynyl. 2' sugar modifications also include but are not limited to $—O[(CH_2)_nO]_m CH_3$, $—O(CH_2)_nOCH_3$, $—O(CH_2)_nNH_2$, $—O(CH_2)_nCH_3$, $—O(CH_2)_nONH_2$, and $—O(CH_2)_nON[(CH_2)_n CH_3)]2$, where n and m are from 1 to about 10.

Other modifications at the 2' position include but are not limited to: $C_1$ to $C_{10}$ lower alkyl, substituted lower alkyl, alkaryl, aralkyl, O-alkaryl, O-aralkyl, SH, $SCH_3$, OCN, Cl, Br, CN, $CF_3$, $OCF_3$, $SOCH_3$, $SO_2$ $CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of the 5' terminal nucleotide. Modified sugars also include those that contain modifications at the bridging ring oxygen, such as $CH_2$ and S. Nucleotide sugar analogs may also have sugar mimetics such as cyclobutyl moieties in place of the pentofuranosyl sugar. There are numerous United States patents that teach the preparation of such modified sugar structures and which detail and describe a range of base modifications, such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,700,920, each of which is herein incorporated by reference in its entirety.

Examples of nucleic acids having modified sugar moieties include, without limitation, nucleic acids comprising 5'-vinyl, 5'-methyl (R or S), 4'-S, 2'-F, 2'-$OCH_3$, and 2'-O$(CH_2)_2OCH_3$ substituent groups. The substituent at the 2' position can also be selected from allyl, amino, azido, thio, O-allyl, O—($C_1$-$C_{10}$ alkyl), $OCF_3$, $O(CH_2)_2SCH_3$, $O(CH_2)_2—O—N(R_m)(R_n)$, and $O—CH_2—C(═O)—N(R_m)(R_n)$, where each $R_m$ and $R_n$ is, independently, H or substituted or unsubstituted $C_1$-$C_{10}$ alkyl.

In certain embodiments, nucleic acids described herein include one or more bicyclic nucleic acids. In certain such embodiments, the bicyclic nucleic acid comprises a bridge between the 4' and the 2' ribosyl ring atoms. In certain embodiments, nucleic acids provided herein include one or more bicyclic nucleic acids wherein the bridge comprises a 4' to 2' bicyclic nucleic acid. Examples of such 4' to 2' bicyclic nucleic acids include, but are not limited to, one of the formulae: 4'-$(CH_2)$—O-2' (LNA); 4'-$(CH_2)$—S-2'; 4'-$(CH_2)_2$—O-2' (ENA); 4'-$CH(CH_3)$—O-2' and 4'-$CH(CH_2OCH_3)$—O-2', and analogs thereof (see, U.S. Pat. No. 7,399,845); 4'-$C(CH_3)(CH_3)$—O-2' and analogs thereof, (see WO2009/006478, WO2008/150729, US2004/0171570, U.S. Pat. No. 7,427,672, Chattopadhyaya et al., J. Org. Chem., 209, 74, 118-134, and WO2008/154401). Also see, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 2007, 129(26) 8362-8379; Elayadi et al., Curr. Opinion Invens. Drugs, 2001, 2, 558-561; Braasch et al., Chem. Biol, 2001, 8, 1-7; Oram et al., Curr. Opinion Mol. Ther., 2001, 3, 239-243; U.S. Pat. Nos. 4,849,513; 5,015,733; 5,118,800; 5,118,802; 7,053,207; 6,268,490; 6,770,748; 6,794,499; 7,034,133; 6,525,191; 6,670,461; and 7,399,845; International Publication Nos. WO2004/106356, WO1994/14226, WO2005/021570, WO2007/090071, and WO2007/134181; U.S. Patent Publication Nos. US2004/0171570, US2007/0287831, and US2008/0039618; U.S. Provisional Application Nos. 60/989,574, 61/026,995, 61/026,998, 61/056,564, 61/086,231, 61/097,787, and 61/099,844; and International Applications Nos. PCT/US2008/064591, PCT US2008/066154, PCT US2008/068922, and PCT/DK98/00393.

In certain embodiments, nucleic acids comprise linked nucleic acids. Nucleic acids can be linked together using any inter nucleic acid linkage. The two main classes of inter nucleic acid linking groups are defined by the presence or absence of a phosphorus atom. Representative phosphorus containing inter nucleic acid linkages include, but are not limited to, phosphodiesters, phosphotriesters, methylphosphonates, phosphoramidate, and phosphorothioates (P═S). Representative non-phosphorus containing inter nucleic acid linking groups include, but are not limited to, methylenemethylimino (—$CH_2$—N($CH_3$)—O—$CH_2$—), thiodiester (—O—C(O)—S—), thionocarbamate (—O—C(O)(NH)—S—); siloxane (—O—Si$(H)_2$—O—); and N,N*-dimethylhydrazine (—$CH_2$—N($CH_3$)—N($CH_3$)). In certain embodiments, inter nucleic acids linkages having a chiral atom can be prepared as a racemic mixture, as separate enantiomers, e.g., alkylphosphonates and phosphorothioates. Unnatural nucleic acids can contain a single modification. Unnatural nucleic acids can contain multiple modifications within one of the moieties or between different moieties.

Backbone phosphate modifications to nucleic acid include, but are not limited to, methyl phosphonate, phosphorothioate, phosphoramidate (bridging or non-bridging), phosphotriester, phosphorodithioate, phosphodithioate, and boranophosphate, and may be used in any combination. Other non-phosphate linkages may also be used.

In some embodiments, backbone modifications (e.g., methylphosphonate, phosphorothioate, phosphoroamidate and phosphorodithioate internucleotide linkages) can confer immunomodulatory activity on the modified nucleic acid and/or enhance their stability in vivo.

In some instances, a phosphorous derivative (or modified phosphate group) is attached to the sugar or sugar analog moiety in and can be a monophosphate, diphosphate, triphosphate, alkylphosphonate, phosphorothioate, phosphorodithioate, phosphoramidate or the like. Exemplary polynucleotides containing modified phosphate linkages or non-phosphate linkages can be found in Peyrottes et al., 1996, Nucleic Acids Res. 24: 1841-1848; Chaturvedi et al., 1996, Nucleic Acids Res. 24:2318-2323; and Schultz et al., (1996) Nucleic Acids Res. 24:2966-2973; Matteucci, 1997, "Oligonucleotide Analogs: an Overview" in Oligonucleotides as Therapeutic Agents, (Chadwick and Cardew, ed.) John Wiley and Sons, New York, NY; Zon, 1993, "Oligonucleoside Phosphorothioates" in Protocols for Oligonucleotides and Analogs, Synthesis and Properties, Humana Press, pp. 165-190; Miller et al., 1971, JACS 93:6657-6665; Jager et al., 1988, Biochem. 27:7247-7246; Nelson et al., 1997, JOC 62:7278-7287; U.S. Pat. No. 5,453,496; and Micklefield, 2001, Curr. Med. Chem. 8: 1157-1179.

In some cases, backbone modification comprises replacing the phosphodiester linkage with an alternative moiety such as an anionic, neutral or cationic group. Examples of such modifications include: anionic internucleoside linkage; N3' to P5' phosphoramidate modification; boranophosphate DNA; prooligonucleotides; neutral internucleoside linkages such as methylphosphonates; amide linked DNA; methylene (methylimino) linkages; formacetal and thioformacetal linkages; backbones containing sulfonyl groups; morpholino oligos; peptide nucleic acids (PNA); and positively charged deoxyribonucleic guanidine (DNG) oligos (Micklefield, 2001, Current Medicinal Chemistry 8: 1157-1179). A modified nucleic acid may comprise a chimeric or mixed backbone comprising one or more modifications, e.g. a combination of phosphate linkages such as a combination of phosphodiester and phosphorothioate linkages.

Substitutes for the phosphate include, for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439. It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. See also Nielsen et al., Science, 1991, 254, 1497-1500. It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. KY. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EM5OJ, 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1-di-O-hexadecyl-rac-glycero-S—H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochem. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937). Numerous United States patents teach the preparation of such conjugates and include, but are not limited to U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

In some cases, the unnatural nucleic acids further form unnatural base pairs. Exemplary unnatural nucleotides capable of forming an unnatural DNA or RNA base pair (UBP) under conditions in vivo includes, but is not limited to, TPT3, dTPT3, 5SICS, d5SICS, NaM, dNaM, CNMO, dCNMO, and combinations thereof.

In some cases, the unnatural nucleic acids further form unnatural base pairs. Exemplary unnatural nucleotides capable of forming an unnatural DNA or RNA base pair (UBP) under conditions in vivo includes, but is not limited to, 5SICS, d5SICS, NAM, dNaM, and combinations thereof. Other examples of unnatural nucleotides capable of forming unnatural UBPs that may be used to prepare the IL-2 conjugates disclosed herein may be found in Dien et al., J Am Chem Soc., 2018, 140:16115-16123; Feldman et al., J Am Chem Soc, 2017, 139:11427-11433; Ledbetter et al., J Am Chem Soc., 2018, 140:758-765; Dhami et al., Nucleic Acids Res. 2014, 42:10235-10244; Malyshev et al., Nature, 2014, 509:385-388; Betz et al., J Am Chem Soc., 2013, 135:18637-18643; Lavergne et al., J Am Chem Soc. 2013, 135:5408-5419; and Malyshev et al. Proc Natl Acad Sci USA, 2012, 109:12005-12010. In some embodiments, unnatural nucleotides include:

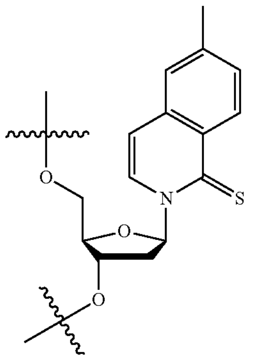

d5SICS

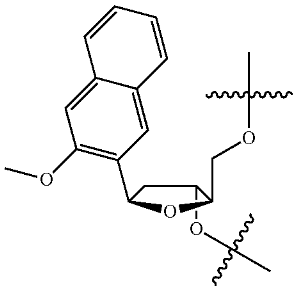

dNAM

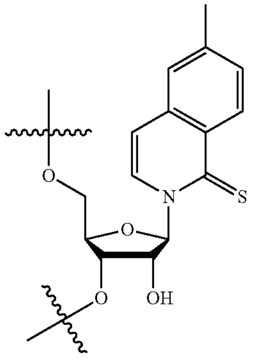

5SICS

-continued

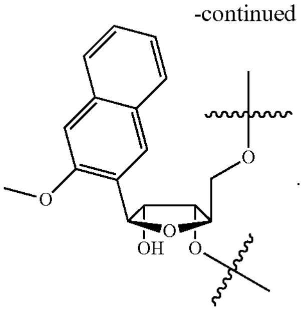

NAM

In some embodiments, the unnatural nucleotides that may be used to prepare the IL-2 conjugates disclosed herein may be derived from a compound of the formula

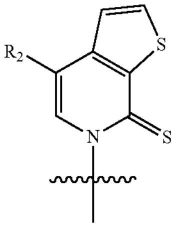

wherein $R_2$ is selected from the group consisting of hydrogen, alkyl, alkenyl, alkynyl, methoxy, methanethiol, methaneseleno, halogen, cyano, and azido; and the wavy line indicates a bond to a ribosyl or 2'-deoxyribosyl, wherein the 5'-hydroxy group of the ribosyl or 2'-deoxyribosyl moiety is in free form, or is optionally bonded to a monophosphate, a diphosphate, or a triphosphate group.

In some embodiments, the unnatural nucleotides that may be used to prepare the IL-2 conjugates disclosed herein may be derived from

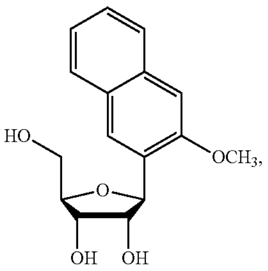

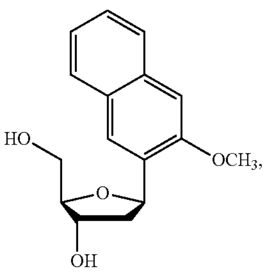

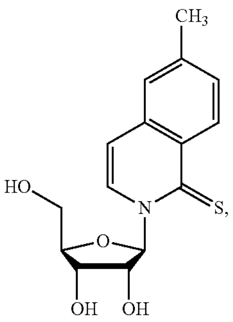

-continued

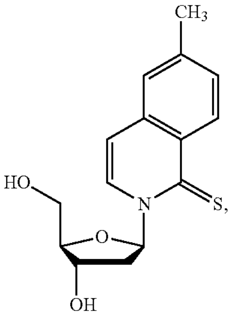

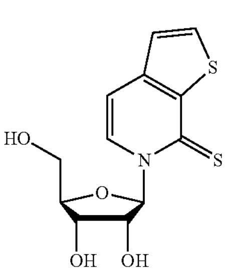

and

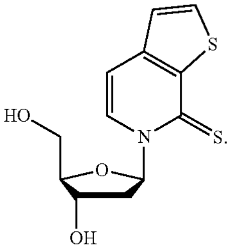

In some embodiments, the unnatural nucleotides that may be used to prepare the IL-2 conjugates disclosed herein include

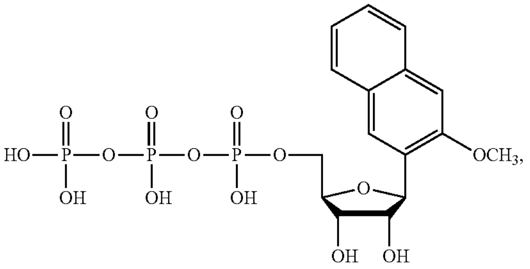

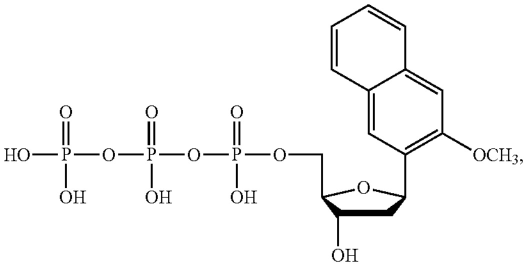

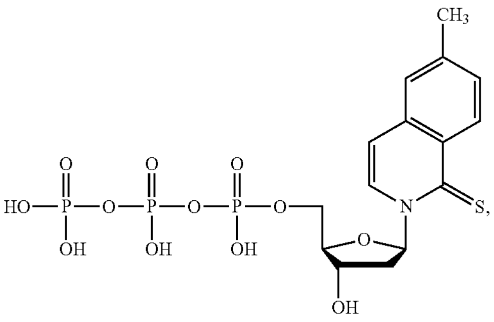

-continued

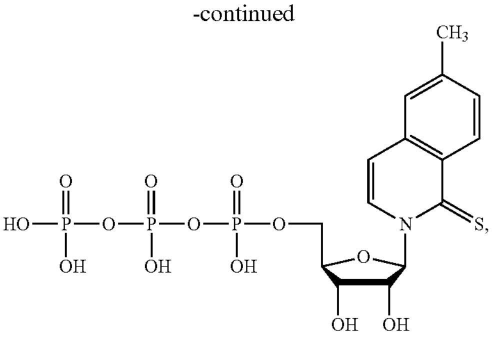

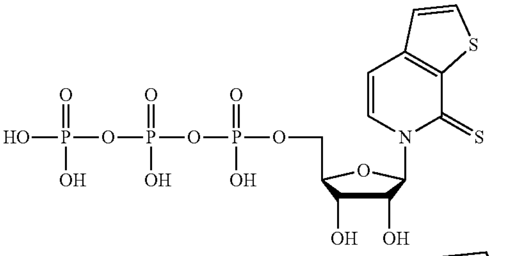

and

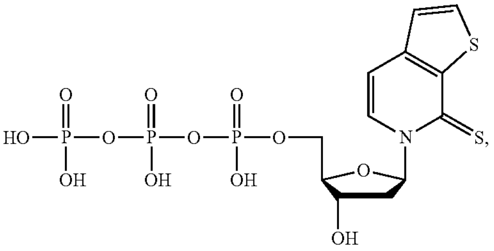

or salts thereof.

In some embodiments, an unnatural base pair generate an unnatural amino acid described in Dumas et al, "Designing logical codon reassignment—Expanding the chemistry in biology," *Chemical Science,* 6: 50-69 (2015).

The host cell into which the constructs or vectors disclosed herein are introduced is cultured or maintained in a suitable medium such that the tRNA, the tRNA synthetase and the protein of interest are produced. The medium also comprises the unnatural amino acid(s) such that the protein of interest incorporates the unnatural amino acid(s). In some embodiments, a nucleoside triphosphate transporter (NTT) from bacteria, plant, or algae is also present in the host cell. In some embodiments, the IL-2 conjugates disclosed herein are prepared by use of a host cell that expresses a NTT. In some embodiments, the nucleotide nucleoside triphosphate transporter used in the host cell may be selected from TpNTT1, TpNTT2, TpNTT3, TpNTT4, TpNTT5, TpNTT6, TpNTT7, TpNTT8 (*T. pseudonana*), PtNTT1, PtNTT2, PtNTT3, PtNTT4, PtNTT5, PtNTT6 (*P. tricornutum*), GsNTT (*Galdieria sulphuraria*), AtNTTT, AtNTT2 (*Arabidopsis thaliana*), CtNTT1, CtNTT2 (*Chlamydia trachomatis*), PamNTT1, PamNTT2 (*Protochlamydia amoebophila*), CcNTT (*Caedibacter caryophilus*), RpNTT1 (*Rickettsia prowazekii*). In some embodiments, the NTT is selected from PtNTT1, PtNTT2, PtNTT3, PtNTT4, PtNTT5, and PtNTT6. In some embodiments, the NTT is PtNTT1. In some embodiments, the NTT is PtNTT2. In some embodiments, the NTT is PtNTT3. In some embodiments, the NTT is PtNTT4. In some embodiments, the NTT is PtNTT5. In some embodiments, the NTT is PtNTT6. Other NTTs that may be used are disclosed in Zhang et al., Nature 2017, 551(7682): 644-647; Malyshev et al. Nature 2014 (509 (7500), 385-388; and Zhang et al. Proc Natl Acad Sci USA, 2017, 114:1317-1322.

The orthogonal tRNA synthetase/tRNA pair charges a tRNA with an unnatural amino acid and incorporates the unnatural amino acid into the polypeptide chain in response to the codon. Exemplary aaRS-tRNA pairs include, but are not limited to, *Methanococcus jannaschii* (Mj-Tyr) aaRS/tRNA pairs, *E. coli* TyrRS (Ec-Tyr)/*B. stearothermophilus* $tRNA_{CUA}$ pairs, *E. coli* LeuRS (Ec-Leu)/*B. stearothermophilus* $tRNA_{CUA}$ pairs, and pyrrolysyl-tRNA pairs. Other aaRS-tRNA pairs that may be used according to the present disclosure include those derived from *M. mazei* those described in Feldman et al., J Am Chem Soc., 2018 140: 1447-1454; and Zhang et al. Proc Natl Acad Sci USA, 2017, 114:1317-1322.

In some embodiments are provided methods of preparing the IL-2 conjugates disclosed herein in a cellular system that expresses a NTT and a tRNA synthetase. In some embodiments described herein, the NTT is selected from PtNTT1, PtNTT2, PtNTT3, PtNTT4, PtNTT5, and PtNTT6, and the tRNA synthetase is selected from *Methanococcus jannaschii, E. coli* TyrRS (Ec-Tyr)/*B. stearothermophilus*, and *M. mazei*. In some embodiments, the NTT is PtNTT1 and the tRNA synthetase is derived from *Methanococcus jannaschii, E. coli* TyrRS (Ec-Tyr)/*B. stearothermophilus*, or *M. mazei*. In some embodiments, the NTT is PtNTT2 and the tRNA synthetase is derived from *Methanococcus jannaschii, E. coli* TyrRS (Ec-Tyr)/*B. stearothermophilus*, or *M. mazei*. In some embodiments, the NTT is PtNTT3 and the tRNA synthetase is derived from *Methanococcus jannaschii, E. coli* TyrRS (Ec-Tyr)/*B. stearothermophilus*, or *M. mazei*. In some embodiments, the NTT is PtNTT3 and the tRNA synthetase is derived from *Methanococcus jannaschii, E. coli* TyrRS (Ec-Tyr)/*B. stearothermophilus*, or *M. mazei*. In some embodiments, the NTT is PtNTT4 and the tRNA synthetase is derived from *Methanococcus jannaschii, E. coli* TyrRS (Ec-Tyr)/*B. stearothermophilus*, or *M. mazei*. In some embodiments, the NTT is PtNTT5 and the tRNA synthetase is derived from *Methanococcus jannaschii, E. coli* TyrRS (Ec-Tyr)/*B. stearothermophilus*, or *M. mazei*. In some embodiments, the NTT is PtNTT6 and the tRNA synthetase is derived from *Methanococcus jannaschii, E. coli* TyrRS (Ec-Tyr)/*B. stearothermophilus*, or *M. mazei*.

A cytokine (e.g., IL-2) polypeptide comprising an unnatural amino acid(s) are prepared by introducing the nucleic acid constructs described herein comprising the tRNA and tRNA synthetase and comprising a nucleic acid sequence of interest with one or more in-frame orthogonal (stop) codons into a host cell. The host cell is exposed to a physiological solution comprising the unnatural amino acid(s), and the host cells are then maintained under conditions which permit expression of the protein of interest's encoding sequence. The unnatural amino acid(s) is incorporated into the polypeptide chain in response to the codon. For example, one or more unnatural amino acids are incorporated into the cytokine (e.g., IL-2) polypeptide. Alternatively, two or more unnatural amino acids may be incorporated into the cytokine (e.g., IL-2) polypeptide at two or more sites in the protein.

In some embodiments, the IL-2 conjugates disclosed herein may be prepared in a cell, such as *E. coli*, comprising (a) nucleoside triphosphate transporter PtNTT2 (including a truncated variant in which the first 65 amino acid residues of the full-length protein are deleted), (b) a plasmid comprising a double-stranded oligonucleotide that encodes an IL-2 variant having a desired amino acid sequence and that contains a unnatural base pair comprising a first unnatural nucleotide and a second unnatural nucleotide to provide a codon at the desired position at which an unnatural amino acid, such as N6-((2-azidoethoxy)-carbonyl)-L-lysine (AzK), will be incorporated, (c) a plasmid encoding a tRNA derived from *M. mazei* and which comprises an unnatural nucleotide to provide a recognized anticodon (to the codon of the IL-2 variant) in place of its native sequence, and (d) a plasmid encoding a *M. barkeri* derived pyrrolysyl-tRNA synthetase (Mb PylRS), which may be the same plasmid that encodes the tRNA or a different plasmid. In some embodiments, the cell is further supplemented with deoxyribo triphosphates comprising one or more unnatural bases. In some embodiments, the cell is further supplemented with ribo triphosphates comprising one or more unnatural bases. In some embodiments, the cells is further supplemented with one or more unnatural amino acids, such as N6-((2-azidoethoxy)-carbonyl)-L-lysine (AzK). In some embodiments, the double-stranded oligonucleotide that encodes the amino acid sequence of the desired IL-2 variant contains a codon AXC at, for example, position 35, 42, 43, 62 or 65 of the sequence that encodes the protein having SEQ ID NO: 4 (IL-2_C125S), or at position 34, 41, 42, 61 or 64 of the sequence that encodes the protein having SEQ ID NO: 3 (aldesleukin), wherein X is an unnatural nucleotide. In some embodiments, the cell further comprises a plasmid, which may be the protein expression plasmid or another plasmid, that encodes an orthogonal tRNA gene from *M. mazei* that comprises an AXC-matching anticodon GYT in place of its native sequence, wherein Y is an unnatural nucleotide that is complementary and may be the same or different as the unnatural nucleotide in the codon. In some embodiments, the unnatural nucleotide in the codon is different than and complimentary to the unnatural nucleotide in the anti-codon. In some embodiments, the unnatural nucleotide in the codon is the same as the unnatural nucleotide in the anti-codon. In some embodiments, the first and second unnatural nucleotides of the unnatural base pair in the double-stranded oligonucleotide may be derived from

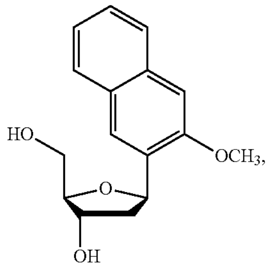

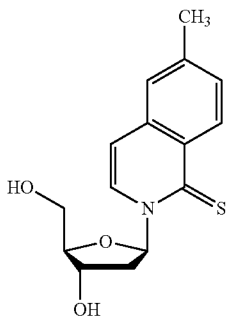
and
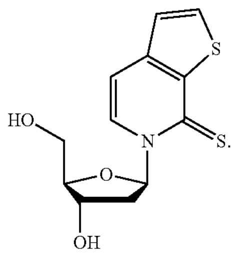

In some embodiments, the first and second unnatural nucleotides of the unnatural base pair in the double-stranded oligonucleotide may be derived from

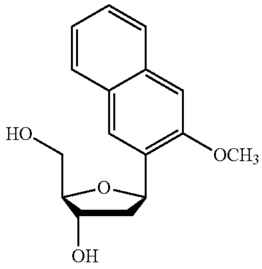

and

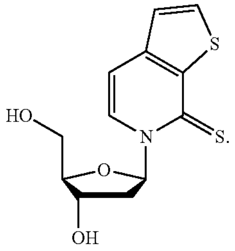

In some embodiments, the triphosphates of the first and second unnatural nucleotides include,

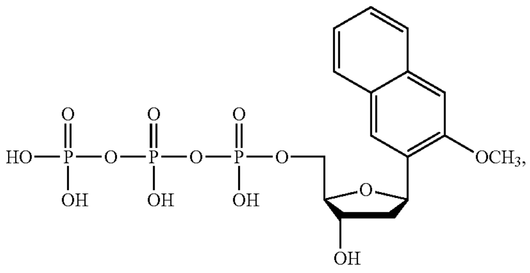

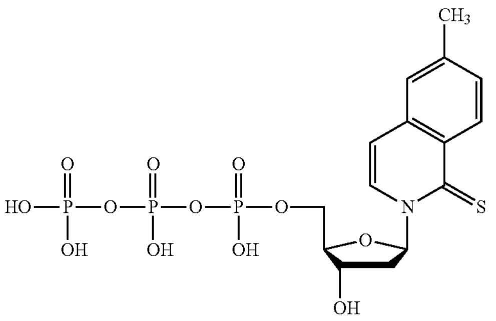

and

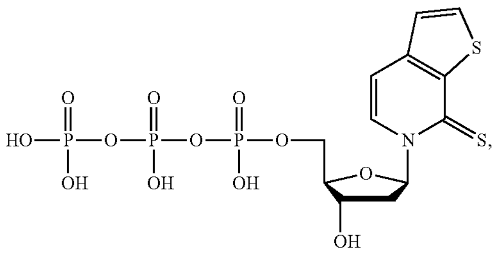

or salts thereof. In some embodiments, the triphosphates of the first and second unnatural nucleotides include,

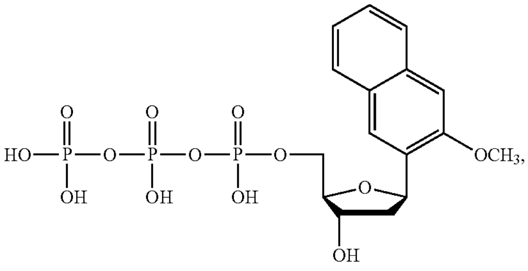

and

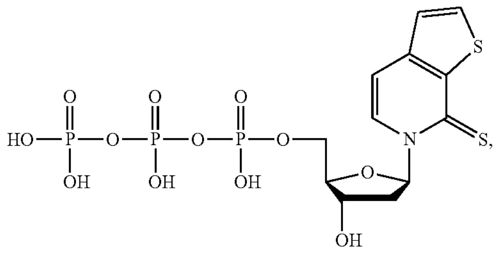

or salts thereof.

In some embodiments, the mRNA derived the double-stranded oligonucleotide comprising a first unnatural nucleotide and a second unnatural nucleotide may comprise a codon comprising an unnatural nucleotide derived from

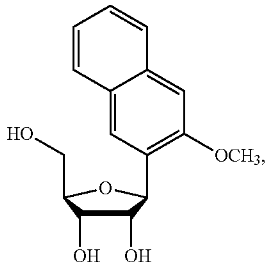

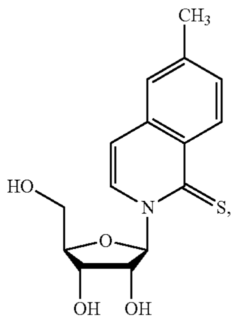

and

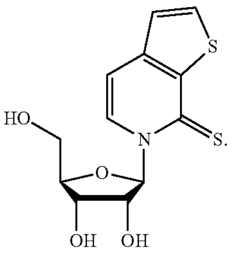

In some embodiments, the *M. mazei* tRNA may comprise an anti-codon comprising an unnatural nucleotide that recognizes the codon comprising the unnatural nucleotide of the mRNA. The anti-codon in the *M. mazei* tRNA may comprise an unnatural nucleotide derived from

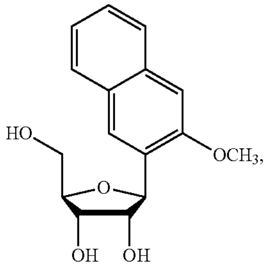

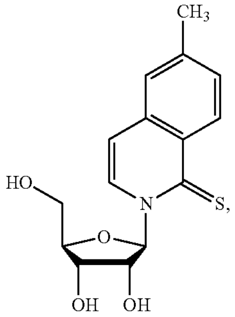

and

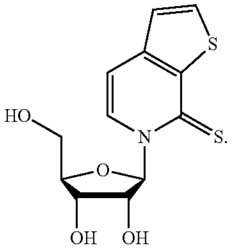

In some embodiments, the mRNA comprises an unnatural nucleotide derived from

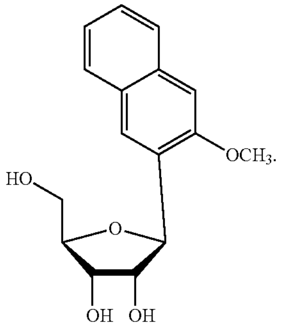

In some embodiments, the mRNA comprises an unnatural nucleotide derived from

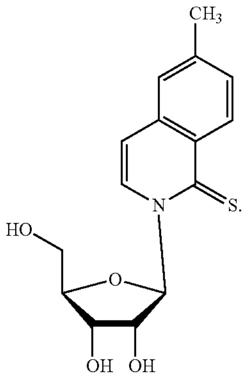

In some embodiments, the mRNA comprises an unnatural nucleotide derived from

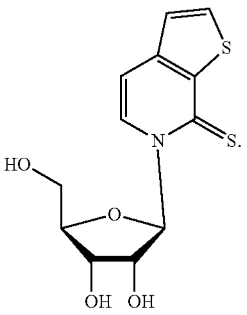

In some embodiments, the tRNA comprises an unnatural nucleotide derived from

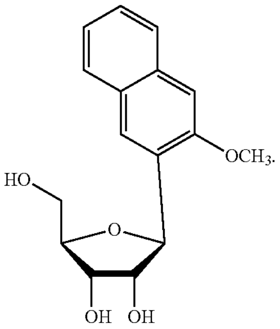

In some embodiments, the tRNA comprises an unnatural nucleotide derived from

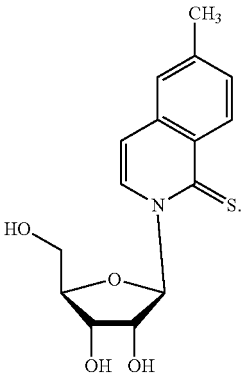

In some embodiments, the tRNA comprises an unnatural nucleotide derived from

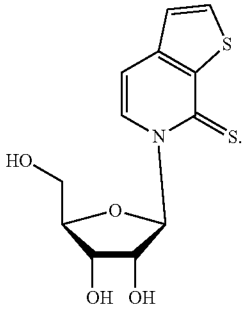

In some embodiments, the mRNA comprises an unnatural nucleotide derived from

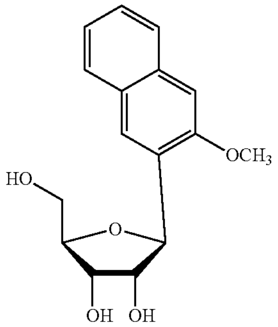

and the tRNA comprises an unnatural nucleotide derived from

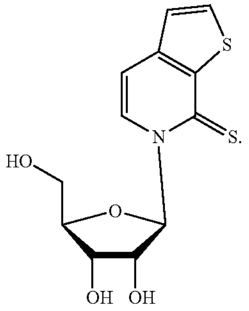

In some embodiments, the mRNA comprises an unnatural nucleotide derived from

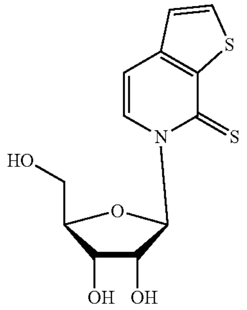

and the tRNA comprises an unnatural nucleotide derived from

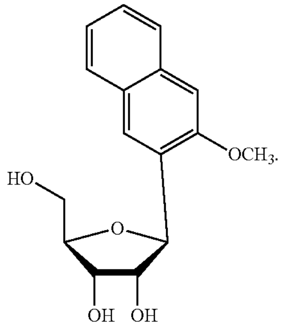

The host cell is cultured in a medium containing appropriate nutrients, and is supplemented with (a) the triphosphates of the deoxyribo nucleosides comprising one or more unnatural bases that are necessary for replication of the plasmid(s) encoding the cytokine gene harboring the codon, (b) the triphosphates of the ribo nucleosides comprising one or more unnatural bases necessary for transcription of (i) the mRNA corresponding to the coding sequence of the cytokine and containing the codon comprising one or more unnatural bases, and (ii) the tRNA containing the anticodon comprising one or more unnatural bases, and (c) the unnatural amino acid(s) to be incorporated in to the polypeptide sequence of the cytokine of interest. The host cells are then maintained under conditions which permit expression of the protein of interest.

In some cases, the codon comprising an unnatural base and the anticodon comprising an unnatural base may be selected from the following pairs, wherein X and Y each comprise a base independently selected from the group consisting of:

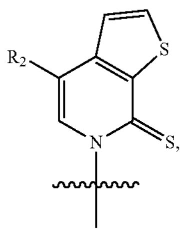

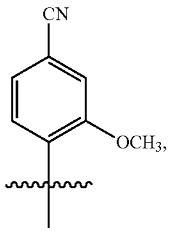

-continued

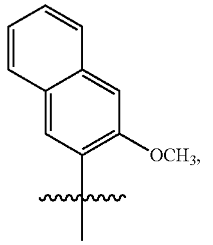
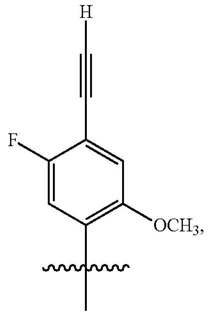
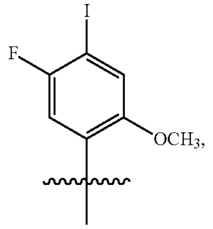
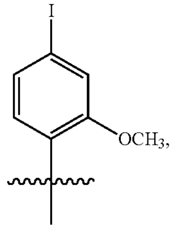
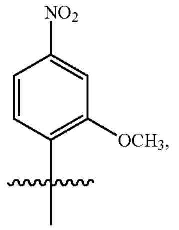
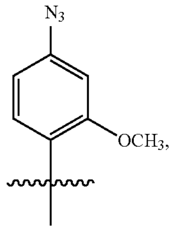
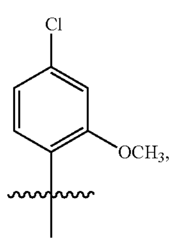
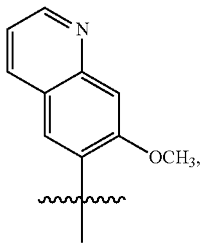
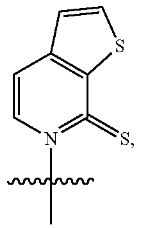
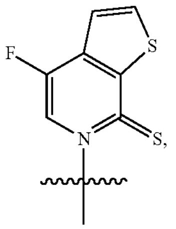
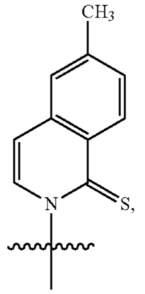
and
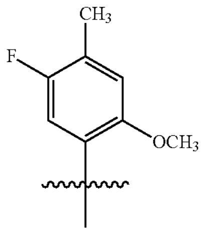

wherein $R_2$ is selected from the group consisting of hydrogen, alkyl, alkenyl, alkynyl, methoxy, methanethiol, methaneseleno, halogen, cyano, and azido; and in each case the wavy line indicates a bond to a ribosyl when X and Y comprise mRNA or tRNA, or 2'-deoxyribosyl when X and Y comprise DNA.

| Codon (mRNA) | Anticodon (tRNA) |
|---|---|
| UUX | YAA or XAA |
| UGX | YCA or XCA |
| CGX | YCG or XCG |
| AGX | YCU or XCU |
| GAX | YUC or XUC |
| CAX | YUG or XUG |
| GXU | AYC |
| CXU | AYG |
| GXG | CYC |
| AXG | CYU |
| GXC | GYC |
| AXC | GYU |
| GXA | UYC |
| CXC | GYG |
| UXC | GYA |
| AUX | YAU or XAU |
| CUX | XAG or YAG |
| GUX | XAC or YAC |
| UAX | XUA or YUA |
| GGX | XCC or YCC |

The resulting protein comprising the one or more unnatural amino acids, Azk for example, that is expressed may be purified by methods known to those of ordinary skill in the art and may then be allowed to react with an alkyne, such as DBCO comprising a PEG chain having a desired average molecular weight as disclosed herein, under conditions known to those of ordinary skill in the art, to afford the IL-2 conjugates disclosed herein. Other methods are known to those of ordinary skill in the art, such as those disclosed in Zhang et al., Nature 2017, 551(7682): 644-647; WO 2015157555; WO 2015021432; WO 2016115168; WO 2017106767; WO 2017223528; WO 2019014262; WO 2019014267; WO 2019028419; and WO2019/028425.

Alternatively, a cytokine (e.g., IL-2) polypeptide comprising an unnatural amino acid(s) are prepared by introducing the nucleic acid constructs described herein comprising the tRNA and aminoacyl tRNA synthetase and comprising a nucleic acid sequence of interest with one or more in-frame orthogonal (stop) codons into a host cell. The host cell is cultured in a medium containing appropriate nutrients, is supplemented with (a) the triphosphates of the deoxyribo nucleosides comprising one or more unnatural bases required for replication of the plasmid(s) encoding the cytokine gene harboring the new codon and anticodon, (b) the triphosphates of the ribo nucleosides required for transcription of the mRNA corresponding to (i) the cyctokine sequence containing the codon, and (ii) the orthogonal tRNA containing the anticodon, and (c) the unnatural amino acid(s). The host cells are then maintained under conditions which permit expression of the protein of interest. The unnatural amino acid(s) is incorporated into the polypeptide chain in response to the unnatural codon. For example, one or more unnatural amino acids are incorporated into the cytokine (e.g., IL-2) polypeptide. Alternatively, two or more unnatural amino acids may be incorporated into the cytokine (e.g., IL-2) polypeptide at two or more sites in the protein.

Once the cytokine (e.g., IL-2) polypeptide incorporating the unnatural amino acid(s) has been produced in the host cell it can be extracted therefrom by a variety of techniques known in the art, including enzymatic, chemical and/or osmotic lysis and physical disruption. The cytokine (e.g., IL-2) polypeptide can be purified by standard techniques known in the art such as preparative ion exchange chromatography, hydrophobic chromatography, affinity chromatography, or any other suitable technique known to those of ordinary skill in the art.

Suitable host cells may include bacterial cells (e.g., *E. coli*, BL21(DE3)), but most suitably host cells are eukaryotic cells, for example insect cells (e.g. *Drosophila* such as *Drosophila melanogaster*), yeast cells, nematodes (e.g. Celegans), mice (e.g. *Mus musculus*), or mammalian cells (such as Chinese hamster ovary cells (CHO) or COS cells, human 293T cells, HeLa cells, NIH 3T3 cells, and mouse erythroleukemia (MEL) cells) or human cells or other eukaryotic cells. Other suitable host cells are known to those skilled in the art. Suitably, the host cell is a mammalian cell—such as a human cell or an insect cell. In some embodiments, the suitable host cells comprise *E coli*.

Other suitable host cells which may be used generally in the embodiments of the invention are those mentioned in the examples section. Vector DNA can be introduced into host cells via conventional transformation or transfection techniques. As used herein, the terms "transformation" and "transfection" are intended to refer to a variety of well-recognized techniques for introducing a foreign nucleic acid molecule (e.g., DNA) into a host cell, including calcium phosphate or calcium chloride co-precipitation, DEAE-dextran-mediated transfection, lipofection, or electroporation. Suitable methods for transforming or transfecting host cells are well known in the art.

When creating cell lines, it is generally preferred that stable cell lines are prepared. For stable transfection of mammalian cells for example, it is known that, depending upon the expression vector and transfection technique used, only a small fraction of cells may integrate the foreign DNA into their genome. In order to identify and select these integrants, a gene that encodes a selectable marker (for example, for resistance to antibiotics) is generally introduced into the host cells along with the gene of interest. Preferred selectable markers include those that confer resistance to drugs, such as G418, hygromycin, or methotrexate. Nucleic acid molecules encoding a selectable marker can be introduced into a host cell on the same vector or can be introduced on a separate vector. Cells stably transfected with the introduced nucleic acid molecule can be identified by drug selection (for example, cells that have incorporated the selectable marker gene will survive, while the other cells die).

In one embodiment, the constructs described herein are integrated into the genome of the host cell. An advantage of stable integration is that the uniformity between individual cells or clones is achieved. Another advantage is that selection of the best producers may be carried out. Accordingly, it is desirable to create stable cell lines. In another embodiment, the constructs described herein are transfected into a host cell. An advantage of transfecting the constructs into the host cell is that protein yields may be maximized. In one aspect, there is described a cell comprising the nucleic acid construct or the vector described herein.

When multiple unnatural amino acids are to be incorporated into a cytokine (e.g., IL-2) polypeptide, it will be understood that multiple codons will need to be incorporated into the encoding nucleic acid sequence at the desired positions such that the tRNA synthetase/tRNA pairs can direct the incorporation of the unnatural amino acids in response to the codon(s). At least 1, 2, 3, 4, or more codon encoding nucleic acids maybe incorporated into the nucleic acid sequence of interest.

When it is desired to incorporate more than one type of unnatural amino acid into the protein of interest into a single protein, a second or further orthogonal tRNA-tRNA synthetase pair may be used to incorporate the second or further unnatural amino acid; suitably said second or further orthogonal tRNA-tRNA synthetase pair recognizes a different codon in the nucleic acid encoding the protein of interest so that the two or more unnatural amino acids can be specifically incorporated into different defined sites in the protein in a single manufacturing step. In certain embodiments, two or more orthogonal tRNA-tRNA synthetase pairs may therefore be used.

Once the cytokine (e.g., IL-2) polypeptide incorporating the unnatural amino acid(s) has been produced in the host cell it can be extracted therefrom by a variety of techniques known in the art, including enzymatic, chemical and/or osmotic lysis and physical disruption. The cytokine (e.g., IL-2) polypeptide can be purified by standard techniques known in the art such as preparative chromatography, affinity purification or any other suitable technique.

Suitable host cells may include bacterial cells (e.g., *E. coli*, BL21(DE3)), but most suitably host cells are eukaryotic cells, for example insect cells (e.g. *Drosophila* such as *Drosophila melanogaster*), yeast cells, nematodes (e.g. Celegans), mice (e.g. *Mus musculus*), or mammalian cells (such as Chinese hamster ovary cells (CHO) or COS cells, human 293T cells, HeLa cells, NIH 3T3 cells, and mouse erythroleukemia (MEL) cells) or human cells or other eukaryotic cells. Other suitable host cells are known to those skilled in the art. Suitably, the host cell is a mammalian cell—such as a human cell or an insect cell.

Other suitable host cells which may be used generally in the embodiments of the invention are those mentioned in the examples section. Vector DNA can be introduced into host cells via conventional transformation or transfection techniques. As used herein, the terms "transformation" and "transfection" are intended to refer to a variety of well-recognized techniques for introducing a foreign nucleic acid molecule (e.g., DNA) into a host cell, including calcium phosphate or calcium chloride co-precipitation, DEAE-dextran-mediated transfection, lipofection, or electroporation. Suitable methods for transforming or transfecting host cells are well known in the art.

When creating cell lines, it is generally preferred that stable cell lines are prepared. For stable transfection of mammalian cells for example, it is known that, depending upon the expression vector and transfection technique used, only a small fraction of cells may integrate the foreign DNA into their genome. In order to identify and select these integrants, a gene that encodes a selectable marker (for example, for resistance to antibiotics) is generally introduced into the host cells along with the gene of interest. Preferred selectable markers include those that confer resistance to drugs, such as G418, hygromycin, or methotrexate. Nucleic acid molecules encoding a selectable marker can be introduced into a host cell on the same vector or can be introduced on a separate vector. Cells stably transfected with the introduced nucleic acid molecule can be identified by drug selection (for example, cells that have incorporated the selectable marker gene will survive, while the other cells die).

In one embodiment, the constructs described herein are integrated into the genome of the host cell. An advantage of stable integration is that the uniformity between individual cells or clones is achieved. Another advantage is that selection of the best producers maybe carried out. Accordingly, it is desirable to create stable cell lines. In another embodiment, the constructs described herein are transfected into a host cell. An advantage of transfecting the constructs into the host cell is that protein yields may be maximized. In one aspect, there is described a cell comprising the nucleic acid construct or the vector described herein.

Pharmaceutical Compositions and Formulations

In some embodiments, the pharmaceutical composition and formulations described herein are administered to a subject by multiple administration routes, including but not limited to, parenteral, oral, buccal, rectal, sublingual, or transdermal administration routes. In some cases, parenteral administration comprises intravenous, subcutaneous, intramuscular, intracerebral, intranasal, intra-arterial, intra-articular, intradermal, intravitreal, intraosseous infusion, intraperitoneal, or intrathecal administration. In some instances, the pharmaceutical composition is formulated for local administration. In other instances, the pharmaceutical composition is formulated for systemic administration. In some embodiments, the pharmaceutical composition and formulations described herein are administered to a subject by intravenous, subcutaneous, and intramuscular administration. In some embodiments, the pharmaceutical composition and formulations described herein are administered to a subject by intravenous administration. In some embodiments, the pharmaceutical composition and formulations described herein are administered to a subject by administration. In some embodiments, the pharmaceutical composition and formulations described herein are administered to a subject by intramuscular administration.

In some embodiments, the pharmaceutical formulations include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations (e.g., nanoparticle formulations), and mixed immediate and controlled release formulations.

In some embodiments, the pharmaceutical formulations include a carrier or carrier materials selected on the basis of compatibility with the composition disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. Pharmaceutically compatible carrier materials include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995), Hoover, John E., *Remington's Pharmaceutical Sciences*, Mack Publishing Co., Easton, Pennsylvania 1975, Liberman, H. A. and Lachman, L., Eds., *Pharmaceutical Dosage Forms*, Marcel Decker, New York, N.Y., 1980, and *Pharmaceutical Dosage Forms and Drug Delivery Systems*, Seventh Ed. (Lippincott Williams & Wilkins 1999).

In some cases, the pharmaceutical composition is formulated as an immunoliposome, which comprises a plurality of IL-2 conjugates bound either directly or indirectly to lipid bilayer of liposomes. Exemplary lipids include, but are not limited to, fatty acids; phospholipids; sterols such as cholesterols; sphingolipids such as sphingomyelin; glycosphingolipids such as gangliosides, globocides, and cerebrosides; surfactant amines such as stearyl, oleyl, and linoleyl amines. In some instances, the lipid comprises a cationic lipid. In some instances, the lipid comprises a phospholipid. Exemplary phospholipids include, but are not limited to, phosphatidic acid ("PA"), phosphatidylcholine ("PC"), phosphatidylglycerol ("PG"), phophatidylethanolamine ("PE"), phophatidylinositol ("PI"), and phosphatidylserine ("PS"), sphingomyelin (including brain sphingomyelin), lecithin, lysolecithin, lysophosphatidylethanolamine, cerebrosides, diarachidoylphosphatidylcholine ("DAPC"), didecanoyl-L-alpha-phosphatidylcholine ("DDPC"), dielaidoylphosphatidylcholine ("DEPC"), dilauroylphosphatidylcholine ("DLPC"), dilinoleoylphosphatidylcholine, dimyristoylphosphatidylcholine ("DMPC"), dioleoylphosphatidylcholine ("DOPC"), dipalmitoylphosphatidylcholine ("DPPC"), distearoylphosphatidylcholine ("DSPC"), 1-palmitoyl-2-oleoyl-phosphatidylcholine ("POPC"), diarachidoylphosphatidylglycerol ("DAPG"), didecanoyl-L-alpha-phosphatidylglycerol ("DDPG"), dielaidoylphosphatidylglycerol ("DEPG"), dilauroylphosphatidylglycerol ("DLPG"), dilinoleoylphosphatidylglycerol, dimyristoylphosphatidylglycerol ("DMPG"), dioleoylphosphatidylglycerol ("DOPG"), dipalmitoylphosphatidylglycerol ("DPPG"), distearoylphosphatidylglycerol ("DSPG"), 1-palmitoyl-2-oleoyl-phosphatidylglycerol ("POPG"), diarachidoylphosphatidylethanolamine ("DAPE"), didecanoyl-L-alpha-phosphatidylethanolamine ("DDPE"), dielaidoylphosphatidylethanolamine ("DEPE"), dilauroylphosphatidylethanolamine ("DLPE"), dilinoleoylphosphatidylethanolamine, dimyristoylphosphatidylethanolamine ("DMPE"), dioleoylphosphatidylethanolamine ("DOPE"), dipalmitoylphosphatidylethanolamine ("DPPE"), distearoylphosphatidylethanolamine ("DSPE"), 1-palmitoyl-2-oleoyl-phosphatidylethanolamine ("POPE"), diarachidoylphosphatidylinositol ("DAPI"), didecanoyl-L-alpha-phosphatidylinositol ("DDPI"), dielaidoylphosphatidylinositol ("DEPI"), dilauroylphosphatidylinositol ("DLPI"), dilinoleoylphosphatidylinositol, dimyristoylphosphatidylinositol ("DMPI"), dioleoylphosphatidylinositol ("DOPI"), dipalmitoylphosphatidylinositol ("DPPI"), distearoylphosphatidylinositol ("DSPI"), 1-palmitoyl-2-oleoyl-phosphatidylinositol ("POPI"), diarachidoylphosphatidylserine ("DAPS"), didecanoyl-L-alpha-phosphatidylserine ("DDPS"), dielaidoylphosphatidylserine ("DEPS"), dilauroylphosphatidylserine ("DLPS"), dilinoleoylphosphatidylserine, dimyristoylphosphatidylserine ("DMPS"), dioleoylphosphatidylserine ("DOPS"), dipalmitoylphosphatidylserine ("DPPS"), distearoylphosphatidylserine ("DSPS"), 1-palmitoyl-2-oleoyl-phosphatidylserine ("POPS"), diarachidoyl sphingomyelin, didecanoyl sphingomyelin, dielaidoyl sphingomyelin, dilauroyl sphingomyelin, dilinoleoyl sphingomyelin, dimyristoyl sphingomyelin, sphingomyelin, dioleoyl sphingomyelin, dipalmitoyl sphingomyelin, distearoyl sphingomyelin, and 1-palmitoyl-2-oleoyl-sphingomyelin.

In some instances, the pharmaceutical formulations further include pH adjusting agents or buffering agents which include acids such as acetic, boric, citric, lactic, phosphoric and hydrochloric acids, bases such as sodium hydroxide, sodium phosphate, sodium borate, sodium citrate, sodium acetate, sodium lactate and tris-hydroxymethylaminomethane, and buffers such as citrate/dextrose, sodium bicarbonate and ammonium chloride. Such acids, bases and buffers are included in an amount required to maintain pH of the composition in an acceptable range.

In some instances, the pharmaceutical formulation includes one or more salts in an amount required to bring osmolality of the composition into an acceptable range.

Such salts include those having sodium, potassium or ammonium cations and chloride, citrate, ascorbate, borate, phosphate, bicarbonate, sulfate, thiosulfate or bisulfite anions, suitable salts include sodium chloride, potassium chloride, sodium thiosulfate, sodium bisulfite and ammonium sulfate.

In some embodiments, the pharmaceutical formulations include, but are not limited to, sugars like trehalose, sucrose, mannitol, maltose, glucose, or salts like potassium phosphate, sodium citrate, ammonium sulfate and/or other agents such as heparin to increase the solubility and in vivo stability of polypeptides.

In some instances, the pharmaceutical formulations further include diluent which are used to stabilize compounds because they can provide a more stable environment. Salts dissolved in buffered solutions (which also can provide pH control or maintenance) are utilized as diluents in the art, including, but not limited to a phosphate buffered saline solution. In certain instances, diluents increase bulk of the composition to facilitate compression or create sufficient bulk for homogenous blend for capsule filling. Such compounds can include e.g., lactose, starch, mannitol, sorbitol, dextrose, microcrystalline cellulose such as Avicel®, dibasic calcium phosphate, dicalcium phosphate dihydrate, tricalcium phosphate, calcium phosphate, anhydrous lactose, spray-dried lactose, pregelatinized starch, compressible sugar, such as Di-Pac® (Amstar), mannitol, hydroxypropylmethylcellulose, hydroxypropylmethylcellulose acetate stearate, sucrose-based diluents, confectioner's sugar, monobasic calcium sulfate monohydrate, calcium sulfate dihydrate, calcium lactate trihydrate, dextrates, hydrolyzed cereal solids, amylose, powdered cellulose, calcium carbonate, glycine, kaolin, mannitol, sodium chloride, inositol, bentonite, and the like. In some embodiments, the IL-2 conjugates disclosed herein may be used in pharmaceutical formulations comprising histidine, sorbitol, and polysorbate 80, or any combination that affords a stable formulation and can be administered to subjects in need thereof. In one embodiment, the IL-2 conjugates disclosed herein may be presented as a finished drug product in a suitable container, such as a vial, as follows: IL-2 conjugate (about 2 mg to about 10 mg); L-histidine (about 0.5 mg to about 2 mg); L-histidine hydrochloride (about 1 mg to about 2 mg); sorbitol (about 20 mg to about 80 mg); and polysorbate 80 (about 0.1 mg to about 0.2 mg); with a sufficient quantity of water for injection to provide a liquid formulation suitable for use in the disclosed methods.

In some cases, the pharmaceutical formulations include disintegration agents or disintegrants to facilitate the breakup or disintegration of a substance. The term "disintegrate" include both the dissolution and dispersion of the dosage form when contacted with gastrointestinal fluid. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel®PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

In some instances, the pharmaceutical formulations include filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

Lubricants and glidants are also optionally included in the pharmaceutical formulations described herein for preventing, reducing or inhibiting adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil©, a starch such as corn starch, silicone oil, a surfactant, and the like.

Plasticizers include compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. Plasticizers can also function as dispersing agents or wetting agents.

Solubilizers include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

Stabilizers include compounds such as any antioxidation agents, buffers, acids, preservatives and the like. Exemplary stabilizers include L-arginine hydrochloride, tromethamine, albumin (human), citric acid, benzyl alcohol, phenol, disodium biphosphate dehydrate, propylene glycol, metacresol or *m*-cresol, zinc acetate, polysorbate-20 or Tween® 20, or trometamol.

Suspending agents include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Surfactants include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Additional surfactants include polyoxyethylene fatty acid glycerides and vegetable oils, e.g., polyoxyethylene (60) hydrogenated castor oil, and polyoxyethylene alkylethers and alkylphenyl ethers, e.g., octoxynol 10, octoxynol 40. Sometimes, surfactants is included to enhance physical stability or for other purposes.

Viscosity enhancing agents include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

Wetting agents include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Therapeutic Regimens

In some embodiments, the pharmaceutical compositions described herein are administered for therapeutic applications. In some embodiments, the pharmaceutical composition is administered once per day, twice per day, three times per day or more. The pharmaceutical composition is administered daily, every day, every alternate day, five days a week, once a week, every other week, two weeks per month, three weeks per month, once a month, twice a month, three times per month, or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In the case wherein the patient's status does improve, upon the doctor's discretion the administration of the composition is given continuously, alternatively, the dose of the composition being administered is temporarily reduced or temporarily suspended for a certain length of time (i.e., a "drug holiday"). In some instances, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

In some embodiments, an effective amount of the IL-2 conjugate is administered to a subject in need thereof once per week, once every two weeks, once every three weeks, once every 4 weeks, once every 5 weeks, once every 6 weeks, once every 7 weeks, once every 8 weeks, once every 9 weeks, once every 10 weeks, once every 11 weeks, once every 12 weeks, once every 13 weeks, once every 14 weeks, once every 15 weeks, once every 16 weeks, once every 17 weeks, once every 18 weeks, once every 19 weeks, once every 20 weeks, once every 21 weeks, once every 22 weeks, once every 23 weeks, once ever 24 weeks, once every 25 weeks, once every 26 weeks, once every 27 weeks, or once every 28 weeks. In some embodiments, an effective amount of the IL-2 conjugate is administered to a subject in need thereof once per week. In some embodiments, an effective amount of the IL-2 conjugate is administered to a subject in need thereof once every two weeks. In some embodiments, an effective amount of the IL-2 conjugate is administered to a subject in need thereof once every three weeks. In some embodiments, an effective amount of the IL-2 conjugate is administered to a subject in need thereof once every 4 weeks. In some embodiments, an effective amount of the IL-2 conjugate is administered to a subject in need thereof once every 5 weeks. In some embodiments, an effective amount of the IL-2 conjugate is administered to a subject in need thereof once every 6 weeks. In some embodiments, an effective amount of the IL-2 conjugate is administered to a subject in need thereof once every 7 weeks. In some embodiments, an effective amount of the IL-2 conjugate is administered to a subject in need thereof once every 8 weeks. In some embodiments, an effective amount of the IL-2 conjugate is administered to a subject in need thereof once every 9 weeks. In some embodiments, an effective amount of the IL-2 conjugate is administered to a subject in need thereof once every 10 weeks. In some embodiments, an effective amount of the IL-2 conjugate is administered to a subject in need thereof once every 11 weeks. In some embodiments, an effective amount of the IL-2 conjugate is administered to a subject in need thereof once every 12 weeks. In some embodiments, an effective amount of the IL-2 conjugate is administered to a subject in need thereof once every 13 weeks. In some embodiments, an effective amount of the IL-2 conjugate is administered to a subject in need thereof once every 14 weeks. In some embodiments, an effective amount of the IL-2 conjugate is administered to a subject in need thereof once every 15 weeks. In some embodiments, an effective amount of the IL-2 conjugate is administered to a subject in need thereof once every 16 weeks. In some embodiments, an effective amount of the IL-2 conjugate is administered to a subject in need thereof once every 17 weeks. In some embodiments, an effective amount of the IL-2 conjugate is administered to a subject in need thereof once every 18 weeks. In some embodiments, an effective amount of the IL-2 conjugate is administered to a subject in need thereof once every 19 weeks. In some embodiments, an effective amount of the IL-2 conjugate is administered to a subject in need thereof once every 20 weeks. In some embodiments, an effective amount of the IL-2 conjugate is administered to a subject in need thereof once every 21 weeks. In some embodiments, an effective amount of the IL-2 conjugate is administered to a subject in need thereof once every 22 weeks. In some embodiments, an effective amount of the IL-2 conjugate is administered to a subject in need thereof once every 23 weeks. In some embodiments, an effective amount of the IL-2 conjugate is administered to a subject in need thereof once every 24 weeks.

In some embodiments, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

In some embodiments, the methods include the dosing of an IL-2 conjugate to a subject in need thereof at a dose in the range from 1 μg of the IL-2 conjugate per kg of the subject's body weight to about 200 μg of the IL-2 conjugate per kg of the subject's body weight, or from about 2 μg of the IL-2 conjugate per kg of the subject's body weight to about 200 μg of the IL-2 conjugate per kg of the subject's body weight, or from about 4 μg of the IL-2 conjugate per kg of the subject's body weight to about 200 μg of the IL-2 conjugate per kg of the subject's body weight, or from about 6 μg of the IL-2 conjugate per kg of the subject's body weight to about 200 μg of the IL-2 conjugate per kg of the subject's body weight, or from about 8 μg of the IL-2 conjugate per kg of the subject's body weight to about 200 μg of the IL-2 conjugate per kg of the subject's body weight, or from about 10 μg of the IL-2 conjugate per kg of the subject's body weight to about 200 μg of the IL-2 conjugate per kg of the subject's body weight, or from about 12 μg of the IL-2 conjugate per kg of the subject's body weight to about 200 μg of the IL-2 conjugate per kg of the subject's body weight, or from about 14 μg of the IL-2 conjugate per kg of the subject's body weight to about 200 μg of the IL-2 conjugate per kg of the subject's body weight, or from about 16 μg of the IL-2 conjugate per kg of the subject's body weight to about 200 μg of the IL-2 conjugate per kg of the subject's body weight, or from about 18 μg of the IL-2 conjugate per kg of the subject's body weight to about 200 μg of the IL-2 conjugate per kg of the subject's body weight, or from about 20 μg of the IL-2 conjugate per kg of the subject's body weight to about 200 μg of the IL-2 conjugate per kg of the subject's body weight, or from about 22 μg of the IL-2 conjugate per kg of the subject's body weight to about 200 μg of the IL-2 conjugate per kg of the subject's body weight, or from about 24 μg of the IL-2 conjugate per kg of the subject's body weight to about 200 μg of the IL-2 conjugate per kg of the subject's body weight, or from about 26 μg of the IL-2 conjugate per kg of the subject's body weight to about 200 μg of the IL-2 conjugate per kg of the subject's body weight, or from about 28 μg of the IL-2 conjugate per kg of the subject's body weight to about 200 μg of the IL-2 conjugate per kg of the subject's body weight, or from about 32 μg of the IL-2 conjugate per kg of the subject's body weight to about 200 μg of the IL-2 conjugate per kg of the subject's body weight, or from about 34 μg of the IL-2 conjugate per kg of the subject's body weight to about 200 μg of the IL-2 conjugate per kg of the subject's body weight, or from about 36 μg of the IL-2 conjugate per kg of the subject's body weight to about 200 μg of the IL-2 conjugate per kg of the subject's body weight, or from about 40 μg of the IL-2 conjugate per kg of the subject's body weight to about 200 μg of the IL-2 conjugate per kg of the subject's body weight, or from about 45 μg of the IL-2 conjugate per kg of the subject's body weight to about 200 μg of the IL-2 conjugate per kg of the subject's body weight, or from about 50 μg of the IL-2 conjugate per kg of the subject's body weight to about 200 μg of the IL-2 conjugate per kg of the subject's body weight, or from about 55 μg of the IL-2 conjugate per kg of the subject's body weight to about 200 μg of the IL-2 conjugate per kg of the subject's body weight, or from about 60 μg of the IL-2 conjugate per kg of the subject's body weight to about 200 μg of the IL-2 conjugate per kg of the subject's body weight, or from about 65 μg of the IL-2 conjugate per kg of the subject's body weight to about 200 μg of the IL-2 conjugate per kg of the subject's body weight, or from about 70 μg of the IL-2 conjugate per kg of the subject's body weight to about 200 μg of the IL-2 conjugate per kg of the subject's body weight, or from about 75 μg of the IL-2 conjugate per kg of the subject's body weight to about 200 μg of the IL-2 conjugate per kg of the subject's body weight, or from about 80 μg of the IL-2 conjugate per kg of the subject's body weight to about 200 μg of the IL-2 conjugate per kg of the subject's body weight, or from about 85 μg of the IL-2 conjugate per kg of the subject's body weight to about 200 μg of the IL-2 conjugate per kg of the subject's body weight, or from about 90 μg of the IL-2 conjugate per kg of the subject's body weight to about 200 μg of the IL-2 conjugate per kg of the subject's body weight, or from about 95 μg of the IL-2 conjugate per kg of the subject's body weight to about 200 μg of the IL-2 conjugate per kg of the subject's body weight, or from about 100 μg of the IL-2 conjugate per kg of the subject's body weight to about 200 μg of the IL-2 conjugate per kg of the subject's body weight, or from about 110 μg of the IL-2 conjugate per kg of the subject's body weight to about 200 μg of the IL-2 conjugate per kg of the subject's body weight, or from about 120 μg of the IL-2 conjugate per kg of the subject's body weight to about 200 μg of the IL-2 conjugate per kg of the subject's body weight, or from about 130 μg of the IL-2 conjugate per kg of the subject's body weight to about 200 μg of the IL-2 conjugate per kg of the subject's body weight, or from about 140 μg of the IL-2 conjugate per kg of the subject's body weight to about 200 μg of the IL-2 conjugate per kg of the subject's body weight, or from about 150 μg of the IL-2 conjugate per kg of the subject's body weight to about 200 μg of the IL-2 conjugate per kg of the subject's body weight, or from about 160 μg of the IL-2 conjugate per kg of the subject's body weight to about 200 μg of the IL-2 conjugate per kg of the subject's body weight, or from about 170 μg of the IL-2 conjugate per kg of the subject's body weight to about 200 μg of the IL-2 conjugate per kg of the subject's body weight, or from about 180 μg of the IL-2 conjugate per kg of the subject's body weight to about 200 μg of the IL-2 conjugate per kg of the subject's body weight, or from about 190 μg of the IL-2 conjugate per kg of the subject's body weight to about 200 μg of the IL-2 conjugate per kg of the subject's body weight. The foregoing ranges are merely suggestive, as the number of variables in regard to an individual treatment regime is large, and considerable excursions from these recommended values are not uncommon. Such dosages are altered depending on a number of variables, not limited to the activity of the compound used, the disease or condition to be treated, the mode of administration, the requirements of the individual subject, the severity of the disease or condition being treated, and the judgment of the practitioner. In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

In some embodiments, the methods include the dosing of an IL-2 conjugate to a subject in need thereof at a dose of about 1 μg of the IL-2 conjugate per kg of the subject's body weight, or about 2 μg of the IL-2 conjugate per kg of the subject's body weight, about 4 μg of the IL-2 conjugate per kg of the subject's body weight, about 6 μg of the IL-2 conjugate per kg of the subject's body weight, about 8 μg of the IL-2 conjugate per kg of the subject's body weight, about 10 μg of the IL-2 conjugate per kg of the subject's body weight, about 12 μg of the IL-2 conjugate per kg of the subject's body weight, about 14 μg of the IL-2 conjugate per kg of the subject's body weight, about 16 μg of the IL-2 conjugate per kg of the subject's body weight, about 18 μg of the IL-2 conjugate per kg of the subject's body weight, about 20 μg of the IL-2 conjugate per kg of the subject's body weight, about 22 μg of the IL-2 conjugate per kg of the subject's body weight, about 24 μg of the IL-2 conjugate per kg of the subject's body weight, about 26 μg of the IL-2 conjugate per kg of the subject's body weight, about 28 μg of the IL-2 conjugate per kg of the subject's body weight, about 30 μg of the IL-2 conjugate per kg of the subject's body weight, about 32 μg of the IL-2 conjugate per kg of the subject's body weight, about 34 μg of the IL-2 conjugate per kg of the subject's body weight, about 36 μg of the IL-2 conjugate per kg of the subject's body weight, about 38 μg of the IL-2 conjugate per kg of the subject's body weight, about g of the IL-2 conjugate per kg of the subject's body weight, about 42 μg of the IL-2 conjugate per kg of the subject's body weight, about 44 μg of the IL-2 conjugate per kg of the subject's body weight, about 46 μg of the IL-2 conjugate per kg of the subject's body weight, about 48 μg of the IL-2 conjugate per kg of the subject's body weight, about 50 μg of the IL-2 conjugate per kg of the subject's body weight, about 55 μg of the IL-2 conjugate per kg of the subject's body weight, about 60 μg of the IL-2 conjugate per kg of the subject's body weight, about 65 μg of the IL-2 conjugate per kg of the subject's body weight, about 70 μg of the IL-2 conjugate per kg of the subject's body weight, about 75 μg of the IL-2 conjugate per kg of the subject's body weight, about 80 μg of the IL-2 conjugate per kg of the subject's body weight, about 85 μg of the IL-2 conjugate per kg of the subject's body weight, about 90 μg of the IL-2 conjugate per kg of the subject's body weight, about 95 μg of the IL-2 conjugate per kg of the subject's body weight, about 100 μg of the IL-2 conjugate per kg of the subject's body weight, about 110 μg of the IL-2 conjugate per kg of the subject's body weight, about 120 μg of the IL-2 conjugate per kg of the subject's body weight, about 130 μg of the IL-2 conjugate per kg of the subject's body weight, about 140 μg of the IL-2 conjugate per kg of the subject's body weight, about 150 μg of the IL-2 conjugate per kg of the subject's body weight, about 160 μg of the IL-2 conjugate per kg of the subject's body weight, about 170 μg of the IL-2 conjugate per kg of the subject's body weight, about 180 μg of the IL-2 conjugate per kg of the subject's body weight, about 190 μg of the IL-2 conjugate per kg of the subject's body weight, or about 200 μg of the IL-2 conjugate per kg of the subject's body weight. The foregoing ranges are merely suggestive, as the number of variables in regard to an individual treatment regime is large, and considerable excursions from these recommended values are not uncommon. Such dosages are altered depending on a number of variables, not limited to the activity of the compound used, the disease or condition to be treated, the mode of administration, the requirements of the individual subject, the severity of the disease or condition being treated, and the judgment of the practitioner. In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained.

In some embodiments, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages are altered depending on a number of variables, not limited to the activity of the compound used, the disease or condition to be treated, the mode of administration, the requirements of the individual subject, the severity of the disease or condition being treated, and the judgment of the practitioner.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Kits/Article of Manufacture

Disclosed herein, in certain embodiments, are kits and articles of manufacture for use with one or more methods and compositions described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

In some embodiments, the kits comprise articles of manufacture that are useful for developing adoptive cell therapies. In some embodiments, kits comprise one or more of the cytokine (e.g., IL-2) polypeptides or cytokine (e.g., IL-2) conjugates disclosed herein, and optionally one or more pharmaceutical excipients described herein to facilitate the delivery of cytokine (e.g., IL-2) polypeptides or cytokine (e.g., IL-2) conjugates. Such kits might optionally include one or more accessory components comprising inducers of T cell receptor signaling or modulation (e.g., checkpoint antibodies, CD3/CD28 antibodies, major histocompatibility complexes (MHC), and the like), or alternative cytokines or cytokine receptor agonists. Such kits further optionally include an identifying description or label or instructions relating to its use in the methods described herein. In some embodiments, kits comprise one or more polynucleic acid sequences encoding the IL-2 conjugates disclosed herein, an activator of a CD4+ helper cell, CD8+ effector naïve and memory cell, Natural Killer (NK) cell, or Natural killer T (NKT) cell and/or a pharmaceutical composition thereof.

Proliferative and Infectious Disease Kits and Articles of Manufacture

Disclosed herein, in some embodiments are kits comprising an isolated and modified interleukin 2 (IL-2) polypeptide comprising at least one unnatural amino acid at a position on the polypeptide that reduces binding between the modified IL-2 polypeptide and interleukin 2 receptor α (IL-2Rα) but retains significant binding with interleukin 2 βγ receptor (IL-2Rβγ) signaling complex to form an IL-2/IL-2Rβγ complex, wherein the reduced binding to IL-2Rα is compared to binding between a wild-type IL-2 polypeptide and IL-2Rα. In some embodiments, the reduction in binding to IL-2Rα comprises a decrease in binding affinity of about 30%, 40%, 50%, 60%, 70%, 80%, 90%, 95%, 99%, or 100% relative to a wild-type IL-2 polypeptide. In some embodiments, the reduction in binding to IL-2Rα comprises a decrease of 3-fold, 4-fold, 5-fold, 6-fold, 7-fold, 8-fold, 9-fold, 10-fold, or more relative to a wild-type IL-2 polypeptide.

Disclosed herein, in some embodiments are kits comprising isolated and modified interleukin 2 (IL-2) polypeptide comprising at least one unnatural amino acid, wherein the isolated and modified IL-2 polypeptide exhibits a first receptor signaling potency to an IL-2βγ signaling complex and a second receptor signaling potency to an IL-2αβγ signaling complex, and wherein a difference between the first receptor signaling potency and the second receptor signaling potency is less than 10-fold. In some embodiments, the difference in receptor signaling potency is less than 5-fold, less than 4-fold, less than 3-fold, less than 2-fold, or less than 1-fold.

Disclosed herein, in some embodiments, are kits comprising a polynucleotide sequence encoding a modified interleukin 2 (IL-2) polypeptide comprising at least one unnatural amino acid at a position on the polypeptide that reduces binding between the modified IL-2 polypeptide and interleukin 2 receptor α (IL-2Rα) but retains significant binding with interleukin 2 βγ receptor (IL-2Rβγ) signaling complex to form an IL-2/IL-2Rβγ complex, wherein the reduced binding to IL-2Rα is compared to binding between a wild-type IL-2 polypeptide and IL-2Rα.

Disclosed herein, in some embodiments, are kits comprising a polynucleotide sequence encoding a modified interleukin 2 (IL-2) polypeptide comprising at least one unnatural amino acid, wherein the isolated and modified IL-2 polypeptide exhibits a first receptor signaling potency to an IL-2βγ signaling complex and a second receptor signaling potency to an IL-2αβγ signaling complex, and wherein a difference between the first receptor signaling potency and the second receptor signaling potency is less than 10-fold. In some embodiments, the difference in receptor signaling potency is less than 5-fold, less than 4-fold, less than 3-fold, less than 2-fold, or less than 1-fold.

Autoimmune Kits and Articles of Manufacture

Disclosed herein, in some embodiments are kits comprising an isolated and modified interleukin 2 (IL-2) polypeptide comprising at least one unnatural amino acid at a position on the polypeptide reduces receptor signaling potency to interleukin 2 receptor βγ (IL-2Rβγ) or reduces a recruitment of an IL-2Rγ subunit to the IL-2/IL-2R3 complex, but retains significant activation of interleukin 2 αβγ receptor (IL-2Rαβγ), wherein the reduced receptor signaling potency is compared to the receptor signaling potency between a wild-type IL-2 polypeptide and IL-2Rβγ, and wherein the recruitment is compared to a recruitment of an IL-2Rγ subunit by a wild-type IL-2 polypeptide.

Disclosed herein, in some embodiments are kits comprising an isolated and modified interleukin 2 (IL-2) polypeptide comprising at least one unnatural amino acid at a position on the polypeptide increases a recruitment of an IL-2Rα subunit to the IL-2 polypeptide leading to activation of interleukin 2 αβγ receptor (IL-2Rαβγ), wherein the increase in recruitment is compared to a recruitment of an IL-2Rα subunit by a wild-type IL-2 polypeptide.

In some embodiments, the modified IL-2 polypeptide with the decrease in receptor signaling potency to IL-2Rβγ is capable of expanding CD4+ T regulatory (Treg) cells. In some embodiments, the conjugating moiety impairs or blocks the receptor signaling potency of IL-2 with IL-2Rβγ, or reduces recruitment of the IL-2Rγ subunit to the IL-2/IL-2R3 complex. In some embodiments, CD4+ Treg cell proliferation by the modified IL-2/IL-2Rαβγ complex is equivalent or greater to that of a wild-type IL-2 polypeptide. In some embodiments, the modified IL-2/IL-2Rαβγ complex induces proliferation of the CD4+ Treg cells to a population that is sufficient to modulate a disease course in an animal model. In some embodiments, the modified IL-2 polypeptide exhibits a first receptor signaling potency to IL-2Rβγ and a second receptor signaling potency to IL-2Rαβγ, wherein the first receptor signaling potency is at least 1-fold, 2-fold, 3-fold, 4-fold, 5-fold, 6-fold, 7-fold, 8-fold, 9-fold, 10-fold, 20-fold, 30-fold, 50-fold, 100-fold, 500-fold, 1000-fold, or lower than the second receptor signaling potency. In some embodiments, the first receptor signaling potency of the modified IL-2 polypeptide is lower than a receptor signaling potency of the wild-type IL-2 polypeptide to IL-2Rβγ. In some embodiments, the second receptor signaling potency of the modified IL-2 polypeptide is lower than a receptor signaling potency of the wild-type IL-2 polypeptide to IL-2Rαβγ. In some embodiments, the modified IL-2 polypeptide further provides an increase in a recruitment of an IL-2Rα subunit to the IL-2 polypeptide leading to activation of interleukin 2 αβγ receptor (IL-2Rαβγ), wherein the increase in recruitment is compared to a recruitment of an IL-2Rα subunit by a wild-type IL-2 polypeptide. In some embodiments, the modified IL-2 polypeptide further provides a decrease in a recruitment of an IL-2Rγ subunit to the IL-2/IL-2R3 complex, wherein the reduced recruitment is compared to a recruitment of an IL-2Rβ subunit and/or IL-2Rγ subunit by a wild-type IL-2 polypeptide.

In some embodiments, position of the at least one unnatural amino acid in the above modified IL-2 polypeptides is selected from K35, T37, R38, T41, F42, K43, F44, Y45, E60, E61, E62, K64, P65, E68, V69, N71, L72, M104, C105, and Y107, wherein the residue positions correspond to the positions 35, 37, 38, 41, 42, 43, 44, 45, 61, 62, 64, 65, 68, 69, 71, 72, 104, 105, and 107 as set forth in SEQ ID NO: 1. In some embodiments, the position of the at least one unnatural amino acid is selected from T37, R38, T41, F42, K43, F44, Y45, E61, E62, P65, E68, and L72, wherein the residue positions correspond to the positions 37, 38, 41, 42, 43, 44, 45, 61, 62, 65, 68, and 72 as set forth in SEQ ID NO: 1. In some embodiments, the position of the at least one unnatural amino acid is selected from K35, K64, V69, N71, M104, C105, and Y107, wherein the residue positions correspond to the positions 35, 64, 69, 71, 104, 105, and 107 as set forth in SEQ ID NO: 1. In some embodiments, the position of the at least one unnatural amino acid is selected from T37, R38, T41, Y45, E61, E68, and L72, wherein the residue positions correspond to the positions 37, 38, 41, 45, 61, 68, and 72 as set forth in SEQ ID NO: 1. In some embodiments, the position of the at least one unnatural amino acid is selected from F42, K43, F44, E62, and P65, wherein the residue positions correspond to the positions 42, 43, 44, 62, and 65 as set forth in SEQ ID NO: 1. In some embodiments, the position of the at least one unnatural amino acid is selected from P2, T3, S4, S5, S6, T7, K8, K9, Q11, L12, E15, H16, L18, L19, D20, Q22, M23, N26, G27, N29, N30, Y31, K32, K35, T37, M46, K47, K48, A50, T51, E52, K53, H55, Q57, E60, E67, N71, Q74, S75, K76, N77, F78, H79, R81, P82, R83, D84, S87, N88, N89, V91, 192, L94, E95, K97, G98, S99, E100, T101, T102, F103, M104, C105, E106, Y107, A108, D109, E110, T111, A112, T113, E116, N119, R120, T123, A125, Q126, S127, S130, T131, L132, and T133, wherein the numbering of the amino acid residues corresponds to SEQ ID NO: 1. In some embodiments, the position of the at least one unnatural amino acid is selected from K8, K9, Q11, L12, E15, H16, L18, L19, D20, Q22, M23, N26, R81, D84, S87, N88, V91, 192, L94, E95, E116, N119, R120, T123, A125, Q126, S127, S130, T131, L132, and T133, wherein the numbering of the amino acid residues corresponds to SEQ ID NO: 1. In some embodiments, the position of the at least one unnatural amino acid is selected from P2, T3, S4, S5, S6, T7, G27, N29, N30, Y31, K32, K35, T37, M46, K47, K48, A50, T51, E52, K53, H55, Q57, E60, E67, N71, Q74, S75, K76, N77, F78, H79, P82, R83, N89, K97, G98, S99, E100, T101, T102, F103, M104, C105, E106, Y107, A108, D109, E110, T111, A112, and T113, wherein the numbering of the amino acid residues corresponds to SEQ ID NO: 1. In some embodiments, the position of the at least one unnatural amino acid is selected from K8, K9, L12, E15, H16, L19, D20, Q22, M23, N26, D84, N88, E95, and Q126, wherein the numbering of the amino acid residues corresponds to SEQ ID NO: 1. In some embodiments, the position of the at least one unnatural amino acid is selected from K8, K9, and H16, wherein the numbering of the amino acid residues corresponds to SEQ ID NO: 1. In some embodiments, the position of the at least one unnatural amino acid is selected from Q22, N26, N88, and Q126, wherein the numbering of the amino acid residues corresponds to SEQ ID NO: 1. In some embodiments, the position of the at least one unnatural amino acid is selected from E15, D20, D84, and E95, wherein the numbering of the amino acid residues corresponds to SEQ ID NO: 1. In some embodiments, the position of the at least one unnatural amino acid is selected from L12, L19, and M23, wherein the numbering of the amino acid residues corresponds to SEQ ID NO: 1. In some embodiments, the position of the at least one unnatural amino acid is selected from Q22 and N26, wherein the numbering of the amino acid residues corresponds to SEQ ID NO: 1.

Kits and Articles of Manufacture Generally

In some embodiments, the at least one unnatural amino acid: is a lysine analogue; comprises an aromatic side chain; comprises an azido group; comprises an alkyne group; or comprises an aldehyde or ketone group. In some embodiments, the at least one unnatural amino acid does not comprise an aromatic side chain. In some embodiments, the at least one unnatural amino acid comprises N6-((2-azidoethoxy)-carbonyl)-L-lysine (AzK; the chemical structure of which is shown as compound 90 in FIG. 3C), N6-(propargyloxy)-carbonyl)-L-lysine (PraK; the chemical structure of which is shown as compound 112 in FIG. 3C), BCN-L-lysine, norbornene lysine, TCO-lysine, methyltetrazine lysine, allyloxycarbonyllysine, 2-amino-8-oxononanoic acid, 2-amino-8-oxooctanoic acid, p-acetyl-L-phenylalanine, p-azidomethyl-L-phenylalanine (pAMF), p-iodo-L-phenylalanine, *m*-acetylphenylalanine, 2-amino-8-oxononanoic acid, p-propargyloxyphenylalanine, p-propargyl-phenylalanine, 3-methyl-phenylalanine, L-Dopa, fluorinated phenylalanine, isopropyl-L-phenylalanine, p-azido-L-phenylalanine, p-acyl-L-phenylalanine, p-benzoyl-L-phenylalanine, p-bromophenylalanine, p-amino-L-phenylalanine, isopropyl-L-phenylalanine, O-allyltyrosine, O-methyl-L-tyrosine, O-4-allyl-L-tyrosine, 4-propyl-L-tyrosine, phosphonotyrosine, tri-O-acetyl-GlcNAcp-serine, L-phosphoserine, phosphonoserine, L-3-(2-naphthyl)alanine, 2-amino-3-((2-((3-(benzyloxy)-3-oxopropyl)amino)ethyl)selanyl)propanoic acid, 2-amino-3-(phenylselanyl)propanoic, or selenocysteine. In some embodiments, the at least one unnatural amino acid comprises N6-((2-azidoethoxy)-carbonyl)-L-lysine (AzK; the chemical structure of which is shown as compound 90 in FIG. 3C) or N6-(propargyloxy)-carbonyl)-L-lysine (PraK; the chemical structure of which is shown as compound 112 in FIG. 3C). In some embodiments, the at least one unnatural amino acid comprises N6-((2-azidoethoxy)-carbonyl)-L-lysine (AzK; the chemical structure of which is shown as compound 90 in FIG. 3C). In some embodiments, the at least one unnatural amino acid comprises N6-(propargyloxy)-carbonyl)-L-lysine (PraK; the chemical structure of which is shown as compound 112 in FIG. 3C).

In some embodiments, the at least one unnatural amino acid comprises an alkyne that is allowed to react with a conjugating moiety that comprises a water-soluble polymer comprises polyethylene glycol (PEG), poly(propylene glycol) (PPG), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), or a combination thereof. In some embodiments, the water-soluble polymer comprises a PEG molecule In some embodiments, the modified IL-2 polypeptide comprises a conjugating moiety. In some embodiments, the conjugating moiety comprises a water-soluble polymer, a lipid, a protein, and/or a peptide. In some embodiments, the water-soluble polymer comprises polyethylene glycol (PEG), poly(propylene glycol) (PPG), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), or a combination thereof. In some embodiments, the water-soluble polymer comprises a PEG molecule.

In some embodiments, the molecular weight of the PEG determines, at least in part, the in vivo plasma half-life of the modified IL-2 polypeptide. In some instances, the conjugating moiety comprises a PEG molecule that corresponds with a longer in vivo plasma half-life of the modified IL-2 polypeptide, as compared to the in vivo plasma half-life of a PEG that is smaller than the conjugating moiety. In some instances, the conjugating moiety comprises a PEG molecule that corresponds with a shorter in vivo plasma half-life of the modified IL-2 polypeptide, as compared to the in vivo plasma half-life of a PEG that is larger than the conjugating moiety.

In some embodiments, the molecular weight of the PEG does not affect, or has minimal affect, on the receptor signaling potency to the IL-2βγ or IL-2αβγ signaling complexes. In some embodiments, the molecular weight of the PEG does not affect, or has minimal affect, on the desired reduced binding to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2/IL-2Rβγ complex, wherein the reduced binding to IL-2Rα is compared to binding between a wild-type IL-2 polypeptide and IL-2Rα.

In some embodiments, the PEG molecule is a linear PEG. In some embodiments, wherein the PEG molecule is a branched PEG. In some embodiments, the PEG comprises between about 2,000-50,000 Daltons (Da). In some embodiments, the PEG has a molecular weight comprising about 5,000 Da, 10,000 Da, 15,000 Da, 20,000 Da, 25,000 Da, 30,000 Da, 35,000 Da, 40,000 Da, 45,000 Da, or 50,000 Da. In some instances, the PEG is 5,000 Da. In some instances, the PEG is 10,000 Da. In some instances, the PEG is 15,000 Da. In some instances, the PEG is 20,000 Da. In some instances, the PEG is 25,000 Da. In some instances, the PEG is 30,000 Da. In some instances, the PEG is 35,000 Da. In some instances, the PEG is 40,000 Da. In some instances, the PEG is 45,000 Da. In some instances, the PEG is 50,000 Da.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include one or more modified IL-2 polypeptides comprising a K35, T37, R38, T41, F42, K43, F44, Y45, E60, E61, E62, K64, P65, E68, V69, N71, L72, M104, C105, or Y107 with residue positions corresponding with 35, 37, 38, 41, 42, 43, 44, 45, 61, 62, 64, 65, 68, 69, 71, 72, 104, 105, and 107 as set forth in SEQ ID NO: 1. In some embodiments, the modified IL-2 polypeptide comprising the T37 with residue positions correspond to the positions 35, 37, 38, 41, 42, 43, 44, 45, 61, 62, 64, 65, 68, 69, 71, 72, 104, 105, and 107 as set forth in SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal affect, on the receptor signaling potency of the modified IL-2 polypeptide to the IL-2βγ or IL-2αβγ signaling complexes. In some embodiments, the molecular weight of the PEG does not affect, or has minimal affect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα

In some embodiments, the modified IL-2 polypeptide comprising a mutation at residue R38 corresponding to position 38 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal affect, on the receptor signaling potency of the modified IL-2 polypeptide to the IL-2βγ or IL-2αβγ signaling complexes. In some embodiments, the molecular weight of the PEG does not affect, or has minimal affect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα

In some embodiments, the modified IL-2 polypeptide comprising a mutation at residue T41 corresponding to position 41 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal affect, on the receptor signaling potency of the modified IL-2 polypeptide to the IL-2βγ or IL-2αβγ signaling complexes. In some embodiments, the molecular weight of the PEG does not affect, or has minimal affect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα

In some embodiments, the modified IL-2 polypeptide comprising a mutation at residue F42 corresponding to position 42 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal affect, on the receptor signaling potency of the modified IL-2 polypeptide to the IL-2βγ or IL-2αβγ signaling complexes. In some embodiments, the molecular weight of the PEG does not affect, or has minimal affect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα

In some embodiments, the modified IL-2 polypeptide comprising a mutation at residue K43 corresponding to position 43 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal affect, on the receptor signaling potency of the modified IL-2 polypeptide to the IL-2βγ or IL-2αβγ signaling complexes. In some embodiments, the molecular weight of the PEG does not affect, or has minimal affect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα

In some embodiments, the modified IL-2 polypeptide comprising a mutation at residue F44 corresponding to position 44 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal affect, on the receptor signaling potency of the modified IL-2 polypeptide to the IL-2βγ or IL-2αβγ signaling complexes. In some embodiments, the molecular weight of the PEG does not affect, or has minimal affect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα

In some embodiments, the modified IL-2 polypeptide comprising a mutation at residue Y45 corresponding to position 45 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal affect, on the receptor signaling potency of the modified IL-2 polypeptide to the IL-2βγ or IL-2αβγ signaling complexes. In some embodiments, the molecular weight of the PEG does not affect, or has minimal affect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα

In some embodiments, the modified IL-2 polypeptide comprising a mutation at residue E60 corresponding to position 60 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal affect, on the receptor signaling potency of the modified IL-2 polypeptide to the IL-2βγ or IL-2αβγ signaling complexes. In some embodiments, the molecular weight of the PEG does not affect, or has minimal affect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα

In some embodiments, the modified IL-2 polypeptide comprising a mutation at residue E61 corresponding to position 61 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal affect, on the receptor signaling potency of the modified IL-2 polypeptide to the IL-2βγ or IL-2αβγ signaling complexes. In some embodiments, the molecular weight of the PEG does not affect, or has minimal affect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα

In some embodiments, the modified IL-2 polypeptide comprising a mutation at residue E62 corresponding to position 62 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal affect, on the receptor signaling potency of the modified IL-2 polypeptide to the IL-2βγ or IL-2αβγ signaling complexes. In some embodiments, the molecular weight of the PEG does not affect, or has minimal affect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα

In some embodiments, the modified IL-2 polypeptide comprising a mutation at residue K64 corresponding to position 64 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal affect, on the receptor signaling potency of the modified IL-2 polypeptide to the IL-2βγ or IL-2αβγ signaling complexes. In some embodiments, the molecular weight of the PEG does not affect, or has minimal affect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα

In some embodiments, the modified IL-2 polypeptide comprising a mutation at residue P65 corresponding to position 65 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal affect, on the receptor signaling potency of the modified IL-2 polypeptide to the IL-2βγ or IL-2αβγ signaling complexes. In some embodiments, the molecular weight of the PEG does not affect, or has minimal affect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα

In some embodiments, the modified IL-2 polypeptide comprising a mutation at residue E68 corresponding to position 68 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal affect, on the receptor signaling potency of the modified IL-2 polypeptide to the IL-2βγ or IL-2αβγ signaling complexes. In some embodiments, the molecular weight of the PEG does not affect, or has minimal affect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα

In some embodiments, the modified IL-2 polypeptide comprising a mutation at residue V69 corresponding to positions 69 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal affect, on the receptor signaling potency of the modified IL-2 polypeptide to the IL-2βγ or IL-2αβγ signaling complexes. In some embodiments, the molecular weight of the PEG does not affect, or has minimal affect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα

In some embodiments, the modified IL-2 polypeptide comprising a mutation at residue N71 corresponding to position 71 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal affect, on the receptor signaling potency of the modified IL-2 polypeptide to the IL-2βγ or IL-2αβγ signaling complexes. In some embodiments, the molecular weight of the PEG does not affect, or has minimal affect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα

In some embodiments, the modified IL-2 polypeptide comprising a mutation at residue L72 corresponding to position 72 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal affect, on the receptor signaling potency of the modified IL-2 polypeptide to the IL-2βγ or IL-2αβγ signaling complexes. In some embodiments, the molecular weight of the PEG does not affect, or has minimal affect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα

In some embodiments, the modified IL-2 polypeptide comprising a mutation at residue M104 corresponding to position 104 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal affect, on the receptor signaling potency of the modified IL-2 polypeptide to the IL-2βγ or IL-2αβγ signaling complexes. In some embodiments, the molecular weight of the PEG does not affect, or has minimal affect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα

In some embodiments, the modified IL-2 polypeptide comprising a mutation at residue C105 corresponding to position 105 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal affect, on the receptor signaling potency of the modified IL-2 polypeptide to the IL-2βγ or IL-2αβγ signaling complexes. In some embodiments, the molecular weight of the PEG does not affect, or has minimal affect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue Y107 corresponding to a position 107 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal affect, on the receptor signaling potency of the modified IL-2 polypeptide to the IL-2βγ or IL-2αβγ signaling complexes. In some embodiments, the molecular weight of the PEG does not affect, or has minimal affect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2 polypeptide/IL-2Rβγ complex, wherein the reduced binding to IL-2Rα is compared to binding between a wild-type IL-2 polypeptide and IL-2Rα.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself, a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for drugs, or the approved product insert. In one embodiment, compositions containing a compound provided herein formulated in a compatible pharmaceutical carrier are also prepared, placed in an appropriate container, and labeled for treatment of an indicated condition.

Embodiments

Disclosed herein, in certain embodiments, are cytokine conjugates and use in the treatment of one or more indication. In some embodiments, also described herein include interleukin 2 (IL-2) conjugates and use in the treatment of one or more indications. In some instances, the one or more indications comprise cancer, a pathogenic infection, or an autoimmune disease. In some cases, described herein are methods of modulating the interaction between IL-2 and IL-2 receptor to stimulate or expand specific T cell, Natural Killer (NK) cell, and/or Natural killer T (NKT) cell populations. In some embodiments, the IL-2 conjugates comprise conjugating moieties (e.g., a PEG) that contribute to an increase or a decrease in an in vivo plasma half-life, without affecting the pharmacokinetics, including the desired cytokine-receptor interactions and immune cell expansion. In additional cases, further described herein are pharmaceutical compositions and kits that comprise one or more interleukin conjugates (e.g., IL-2 conjugates) described herein that may be useful as reagents for developing adoptive cell therapies to treat the one or more indications described herein.

Aspects disclosed herein provide isolated and modified interleukin 2 (IL-2) polypeptides comprising at least one unnatural amino acid at a position on the polypeptide that reduces binding between the modified IL-2 polypeptide and interleukin 2 receptor α (IL-2Rα) but retains significant binding with interleukin 2 βγ receptor (IL-2Rβγ) signaling complex to form an IL-2/IL-2Rβγ complex, wherein the reduced binding to IL-2Rα is compared to binding between a wild-type IL-2 polypeptide and IL-2Rα. In some embodiments, difference in receptor signaling potency is less than 5-fold, less than 4-fold, less than 3-fold, less than 2-fold, or less than 1-fold. In some embodiments, the position of the at least one unnatural amino acid is selected from K35, T37, R38, T41, F42, K43, F44, Y45, E60, E61, E62, K64, P65, E68, V69, N71, L72, M104, C105, Y107, wherein the residue positions correspond to the positions 35, 37, 38, 41, 42, 43, 44, 45, 61, 62, 64, 65, 68, 69, 71, 72, 104, 105, and 107 as set forth in SEQ ID NO: 1. In some embodiments, the position of the at least one unnatural amino acid is selected from T37, R38, T41, F42, K43, F44, Y45, E61, E62, P65, E68, and L72, wherein the residue positions correspond to the positions 37, 38, 41, 42, 43, 44, 45, 61, 62, 65, 68, and 72 as set forth in SEQ ID NO: 1. In some embodiments, the position of the at least one unnatural amino acid is selected from K35, K64, V69, N71, M104, C105, and Y107, wherein the residue positions correspond to the positions 35, 64, 69, 71, 104, 105, and 107 as set forth in SEQ ID NO: 1. In some embodiments, the position of the at least one unnatural amino acid is selected from T37, R38, T41, Y45, E61, E68, and L72, wherein the residue positions correspond to the positions 37, 38, 41, 45, 61, 68, and 72 as set forth in SEQ ID NO: 1. In some embodiments, the position of the at least one unnatural amino acid is selected from F42, K43, F44, E62, and P65, wherein the residue positions correspond to the positions 42, 43, 44, 62, and 65 as set forth in SEQ ID NO: 1. In some embodiments, the at least one unnatural amino acid: is a lysine analogue; comprises an aromatic side chain; comprises an azido group; comprises an alkyne group; or comprises an aldehyde or ketone group. In some embodiments, the at least one unnatural amino acid does not comprise an aromatic side chain. In some embodiments, the at least one unnatural amino acid comprises N6-((2-azidoethoxy)-carbonyl)-L-lysine (AzK; the chemical structure of which is shown as compound 90 in FIG. 3C), N6-(propargyloxy)-carbonyl-L-lysine (PraK), BCN-L-lysine, norbornene lysine, TCO-lysine, methyltetrazine lysine, allyloxycarbonyllysine, 2-amino-8-oxononanoic acid, 2-amino-8-oxooctanoic acid, p-acetyl-L-phenylalanine, p-azidomethyl-L-phenylalanine (p MF), p-iodo-L-phenylalanine, *m*-acetylphenylalanine, 2-amino-8-oxononanoic acid, p-propargyloxyphenylalanine, p-propargyl-phenylalanine, 3-methyl-phenylalanine, L-Dopa, fluorinated phenylalanine, isopropyl-L-phenylalanine, p-azido-L-phenylalanine, p-acyl-L-phenylalanine, p-benzoyl-L-phenylalanine, p-bromophenylalanine, p-amino-L-phenylalanine, isopropyl-L-phenylalanine, 0-allyltyrosine, O-methyl-L-tyrosine, O-4-allyl-L-tyrosine, 4-propyl-L-tyrosine, phosphonotyrosine, tri-O-acetyl-GlcNcp-serine, L-phosphoserine, phosphonoserine, L-3-(2-naphthyl)alanine, 2-amino-3-((2-((3-(benzyloxy)-3-oxopropyl)amino)ethyl)selanyl)propanoic acid, 2-amino-3-(phenylselanyl)propanoic, or selenocysteine. In some embodiments, the at least one unnatural amino acid is incorporated into the modified IL-2 polypeptide by an orthogonal tRNA synthetase/tRNA pair. In some embodiments, n the orthogonal tRNA of the orthogonal synthetase/tRNA pair comprises at least one unnatural nucleobase. In some embodiments, the modified IL-2 polypeptide is covalently attached to a conjugating moiety through the at least one unnatural amino acid. In some embodiments, the conjugating moiety comprises a water-soluble polymer, a lipid, a protein, and/or a peptide. In some embodiments, the water-soluble polymer comprises polyethylene glycol (PEG), poly(propylene glycol) (PPG), copolymers of ethylene glycol and propylene glycol, poly(oxyethylated polyol), poly(olefinic alcohol), poly (vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), or a combination thereof. In some embodiments, the water-soluble polymer comprises a PEG molecule. In some embodiments, the PEG molecule is a linear PEG. In some embodiments, the PEG molecule is a branched PEG. In some embodiments, the PEG comprises between about 2,000-50,000 Daltons (Da). In some embodiments, the PEG has a molecular weight comprising about 5,000 Da, 10,000 Da, 15,000 Da, 20,000 Da, 25,000 Da, 30,000 Da, 35,000 Da, 40,000 Da, 45,000 Da, or 50,000 Da. In some embodiments, the molecular weight determines, at least in part, the in vivo plasma half-life of the IL-2 polypeptide. In some embodiments, the water-soluble polymer comprises a polysaccharide. In some embodiments, the polysaccharide comprises dextran, polysialic acid (PSA), hyaluronic acid (HA), amylose, heparin, heparan sulfate (HS), dextrin, or hydroxyethyl-starch (HES). In some embodiments, the lipid comprises a fatty acid. In some embodiments, n the fatty acid comprises from about 6 to about 26 carbon atoms, from about 6 to about 24 carbon atoms, from about 6 to about 22 carbon atoms, from about 6 to about 20 carbon atoms, from about 6 to about 18 carbon atoms, from about 20 to about 26 carbon atoms, from about 12 to about 26 carbon atoms, from about 12 to about 24 carbon atoms, from about 12 to about 22 carbon atoms, from about 12 to about 20 carbon atoms, or from about 12 to about 18 carbon atoms. In some embodiments, the fatty acid is a saturated fatty acid. In some embodiments, the protein comprises an albumin, a transferrin, or a transthyretin. In some embodiments, the conjugating moiety comprises a TLR agonist. In some embodiments, the protein comprises an antibody or its binding fragments thereof. In some embodiments, the antibody or its binding fragments thereof comprises an Fc portion of an antibody. In some embodiments, the peptide comprises a XTEN peptide, a glycine-rich homoamino acid polymer (HAP), a PAS polypeptide, an elastin-like polypeptide (ELP), a CTP peptide, or a gelatin-like protein (GLK) polymer. In some embodiments, the conjugating moiety is indirectly bound to the at least one unnatural amino acid of the modified IL-2 through a linker. In some embodiments, the linker comprises a homobifunctional linker, a heterobifunctional linker, a zero-length linker, a cleavable or a non-cleavable dipeptide linker, a maleimide group, a spacer, or a combination thereof. In some embodiments, the decrease in binding affinity is about 30%, 40%, 50%, 60%, 70%, 80%, 90%, 95%, 99%, or 100% decrease in binding affinity to IL-2Rα relative to a wild-type IL-2 polypeptide. In some embodiments, the decrease in binding affinity is about 3-fold, 4-fold, 5-fold, 6-fold, 7-fold, 8-fold, 9-fold, 10-fold, or more to IL-2Rα relative to a wild-type IL-2 polypeptide. In some embodiments, the modified IL-2 polypeptide is: a functionally active fragment of a full-length IL-2 polypeptide; a recombinant IL-2 polypeptide; or a recombinant human IL-2 polypeptide. In some embodiments, the modified IL-2 polypeptide comprises an N-terminal deletion, a C-terminal deletion, or a combination thereof. In some embodiments, the N-terminal deletion comprises a deletion of the first 1, 2, 3, 4, 5, 6, 7, 8, 9, 10, 11, 12, 13, 14, 15, 20, 25, or 30 residues from the N-terminus, wherein the residue positions are in reference to the positions in SEQ ID NO: 1. In some embodiments, the C-terminal deletion comprises a deletion of the last 1, 2, 3, 4, 5, 6, 7, 8, 9, 10, 11, 12, 13, 14, 15, 20, or more residues from the C-terminus, wherein the residue positions are in reference to the positions in SEQ ID NO: 1. In some embodiments, the functionally active fragment comprises IL-2 region 10-133, 20-133, 30-133, 10-130, 20-130, 30-130, 10-125, 20-125, 30-125, 1-130, or 1-125, wherein the residue positions are in reference to the positions in SEQ ID NO: 1. In some embodiments, the modified IL-2 polypeptide comprises about 80%, 85%, 90%, 95%, 96%, 97%, 98%, or 99% sequence identity to SEQ ID NO: 1. In some embodiments, the modified IL-2 polypeptide with the decrease in binding affinity to IL-2Rα is capable of expanding CD4+ helper cell, CD8+ effector naïve and memory cell, CD8+ T cell, Natural Killer (NK) cell, Natural killer T (NKT) cell populations, or a combination thereof. In some embodiments, the conjugating moiety or the unnatural amino acid impairs or blocks the binding of IL-2 with IL-2Rα. In some embodiments, activation of CD4+ helper cell, CD8+ effector naïve and memory cell, Natural Killer (NK) cell, or Natural killer T (NKT) cell population via the IL-2Rβγ complex by the modified IL-2 polypeptide retains significant potency of activation of said cell population relative to a wild-type IL-2 polypeptide. In some embodiments, a receptor signaling potency of the modified IL-2 polypeptide to the IL-2Rβγ complex is higher than a receptor signaling potency of the wild-type IL-2 polypeptide to the IL-2Rβγ complex. In some embodiments, a receptor signaling potency of the modified IL-2 polypeptide the IL-2Rβγ complex is lower than a receptor signaling potency of the wild-type IL-2 polypeptide the IL-2Rβγ complex. In some embodiments, the modified IL-2 polypeptide exhibits a first receptor signaling potency to IL-2Rβγ and a second receptor signaling potency to IL-2Rαβγ, and wherein the first receptor signaling potency is at least 1-fold, 2-fold, 3-fold, 4-fold, 5-fold, 6-fold, 7-fold, 8-fold, 9-fold, 10-fold, 20-fold, 30-fold, 50-fold, 100-fold, 500-fold, or higher than the second receptor signaling potency. wherein the first receptor signaling potency of the modified IL-2 polypeptide is higher than a receptor signaling potency of the wild-type IL-2 polypeptide to the IL-2Rβγ, and the second receptor signaling potency of the modified IL-2 polypeptide is lower than a receptor signaling potency of the wild-type IL-2 polypeptide to the IL-2Rαβγ. In some embodiments, the first receptor signaling potency of the modified IL-2 polypeptide is at least 1-fold lower than a receptor signaling potency of the wild-type IL-2 polypeptide.

Aspects disclosed herein provide isolated and modified interleukin 2 (IL-2) polypeptides comprising at least one unnatural amino acid, wherein the isolated and modified IL-2 polypeptide exhibits a first receptor signaling potency to an IL-2βγ signaling complex and a second receptor signaling potency to an IL-2αβγ signaling complex, and wherein a difference between the first receptor signaling potency and the second receptor signaling potency is less than 10-fold. In some embodiments, difference in receptor signaling potency is less than 5-fold, less than 4-fold, less than 3-fold, less than 2-fold, or less than 1-fold. In some embodiments, the position of the at least one unnatural amino acid is selected from K35, T37, R38, T41, F42, K43, F44, Y45, E60, E61, E62, K64, P65, E68, V69, N71, L72, M104, C105, Y107, wherein the residue positions correspond to the positions 35, 37, 38, 41, 42, 43, 44, 45, 61, 62, 64, 65, 68, 69, 71, 72, 104, 105, and 107 as set forth in SEQ ID NO: 1. In some embodiments, the position of the at least one unnatural amino acid is selected from T37, R38, T41, F42, K43, F44, Y45, E61, E62, P65, E68, and L72, wherein the residue positions correspond to the positions 37, 38, 41, 42, 43, 44, 45, 61, 62, 65, 68, and 72 as set forth in SEQ ID NO: 1. In some embodiments, the position of the at least one unnatural amino acid is selected from K35, K64, V69, N71, M104, C105, and Y107, wherein the residue positions correspond to the positions 35, 64, 69, 71, 104, 105, and 107 as set forth in SEQ ID NO: 1. In some embodiments, the position of the at least one unnatural amino acid is selected from T37, R38, T41, Y45, E61, E68, and L72, wherein the residue positions correspond to the positions 37, 38, 41, 45, 61, 68, and 72 as set forth in SEQ ID NO: 1. In some embodiments, the position of the at least one unnatural amino acid is selected from F42, K43, F44, E62, and P65, wherein the residue positions correspond to the positions 42, 43, 44, 62, and 65 as set forth in SEQ ID NO: 1. In some embodiments, the at least one unnatural amino acid: is a lysine analogue; comprises an aromatic side chain; comprises an azido group; comprises an alkyne group; or comprises an aldehyde or ketone group. In some embodiments, the at least one unnatural amino acid does not comprise an aromatic side chain. In some embodiments, the at least one unnatural amino acid comprises N6-((2-azidoethoxy)-carbonyl)-L-lysine (AzK; the chemical structure of which is shown as compound 90 in FIG. 3C), N6-(propargyloxy)-carbonyl-L-lysine (PraK), BCN-L-lysine, norbornene lysine, TCO-lysine, methyltetrazine lysine, allyloxycarbonyllysine, 2-amino-8-oxononanoic acid, 2-amino-8-oxooctanoic acid, p-acetyl-L-phenylalanine, p-azidomethyl-L-phenylalanine (pAMF), p-iodo-L-phenylalanine, *m*-acetylphenylalanine, 2-amino-8-oxononanoic acid, p-propargyloxyphenylalanine, p-propargyl-phenylalanine, 3-methyl-phenylalanine, L-Dopa, fluorinated phenylalanine, isopropyl-L-phenylalanine, p-azido-L-phenylalanine, p-acyl-L-phenylalanine, p-benzoyl-L-phenylalanine, p-bromophenylalanine, p-amino-L-phenylalanine, isopropyl-L-phenylalanine, 0-allyltyrosine, O-methyl-L-tyrosine, O-4-allyl-L-tyrosine, 4-propyl-L-tyrosine, phosphonotyrosine, tri-O-acetyl-GlcNAcp-serine, L-phosphoserine, phosphonoserine, L-3-(2-naphthyl)alanine, 2-amino-3-((2-((3-(benzyloxy)-3-oxopropyl)amino)ethyl)selanyl)propanoic acid, 2-amino-3-(phenylselanyl)propanoic, or selenocysteine. In some embodiments, the at least one unnatural amino acid is incorporated into the modified IL-2 polypeptide by an orthogonal tRNA synthetase/tRNA pair. In some embodiments, the orthogonal tRNA of the orthogonal synthetase/tRNAspects comprises at least one unnatural nucleobase. In some embodiments, the modified IL-2 polypeptide is covalently attached to a conjugating moiety through the at least one unnatural amino acid. In some embodiments, the conjugating moiety comprises a water-soluble polymer, a lipid, a protein, and/or a peptide. In some embodiments, the water-soluble polymer comprises polyethylene glycol (PEG), poly(propylene glycol) (PPG), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), or a combination thereof. In some embodiments, the water-soluble polymer comprises a PEG molecule. In some embodiments, the PEG molecule is a linear PEG. In some embodiments, the PEG molecule is a branched PEG. In some embodiments, the PEG comprises between about 2,000-50,000 Daltons (Da). In some embodiments, the PEG has a molecular weight comprising about 5,000 Da, 10,000 Da, 15,000 Da, 20,000 Da, 25,000 Da, 30,000 Da, 35,000 Da, 40,000 Da, 45,000 Da, or 50,000 Da. In some embodiments, the molecular weight determines, at least in part, the in vivo plasma half-life of the IL-2 polypeptide. In some embodiments, the water-soluble polymer comprises a polysaccharide. In some embodiments, the polysaccharide comprises dextran, polysialic acid (PSA), hyaluronic acid (HA), amylose, heparin, heparan sulfate (HS), dextrin, or hydroxyethyl-starch (HES). In some embodiments, the lipid comprises a fatty acid. In some embodiments, n the fatty acid comprises from about 6 to about 26 carbon atoms, from about 6 to about 24 carbon atoms, from about 6 to about 22 carbon atoms, from about 6 to about 20 carbon atoms, from about 6 to about 18 carbon atoms, from about 20 to about 26 carbon atoms, from about 12 to about 26 carbon atoms, from about 12 to about 24 carbon atoms, from about 12 to about 22 carbon atoms, from about 12 to about 20 carbon atoms, or from about 12 to about 18 carbon atoms. In some embodiments, the fatty acid is a saturated fatty acid. In some embodiments, the protein comprises an albumin, a transferrin, or a transthyretin. In some embodiments, the conjugating moiety comprises a TLR agonist. In some embodiments, the protein comprises an antibody or its binding fragments thereof. In some embodiments, the antibody or its binding fragments thereof comprises an Fc portion of an antibody. In some embodiments, the peptide comprises a XTEN peptide, a glycine-rich homoamino acid polymer (HAP), a PAS polypeptide, an elastin-like polypeptide (ELP), a CTP peptide, or a gelatin-like protein (GLK) polymer. In some embodiments, the conjugating moiety is indirectly bound to the at least one unnatural amino acid of the modified IL-2 through a linker. In some embodiments, the linker comprises a homobifunctional linker, a heterobifunctional linker, a zero-length linker, a cleavable or a non-cleavable dipeptide linker, a maleimide group, a spacer, or a combination thereof. In some embodiments, the decrease in binding affinity is about 30%, 40%, 50%, 60%, 70%, 80%, 90%, 95%, 99%, or 100% decrease in binding affinity to IL-2Rα relative to a wild-type IL-2 polypeptide. In some embodiments, the decrease in binding affinity is about 3-fold, 4-fold, 5-fold, 6-fold, 7-fold, 8-fold, 9-fold, 10-fold, or more to IL-2Rα relative to a wild-type IL-2 polypeptide. In some embodiments, the modified IL-2 polypeptide is: a functionally active fragment of a full-length IL-2 polypeptide; a recombinant IL-2 polypeptide; or a recombinant human IL-2 polypeptide. In some embodiments, the modified IL-2 polypeptide comprises an N-terminal deletion, a C-terminal deletion, or a combination thereof. In some embodiments, the N-terminal deletion comprises a deletion of the first 1, 2, 3, 4, 5, 6, 7, 8, 9, 10, 11, 12, 13, 14, 15, 20, 25, or 30 residues from the N-terminus, wherein the residue positions are in reference to the positions in SEQ ID NO: 1. In some embodiments, the C-terminal deletion comprises a deletion of the last 1, 2, 3, 4, 5, 6, 7, 8, 9, 10, 11, 12, 13, 14, 15, 20, or more residues from the C-terminus, wherein the residue positions are in reference to the positions in SEQ ID NO: 1. In some embodiments, the functionally active fragment comprises IL-2 region 10-133, 20-133, 30-133, 10-130, 20-130, 30-130, 10-125, 20-125, 30-125, 1-130, or 1-125, wherein the residue positions are in reference to the positions in SEQ ID NO: 1. In some embodiments, the modified IL-2 polypeptide comprises about 80%, 85%, 90%, 95%, 96%, 97%, 98%, or 99% sequence identity to SEQ ID NO: 1. In some embodiments, the modified IL-2 polypeptide with the decrease in binding affinity to IL-2Rα is capable of expanding CD4+ helper cell, CD8+ effector naïve and memory cell, CD8+ T cell, Natural Killer (NK) cell, Natural killer T (NKT) cell populations, or a combination thereof. In some embodiments, the conjugating moiety or the unnatural amino acid impairs or blocks the binding of IL-2 with IL-2Rα. In some embodiments, activation of CD4+ helper cell, CD8+ effector naïve and memory cell, Natural Killer (NK) cell, or Natural killer T (NKT) cell population via the IL-2Rβγ complex by the modified IL-2 polypeptide retains significant potency of activation of said cell population relative to a wild-type IL-2 polypeptide. In some embodiments, a receptor signaling potency of the modified IL-2 polypeptide to the IL-2Rβγ complex is higher than a receptor signaling potency of the wild-type IL-2 polypeptide to the IL-2Rβγ complex. In some embodiments, a receptor signaling potency of the modified IL-2 polypeptide the IL-2Rβγ complex is lower than a receptor signaling potency of the wild-type IL-2 polypeptide the IL-2Rβγ complex. In some embodiments, the modified IL-2 polypeptide exhibits a first receptor signaling potency to IL-2Rβγ and a second receptor signaling potency to IL-2Rαβγ, and wherein the first receptor signaling potency is at least 1-fold, 2-fold, 3-fold, 4-fold, 5-fold, 6-fold, 7-fold, 8-fold, 9-fold, 10-fold, 20-fold, 30-fold, 50-fold, 100-fold, 500-fold, or higher than the second receptor signaling potency. wherein the first receptor signaling potency of the modified IL-2 polypeptide is higher than a receptor signaling potency of the wild-type IL-2 polypeptide to the IL-2Rβγ, and the second receptor signaling potency of the modified IL-2 polypeptide is lower than a receptor signaling potency of the wild-type IL-2 polypeptide to the IL-2Rαβγ. In some embodiments, the first receptor signaling potency of the modified IL-2 polypeptide is at least 1-fold lower than a receptor signaling potency of the wild-type IL-2 polypeptide.

Aspects disclosed herein provide interleukin 2 (IL-2) conjugates comprising an unnatural amino acid covalently attached to a conjugating moiety, wherein the unnatural amino acid is located in region 35-107, and wherein the region 35-107 corresponds to residues K35-Y107 of SEQ ID NO: 1. In some embodiments, the unnatural amino acid is located in region 42, and wherein the region 42 corresponds to a residue F42. In some embodiments, the conjugating moiety comprises a water-soluble polymer having a molecular weight of 2,000-50,000 Daltons (Da). In some embodiments, the conjugating moiety comprises a water-soluble polymer having a molecular weight of 5,000 Da, 10,000 Da, 15,000 Da, 20,000 Da, 25,000 Da, 30,000 Da, 35,000 Da, 40,000 Da, 45,000 Da, or 50,000 Da. In some embodiments, the water-soluble polymer comprises polyethylene glycol (PEG), poly(propylene glycol) (PPG), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), or a combination thereof. In some embodiments, the molecular weight determines, at least in part, the in vivo plasma half-life of the IL-2 conjugate. In some embodiments, the IL-2 conjugate comprises a mutation at residue P65 corresponding to a residue position 65 of SEQ ID NO: 1, and a conjugating moiety comprising a PEG, the PEG having a molecular weight comprising about 5,000 Daltons (Da), 10,000 Da, 15,000 Da, 20,000 Da, 25,000 Da, 30,000 Da, 35,000 Da, 40,000 Da, 45,000 Da, or 50,000 Da. In some embodiments, the IL-2 conjugate comprises a mutation at residue E61 corresponding to a residue position 61 of SEQ ID NO: 1, and a conjugating moiety comprising a PEG, the PEG having a molecular weight comprising about 5,000 Daltons (Da), 10,000 Da, 15,000 Da, 20,000 Da, 25,000 Da, 30,000 Da, 35,000 Da, 40,000 Da, 45,000 Da, or 50,000 Da. In some embodiments, the IL-2 conjugate comprises a mutation at residue F42 corresponding to a residue position 42 of SEQ ID NO: 1, and a conjugating moiety comprising a PEG, the PEG having a molecular weight comprising about 5,000 Daltons (Da), 10,000 Da, 15,000 Da, 20,000 Da, 25,000 Da, 30,000 Da, 35,000 Da, 40,000 Da, 45,000 Da, or 50,000 Da.

Aspects disclosed herein provide interleukin 2 βγ receptor (IL-2Rβγ) binding proteins, wherein the binding affinity for an interleukin 2α receptor (IL-2Rα) of said binding protein is less than that of wild-type human IL-2 (hIL-2), and wherein said binding protein comprises at least one unnatural amino acid. In some embodiments, said binding protein is a modified IL-2 polypeptide or a functionally active fragment thereof, wherein the modified IL-2 polypeptide comprises at least one unnatural amino acid. In some embodiments, the at least one unnatural amino acid is located in region 35-107, and wherein the region 35-107 corresponds to residues K35-Y107 of SEQ ID NO: 1.

Aspects disclosed herein provide IL-2/IL-2Rβγ complexes comprising a modified IL-2 polypeptide comprising an unnatural amino acid and an IL-2Rβγ, wherein the modified IL-2 polypeptide has a reduced binding affinity toward IL-2Rα, and wherein the reduced binding affinity is compared to a binding affinity between a wild-type IL-2 polypeptide and IL-2Rα. In some embodiments, the modified IL-2 polypeptide further comprises a conjugating moiety covalently attached to the unnatural amino acid.

Aspects disclosed herein provide activators of a CD4+ helper cell, CD8+ effector naïve and memory cell, CD8+ T cell, Natural Killer (NK) cell, or Natural killer T (NKT) cell that selectively expands CD4+ helper cells, CD8+ effector naïve and memory cells, Natural Killer (NK) cells, or Natural killer T (NKT) cells in a cell population, wherein said activator comprises a modified interleukin 2 (IL-2) polypeptide comprising at least one unnatural amino acid. In some embodiments, said activator expands CD4+ T regulatory (Treg) cells by less than 20%, 15%, 10%, 5%, 1%, or 0.1% when said activator is in contact with said cell population. In some embodiments, said activator does not expand Treg cells in said cell population. In some embodiments, said cell population is an in vivo cell population. In some embodiments, said cell population is an in vitro cell population. In some embodiments, said cell population is an ex vivo cell population.

Aspects disclosed herein provide pharmaceutical composition comprising: an isolated and modified IL-2 polypeptide described herein, an IL-2 conjugate described herein, an IL-2Rβγ binding protein described herein or an activator of a CD4+ helper cell, CD8+ effector naïve and memory cell, Natural Killer (NK) cell, or Natural killer T (NKT) cell described herein; and a pharmaceutically acceptable excipient. In some embodiments, the pharmaceutical composition is formulated for systemic delivery. In some embodiments, the pharmaceutical composition is formulated for parenteral administration. In some embodiments, n the IL-2 polypeptide or the IL-2 conjugate comprises a mutation at residue F42 corresponding with residue position 42 of SEQ ID NO: 1, and a conjugating moiety comprising a PEG, the PEG having a molecular weight comprising about 5,000 Daltons (Da). In some embodiments, wherein the IL-2 polypeptide or the IL-2 conjugate comprises a mutation at residue F42 corresponding with residue position 42 of SEQ ID NO: 1, and a conjugating moiety comprising a PEG, the PEG having a molecular weight comprising about 10,000 Daltons (Da). In some embodiments, the IL-2 polypeptide or the IL-2 conjugate comprises a mutation at residue F42 corresponding with residue position 42 of SEQ ID NO: 1, and a conjugating moiety comprising a PEG, the PEG having a molecular weight comprising about 15,000 Daltons (Da). In some embodiments, the IL-2 polypeptide or the IL-2 conjugate comprises a mutation at residue F42 corresponding with residue position 42 of SEQ ID NO: 1, and a conjugating moiety comprising a PEG, the PEG having a molecular weight comprising about 20,000 Daltons (Da). In some embodiments, the IL-2 polypeptide or the IL-2 conjugate comprises a mutation at residue F42 corresponding with residue position 42 of SEQ ID NO: 1, and a conjugating moiety comprising a PEG, the PEG having a molecular weight comprising about 25,000 Daltons (Da). In some embodiments, n the IL-2 polypeptide or the IL-2 conjugate comprises a mutation at residue F42 corresponding with residue position 42 of SEQ ID NO: 1, and a conjugating moiety comprising a PEG, the PEG having a molecular weight comprising about 30,000 Daltons (Da). In some embodiments the IL-2 polypeptide or the IL-2 conjugate comprises a mutation at residue P65 corresponding with residue position 65 of SEQ ID NO: 1, and a conjugating moiety comprising a PEG, the PEG having a molecular weight comprising about 5,000 Daltons (Da). In some embodiments, t the IL-2 polypeptide or the IL-2 conjugate comprises a mutation at residue P65 corresponding with residue position 65 of SEQ ID NO: 1, and a conjugating moiety comprising a PEG, the PEG having a molecular weight comprising about 10,000 Daltons (Da). In some embodiments, the IL-2 polypeptide or the IL-2 conjugate comprises a mutation at residue P65 corresponding with residue position 65 of SEQ ID NO: 1, and a conjugating moiety comprising a PEG, the PEG having a molecular weight comprising about 15,000 Daltons (Da). In some embodiments, the IL-2 polypeptide or the IL-2 conjugate comprises a mutation at residue P65 corresponding with residue position 65 of SEQ ID NO: 1, and a conjugating moiety comprising a PEG, the PEG having a molecular weight comprising about 20,000 Daltons (Da). In some embodiments, the IL-2 polypeptide or the IL-2 conjugate comprises a mutation at residue P65 corresponding with residue position 65 of SEQ ID NO: 1, and a conjugating moiety comprising a PEG, the PEG having a molecular weight comprising about 25,000 Daltons (Da). In some embodiments, the IL-2 polypeptide or the IL-2 conjugate comprises a mutation at residue P65 corresponding with residue position 65 of SEQ ID NO: 1, and a conjugating moiety comprising a PEG, the PEG having a molecular weight comprising about 30,000 Daltons (Da). In some embodiments, the IL-2 polypeptide or the IL-2 conjugate comprises a mutation at residue E62 corresponding with residue position 62 of SEQ ID NO: 1, and a conjugating moiety comprising a PEG, the PEG having a molecular weight comprising about 5,000 Daltons (Da). In some embodiments, the IL-2 polypeptide or the IL-2 conjugate comprises a mutation at residue E62 corresponding with residue position 62 of SEQ ID NO: 1, and a conjugating moiety comprising a PEG, the PEG having a molecular weight comprising about 10,000 Daltons (Da). In some embodiments, the IL-2 polypeptide or the IL-2 conjugate comprises a mutation at residue E62 corresponding with residue position 62 of SEQ ID NO: 1, and a conjugating moiety comprising a PEG, the PEG having a molecular weight comprising about 15,000 Daltons (Da). In some embodiments the IL-2 polypeptide or the IL-2 conjugate comprises a mutation at residue E62 corresponding with residue position 62 of SEQ ID NO: 1, and a conjugating moiety comprising a PEG, the PEG having a molecular weight comprising about 20,000 Daltons (Da). In some embodiments, the IL-2 polypeptide or the IL-2 conjugate comprises a mutation at residue E62 corresponding with residue position 62 of SEQ ID NO: 1, and a conjugating moiety comprising a PEG, the PEG having a molecular weight comprising about 25,000 Daltons (Da). In some embodiments, the IL-2 polypeptide or the IL-2 conjugate comprises a mutation at residue E62 corresponding with residue position 62 of SEQ ID NO: 1, and a conjugating moiety comprising a PEG, the PEG having a molecular weight comprising about 30,000 Daltons (Da).

Aspects disclosed herein provide method of treating a disease or condition in a subject in need thereof, comprising administering to the subject a therapeutically effective amount of an isolated and modified IL-2 polypeptide described herein, an IL-2 conjugate described herein, an IL-2Rβγ binding protein described herein, an activator of a CD4+ helper cell, CD8+ effector naïve and memory cell, Natural Killer (NK) cell, or Natural killer T (NKT) cell described herein, or a pharmaceutical composition described herein. In some embodiments, the disease or condition is a cancer. In some embodiments, the cancer is a solid tumor cancer. In some embodiments, the solid tumor cancer is bladder cancer, bone cancer, brain cancer, breast cancer, colorectal cancer, esophageal cancer, eye cancer, head and neck cancer, kidney cancer, lung cancer, melanoma, ovarian cancer, pancreatic cancer, or prostate cancer. In some embodiments, the cancer is a hematologic malignancy. In some embodiments, the hematologic malignancy is chronic lymphocytic leukemia (CLL), small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some embodiments, the disease or condition comprises a pathogenic infection. In some embodiments, the pathogenic infection comprises a retrovirus, virus, deoxyribonucleic acid (DNA) virus, or ribonucleic acid (RNA) virus, or a combination thereof. In some embodiments, the RNA virus comprises a negative-sense single-stranded (ss)RNA virus, a positive-sense ssRNA virus, or a double-stranded (ds)RNA virus. In some embodiments, the DNA virus comprises a single-stranded (ss)DNA virus or a double-stranded (ds)DNA virus. In some embodiments, the disease or condition comprises an autoimmune disease. In some embodiments, the disease or condition comprises alopecia areata, autoimmune hemolytic anemia, autoimmune hepatitis, dermatomyositis, type 1 diabetes, juvenile idiopathic arthritis, glomerulonephritis, Graves' disease, Guillain-Barré syndrome, idiopathic thrombocytepenic purpura, myasthenia gravis, multiple sclerosis, pemphigus/pemphigoid, pernicious anemia, polyarteritis *nodosa*, polymyositis, primary biliary cirrhosis, psoriasis, rheumatoid arthritis, scleroderma, Sjögren's syndrome, systemic lupus erythematosus, thyroiditis, uveitis, vitiligo, or Wegener's granulomatosis, or a combination thereof. In some embodiments, the methods further comprise administering an additional therapeutic agent. In some embodiments, the isolated and modified IL-2 polypeptide, the IL-2 conjugate, the IL-2Rβγ binding protein, the activator of a CD4+ helper cell, CD8+ effector naïve and memory cell, Natural Killer (NK) cell, or Natural killer T (NKT) cell, or the pharmaceutical composition and the additional therapeutic agent are administered simultaneously. In some embodiments, the isolated and modified IL-2 polypeptide, the IL-2 conjugate, the IL-2Rβγ binding protein, the activator of a CD4+ helper cell, CD8+ effector naïve and memory cell, Natural Killer (NK) cell, or Natural killer T (NKT) cell, or the pharmaceutical composition and the additional therapeutic agent are administered sequentially. In some embodiments, the isolated and modified IL-2 polypeptide, the IL-2 conjugate, the IL-2Rβγ binding protein, the activator of a CD4+ helper cell, CD8+ effector naïve and memory cell, Natural Killer (NK) cell, or Natural killer T (NKT) cell, or the pharmaceutical composition is administered prior to the additional therapeutic agent. In some embodiments, the isolated and modified IL-2 polypeptide, the IL-2 conjugate, the IL-2Rβγ binding protein, the activator of a CD4+ helper cell, CD8+ effector naïve and memory cell, Natural Killer (NK) cell, or Natural killer T (NKT) cell, or the pharmaceutical composition is administered after the administration of the additional therapeutic agent.

Aspects disclosed herein provide methods of expanding a CD4+ helper cell, CD8+ effector naïve and memory cell, Natural Killer (NK) cell, or Natural killer T (NKT) cell population, comprising: contacting a cell population with an isolated and modified IL-2 polypeptide described herein, an IL-2 conjugate of any one described herein, an IL-2 conjugate described herein, an IL-2Rβγ binding protein described herein, an activator of a CD4+ helper cell, CD8+ effector naïve and memory cell, CD8+ T cell, Natural Killer (NK) cell, or Natural killer T (NKT) cell described herein, or a pharmaceutical composition described herein, for a time sufficient to induce formation of a complex with an IL-2Rβγ, thereby stimulating the expansion of the Teff, the CD8+ T Cell and/or NK cell population. In some embodiments, the isolated and modified IL-2 polypeptide, an IL-2 conjugate, an IL-2Rβγ binding protein, an activator of a CD4+ helper cell, CD8+ effector naïve and memory cell, Natural Killer (NK) cell, or Natural killer T (NKT) cell, or a pharmaceutical composition, expands CD4+ T regulatory (Treg) cells by less than 20%, 15%, 10%, 5%, or 1% in the CD3+ cell population compared to an expansion of CD4+ Treg cells in the CD3+ cell population contacted with a wild-type IL-2 polypeptide. In some embodiments the isolated and modified IL-2 polypeptide, an IL-2 conjugate, an IL-2Rβγ binding protein, an activator of a CD4+ helper cell, CD8+ effector naïve and memory cell, Natural Killer (NK) cell, or Natural killer T (NKT) cell, or a pharmaceutical composition, does not expand CD4+ Treg cells in the cell population. In some embodiments, the ratio of the Teff cells to Treg cells in the cell population after incubation with the isolated and modified IL-2 polypeptide, an IL-2 conjugate, an IL-2Rβγ binding protein, an activator of a CD4+ helper cell, CD8+ effector naïve and memory cell, Natural Killer (NK) cell, or Natural killer T (NKT) cell, or a pharmaceutical composition, is about or at least 2:1, 3:1, 4:1, 5:1, 6:1, 7:1, 8:1, 9:1, 10:1, 20:1, 50:1, or 100:1. In some embodiments, the method is an in vivo method. In some embodiments, the method is an in vitro method. In some embodiments, the method is an ex vivo method. In some embodiments, the subject is a human.

Aspects disclosed herein provide kits comprising one or more of the isolated and modified the IL-2 polypeptide described herein, an IL-2 conjugate described herein, an IL-2Rβγ binding protein described herein 0, an activator of a CD4+ helper cell, CD8+ effector naïve and memory cell, Natural Killer (NK) cell, or Natural killer T (NKT) cell described herein, and/or a pharmaceutical composition described herein. In some embodiments, the modified IL-2 polypeptide comprises a mutation at residue F42 corresponding to a residue position 42 of SEQ ID NO: 1, and a conjugating moiety comprising a PEG, the PEG having a molecular weight comprising about 5,000 Daltons (Da), 10,000 Da, 15,000 Da, 20,000 Da, 25,000 Da, 30,000 Da, 35,000 Da, 40,000 Da, 45,000 Da, or 50,000 Da. In some embodiments, the PEG corresponds with a longer in vivo plasma half-life of the modified IL-2 polypeptide, as compared to the in vivo plasma half-life of a smaller PEG. In some embodiments, the PEG corresponds with a shorter in vivo plasma half-life of the modified IL-2 polypeptide, as compared to the in vivo plasma half-life of a larger PEG. In some embodiments, the molecular weight of the PEG does not affect a receptor signaling potency of the modified IL-2 polypeptide to the IL-2βγ or IL-2αβγ signaling complexes. In some embodiments, the molecular weight of the PEG does not affect, or has minimal effect on, a desired reduced binding of the modified IL-2 polypeptide to IL-2Rα or a desired maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of a modified IL-2 polypeptide/IL-2Rβγ complex. In some embodiments, the IL-2 conjugate comprises a mutation at residue F42 corresponding to a residue position 42 of SEQ ID NO: 1, and a conjugating moiety comprising a PEG, the PEG having a molecular weight comprising about 5,000 Daltons (Da), 10,000 Da, 15,000 Da, 20,000 Da, 25,000 Da, 30,000 Da, 35,000 Da, 40,000 Da, 45,000 Da, or 50,000 Da. In some embodiments, the PEG corresponds with a longer in vivo plasma half-life of the modified IL-2 polypeptide, as compared to the in vivo plasma half-life of a smaller PEG. In some embodiments, the PEG corresponds with a shorter in vivo plasma half-life of the modified IL-2 polypeptide, as compared to the in vivo plasma half-life of a larger PEG. In some embodiments, t the molecular weight of the PEG does not affect a receptor signaling potency of the modified IL-2 polypeptide to the IL-2βγ or IL-2αβγ signaling complexes. In some embodiments, the molecular weight of the PEG does not affect, or has minimal effect on, a desired reduced binding of the modified IL-2 polypeptide to IL-2Rα or a desired maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of a modified IL-2 polypeptide/IL-2Rβγ complex. In some embodiments, the modified IL-2 polypeptide comprises a mutation at residue E62 corresponding to a residue position 62 of SEQ ID NO: 1, and a conjugating moiety comprising a PEG, the PEG having a molecular weight comprising about 5,000 Daltons (Da), 10,000 Da, 15,000 Da, 20,000 Da, 25,000 Da, 30,000 Da, 35,000 Da, 40,000 Da, 45,000 Da, or 50,000 Da. In some embodiments, the PEG corresponds with a longer in vivo plasma half-life of the modified IL-2 polypeptide, as compared to the in vivo plasma half-life of a smaller PEG. In some embodiments, the PEG corresponds with a shorter in vivo plasma half-life of the modified IL-2 polypeptide, as compared to the in vivo plasma half-life of a larger PEG. In some embodiments, the molecular weight of the PEG does not affect a receptor signaling potency of the modified IL-2 polypeptide to the IL-2βγ or IL-2αβγ signaling complexes. In some embodiments, the molecular weight of the PEG does not affect, or has minimal effect on, a desired reduced binding of the modified IL-2 polypeptide to IL-2Rα or a desired maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of a modified IL-2 polypeptide/IL-2Rβγ complex. In some embodiments, the IL-2 conjugate comprises a mutation at residue E62 corresponding to a residue position 62 of SEQ ID NO: 1, and a conjugating moiety comprising a PEG, the PEG having a molecular weight comprising about 5,000 Daltons (Da), 10,000 Da, 15,000 Da, 20,000 Da, 25,000 Da, 30,000 Da, 35,000 Da, 40,000 Da, 45,000 Da, or 50,000 Da. In some embodiments, the PEG corresponds with a longer in vivo plasma half-life of the modified IL-2 polypeptide, as compared to the in vivo plasma half-life of a smaller PEG. In some embodiments, the PEG corresponds with a shorter in vivo plasma half-life of the modified IL-2 polypeptide, as compared to the in vivo plasma half-life of a larger PEG. In some embodiments, the molecular weight of the PEG does not affect a receptor signaling potency of the modified IL-2 polypeptide to the IL-2βγ or IL-2αβγ signaling complexes. In some embodiments, the molecular weight of the PEG does not affect, or has minimal effect on, a desired reduced binding of the modified IL-2 polypeptide to IL-2Rα or a desired maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of a modified IL-2 polypeptide/IL-2Rβγ complex. In some embodiments, the modified IL-2 polypeptide comprises a mutation at residue P65 corresponding to a residue position 65 of SEQ ID NO: 1, and a conjugating moiety comprising a PEG, the PEG having a molecular weight comprising about 5,000 Daltons (Da), 10,000 Da, 15,000 Da, 20,000 Da, 25,000 Da, 30,000 Da, 35,000 Da, 40,000 Da, 45,000 Da, or 50,000 Da. In some embodiments, the PEG corresponds with a longer in vivo plasma half-life of the modified IL-2 polypeptide, as compared to the in vivo plasma half-life of a smaller PEG. In some embodiments, the PEG corresponds with a shorter in vivo plasma half-life of the modified IL-2 polypeptide, as compared to the in vivo plasma half-life of a larger PEG. In some embodiments, the molecular weight of the PEG does not affect a receptor signaling potency of the modified IL-2 polypeptide to the IL-2βγ or IL-2αβγ signaling complexes. In some embodiments, the molecular weight of the PEG does not affect, or has minimal effect on, a desired reduced binding of the modified IL-2 polypeptide to IL-2Rα or a desired maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of a modified IL-2 polypeptide/IL-2Rβγ complex. In some embodiments, the IL-2 conjugate comprises a mutation at residue P65 corresponding to a residue position 65 of SEQ ID NO: 1, and a conjugating moiety comprising a PEG, the PEG having a molecular weight comprising about 5,000 Daltons (Da), 10,000 Da, 15,000 Da, 20,000 Da, 25,000 Da, 30,000 Da, 35,000 Da, 40,000 Da, 45,000 Da, or 50,000 Da. In some embodiments, the PEG corresponds with a longer in vivo plasma half-life of the modified IL-2 polypeptide, as compared to the in vivo plasma half-life of a smaller PEG. In some embodiments, the PEG corresponds with a shorter in vivo plasma half-life of the modified IL-2 polypeptide, as compared to the in vivo plasma half-life of a larger PEG. In some embodiments, the molecular weight of the PEG does not affect a receptor signaling potency of the modified IL-2 polypeptide to the IL-2βγ or IL-2αβγ signaling complexes. In some embodiments, the molecular weight of the PEG does not affect, or has minimal effect on, a desired reduced binding of the modified IL-2 polypeptide to IL-2Rα or a desired maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of a modified IL-2 polypeptide/IL-2Rβγ complex.

Aspects disclosed herein provide kit comprising one or more polynucleic acid sequences encoding the IL-2 polypeptide described herein, an IL-2 conjugate described herein, an IL-2Rβγ binding protein described herein, an activator of a CD4+ helper cell, CD8+ effector naïve and memory cell, Natural Killer (NK) cell, or Natural killer T (NKT) cell described herein, and/or a pharmaceutical composition described herein. In some embodiments, the modified IL-2 polypeptide comprises a mutation at residue F42 corresponding to a residue position 42 of SEQ ID NO: 1, and a conjugating moiety comprising a PEG, the PEG having a molecular weight comprising about 5,000 Daltons (Da), 10,000 Da, 15,000 Da, 20,000 Da, 25,000 Da, 30,000 Da, 35,000 Da, 40,000 Da, 45,000 Da, or 50,000 Da. In some embodiments, the PEG corresponds with a longer in vivo plasma half-life of the modified IL-2 polypeptide, as compared to the in vivo plasma half-life of a smaller PEG. In some embodiments, the PEG corresponds with a shorter in vivo plasma half-life of the modified IL-2 polypeptide, as compared to the in vivo plasma half-life of a larger PEG. In some embodiments, the molecular weight of the PEG does not affect a receptor signaling potency of the modified IL-2 polypeptide to the IL-2βγ or IL-2αβγ signaling complexes. In some embodiments, the molecular weight of the PEG does not affect, or has minimal effect on, a desired reduced binding of the modified IL-2 polypeptide to IL-2Rα or a desired maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of a modified IL-2 polypeptide/IL-2Rβγ complex. In some embodiments, the IL-2 conjugate comprises a mutation at residue F42 corresponding to a residue position 42 of SEQ ID NO: 1, and a conjugating moiety comprising a PEG, the PEG having a molecular weight comprising about 5,000 Daltons (Da), 10,000 Da, 15,000 Da, 20,000 Da, 25,000 Da, 30,000 Da, 35,000 Da, 40,000 Da, 45,000 Da, or 50,000 Da. In some embodiments, the PEG corresponds with a longer in vivo plasma half-life of the modified IL-2 polypeptide, as compared to the in vivo plasma half-life of a smaller PEG. In some embodiments, the PEG corresponds with a shorter in vivo plasma half-life of the modified IL-2 polypeptide, as compared to the in vivo plasma half-life of a larger PEG. In some embodiments, t the molecular weight of the PEG does not affect a receptor signaling potency of the modified IL-2 polypeptide to the IL-2βγ or IL-2αβγ signaling complexes. In some embodiments, the molecular weight of the PEG does not affect, or has minimal effect on, a desired reduced binding of the modified IL-2 polypeptide to IL-2Rα or a desired maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of a modified IL-2 polypeptide/IL-2Rβγ complex. In some embodiments, the modified IL-2 polypeptide comprises a mutation at residue E62 corresponding to a residue position 62 of SEQ ID NO: 1, and a conjugating moiety comprising a PEG, the PEG having a molecular weight comprising about 5,000 Daltons (Da, e.g., 5 kD or 5 kDa), 10,000 Da, 15,000 Da, 20,000 Da, 25,000 Da, 30,000 Da, 35,000 Da, 40,000 Da, 45,000 Da, or 50,000 Da. In some embodiments, the PEG corresponds with a longer in vivo plasma half-life of the modified IL-2 polypeptide, as compared to the in vivo plasma half-life of a smaller PEG. In some embodiments, the PEG corresponds with a shorter in vivo plasma half-life of the modified IL-2 polypeptide, as compared to the in vivo plasma half-life of a larger PEG. In some embodiments, the molecular weight of the PEG does not affect a receptor signaling potency of the modified IL-2 polypeptide to the IL-2βγ or IL-2αβγ signaling complexes. In some embodiments, the molecular weight of the PEG does not affect, or has minimal effect on, a desired reduced binding of the modified IL-2 polypeptide to IL-2Rα or a desired maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of a modified IL-2 polypeptide/IL-2Rβγ complex. In some embodiments, the IL-2 conjugate comprises a mutation at residue E62 corresponding to a residue position 62 of SEQ ID NO: 1, and a conjugating moiety comprising a PEG, the PEG having a molecular weight comprising about 5,000 Daltons (Da), 10,000 Da, 15,000 Da, 20,000 Da, 25,000 Da, 30,000 Da, 35,000 Da, 40,000 Da, 45,000 Da, or 50,000 Da. In some embodiments, the PEG corresponds with a longer in vivo plasma half-life of the modified IL-2 polypeptide, as compared to the in vivo plasma half-life of a smaller PEG. In some embodiments, the PEG corresponds with a shorter in vivo plasma half-life of the modified IL-2 polypeptide, as compared to the in vivo plasma half-life of a larger PEG. In some embodiments, the molecular weight of the PEG does not affect a receptor signaling potency of the modified IL-2 polypeptide to the IL-2βγ or IL-2αβγ signaling complexes. In some embodiments, the molecular weight of the PEG does not affect, or has minimal effect on, a desired reduced binding of the modified IL-2 polypeptide to IL-2Rα or a desired maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of a modified IL-2 polypeptide/IL-2Rβγ complex. In some embodiments, the modified IL-2 polypeptide comprises a mutation at residue P65 corresponding to a residue position 65 of SEQ ID NO: 1, and a conjugating moiety comprising a PEG, the PEG having a molecular weight comprising about 5,000 Daltons (Da), 10,000 Da, 15,000 Da, 20,000 Da, 25,000 Da, 30,000 Da, 35,000 Da, 40,000 Da, 45,000 Da, or 50,000 Da. In some embodiments, the PEG corresponds with a longer in vivo plasma half-life of the modified IL-2 polypeptide, as compared to the in vivo plasma half-life of a smaller PEG. In some embodiments, the PEG corresponds with a shorter in vivo plasma half-life of the modified IL-2 polypeptide, as compared to the in vivo plasma half-life of a larger PEG. In some embodiments, the molecular weight of the PEG does not affect a receptor signaling potency of the modified IL-2 polypeptide to the IL-2βγ or IL-2αβγ signaling complexes. In some embodiments, the molecular weight of the PEG does not affect, or has minimal effect on, a desired reduced binding of the modified IL-2 polypeptide to IL-2Rα or a desired maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of a modified IL-2 polypeptide/IL-2Rβγ complex. In some embodiments, the IL-2 conjugate comprises a mutation at residue P65 corresponding to a residue position 65 of SEQ ID NO: 1, and a conjugating moiety comprising a PEG, the PEG having a molecular weight comprising about 5,000 Daltons (Da), 10,000 Da, 15,000 Da, 20,000 Da, 25,000 Da, 30,000 Da, 35,000 Da, 40,000 Da, 45,000 Da, or 50,000 Da. In some embodiments, the PEG corresponds with a longer in vivo plasma half-life of the modified IL-2 polypeptide, as compared to the in vivo plasma half-life of a smaller PEG. In some embodiments, the PEG corresponds with a shorter in vivo plasma half-life of the modified IL-2 polypeptide, as compared to the in vivo plasma half-life of a larger PEG. In some embodiments, the molecular weight of the PEG does not affect a receptor signaling potency of the modified IL-2 polypeptide to the IL-2βγ or IL-2αβγ signaling complexes. In some embodiments, the molecular weight of the PEG does not affect, or has minimal effect on, a desired reduced binding of the modified IL-2 polypeptide to IL-2Rα or a desired maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of a modified IL-2 polypeptide/IL-2Rβγ complex.

Aspects disclosed herein provide cell culture system comprising an immune cell and the isolated and modified IL-2 polypeptide described herein, and/or the IL-2 conjugate described herein. In some embodiments, the immune cell comprises a CD4+ helper cell, CD8+ effector naïve and memory T cell, a CD8+ cell, a Natural Killer (NK) cell, or a Natural killer T (NKT) cell. In some embodiments, the modified IL-2 polypeptide or the IL-2 conjugate is effective to enhance expansion of the immune cell.

Aspects disclosed herein provide reagents for manufacturing an adoptive cell therapy the isolated and modified IL-2 polypeptide described herein, and/or the IL-2 conjugate described herein. In some embodiments, the isolated and modified IL-2 polypeptide, and/or the IL-2 conjugate comprises a mutation at residue P65 corresponding to a residue position 65 of SEQ ID NO: 1, and a conjugating moiety comprising a PEG, the PEG having a molecular weight comprising about 5,000 Daltons (Da), 10,000 Da, 15,000 Da, 20,000 Da, 25,000 Da, 30,000 Da, 35,000 Da, 40,000 Da, 45,000 Da, or 50,000 Da. In some embodiments, the isolated and modified IL-2 polypeptide, and/or the IL-2 conjugate comprises a mutation at residue E61 corresponding to a residue position 61 of SEQ ID NO: 1, and a conjugating moiety comprising a PEG, the PEG having a molecular weight comprising about 5,000 Daltons (Da), 10,000 Da, 15,000 Da, 20,000 Da, 25,000 Da, 30,000 Da, 35,000 Da, 40,000 Da, 45,000 Da, or 50,000 Da. In some embodiments, the isolated and modified IL-2 polypeptide, and/or the IL-2 conjugate comprises a mutation at residue F42 corresponding to a residue position 42 of SEQ ID NO: 1, and a conjugating moiety comprising a PEG, the PEG having a molecular weight comprising about 5,000 Daltons (Da), 10,000 Da, 15,000 Da, 20,000 Da, 25,000 Da, 30,000 Da, 35,000 Da, 40,000 Da, 45,000 Da, or 50,000 Da. In some embodiments, the molecular weight of the PEG is effective to improve solubility of the isolated and modified IL-2 polypeptide and/or IL-2 conjugate. In some embodiments, the molecular weight of the PEG is effective to increase stability of the isolated and modified IL-2 polypeptide and/or IL-2 conjugate. In some embodiments, the molecular weight of the PEG is effective to improve an efficiency of manufacturing of the adoptive cell therapy of the isolated and modified IL-2 polypeptide and/or IL-2 conjugate.

Aspects disclosed herein provide an isolated and modified interleukin 2 (IL-2) polypeptide comprising at least one unnatural amino acid at a position that reduces receptor signaling potency to interleukin 2 receptor βγ (IL-2Rβγ) or reduces a recruitment of an IL-2Rγ subunit to the IL-2/IL-2R3 complex, but retains significant activation of interleukin 2 αβγ receptor (IL-2Rαβγ), wherein the reduced receptor signaling potency is compared to the receptor signaling potency between a wild-type IL-2 polypeptide and IL-2Rβγ, and wherein the recruitment is compared to a recruitment of an IL-2Rγ subunit by a wild-type IL-2 polypeptide.

Aspects disclosed herein provide an isolated and modified interleukin 2 (IL-2) polypeptide comprising at least one unnatural amino acid at a position that increases a recruitment of an IL-2Rα subunit to the IL-2 polypeptide leading to activation of interleukin 2 αβγ receptor (IL-2Rαβγ), wherein the increase in recruitment is compared to a recruitment of an IL-2Rα subunit by a wild-type IL-2 polypeptide. In some embodiments, the position of the at least one unnatural amino acid is selected from A108, D109, E110, T111, A112, T113, E116, N119, R120, T123, A125, Q126, 5127, 5130, T131, L132, and T133, wherein the numbering of the amino acid residues corresponds to SEQ ID NO: 1. In some embodiments, the position of the at least one unnatural amino acid is selected from K8, K9, Q11, L12, E15, H16, L18, L19, D20, Q22, M23, N26, R81, D84, 587, N88, V91, 192, L94, E95, E116, N119, R120, T123, A125, Q126, 5127, S130, T131, L132, and T133, wherein the numbering of the amino acid residues corresponds to SEQ ID NO: 1. In some embodiments, the position of the at least one unnatural amino acid is selected from P2, T3, S4, S5, S6, T7, K8, K9, Q11, L12, E15, H16, L18, L19, D20, Q22, M23, N26, G27, N29, N30, Y31, K32, K35, T37, M46, K47, K48, A50, T51, E52, K53, H55, Q57, E60, E67, N71, Q74, S75, K76, N77, F78, H79, R81, P82, R83, D84, S87, N88, N89, V91, 192, L94, E95, K97, G98, S99, E100, T101, T102, F103, M104, C105, E106, Y107, In some embodiments, the position of the at least one unnatural amino acid is selected from K8, K9, Q11, L12, E15, H16, L18, L19, D20, Q22, M23, N26, R81, D84, S87, N88, V91, 192, L94, E95, E116, N119, R120, T123, A125, Q126, S127, S130, T131, L132, and T133, wherein the numbering of the amino acid residues corresponds to SEQ ID NO: 1. In some embodiments, the position of the at least one unnatural amino acid is selected from P2, T3, S4, S5, S6, T7, G27, N29, N30, Y31, K32, K35, T37, M46, K47, K48, A50, T51, E52, K53, H55, Q57, E60, E67, N71, Q74, S75, K76, N77, F78, H79, P82, R83, N89, K97, G98, S99, E100, T101, T102, F103, M104, C105, E106, Y107, A108, D109, E110, T111, A112, and T113, wherein the numbering of the amino acid residues corresponds to SEQ ID NO: 1. In some embodiments, the position of the at least one unnatural amino acid is selected from K8, K9, L12, E15, H16, L19, D20, Q22, M23, N26, D84, N88, E95, and Q126, wherein the numbering of the amino acid residues corresponds to SEQ ID NO: 1. In some embodiments, the position of the at least one unnatural amino acid is selected from K8, K9, and H16, wherein the numbering of the amino acid residues corresponds to SEQ ID NO: 1. In some embodiments, the position of the at least one unnatural amino acid is selected from Q22, N26, N88, and Q126, wherein the numbering of the amino acid residues corresponds to SEQ ID NO: 1. In some embodiments, the position of the at least one unnatural amino acid is selected from E15, D20, D84, and E95, wherein the numbering of the amino acid residues corresponds to SEQ ID NO: 1. In some embodiments, the position of the at least one unnatural amino acid is selected from L12, L19, and M23, wherein the numbering of the amino acid residues corresponds to SEQ ID NO: 1. In some embodiments, the position of the at least one unnatural amino acid is selected from Q22 and N26, wherein the numbering of the amino acid residues corresponds to SEQ ID NO: 1. In some embodiments, the at least one unnatural amino acid: is a lysine analogue; is a cysteine analogue or a histidine analogue; comprises an aromatic side chain; comprises an azido group; comprises an alkyne group; or comprises an aldehyde or ketone group. In some embodiments, the at least one unnatural amino acid does not comprise an aromatic side chain. In some embodiments, the at least one unnatural amino acid comprises N6-((2-azidoethoxy)-carbonyl)-L-lysine (AzK; the chemical structure of which is shown as compound 90 in FIG. 3C), N6-(propargyloxy)-carobonyl-L-lysine (PraK), BCN-L-lysine, norbornene lysine, TCO-lysine, methyltetrazine lysine, allyloxycarbonyllysine, 2-amino-8-oxononanoic acid, 2-amino-8-oxooctanoic acid, p-acetyl-L-phenylalanine, p-azidomethyl-L-phenylalanine (AMF), p-iodo-L-phenylalanine, *m*-acetylphenylalanine, 2-amino-8-oxononanoic acid, p-propargyloxyphenylalanine, p-propargyl-phenylalanine, 3-methyl-phenylalanine, L-Dopa, fluorinated phenylalanine, isopropyl-L-phenylalanine, p-azido-L-phenylalanine, p-acyl-L-phenylalanine, p-benzoyl-L-phenylalanine, p-bromophenylalanine, p-amino-L-phenylalanine, isopropyl-L-phenylalanine, 0-allyltyrosine, O-methyl-L-tyrosine, O-4-allyl-L-tyrosine, 4-propyl-L-tyrosine, phosphonotyrosine, tri-O-acetyl-GlcNA, cp-serine, L-phosphoserine, phosphonoserine, L-3-(2-naphthyl)alanine, 2-amino-3-((2-((3-(benzyloxy)-3-oxopropyl)amino)ethyl)selanyl)propanoic acid, 2-amino-3-(phenylselanyl)propanoic, or selenocysteine. In some embodiments, the at least one unnatural amino acid is incorporated into the modified IL-2 polypeptide by an orthogonal tRNA. In some embodiments, the orthogonal tRNA disclosed herein comprises at least one unnatural nucleobase. In some embodiments, the modified IL-2 polypeptide is covalently attached to a conjugating moiety through the at least one unnatural amino acid. In some embodiments, the conjugating moiety comprises a water-soluble polymer, a lipid, a protein, or a peptide. In some embodiments, the water-soluble polymer comprises polyethylene glycol (PEG), poly(propylene glycol) (PPG), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), or a combination thereof. In some embodiments, the water-soluble polymer comprises a PEG molecule. In some embodiments, the PEG molecule is a linear PEG. In some embodiments, the PEG molecule is a branched PEG. In some embodiments, the PEG comprises between about 2,000-50,000 Daltons (Da). In some embodiments, the PEG has a molecular weight comprising about 5,000 Da, 10,000 Da, 15,000 Da, 20,000 Da, 25,000 Da, 30,000 Da, 35,000 Da, 40,000 Da, 45,000 Da, or 50,000 Da. In some embodiments, the unnatural amino acid comprises F42 in a residue position 42 of SEQ ID NO: 1. In some embodiments, the unnatural amino acid comprises P65 in a residue position 65 of SEQ: 1. In some embodiments, the unnatural amino acid comprises E62 in a residue position 62 of SEQ ID NO: 1. In some embodiments, herein the molecular weight determines, at least in part, the in vivo plasma half-life of the IL-2 polypeptide. In some embodiments, the PEG corresponds with a longer in vivo plasma half-life of the modified IL-2 polypeptide, as compared to the in vivo plasma half-life of a smaller PEG. In some embodiments, the PEG corresponds with a shorter in vivo plasma half-life of the modified IL-2 polypeptide, as compared to the in vivo plasma half-life of a larger PEG. In some embodiments, the molecular weight of the PEG does not affect a receptor signaling potency of the modified IL-2 polypeptide to the IL-2βγ or IL-2αβγ signaling complexes. In some embodiments, the molecular weight of the PEG does not affect, or has minimal effect on, a desired reduced binding of the modified IL-2 polypeptide to IL-2Rβγ or a desired maintained binding with to IL-2Rβγα signaling complex, wherein the reduced binding to IL-2Rβγ is compared to binding between a wild-type IL-2 polypeptide and IL-2Rβγα. In some embodiments, the molecular weight of the PEG does not affect the formation of a modified IL-2 polypeptide/IL-2Rβγ complex. In some embodiments, the water-soluble polymer comprises a polysaccharide. In some embodiments, the polysaccharide comprises dextran, polysialic acid (PSAs), hyaluronic acid (HA), amylose, heparin, heparan sulfate (HS), dextrin, or hydroxyethyl-starch (HES). In some embodiments, the lipid comprises a fatty acid. In some embodiments, the fatty acid comprises from about 6 to about 26 carbon atoms, from about 6 to about 24 carbon atoms, from about 6 to about 22 carbon atoms, from about 6 to about 20 carbon atoms, from about 6 to about 18 carbon atoms, from about 20 to about 26 carbon atoms, from about 12 to about 26 carbon atoms, from about 12 to about 24 carbon atoms, from about 12 to about 22 carbon atoms, from about 12 to about 20 carbon atoms, or from about 12 to about 18 carbon atoms. In some embodiments, the fatty acid is a saturated fatty acid. In some embodiments, the protein comprises an albumin, a transferrin, or a transthyretin. In some embodiments, the protein comprises an antibody or its binding fragments thereof. In some embodiments, herein the antibody or its binding fragments thereof comprises an Fc portion of an antibody. In some embodiments, the peptide comprises a XTEN peptide, a glycine-rich homoamino acid polymer (HAP), a PAS polypeptide, an elastin-like polypeptide (ELP), a CTP peptide, or a gelatin-like protein (GLK) polymer. In some embodiments, the conjugating moiety is indirectly bound to the at least one unnatural amino acid of the modified IL-2 through a linker. In some embodiments, the linker comprises a homobifunctional linker, a heterobifunctional linker, a zero-length linker, a cleavable or a non-cleavable dipeptide linker, a maleimide group, a spacer, or a combination thereof. In some embodiments, the isolated and modified IL-2 polypeptide has a decrease in receptor signaling potency to IL-2Rβγ, and the decrease in receptor signaling potency is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 400-fold, 500-fold, 1000-fold, or more to IL-2Rβγ relative to a wild-type IL-2 polypeptide. In some embodiments, the modified IL-2 polypeptide is: a functionally active fragment of a full-length IL-2 polypeptide; a recombinant IL-2 polypeptide; or a recombinant human IL-2 polypeptide. In some embodiments, the modified IL-2 polypeptide comprises an N-terminal deletion, a C-terminal deletion, or a combination thereof. In some embodiments, the N-terminal deletion comprises a deletion of the first 1, 2, 3, 4, 5, 6, 7, 8, 9, 10, 11, 12, 13, 14, 15, 20, 25, or 30 residues from the N-terminus, wherein the residue positions are in reference to the positions in SEQ ID NO: 1. In some embodiments, the C-terminal deletion comprises a deletion of the last 1, 2, 3, 4, 5, 6, 7, 8, 9, 10, 11, 12, 13, 14, 15, 20, or more residues from the C-terminus, wherein the residue positions are in reference to the positions in SEQ ID NO: 1. In some embodiments, the functionally active fragment comprises IL-2 region 10-133, 20-133, 30-133, 10-130, 20-130, 30-130, 10-125, 20-125, 30-125, 1-130, or 1-125, wherein the residue positions are in reference to the positions in SEQ ID NO: 1. In some embodiments, the modified IL-2 polypeptide comprises about 80%, 85%, 90%, 95%, 96%, 97%, 98%, or 99% sequence identity to SEQ ID NO: 1. In some embodiments, the modified IL-2 polypeptide with the decrease in receptor signaling potency to IL-2Rβγ is capable of expanding CD4+ T regulatory (Treg) cells. In some embodiments, the conjugating moiety impairs or blocks the receptor signaling potency of IL-2 with IL-2Rβγ, or reduces recruitment of the IL-2Rγ subunit to the IL-2/IL-2Rβ complex. In some embodiments, the CD4+ Treg cell proliferation by the modified IL-2/IL-2Rαβγ complex is equivalent or greater to that of a wild-type IL-2 polypeptide. In some embodiments, the modified IL-2/IL-2Rαβγ complex induces proliferation of the CD4+ Treg cells to a population that is sufficient to modulate a disease course in an animal model. In some embodiments, the modified IL-2 polypeptide exhibits a first receptor signaling potency to IL-2Rβγ and a second receptor signaling potency to IL-2Rαβγ, wherein the first receptor signaling potency is at least 1-fold, 2-fold, 3-fold, 4-fold, 5-fold, 6-fold, 7-fold, 8-fold, 9-fold, 10-fold, 20-fold, 30-fold, 50-fold, 100-fold, 500-fold, 1000-fold, or lower than the second receptor signaling potency. In some embodiments, the first receptor signaling potency of the modified IL-2 polypeptide is lower than a receptor signaling potency of the wild-type IL-2 polypeptide to IL-2Rβγ. In some embodiments, the second receptor signaling potency of the modified IL-2 polypeptide is lower than a receptor signaling potency of the wild-type IL-2 polypeptide to IL-2Rαβγ. In some embodiments, wherein the modified IL-2 polypeptide further provides an increase in a recruitment of an IL-2Rα subunit to the IL-2 polypeptide leading to activation of interleukin 2 αβγ receptor (IL-2Rαβγ), wherein the increase in recruitment is compared to a recruitment of an IL-2Rα subunit by a wild-type IL-2 polypeptide. In some embodiments, the modified IL-2 polypeptide further provides a decrease in a recruitment of an IL-2Rγ subunit to the IL-2/IL-2Rβ complex, wherein the reduced recruitment is compared to a recruitment of an IL-2Rβ subunit and/or IL-2Rγ subunit by a wild-type IL-2 polypeptide.

Aspects disclosed herein provide an interleukin 2 αβγ receptor (IL-2Rαβγ) binding protein, wherein the receptor signaling potency for an interleukin 2 βγ receptor (IL-2Rβγ) of said binding protein is less than that of wild-type human IL-2 (hTL-2), and wherein said binding protein comprises at least one unnatural amino acid.

Aspects disclosed herein provide an interleukin 2 αβγ receptor (IL-2Rαβγ) binding protein, wherein a recruitment of an IL-2Rγ subunit to an IL-2/IL-2Rβ complex by said binding protein is less than that of wild-type human IL-2 (hIL-2), and wherein said binding protein comprises at least one unnatural amino acid. In some embodiments, said binding protein is a modified IL-2 polypeptide or a functionally active fragment thereof, wherein the modified IL-2 polypeptide comprises at least one unnatural amino acid.

Aspects disclosed herein provide IL-2/IL-2Rαβγ complexes comprising a modified IL-2 polypeptide comprising an unnatural amino acid and an IL-2Rαβγ, wherein the modified IL-2 polypeptide has a reduced receptor signaling potency toward IL-2Rβγ, and wherein the reduced receptor signaling potency is compared to a binding affinity between a wild-type IL-2 polypeptide and IL-2Rβγ. In some embodiments, said activator expands CD8+ effector T cell and/or Natural Killer cells by less than 20%, 15%, 10%, 5%, 1%, or 0.1% in the CD3+ cell population when said activator is in contact with said CD3+ cell population, relative to an expansion of CD8+ effector T cell and/or Natural Killer cells in the CD3+ cell population contacted by a wild-type IL-2 polypeptide. In some embodiments, said activator does not expand CD8+ effector T cell and/or Natural Killer cells. In some embodiments, said cell population is an in vivo cell population. In some embodiments, said cell population is an in vitro cell population. In some embodiments, said cell population is an ex vivo cell population.

Aspects disclosed herein provide IL-2/IL-2Rαβγ complexes comprising a modified IL-2 polypeptide comprising an unnatural amino acid and an IL-2Rαβγ, wherein a recruitment of an IL-2Rγ subunit to an IL-2/IL-2Rβ complex by said modified IL-2 polypeptide is less than that of a wild-type IL-2 polypeptide. In some embodiments, the modified IL-2 polypeptide further comprises a conjugating moiety covalently attached to the unnatural amino acid. In some embodiments, said activator expands CD8+ effector T cell and/or Natural Killer cells by less than 20%, 15%, 10%, 5%, 1%, or 0.1% in the CD3+ cell population when said activator is in contact with said CD3+ cell population, relative to an expansion of CD8+ effector T cell and/or Natural Killer cells in the CD3+ cell population contacted by a wild-type IL-2 polypeptide. In some embodiments, said activator does not expand CD8+ effector T cell and/or Natural Killer cells. In some embodiments, said cell population is an in vivo cell population. In some embodiments, said cell population is an in vitro cell population. In some embodiments, said cell population is an ex vivo cell population.

Aspects disclosed herein provide CD4+ Treg cell activator that selectively expands CD4+ Treg cells in a cell population, wherein said activator comprises a modified IL-2 polypeptide comprising at least one unnatural amino acid. In some embodiments, said activator expands CD8+ effector T cell and/or Natural Killer cells by less than 20%, 15%, 10%, 5%, 1%, or 0.1% in the CD3+ cell population when said activator is in contact with said CD3+ cell population, relative to an expansion of CD8+ effector T cell and/or Natural Killer cells in the CD3+ cell population contacted by a wild-type IL-2 polypeptide. In some embodiments, said activator does not expand CD8+ effector T cell and/or Natural Killer cells. In some embodiments, said cell population is an in vivo cell population. In some embodiments, said cell population is an in vitro cell population. In some embodiments, said cell population is an ex vivo cell population.

Aspects disclosed herein provide pharmaceutical composition comprising: an isolated and modified IL-2 polypeptide described herein, an IL-2Rαβγ binding protein described herein, or a CD4+ Treg described herein; and a pharmaceutically acceptable excipient. In some embodiments, the pharmaceutical composition is formulated for systemic delivery. In some embodiments, the pharmaceutical composition is formulated for parenteral administration. In some embodiments, the autoimmune disease or disorder comprises alopecia areata, autoimmune hemolytic anemia, autoimmune hepatitis, dermatomyositis, type 1 diabetes, juvenile idiopathic arthritis, glomerulonephritis, Graves' disease, Guillain-Barré syndrome, idiopathic thrombocytepenic purpura, myasthenia gravis, multiple sclerosis, pemphigus/pemphigoid, pernicious anemia, polyarteritis *nodosa*, polymyositis, primary biliary cirrhosis, psoriasis, rheumatoid arthritis, scleroderma, Sjögren's syndrome, systemic lupus erythematosus, thyroiditis, uveitis, vitiligo, or Wegener's granulomatosis. In some embodiments, the methods further comprise administering an additional therapeutic agent. In some embodiments, the IL-2 conjugate and the additional therapeutic agent are administered simultaneously. In some embodiments, the IL-2 conjugate and the additional therapeutic agent are administered sequentially. In some embodiments, the IL-2 conjugate is administered prior to the additional therapeutic agent. In some embodiments, the IL-2 conjugate is administered after the administration of the additional therapeutic agent. In some embodiments, the subject is a human.

Aspects disclosed herein provide methods of treating an autoimmune disease or disorder in a subject in need thereof, comprising administering to the subject a therapeutically effective amount of an isolated and modified IL-2 polypeptide described herein, an IL-2Rαβγ binding protein described herein, a CD4+ Treg cell described herein, or a pharmaceutical composition of described herein. In some embodiments, the autoimmune disease or disorder comprises alopecia areata, autoimmune hemolytic anemia, autoimmune hepatitis, dermatomyositis, type 1 diabetes, juvenile idiopathic arthritis, glomerulonephritis, Graves' disease, Guillain-Barré syndrome, idiopathic thrombocytepenic purpura, myasthenia gravis, multiple sclerosis, pemphigus/pemphigoid, pernicious anemia, polyarteritis *nodosa*, polymyositis, primary biliary cirrhosis, psoriasis, rheumatoid arthritis, scleroderma, Sjögren's syndrome, systemic lupus erythematosus, thyroiditis, uveitis, vitiligo, or Wegener's granulomatosis. In some embodiments, the methods further comprise administering an additional therapeutic agent. In some embodiments, the IL-2 conjugate and the additional therapeutic agent are administered simultaneously. In some embodiments, the IL-2 conjugate and the additional therapeutic agent are administered sequentially. In some embodiments, the IL-2 conjugate is administered prior to the additional therapeutic agent. In some embodiments, the IL-2 conjugate is administered after the administration of the additional therapeutic agent. In some embodiments, the subject is a human.

Aspects disclosed herein provide method of expanding CD4+ regulatory T (Treg) cell population, comprising: contacting a cell with an isolated and modified IL-2 polypeptide described herein, an IL-2Rαβγ binding protein described herein, a CD4+ Treg cell described herein, or a pharmaceutical composition described herein for a time sufficient to induce formation of a complex with an IL-2Rαβγ, thereby stimulating the expansion of the Treg cell population. In some embodiments, the method is an in vivo method. In some embodiments, the method is an in vitro method. In some embodiments, the method is an ex vivo method.

Aspects disclosed herein provide kits comprising an isolated and modified IL-2 polypeptide of described herein, an IL-2Rαβγ binding protein described herein, a CD4+ Treg cell described herein, or a pharmaceutical composition described herein. In some embodiments, the isolated and modified IL-2 polypeptide comprises a mutation at residue P65 corresponding to a residue position 65 of SEQ ID NO: 1, and a conjugating moiety comprising a PEG, the PEG having a molecular weight comprising about 5,000 Daltons (Da), 10,000 Da, 15,000 Da, 20,000 Da, 25,000 Da, 30,000 Da, 35,000 Da, 40,000 Da, 45,000 Da, or 50,000 Da. In some embodiments, the isolated and modified IL-2 polypeptide comprises a mutation at residue E61 corresponding to a residue position 61 of SEQ ID NO: 1, and a conjugating moiety comprising a PEG, the PEG having a molecular weight comprising about 5,000 Daltons (Da), 10,000 Da, 15,000 Da, 20,000 Da, 25,000 Da, 30,000 Da, 35,000 Da, 40,000 Da, 45,000 Da, or 50,000 Da. In some embodiments, the isolated and modified IL-2 polypeptide comprises a mutation at residue F42 corresponding to a residue position 42 of SEQ ID NO: 1, and a conjugating moiety comprising a PEG, the PEG having a molecular weight comprising about 5,000 Daltons (Da), 10,000 Da, 15,000 Da, 20,000 Da, 25,000 Da, 30,000 Da, 35,000 Da, 40,000 Da, 45,000 Da, or 50,000 Da. In some embodiments, the molecular weight of the PEG is effective to improve solubility of the isolated and modified IL-2 polypeptide and/or IL-2 conjugate. In some embodiments, the molecular weight of the PEG is effective to increase stability of the isolated and modified IL-2 polypeptide and/or IL-2 conjugate. In some embodiments, the molecular weight of the PEG is effective to improve an efficiency of manufacturing of the adoptive cell therapy of the isolated and modified IL-2 polypeptide and/or IL-2 conjugate.

Aspects disclosed herein provide reagents for manufacturing an adoptive cell therapy comprising the isolated and modified IL-2 polypeptide described herein, an IL-2Rαβγ binding protein described herein, a CD4+ Treg cell described herein, or a pharmaceutical composition described herein. In some embodiments, the isolated and modified IL-2 polypeptide comprises a mutation at residue P65 corresponding to a residue position 65 of SEQ ID NO: 1, and a conjugating moiety comprising a PEG, the PEG having a molecular weight comprising about 5,000 Daltons (Da), 10,000 Da, 15,000 Da, 20,000 Da, 25,000 Da, 30,000 Da, 35,000 Da, 40,000 Da, 45,000 Da, or 50,000 Da. In some embodiments, the isolated and modified IL-2 polypeptide comprises a mutation at residue E61 corresponding to a residue position 61 of SEQ ID NO: 1, and a conjugating moiety comprising a PEG, the PEG having a molecular weight comprising about 5,000 Daltons (Da), 10,000 Da, 15,000 Da, 20,000 Da, 25,000 Da, 30,000 Da, 35,000 Da, 40,000 Da, 45,000 Da, or 50,000 Da. In some embodiments, the isolated and modified IL-2 polypeptide comprises a mutation at residue F42 corresponding to a residue position 42 of SEQ ID NO: 1, and a conjugating moiety comprising a PEG, the PEG having a molecular weight comprising about 5,000 Daltons (Da), 10,000 Da, 15,000 Da, 20,000 Da, 25,000 Da, 30,000 Da, 35,000 Da, 40,000 Da, 45,000 Da, or 50,000 Da. In some embodiments, the molecular weight of the PEG is effective to improve solubility of the isolated and modified IL-2 polypeptide and/or IL-2 conjugate. In some embodiments, the molecular weight of the PEG is effective to increase stability of the isolated and modified IL-2 polypeptide and/or IL-2 conjugate. In some embodiments, the molecular weight of the PEG is effective to improve an efficiency of manufacturing of the adoptive cell therapy of the isolated and modified IL-2 polypeptide and/or IL-2 conjugate.

Certain Terminologies

Unless defined otherwise, all technical and scientific terms used herein have the same meaning as is commonly understood by one of skill in the art to which the claimed subject matter belongs. It is to be understood that the detailed description are exemplary and explanatory only and are not restrictive of any subject matter claimed. In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

As used herein, ranges and amounts can be expressed as "about" a particular value or range. About also includes the exact amount. Hence "about 5 μL" means "about 5 μL" and also "5 μL." Generally, the term "about" includes an amount that would be expected to be within experimental error, such as for example, within 15%, 10%, or 5%.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

As used herein, the term "significant" or "significantly" in reference to binding affinity means a change in the binding affinity of the cytokine (e.g., IL-2 polypeptide) sufficient to impact binding of the cytokine (e.g., IL-2 polypeptide) to a target receptor. In some instances, the term refers to a change of at least 10%, 20%, 30%, 40%, 50%, 60%, 70%, 80%, 90%, 95%, or more. In some instances, the term means a change of at least 2-fold, 3-fold, 4-fold, 5-fold, 6-fold, 7-fold, 8-fold, 9-fold, 10-fold, 50-fold, 100-fold, 500-fold, 1000-fold, or more.

In some instances, the term "significant" or "significantly" in reference to activation of one or more cell populations via a cytokine signaling complex means a change sufficient to activate the cell population. In some cases, the change to activate the cell population is measured as a receptor signaling potency. In such cases, an EC50 value may be provided. In other cases, an ED50 value may be provided. In additional cases, a concentration or dosage of the cytokine may be provided.

As used herein, the term "potency" refers to the amount of a cytokine (e.g., IL-2 polypeptide) required to produce a target effect. In some instances, the term "potency" refers to the amount of cytokine (e.g., IL-2 polypeptide) required to activate a target cytokine receptor (e.g., IL-2 receptor). In other instances, the term "potency" refers to the amount of cytokine (e.g., IL-2 polypeptide) required to activate a target cell population. In some cases, potency is measured as ED50 (Effective Dose 50), or the dose required to produce 50% of a maximal effect. In other cases, potency is measured as EC50 (Effective Concentration 50), or the dose required to produce the target effect in 50% of the population.

Numbered Embodiments

The present disclosure provided the following non-limiting numbered embodiments: Embodiment 1. An IL-2 conjugate comprising the amino acid sequence of SEQ ID NO: 3 in which at least one amino acid residue in the IL-2 conjugate is replaced by the structure of Formula (I):

Formula (I)

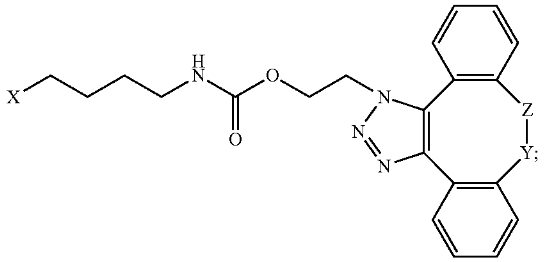

wherein:

Z is $CH_2$ and Y is

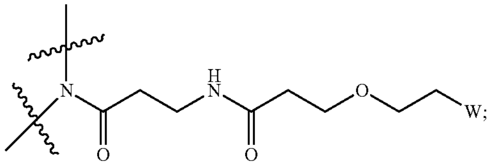

Y is $CH_2$ and Z is

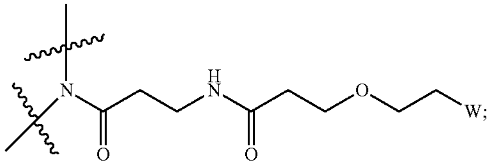

Z is $CH_2$ and Y is

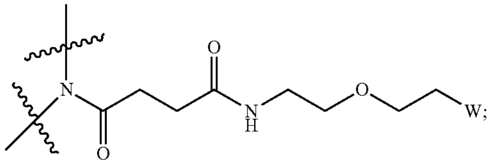

or

Y is $CH_2$ and Z is

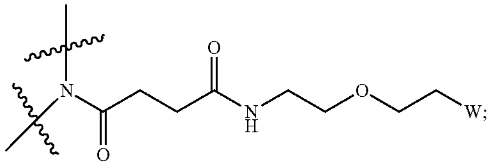

W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and X has the structure:

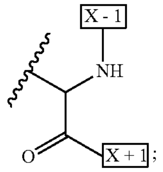 [SMILES: *C(NC)C(C)=O]

or a pharmaceutically acceptable salt, solvate, or hydrate thereof.

Embodiment 2. An IL-2 conjugate comprising the amino acid sequence of SEQ ID NO: 4 in which at least one amino acid residue in the IL-2 conjugate is replaced by the structure of Formula (I):

Formula (I)

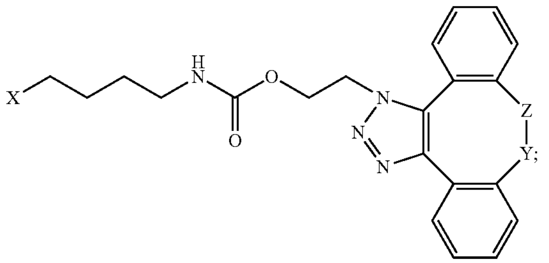

wherein:

Z is $CH_2$ and Y is

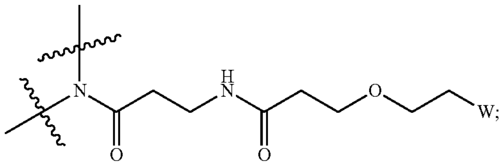

Y is $CH_2$ and Z is

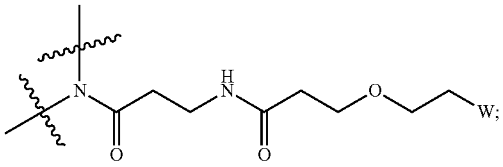

Z is $CH_2$ and Y is

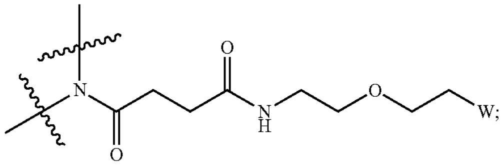

or

Y is $CH_2$ and Z is

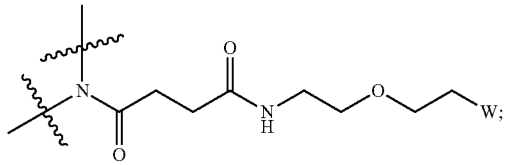

W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa;

X has the structure:

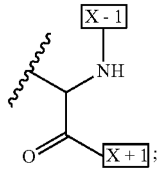 [SMILES: *C(NC)C(C)=O]

and wherein the position of the structure of Formula (I) in the amino acid sequence of the IL-2 conjugate is in reference to the positions in SEQ ID NO: 1; or a pharmaceutically acceptable salt, solvate, or hydrate thereof.

Embodiment 3. The IL-2 conjugate of embodiment 1 or 2 wherein Z is $CH_2$ and Y is

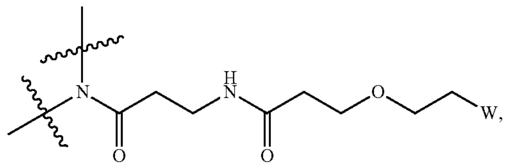

or a pharmaceutically acceptable salt, solvate, or hydrate thereof.

Embodiment 4. The IL-2 conjugate of embodiment 1 or 2 wherein Y is $CH_2$ and Z is

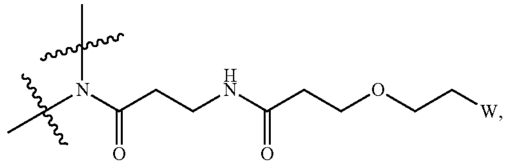

or a pharmaceutically acceptable salt, solvate, or hydrate thereof.

Embodiment 5. The IL-2 conjugate of embodiment 1 or 2 wherein Z is $CH_2$ and Y is

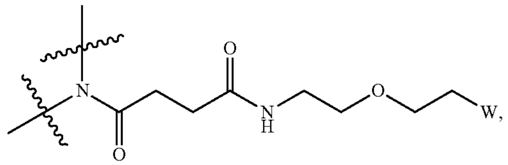

or a pharmaceutically acceptable salt, solvate, or hydrate thereof.

Embodiment 6. The IL-2 conjugate of embodiment 1 or 2 wherein Z is $CH_2$ and Y is

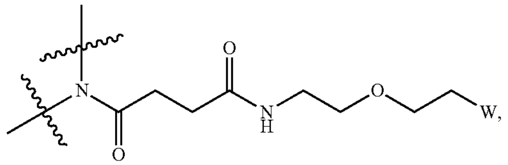

or a pharmaceutically acceptable salt, solvate, or hydrate thereof.

Embodiment 7. The IL-2 conjugate of embodiment 1 or 2 wherein Y is $CH_2$ and Z is

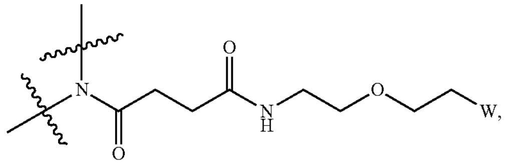

or a pharmaceutically acceptable salt, solvate, or hydrate thereof.

Embodiment 8. The IL-2 conjugate of embodiment 1 or 2 wherein the PEG group has an average molecular weight selected from 5 kDa, 10 kDa, 20 kDa and 30 kDa, or a pharmaceutically acceptable salt, solvate, or hydrate thereof.

Embodiment 9. The IL-2 conjugate of embodiment 8 wherein the PEG group has an average molecular weight of 5 kDa, or a pharmaceutically acceptable salt, solvate, or hydrate thereof.

Embodiment 10. The IL-2 conjugate of embodiment 8 wherein the PEG group has an average molecular weight of 30 kDa, or a pharmaceutically acceptable salt, solvate, or hydrate thereof.

Embodiment 11. The IL-2 conjugate of embodiment 1 or 2 wherein the position of the structure of Formula (I) in the amino acid sequence of the IL-2 conjugate is selected from K35, F42, F44, K43, E62, P65, R38, T41, E68, Y45, V69, and L72, wherein the position of the structure of Formula (I) in the amino acid sequence of the IL-2 conjugate is in reference to the positions in SEQ ID NO: 1, or a pharmaceutically acceptable salt, solvate, or hydrate thereof.

Embodiment 12. The IL-2 conjugate of embodiment 11 wherein the position of the structure of Formula (I) in the amino acid sequence of the IL-2 conjugate is selected from F42, E62, and P65, wherein the position of the structure of Formula (I) in the amino acid sequence of the IL-2 conjugate is in reference to the positions in SEQ ID NO: 1, or a pharmaceutically acceptable salt, solvate, or hydrate thereof.

Embodiment 13. An IL-2 conjugate comprising the amino acid sequence of any one of SEQ ID NOS: 15-19, wherein [AzK_PEG] has the structure of Formula (II) or Formula (III), or a mixture of Formula (II) and Formula (III):

Formula (II)

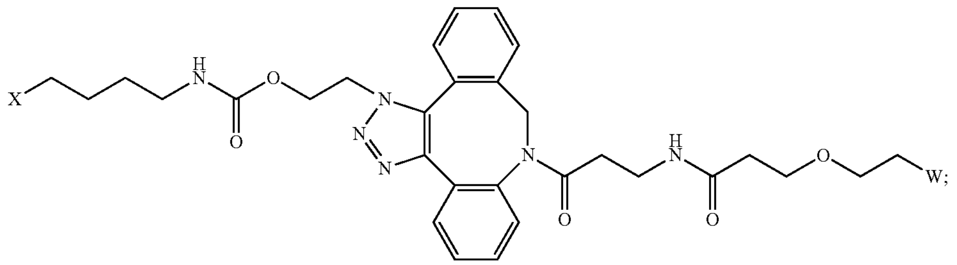

Formula (III)

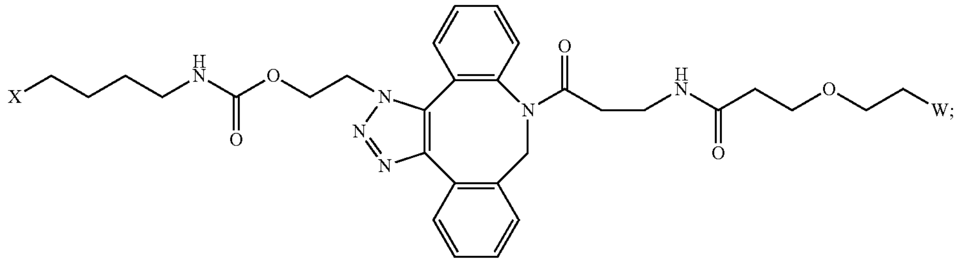

wherein:

W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and X has the structure:

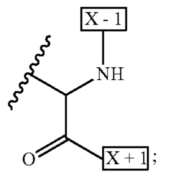 [SMILES: *C(NC)C(C)=O]

or a pharmaceutically acceptable salt, solvate, or hydrate thereof.

Embodiment 14. The IL-2 conjugate of embodiment 13, wherein the [AzK_PEG] is a mixture of Formula (II) and Formula (III), or a pharmaceutically acceptable salt, solvate, or hydrate thereof.

Embodiment 15. The IL-2 conjugate of embodiment 13, wherein the [AzK_PEG] has the structure of formula (II):

Formula (II)

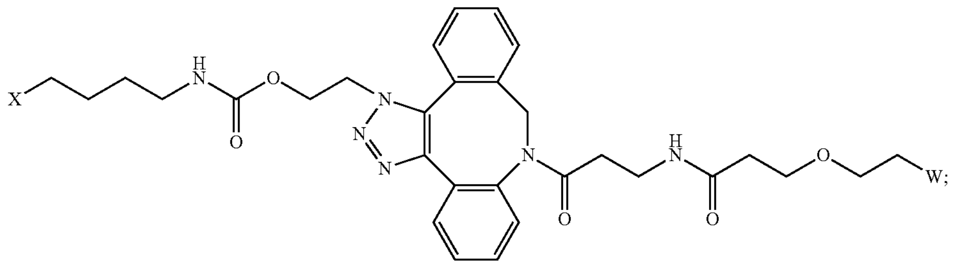

or a pharmaceutically acceptable salt, solvate, or hydrate thereof.

Embodiment 16. The IL-2 conjugate of embodiment 15, wherein the IL-2 conjugate has the amino acid sequence of SEQ ID NO: 15, or a pharmaceutically acceptable salt, solvate, or hydrate thereof.

Embodiment 17. The IL-2 conjugate of embodiment 16, wherein W is a PEG group having an average molecular weight selected from 5 kDa, 10 kDa, 15 kDa, 20 kDa, 25 kDa, and 30 kDa, or a pharmaceutically acceptable salt, solvate, or hydrate thereof.

Embodiment 18. The IL-2 conjugate of embodiment 17, wherein W is a PEG group having an average molecular weight selected from 5 kDa and 30 kDa, or a pharmaceutically acceptable salt, solvate, or hydrate thereof.

Embodiment 19. The IL-2 conjugate of embodiment 17, wherein W is a PEG group having an average molecular weight of 5 kDa, or a pharmaceutically acceptable salt, solvate, or hydrate thereof.

Embodiment 20. The IL-2 conjugate of embodiment 17, wherein W is a PEG group having an average molecular weight of 30 kDa, or a pharmaceutically acceptable salt, solvate, or hydrate thereof.

Embodiment 21. The IL-2 conjugate of embodiment 15, wherein the IL-2 conjugate has the amino acid sequence of SEQ ID NO: 16, or a pharmaceutically acceptable salt, solvate, or hydrate thereof.

Embodiment 22. The IL-2 conjugate of embodiment 21, wherein W is a PEG group having an average molecular weight selected from 5 kDa, 10 kDa, 15 kDa, 20 kDa, 25 kDa, and 30 kDa, or a pharmaceutically acceptable salt, solvate, or hydrate thereof.

Embodiment 23. The IL-2 conjugate of embodiment 22, wherein W is a PEG group having an average molecular weight selected from 5 kDa and 30 kDa, or a pharmaceutically acceptable salt, solvate, or hydrate thereof.

Embodiment 24. The IL-2 conjugate of embodiment 23, wherein W is a PEG group having an average molecular weight of 5 kDa, or a pharmaceutically acceptable salt, solvate, or hydrate thereof.

Embodiment 25. The IL-2 conjugate of embodiment 23, wherein W is a PEG group having an average molecular weight of 30 kDa, or a pharmaceutically acceptable salt, solvate, or hydrate thereof.

Embodiment 26. The IL-2 conjugate of embodiment 15, wherein the IL-2 conjugate has the amino acid sequence of SEQ ID NO: 17, or a pharmaceutically acceptable salt, solvate, or hydrate thereof.

Embodiment 27. The IL-2 conjugate of embodiment 26, wherein W is a PEG group having an average molecular weight selected from 5 kDa, 10 kDa, 15 kDa, 20 kDa, 25 kDa, and 30 kDa, or a pharmaceutically acceptable salt, solvate, or hydrate thereof.

Embodiment 28. The IL-2 conjugate of embodiment 27, wherein W is a PEG group having an average molecular weight selected from 5 kDa and 30 kDa, or a pharmaceutically acceptable salt, solvate, or hydrate thereof.

Embodiment 29. The IL-2 conjugate of embodiment 27, wherein W is a PEG group having an average molecular weight of 5 kDa, or a pharmaceutically acceptable salt, solvate, or hydrate thereof.

Embodiment 30. The IL-2 conjugate of embodiment 27, wherein W is a PEG group having an average molecular weight of 30 kDa, or a pharmaceutically acceptable salt, solvate, or hydrate thereof.

Embodiment 31. The IL-2 conjugate of embodiment 15, wherein the IL-2 conjugate has the amino acid sequence of SEQ ID NO: 18, or a pharmaceutically acceptable salt, solvate, or hydrate thereof.

Embodiment 32. The IL-2 conjugate of embodiment 31, wherein W is a PEG group having an average molecular weight selected from 5 kDa, 10 kDa, 15 kDa, 20 kDa, 25 kDa, and 30 kDa, or a pharmaceutically acceptable salt, solvate, or hydrate thereof.

Embodiment 33. The IL-2 conjugate of embodiment 32, wherein W is a PEG group having an average molecular weight selected from 5 kDa and 30 kDa, or a pharmaceutically acceptable salt, solvate, or hydrate thereof.

Embodiment 34. The IL-2 conjugate of embodiment 33, wherein W is a PEG group having an average molecular weight of 5 kDa, or a pharmaceutically acceptable salt, solvate, or hydrate thereof.

Embodiment 35. The IL-2 conjugate of embodiment 33, wherein W is a PEG group having an average molecular weight of 30 kDa, or a pharmaceutically acceptable salt, solvate, or hydrate thereof.

Embodiment 36. The IL-2 conjugate of embodiment 15, wherein the IL-2 conjugate has the amino acid sequence of SEQ ID NO: 19, or a pharmaceutically acceptable salt, solvate, or hydrate thereof.

Embodiment 37. The IL-2 conjugate of embodiment 36, wherein W is a PEG group having an average molecular weight selected from 5 kDa, 10 kDa, 15 kDa, 20 kDa, 25 kDa, and 30 kDa, or a pharmaceutically acceptable salt, solvate, or hydrate thereof.

Embodiment 38. The IL-2 conjugate of embodiment 37, wherein W is a PEG group having an average molecular weight selected from 5 kDa and 30 kDa, or a pharmaceutically acceptable salt, solvate, or hydrate thereof.

Embodiment 39. The IL-2 conjugate of embodiment 38, wherein W is a PEG group having an average molecular weight of 5 kDa, or a pharmaceutically acceptable salt, solvate, or hydrate thereof.

Embodiment 40. The IL-2 conjugate of embodiment 38, wherein W is a PEG group having an average molecular weight of 30 kDa, or a pharmaceutically acceptable salt, solvate, or hydrate thereof.

Embodiment 41. The IL-2 conjugate of embodiment 13, wherein the [AzK_PEG] has the structure of formula (III)

Formula (III)

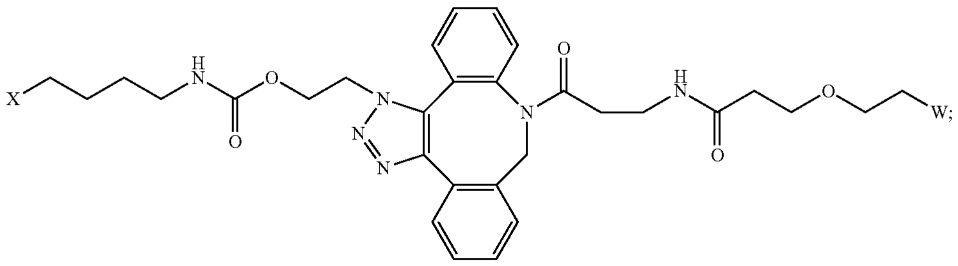

or a pharmaceutically acceptable salt, solvate, or hydrate thereof.

Embodiment 42. The IL-2 conjugate of embodiment 41, wherein the IL-2 conjugate has the amino acid sequence of SEQ ID NO: 15, or a pharmaceutically acceptable salt, solvate, or hydrate thereof.

Embodiment 43. The IL-2 conjugate of embodiment 42, wherein W is a PEG group having an average molecular weight selected from 5 kDa, 10 kDa, 15 kDa, 20 kDa, 25 kDa, and 30 kDa, or a pharmaceutically acceptable salt, solvate, or hydrate thereof.

Embodiment 44. The IL-2 conjugate of embodiment 43, wherein W is a PEG group having an average molecular weight selected from 5 kDa and 30 kDa, or a pharmaceutically acceptable salt, solvate, or hydrate thereof.

Embodiment 45. The IL-2 conjugate of embodiment 44, wherein W is a PEG group having an average molecular weight of 5 kDa, or a pharmaceutically acceptable salt, solvate, or hydrate thereof.

Embodiment 46. The IL-2 conjugate of embodiment 44, wherein W is a PEG group having an average molecular weight of 30 kDa, or a pharmaceutically acceptable salt, solvate, or hydrate thereof.

Embodiment 47. The IL-2 conjugate of embodiment 41, wherein the IL-2 conjugate has the amino acid sequence of SEQ ID NO: 16, or a pharmaceutically acceptable salt, solvate, or hydrate thereof.

Embodiment 48. The IL-2 conjugate of embodiment 47, wherein W is a PEG group having an average molecular weight selected from 5 kDa, 10 kDa, 15 kDa, 20 kDa, 25 kDa, and 30 kDa, or a pharmaceutically acceptable salt, solvate, or hydrate thereof.

Embodiment 49. The IL-2 conjugate of embodiment 48, wherein W is a PEG group having an average molecular weight selected from 5 kDa and 30 kDa, or a pharmaceutically acceptable salt, solvate, or hydrate thereof.

Embodiment 50. The IL-2 conjugate of embodiment 49, wherein W is a PEG group having an average molecular weight of 5 kDa, or a pharmaceutically acceptable salt, solvate, or hydrate thereof.

Embodiment 51. The IL-2 conjugate of embodiment 49, wherein W is a PEG group having an average molecular weight of 30 kDa, or a pharmaceutically acceptable salt, solvate, or hydrate thereof.

Embodiment 52. The IL-2 conjugate of embodiment 41, wherein the IL-2 conjugate has the amino acid sequence of SEQ ID NO: 17, or a pharmaceutically acceptable salt, solvate, or hydrate thereof.

Embodiment 53. The IL-2 conjugate of embodiment 52, wherein W is a PEG group having an average molecular weight selected from 5 kDa, 10 kDa, 15 kDa, 20 kDa, 25 kDa, and 30 kDa, or a pharmaceutically acceptable salt, solvate, or hydrate thereof.

Embodiment 54. The IL-2 conjugate of embodiment 53, wherein W is a PEG group having an average molecular weight selected from 5 kDa and 30 kDa, or a pharmaceutically acceptable salt, solvate, or hydrate thereof.

Embodiment 55. The IL-2 conjugate of embodiment 54, wherein W is a PEG group having an average molecular weight of 5 kDa, or a pharmaceutically acceptable salt, solvate, or hydrate thereof.

Embodiment 56. The IL-2 conjugate of embodiment 54, wherein W is a PEG group having an average molecular weight of 30 kDa, or a pharmaceutically acceptable salt, solvate, or hydrate thereof.

Embodiment 57. The IL-2 conjugate of embodiment 41, wherein the IL-2 conjugate has the amino acid sequence of SEQ ID NO: 18, or a pharmaceutically acceptable salt, solvate, or hydrate thereof.

Embodiment 58. The IL-2 conjugate of embodiment 57, wherein W is a PEG group having an average molecular weight selected from 5 kDa, 10 kDa, 15 kDa, 20 kDa, 25 kDa, and 30 kDa, or a pharmaceutically acceptable salt, solvate, or hydrate thereof.

Embodiment 59. The IL-2 conjugate of embodiment 58, wherein W is a PEG group having an average molecular weight selected from 5 kDa and 30 kDa, or a pharmaceutically acceptable salt, solvate, or hydrate thereof.

Embodiment 60. The IL-2 conjugate of embodiment 59, wherein W is a PEG group having an average molecular weight of 5 kDa, or a pharmaceutically acceptable salt, solvate, or hydrate thereof.

Embodiment 61. The IL-2 conjugate of embodiment 59, wherein W is a PEG group having an average molecular weight of 30 kDa, or a pharmaceutically acceptable salt, solvate, or hydrate thereof.

Embodiment 62. The IL-2 conjugate of embodiment 41, wherein the IL-2 conjugate has the amino acid sequence of SEQ ID NO: 19, or a pharmaceutically acceptable salt, solvate, or hydrate thereof.

Embodiment 63. The IL-2 conjugate of embodiment 62, wherein W is a PEG group having an average molecular weight selected from 5 kDa, 10 kDa, 15 kDa, 20 kDa, 25 kDa, and 30 kDa, or a pharmaceutically acceptable salt, solvate, or hydrate thereof.

Embodiment 64. The IL-2 conjugate of embodiment 63, wherein W is a PEG group having an average molecular weight selected from 5 kDa and 30 kDa, or a pharmaceutically acceptable salt, solvate, or hydrate thereof.

Embodiment 65. The IL-2 conjugate of embodiment 64, wherein W is a PEG group having an average molecular weight of 5 kDa, or a pharmaceutically acceptable salt, solvate, or hydrate thereof.

Embodiment 66. The IL-2 conjugate of embodiment 64, wherein W is a PEG group having an average molecular weight of 30 kDa, or a pharmaceutically acceptable salt, solvate, or hydrate thereof.

Embodiment 67. The IL-2 conjugate according to any one of embodiments 1 to 66, wherein W is a linear or branched PEG group, or a pharmaceutically acceptable salt, solvate, or hydrate thereof.

Embodiment 68. The IL-2 conjugate according to any one of embodiments 1 to 66, wherein W is a linear PEG group, or a pharmaceutically acceptable salt, solvate, or hydrate thereof.

Embodiment 69. The IL-2 conjugate according to any one of embodiments 1 to 66, wherein W is a branched PEG group, or a pharmaceutically acceptable salt, solvate, or hydrate thereof.

Embodiment 70. The IL-2 conjugate according to any one of embodiments 1 to 66, wherein W is a methoxy PEG group, or a pharmaceutically acceptable salt, solvate, or hydrate thereof.

Embodiment 71. The IL-2 conjugate according to embodiment 70, wherein the methoxy PEG group is linear or branched, or a pharmaceutically acceptable salt, solvate, or hydrate thereof.

Embodiment 72. The IL-2 conjugate according to embodiment 71, wherein the methoxy PEG group is linear, or a pharmaceutically acceptable salt, solvate, or hydrate thereof.

Embodiment 73. The IL-2 conjugate according to embodiment 71, wherein the methoxy PEG group is branched, or a pharmaceutically acceptable salt, solvate, or hydrate thereof.

Embodiment 74. An IL-2 conjugate comprising the amino acid sequence of any one of SEQ ID NOS: 20-24, wherein [AzK_PEG5kD] has the structure of Formula (II) or Formula (III), or a mixture of Formula (II) and Formula (III):

Formula (II)

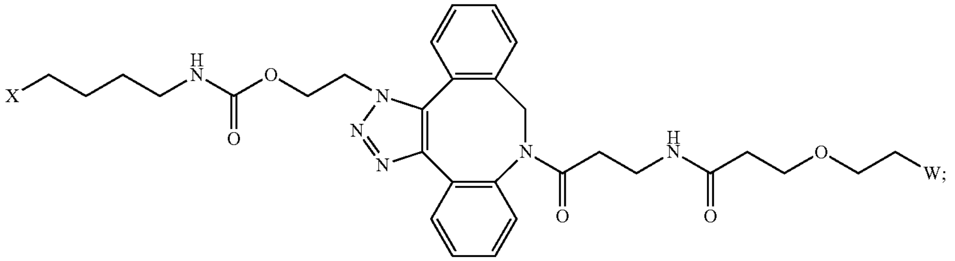

Formula (III)

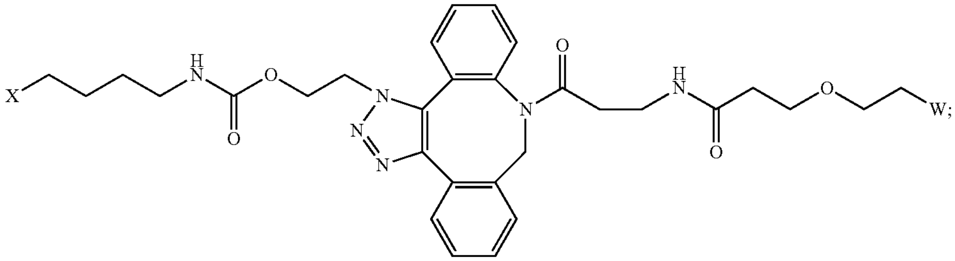

wherein:

W is a PEG group having an average molecular weight of 5 kDa; and

X has the structure:

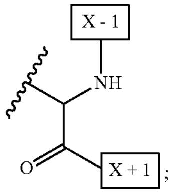

or a pharmaceutically acceptable salt, solvate, or hydrate thereof.

Embodiment 75. The IL-2 conjugate of embodiment 74, wherein the IL-2 conjugate has the amino acid sequence of SEQ ID NO: 20, or a pharmaceutically acceptable salt, solvate, or hydrate thereof.

Embodiment 76. The IL-2 conjugate of embodiment 74, wherein the IL-2 conjugate has the amino acid sequence of SEQ ID NO: 21, or a pharmaceutically acceptable salt, solvate, or hydrate thereof.

Embodiment 77. The IL-2 conjugate of embodiment 74, wherein the IL-2 conjugate has the amino acid sequence of SEQ ID NO: 22, or a pharmaceutically acceptable salt, solvate, or hydrate thereof.

Embodiment 78. The IL-2 conjugate of embodiment 74, wherein the IL-2 conjugate has the amino acid sequence of SEQ ID NO: 23, or a pharmaceutically acceptable salt, solvate, or hydrate thereof.

Embodiment 79. The IL-2 conjugate of embodiment 74, wherein the IL-2 conjugate has the amino acid sequence of SEQ ID NO: 24, or a pharmaceutically acceptable salt, solvate, or hydrate thereof.

Embodiment 80. The IL-2 conjugate of embodiment 74, wherein the [AzK_PEG5kD] has the structure of formula (II)

Formula (II)

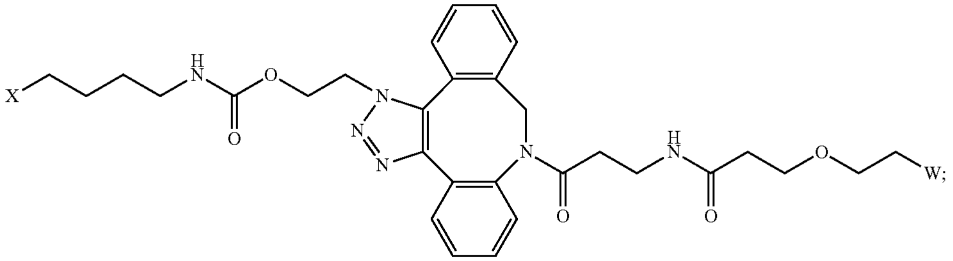

or a pharmaceutically acceptable salt, solvate, or hydrate thereof.

Embodiment 81. The IL-2 conjugate of embodiment 80, wherein the IL-2 conjugate has the amino acid sequence of SEQ ID NO: 20, or a pharmaceutically acceptable salt, solvate, or hydrate thereof.

Embodiment 82. The IL-2 conjugate of embodiment 80, wherein the IL-2 conjugate has the amino acid sequence of SEQ ID NO: 21, or a pharmaceutically acceptable salt, solvate, or hydrate thereof.

Embodiment 83. The IL-2 conjugate of embodiment 80, wherein the IL-2 conjugate has the amino acid sequence of SEQ ID NO: 22, or a pharmaceutically acceptable salt, solvate, or hydrate thereof.

Embodiment 84. The IL-2 conjugate of embodiment 80, wherein the IL-2 conjugate has the amino acid sequence of SEQ ID NO: 23, or a pharmaceutically acceptable salt, solvate, or hydrate thereof.

Embodiment 85. The IL-2 conjugate of embodiment 80, wherein the IL-2 conjugate has the amino acid sequence of SEQ ID NO: 24, or a pharmaceutically acceptable salt, solvate, or hydrate thereof.

Embodiment 86. The IL-2 conjugate of embodiment 74, wherein the [AzK_PEG5kD] has the structure of formula (III)

Formula (III)

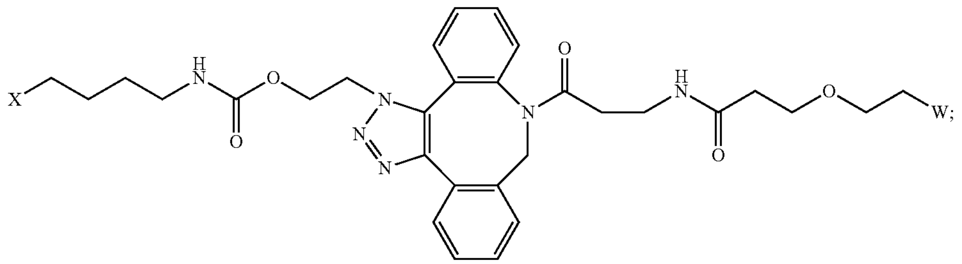

or a pharmaceutically acceptable salt, solvate, or hydrate thereof.

Embodiment 87. The IL-2 conjugate of embodiment 86, wherein the IL-2 conjugate has the amino acid sequence of SEQ ID NO: 20, or a pharmaceutically acceptable salt, solvate, or hydrate thereof.

Embodiment 88. The IL-2 conjugate of embodiment 86, wherein the IL-2 conjugate has the amino acid sequence of SEQ ID NO: 21, or a pharmaceutically acceptable salt, solvate, or hydrate thereof.

Embodiment 89. The IL-2 conjugate of embodiment 86, wherein the IL-2 conjugate has the amino acid sequence of SEQ ID NO: 22, or a pharmaceutically acceptable salt, solvate, or hydrate thereof.

Embodiment 90. The IL-2 conjugate of embodiment 86, wherein the IL-2 conjugate has the amino acid sequence of SEQ ID NO: 23, or a pharmaceutically acceptable salt, solvate, or hydrate thereof.

Embodiment 91. The IL-2 conjugate of embodiment 86, wherein the IL-2 conjugate has the amino acid sequence of SEQ ID NO: 24, or a pharmaceutically acceptable salt, solvate, or hydrate thereof.

Embodiment 92. An IL-2 conjugate comprising the amino acid sequence of any one of SEQ ID NOS: 25-29, wherein [AzK_PEG30kD] has the structure of Formula (II) or Formula (III), or is a mixture of the structures of Formula (II) and Formula (III):

Formula (II)

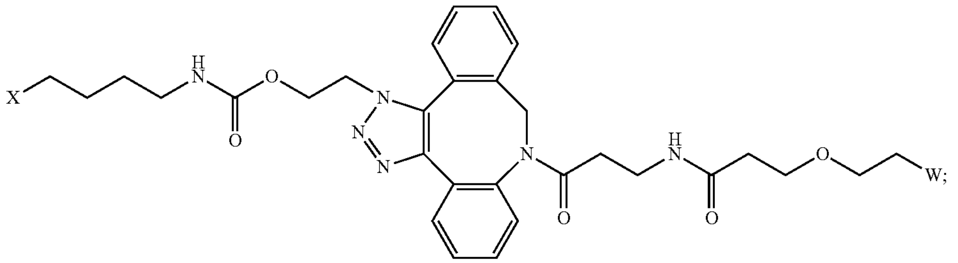

Formula (III)

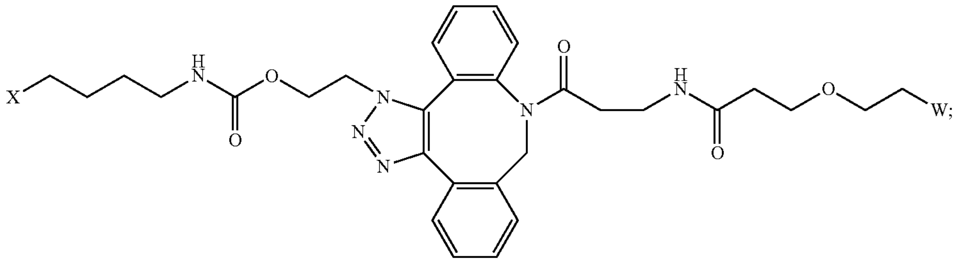

wherein:

W is a PEG group having an average molecular weight of 30 kDa; and

X has the structure:

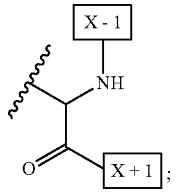

or a pharmaceutically acceptable salt, solvate, or hydrate thereof.

Embodiment 93. The IL-2 conjugate of embodiment 92, wherein the IL-2 conjugate has the amino acid sequence of SEQ ID NO: 25, or a pharmaceutically acceptable salt, solvate, or hydrate thereof.

Embodiment 94. The IL-2 conjugate of embodiment 92, wherein the IL-2 conjugate has the amino acid sequence of SEQ ID NO: 26, or a pharmaceutically acceptable salt, solvate, or hydrate thereof.

Embodiment 95. The IL-2 conjugate of embodiment 92, wherein the IL-2 conjugate has the amino acid sequence of SEQ ID NO: 27, or a pharmaceutically acceptable salt, solvate, or hydrate thereof.

Embodiment 96. The IL-2 conjugate of embodiment 92, wherein the IL-2 conjugate has the amino acid sequence of SEQ ID NO: 28, or a pharmaceutically acceptable salt, solvate, or hydrate thereof.

Embodiment 97. The IL-2 conjugate of embodiment 92, wherein the IL-2 conjugate has the amino acid sequence of SEQ ID NO: 29, or a pharmaceutically acceptable salt, solvate, or hydrate thereof.

Embodiment 98. The IL-2 conjugate of embodiment 92, wherein the [AzK_PEG30kD] has the structure of formula (II):

Formula (II)

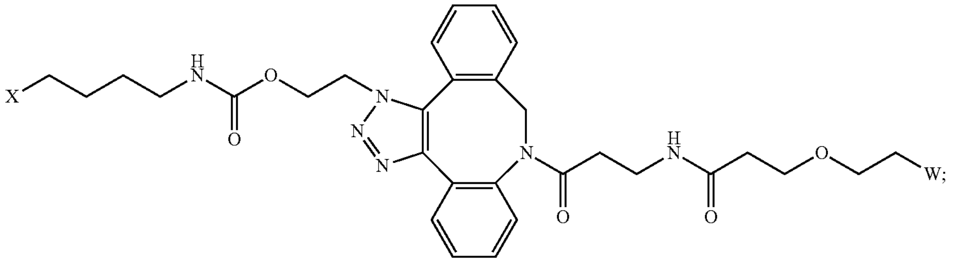

or a pharmaceutically acceptable salt, solvate, or hydrate thereof.

Embodiment 99. The IL-2 conjugate of embodiment 98, wherein the IL-2 conjugate has the amino acid sequence of SEQ ID NO: 25, or a pharmaceutically acceptable salt, solvate, or hydrate thereof.

Embodiment 100. The IL-2 conjugate of embodiment 98, wherein the IL-2 conjugate has the amino acid sequence of SEQ ID NO: 26, or a pharmaceutically acceptable salt, solvate, or hydrate thereof.

Embodiment 101. The IL-2 conjugate of embodiment 98, wherein the IL-2 conjugate has the amino acid sequence of SEQ ID NO: 27, or a pharmaceutically acceptable salt, solvate, or hydrate thereof.

Embodiment 102. The IL-2 conjugate of embodiment 98, wherein the IL-2 conjugate has the amino acid sequence of SEQ ID NO: 28, or a pharmaceutically acceptable salt, solvate, or hydrate thereof.

Embodiment 103. The IL-2 conjugate of embodiment 98, wherein the IL-2 conjugate has the amino acid sequence of SEQ ID NO: 29, or a pharmaceutically acceptable salt, solvate, or hydrate thereof.

Embodiment 104. The IL-2 conjugate of embodiment 92, wherein the [AzK_PEG30kD] has the structure of formula (III)

Formula (III)

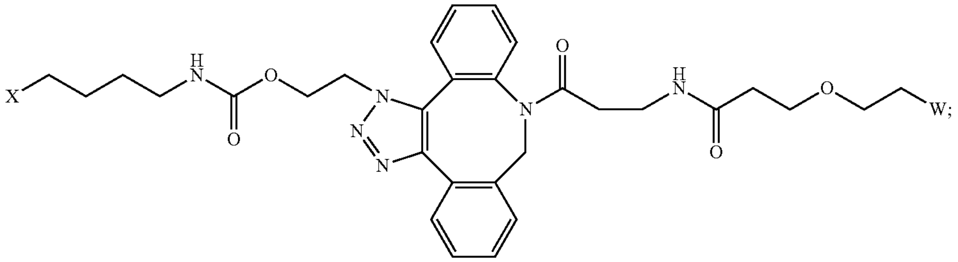

or a pharmaceutically acceptable salt, solvate, or hydrate thereof.

Embodiment 105. The IL-2 conjugate of embodiment 104, wherein the IL-2 conjugate has the amino acid sequence of SEQ ID NO: 25, or a pharmaceutically acceptable salt, solvate, or hydrate thereof.

Embodiment 106. The IL-2 conjugate of embodiment 104, wherein the IL-2 conjugate has the amino acid sequence of SEQ ID NO: 26, or a pharmaceutically acceptable salt, solvate, or hydrate thereof.

Embodiment 107. The IL-2 conjugate of embodiment 104, wherein the IL-2 conjugate has the amino acid sequence of SEQ ID NO: 27, or a pharmaceutically acceptable salt, solvate, or hydrate thereof.

Embodiment 108. The IL-2 conjugate of embodiment 104, wherein the IL-2 conjugate has the amino acid sequence of SEQ ID NO: 28, or a pharmaceutically acceptable salt, solvate, or hydrate thereof.

Embodiment 109. The IL-2 conjugate of embodiment 104, wherein the IL-2 conjugate has the amino acid sequence of SEQ ID NO: 29, or a pharmaceutically acceptable salt, solvate, or hydrate thereof.

Embodiment 110. An IL-2 conjugate comprising the amino acid sequence of any one of SEQ ID NOS: 15-19, wherein [AzK_PEG] is a mixture of the structures of Formula (II) and Formula (III):

wherein:

W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and X has the structure:

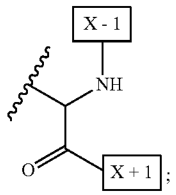

or a pharmaceutically acceptable salt, solvate, or hydrate thereof.

Embodiment 111. The IL-2 conjugate according to embodiment 110, wherein the ratio of the amount of the structure of Formula (II) to the amount of the structure of Formula (III) comprising the total amount of [AzK_PEG] in the IL-2 conjugate is about 1:1.

Embodiment 112. The IL-2 conjugate according to embodiment 110, wherein the ratio of the amount of the structure of Formula (II) to the amount of the structure of Formula (II)

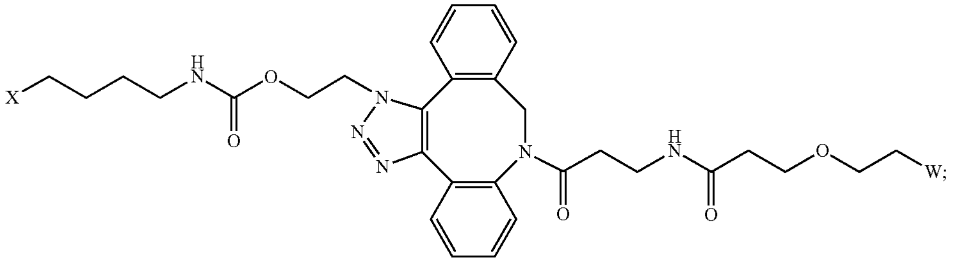

Formula (III)

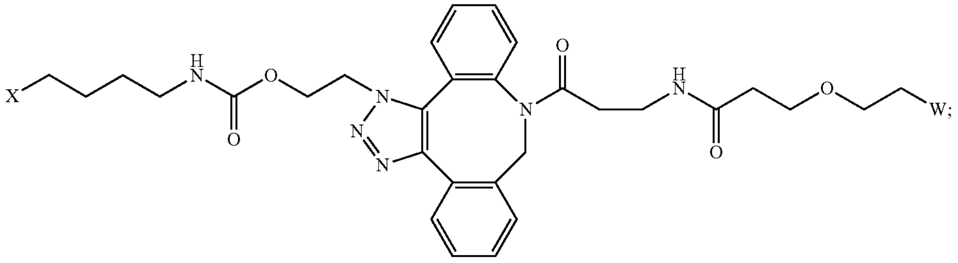

Formula (III) comprising the total amount of [AzK_PEG] in the IL-2 conjugate is greater than 1:1.

Embodiment 113. The IL-2 conjugate according to embodiment 110, wherein the ratio of the amount of the structure of Formula (II) to the amount of the structure of Formula (III) comprising the total amount of [AzK_PEG] in the IL-2 conjugate is less than 1:1.

Embodiment 114. The IL-2 conjugate according to any one of embodiments 110 to 113, wherein W is a linear or branched PEG group, or a pharmaceutically acceptable salt, solvate, or hydrate thereof.

Embodiment 115. The IL-2 conjugate according to any one of embodiments 110 to 113, wherein W is a linear PEG group, or a pharmaceutically acceptable salt, solvate, or hydrate thereof.

Embodiment 116. The IL-2 conjugate according to any one of embodiments 110 to 113, wherein W is a branched PEG group, or a pharmaceutically acceptable salt, solvate, or hydrate thereof.

Embodiment 117. The IL-2 conjugate according to any one of embodiments 110 to 113, wherein W is a methoxy PEG group, or a pharmaceutically acceptable salt, solvate, or hydrate thereof.

Embodiment 118. The IL-2 conjugate according to embodiment 117, wherein the methoxy PEG group is linear or branched, or a pharmaceutically acceptable salt, solvate, or hydrate thereof.

Embodiment 119. The IL-2 conjugate according to embodiment 118, wherein the methoxy PEG group is linear, or a pharmaceutically acceptable salt, solvate, or hydrate thereof.

Embodiment 120. The IL-2 conjugate according to embodiment 118, wherein the methoxy PEG group is branched, or a pharmaceutically acceptable salt, solvate, or hydrate thereof.

Embodiment 121. An IL-2 conjugate comprising the amino acid sequence of any one of SEQ ID NOS: 20 to 24, wherein [AzK_PEG5kD] is a mixture of the structures of Formula (II) and Formula (III):

wherein:

W is a PEG group having an average molecular weight of 5 kDa; and

X has the structure:

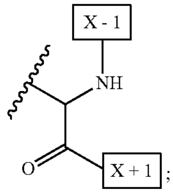

;

or a pharmaceutically acceptable salt, solvate, or hydrate thereof.

Embodiment 122. The IL-2 conjugate according to embodiment 121, wherein the ratio of the amount of the structure of Formula (II) to the amount of the structure of Formula (III) comprising the total amount of [AzK_PEG5kD] in the IL-2 conjugate is about 1:1.

Embodiment 123. The IL-2 conjugate according to embodiment 121, wherein the ratio of the amount of the structure of Formula (II) to the amount of the structure of Formula (III) comprising the total amount of [AzK_PEG5kD] in the IL-2 conjugate is greater than 1:1.

Embodiment 124. The IL-2 conjugate according to embodiment 121, wherein the ratio of the amount of the structure of Formula (II) to the amount of the structure of Formula (III) comprising the total amount of [AzK_PEG5kD] in the IL-2 conjugate is less than 1:1.

Embodiment 125. An IL-2 conjugate comprising the amino acid sequence of any one of SEQ ID NOS: 25-29, wherein [AzK_PEG30kD] is a mixture of the structures of Formula (II) and Formula (III):

Formula (II)

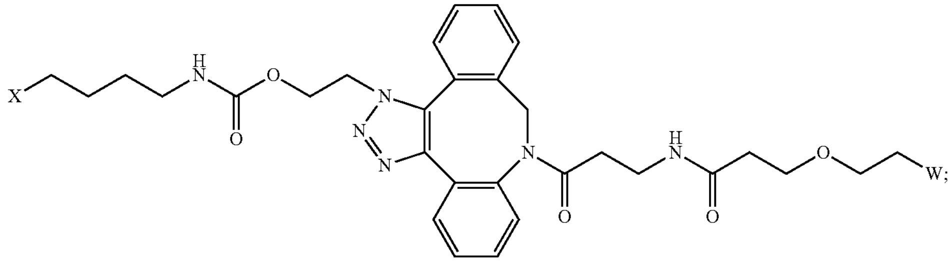

;

Formula (III)

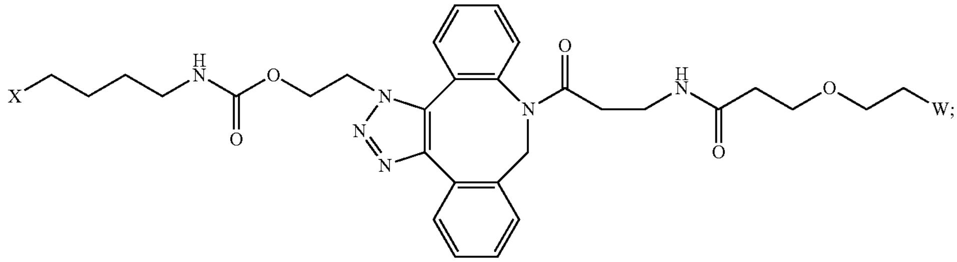

;

Formula (II)

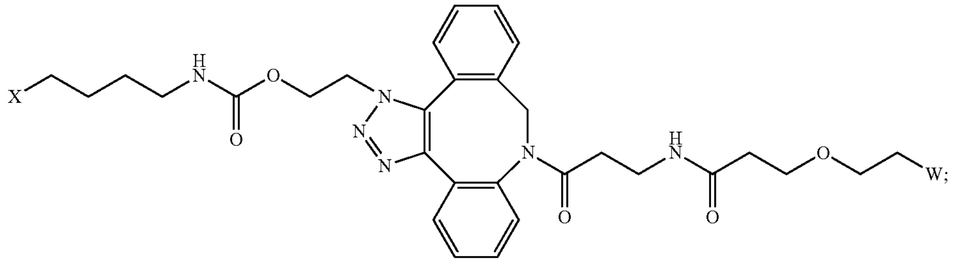

Formula (III)

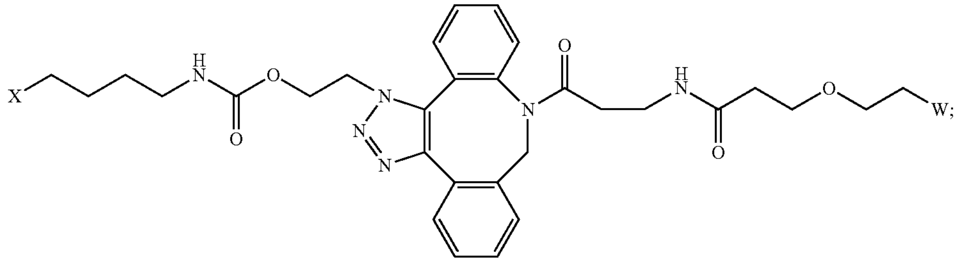

wherein:

W is a PEG group having an average molecular weight of 30 kDa; and

X has the structure:

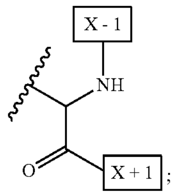

or a pharmaceutically acceptable salt, solvate, or hydrate thereof.

Embodiment 126. The IL-2 conjugate according to embodiment 125, wherein the ratio of the amount of the structure of Formula (II) to the amount of the structure of Formula (III) comprising the total amount of [AzK_PEG30kD] in the IL-2 conjugate is about 1:1.

Embodiment 127. The IL-2 conjugate according to embodiment 125, wherein the ratio of the amount of the structure of Formula (II) to the amount of the structure of Formula (III) comprising the total amount of [AzK_PEG30kD] in the IL-2 conjugate is greater than 1:1.

Embodiment 128. The IL-2 conjugate according to embodiment 125, wherein the ratio of the amount of the structure of Formula (II) to the amount of the structure of Formula (III) comprising the total amount of [AzK_PEG30kD] in the IL-2 conjugate is less than 1:1.

Embodiment 129. An IL-2 conjugate comprising the amino acid sequence of any one of SEQ ID NOS: 40-44, wherein [AzK_L1_PEG] has the structure of Formula (IV) or Formula (V), or a mixture of Formula (IV) and Formula (V):

Formula (IV)

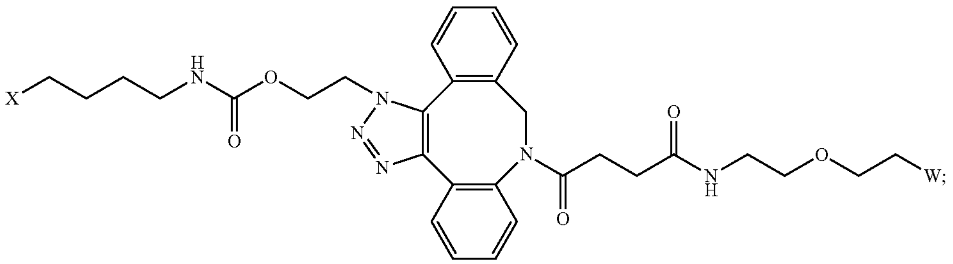

-continued

Formula (V)

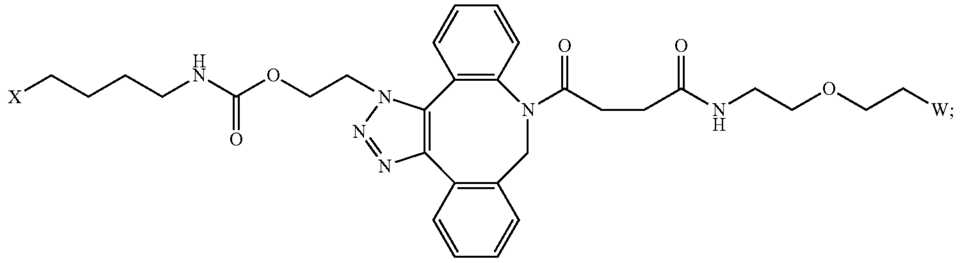

wherein:

W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and X has the structure:

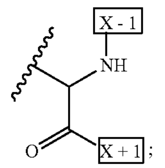

or a pharmaceutically acceptable salt, solvate, or hydrate thereof.

Embodiment 130. The IL-2 conjugate of embodiment 129, wherein the [AzK_L1_PEG] is a mixture of Formula (IV) and Formula (V), or a pharmaceutically acceptable salt, solvate, or hydrate thereof.

Embodiment 131. The IL-2 conjugate of embodiment 129, wherein the [AzK_L1_PEG] has the structure of Formula (IV):

Formula (IV)

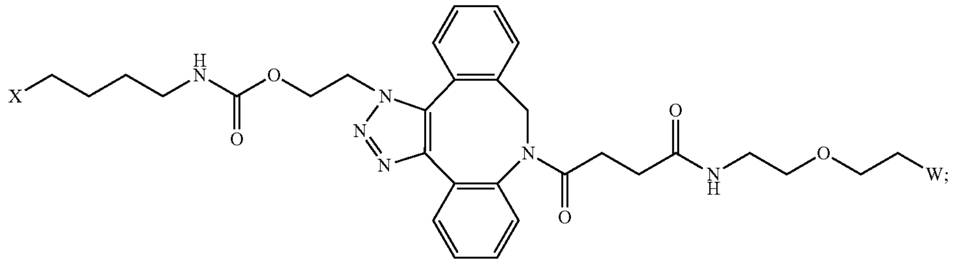

or a pharmaceutically acceptable salt, solvate, or hydrate thereof.

Embodiment 132. The IL-2 conjugate of embodiment 131, wherein the IL-2 conjugate has the amino acid sequence of SEQ ID NO: 40, or a pharmaceutically acceptable salt, solvate, or hydrate thereof.

Embodiment 133. The IL-2 conjugate of embodiment 132, wherein W is a PEG group having an average molecular weight selected from 5 kDa, 10 kDa, 15 kDa, 20 kDa, 25 kDa, and 30 kDa, or a pharmaceutically acceptable salt, solvate, or hydrate thereof.

Embodiment 134. The IL-2 conjugate of embodiment 133, wherein W is a PEG group having an average molecular weight selected from 5 kDa and 30 kDa, or a pharmaceutically acceptable salt, solvate, or hydrate thereof.

Embodiment 135. The IL-2 conjugate of embodiment 133, wherein W is a PEG group having an average molecular weight of 5 kDa, or a pharmaceutically acceptable salt, solvate, or hydrate thereof.

Embodiment 136. The IL-2 conjugate of embodiment 133, wherein W is a PEG group having an average molecular weight of 30 kDa, or a pharmaceutically acceptable salt, solvate, or hydrate thereof.

Embodiment 137. The IL-2 conjugate of embodiment 131, wherein the IL-2 conjugate has the amino acid sequence of SEQ ID NO: 41, or a pharmaceutically acceptable salt, solvate, or hydrate thereof.

Embodiment 138. The IL-2 conjugate of embodiment 137, wherein W is a PEG group having an average molecular weight selected from 5 kDa, 10 kDa, 15 kDa, 20 kDa, 25 kDa, and 30 kDa, or a pharmaceutically acceptable salt, solvate, or hydrate thereof.

Embodiment 139. The IL-2 conjugate of embodiment 138, wherein W is a PEG group having an average molecular weight selected from 5 kDa and 30 kDa, or a pharmaceutically acceptable salt, solvate, or hydrate thereof.

Embodiment 140. The IL-2 conjugate of embodiment 139, wherein W is a PEG group having an average molecular weight of 5 kDa, or a pharmaceutically acceptable salt, solvate, or hydrate thereof.

Embodiment 141. The IL-2 conjugate of embodiment 139, wherein W is a PEG group having an average molecular weight of 30 kDa, or a pharmaceutically acceptable salt, solvate, or hydrate thereof.

Embodiment 142. The IL-2 conjugate of embodiment 129, wherein the IL-2 conjugate has the amino acid sequence of SEQ ID NO: 42, or a pharmaceutically acceptable salt, solvate, or hydrate thereof.

Embodiment 143. The IL-2 conjugate of embodiment 142, wherein W is a PEG group having an average molecular weight selected from 5 kDa, 10 kDa, 15 kDa, 20 kDa, 25 kDa, and 30 kDa, or a pharmaceutically acceptable salt, solvate, or hydrate thereof.

Embodiment 144. The IL-2 conjugate of embodiment 143, wherein W is a PEG group having an average molecular weight selected from 5 kDa and 30 kDa, or a pharmaceutically acceptable salt, solvate, or hydrate thereof.

Embodiment 145. The IL-2 conjugate of embodiment 144, wherein W is a PEG group having an average molecular weight of 5 kDa, or a pharmaceutically acceptable salt, solvate, or hydrate thereof. Embodiment 146. The IL-2 conjugate of embodiment 144, wherein W is a PEG group having an average molecular weight of 30 kDa, or a pharmaceutically acceptable salt, solvate, or hydrate thereof.

Embodiment 147. The IL-2 conjugate of embodiment 129, wherein the IL-2 conjugate has the amino acid sequence of SEQ ID NO: 43, or a pharmaceutically acceptable salt, solvate, or hydrate thereof.

Embodiment 148. The IL-2 conjugate of embodiment 147, wherein W is a PEG group having an average molecular weight selected from 5 kDa, 10 kDa, 15 kDa, 20 kDa, 25 kDa, and 30 kDa, or a pharmaceutically acceptable salt, solvate, or hydrate thereof.

Embodiment 149. The IL-2 conjugate of embodiment 148, wherein W is a PEG group having an average molecular weight selected from 5 kDa and 30 kDa, or a pharmaceutically acceptable salt, solvate, or hydrate thereof.

Embodiment 150. The IL-2 conjugate of embodiment 149, wherein W is a PEG group having an average molecular weight of 5 kDa, or a pharmaceutically acceptable salt, solvate, or hydrate thereof.

Embodiment 151. The IL-2 conjugate of embodiment 149, wherein W is a PEG group having an average molecular weight of 30 kDa, or a pharmaceutically acceptable salt, solvate, or hydrate thereof.

Embodiment 152. The IL-2 conjugate of embodiment 129, wherein the IL-2 conjugate has the amino acid sequence of SEQ ID NO: 44, or a pharmaceutically acceptable salt, solvate, or hydrate thereof.

Embodiment 153. The IL-2 conjugate of embodiment 152, wherein W is a PEG group having an average molecular weight selected from 5 kDa, 10 kDa, 15 kDa, 20 kDa, 25 kDa, and 30 kDa, or a pharmaceutically acceptable salt, solvate, or hydrate thereof.

Embodiment 154. The IL-2 conjugate of embodiment 153, wherein W is a PEG group having an average molecular weight selected from 5 kDa and 30 kDa, or a pharmaceutically acceptable salt, solvate, or hydrate thereof.

Embodiment 155. The IL-2 conjugate of embodiment 154, wherein W is a PEG group having an average molecular weight of 5 kDa, or a pharmaceutically acceptable salt, solvate, or hydrate thereof.

Embodiment 156. The IL-2 conjugate of embodiment 155, wherein W is a PEG group having an average molecular weight of 30 kDa, or a pharmaceutically acceptable salt, solvate, or hydrate thereof.

Embodiment 157. The IL-2 conjugate of embodiment 129, wherein the [AzK_L1_PEG] has the structure of Formula (V)

Formula (V)

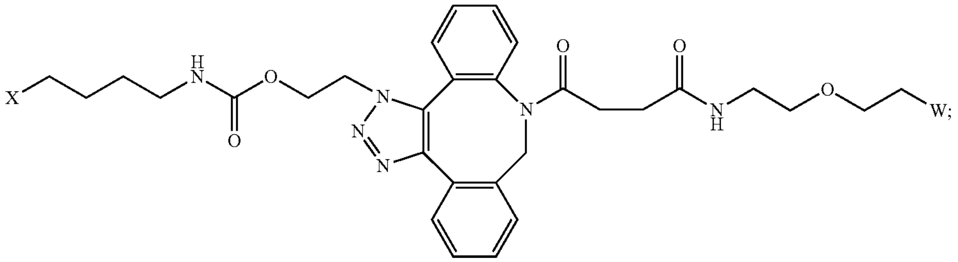

or a pharmaceutically acceptable salt, solvate, or hydrate thereof.

Embodiment 158. The IL-2 conjugate of embodiment 157, wherein the IL-2 conjugate has the amino acid sequence of SEQ ID NO: 40, or a pharmaceutically acceptable salt, solvate, or hydrate thereof.

Embodiment 159. The IL-2 conjugate of embodiment 158, wherein W is a PEG group having an average molecular weight selected from 5 kDa, 10 kDa, 15 kDa, 20 kDa, 25 kDa, and 30 kDa, or a pharmaceutically acceptable salt, solvate, or hydrate thereof.

Embodiment 160. The IL-2 conjugate of embodiment 159, wherein W is a PEG group having an average molecular weight selected from 5 kDa and 30 kDa, or a pharmaceutically acceptable salt, solvate, or hydrate thereof.

Embodiment 161. The IL-2 conjugate of embodiment 160, wherein W is a PEG group having an average molecular weight of 5 kDa, or a pharmaceutically acceptable salt, solvate, or hydrate thereof.

Embodiment 162. The IL-2 conjugate of embodiment 160, wherein W is a PEG group having an average molecular weight of 30 kDa, or a pharmaceutically acceptable salt, solvate, or hydrate thereof.

Embodiment 163. The IL-2 conjugate of embodiment 157, wherein the IL-2 conjugate has the amino acid sequence of SEQ ID NO: 41, or a pharmaceutically acceptable salt, solvate, or hydrate thereof.

Embodiment 164. The IL-2 conjugate of embodiment 163, wherein W is a PEG group having an average molecular weight selected from 5 kDa, 10 kDa, 15 kDa, 20 kDa, 25 kDa, and 30 kDa, or a pharmaceutically acceptable salt, solvate, or hydrate thereof.

Embodiment 165. The IL-2 conjugate of embodiment 164, wherein W is a PEG group having an average molecular weight selected from 5 kDa and 30 kDa, or a pharmaceutically acceptable salt, solvate, or hydrate thereof.

Embodiment 166. The IL-2 conjugate of embodiment 165, wherein W is a PEG group having an average molecular weight of 5 kDa, or a pharmaceutically acceptable salt, solvate, or hydrate thereof.

Embodiment 167. The IL-2 conjugate of embodiment 165, wherein W is a PEG group having an average molecular weight of 30 kDa, or a pharmaceutically acceptable salt, solvate, or hydrate thereof.

Embodiment 168. The IL-2 conjugate of embodiment 157, wherein the IL-2 conjugate has the amino acid sequence of SEQ ID NO: 42, or a pharmaceutically acceptable salt, solvate, or hydrate thereof.

Embodiment 169. The IL-2 conjugate of embodiment 168, wherein W is a PEG group having an average molecular weight selected from 5 kDa, 10 kDa, 15 kDa, 20 kDa, 25 kDa, and 30 kDa, or a pharmaceutically acceptable salt, solvate, or hydrate thereof.

Embodiment 170. The IL-2 conjugate of embodiment 169, wherein W is a PEG group having an average molecular weight selected from 5 kDa and 30 kDa, or a pharmaceutically acceptable salt, solvate, or hydrate thereof.

Embodiment 171. The IL-2 conjugate of embodiment 170, wherein W is a PEG group having an average molecular weight of 5 kDa, or a pharmaceutically acceptable salt, solvate, or hydrate thereof.

Embodiment 172. The IL-2 conjugate of embodiment 170, wherein W is a PEG group having an average molecular weight of 30 kDa, or a pharmaceutically acceptable salt, solvate, or hydrate thereof.

Embodiment 173. The IL-2 conjugate of embodiment 157, wherein the IL-2 conjugate has the amino acid sequence of SEQ ID NO: 43, or a pharmaceutically acceptable salt, solvate, or hydrate thereof.

Embodiment 174. The IL-2 conjugate of embodiment 173, wherein W is a PEG group having an average molecular weight selected from 5 kDa, 10 kDa, 15 kDa, 20 kDa, 25 kDa, and 30 kDa, or a pharmaceutically acceptable salt, solvate, or hydrate thereof.

Embodiment 175. The IL-2 conjugate of embodiment 174, wherein W is a PEG group having an average molecular weight selected from 5 kDa and 30 kDa, or a pharmaceutically acceptable salt, solvate, or hydrate thereof.

Embodiment 176. The IL-2 conjugate of embodiment 175, wherein W is a PEG group having an average molecular weight of 5 kDa, or a pharmaceutically acceptable salt, solvate, or hydrate thereof.

Embodiment 177. The IL-2 conjugate of embodiment 175, wherein W is a PEG group having an average molecular weight of 30 kDa, or a pharmaceutically acceptable salt, solvate, or hydrate thereof.

Embodiment 178. The IL-2 conjugate of embodiment 157, wherein the IL-2 conjugate has the amino acid sequence of SEQ ID NO: 44, or a pharmaceutically acceptable salt, solvate, or hydrate thereof.

Embodiment 179. The IL-2 conjugate of embodiment 178, wherein W is a PEG group having an average molecular weight selected from 5 kDa, 10 kDa, 15 kDa, 20 kDa, 25 kDa, and 30 kDa, or a pharmaceutically acceptable salt, solvate, or hydrate thereof.

Embodiment 180. The IL-2 conjugate of embodiment 179, wherein W is a PEG group having an average molecular weight selected from 5 kDa and 30 kDa, or a pharmaceutically acceptable salt, solvate, or hydrate thereof.

Embodiment 181. The IL-2 conjugate of embodiment 180, wherein W is a PEG group having an average molecular weight of 5 kDa, or a pharmaceutically acceptable salt, solvate, or hydrate thereof.

Embodiment 182. The IL-2 conjugate of embodiment 180, wherein W is a PEG group having an average molecular weight of 30 kDa, or a pharmaceutically acceptable salt, solvate, or hydrate thereof. Embodiment 183. The IL-2 conjugate according to any one of embodiments 129 to 182, wherein W is a linear or branched PEG group, or a pharmaceutically acceptable salt, solvate, or hydrate thereof.

Embodiment 184. The IL-2 conjugate according to any one of embodiments 129 to 182, wherein W is a linear PEG group, or a pharmaceutically acceptable salt, solvate, or hydrate thereof.

Embodiment 185. The IL-2 conjugate according to any one of embodiments 129 to 182, wherein W is a branched PEG group, or a pharmaceutically acceptable salt, solvate, or hydrate thereof.

Embodiment 186. The IL-2 conjugate according to any one of embodiments 129 to 182, wherein W is a methoxy PEG group, or a pharmaceutically acceptable salt, solvate, or hydrate thereof.

Embodiment 187. The IL-2 conjugate according to embodiment 186, wherein the methoxy PEG group is linear or branched, or a pharmaceutically acceptable salt, solvate, or hydrate thereof.

Embodiment 188. The IL-2 conjugate according to embodiment 187, wherein the methoxy PEG group is linear, or a pharmaceutically acceptable salt, solvate, or hydrate thereof.

Embodiment 189. The IL-2 conjugate according to embodiment 187, wherein the methoxy PEG group is branched, or a pharmaceutically acceptable salt, solvate, or hydrate thereof.

Embodiment 190. An IL-2 conjugate comprising the amino acid sequence of any one of SEQ ID NOS: 45-49, wherein [AzK_L1_PEG5kD] has the structure of Formula (IV) or Formula (V), or a mixture of Formula (IV) and Formula (V):

Formula (IV)

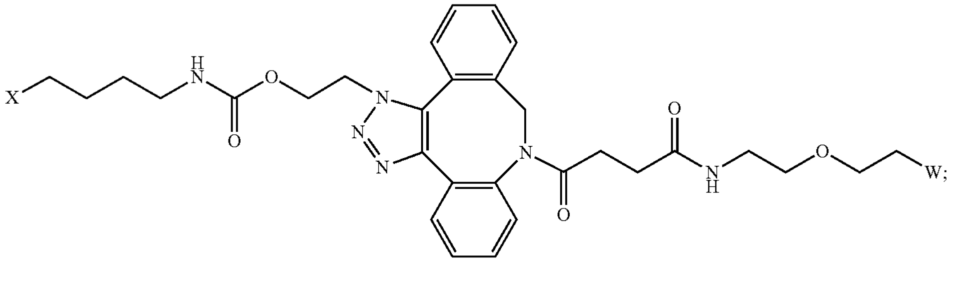

-continued

Formula (V)

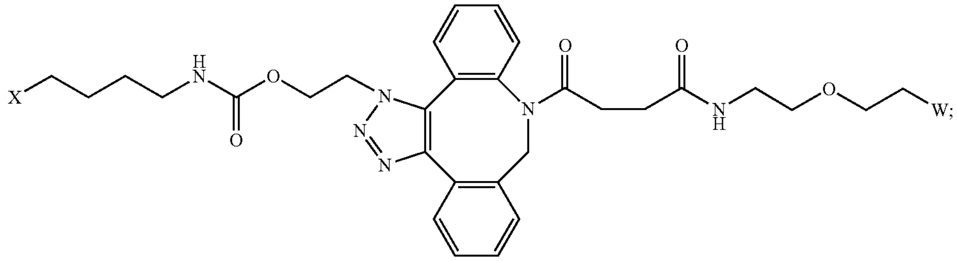

wherein:

W is a PEG group having an average molecular weight of 5 kDa; and

X has the structure:

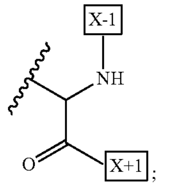

or a pharmaceutically acceptable salt, solvate, or hydrate thereof.

Embodiment 191. The IL-2 conjugate of embodiment 190, wherein the IL-2 conjugate has the amino acid sequence of SEQ ID NO: 45, or a pharmaceutically acceptable salt, solvate, or hydrate thereof.

Embodiment 192. The IL-2 conjugate of embodiment 190, wherein the IL-2 conjugate has the amino acid sequence of SEQ ID NO: 46, or a pharmaceutically acceptable salt, solvate, or hydrate thereof.

Embodiment 193. The IL-2 conjugate of embodiment 190, wherein the IL-2 conjugate has the amino acid sequence of SEQ ID NO: 47, or a pharmaceutically acceptable salt, solvate, or hydrate thereof.

Embodiment 194. The IL-2 conjugate of embodiment 190, wherein the IL-2 conjugate has the amino acid sequence of SEQ ID NO: 48, or a pharmaceutically acceptable salt, solvate, or hydrate thereof.

Embodiment 195. The IL-2 conjugate of embodiment 190, wherein the IL-2 conjugate has the amino acid sequence of SEQ ID NO: 49, or a pharmaceutically acceptable salt, solvate, or hydrate thereof.

Embodiment 196. The IL-2 conjugate of embodiment 190, wherein the [AzK_L1_PEG5kD] has the structure of Formula (IV)

Formula (IV)

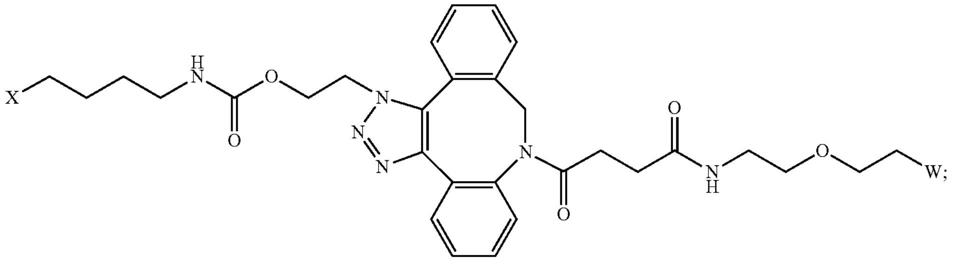

or a pharmaceutically acceptable salt, solvate, or hydrate thereof.

Embodiment 197. The IL-2 conjugate of embodiment 196, wherein the IL-2 conjugate has the amino acid sequence of SEQ ID NO: 45, or a pharmaceutically acceptable salt, solvate, or hydrate thereof.

Embodiment 198. The IL-2 conjugate of embodiment 196, wherein the IL-2 conjugate has the amino acid sequence of SEQ ID NO: 46, or a pharmaceutically acceptable salt, solvate, or hydrate thereof.

Embodiment 199. The IL-2 conjugate of embodiment 196, wherein the IL-2 conjugate has the amino acid sequence of SEQ ID NO: 47, or a pharmaceutically acceptable salt, solvate, or hydrate thereof.

Embodiment 200. The IL-2 conjugate of embodiment 196, wherein the IL-2 conjugate has the amino acid sequence of SEQ ID NO: 48, or a pharmaceutically acceptable salt, solvate, or hydrate thereof.

Embodiment 201. The IL-2 conjugate of embodiment 196, wherein the IL-2 conjugate has the amino acid sequence of SEQ ID NO: 49, or a pharmaceutically acceptable salt, solvate, or hydrate thereof.

Embodiment 202. The IL-2 conjugate of embodiment 190, wherein the [AzK_L1_PEG5kD] has the structure of Formula (V)

Formula (V)

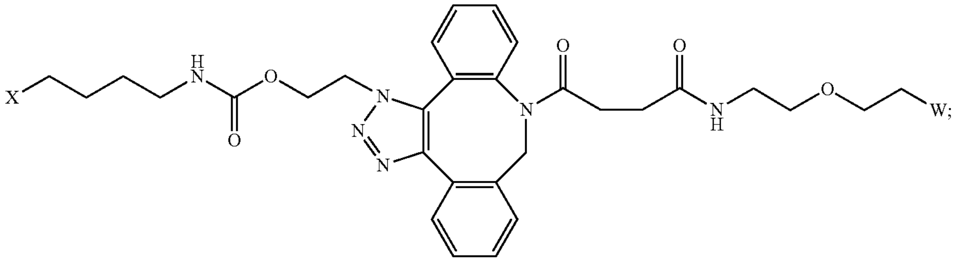

or a pharmaceutically acceptable salt, solvate, or hydrate thereof.

Embodiment 203. The IL-2 conjugate of embodiment 202, wherein the IL-2 conjugate has the amino acid sequence of SEQ ID NO: 45, or a pharmaceutically acceptable salt, solvate, or hydrate thereof.

Embodiment 204. The IL-2 conjugate of embodiment 202, wherein the IL-2 conjugate has the amino acid sequence of SEQ ID NO: 46, or a pharmaceutically acceptable salt, solvate, or hydrate thereof.

Embodiment 205. The IL-2 conjugate of embodiment 202, wherein the IL-2 conjugate has the amino acid sequence of SEQ ID NO: 47, or a pharmaceutically acceptable salt, solvate, or hydrate thereof.

Embodiment 206. The IL-2 conjugate of embodiment 202, wherein the IL-2 conjugate has the amino acid sequence of SEQ ID NO: 48, or a pharmaceutically acceptable salt, solvate, or hydrate thereof.

Embodiment 207. The IL-2 conjugate of embodiment 202, wherein the IL-2 conjugate has the amino acid sequence of SEQ ID NO: 49, or a pharmaceutically acceptable salt, solvate, or hydrate thereof.

Embodiment 208. An IL-2 conjugate comprising the amino acid sequence of any one of SEQ ID NOS: 50-54, wherein [AzK_L1_PEG30kD] has the structure of Formula (IV) or Formula (V), or is a mixture of the structures of Formula (IV) and Formula (V):

Formula (IV)

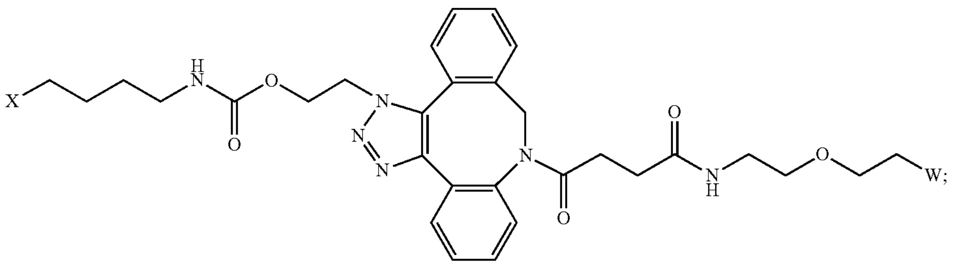

-continued

Formula (V)

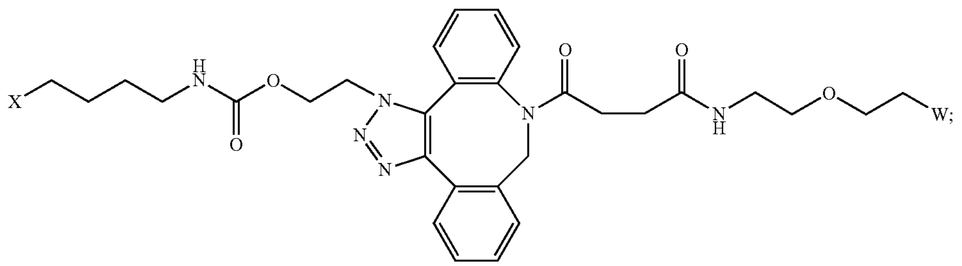

wherein:

W is a PEG group having an average molecular weight of 30 kDa; and

X has the structure:

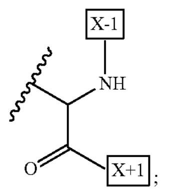

or a pharmaceutically acceptable salt, solvate, or hydrate thereof.

Embodiment 209. The IL-2 conjugate of embodiment 208, wherein the IL-2 conjugate has the amino acid sequence of SEQ ID NO: 50, or a pharmaceutically acceptable salt, solvate, or hydrate thereof.

Embodiment 210. The IL-2 conjugate of embodiment 208, wherein the IL-2 conjugate has the amino acid sequence of SEQ ID NO: 51, or a pharmaceutically acceptable salt, solvate, or hydrate thereof.

Embodiment 211. The IL-2 conjugate of embodiment 208, wherein the IL-2 conjugate has the amino acid sequence of SEQ ID NO: 52, or a pharmaceutically acceptable salt, solvate, or hydrate thereof.

Embodiment 212. The IL-2 conjugate of embodiment 208, wherein the IL-2 conjugate has the amino acid sequence of SEQ ID NO: 53, or a pharmaceutically acceptable salt, solvate, or hydrate thereof.

Embodiment 213. The IL-2 conjugate of embodiment 208, wherein the IL-2 conjugate has the amino acid sequence of SEQ ID NO: 54, or a pharmaceutically acceptable salt, solvate, or hydrate thereof.

Embodiment 214. The IL-2 conjugate of embodiment 208, wherein the [AzK_L1_PEG30kD] has the structure of Formula (IV):

Formula (IV)

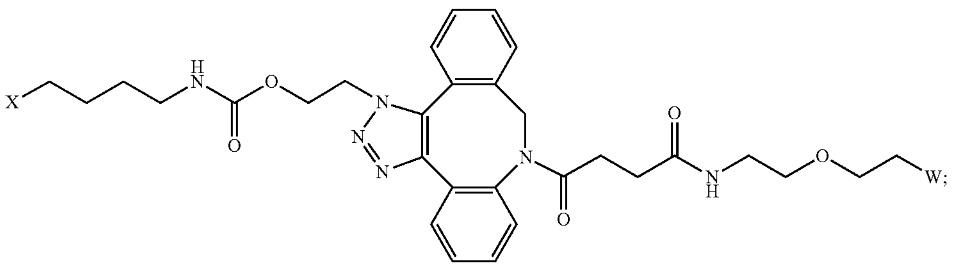

or a pharmaceutically acceptable salt, solvate, or hydrate thereof.

Embodiment 215. The IL-2 conjugate of embodiment 214, wherein the IL-2 conjugate has the amino acid sequence of SEQ ID NO: 50, or a pharmaceutically acceptable salt, solvate, or hydrate thereof.

Embodiment 216. The IL-2 conjugate of embodiment 214, wherein the IL-2 conjugate has the amino acid sequence of SEQ ID NO: 51, or a pharmaceutically acceptable salt, solvate, or hydrate thereof.

Embodiment 217. The IL-2 conjugate of embodiment 214, wherein the IL-2 conjugate has the amino acid sequence of SEQ ID NO: 52, or a pharmaceutically acceptable salt, solvate, or hydrate thereof.

Embodiment 218. The IL-2 conjugate of embodiment 214, wherein the IL-2 conjugate has the amino acid sequence of SEQ ID NO: 53, or a pharmaceutically acceptable salt, solvate, or hydrate thereof.

Embodiment 219. The IL-2 conjugate of embodiment 214, wherein the IL-2 conjugate has the amino acid sequence of SEQ ID NO: 54, or a pharmaceutically acceptable salt, solvate, or hydrate thereof.

Embodiment 220. The IL-2 conjugate of embodiment 214, wherein the [AzK_L1_PEG30kD] has the structure of Formula (V)

Formula (V)

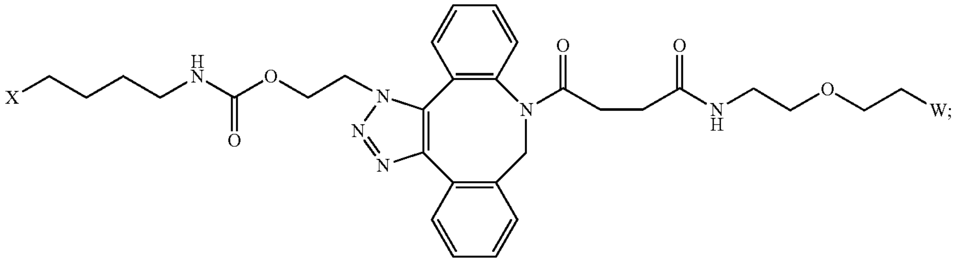

or a pharmaceutically acceptable salt, solvate, or hydrate thereof.

Embodiment 221. The IL-2 conjugate of embodiment 220, wherein the IL-2 conjugate has the amino acid sequence of SEQ ID NO: 50, or a pharmaceutically acceptable salt, solvate, or hydrate thereof.

Embodiment 222. The IL-2 conjugate of embodiment 220, wherein the IL-2 conjugate has the amino acid sequence of SEQ ID NO: 51, or a pharmaceutically acceptable salt, solvate, or hydrate thereof.

Embodiment 223. The IL-2 conjugate of embodiment 220, wherein the IL-2 conjugate has the amino acid sequence of SEQ ID NO: 52, or a pharmaceutically acceptable salt, solvate, or hydrate thereof.

Embodiment 224. The IL-2 conjugate of embodiment 220, wherein the IL-2 conjugate has the amino acid sequence of SEQ ID NO: 53, or a pharmaceutically acceptable salt, solvate, or hydrate thereof.

Embodiment 225. The IL-2 conjugate of embodiment 220, wherein the IL-2 conjugate has the amino acid sequence of SEQ ID NO: 54, or a pharmaceutically acceptable salt, solvate, or hydrate thereof.

Embodiment 226. An IL-2 conjugate comprising the amino acid sequence of any one of SEQ ID NOS: 40-44, wherein [Azk_L1_PEG] is a mixture of the structures of Formula (IV) and Formula (V):

Formula (IV)

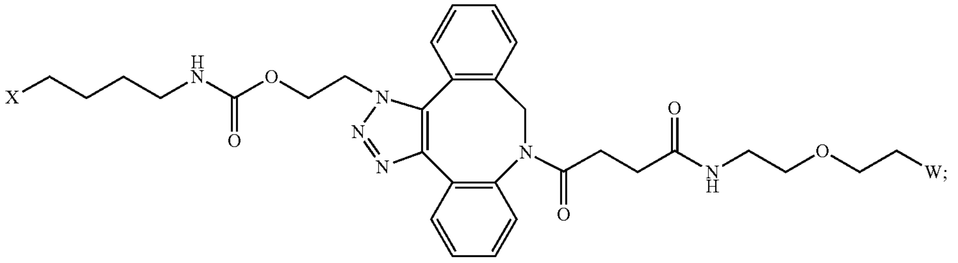

-continued

Formula (V)

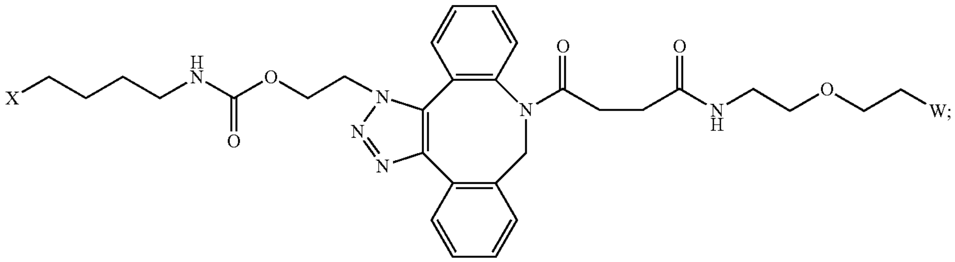

wherein:

W is a PEG group having an average molecular weight selected from 5 kDa, 10 kDa, 15 kDa, 20 kDa, 25 kDa, 30 kDa, 35 kDa, 40 kDa, 45 kDa, 50 kDa, and 60 kDa; and X has the structure:

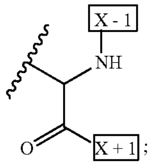

or a pharmaceutically acceptable salt, solvate, or hydrate thereof.

Embodiment 227. The IL-2 conjugate according to embodiment 226, wherein the ratio of the amount of the structure of Formula (IV) to the amount of the structure of Formula (V) comprising the total amount of [AzK_L1_PEG] in the IL-2 conjugate is about 1:1.

Embodiment 228. The IL-2 conjugate according to embodiment 226, wherein the ratio of the amount of the structure of Formula (IV) to the amount of the structure of Formula (V) comprising the total amount of [AzK_L1_PEG] in the IL-2 conjugate is greater than 1:1.

Embodiment 229. The IL-2 conjugate according to embodiment 226, wherein the ratio of the amount of the structure of Formula (IV) to the amount of the structure of Formula (V) comprising the total amount of [AzK_L1_PEG] in the IL-2 conjugate is less than 1:1.

Embodiment 230. The IL-2 conjugate according to any one of embodiments 226 to 229, wherein W is a linear or branched PEG group, or a pharmaceutically acceptable salt, solvate, or hydrate thereof.

Embodiment 231. The IL-2 conjugate according to any one of embodiments 226 to 229, wherein W is a linear PEG group, or a pharmaceutically acceptable salt, solvate, or hydrate thereof.

Embodiment 232. The IL-2 conjugate according to any one of embodiments 226 to 229, wherein W is a branched PEG group, or a pharmaceutically acceptable salt, solvate, or hydrate thereof.

Embodiment 233. The IL-2 conjugate according to any one of embodiments 226 to 229, wherein W is a methoxy PEG group, or a pharmaceutically acceptable salt, solvate, or hydrate thereof.

Embodiment 234. The IL-2 conjugate according to embodiment 233, wherein the methoxy PEG group is linear or branched, or a pharmaceutically acceptable salt, solvate, or hydrate thereof.

Embodiment 235. The IL-2 conjugate according to embodiment 234, wherein the methoxy PEG group is linear, or a pharmaceutically acceptable salt, solvate, or hydrate thereof.

Embodiment 236. The IL-2 conjugate according to embodiment 234, wherein the methoxy PEG group is branched, or a pharmaceutically acceptable salt, solvate, or hydrate thereof.

Embodiment 237. An IL-2 conjugate comprising the amino acid sequence of any one of SEQ ID NOS: 45 to 49, wherein [AzK_L1_PEG5kD] is a mixture of the structures of Formula (IV) and Formula (V):

Formula (IV)

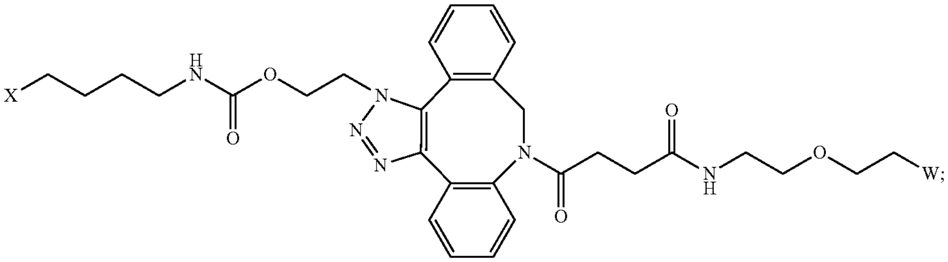

-continued

Formula (V)

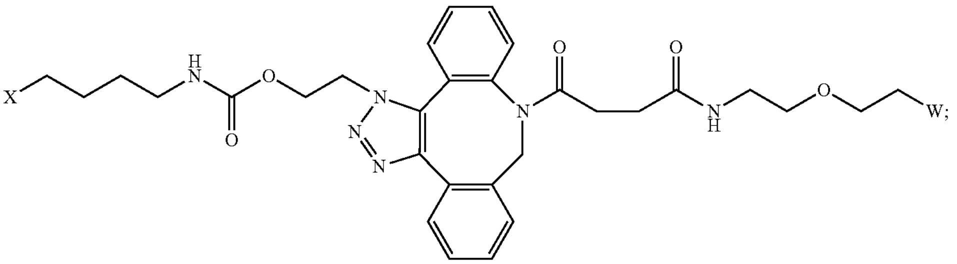

wherein:

W is a PEG group having an average molecular weight of 5 kDa; and

X has the structure:

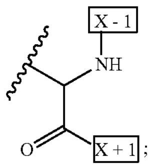

or a pharmaceutically acceptable salt, solvate, or hydrate thereof.

Embodiment 238. The IL-2 conjugate according to embodiment 237, wherein the ratio of the amount of the structure of Formula (IV) to the amount of the structure of Formula (V) comprising the total amount of [AzK_L1_PEG5kD] in the IL-2 conjugate is about 1:1.

Embodiment 239. The IL-2 conjugate according to embodiment 237, wherein the ratio of the amount of the structure of Formula (IV) to the amount of the structure of Formula (V) comprising the total amount of [AzK_L1_PEG5kD] in the IL-2 conjugate is greater than 1:1.

Embodiment 240. The IL-2 conjugate according to embodiment 237, wherein the ratio of the amount of the structure of Formula (IV) to the amount of the structure of Formula (V) comprising the total amount of [AzK_L1_PEG5kD] in the IL-2 conjugate is less than 1:1.

Embodiment 241. An IL-2 conjugate comprising the amino acid sequence of any one of SEQ ID NOS: 50-54, wherein [AzK_L1_PEG30kD] is a mixture of the structures of Formula (IV) and Formula (V):

Formula (IV)

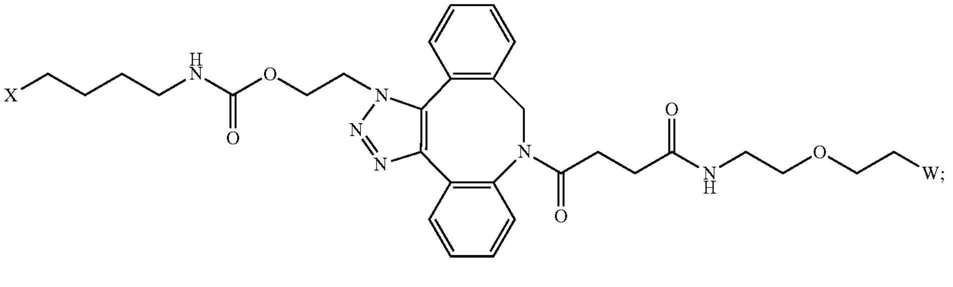

Formula (V)

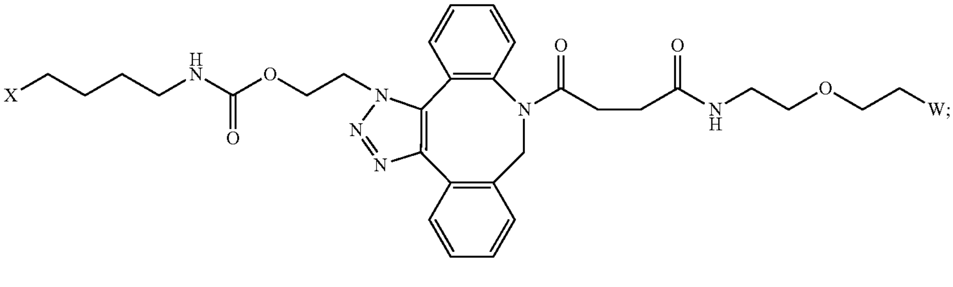

wherein:

W is a PEG group having an average molecular weight of 30 kDa; and

X has the structure:

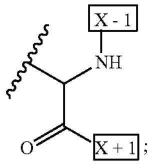

or a pharmaceutically acceptable salt, solvate, or hydrate thereof.

Embodiment 242. The IL-2 conjugate according to embodiment 241, wherein the ratio of the amount of the structure of Formula (IV) to the amount of the structure of Formula (V) comprising the total amount of [AzK_L1_PEG30kD] in the IL-2 conjugate is about 1:1.

Embodiment 243. The IL-2 conjugate according to embodiment 241, wherein the ratio of the amount of the structure of Formula (IV) to the amount of the structure of Formula (V) comprising the total amount of [AzK_L1_PEG30kD] in the IL-2 conjugate is greater than 1:1.

Embodiment 244. The IL-2 conjugate according to embodiment 241, wherein the ratio of the amount of the structure of Formula (IV) to the amount of the structure of Formula (V) comprising the total amount of [AzK_L1_PEG30kD] in the IL-2 conjugate is less than 1:1.

Embodiment 245. A method of treating cancer in a subject, comprising administering to a subject in need thereof an effective amount of an IL-2 conjugate according to any one of embodiments 1 to 244.

Embodiment 246. A method of treating cancer in a subject according to embodiment 245, wherein the cancer in the subject is selected from renal cell carcinoma (RCC), non-small cell lung cancer (NSCLC), head and neck squamous cell cancer (HNSCC), classical Hodgkin lymphoma (cHL), primary mediastinal large B-cell lymphoma (PMBCL), urothelial carcinoma, microsatellite unstable cancer, microsatellite stable cancer, gastric cancer, cervical cancer, hepatocellular carcinoma (HCC), Merkel cell carcinoma (MCC), melanoma, small cell lung cancer (SCLC), esophageal, glioblastoma, mesothelioma, breast cancer, triple-negative breast cancer, prostate cancer, bladder cancer, ovarian cancer, tumors of moderate to low mutational burden, cutaneous squamous cell carcinoma (CSCC), squamous cell skin cancer (SCSC), tumors of low- to non-expressing PD-L1, tumors disseminated systemically to the liver and CNS beyond their primary anatomic originating site, and diffuse large B-cell lymphoma.

Embodiment 247. A method of treating cancer in a subject according to embodiment 246, wherein the cancer in the subject is selected from renal cell carcinoma (RCC), non-small cell lung cancer (NSCLC), urothelial carcinoma, and melanoma.

Embodiment 248. A method of treating cancer in a subject according to any one of embodiments 245 to 247, wherein the IL-2 conjugate is administered to the subject in need thereof once every two weeks, once every three weeks, once every 4 weeks, once every 5 weeks, once every 6 weeks, once every 7 weeks, or once every 8 weeks.

Embodiment 249. A method of treating cancer in a subject according to embodiment 248, wherein the IL-2 conjugate is administered to the subject in need thereof once per week or once every two weeks.

Embodiment 250. A method of treating cancer in a subject according to embodiment 249, wherein the IL-2 conjugate is administered to the subject in need thereof once per week.

Embodiment 251. A method of treating cancer in a subject according to embodiment 249, wherein the IL-2 conjugate is administered to the subject in need thereof once every two weeks.

Embodiment 252. A method of treating cancer in a subject according to any one of embodiments 245 to 251, wherein administration of the effective amount of the IL-2 conjugate to the subject does not cause vascular leak syndrome in the subject.

Embodiment 253. A method of treating cancer in a subject according to any one of embodiments 245 to 251, wherein administration of the effective amount of the IL-2 conjugate to the subject does not cause Grade 2, Grade 3, or Grade 4 vascular leak syndrome in the subject.

Embodiment 254. A method of treating cancer in a subject according to any one of embodiments 245 to 251, wherein administration of the effective amount of the IL-2 conjugate to the subject does not cause Grade 2 vascular leak syndrome in the subject.

Embodiment 255. A method of treating cancer in a subject according to embodiment 253, wherein administration of the effective amount of the IL-2 conjugate to the subject does not cause Grade 3 vascular leak syndrome in the subject.

Embodiment 256. A method of treating cancer in a subject according to embodiment 253, wherein administration of the effective amount of the IL-2 conjugate to the subject does not cause Grade 4 vascular leak syndrome in the subject.

Embodiment 257. A method of treating cancer in a subject according to any one of embodiments 245 to 251, wherein administration of the effective amount of the IL-2 conjugate to the subject does not cause loss of vascular tone in the subject.

Embodiment 258. A method of treating cancer in a subject according to any one of embodiments 245 to 251, wherein administration of the effective amount of the IL-2 conjugate to the subject does not cause extravasation of plasma proteins and fluid into the extravascular space in the subject.

Embodiment 259. A method of treating cancer in a subject according to any one of embodiments 245 to 251, wherein administration of the effective amount of the IL-2 conjugate to the subject does not cause hypotension and reduced organ perfusion in the subject.

Embodiment 260. A method of treating cancer in a subject according to any one of embodiments 245 to 251, wherein administration of the effective amount of the IL-2 conjugate to the subject does not cause impaired neutrophil function in the subject.

Embodiment 261. A method of treating cancer in a subject according to any one of embodiments 245 to 251, wherein administration of the effective amount of the IL-2 conjugate to the subject does not cause reduced chemotaxis in the subject.

Embodiment 262. A method of treating cancer in a subject according to any one of embodiments 245 to 251, wherein administration of the effective amount of the IL-2 conjugate to the subject is not associated with an increased risk of disseminated infection in the subject.

Embodiment 263. The method according to embodiment 262, wherein the disseminated infection is sepsis or bacterial endocarditis.

Embodiment 264. The method according to embodiment 263, wherein the disseminated infection is sepsis.

Embodiment 265. The method according to embodiment 262, wherein the disseminated infection is bacterial endocarditis.

Embodiment 266. A method of treating cancer in a subject according to any one of embodiments 245 to 251, wherein the subject is treated for any preexisting bacterial infections prior to administration of the IL-2 conjugate.

Embodiment 267. The method according to embodiment 266, wherein the subject is treated with an antibacterial agent selected from oxacillin, nafcillin, ciprofloxacin, and vancomycin prior to administration of the IL-2 conjugate.

Embodiment 268. A method of treating cancer in a subject according to any one of embodiments 245 to 251, wherein administration of the effective amount of the IL-2 conjugate to the subject does not exacerbate a pre-existing or initial presentation of an autoimmune disease or an inflammatory disorder in the subject.

Embodiment 269. The method according to embodiment 268, wherein the administration of the effective amount of the IL-2 conjugate to the subject does not exacerbate a pre-existing or initial presentation of an autoimmune disease in the subject.

Embodiment 270. The method according to embodiment 268, wherein the administration of the effective amount of the IL-2 conjugate to the subject does not exacerbate a pre-existing or initial presentation of an inflammatory disorder in the subject.

Embodiment 271. The method according to embodiment 268, wherein the autoimmune disease or inflammatory disorder in the subject is selected from Crohn's disease, scleroderma, thyroiditis, inflammatory arthritis, diabetes mellitus, oculo-bulbar myasthenia gravis, crescentic IgA glomerulonephritis, cholecystitis, cerebral vasculitis, Stevens-Johnson syndrome and bullous pemphigoid.

Embodiment 272. The method according to embodiment 271 wherein the autoimmune disease or inflammatory disorder in the subject is Crohn's disease.

Embodiment 273. The method according to embodiment 271 wherein the autoimmune disease or inflammatory disorder in the subject is scleroderma.

Embodiment 274. The method according to embodiment 271 wherein the autoimmune disease or inflammatory disorder in the subject is thyroiditis.

Embodiment 275. The method according to embodiment 271 wherein the autoimmune disease or inflammatory disorder in the subject is inflammatory arthritis.

Embodiment 276. The method according to embodiment 271 wherein the autoimmune disease or inflammatory disorder in the subject is diabetes mellitus.

Embodiment 277. The method according to embodiment 271 wherein the autoimmune disease or inflammatory disorder in the subject is oculo-bulbar myasthenia gravis.

Embodiment 278. The method according to embodiment 271 wherein the autoimmune disease or inflammatory disorder in the subject is crescentic IgA glomerulonephritis.

Embodiment 279. The method according to embodiment 271 wherein the autoimmune disease or inflammatory disorder in the subject is cholecystitis.

Embodiment 280. The method according to embodiment 271 wherein the autoimmune disease or inflammatory disorder in the subject is cerebral vasculitis.

Embodiment 281. The method according to embodiment 271 wherein the autoimmune disease or inflammatory disorder in the subject is Stevens-Johnson syndrome.

Embodiment 282. The method according to embodiment 271 wherein the autoimmune disease or inflammatory disorder in the subject is bullous pemphigoid.

Embodiment 283. A method of treating cancer in a subject according to any one of embodiments 245 to 251, wherein administration of the effective amount of the IL-2 conjugate to the subject does not cause changes in mental status, speech difficulties, cortical blindness, limb or gait ataxia, hallucinations, agitation, obtundation, or coma in the subject.

Embodiment 284. A method of treating cancer in a subject according to any one of embodiments 245 to 251, wherein administration of the effective amount of the IL-2 conjugate to the subject does not cause seizures in the subject.

Embodiment 285. A method of treating cancer in a subject according to any one of embodiments 245 to 251, wherein administration of the effective amount of the IL-2 conjugate to the subject is not contraindicated in subjects having a known seizure disorder.

Embodiment 286. A method of treating cancer in a subject according to any one of embodiments 245 to 251, wherein administration of the effective amount of the IL-2 conjugate to the subject does not cause capillary leak syndrome in the subject.

Embodiment 287. The method according to embodiment 286, wherein administration of the effective amount of the IL-2 conjugate to the subject does not cause Grade 2, Grade 3, or Grade 4 capillary leak syndrome in the subject.

Embodiment 288. The method according to embodiment 287, wherein administration of the effective amount of the IL-2 conjugate to the subject does not cause Grade 2 capillary leak syndrome in the subject.

Embodiment 289. The method according to embodiment 287, wherein administration of the effective amount of the IL-2 conjugate to the subject does not cause Grade 3 capillary leak syndrome in the subject.

Embodiment 290. The method according to embodiment 287, wherein administration of the effective amount of the IL-2 conjugate to the subject does not cause Grade 4 capillary leak syndrome in the subject.

Embodiment 291. A method of treating cancer in a subject according to any one of embodiments 245 to 251, wherein administration of the effective amount of the IL-2 conjugate to the subject does not cause a drop in mean arterial blood pressure in the subject following administration of the IL-2 conjugate to the subject.

Embodiment 292. The method according to embodiment 291, wherein administration of the effective amount of the IL-2 conjugate to the subject does not cause hypotension in the subject following administration of the IL-2 conjugate to the subject.

Embodiment 293. The method according to embodiment 292, wherein administration of the effective amount of the IL-2 conjugate to the subject does not cause the subject to experience a systolic blood pressure below 90 mm Hg or a 20 mm Hg drop from baseline systolic pressure following administration of the IL-2 conjugate to the subject.

Embodiment 294. A method of treating cancer in a subject according to any one of embodiments 245 to 251, wherein administration of the effective amount of the IL-2 conjugate to the subject does not cause edema in the subject following administration of the IL-2 conjugate to the subject.

Embodiment 295. A method of treating cancer in a subject according to any one of embodiments 245 to 251, wherein administration of the effective amount of the IL-2 conjugate to the subject does not cause impairment of kidney or liver function in the subject following administration of the IL-2 conjugate to the subject.

Embodiment 296. A method of treating cancer in a subject according to any one of embodiments 245 to 251, wherein administration of the effective amount of the IL-2 conjugate to the subject does not cause eosinophilia in the subject following administration of the IL-2 conjugate to the subject.

Embodiment 297. A method of treating cancer in a subject according to any one of embodiments 245 to 251, wherein administration of the effective amount of the IL-2 conjugate to the subject does not cause the eosinophil count in the peripheral blood of the subject to exceed 500 per L following administration of the IL-2 conjugate to the subject.

Embodiment 298. The method according to embodiment 297, wherein administration of the effective amount of the IL-2 conjugate to the subject does not cause the eosinophil count in the peripheral blood of the subject to exceed 500 μL to 1500 per μL following administration of the IL-2 conjugate to the subject.

Embodiment 299. The method according to embodiment 297, wherein administration of the effective amount of the IL-2 conjugate to the subject does not cause the eosinophil count in the peripheral blood of the subject to exceed 1500 per μL to 5000 per μL following administration of the IL-2 conjugate to the subject.

Embodiment 300. The method according to embodiment 297, wherein administration of the effective amount of the IL-2 conjugate to the subject does not cause the eosinophil count in the peripheral blood of the subject to exceed 5000 per L following administration of the IL-2 conjugate to the subject.

Embodiment 301. A method of treating cancer in a subject according to any one of embodiments 245 to 251, wherein administration of the effective amount of the IL-2 conjugate to the subject is not contraindicated in subjects on an existing regimen of psychotropic drugs.

Embodiment 302. A method of treating cancer in a subject according to any one of embodiments 245 to 251, wherein administration of the effective amount of the IL-2 conjugate to the subject is not contraindicated in subjects on an existing regimen of nephrotoxic, myelotoxic, cardiotoxic, or hepatotoxic drugs.

Embodiment 303. The method according to embodiment 302, wherein administration of the effective amount of the IL-2 conjugate to the subject is not contraindicated in subjects on an existing regimen of aminoglycosides, cytotoxic chemotherapy, doxorubicin, methotrexate, or asparaginase.

Embodiment 304. A method of treating cancer in a subject according to any one of embodiments 245 to 251, wherein administration of the effective amount of the IL-2 conjugate to the subject is not contraindicated in subjects receiving combination regimens containing antineoplastic agents.

Embodiment 305. The method according to embodiment 304, wherein the antineoplastic agent is selected from dacarbazine, cis-platinum, tamoxifen and interferon-alfa.

Embodiment 306. A method of treating cancer in a subject according to any one of embodiments 245 to 251, wherein administration of the effective amount of the IL-2 conjugate to the subject does not cause one or more Grade 4 adverse events in the subject following administration of the IL-2 conjugate to the subject.

Embodiment 307. The method according to embodiment 306, wherein the one or more Grade 4 adverse events are selected from hypothermia; shock; bradycardia; ventricular extrasystoles; myocardial ischemia; syncope; hemorrhage; atrial arrhythmia; phlebitis; AV block second degree; endocarditis; pericardial effusion; peripheral gangrene; thrombosis; coronary artery disorder; stomatitis; nausea and vomiting; liver function tests abnormal; gastrointestinal hemorrhage; hematemesis; bloody diarrhea; gastrointestinal disorder; intestinal perforation; pancreatitis; anemia; leukopenia; leukocytosis; hypocalcemia; alkaline phosphatase increase; blood urea nitrogen (BUN) increase; hyperuricemia; non-protein nitrogen (NPN) increase; respiratory acidosis; somnolence; agitation; neuropathy; paranoid reaction; convulsion; grand mal convulsion; delirium; asthma, lung edema; hyperventilation; hypoxia; hemoptysis; hypoventilation; pneumothorax; mydriasis; pupillary disorder; kidney function abnormal; kidney failure; and acute tubular necrosis.

Embodiment 308. A method of treating cancer in a subject according to any one of embodiments 245 to 251, wherein administration of the effective amount of the IL-2 conjugate to a group of subjects does not cause one or more Grade 4 adverse events in greater than 1% of the subjects following administration of the IL-2 conjugate to the subjects.

Embodiment 309. The method according to embodiment 307, wherein the one or more Grade 4 adverse events are selected from hypothermia; shock; bradycardia; ventricular extrasystoles; myocardial ischemia; syncope; hemorrhage; atrial arrhythmia; phlebitis; AV block second degree; endocarditis; pericardial effusion; peripheral gangrene; thrombosis; coronary artery disorder; stomatitis; nausea and vomiting; liver function tests abnormal; gastrointestinal hemorrhage; hematemesis; bloody diarrhea; gastrointestinal disorder; intestinal perforation; pancreatitis; anemia; leukopenia; leukocytosis; hypocalcemia; alkaline phosphatase increase; blood urea nitrogen (BUN) increase; hyperuricemia; non-protein nitrogen (NPN) increase; respiratory acidosis; somnolence; agitation; neuropathy; paranoid reaction; convulsion; grand mal convulsion; delirium; asthma, lung edema; hyperventilation; hypoxia; hemoptysis; hypoventilation; pneumothorax; mydriasis; pupillary disorder; kidney function abnormal; kidney failure; and acute tubular necrosis.

Embodiment 310. A method of treating cancer in a subject according to any one of embodiments 245 to 251, wherein administration of the effective amount of the IL-2 conjugate to a group of subjects does not cause one or more adverse events in greater than 1% of the subjects following administration of the IL-2 conjugate to the subjects, wherein the one or more adverse events is selected from duodenal ulceration; bowel necrosis; myocarditis; supraventricular tachycardia; permanent or transient blindness secondary to optic neuritis; transient ischemic attacks; meningitis; cerebral edema; pericarditis; allergic interstitial nephritis; and tracheo-esophageal fistula.

Embodiment 311. A method of treating cancer in a subject according to any one of embodiments 245 to 251, wherein administration of the effective amount of the IL-2 conjugate to a group of subjects does not cause one or more adverse events in greater than 1% of the subjects following administration of the IL-2 conjugate to the subjects, wherein the one or more adverse events is selected from malignant hyperthermia; cardiac arrest; myocardial infarction; pulmonary emboli; stroke; intestinal perforation; liver or renal failure; severe depression leading to suicide; pulmonary edema; respiratory arrest; respiratory failure.

Embodiment 312. A method of treating cancer in a subject according to any one of embodiments 245 to 251, wherein administration of the effective amount of the IL-2 conjugate to a subject does not result in the production of neutralizing antibodies to the IL-2 conjugate.

Embodiment 313. A method of treating cancer in a subject according to any one of embodiments 245 to 256, wherein administration of the IL-2 conjugate to the subject increases the number of peripheral CD8+ T and NK cells in the subject without increasing the number of peripheral CD4+ regulatory T cells in the subject.

Embodiment 314. A method of treating cancer in a subject according to any one of embodiments 245 to 256, wherein administration of the IL-2 conjugate to the subject increases the number of peripheral CD8+ T and NK cells in the subject without increasing the number of peripheral eosinophils in the subject.

Embodiment 315. A method of treating cancer in a subject according to any one of embodiments 245 to 256, wherein administration of the IL-2 conjugate to the subject increases the number of intratumoral CD8+ T and NK cells in the subject without increasing the number of intratumoral CD4+ regulatory T cells in the subject.

Embodiment 316. A pharmaceutical composition comprising an effective amount of an IL-conjugate according to any one of embodiments 1 to 244 and one or more pharmaceutically acceptable excipients.

Embodiment 317. A method of treating cancer in a subject according to any one of embodiments 245 to 251, wherein administration of the effective amount of the IL-2 conjugate to the subject does not require the availability of an intensive care facility or skilled specialists in cardiopulmonary or intensive care medicine.

Embodiment 318. The method according to embodiment 317, wherein administration of the effective amount of the IL-2 conjugate to the subject does not require the availability of an intensive care facility.

Embodiment 319. The method according to embodiment 317, wherein administration of the effective amount of the IL-2 conjugate to the subject does not require the availability of skilled specialists in cardiopulmonary or intensive care medicine.

EXAMPLES

These examples are provided for illustrative purposes only and not to limit the scope of the claims provided herein.

Each of the compounds disclosed in Examples 2 to 12 utilized SEQ ID NO: 4 and the [AzK_PEG] moiety, wherein the position of the substituted amino acid in the IL-2 conjugate is in reference to the positions in SEQ ID NO: 4.

For example, the compound labelled "P65_5kD" in Tables 2A and 2B, was prepared using methods similar to those disclosed in Example 2, wherein a protein was first prepared having SEQ ID NO: 4 in which the proline at position 65 was replaced by AzK. The AzK-containing protein was then allowed to react under click chemistry conditions with DBCO comprising a methoxy, linear PEG group having an average molecular weight of 5 kDa to afford a product having SEQ ID NO: 20 comprising Formula (II), Formula (III), or a mixture of Formula (II) and (III), wherein W is a methoxy, linear PEG group having an average molecular weight of 5 kDa.

In another example, the compound labelled "P65_30kD" in Tables 2A and 2B was prepared by first preparing a protein having SEQ ID NO: 4 in which the proline at position 65 was replaced by AzK. The AzK-containing protein was then allowed to react under click chemistry conditions with DBCO comprising a methoxy, linear PEG group having an average molecular weight of 30 kDa to afford a product having SEQ ID NO: 25 comprising Formula (II), Formula (III), or a mixture of Formula (II) and (III), wherein W is a methoxy, linear PEG group having an average molecular weight of 30 kDa.

Similarly, the compound the compound labelled "P65_30kD" was prepared by preparing a protein having SEQ ID NO: 4 in which the proline at position 65 was replaced by N6-((2-azidoethoxy)-carbonyl)-L-lysine (AzK) (SEQ ID NO: 10). The compound can also be defined as comprising the amino acid sequence of SEQ ID NO: 4 in which the proline at position 65 (P65) is replaced by the structure of Formula (VI) or (VII), or a mixture of (VI) and (VII), and wherein n is an integer such that the PEG group has a molecular weight of about 30 kDa. The compound can also be defined as comprising the amino acid sequence of SEQ ID NO: 4 in which the proline at position 65 (P65) is replaced by the structure of Formula (X) or (XI), or a mixture of (X) and (XI), and wherein n is an integer such that the PEG group has a molecular weight of about 30 kDa. The compound P65_30kD was utilized in Examples 5, 6, 7, and 8.

In another example, the compound labelled "E62_5kD" in Tables 2A and 2B was prepared by first preparing a protein having SEQ ID NO: 4 in the glutamic acid at position 62 was replaced by AzK. The AzK-containing protein was then allowed to react under click chemistry conditions with DBCO comprising a methoxy, linear PEG group having an average molecular weight of 5 kDa to afford a product having SEQ ID NO: 21 comprising Formula (II), Formula (III), or a mixture of Formula (II) and (III), wherein W is a methoxy, linear PEG group having an average molecular weight of 5 kDa.

Similarly, the compound labelled "E62_5kD" was prepared by first preparing a protein having SEQ ID NO: 4 in the glutamic acid at position 62 (E62) was replaced by N6-((2-azidoethoxy)-carbonyl)-L-lysine AzK (SEQ ID NO: 11). The AzK-containing protein was then allowed to react under click chemistry conditions with DBCO comprising a methoxy, linear PEG group having an average molecular weight of 5 kDa to afford a product having SEQ ID NO: 21 comprising Formula (II), Formula (III), or a mixture of Formula (II) and (III), wherein W is a methoxy, linear PEG group having an average molecular weight of 5 kDa. The compound E62_5kD was utilized in Example 9.

In another example, the compound labelled "E62_30kD" in Tables 2A and 2B was prepared by first preparing a protein having SEQ ID NO: 4 in the glutamic acid at position 62 was replaced by AzK. The AzK-containing protein was then allowed to react under click chemistry conditions with DBCO comprising a methoxy, linear PEG group having an average molecular weight of 30 kDa to afford a product having SEQ ID NO: 26 comprising Formula (II), Formula (III), or a mixture of Formula (II) and (III), wherein W is a methoxy, linear PEG group having an average molecular weight of 30 kDa.

Similarly, the compound labelled "E62_30kD" was prepared by first preparing a protein having SEQ ID NO: 4 in which the glutamic acid at position 62 (E62) was replaced by N6-((2-azidoethoxy)-carbonyl)-L-lysine (AzK) (SEQ ID NO: 11). The AzK-containing protein was then allowed to react under click chemistry conditions with DBCO comprising a methoxy, linear PEG group having an average molecular weight of 30 kDa to afford a product having SEQ ID NO: 26 comprising Formula (II), Formula (III), or a mixture of Formula (II) and (III), wherein W is a methoxy, linear PEG group having an average molecular weight of 30 kDa. The compound can also be defined as comprising the amino acid sequence of SEQ ID NO: 4 in which the glutamic acid at position 62 (E62) is replaced by the structure of Formula (VI) or (VII), or a mixture of (VI) and (VII), and wherein n is an integer such that the PEG group has a molecular weight of about 30 kDa. The compound can also be defined as comprising the amino acid sequence of SEQ ID NO: 4 in which the glutamic acid at position 62 (E62) is replaced by the structure of Formula (X) or (XI), or a mixture of (X) and (XI), and wherein n is an integer such that the PEG group has a molecular weight of about 30 kDa. The compound E62_30kD was utilized in Examples 3, 5, and 9.

In another example, the compound labelled "K35_30kD," and used in Example 12, was prepared by first preparing a protein having SEQ ID NO: 4 in which the lysine at position 35 was replaced by N6-((2-azidoethoxy)-carbonyl)-L-lysine (AzK) (SEQ ID NO: 14). The AzK-containing protein was then allowed to react under click chemistry conditions with DBCO comprising a methoxy, linear PEG group having an average molecular weight of 30 kDa to afford a product having SEQ ID NO: 29 comprising Formula (II), Formula (III), or a mixture of Formula (II) and (III), wherein W is a methoxy, linear PEG group having an average molecular weight of 30 kDa. The compound can also be defined as comprising the amino acid sequence of SEQ ID NO: 4 in which the lysine at position 35 (K35) is replaced by the structure of Formula (VI) or (VII), or a mixture of (VI) and (VII), and wherein n is an integer such that the PEG group has a molecular weight of about 30 kDa. The compound can also be defined as comprising the amino acid sequence of SEQ ID NO: 4 in which the lysine at position 35 (K35) is replaced by the structure of Formula (X) or (XI), or a mixture of (X) and (XI), and wherein n is an integer such that the PEG group has a molecular weight of about 30 kDa.

The compound disclosed in Examples 13 and 14 labelled "IL2_P65_[AzK_L1_PEG30kD]-1" was prepared using methods similar to those disclosed in Example 2, wherein a protein was first prepared having SEQ ID NO: 3 in which the proline at position 64 was replaced by AzK. The AzK-containing protein was then allowed to react under click chemistry conditions with DBCO comprising a methoxy, linear PEG group having an average molecular weight of 30 kDa to afford a product having SEQ ID NO:50 comprising Formula (IV), Formula (V), or a mixture of Formula (IV) and (V), wherein W is a methoxy, linear PEG group having an average molecular weight of 30 kDa.

Similarly, the compound labelled "IL2_P65_[AzK_L1_PEG30kD]-1" was prepared using methods similar to those disclosed in Example 2, wherein a protein was first prepared having SEQ ID NO: 3 in which the proline at position 64 was replaced by N6-((2-azidoethoxy)-carbonyl)-L-lysine AzK (SEQ ID NO: 35). The AzK-containing protein was then allowed to react under click chemistry conditions with DBCO comprising a methoxy, linear PEG group having an average molecular weight of 30 kDa. Compound IL-2_P65[AzK_L1_PEG30kD]-1 is also defined as the compound comprising SEQ ID NO: 3 in which the proline residue at position 64 (P64) is replaced by the structure of Formula (VIII) or (IX), or a mixture of (VIII) and (IX), and wherein n is an integer such that the molecular weight of the PEG group is about 30 kDa. Compound IL-2_P65 [AzK_L1_PEG30kD]-1 is also defined as the compound comprising SEQ ID NO: 3 in which the proline residue at position 64 (P64) is replaced by the structure of Formula (XII) or (XIII), or a mixture of (XII) and (XIII), and wherein n is an integer such that the molecular weight of the PEG group is about 30 kDa. The compound IL2_P65_[AzK_L1_PEG30kD]-1 was utilized in Examples 13, 14, and 15.

Example 1

Kinase and Cytokine Receptor Dimerization Assays

Cell Handling

PathHunter cell lines were expanded from freezer stocks according to standard procedures. Cells were seeded in a total volume of 20 μL into white walled, 384-well microplates and incubated for the appropriate time prior to testing.

Agonist Format

For agonist determination, cells were incubated with sample to induce response. Intermediate dilution of sample stocks was performed to generate 5× sample in assay buffer. About 5 μL of 5× sample was added to cells and incubated at 37° C. for 6 to 16 hours depending on the assay. Vehicle concentration was 1%.

Signal Detection

Assay signal was generated through a single addition of 12.5 or 15 μL (50% v/v) of PathHunter Detection reagent cocktail for agonist and antagonist assays respectively, followed by a one hour incubation at room temperature. For some assays, activity was detected using a high sensitivity detection reagent (PathHunter Flash Kit) to improve assay performance. In these assays, an equal volume of detection reagent (25 or 30 uL) was added to the wells, followed by a one hour incubation at room temperature. Microplates were read following signal generation with a PerkinElmer Envision™ instrument for chemilumine-scent signal detection.

Data Analysis

Compound activity was analyzed using CBIS data analysis suite (ChemInnovation, CA). For agonist mode assays, percentage activity was calculated using the following formula:

% Activity=100%×(mean RLU of test sample−mean RLU of vehicle control)/(mean MAX RLU control ligand−mean RLU of vehicle control).

For antagonist mode assays, percentage inhibition was calculated using the following formula:

% Inhibition=100%×(1−(mean RLU of test sample−mean RLU of vehicle control)/(mean RLU of EC80 control−mean RLU of vehicle control)).

Example 2

Cell-Based Screening for Identification of Pegylated IL-2 Compounds with No IL-2Rα Engagement Structural data of the IL-2/heterotrimeric receptor signaling complex (PDB: 2ERJ) were used to guide design of nAA-pegylation sites to specifically abrogate the interaction of IL-2 and IL-2 receptor α subunit (IL-2Rα). Exemplary IL-2 conjugates were subjected to functional analysis: K35, F42, K43, E62, and P65. The IL-2 conjugates were expressed as inclusion bodies in *E. coli*, purified and re-folded using standard procedures before site-specifically pegylating the IL-2 product using DBCO-mediated copper-free click chemistry to attach stable, covalent mPEG moieties to the AzK (Scheme 1).

Scheme 1. Exemplary synthesis of AzK_PEG interleukin variants (wherein n indicates the number of repeating PEG units). Regioisomers
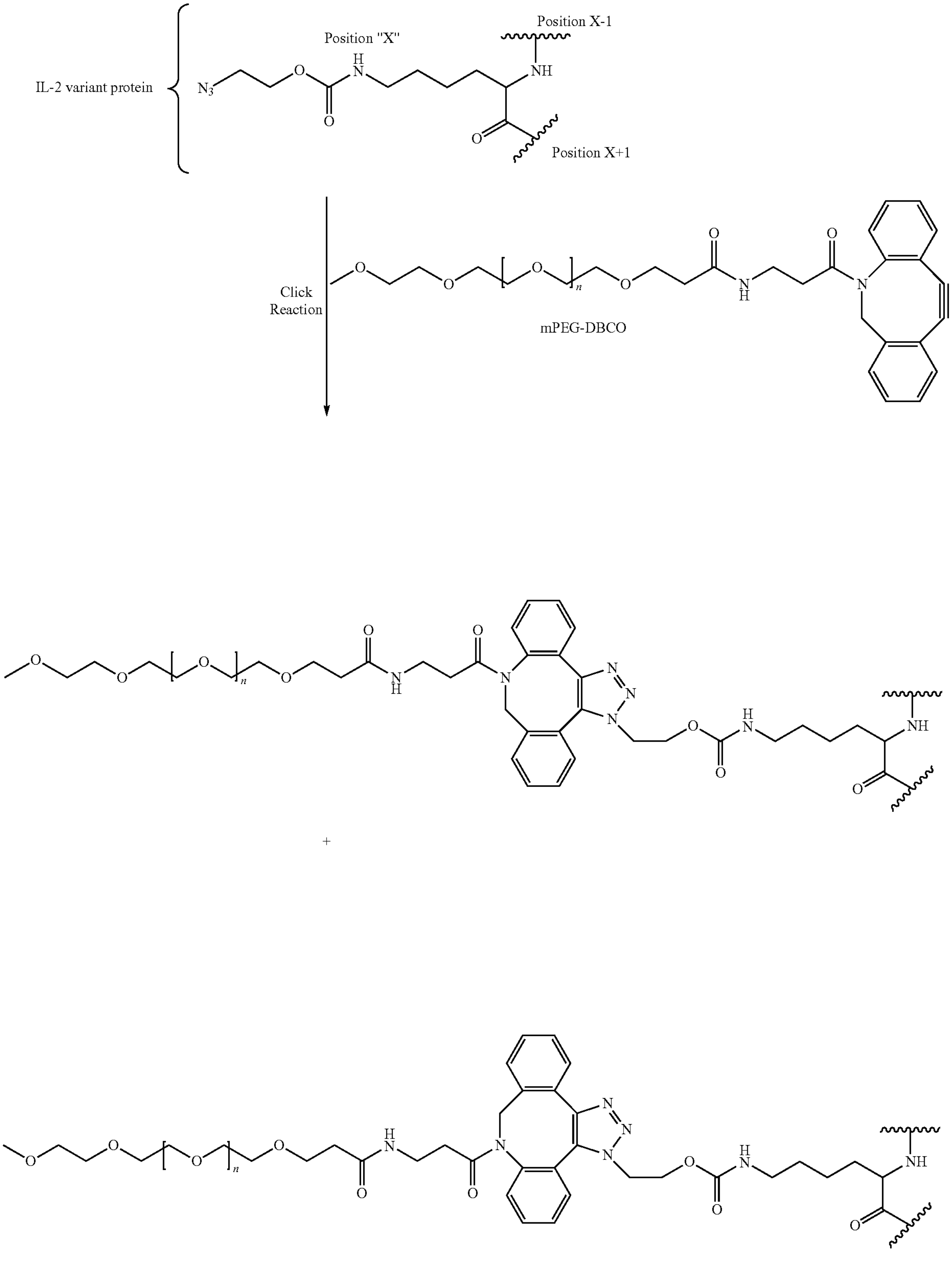
IL-2 Azk_PEG variant proteins Scheme 2. Exemplary synthesis of AzK_PEG interleukin variants (wherein n indicates the number of repeating PEG units). A mixture of regioisomers may be produced.

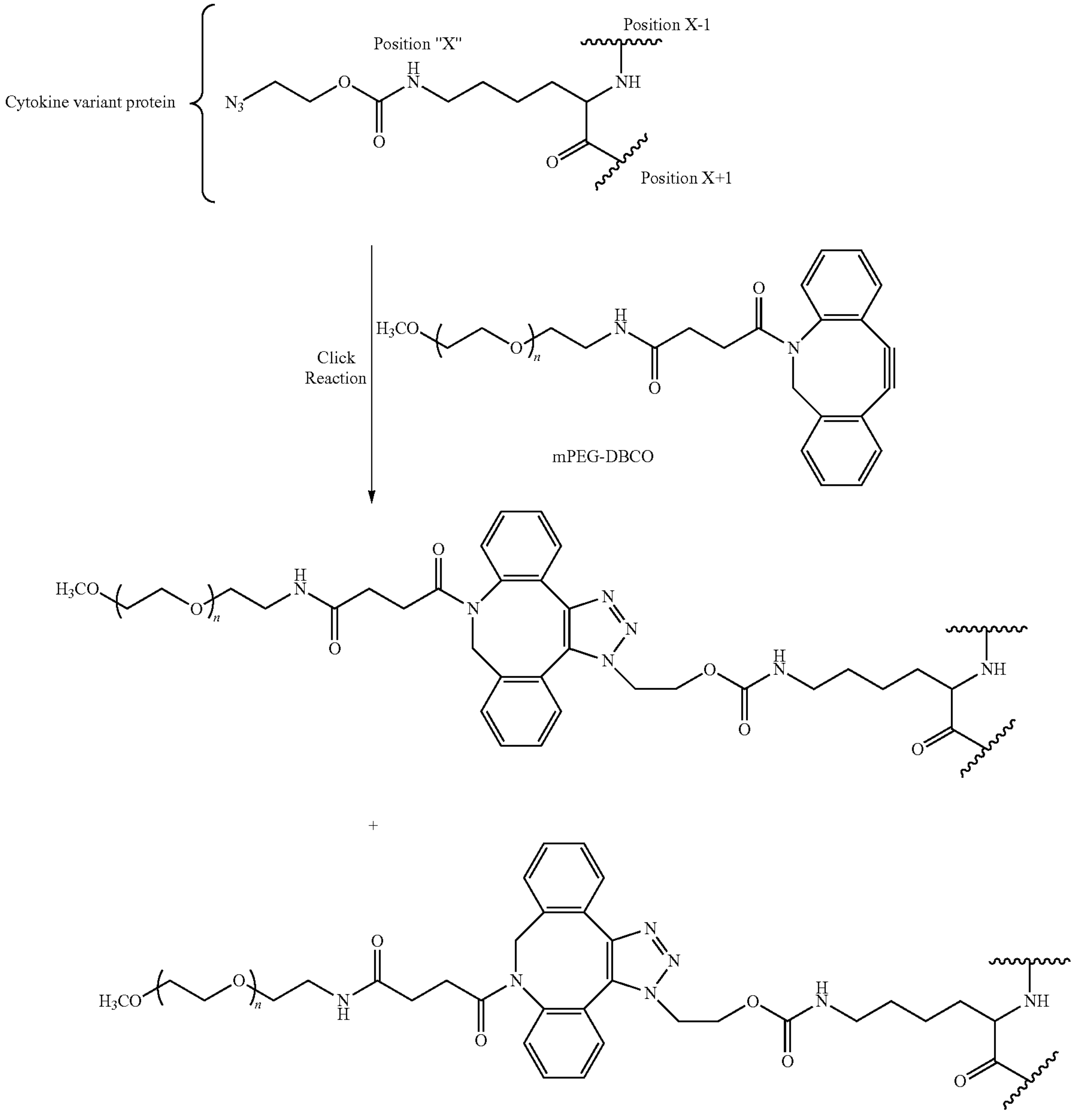

Cytokine Azk_L1_PEG variant proteins

The IL-2 conjugates were screened for functional activity at Discoverx (Fremont CA) using the PathHunter IL-2 Cytokine Receptor assay. This assay uses recombinant human U2OS cell line that expresses the IL-2 receptor β (IL-2Rβ) and γ (IL-2Rγ) subunits, each fused to half of the split reporter enzyme β-galactosidase. A second cell line has been further engineered to express the IL-2Rα subunit. Parallel testing with these two cell lines allows assessment of variant activation of the IL-2 receptor αβγ as well as the basal βγ complex. IL-2 agonist activity on the IL-2 βγ receptor complex stimulates receptor dimerization and reporter β-galactosidase reconstitution that results in a chemiluminescent signal. The assay was run in agonist mode to determine the $EC_{50}$ of each test article, and comparison of dose-response curve profiles between IL2Rα positive and negative cell types allows determination of the contribution of IL2Rα to the observed activity.

TABLE 1 shows the EC50 data for IL-2 receptor agonism in cell-based screen for 10 kD (except where noted) PEGylated IL-2 conjugates.

| Site | βγ EC50 (nM) | αβγ EC50 (nM) | βγ/αβγ ratio |
|---|---|---|---|
| Native | 1.68 | 0.074 | 23 |
| Ideal | 1.68 | 1.68 | 1 |

TABLE 1-continued shows the EC50 data for IL-2 receptor agonism in cell-based screen for 10 kD (except where noted) PEGylated IL-2 conjugates.

| Site | βγ EC50 (nM) | αβγ EC50 (nM) | βγ/αβγ ratio |
|---|---|---|---|
| K35 | 6.75 | 0.15 | 45 |
| F42 | 6.09 | 0.515 | 12 |
| K43 | 9.84 | 0.131 | 75 |
| E62 | 3 | 1.5 | 2 |
| P65* | 23.8 | 4.44 | 5 |
| R38 | 4.16 | 0.165 | 25 |
| T41 | 6.37 | 0.0489 | 130 |
| E68 | 7.70 | 0.0893 | 86 |
| Y45* | 9.06 | 0.110 | 83 |
| V69* | 9.99 | 0.083 | 121 |

*Indicates a 30 kD PEGylated IL-2 conjugate.

Biochemical Interactions of PEGylated IL-2 with Human IL-2 Receptor Subunits

The kinetics of PEGylated IL-2 compound interactions with human IL-2 receptor subunits were measured using Surface Plasmon Resonance (SPR) at Biosensor Tools LLC (Salt Lake City, UT). For these studies, human IgG1 Fc-fused IL-2 Ra (Sino Biological #10165-H02H) and R (Sino Biological #10696-H02H) extracellular domains were captured on the surface of a Biacore Protein A-coated CM4 sensor chip. These surfaces were probed in duplicate, with two-fold dilution series starting at 2 μM of either native IL-2 (wild-type IL-2; Thermo #PHC0021), P65_30kD, P65_5kD, E62_30kD, or E62_5kD using a Biacore 2000 SPR instrument. Test samples were injected for 60 seconds to allow measurement of association, followed by buffer only (wash) for 30 s to measure dissociation. Response units (RU, Y-axis) are plotted versus time (s, X-axis).

To evaluate the effect of IL-2 receptor α subunit on IL-2 binding to β, α was captured in about two-fold excess relative to β. To these surfaces, native IL-2 (wild-type IL-2), P65_30kD, P65_5kD, E62_30kD, or E62_5kD were applied in a three-fold dilution series beginning at 2.5 μM. The binding data were fit to a 1:1 interaction model that included a bulk shift, and the extracted kinetic parameters are summarized in Table 2A and Table 2B. As shown in Table 2A and Table 2B, as well as FIGS. 4A-4B, small PEGs abrogate IL2R alpha engagement, but have less non-specific effect on IL2R beta engagement.

TABLE 2A

Kinetic parameters for IL-2 variant interactions with individual IL-2 receptor subunit surfaces IL-2 receptor α surface

| | $k_a$ ($M^{-1}s^{-1}$) | $k_d$ ($s^{-1}$) | $K_D$ (μM) |
|---|---|---|---|
| IL-2 native | 4.5 ± 0.3 × $10^7$ | 0.410 ± 0.01 | 0.009 ± 0.002 |
| P65_30 kD | 114 ± 36 × $10^7$ | 0.018 ± 0.008 | 158 ± 21 |
| P65_5 kD | 797 ± 226 × $10^7$ | 0.033 ± 0.004 | 42 ± 7 |
| E62_30 kD | 333 ± 88 × $10^7$ | 0.050 ± 0.01 | 162 ± 07 |
| E62_5 kD | 1010 ± 41 × $10^7$ | 0.035 ± 0.002 | 34.4 ± 0.3 |

TABLE 2B

Kinetic parameters for IL-2 variant interactions with individual IL-2 receptor subunit surfaces IL-2 receptor β surface

| | $k_a$ ($M^{-1}s^{-1}$) | $k_d$ ($s^{-1}$) | $K_D$ (μM) |
|---|---|---|---|
| IL-2 native | 1.3 ± 0.2 × $10^6$ | 0.185 ± 0.009 | 0.145 ± 0.005 |
| P65_30 kD | 1.8 ± 0.2 × $10^5$ | 0.370 ± 0.01 | 2.09 ± 0.09 |
| P65_5 kD | 9.0 ± 0.4 × $10^5$ | 0.270 ± 0.01 | 0.305 ± 0.002 |
| E62_30 kD | 1.8 ± 0.4 × $10^5$ | 0.208 ± 0.006 | 1.14 ± 0.01 |
| E62_5 kD | 6.6 ± 0.8 × $10^5$ | 0.281 ± 0.004 | 0.428 ± 0.00 |

Figure 4A:
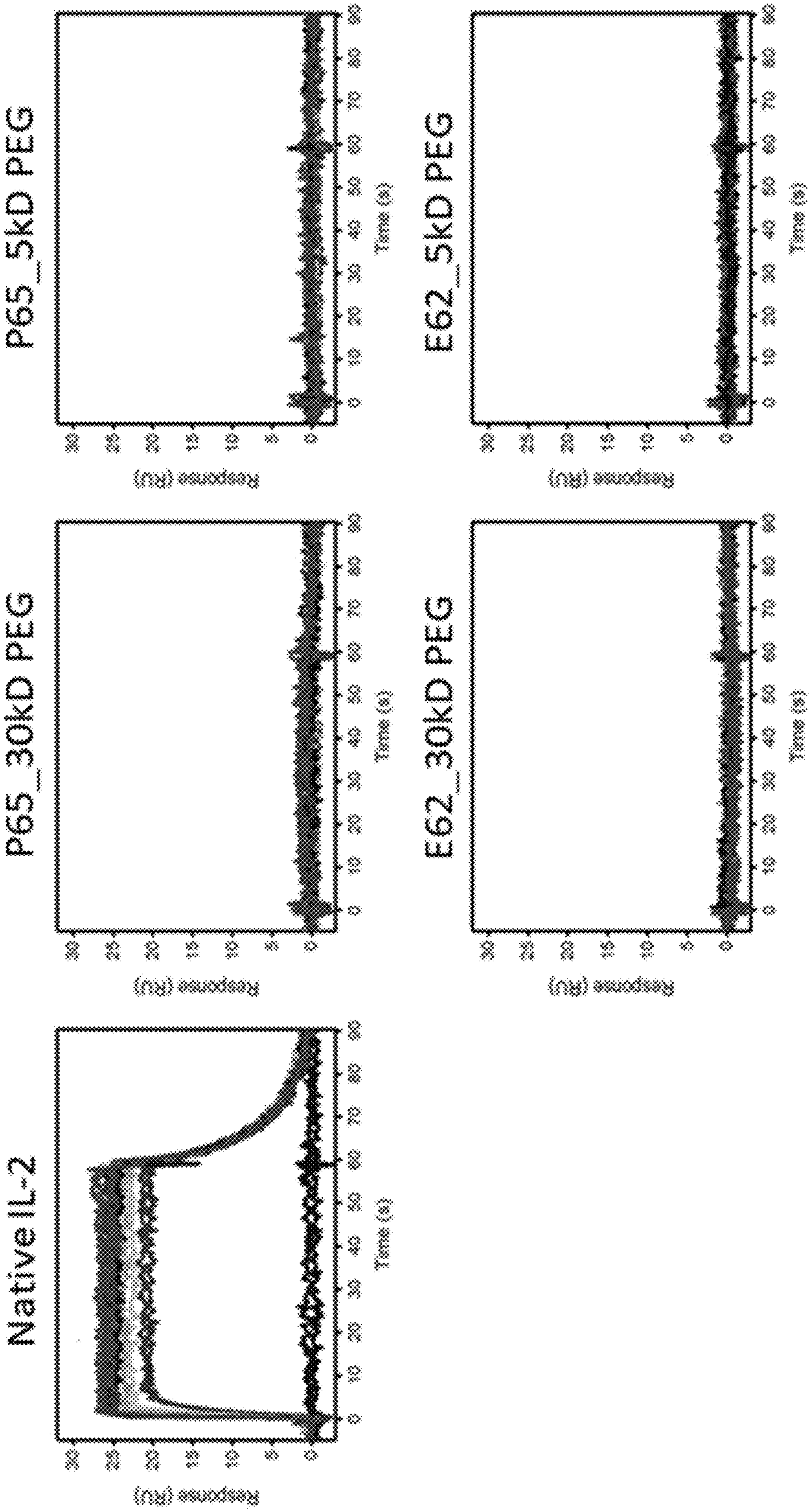
FIGS. 4A-FIG. 4C show surface plasmon resonance (SPR) analysis of native IL-2, P65_30kD, P65_5kD, E62_30kD, E62_5kD, and F42_30kD PEG conjugates.
Figure 4B:
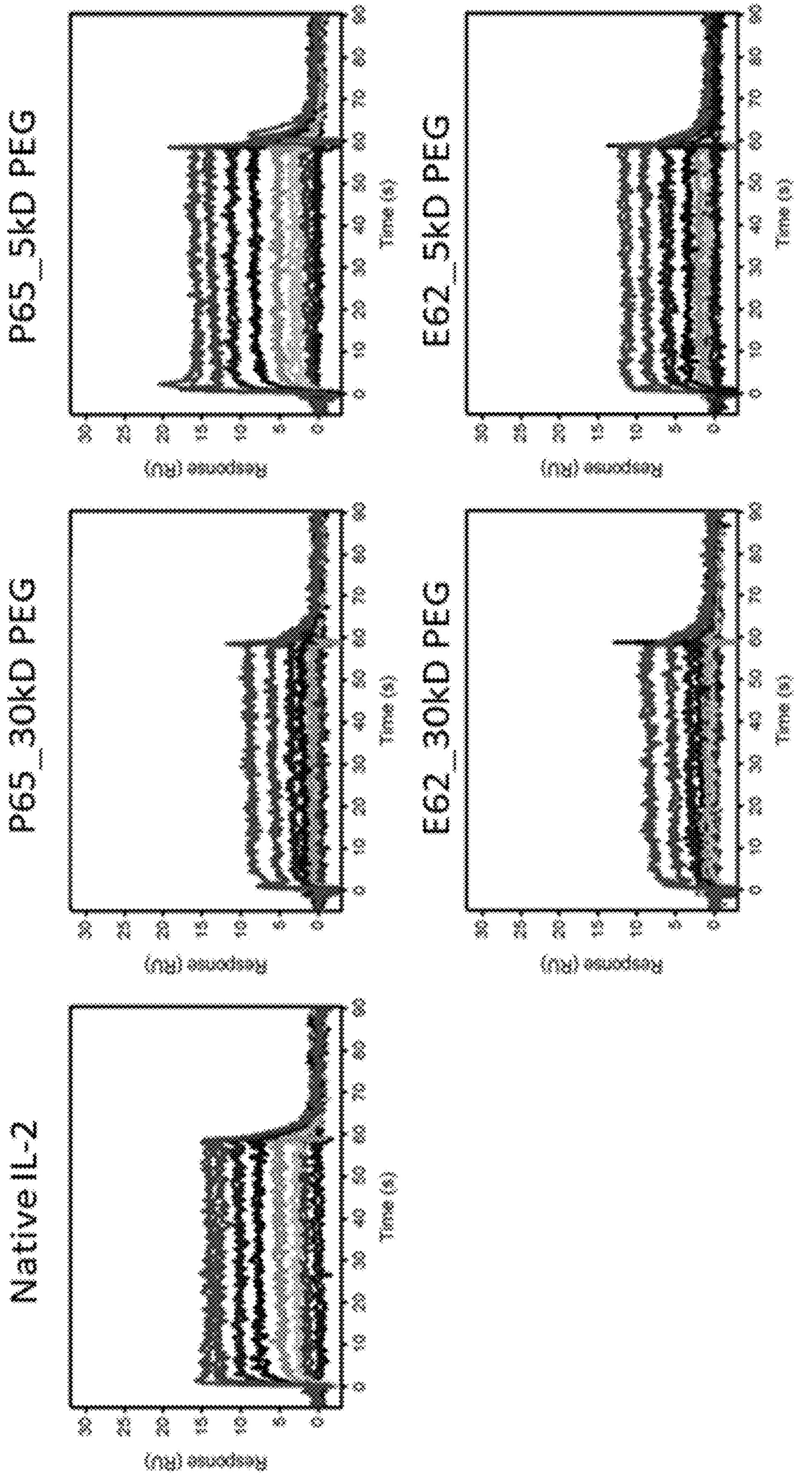
Figure 4C:
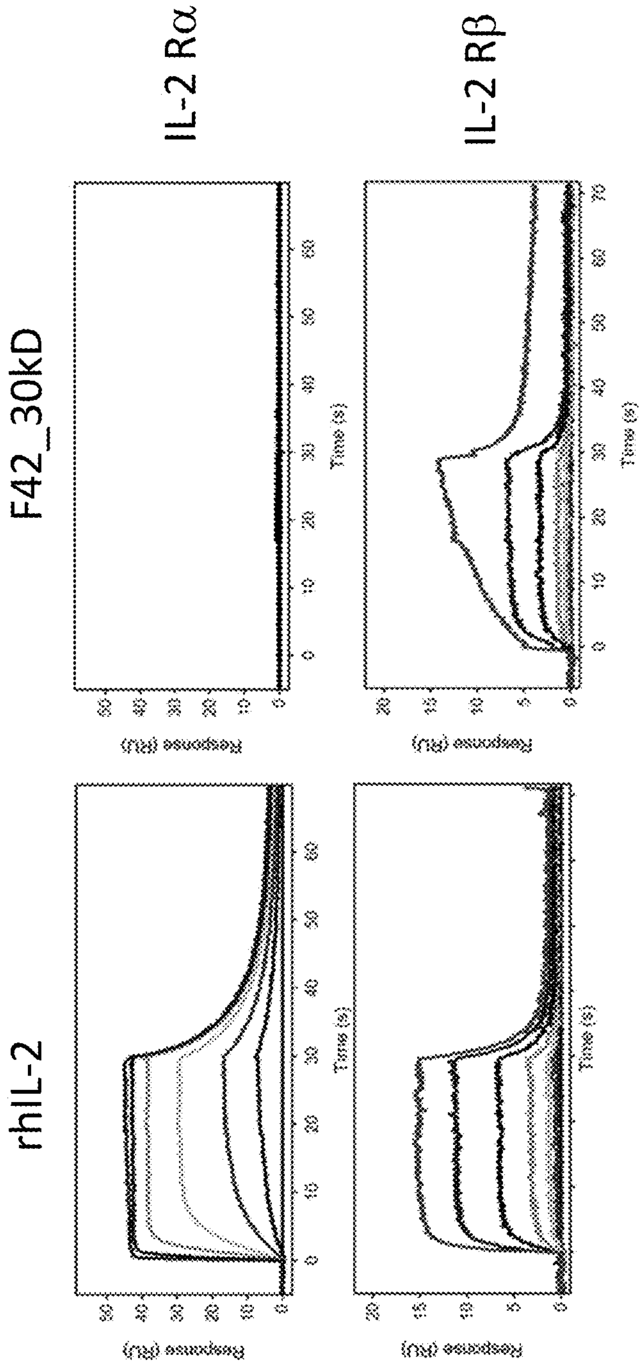

On sensor surfaces containing immobilized IL-2Rα, native IL-2 showed rapid association and slow dissociation kinetics, demonstrating high-affinity binding (FIG. 4A). In contrast, neither P65_30kD nor E62_30kD interact with the IL-2Rα surface even at the highest test concentration of 2 μM (FIG. 4A). Similarly, F42_30kD did not interact with the IL-2 IL-2Rα surface (FIG. 4C). Surfaces containing immobilized IL-2 RR showed comparable association and dissociation responses with both native IL-2 (wild-type IL-2) and IL-2 P65_30kD (FIG. 4B), as well as F42_30kD (FIG. 4C). The modest difference in $K_D$ observed between compounds for the R subunit is due to the decreased on-rate of IL-2 P65_30kD relative to native IL-2, expected from the change in the hydrodynamic radius of this pegylated compound (lower diffusion coefficient) as well as non-specific shielding effects of the large PEG moiety on distant binding surfaces. These results suggest that P65_30kD, E62_30kD, and F42_30kD are defective in IL-2Rα interactions while largely retaining binding to IL-2Rβ.

Ex-Vivo Immune Response Profiling of IL-2 Compounds in Primary Human Leukocyte Reduction System (LRS)-Derived PBMC Samples To determine how the differential receptor specificity of IL-2 P65_30kD, K64_30kD, K43_30kD, K35_30kD, and F42_30kD, effects activation of primary immune cell subpopulations, concentration-response profiling of lymphocyte activation in human LRS-derived peripheral blood mononuclear cell (PBMC) samples were performed using multicolor flow cytometry. These studies were performed at PrimityBio LLC (Fremont, CA). Fresh LRS-derived samples were treated with native IL-2, L-2 P65_30kD, K64_30kD, K43_30kD, K35_30kD, and F42_30kD in 5-fold dilution series starting with a top concentration of 30 μg/mL. After a 45 min incubation, samples were fixed and stained with antibodies to detect the phosphorylated form of the transcription factor STAT5 (pSTAT5), a marker of upstream engagement and activation of IL-2 receptor signaling complexes, and a panel of surface markers to follow pSTAT5 formation in specific Tcell and natural killer (NK) cell subpopulations. Staining panel for flow cytometry study of LRS-derived PBMC samples include markers for Effector T cells (Teff: CD3+, CD4+, CD8+, CD127+), NK cells (CD3-, CD16+), and Regulatory T cells (Treg: CD3+, CD4+, CD8-, IL-2Rα+, CD127-1).

Figure 5A:
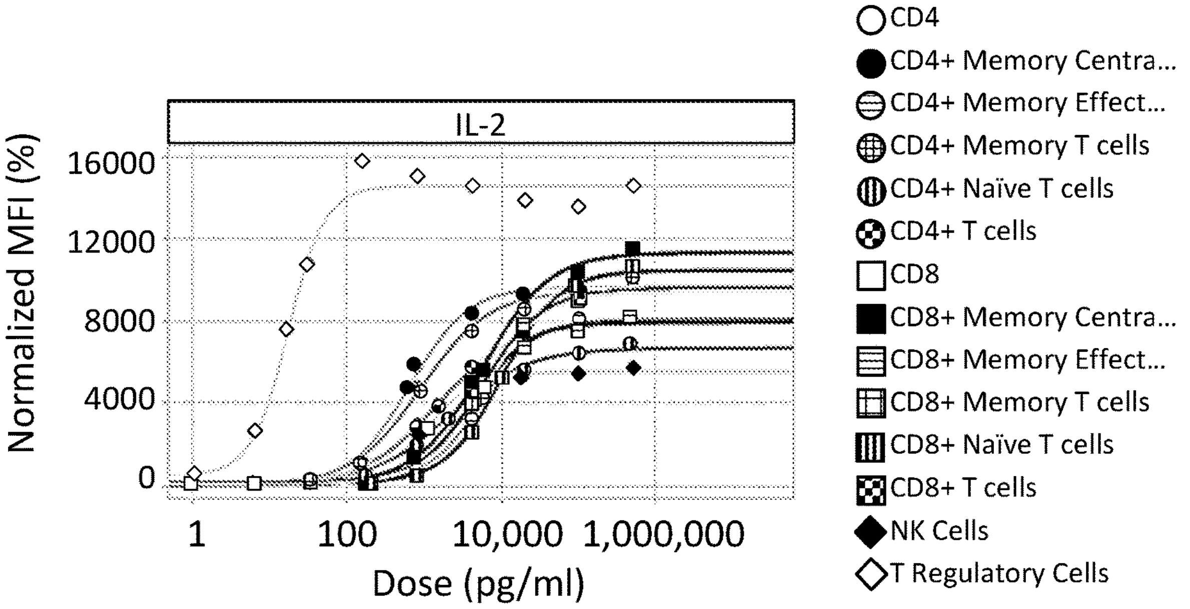
FIGS. 5A-FIG. 5F show exemplary IL-2 variant dose response curves for pSTAT5 signaling in human LRS primary cell populations.
Figure 5B:
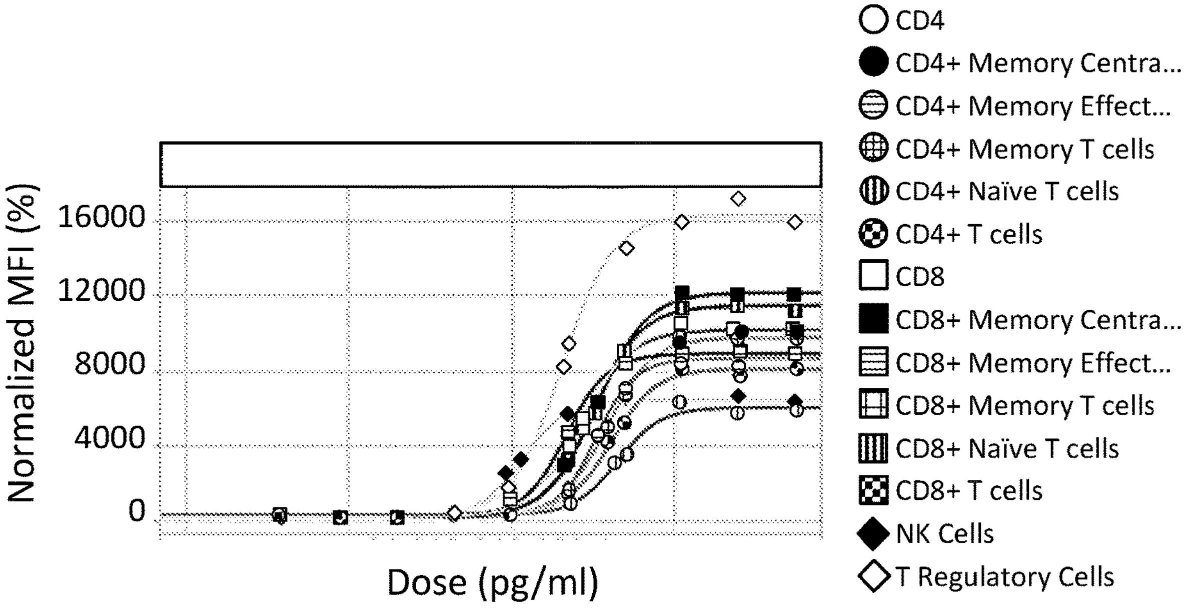
Figure 5C:
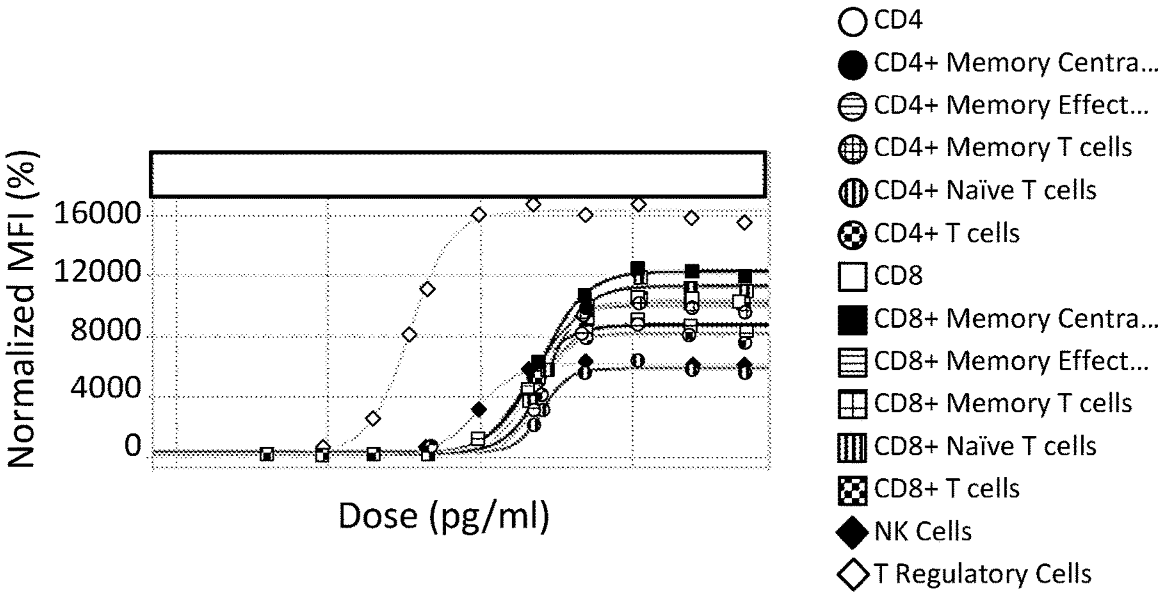
Figure 5D:
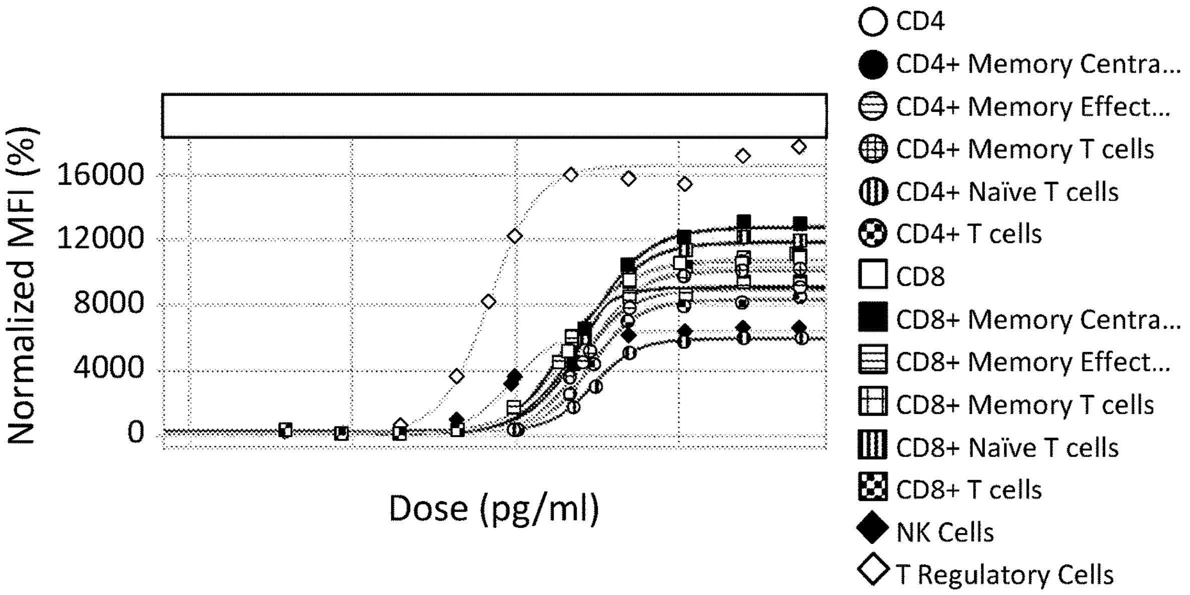
Figure 5E:
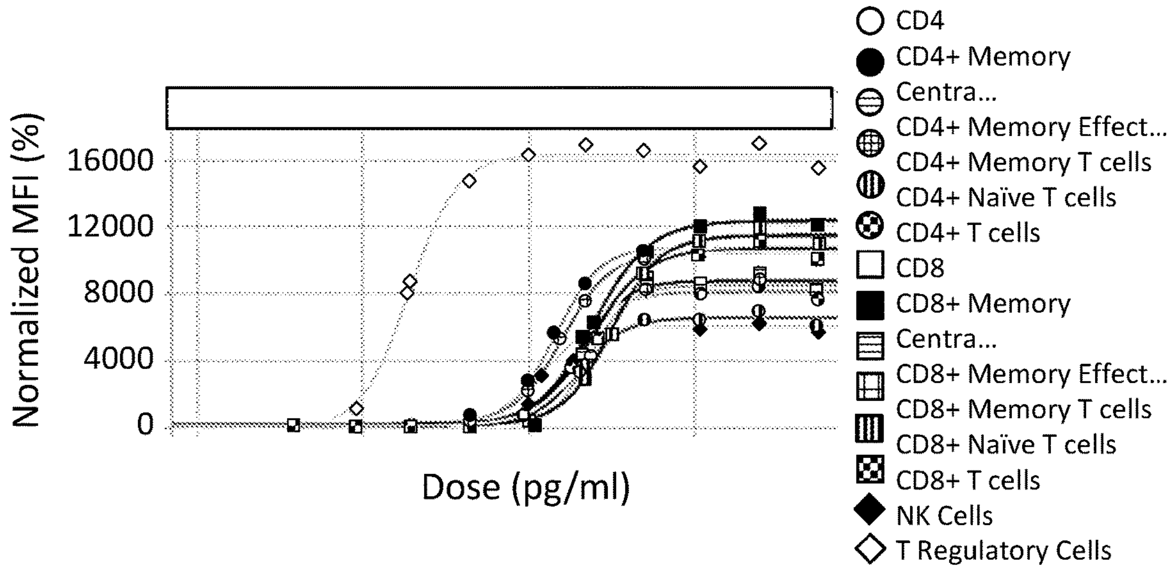
Figure 5F:
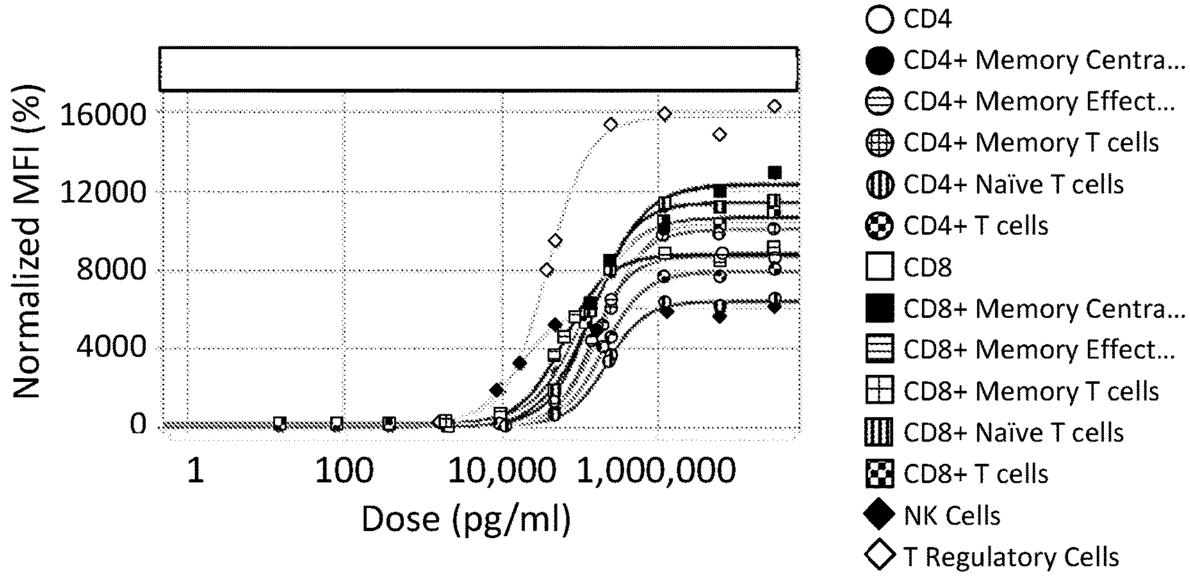

Flow cytometry data were analyzed for activation of different T and NK cell subsets in concentration-response mode, reading pSTAT5 accumulation after treatment with native IL-2 (FIGS. 5A and 5G), E62_30kD (FIG. 5H), P65_30kD (FIGS. 5B and 5I), K64_30kD (FIG. 5C), K43_30kD (FIG. 5D), K35_kDa (FIG. 5E), and F42_30 kDa (FIG. 5F). As a result of Treg-specific expression of IL-2 Rα, native IL-2 demonstrated an increased potency for pSTAT5 stimulation in Tregs compared with CD8 Teff and NK cells. Compared to the native compound, the PEGylated variants shown in FIG. 5B-5F demonstrate modestly-reduced potencies on CD8 Tcells and NK cell populations, but show differential reduction in potency in IL-2 Ra expressing Treg cells with respect to native IL-2.

Table 3 provides the dose response EC50 for pSTAT5 signaling (EC50) in human LRS samples or CTLL-2 proliferation treated with indicated IL-2 variant.

TABLE 3

Dose response EC50 for pSTAT5 signaling (EC50) in human LRS samples or CTLL-2 proliferation treated with indicated IL-2 variant

| treatment | NK Cells | Treg Cells | CD8 + T Cells | CD8/ Treg ratio | CTLL-2 |
|---|---|---|---|---|---|
| Native IL-2 | 5150.5 | 62.5 | 25703.5 | 411.3 | 846 |
| E62_30 kD | 12834 | 37213 | 66644 | 1.8 | 398,012 |
| E62_5 kD | 5327.5 | 18146 | 41552.5 | 2.3 | 275,590 |
| E62K | 10305 | 11086 | 64037 | 5.8 | 58,213 |
| P65_30 kD | 15741 | 40740.5 | 113638 | 2.8 | 677,198 |
| P65_5 kD | 1920 | 6324.5 | 13769.5 | 2.2 | 194,924 |
| K35_30 kD | 14021 | 358 | 63023 | 176.0 | N.D. |
| F42_30 kD | 16397 | 36856 | 107944 | 2.9 | 123,936 |
| K43_30 kD | 9004 | 4797 | 50504 | 10.5 | N.D. |

The EC50 values (pg/mL) was calculated from dose response curves generated from MFI plots.

Example 3

PEG and Residue Substitution Contribute to No-Alpha Pharmacology

To determine whether the PEG and residue substitution impacted the no-alpha pharmacology of IL-2 E62, concentration-response profiling of lymphocyte activation in human LRS-derived peripheral blood mononuclear cell (PBMC) samples were performed using multi-color flow cytometry. These studies were performed at PrimityBio LLC (Fremont, CA). Fresh LRS-derived samples were treated with native IL-2, E62K, or E62_30kD in 5-fold dilution series starting with a top concentration of 30 μg/mL. After a 45 min incubation, samples were fixed and stained with antibodies to detect the phosphorylated form of the transcription factor STAT5 (pSTAT5), a marker of upstream engagement and activation of IL-2 receptor signaling complexes, and a panel of surface markers to follow pSTAT5 formation in specific Tcell and natural killer (NK) cell subpopulations. Staining panel for flow cytometry study of LRS-derived PBMC samples include markers CD4, CD4+ memory central, CD4+ memory effect, CD4+ memory T cells, CD4+ Naive T cells, CD4+ T cells, CD8, CD8+ memory central, CD8+ memory effect, CD8+ memory T cells, CD8+ Naive T cells, CD8+ T cells, NK cells, and T regulatory cells.

Figure 6A:
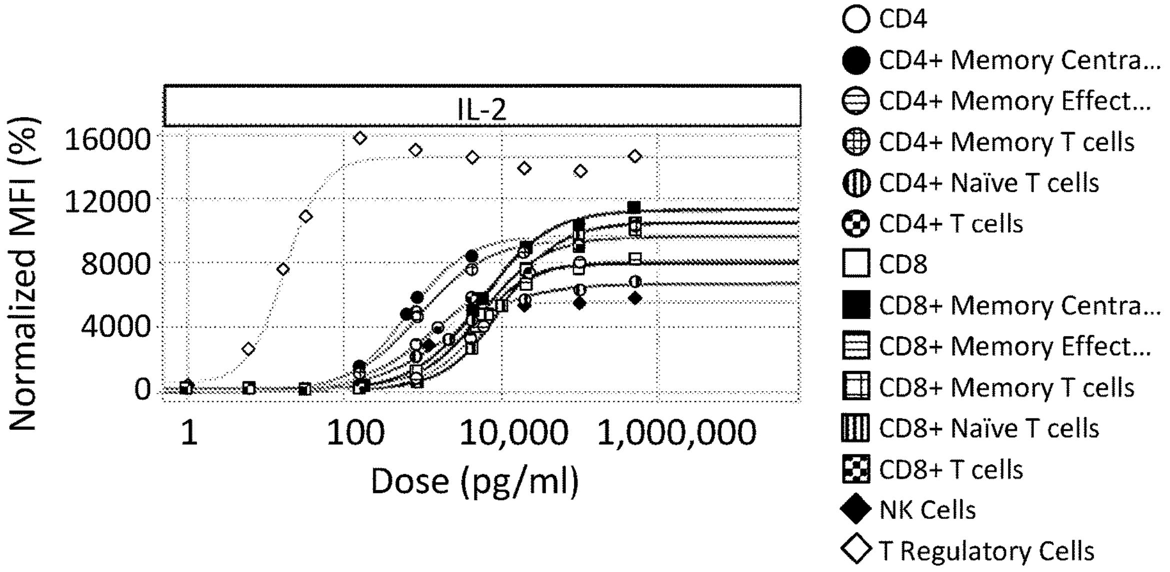
FIGS. 6A-C show that PEG and residue substitution contribute to no-alpha pharmacology of IL-2 variants.
Figure 6B:
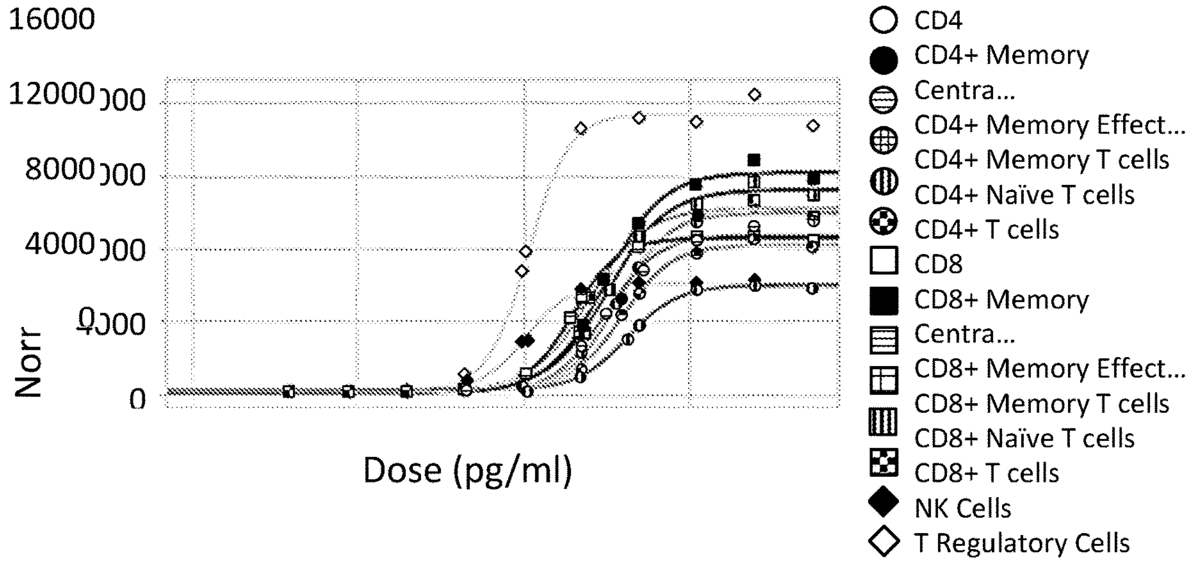
Figure 6C:
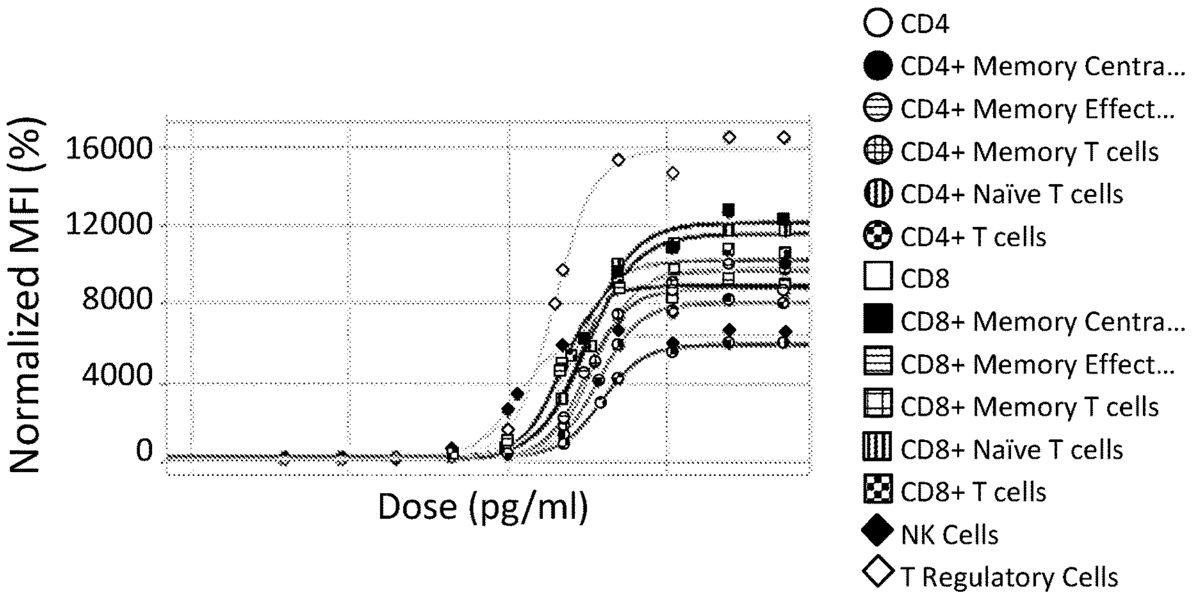

Flow cytometry data were analyzed for activation of different T and NK cell subsets in IL-2 (FIG. 6A), E62K (FIG. 6B), or E62_30kD (FIG. 6C). These results demonstrate that the amino acid residue substitution at position 62 as well as the AzK-PEGylation at the modified position can contribute to reduction of the IL-2 Ra engagement and resulting differential potency on primary lymphocytes that express these receptors.

TABLE 4

Dose response EC50 for pSTAT5 signaling (EC50) in human LRS samples proliferation treated with indicated IL-2 variant

| treatment | Treg Cells | CD8 + T Cells | CD8/Treg ratio |
|---|---|---|---|
| Native IL-2 | 17 | 6092 | 358 |
| E62_30 kD | 33580 | 64134 | 1.9 |
| E62K | 11086 | 64037 | 5.8 |

Example 4

No-Alpha Pharmacology is PEG Size Independent

The IL-2 conjugates were screened for functional activity at Discoverx (Fremont CA) using the PathHunter IL-2 Cytokine Receptor assay. This assay uses recombinant human U20S cell line that expresses the IL-2 receptor β (IL-2Rβ) and γ (IL-2Rγ) subunits, each fused to half of the split reporter enzyme β-galactosidase. A second cell line has been further engineered to express the IL-2Rα subunit. Parallel testing with these two cell lines allows assessment of variant activation of the IL-2 receptor αβγ as well as the basal βγ complex. IL-2 agonist activity on the IL-2 βγ receptor complex stimulates receptor dimerization and reporter β-galactosidase reconstitution that results in a chemiluminescent signal. The assay was run in agonist mode to determine the $EC_{50}$ of each test article, and comparison of dose-response curve profiles between IL2Rα positive and negative cell types allows determination of the contribution of IL2Rα to the observed activity.

Figure 7:
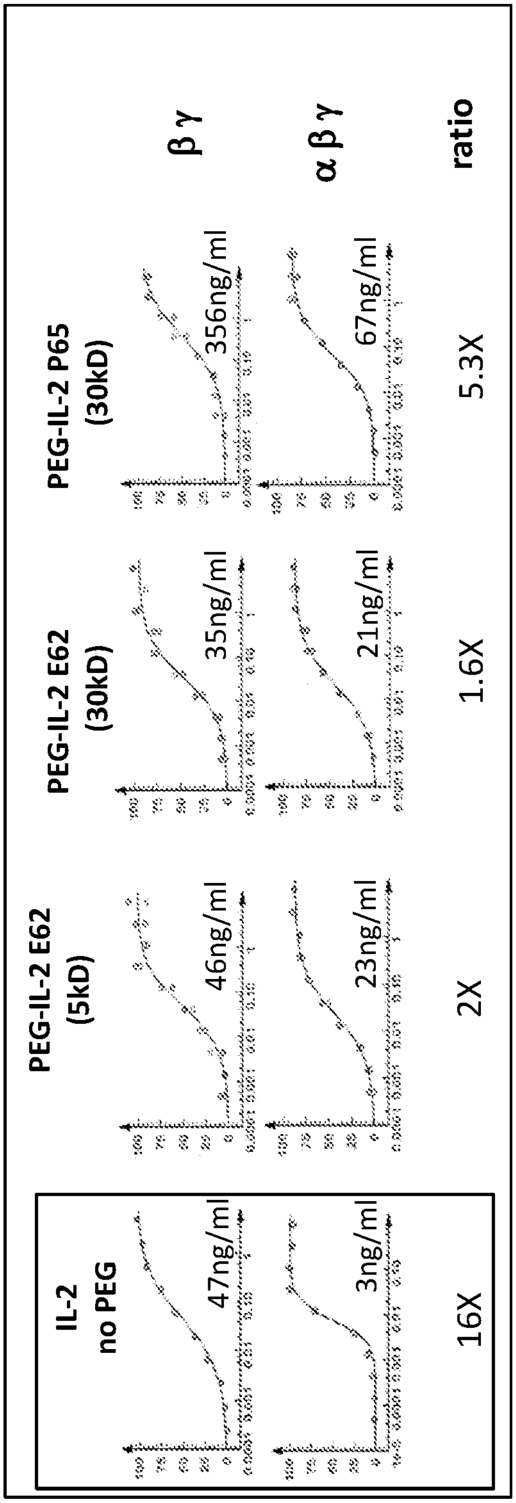
FIG. 7 shows that no-alpha pharmacology of IL-2 variants is PEG size independent.

FIG. 7 shows the observed potencies of the compounds PEGylated with 5kD and 30kD PEG were similar on cells expressing IL-2 Ra as well as those expressing only IL-2 Roy. These results suggest that the reduction in IL-2 Ra engagement by these compounds is insensitive to the molecular weight of the PEG conjugate.

Example 5

PK/PD Studies in Naïve (E3826-U1704) and B16-F10 Tumor-Bearing (E3826-U1803) C57BL/6 mice The study designs are summarized in Tables 5 and 6, wherein the dose was calculated by reference to the mass of the protein component not including the mass of the PEG moiety. Terminal blood samples were collected via cardiac puncture at the points indicated. Study E3826-U1704, included 13 time points (0.13, 0.25, 0.5, 1, 2, 4, 8, 12, 24, 48, 72, 96 and 120 h) sacrificing 3 mice per each time point and study E3826-U1803 included 9 time points (2, 8, 12, 24, 48, 72, 120, 168, and 240 h) sacrificing 4-7 mice per each time point. Plasma and blood cells (in both studies) and tumors in study E3826-U1803 were collected for PK and PD analyses.

Bioanalysis of plasma samples was performed using a qualified human IL-2 ELISA assay (Abcam, Cambridge, UK). Concentrations of Aldesleukin, E62_30kD and P65_30kD and the internal standard in samples derived from plasma were determined using an ELISA assay. PK data analysis was performed at NW Solutions (Seattle, WA). The PK data were imported into Phoenix WinNonlin v6.4 (Certara/Pharsight, Princeton, NJ) for analysis. The group mean plasma concentration versus time data were analyzed with noncompartmental methods using an IV bolus administration model.

TABLE 5

| PK/PD Study No. E3826-U1704—Control and Test Treatment groups in Naïve C57/BL6 Mice | | | | |
|---|---|---|---|---|
| Treatment | Dose*(mg/Kg) | Route, Schedule | Time Points | N |
| Control | 0 | IV, single dose | 13 | 3 |
| Aldesleukin | 0.3 | IV, single dose | 13 | 3 |
| P65_30 kD | 0.3 | IV, single dose | 13 | 3 |
| E62_30 kD | 0.3 | IV, single dose | 13 | 3 |

*Dose refers to P65 30 kD IL-2 polypeptide amount, wherein the dose was calculated by reference to the mass of the protein component not including the mass of the PEG moiety

TABLE 6

| PK/PD Study No. E3826-U1803-Control and Test Treatment groups-B16F-10 Melanoma Tumor-Bearing Mice (wherein the dose was calculated by reference to the mass of the protein component not including the mass of the PEG moiety) | | | | |
|---|---|---|---|---|
| Treatment | Dose (mg/kg) | Route, Schedule | Time Point | N |
| None (pre-dose) | 0 mg/kg | None | 1 | 6 |
| Vehicle Control | 0 mg/kg | IV, single dose | 9 | 3 |
| P65_30kD | 1 mg/kg | IV, single dose | 9 | 4 |
| P65_30kD | 3 mg/kg | IV, single dose | 9 | 4 |

Figure 8:
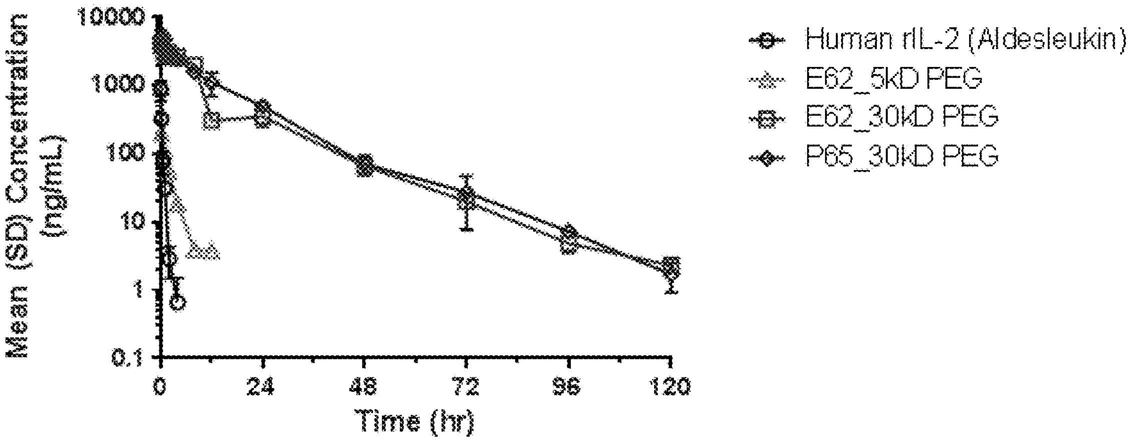
FIG. 8 shows the mean (±SD) plasma concentration versus time profiles following a single IV bolus dose of aldesleukin (IL-2), E62_5kD, E62_30 kD and P65_30 kD to C57BL/6 mice.

The plasma concentration profiles of P65_30 kD, E62_30 kD, E62_5kD and aldesleukin at 0.3 mg/kg are plotted in FIG. 8.

In study E3826-U1704, both P65_30 kD and E62_30 kD exhibits a superior PK profile relative to aldesleukin as summarized on Table 5. Following a single IV bolus dose of aldesleukin, the $T_{max}$ was observed at 0.03 h post-dose (the first measured timepoint after dosing) and mean plasma concentrations were measurable out to 4 h post-dose. After single IV bolus dosing of P65_30 kD and E62_30 kD, the Tmax was observed at 0.03 h post-dose and mean plasma concentrations were measurable out to 120 h post-dose (the last measured timepoint). In a separate study, after IV dosing of E62_5kD, the $T_{max}$ was observed at 0.133 hr post-dose and mean plasma concentrations were measurable out to 12 hr post-dose.

Exposure based on $C_{max}$ and $AUC_{0-t}$, was as follows: P65_30 kD>E62_30 kD>>E62_5kD> aldesleukin. E62_5kD with a smaller PEG had a PK profile closer to rIL-2. P65_30 kD exposure was 5.5 and 200 times higher than aldesleukin based on $C_{max}$ and $AUC_{0-t}$, respectively. In addition, P65_30 kD demonstrated 23-fold extended t½ (13.3 h vs. 0.57 h) and about 198-fold reduced CL (6.58 vs 1300 mL/h/Kg) compared to the aldesleukin. For both P65_30 kD and E62_30 kD, the distribution volume (82.4 and 92.3 mL/Kg respectively) was about 4.2 to 4.7-fold reduced relative to aldesleukin, and similar to the blood volume in a mouse (85 mL/Kg; [Boersen 2013]). This suggests that P65_30 kD and E62_30 kD are mostly distributed within systemic circulation.

TABLE 7

| P65 30kD PK Parameters in C57BL/6 Female Mice | | | | | |
|---|---|---|---|---|---|
| Parameter | Units | P65_30kD | E62_30kD | E62_5kD | Aldesleukin |
| $T_{max}$ | h | 0.030 | 0.030 | 0.133 | 0.030 |
| $C_{max}$ | ng/mL | 4,870 | 4,230 | 936 | 884 |
| $AUC_{0-t}$ | h*ng/mL | 45,600 | 37,100 | 798 | 229 |
| $R^2$ | | 0.992 | 0.986 | 0.851 | 0.900 |
| $AUC_{INF}$ | h*ng/mL | 45,600 | 37,100 | 807 | 230 |
| $t_{1/2}$ | h | 13.300 | 14.500 | 2.56 | 0.573 |
| CL | mL/h/Kg | 6.580 | 8.07 | 372 | 1300 |
| $V_{ss}$ | mL/Kg | 82.4 | 92.3 | 404 | 390 |

Note:

$R^2$ is the goodness-of-fit parameter for the terminal phase of each concentration versus time profile All parameters shown to 3 significant figures.

Example 6

Pharmacodynamics Observations in Peripheral Blood Compartment

Figure 9:
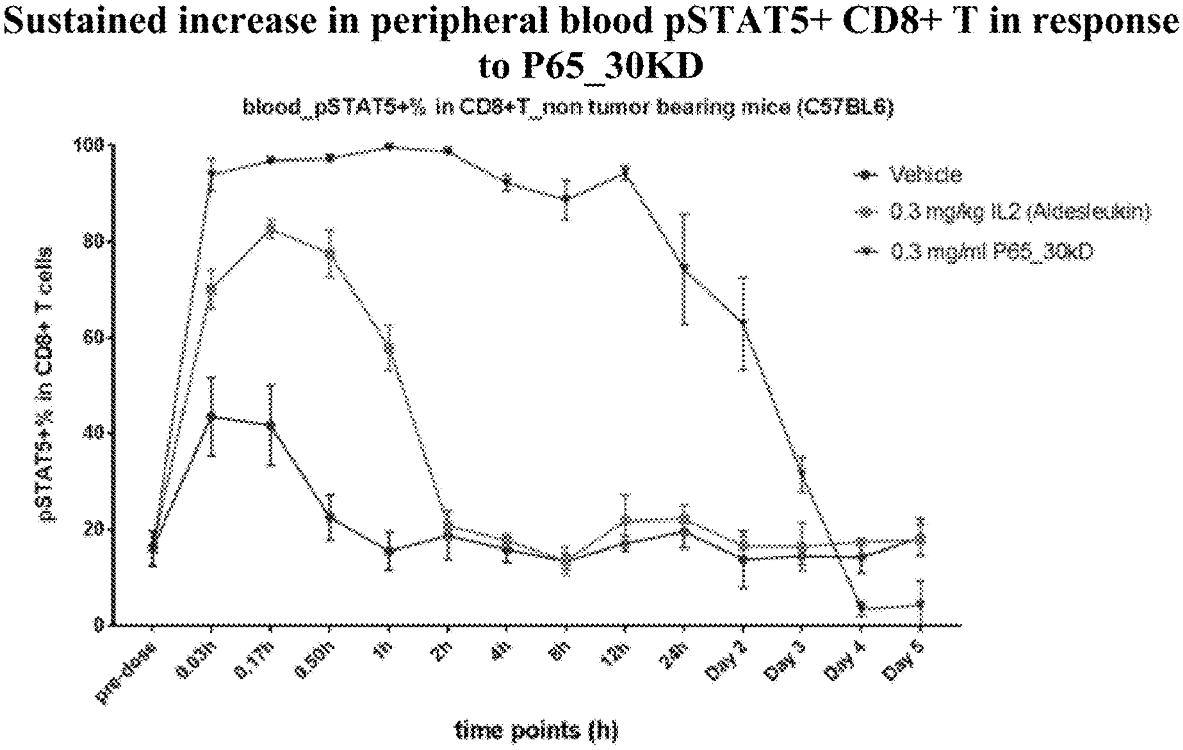
FIG. 9 shows percentage of pSTAT5+CD8+ T cells vs time cells in peripheral blood following treatment with a single IV bolus dose of P65_30 kD or aldesleukin to C57BL/6 mice.
Figure 10A:
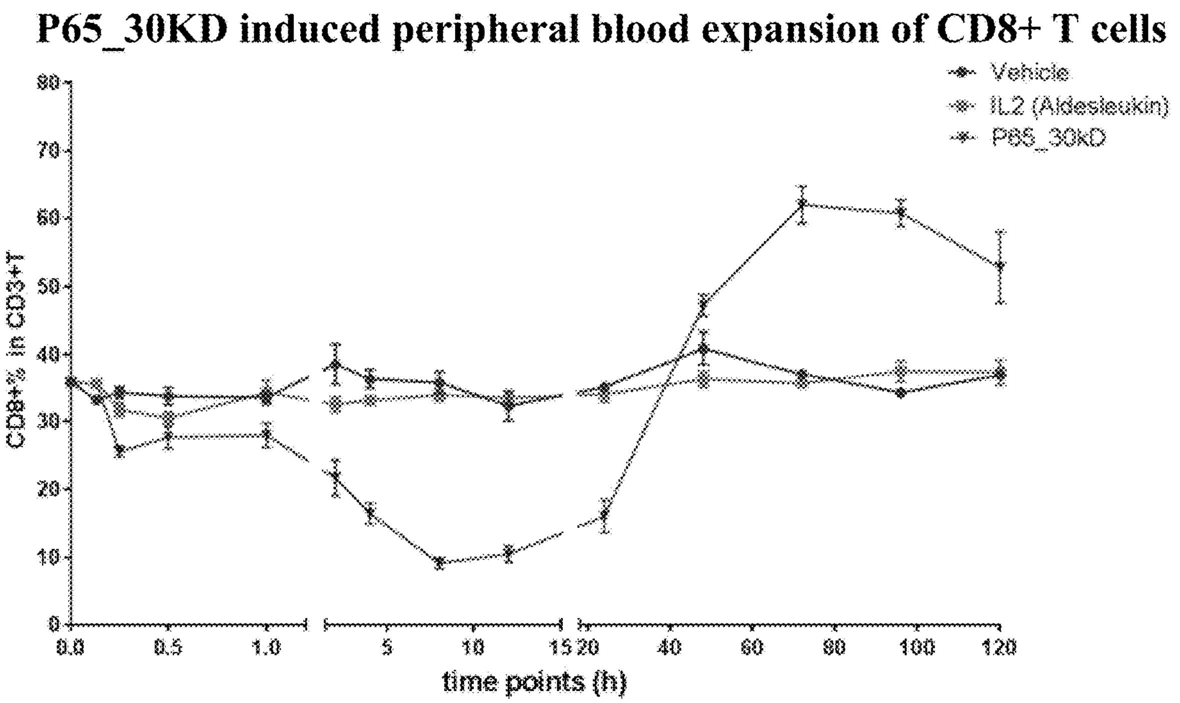
FIGS. 10A-FIG. 10C show percentage of CD8+ T cells (FIG. 10A), NK cells (FIG. 10B) and CD4+ Treg cells (FIG. 10C) in the PBMC population following treatment with a single IV bolus dose of P65_30 kD or aldesleukin (IL-2). Blood was drawn via cardiac puncture at the time points indicated and immune cell populations were assessed by flow cytometry. Each data point represents an average from 3 replicates at each time point, ±SEM.
Figure 10B:
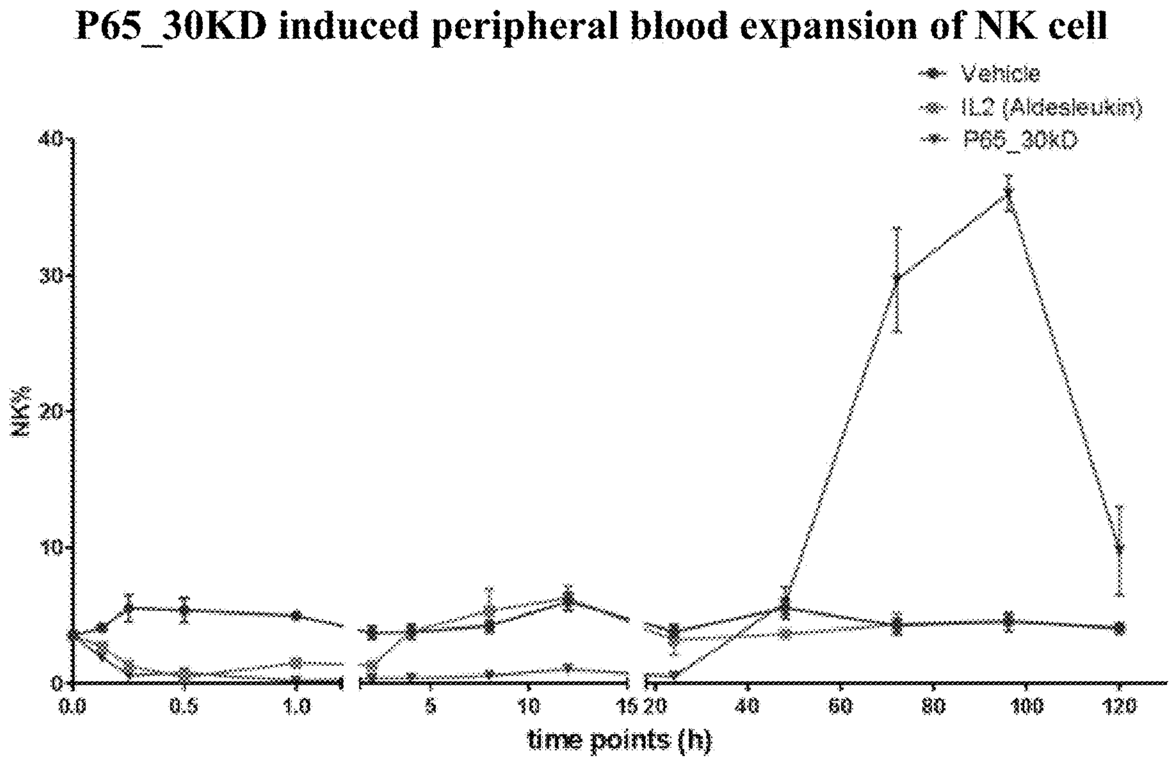
Figure 10C:
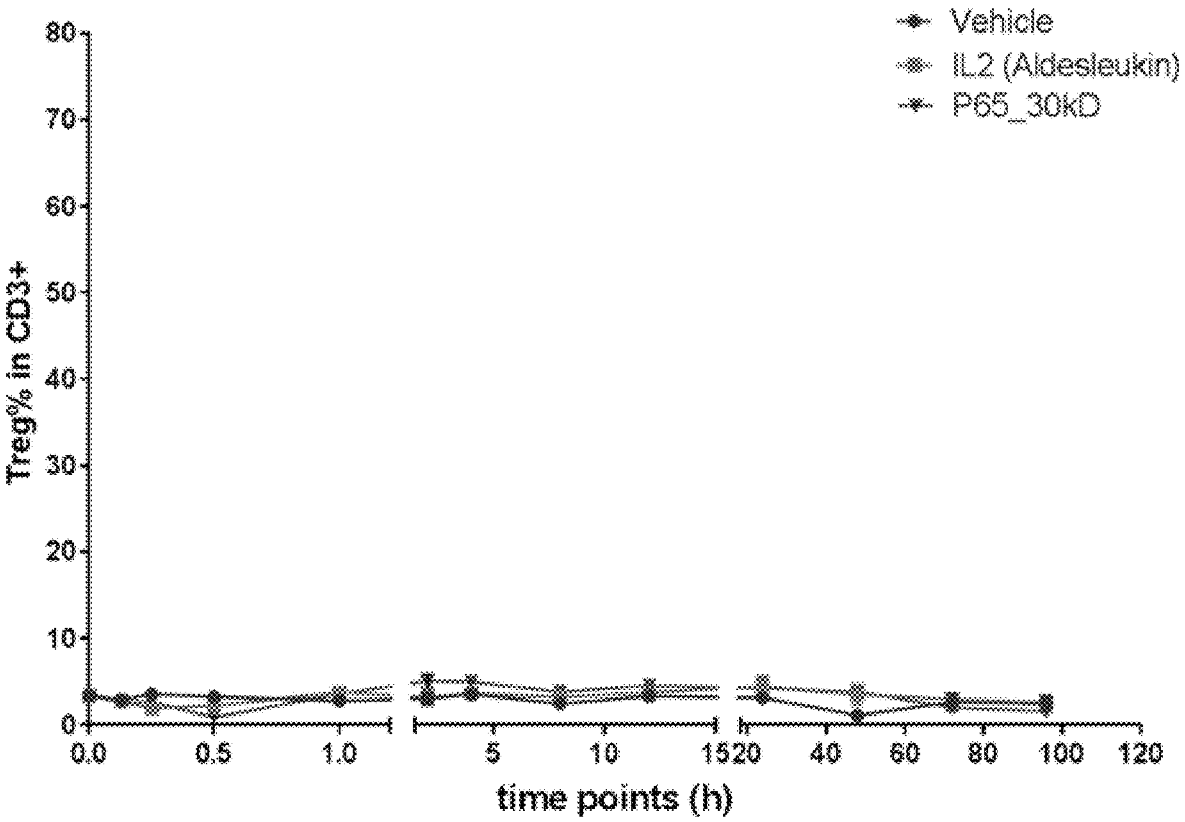

STAT5 phosphorylation and induction of cell proliferation (the early molecular marker Ki-67 and cell counts) was used as pharmacodynamics readouts to assess the pharmacological profile of P65_30kD relative to its pharmacokinetics. The pSTAT5 PD marker showed good correlation with PK for both P65_30kD and aldesleukin in CD8+ effector T cells (Table 7). Persistent elevation of pSTAT5 was observed in both NK and CD8+ T cells up to 72 h, and up to 24 h in Tregs. pSTAT5 induction returned to baseline after only 2 h in mice dosed with aldesleukin (FIG. 8). STAT5 phosphorylation translated into proliferative responses (72-120 hrs) of CD8+ effector T cells and NK cells but not with T regs (FIGS. 9A-9C), Phenotypic analysis of CD8+ effector T cells revealed substantial expansion of CD44+ memory cells within this population (FIGS. 10A-10B).

Pharmacodynamics Observations in Tumor Compartment in B16-F10 Tumor-Bearing (E3826-U1803) C57BL/6 Mice Table 8 shows the plasma and tumor drug concentration following a single dose of P65_30kD at 3 mg/kg in B16-F10 tumor-bearing mice, wherein the dose was calculated by reference to the mass of the protein component not including the mass of the PEG moiety. The tumor half-life was twice the plasma half-life (24.4 vs 12.6), indicating that the P65_30kD penetrates the tumor and is retained in the tumor. The tail end of the curves cross showing the plasma eliminates faster than the tumor (data not shown). The tumor: plasma AUC ratio was 9.7% and 8.4% for the 1 and 3 mg/kg doses respectively.

TABLE 8

| P65_30kD Plasma and Tumor PK Parameters B16-F10 tumor-bearing C57BL/6 Female Mice | | |
|---|---|---|
| | P65_30kD (3 mg/kg) | |
| Parameter | Plasma | Tumor |
| $T_{max}$ (II) | *2.00 | 8 |
| $C_{max}$ (ng/mL) | 40000 | 1550 |
| t1/2 (h) | 12.60 | 24.4 |

TABLE 8-continued

P65_30kD Plasma and Tumor PK Parameters
B16-F10 tumor-bearing C57BL/6 Female Mice

| Parameter | P65_30kD (3 mg/kg) Plasma | Tumor |
|---|---|---|
| $AUC_{0-t}$ (h*ng/mL) | 656,000 | 55200 |
| $R^2$ | 0.974 | 0.988 |
| $AUC_{INF}$ (h*ng/mL) | 656,000 | 55200 |

Figure 11A:
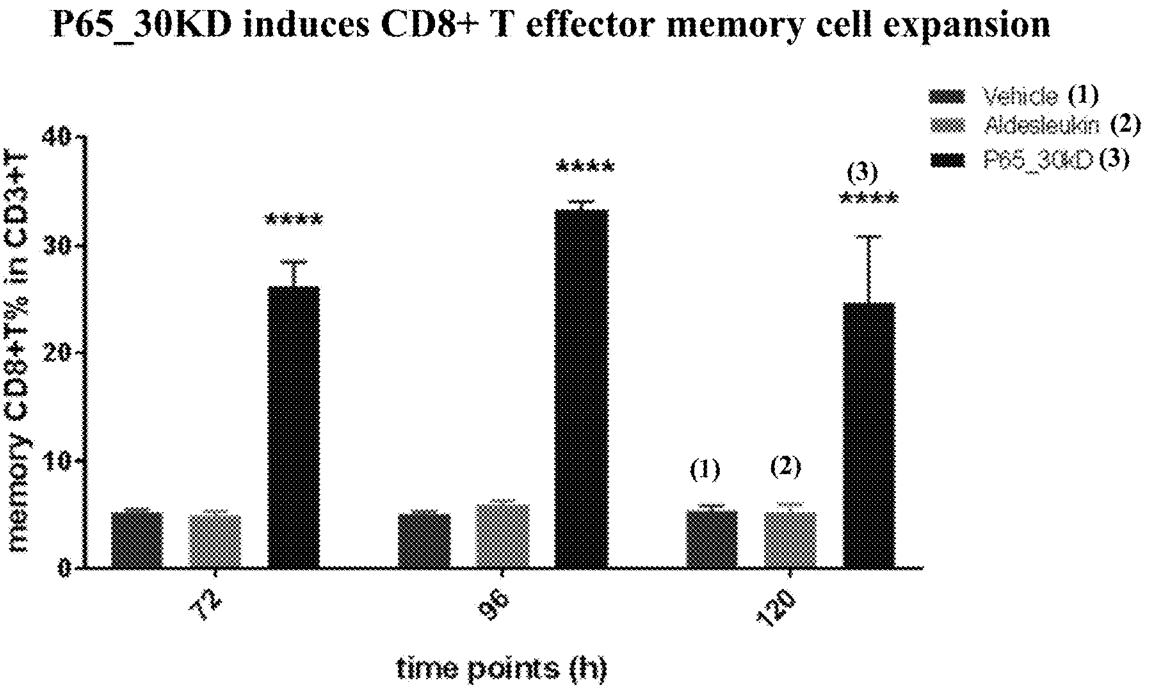
FIGS. 11A-FIG. 11B show differences between P65_30 kD and IL-2 (aldesleukin) in the stimulation of memory CD8+CD44+ T cell proliferation within the CD3+ population following treatment with a single IV bolus dose of P65_30 kD or aldesleukin (IL-2). Blood was drawn via cardiac puncture at the time points indicated and immune cell populations were assessed by flow cytometry. Data were analyzed using unpaired Student t test. *** designate P values<0.001.
Figure 11B:
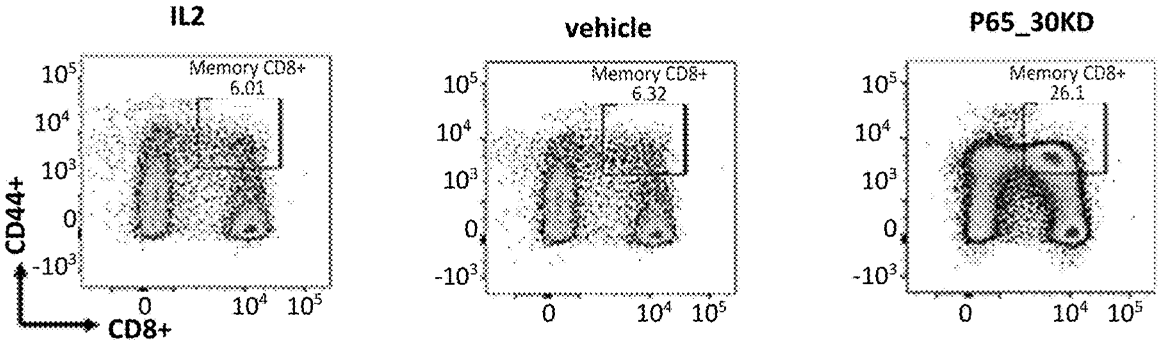

FIG. 11A-FIG. 11B show the expansion of NK and CD+ T cells by P65_30kD in B16F10 tumors. FIG. 11A shows of the percentage of NK cells, CD8+ cells and Tregs in the tumor CD3+ T cell population following treatment with a single IV bolus dose of P65_30kD at 3 g/kg. Tumor samples were analyzed for immune cell populations 5 days after treatment by flow cytometry. Each data point represents an average from 3 replicates at each time point, ±SEM. The cell population data represented is from day 5 Tumor samples and the CD8/Treg ratio was calculated from the day 7 samples. FIG. 11B shows the ratio of CD8+ effector over CD4+ regulatory T cells 7 days following treatment with a single IV bolus dose of P65_30kD at 3 mg/kg. Each data point represents an average from 3 replicates at each time point, ±SEM.

MTD Study in Balb/c Mice E3826-U1802

A dose ranging study of P65_30kD was conducted in naïve female Balb/c mice at Crown Biosciences, Inc. (San Diego, CA). The study design is shown in Table 9, wherein the dose was calculated by reference to the mass of the protein component not including the mass of the PEG moiety. Blood samples were drawn via sub mandibular vein at 7 time points (0.25, 1, 4, 12, 24, 34, 48 & 72 h). Both plasma and blood cells were collected for PK and PD analyses.

All plasma samples were analyzed for human IL-2 as well as mouse IL-2, TNF-α, IFNγ, IL-5, and IL-6 cytokines, employing commercially-available ELISA kits.

TABLE 9

PK/PD and MTD Study No. E3826-U1802-
Control and Test Treatment groups in Naïve Balb/C Mice

| Treatment | Dose (mg/kg) | Route, Schedule | Time Point | N |
|---|---|---|---|---|
| Naive | 0 mg/kg | | 0 | 3 |
| Vehicle Control | 0 mg/kg | IV, BID × 3 | 3 | 3 |
| Aldesleukin | 0.01 mg/kg | IV, BID × 3 | 3 | 3 |
| Aldesleukin | 0.03 mg/kg | IV, BID × 3 | 3 | 3 |
| Aldesleukin | 0.1 mg/kg | IV, BID × 3 | 3 | 3 |
| Aldesleukin | 1.0 mg/kg | IV, BID × 3 | 3 | 3 |
| Aldesleukin | 3.0 mg/kg | IV, BID × 3 | 3 | 3 |
| Aldesleukin | 5.0 mg/kg | IV, BID × 3 | 3 | 3 |
| P65_30kD | 0.01 mg/kg | IV, single dose | 3 | 3 |

TABLE 9-continued

PK/PD and MTD Study No. E3826-U1802-
Control and Test Treatment groups in Naïve Balb/C Mice

| Treatment | Dose (mg/kg) | Route, Schedule | Time Point | N |
|---|---|---|---|---|
| P65_30kD | 0.03 mg/kg | IV, single dose | 3 | 3 |
| P65_30kD | 0.1 mg/kg | IV, single dose | 3 | 3 |
| P65_30kD | 1.0 mg/kg | IV, single dose | 3 | 3 |
| P65_30kD | 3.0 mg/kg | IV, single dose | 3 | 3 |
| P65_30kD | 5.0 mg/kg | IV, single dose | 3 | 3 |
| #P65_30kD | 0.3 mg/kg | IV, single dose | 8 | 3 |

Figure 12A:
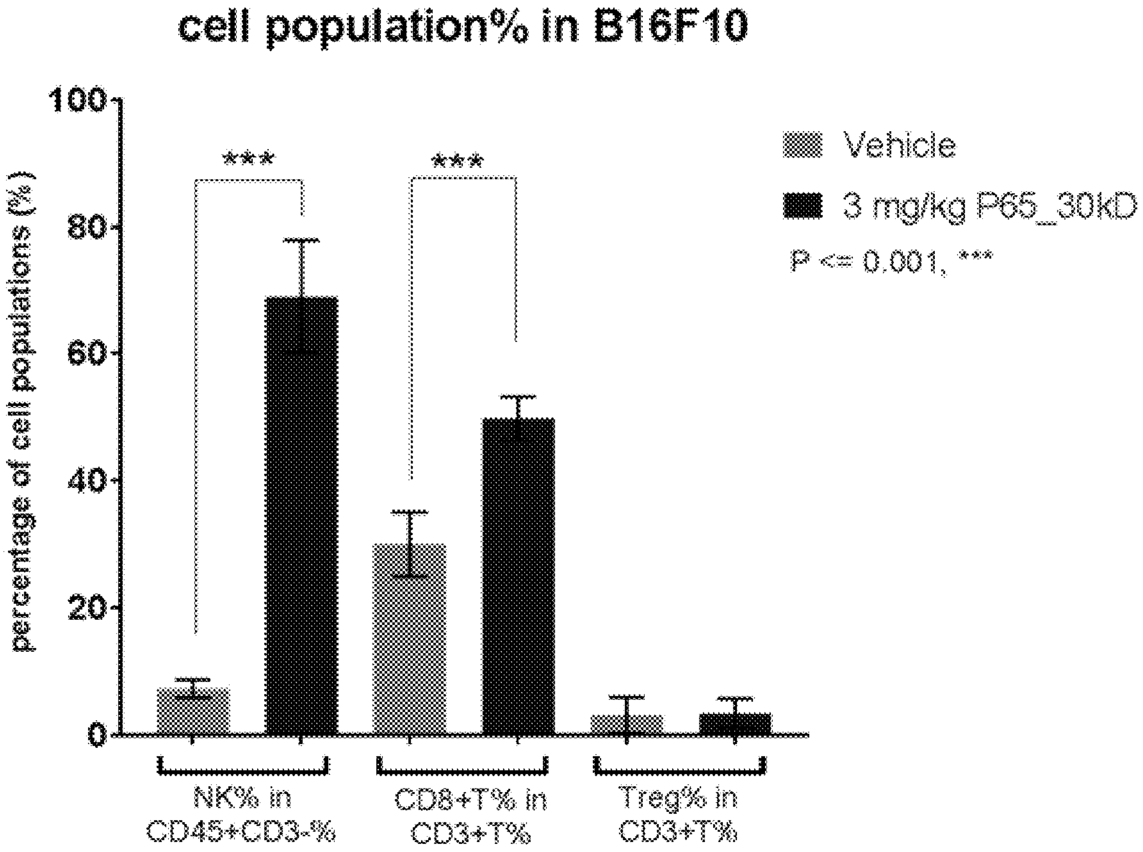
FIGS. 12A-FIG. 12B show the increase in tumor-infiltrating lymphocytes (TILs) vs time in C57B16 mice bearing syngeneic B16F10 tumors following treatment with a single IV bolus dose of P65_30 kD.
Figure 12B:
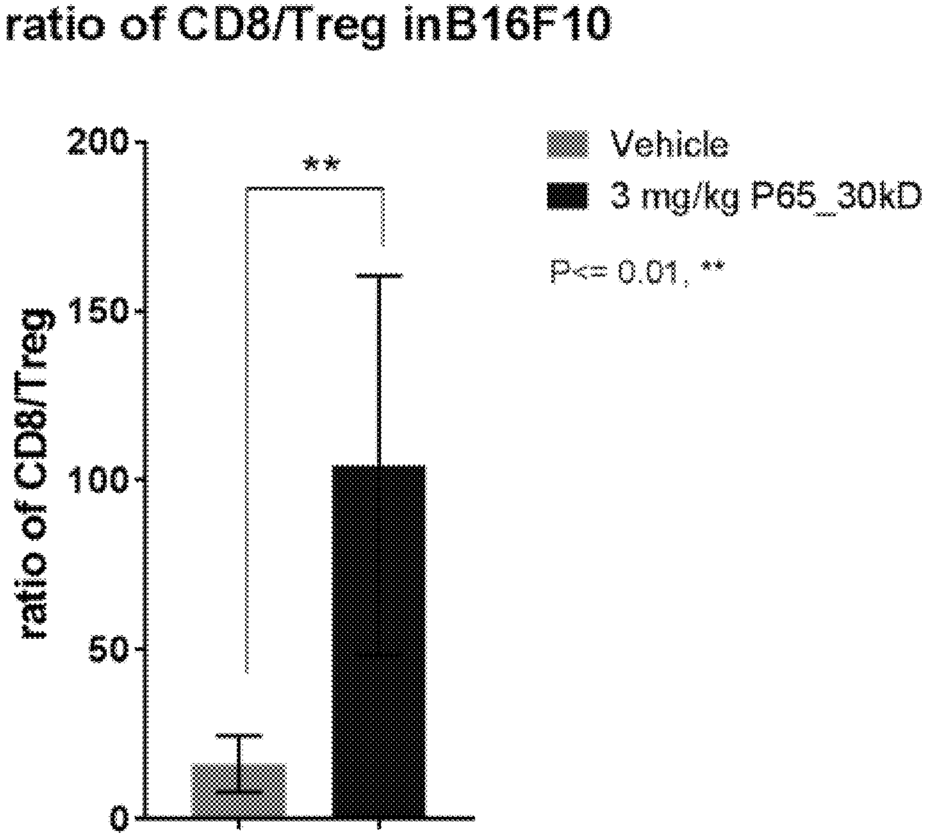

*All time point except the 72 hr time point blood collection was via the sub mandibular vein. The 72 hr time point was terminal blood collection.
#Only the 0.3 mg/kg dose of P65_30kD was used for the PK/PD evaluation Toxicology Observations in the MTD Study Using Balb/c Mice A major of toxicity associated with high-dose aldesleukin is vascular leak syndrome and associated Cytokine Release Syndrome (CRS). To evaluate the potential for this effect in mice, a single dose IV administration of P65_30kD at doses ranging from 0.01-5.0 mg/kg dose was performed (Table 10), wherein the dose was calculated by reference to the mass of the protein component not including the mass of the PEG moiety. The analysis performed was hematology, histopathology, organ weight, and cytokine analyses. Abnormalities were not observed with hematology, histopathology or body weights relative to the vehicle control mice with both P65_30kD or aldesleukin. With respect to the cytokine analysis, it was observed that aldesleukin elevated plasma IL-5 levels starting at 1 mg/kg to 5 mg/kg (FIG. 12A). With P65_30kD, a moderate increase in IL-5 (but less compared to aldesleukin) was seen only at 5 mg/kg dose (FIG. 12B). A transient elevation in the systemic levels of IFNγ was observed with both aldesleukin and P65_30kD.

Example 7

PK/PD in Cynomolgus Monkeys—Study No.: 20157276

The pharmacokinetic and pharmacodynamics profile of P65_30kD was evaluated in non-naïve cynomolgus monkeys following administration of a single intravenous dose at 0.3 mg/kg, wherein the dose was calculated by reference to the mass of the protein component not including the mass of the PEG moiety. The study was conducted at Charles River Laboratories, Inc. (Reno, NV) and PK data analysis was performed at NW Solutions (Seattle, WA). Blood samples were collected pre-dose and at 21 time points (0.5, 1, 2, 4, 8, 12, 24, 36, 48, 72, 120, 144, 168, 192 and 240 h post-dose. Both plasma and blood cells were collected for PK and PD analyses. Selected time points were used for PK, PD, cell population and hematology analysis.

All plasma samples were analyzed for human IL-2 (PK readout) employing commercially-available ELISA kits.

Table 10 shows P65_30kD PK Parameters in Cynomolgus monkey.

TABLE 10

| ROA | Parameter | Units | 0.3 mg/kg Animal 2699 | Animal 2705 Estimate | Mean |
|---|---|---|---|---|---|
| IV | $T_{max}$ | hr | 0.500 | 0.500 | 0.500 |
| | $C_{max}$ | ng/mL | 11000 | 11400 | 11200 |
| | $AUC_{0-t}$ | hr*ng/mL | 121000 | 120000 | 121000 |
| | $t_{1/2}$ | hr | 13.4 | 13.9 | 13.6 |
| | CL | mL/hr/kg | 2.47 | 2.49 | 2.48 |
| | $V_{ss}$ | mL/kg | 29.0 | 32.1 | 30.5 |

After single IV bolus dosing Tmax was observed at 0.5 h post-dose (the first measured timepoint after dosing) and mean plasma concentrations were measurable out to 168 h post-dose (the last measure) The $t_{1/2}$ and AUC for P65_30kD were 13.6 h and 121000 hr*ng/mL respectively.

Hematology Parameters—Cynomolgus Monkeys—Study No.: 20157276

For hematologic parameters the evaluation time points correspond to pre-dose at day −1 and 1, 3, 6, 8, 10, 12, 14, 17, 19, 21 post-dose.

Figure 13A:
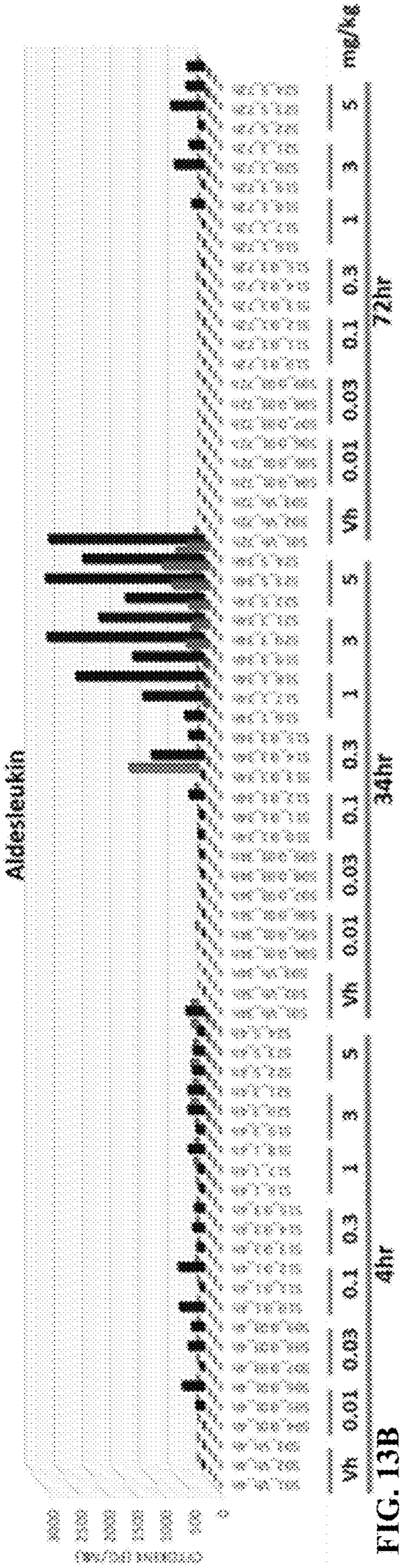
FIGS. 13A-FIG. 13B show plasma levels of mouse IL-2, TNF-α, IFNγ, IL-5 and IL-6 following treatment with a single IV bolus dose of P65_30 kD or aldesleukin (IL-2) at increasing levels (0.01-5 mg/kg). The concentration of each cytokine in plasma was determined via ELISA (Abcam, Cambridge, UK). For each dose group N=3 mice and samples were collected at 4, 34 and 72 h post-dose.
Figure 13B:
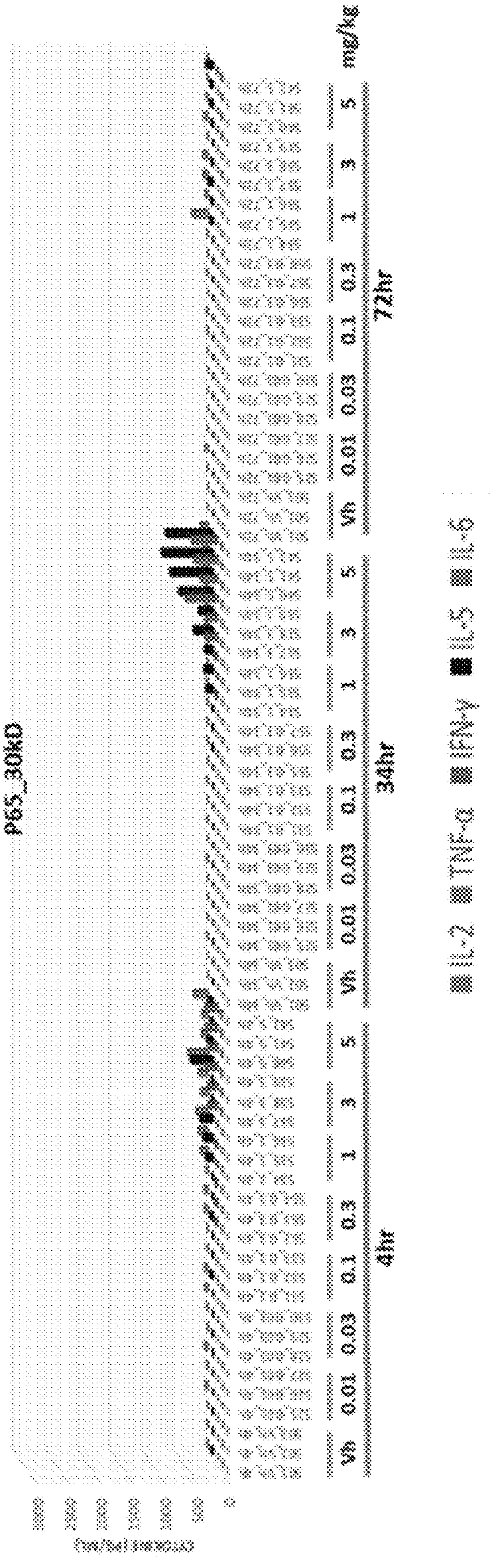
Figure 14:
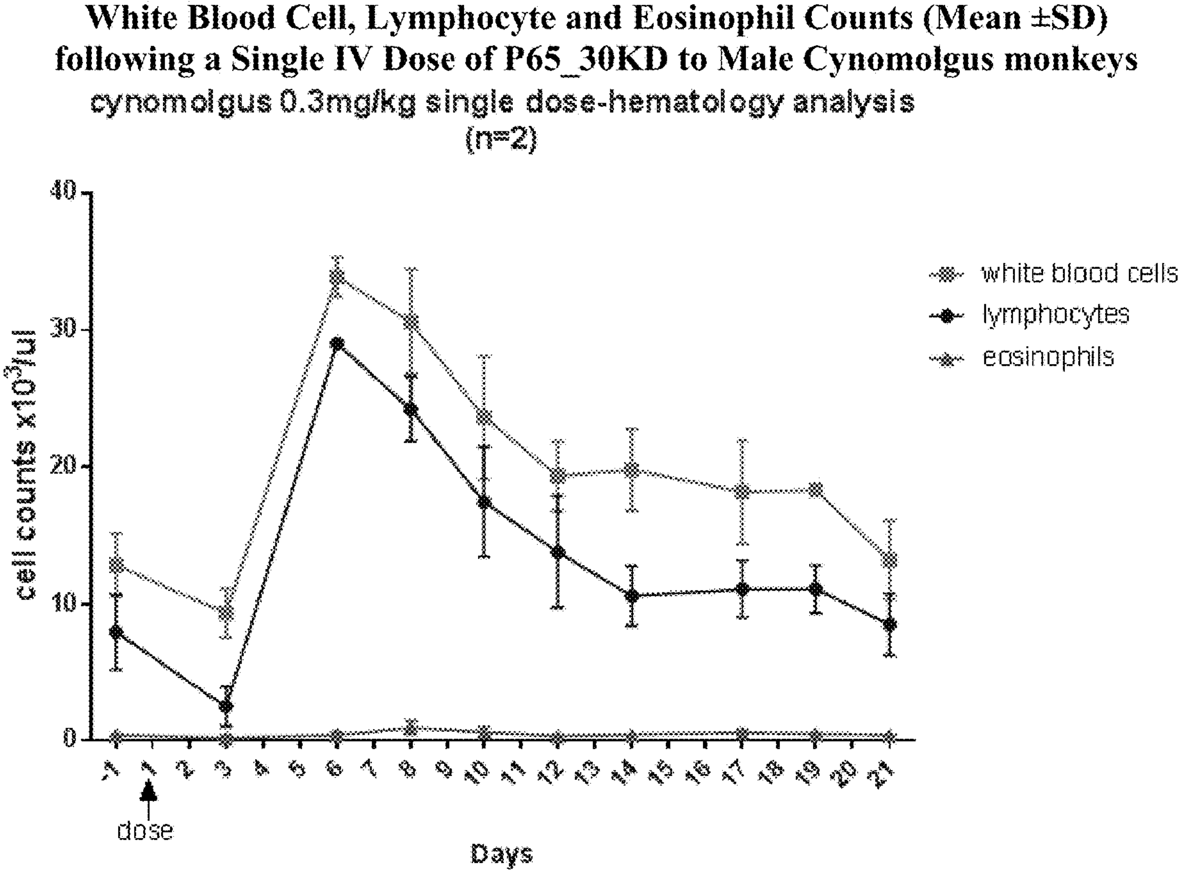
FIG. 14 shows white blood cell, lymphocyte, and eosinophil counts (mean±SD) following a single IV dose of P65_30 kD to male Cynomolgus monkeys.

FIG. 13 shows the absolute white blood cell and differential counts. Data represents mean±SD (N=2 animals/dose group).

Analysis of the white blood cell (WBC) subpopulations revealed major increase in WBC count was due an expansion of Lymphocyte cell population which is consistent with the mechanism of P65_30kD. There is no elevation of eosinophils.

Example 8

Figure 16A:
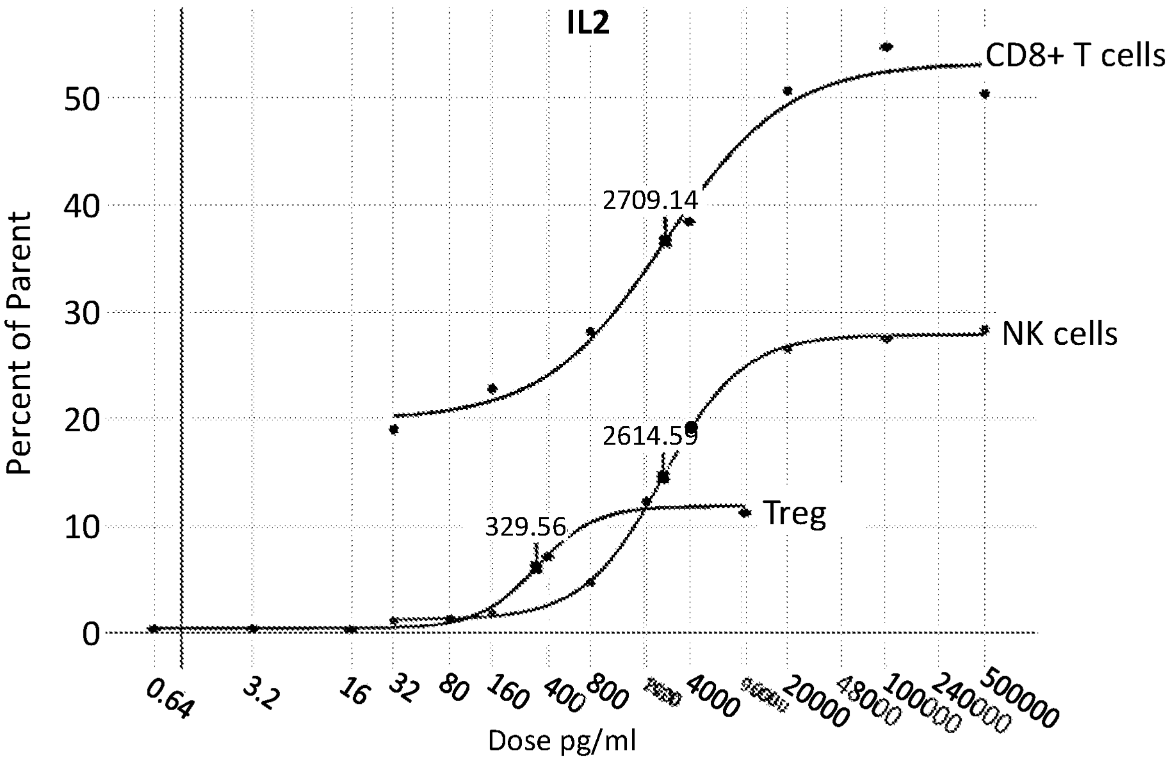
FIGS. 16A-FIG. 16B show PEG IL-2 compounds can specifically expand immune cell populations ex vivo in primary lymphocytes, as compared to a normal IL-2 control.
Figure 16B:
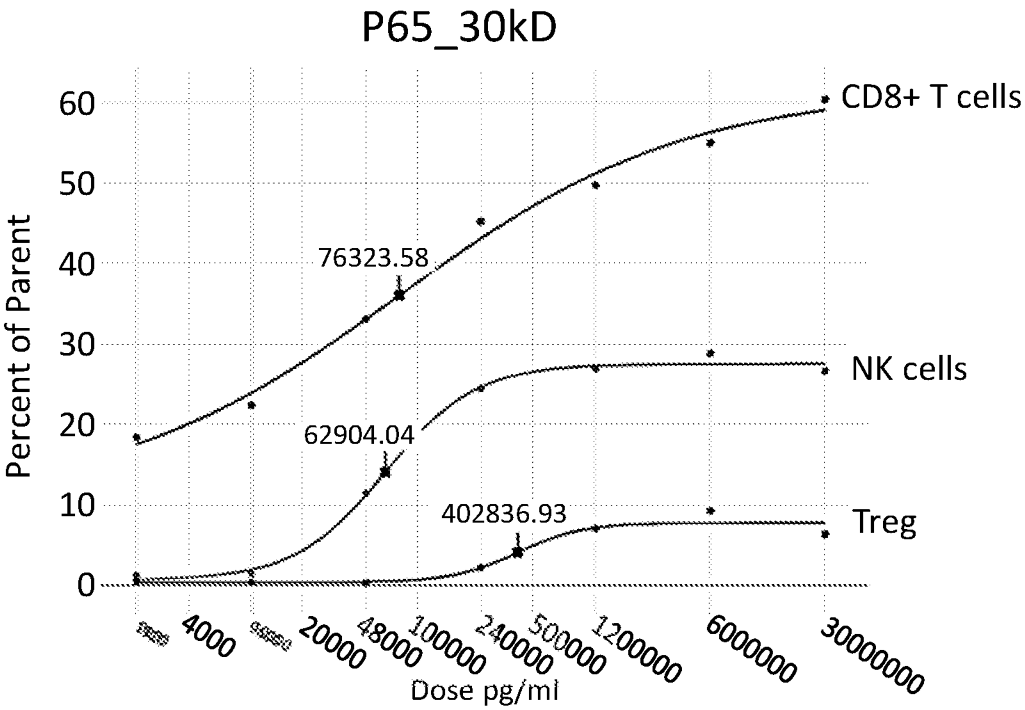

Markers of Treg Expansion in Primary Lymphocytes Treated with Various PEG IL-2 Compounds Primary lymphocytes from fresh human leucocyte reduction system (LRS) were harvested, ficoll prepped, and rested at 4 C overnight. The following day, FACS was used to sort the lymphocyte populations including CD8 positive Tcells, NK cells, and Tregs. Isolated populations were stimulated with plate-bound anti-CD8/CD28 for two days. Dose curves of native IL-2 and K9_30kD were incubated at 37 C. On the third day, the media was refreshed and dose curves of compounds were added again. On day 6, cells were harvested and analyzed using Flow cytometry to profile CD25 levels and Ki-67 as a measure of proliferation. FIG. 16 shows PEG IL-2 compounds can specifically expand immune cell populations ex vivo in primary lymphocytes, as compared to a normal IL-2 control. FIG. 16A shows markers for immune cell expansion Ki67 after treatment with IL-2 (control). FIG. 16B shows markers for immune cell expansion Ki67 after treatment with P65_30kD.

Example 9

PEG Size can be Dialed to Adjust Pharmacokinetics for Clearance Rate In Vivo

The PK/PD relationship of the pegylated IL-2 variant E62 modified with 5kD and 30kD mPEGs, compared to the reference compound Aldesleukin (Proleukin), was investigated. There were 4 groups of 6-8 week old C57/B16 mice ranging from 16-22 g, each group contained 12 mice. Mice received doses via single IV injection on day 0, time 0. At the indicated time points, approximately 100 ul of whole blood were collected in EDTA tubes for processing: 50 ul was fixed in buffer for Flow cytometry, and plasma was extracted from the remaining sample for ELISA analysis. For terminal blood collection, approximately 300 ul of whole blood was fixed, the remaining sample was spun down for plasma and used for ELISA.

Test articles were formulated to 37.5 ug/ml in PBS prior to IV dosing at 10 mL/kg, and 100 μL samples were collected at t=8 min, 15 min, 30 min, and 1, 2, 4, 8, 12, 24, 48, 72, 96, and 120 hours post dose. Table 11 illustrates the treatment regimen, wherein the dose was calculated by reference to the mass of the protein component not including the mass of the PEG moiety. Table 12 illustrates the various clearance rates in vivo.

TABLE 11 illustrates treatments of mice in vivo with IL2 variant

| Group | Treatment | Dose (mg/kg) |
|---|---|---|
| 1 | Vehicle | 0.0 |
| 2 | Aldesleukin | 0.3 |
| 3 | E62 (30kDa PEG) | 0.3 |
| 4 | E62 (5kDa PEG) | 0.3 |

TABLE 12 illustrates clearance rates for IL variants in comparison to Aldesleukin control

| Treatment | Aldesleukin | E62 (30kDa PEG) | E62 (5kDa PEG) |
|---|---|---|---|
| Cmax, n/g/mL | 745 | 8,450 | 936 |
| $AUC_{0-t}$ (ng*h/mL) | 432 | 81,900 | 807 |
| $t_{1/2}$ (h) | 0.576 | 10.4 | 2.56 |
| Vss (mL/Kg) | 232 | 48.9 | 404 |
| CL (mL/g/Kg) | 694 | 3.66 | 373 |

Example 10

TABLE 11 illustrates IL-2 sequences and compounds described herein.

| Name | Sequence | SEQ ID NO: |
|---|---|---|
| IL-2 (*homo sapiens*) (mature form) | APTSSSTKKTQLQLEFILLLDLQMILNGINNYKNPKLTRMLTFKFYMPKKATELKEILQCLEEELKPLEEVLNLAQSKNFEILRPRDLISNINVIVLELKGSETTFMCEYADETATIVEFLNRWITFCQSIISTLT | 1 |
| IL-2 (*homo sapiens*) (precursor) NCBI Accession No.: AAB46883.1 | MYRMQLLSCIALSLALVTNSAPTSSSTKKTQLQLEFILLLDLQMILNGINNYKNPKLTRMLTFKFYMPKKATELKEILQCLEEELKPLEEVLNLAQSKNFEILRPRDLISNINVIVLELKGSETTFMCEYADETATIVEFLNRWITFCQSI-ISTLT | 2 |

Example 11

Ex-Vivo Immune Response Profiling of Exemplary IL-2 Compounds in Primary Human Leukocyte Reduction System (LRS)-Derived PBMC Samples To determine how the differential receptor specificity of exemplary IL-2 compounds affects activation of primary immune cell subpopulations, concentration-response profiling of lymphocyte activation in human LRS-derived peripheral blood mononuclear cell (PBMC) samples were performed using multi-color flow cytometry. Conjugates of Table 13 were synthesized by modification of SEQ NO. 1. These studies were performed at PrimityBio LLC (Fremont, CA). Primary lymphocytes derived from human LRS samples were treated with dilutions series of exemplary IL-2 compounds and quantified based on pSTAT5 signaling in each lymphocyte cell type using the panel shown in Table 12.

TABLE 12

| Key indicating cell populations | |
|---|---|
| Marker | Cell population |
| CD3 | T cells |
| CD4 | Th cells |
| CD8 | T effector cells |
| CD45RA | Naïve T cells |
| CD56 | NK cells |
| CD14/19 | Monocyte/B cells |
| CD25 | Tregs or experienced T cell |
| CD127 | Not Treg |
| CD62L | Memory T vs effector memory T cell |
| pSTAT5 (Y694) | Activation marker |

Flow cytometry data were analyzed for activation of different T and NK cell subsets in concentration-response mode, reading pSTAT5 accumulation after treatment with an exemplary IL-2 variant K9_30 kD.

Figure 15A:
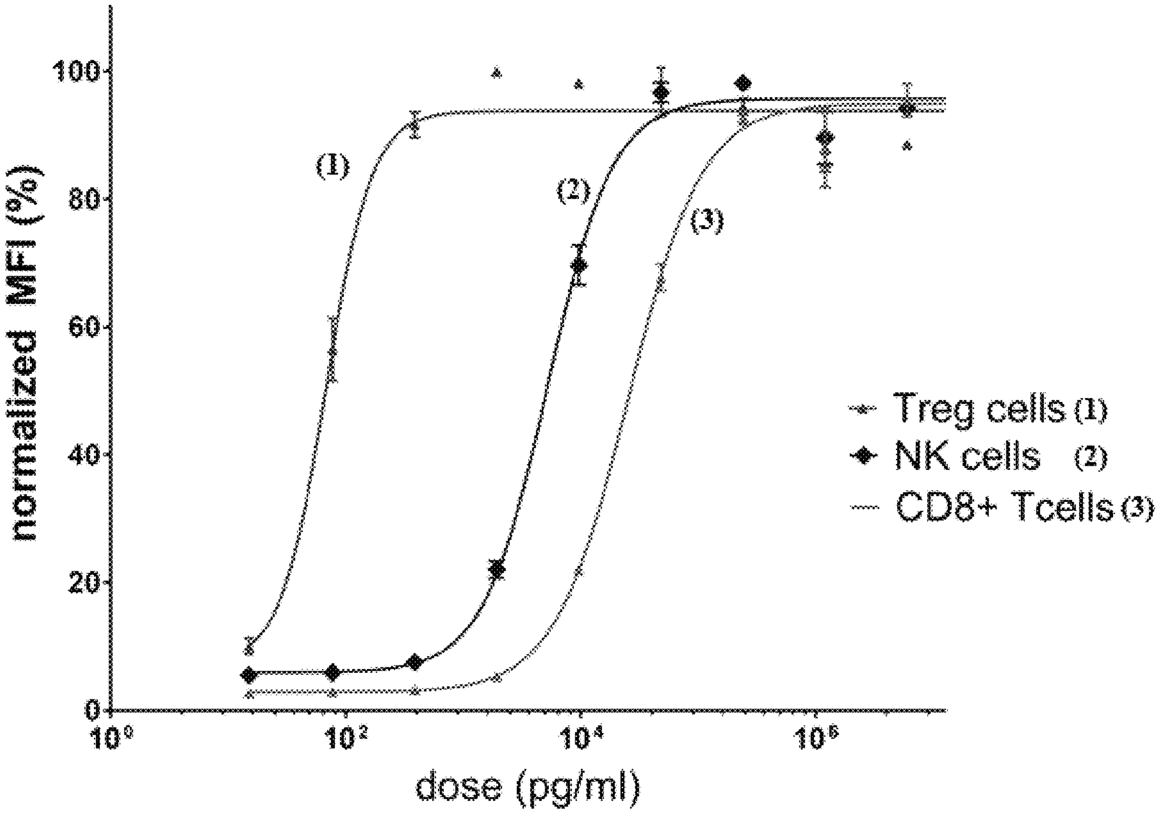
FIGS. 15A-FIG. 15B show the dose response curves of an exemplary IL-2 variant for pSTAT5 signaling in human LRS primary cell (FIG. 15A) and proliferation response in mouse CTLL-2 populations (FIG. 15B).
Figure 15B:
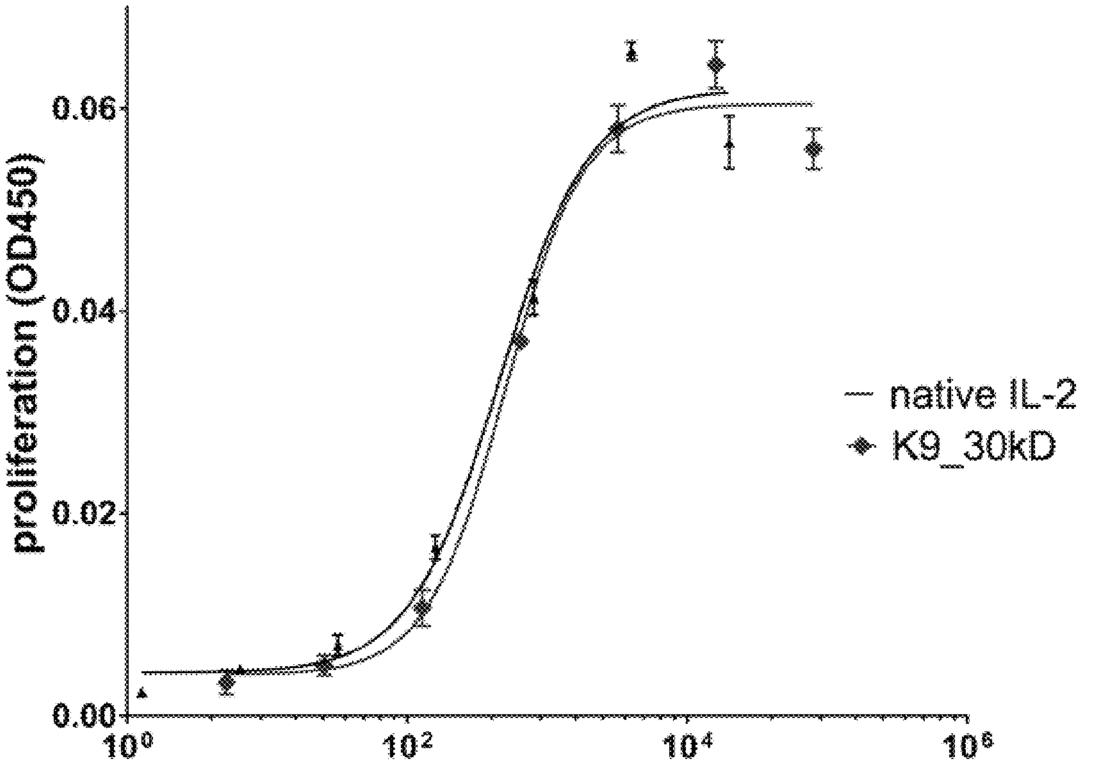

FIG. 15A-FIG. 15B show the dose response curves for pSTAT5 signaling in human LRS primary cell (FIG. 15A) and proliferation response in mouse CTLL-2 populations (FIG. 15B).

Table 13 shows the dose response EC50 for pSTAT5 signaling (EC50) in human LRS samples or CTLL-2 proliferation treated with indicated IL-2 variant.

TABLE 13

Dose response EC50 for pSTAT5 signaling (EC50) in human LRS samples or CTLL-2 proliferation treated with indicated IL-2 variant

| Compound | NK cells | CD8 + Tcells | Treg cells | CD8 +/Treg ratio | Fold increase in Treg EC50 vs native IL-2 | CTLL-2 proliferation |
|---|---|---|---|---|---|---|
| native IL-2 | 4586 | 31024 | 75 | 414 | 1 | 455.8 |
| K9_30kD | 169578 | 1100679 | 2217 | 496 | 30 | 504 |
| H16_30kD | 2545257 | 12070108 | 34976 | 345 | 466 | 80755 |
| L19_30kD | 6756768 | 22436430 | 93205 | 241 | 1243 | 3510 |
| D20_30kD | 2643930 | 9505217 | 1129455 | 8 | 15059 | 689939 |
| M23_30kD | 143620 | 539824 | 1030 | 524 | 14 | 1102 |
| N26_30kD | 258531 | 1188859 | 2459 | 483 | 33 | 2594 |
| N88_30kD | 3298113 | 11111537 | 323201 | 34 | 4309 | 66606 |
| E100_30kD | 35088 | 195823 | 483 | 405 | 6 | 1676 |
| N119_30kD | 34010 | 143380 | 535 | 268 | 11 | 1215 |
| T123_30kD | 33396 | 152928 | 269 | 569 | 6 | 255 |
| Q126_30kD | 3676807 | 19722480 | 29454 | 670 | 393 | 3584 |
| S127_30kD | 20210 | 92190 | 150 | 615 | 3 | 123 |
| T131_30kD | 24207 | 132922 | 258 | 515 | 3 | 641 |
| N88R/D109_30kD | 2780819 | 12503386 | 175805 | 71 | 3663 | 59577 |
| V91K | 20537 | 102255 | 142 | 720 | 3 | 99.5 |
| N88R | 2312847 | 15025734 | 11082 | 1356 | 148 | 363 |

The EC50 values (pg/ml) were calculated from dose response curves generated from the MFI plots.

*Treg potency change compared to native IL-2 (wild-type IL-2) run in each individual experiment.

Example 12

PK Study in C57BL/6 Mice

Experimental details are summarized in Table 14, wherein the dose was calculated by reference to the mass of the protein component not including the mass of the PEG moiety.

TABLE 14

| Group | Number of Animals | Test/Control Article (dose) | Route, Dosing Regimen | End Point(s) |
|---|---|---|---|---|
| 1 | 9 | Native IL-2 (wild-type) (3.0 mg/kg) Concentration: 0.6 mg/mL | IV, single dose on Day 0 at T = 0 at 5 mL/kg | Blood collection at 0.08, 0.25, 0.5, 1, 2, 4, 8, 12, and 24 hours post dose |
| 2 | 9 | K35_30kD (3.0 mg/kg) Concentration: 0.6 mg/mL | IV, single dose on Day 0 at T = 0 at 5 mL/kg | |
| 3 | 9 | K35_30kD (0.3 mg/kg) Concentration: 0.6 mg/mL | IV, single dose on Day 0 at T = 0 at 5 mL/kg | |

TABLE 14-continued

| Group | Number of Animals | Test/Control Article (dose) | Route, Dosing Regimen | End Point(s) |
|---|---|---|---|---|
| Extra | 6 | N/A | N/A | Blank Matrix Collection (untimed) |
| Total | 33 | | | |

The pharmacokinetic properties of an exemplary PEGylated IL-2 compound K35_30 kD at two dose levels were evaluated. The lyophilized test article was reconstituted in PBS, and nine male C57BL/6 mice were dosed with 0.3 and 3 mg/kg via intravenous tail vein injection for each dose group (see collection details below). Blood samples were collected at 0.08, 0.25, 0.5, 1, 2, 4, 8, 12, and 24 hours post dose. The hIL-2 ELISA kit from Abcam (ab100566), which does not cross-react with native mouse IL-2, was used for detection and quantitation of test articles. To adjust for ELISA-specific differences in sensitivity of kit detection of native and PEGylated compounds, native IL0-2 and K35_3kD test article standard curves were generated using the test article diluent buffer, and data were analyzed with respect to respective standard curves. The data plotted represent the mean and SEM of three individual samples (biological replicates) as described above, and PK parameters for K35_30 kD test articles were extracted and summarized in Table 15.

TABLE 15

| Analyte | Parameter | Unit | Dose 0.3 mg/kg Estimate | Dose 3 mg/kg Estimate |
|---|---|---|---|---|
| IL-2 K35-mPEG30kD | $T_{max}$ | hr | 0.250 | 0.250 |
| | $C_{max}$ | ng/mL | 6080 | 57700 |
| | $AUC_{0-t}$ | hr*/ng/mL | 38500 | 425000 |
| | $R^2$ | | 0.994 | 0.947 |
| | $AUC_{1/2extrap}$ | % | 35.3 | 37.4 |
| | $AUC_{0-\infty}$ | h*ng/mL | 59600 | 679000 |
| | $t_{1/2}$ | hr | 18.2 | 19.5 |
| | $C_{max}/D$ | kg*ng/mL/mg | 20300 | 19200 |
| | $AUC_{0-t}/D$ | hr*ng/mL | 128000 | 142000 |

Example 13

Characterization of Binding to Human IL-2R Alpha and IL-2R Beta

A study was conducted to characterize the binding of an exemplary IL-2 conjugate IL-2_P65[AzK_L1_PEG30kD]-1 to human IL-2R alpha and IL-2R beta.

Figure 17A:
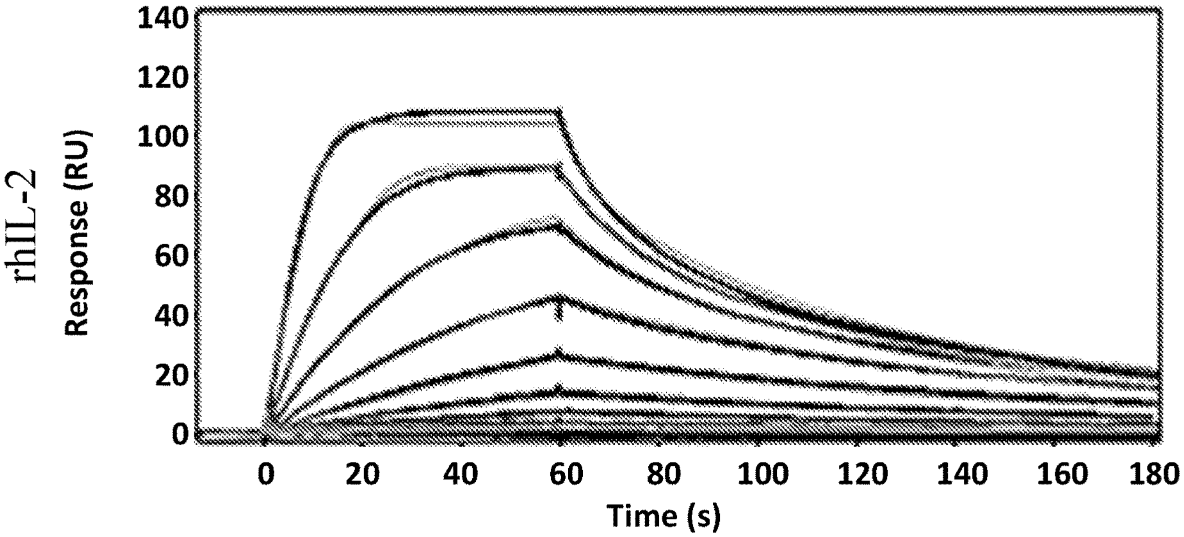
FIGS. 17A-FIG. 17B show sensorgrams of the binding responses for rhIL-2 (recombinant human interleukin-2, FIG. 17A) and synthetic conjugate IL-2_P65 [AzK_L1_PEG30kD]-1 (FIG. 17B) over the IL-2R alpha surfaces. No significant binding response was detected for IL-2_P65[AzK_L1_PEG30kD]-1 under these conditions.
Figure 17B:
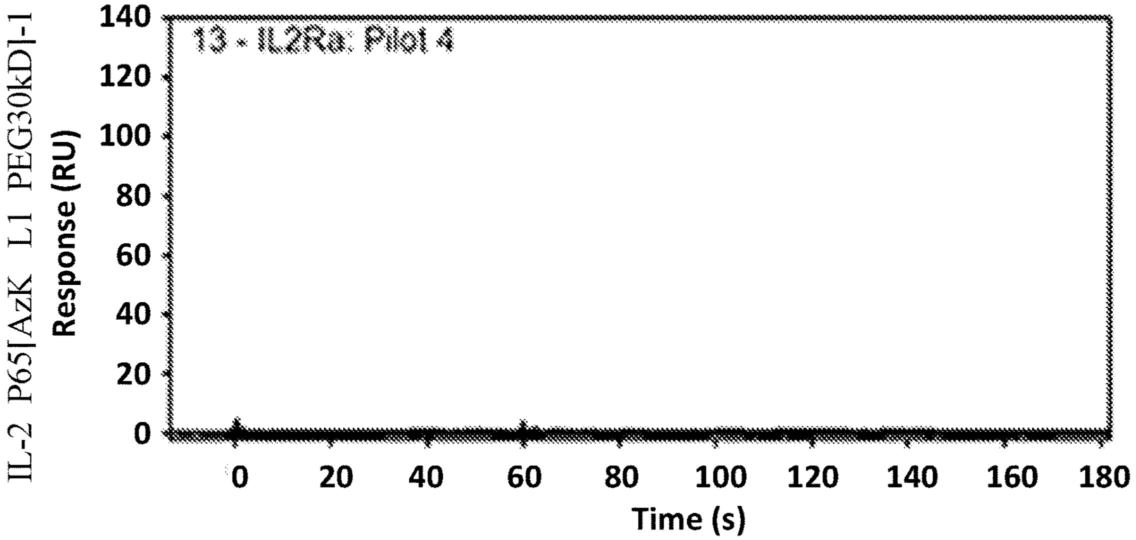

Test article samples binding to IL-2R alpha. The test article samples in solution were tested for binding over the IL-2R alpha receptor surfaces. Response data were processed by subtracting the signals from a reference surface without receptor as well as an average of buffer injections using Scrubber-2 (Biologic Software Pty Ltd). Responses for the rhIL-2 concentration series were globally fit to a 1:1 interaction model including a step for mass transport (FIG. 17A-17B). A summary of the binding constants is provided in Table 16.

TABLE 16

| | $K_D$ (nM) IL-2 R alpha | $K_D$ (nM) IL-2 R beta |
|---|---|---|
| rhIL-2 | 11 ± 1 | 0.7 ± 1 |
| IL-2_P65 [AzK_L1_PEG30kD]-1 | n.d. | 3.1 ± 0.3 |

Capture of Fc-tagged IL-2R beta on Protein coated CM4 sensor chip. A CM4 sensor chip was docked into the Biacore 4000 optical biosensor and the instrument was primed three times with HBS-P running buffer (HBS-P is 1×HBS-N with 0.005% Tween-20 added). Protein A was coupled using standard NHS/EDC coupling conditions. IL-2R beta-Fc was dissolved in water to a concentration of 0.1 mg/ml and then diluted 1/1000 into the HBS-P running buffer. IL-2R beta-Fc was injected for different lengths of time to create 2 different density receptor surfaces (~750 RU and 1500 RU, data not shown).

Figure 17C:
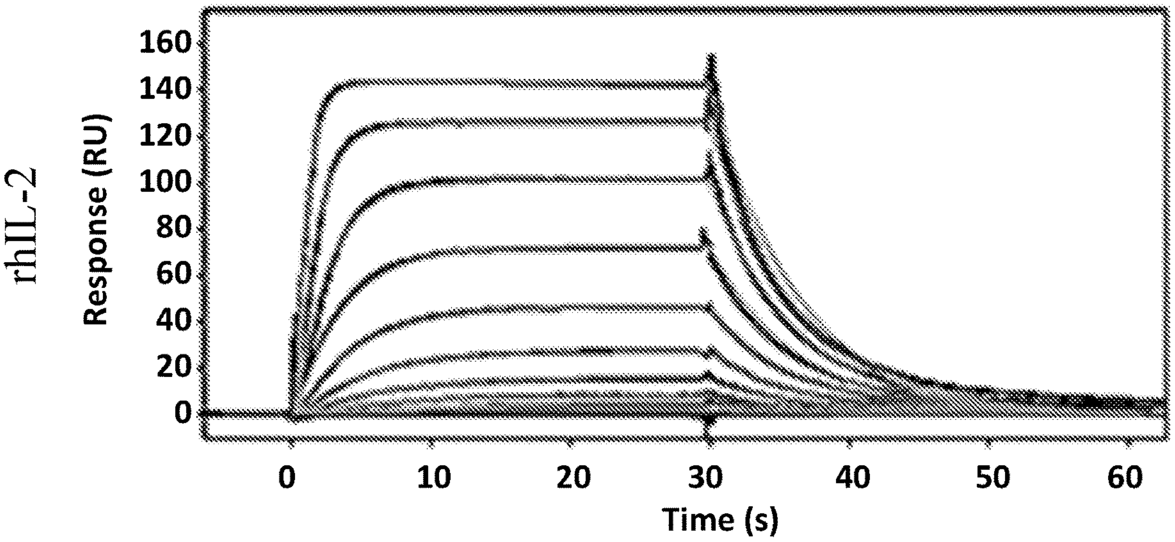
FIGS. 17C-FIG. 17D shows sensorgrams of rhIL-2 (recombinant human interleukin-2, FIG. 17C) and synthetic conjugate IL-2_P65[AzK_L_PEG30kD]-1 (FIG. 17D) samples binding to IL-2R beta surfaces.
Figure 17D:
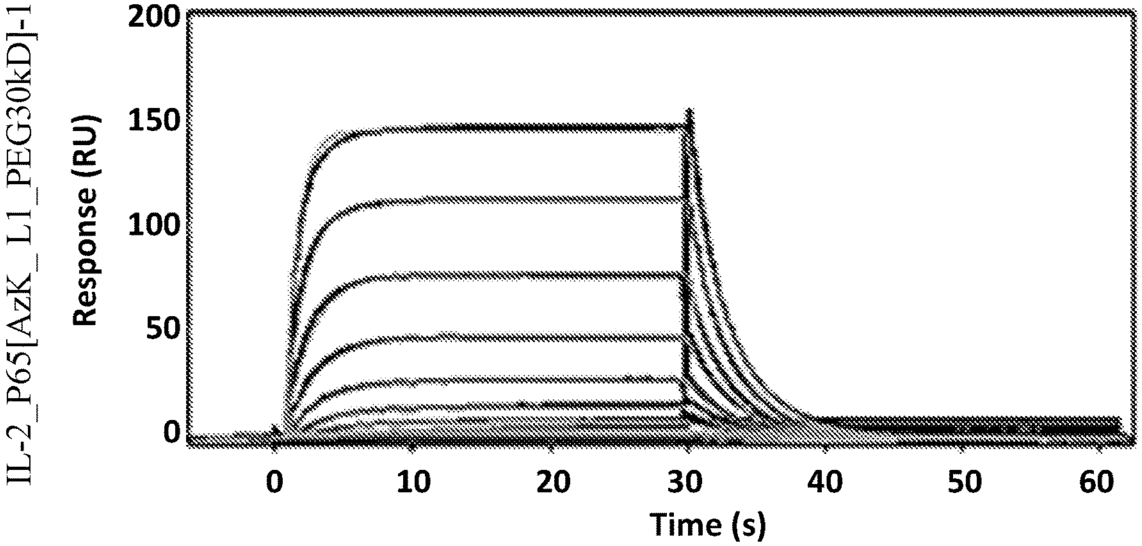

Characterization of samples binding to IL-2R beta. The test article samples in solution were tested for binding over the IL-2R beta receptor surfaces. Response data were processed by subtracting the signals from a reference surface without receptor as well as an average of buffer injections using Scrubber-2 (Biologic Software Pty Ltd). Responses for the rhIL-2 (4 uM highest concentration 2-fold dilutions) and IL-2_P65[AzK_L1_PEG30kD]-1 samples (8 uM highest concentration 2-fold dilutions) tested in duplicate were globally fit to a 1:1 interaction model including a step for mass transport as shown in FIGS. 17C-17D. A summary of the binding constants is provided in Table 16.

Results. His-tagged IL-2R alpha was captured at different densities on a nickel charged NTA sensor chip within a Biacore SPR biosensor system. Fc-tagged IL-2R beta was captured at different densites on a Protein A coated CM4 sensor chip. Response data were fit to a 1:1 interaction model to determine binding constants for each interaction. Recombinant human IL-2 (rhIL-2) bound to IL-2R alpha with an affinity of ~11 nM, while no binding of IL-2_P65 [AzK_L1_PEG30 kD]-1 samples could be detected to the IL-2R alpha. The rhIL-2 bound to IL-2R beta with an affinity of ~700 nM, and IL-2_P65[AzK_L1_PEG30 kD]-1 bound to IL-2R beta with an affinity of ~3 uM under these test conditions.

Example 14

A study was conducted to determine the potency and differential cell-type specificity of IL-2_P65 [AzK_L1_PEG30 kD]-1 vs. recombinant human interleukin-2 (hIL-2) for the phosphorylated form of the transcription factor STAT5 (pSTAT5) signaling potency human primary immune cell types.

Human PBMC sample Treatment Methods. Stocks of IL-2 (control, 1 mg/mL), and IL-2_P65[AzK_L1_PEG30 kD]-1 ("lot 1": 1.27 mg/mL; "lot 2": 2.29 mg/mL) were stored as stock solutions frozen at −20° C.

The IL-2 P65[AzK_L1_PEG30 kD]-1 lot 1 and lot 2 compounds were diluted in PBS and the IL-2 was diluted using PBS+0.1% BSA to create 10× stocks. The 10× IL-2 stock concentration was 5 ug/ml and the GLP-1 and GLP-2 stocks were between 6-300 μg/ml, depending on the experiment. The 10× stocks were diluted in successive 5-fold dilutions to create a 10-point dose titration. The top dose of the IL-2 was 5 ug/ml and the lot 1 and lot 2 stocks were between 6-300 μg/ml depending on the experiment. 10 ul of each stock was added to 90 μl of cell samples to achieve a final top dose for IL-2 of 500 ng/ml and 0.6-30 g/ml for each of lot 1 and lot 2.

Sample Stimulation. To stimulate, 10 μl of the dose titration outlined above was added to 90 d of blood sample pre-equilibrated to 37° C. The samples were incubated at 37° C. for 45 minutes. At the end of the incubation period, the red blood cells were lysed and the cells were fixed simultaneously as follows:

100 μl cells were transferred to 900 μl of BD Lyse/Fix Buffer (Beckton Dickinson, Cat #558049) and vortexed immediately. The BD Lyse/Fix was prepared by diluting the stock 1:5 with cell culture water just prior to addition. Samples were incubated 10 minutes at room temperature, then centrifuged at 450×g for 5 minutes to pellet cells. Pelleted cells were washed with PBS+0.5% BSA and stored at −37° C. until analysis.

Staining Protocol.

Step 1. Thaw cells at room temperature. Step 2. Add the Fc Block (TruStain FcX™). Step 3. Incubate at room temperature for 5 minutes. Step 4. Add the following antibodies from Table 17:

TABLE 17

Antibodies for Human panel.

| | Fluorophore |
|---|---|
| CD4 | BUV737 |
| CD56 | BV711 |
| CD16 | BV711 |
| CD8 | BUV805 |
| CD27 | BV786 |
| CD45RA | BUV395 |
| CD127 | FITC |
| CD25 | Biotin |

Step 5. Incubate for 20 minutes at room temperature. Step 6. Wash cells two times with PBS+0.5% BSA. Step 7. Permeabilize cells by adding 10 volumes of Methanol to one volumes of cells. Step 8. Incubate cells for 10 minutes at 4° C. Step 9. Wash with PBS. Step 10. Wash cells with PBS w/0.5% BSA. Step 11. Add the Fc Block (TruStain FcX™). Step 12. Add the following post-permeabilization staining panel from Table 18:

TABLE 18

Staining reagents.

| | Fluorophore |
|---|---|
| CD3 | PE-Cy7 |
| STAT5 | Ax647 |
| Streptavidin | BV421 |
| FOXp3 | PE |

Flow Cytometry and data analysis. Samples were run on Becton Dickinson Fortessa and LSR II instrument with five lasers (372 nM, 405 nM, 488 nM, 561 nM, and 640 nM). The instruments are equipped with 20 detectors including the scatter parameters. The instruments are regularly calibrated using Becton Dickinson Cytometer Setup & Tracking Beads. The 96 well plates containing the stained samples were run at less than 8,000 cells/second using the 96-well high throughput sampler.

Figure 18:
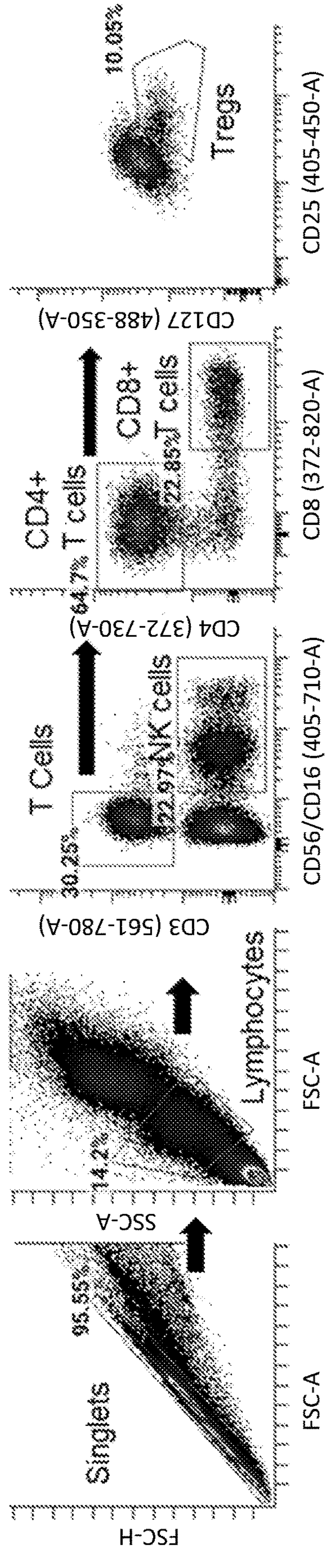
FIG. 18 shows a gating strategy for flow cytometry cell sorting of Tregs. The cells were first gated on singlets using FSC-A by FSC-H to exclude any aggregates or doublets (Singlets gate, $1^{st}$ panel). Within this gate the cells were gated on mid to high forward scatter (FSC-A) and side scatter (SSC-A) to exclude the red blood cells, debris, and granulocytes (Lymphocyte gate, $2^{nd}$ panel). The T cells were then gated as the CD3+, CD56/16 negative population $3^{rd}$ panel. The NK cells were identified as the CD3 negative, CD56/16 high population, $3^{rd}$ panel. The T cells were then divided into CD4+ T cells and CD8+ T cells ($4^{th}$ panel). The Tregs were then gated from the CD4+ T cells as the $CD25^{hi}$x$C127^{lo}$ population, $5^{th}$ panel.

The data is exported as .fcs files to a network drive and compensated to account for spillover of the fluorophores and the fcs files are annotated. The fcs files are then gated according to the strategies described FIG. 18. The cells are first gated on singlets using FSC-A by FSC-H to exclude any aggregates or doublets (FIG. 18, Singlets gate, $1^{st}$ panel). Within this gate the cells are gated on mid to high forward scatter (FSC-A) and side scatter (SSC-A) to exclude the red blood cells, debris, and granulocytes (FIG. 18, Lymphocyte gate, $2^{nd}$ panel). The T cells are then gated as the CD3+, CD56/16 negative population $3^{rd}$ panel. The NK cells are identified as the CD3 negative, CD56/16 high population, $3^{rd}$ panel. The T cells are then divided into CD4+ T cells and CD8+ T cells (FIG. 18, $4^{th}$ panel). The Tregs are then gated from the CD4+ T cells as the $CD25^{hi}$×$C127^{lo}$ population, FIG. 18, $5^{th}$ panel.

Statistics and plotting for derivation of EC50 values. The Median Fluorescence Intensity (MFI) for each of the cell population, donor, and compound treatment was calculated from the signal in the channel detecting phosphorylated. The statistics were analyzed using Spotfire. Within Spotfire, the data was plotted on a log scale for the compound doses and a linear scale for the MFI readings. These data were fit using a 4-parameter logistic regression equation. The EC50 was calculated as the inflection point of the curve.

Results. Human IL-2 and IL-2 P65 [AzK_L1_PEG30kD]-1 samples were diluted and tested in triplicate against each of three individual donors as described above. The calculated half-maximal effective concentration (EC50) values are listed in Table 19. Results demonstrate that IL-2_P65[AzK_L1_PEG30kD]-1 is a potent agonist of IL-2 receptor signaling in lymphocytes from human. Consistent with previous in vitro binding studies that showed IL-2_P65[AzK_L1_PEG30kD]-1 specifically engages the IL-2Rβ subunit and not IL2Rα, it demonstrated specifically reduced signaling potency in Treg cells that rely on IL-2Rα engagement for potency, compared to Teff and NK cells that do not constitutively express high levels of IL-2Rα.

TABLE 19

| Potency Characteristics for hIL-2 and IL-2_P65 [AzK_Ll_PEG30kD]-1 Lots Against Primary CD8 + T Cell, NK Cell, and Treg Cell Subpopulations from Human donors. Human Cell EC50 (ng/mL) | | | | | |
|---|---|---|---|---|---|
| Material | CD8 + T | Mem CD8 + T | NK | Treg | CD8/Treg ratio |
| Human IL-2 | 12.4 ± 1.29 | 11.3 ± 1.63 | 2.88 ± 1.63 | 0.027 ± 0.005 | 460 |
| lot 1* | 224 ± 25.3 | 240 ± 27.3 | 54.7 ± 6.55 | 114 ± 20.3 | 2.0 |
| lot 2* | 265 ± 12.4 | 284 ± 18.3 | 55.7 ± 8.62 | 132 ± 24.0 | 2.0 |

Data are mean ± standard error of the mean (SEM) calculated from triplicate testing of samples from three independent donors.
*IL-2_P65 [AzK_L1_PEG30kD]-1.

Example 15: Stability of Il-2_P65[Azk_L1_Peg30kD]-1 in Human Serum

A study was conducted to evaluate the stability of compound IL-2_P65[AzK_L1_PEG30kD]-1 in human serum over time.

The following materials were used for the study:

| Reagent | Source | Cat # |
|---|---|---|
| Compound IL-2_P65 [AzK_L1_PEG30kD]-1 | Synthorx | Lot 19-1756 |
| HUMAN A/B SERUM, pooled | Fischer Sci | NC9370648 |
| Goat Anti-human IL2 antibody | Abcam | Ab10752 |
| PEG Polyclonal antibody | ThermoFisher | PA5-32247 |
| Mouse Anti-Rabbit IgG-HRP | Southern Biotech | 4090-05 |
| Blocker ™ Casein in PBS, 1% | ThermoFisher | 37528 |
| 1-Step ™ Ultra TMB-ELISA Substrate Solution | ThermoFisher | 34028 |
| Stop Solution for TMB Substrates | ThermoFisher | N600 |
| PBS (10X), pH 7.4 | ThermoFisher | 70011044 |

Compound IL-2 P65[AzK_L1_PEG30kD]-1 was spiked into human A/B pooled serum at three (3) concentrations (2590 ng/mL, 847 ng/mL, and 212 ng/mL) in PCR tubes. Each concentration timepoint was prepared in triplicate. Compound IL-2_P65[AzK_L1_PEG30kD]-1 was prepared in stock concentrations of 25900 ng/mL, 8470 ng/mL, and 2120 ng/mL and 20 μL of each stock solution were added to 180 μL of human pooled serum, mixed well, and incubated at 37° C. for up to 168 hours. Samples were collected at timepoints corresponding to 0, 6, 24, 48, 72, 96, 120, and 168 hours post-incubation, were divided into two aliquots, and frozen at −80° C. for batch analysis. The first set of samples were analyzed on one day and the second set of samples were analyzed on another day.

Figure 19:
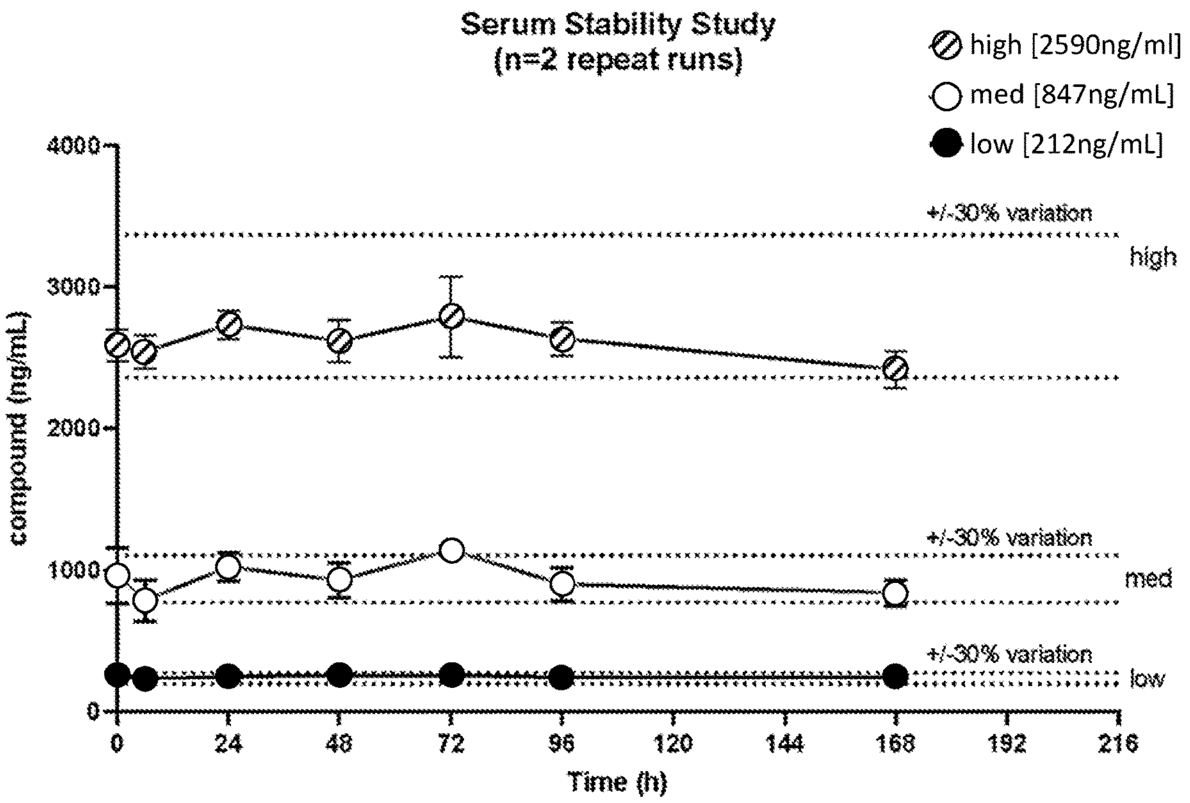
FIG. 19 shows the stability of compound IL-2_P65 [AzK_L1_PEG30kD]-1 in human serum at three concentrations up to 168 hours, as described in Example 15.

Samples were thawed at room temperature on the day of the assay using a custom ELISA format utilizing a goat anti-human IL-2 and a PEG polyclonal antibody. The ELISA plate was coated overnight at 4° C. with 1 μg/mL α-human IL2 antibody and washed with 1×PBS for 3×300 μL with a plate washer. The assay plate was blocked for one (1) hour with 1% casein in PBS. Test samples were pre-diluted with human serum to bring them into the detection range of the ELISA. Calibration standard and QC samples were also prepared with human serum matrix into neat concentration. All the samples were diluted 25-fold in assay buffer (1% casein) into MRD (minimum required dilution). Samples were added to the plate and sealed for two (2) hours at room temperature on a plate shaker and washed with 1×PBS for 3×300 μL with a plate washer. Secondary detection antibody, α-PEG (rabbit) at 1 μg/mL was added at 100 μL per well and sealed for one (1) hour at room temperature on a plate shaker and washed with 1×PBS for 3×300 μL with a plate washer. The final detection antibody, α-rabbit-HRP, was prepared as a 1:5000 dilution and added at 100 μL per well and sealed for 45 minutes at room temperature on a plate shaker and washed with 1×PBS for 3×300 μL with a plate washer. The substrate was added at 100 μL per well and placed away from light for 30 minutes without sealing or shaking. Finally, 50 μL of stop solution was added to each well and the plate was immediately read in a Spectramax iD5 plate reader to obtain OD450 values for all samples. Raw reads were interpolated to corresponding concentrations using 4-parameter logistic fit curve methods to determine sample concentrations. The data represented in FIG. 19 is the result of two repeat ELISA runs. These results demonstrate that compound IL-2_P65[AzK_L1_PEG30kD]-1 is stable in a human serum matrix up to the last time point analyzed, which was 168 hours.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of making an IL-2 conjugate, comprising:

reacting an IL-2 polypeptide, or a pharmaceutically acceptable salt, solvate, or hydrate thereof, comprising an unnatural amino acid having the structure:

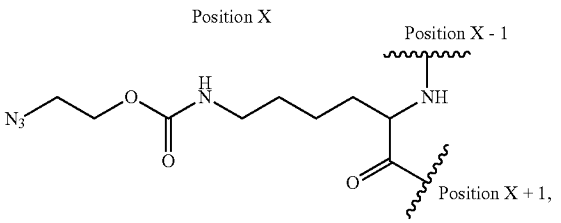 [SMILES: *NC(CCCCNC(=O)OCCN=[N+]=[N-])C(*)=O]

wherein the IL-2 polypeptide, or a pharmaceutically acceptable salt, solvate, or hydrate thereof, comprises an amino acid sequence having at least 80% sequence identity to SEQ ID NO: 1, and the unnatural amino acid substitutes for an amino acid residue within the amino acid sequence of SEQ ID NO: 1 at Position X, wherein Position X is K35, F42, F44, K43, E62, P65, R38, T41, E68, Y45, V69, L72, or Y107 in reference to the amino acid positions within SEQ ID NO: 1, Position X−1 indicates the position of the first preceding amino acid residue, Position X+1 indicates the position of the first following amino acid residue, and the wavy lines indicate covalent bonds to the amino acid residues at Position X+1 and at Position X−1, respectively, with an mPEG-DBCO of formula

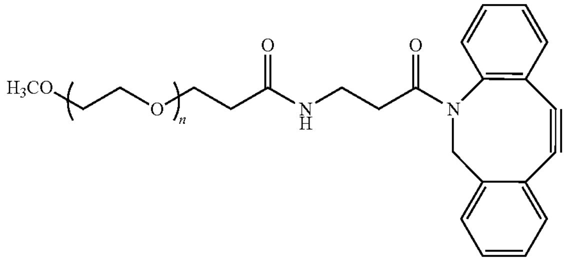

or

-continued

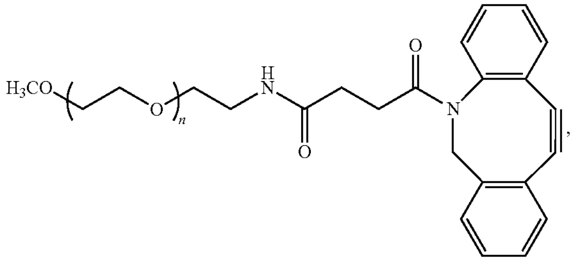

wherein n is an integer such that the mPEG-DBCO comprises an mPEG having a molecular weight of about 5 kDa, about 10 kDa, about 15 kDa, about 20 kDa, about 25 kDa, about 30 kDa, about 35 kDa, about 40 kDa, about 45 kDa, or about 50 kDa, to form an IL-2 conjugate.

2. The method of claim 1, wherein Position X is P65 in reference to the amino acid position within SEQ ID NO: 1.

3. The method of claim 1, wherein the IL-2 polypeptide, or a pharmaceutically acceptable salt, solvate, or hydrate thereof, comprises an N-terminal deletion of one residue relative to SEQ ID NO: 1.

4. The method of claim 3, wherein the IL-2 polypeptide, or a pharmaceutically acceptable salt, solvate, or hydrate thereof, comprises the amino acid sequence of SEQ ID NO: 3 in which the unnatural amino acid substitutes for an amino acid residue within the amino acid sequence of SEQ ID NO: 3 at Position X, wherein Position X is K34, F41, F43, K42, E61, P64, R37, T40, E67, Y44, V68, L71, Y106 or in reference to the amino acid positions within SEQ ID NO: 3.

5. The method of claim 1, wherein n is an integer such that the mPEG-DBCO comprises an mPEG having a molecular weight of about 30 kDa.

6. The method of claim 1, wherein the mPEG-DBCO is of formula

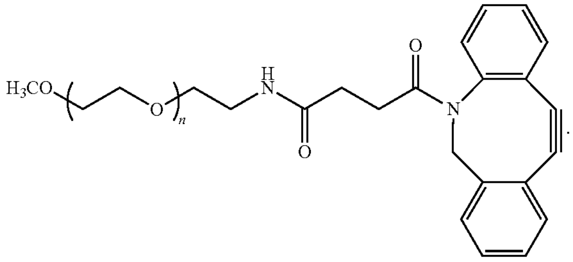

7. The method of claim 4, wherein the IL-2 conjugate comprises the unnatural amino acid and the mPEG, wherein the unnatural amino acid covalently attached to the mPEG is collectively represented by the structure of is of Formula (XII) or (XIII):

Formula (XII)

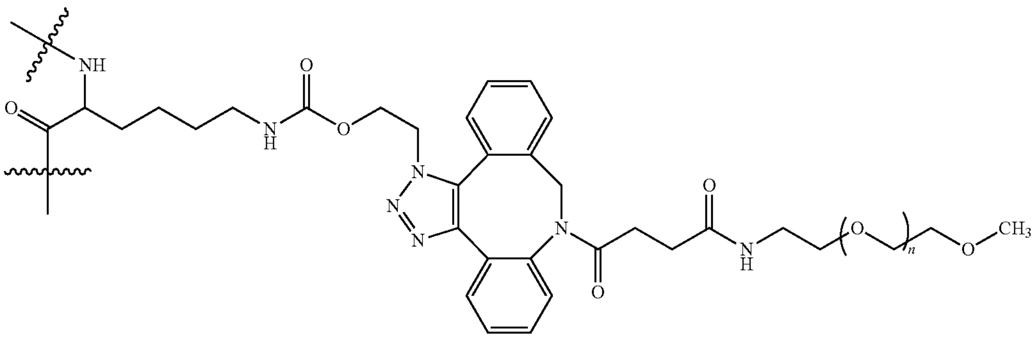

Formula (XIII)

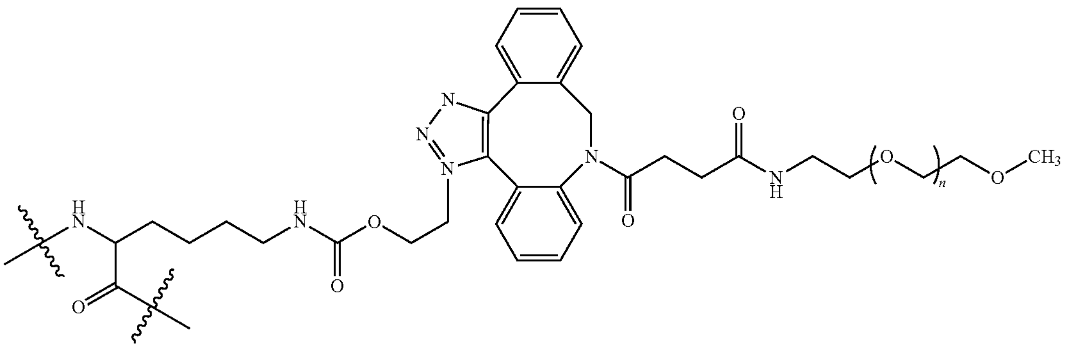

wherein n is an integer such that the mPEG having the structure of $-(OCH_2CH_2)_n-OCH_3$ has a molecular weight of about 5 kDa, about 10 kDa, about 15 kDa, about 20 kDa, about 25 kDa, about 30 kDa, about 35 kDa, about 40 kDa, about 45 kDa, or about 50 kDa, and the wavy lines indicate covalent bonds to the amino acid residues at Position X+1 and at Position X−1, respectively.

8. The method of claim 7, wherein Position X is P64 in reference to the amino acid position within SEQ ID NO: 3.

9. The method of claim 1, wherein the IL-2 polypeptide, or a pharmaceutically acceptable salt, solvate, or hydrate thereof, comprises an amino acid sequence having about 95% sequence identity to SEQ ID NO: 1.

10. The method of claim 9, wherein the IL-2 polypeptide, or a pharmaceutically acceptable salt, solvate, or hydrate thereof, comprises an amino acid sequence having about 97% sequence identity to SEQ ID NO: 1.

11. The method of claim 8, wherein n is an integer such that the mPEG having the structure of $-(OCH_2CH_2)_n-OCH_3$ has a molecular weight of about 30 kDa.

12. A method of making an IL-2 conjugate, comprising:

reacting an IL-2 polypeptide, or a pharmaceutically acceptable salt, solvate, or hydrate thereof, comprising an unnatural amino acid having the structure:

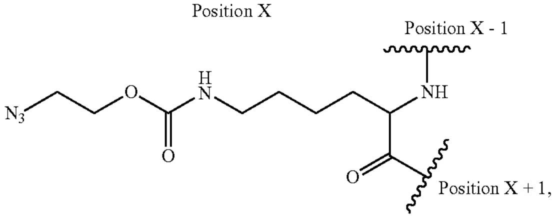 [SMILES: *NC(CCCCNC(=O)OCCN=[N+]=[N-])C(*)=O]

wherein the IL-2 polypeptide, or a pharmaceutically acceptable salt, solvate, or hydrate thereof, comprises the amino acid sequence of SEQ ID NO: 3 in which the unnatural amino acid substitutes for an amino acid residue within the amino acid sequence of SEQ ID NO: 3 at Position X, wherein Position X is P64 in reference to the amino acid position within SEQ ID NO: 3, Position X−1 indicates the position of the first preceding amino acid residue, Position X+1 indicates the position of the first following amino acid residue, and the wavy lines indicate covalent bonds to the amino acid residues at Position X+1 and at Position X−1, respectively, the following amino acid residue, with an mPEG-DBCO having the structure:

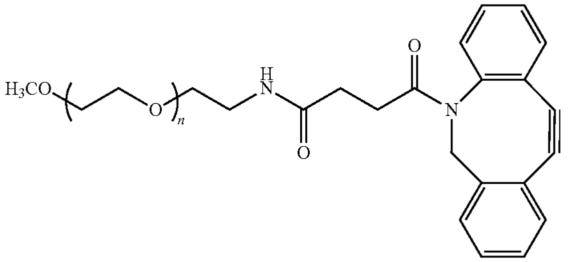

wherein n is an integer such that the mPEG-DBCO comprises a PEG having a molecular weight of about 30 kDa, to form an IL-2 conjugate comprising the unnatural amino acid and the mPEG, wherein the unnatural amino acid covalently attached to the mPEG is collectively represented by the structure of Formula (XII) or Formula (XIII):

Formula (XII)

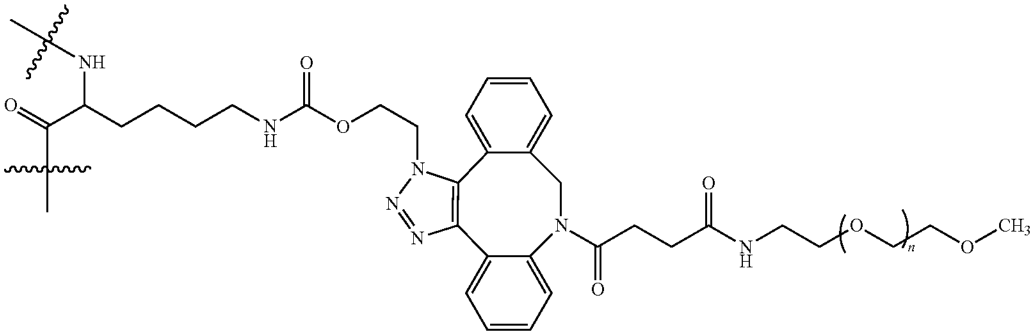

Formula (XIII)

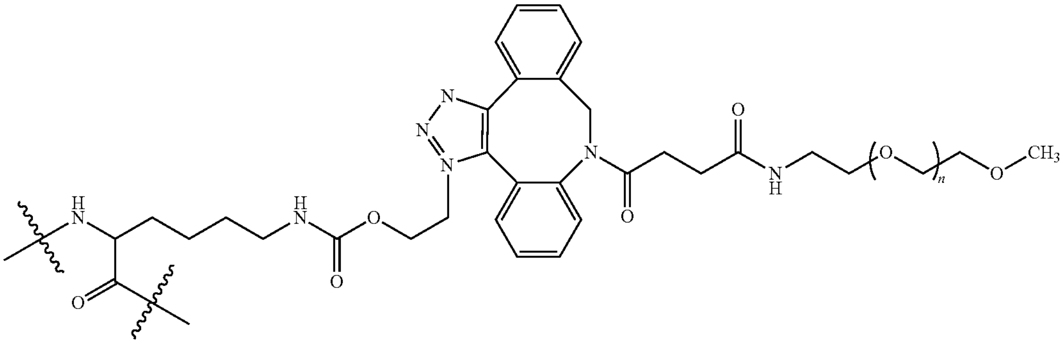

wherein n is an integer such that the mPEG having the structure of —$(OCH_2CH_2)_n$—$OCH_3$ has a molecular weight of about 5 kDa, about 10 kDa, about 15 kDa, about 20 kDa, about 25 kDa, about 30 kDa, about 35 kDa, about 40 kDa, about 45 kDa, or about 50 kDa, and the wavy lines indicate covalent bonds to the amino acid residues at Position X+1 and at Position X−1, respectively.

13. The method of claim 1, wherein Position X is K43 in reference to the amino acid position within SEQ ID NO: 1.

14. The method of claim 1, wherein Position X is Y107 in reference to the amino acid position within SEQ ID NO: 1.

15. The method of claim 4, wherein Position X is K42 in reference to the amino acid position within SEQ ID NO: 3.

16. The method of claim 4, wherein Position X is Y106 in reference to the amino acid position within SEQ ID NO: 3.

17. A method of making an IL-2 conjugate, comprising:

reacting an IL-2 polypeptide, or a pharmaceutically acceptable salt, solvate, or hydrate thereof, comprising an amino acid sequence having at least 80% sequence identity to SEQ ID NO: 1 and an unnatural amino acid having the structure:

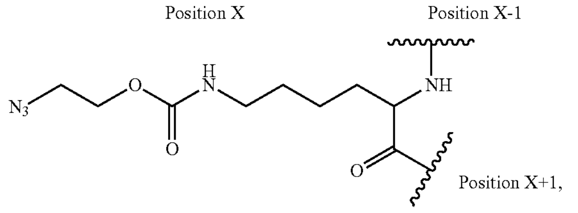 [SMILES: *NC(CCCCNC(=O)OCCN=[N+]=[N-])C(*)=O]

wherein the unnatural amino acid substitutes for an amino acid residue within the amino acid sequence of SEQ ID NO: 1 at Position X, wherein Position X is K35, F42, F44, K43, E62, P65, R38, T41, E68, Y45, V69, L72, or Y107 in reference to the amino acid positions within SEQ ID NO: 1, Position X-1 indicates the position of the first preceding amino acid residue, Position X+1 indicates the position of the first following amino acid residue, and the wavy lines indicate covalent bonds to the amino acid residues at Position X+1 and at Position X−1, respectively, with a moiety comprising a dibenzocyclooctyne group and a PEG group having a molecular weight of about 5 kDa to about 50 kDa, thereby forming an IL-2 conjugate.

18. The method of claim 17, wherein the PEG group has a molecular weight of about 30 kDa.

19. The method of claim 17, wherein Position X is P65 in reference to the amino acid position within SEQ ID NO: 1.

20. The method of claim 17, wherein Position X is K43 or Y107 in reference to the amino acid position within SEQ ID NO: 1.

21. The method of claim 17, wherein the IL-2 polypeptide, or a pharmaceutically acceptable salt, solvate, or hydrate thereof, comprises an amino acid sequence having about 95% sequence identity to SEQ ID NO: 1.

22. The method of claim 17, wherein the IL-2 polypeptide, or a pharmaceutically acceptable salt, solvate, or hydrate thereof, comprises the amino acid sequence of SEQ ID NO: 3in which the unnatural amino acid substitutes for an amino acid residue within the amino acid sequence of SEQ ID NO: 3 at Position X, wherein Position X is K34, F41, F43, K42, E61, P64, R37, T40, E67, Y44, V68, L71, or Y106 in reference to the amino acid positions within SEQ ID NO: 3.

23. The method of claim 22, wherein Position X is P64 in reference to the amino acid position within SEQ ID NO: 3.

24. The method of claim 22, wherein Position X is K42 or Y106 in reference to the amino acid position within SEQ ID NO: 3.

25. A method of making an IL-2 conjugate, comprising:

reacting an IL-2 polypeptide, or a pharmaceutically acceptable salt, solvate, or hydrate thereof, comprising an amino acid sequence having at least 80% sequence identity to SEQ ID NO: 1 and an unnatural amino acid having an azido group, wherein the unnatural amino acid substitutes for an amino acid residue within the amino acid sequence of SEQ ID NO: 1 at a position selected from K35, F42, F44, K43, E62, P65, R38, T41, E68, Y45, V69, L72, and Y107 in reference to the amino acid positions within SEQ ID NO: 1, with a moiety comprising a dibenzocyclooctyne group and a PEG group, wherein the dibenzocyclooctyne group and the PEG group are collectively represented by the structure:

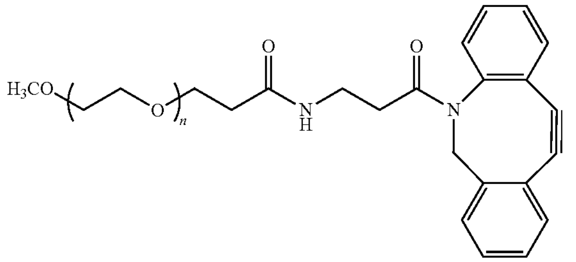

or

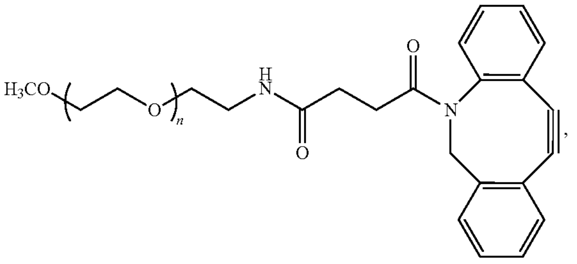

wherein n is an integer such that the PEG group having the structure of —$(OCH_2CH_2)_n$—$OCH_3$ has a molecular weight of about 5 kDa to about 50 kDa, thereby forming an IL-2 conjugate.

26. The method of claim 25, wherein n is an integer such that the PEG group having the structure of —$(OCH_2CH_2)_n$—$OCH_3$ has a molecular weight of about 30 kDa.

27. The method of claim 25, wherein Position X is P65 in reference to the amino acid position within SEQ ID NO: 1.

28. The method of claim 25, wherein Position X is K43 or Y107 in reference to the amino acid position within SEQ ID NO: 1.

29. The method of claim 25, wherein the dibenzocyclooctyne group and the PEG group are collectively represented by the structure:

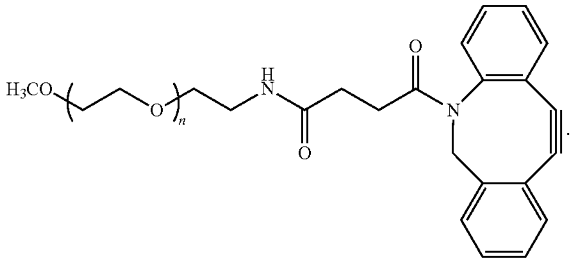

30. The method of claim 25, wherein the IL-2 polypeptide, or a pharmaceutically acceptable salt, solvate, or hydrate thereof, comprises an amino acid sequence having about 95% sequence identity to SEQ ID NO: 1.

31. The method of claim 25, wherein the IL-2 polypeptide, or a pharmaceutically acceptable salt, solvate, or hydrate thereof, comprises the amino acid sequence of SEQ ID NO: 3 in which the unnatural amino acid substitutes for an amino acid residue within the amino acid sequence of SEQ ID NO: 3 at a position selected from K34, F41, F43, K42, E61, P64, R37, T40, E67, Y44, V68, L71, and Y106 in reference to the amino acid positions within SEQ ID NO: 3.

32. The method of claim 31, wherein Position X is P64 in reference to the amino acid position within SEQ ID NO: 3.

33. The method of claim 31, wherein Position X is K42 or Y106 in reference to the amino acid position within SEQ ID NO: 3.

* * * * *